(12) United States Patent
Ackermann et al.

(10) Patent No.: US 8,440,710 B2
(45) Date of Patent: May 14, 2013

(54) HSL INHIBITORS USEFUL IN THE TREATMENT OF DIABETES

(75) Inventors: Jean Ackermann, Riehen (CH);
Stephan Brugger, Grenzach-Wyhlen (DE); Aurelia Conte, Basel (CH);
Daniel Hunziker, Moehlin (CH);
Werner Neidhart, Haganthal-le-Bas (FR); Matthias Nettekoven, Grenzach-Wyhlen (DE); Tanja Schulz-Gasch, Ziefen (CH); Stanley Wertheimer, Croton, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 103 days.

(21) Appl. No.: 12/900,621

(22) Filed: Oct. 8, 2010

(65) Prior Publication Data

US 2011/0092512 A1     Apr. 21, 2011

(30) Foreign Application Priority Data

Oct. 15, 2009   (EP) ..................... 09173178

(51) Int. Cl.
*A61K 31/4015* (2006.01)
*C07D 209/96* (2006.01)

(52) U.S. Cl.
USPC ............................ 514/409; 548/407; 548/408

(58) Field of Classification Search ................ 548/407, 548/408; 514/409
See application file for complete search history.

(56) References Cited

U.S. PATENT DOCUMENTS

| 7,968,585 B2 * | 6/2011 | Mabry et al. ............. 514/409 |
| 7,994,176 B2 * | 8/2011 | Li et al. ............... 514/254.01 |

FOREIGN PATENT DOCUMENTS

| AU | 2003/275997 | 6/2004 |
| WO | 2004/035550 | 4/2004 |
| WO | 2007/103719 | 9/2007 |
| WO | 2007/127763 | 11/2007 |

OTHER PUBLICATIONS

Wang et al., Chemical Biology (2006) vol. 13 pp. 1019-1027.
Gregoire et al., Physiol. Review (1998) vol. 78 pp. 783-809.
Unger et al., Annual Review Med. (2002) vol. 53 pp. 319-336.
Large et al., J. Lipid. Res. vol. 39 (1998) pp. 1688-1695.
Hotamisigil, G. S., J. Clin. Invest. vol. 95 (1995) pp. 2409-2415.
Gao et al., Mol. Endocrinol. vol. 18 (2004) pp. 2024-2034.
Stanley et al., Physiol. Review vol. 85 (2005) pp. 1093-1129.
Oliver, M. F., QJM vol. 99 (2006) pp. 701-709.
Cusi et al., J. Cardiometab Syndr. vol. 3 (2009) pp. 141-146.
Atgie et al., J. Physiol. Biochem. vol. 65 (2009) pp. 33-41.
Lewis, et al., Dig. Dis. Sol. vol. 55 (2010) pp. 560-578.
Sueess, R., Helvetica Chimica Acta (1997) vol. 60, No. 5, pp. 1650-1656.
Rigby, et al., Tetrahedron Letters (1998) vol. 39, No. 46, pp. 8413-8416.
Kraft et al., Tetrahedron Letters (1998) vol. 29, No. 49, pp. 6421-6424.

* cited by examiner

*Primary Examiner* — Golam M M Shameem

(57) ABSTRACT

The present invention relates to compounds of formula (I)

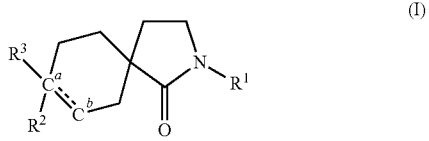

(I)

as well as pharmaceutically acceptable salts thereof. The are useful as HSL inhibitors and may, for example, be used in treatment of diabetes, metabolic syndrome, dyslipidemia, atherosclerosis, and obesity.

57 Claims, No Drawings

HSL INHIBITORS USEFUL IN THE TREATMENT OF DIABETES

PRIORITY TO RELATED APPLICATION(S)

This application claims the benefit of European Patent Application No. 09173178.6, filed Oct. 15, 2009, which is hereby incorporated by reference in its entirety.

FIELD OF THE INVENTION

The present invention is concerned with novel spiro derivatives useful as HSL inhibitors. The compounds of the present invention are useful in the treatment or prophylaxis of illnesses, for example, in the treatment or prophylaxis of diabetes, metabolic syndrome, dyslipidemia, atherosclerosis, obesity, cardiovascular diseases, myocardial dysfunction, inflammation, nonalkoholic fatty liver disease and nonalkoholic steatohepatitis.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess (Wang M. et al., Chem. Biol., 2006, 13, 1019-1027; Gregoire F. M. et al., Physiol. Rev., 1998, 78, 783-809). However, unlike TAG synthesis that also occurs at high levels in liver for very low density lipoprotein (VLDL) production, lipolysis for the provision of fatty acids as an energy source for use by other organs is unique to adipocytes. The release of free fatty acids (FFA) from TAG proceeds in an orderly and regulated manner (Unger R. H, Annu. Rev. Med. 2002, 53, 319-336; Duncan R. E. et al, 2007, Annu Rev Nutr, 27, 79-101; Jaworski K. Et al, 2007, Am J Physiol Gastrointest Liver Physiol, 293, G1-4), stimulated by catecholamines and regulated by hormones such as insulin, glucagon and epinephrine.

The most important enzyme in WAT believed responsible for hormone regulated hydrolysis of triglyceride is hormone sensitive lipase (HSL). This enzyme is also present in the liver, skeletal muscle, pancreas and adrenal glands. In the basal state, it has minimal activity against its substrate. Stimulation of adipocytes by hormones activates protein kinase A resulting in the phosphorylation of HSL and the lipid droplet coating protein perilipin. Phosphorylation of perilipin leads to its removal from the lipid droplet and migration of phosphorylated HSL from the cytosol to the lipid droplet where it catalyzes the hydrolysis of triglycerides (Wang M. et al., Chem. Biol., 2006, 13, 1019-1027).

Dysregulation of adipocyte lipolysis, resulting in elevated circulating non-esterified fatty acids (NEFA) is associated with obesity and co-morbidities including the development of type 2 diabetes (Unger R. H, Annu. Rev. Med. 2002, 53, 319-336). Obese or insulin resistant subjects have increased visceral adipose tissue depots. These depots contain elevated levels of HSL protein (Large, V. et al., 1998, J. Lipid. Res. 39, 1688-1695) and exhibit enhanced lipolytic activity as they are resistant to the insulin-mediated suppression of lipolysis. This results in increased plasma levels of free fatty acids, which further exacerbates insulin resistance due to the accumulation of triglycerides in tissues other than WAT such as liver, pancreas and muscle. The ectopic deposition of triglycerides results in pathological effects such as increased glucose production in the liver, decreased insulin secretion from the pancreas, and reduced glucose uptake and fatty acid oxidation in skeletal muscle. Thus, the elevated plasma levels of FFA due to increased HSL activity contributes to and worsens insulin resistance in obese and type 2 diabetic individuals. In addition, elevated FFA is related to increased production of the inflammatory cytokine TNF-alpha, by the adipose tissue (Hotamisigil, G. S., 1995, J. Clin. Invest. 95, 2409-2415). TNF-alpha further disrupts insulin signaling by the activation of serine kinases, such as JNK-1, which phosphorylated IRS-1 which depresses insulin signaling (Gao, Z. et. al., Mol Endocrinol, 2004, 18, 2024-2034). Thus, restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function. Inflammatory cytokine production would also be lessened, leading to further reductions in FFA production and improved insulin signaling. Elevated FFAs are also associated with increased cardiovascular risk, including atherosclerosis and myocardial dysfunction (Lopaschuk, et. al., Physiol Rev 2005, 85, 1093-129; Oliver, M F, QJM 2006, 99, 701-9) It has also been demonstrated that chronic low-dose lipid infusion in healthy patients induces markers of endothelial activation independent of its metabolic effects (Cusi, et. al., J. Cardiometab. Syndr. 2009, 3, 141-6). Here it was shown that modest lipid infusion elevates markers of endothelial activation-ET-1, ICAM-1, VCAM-1. Furthermore high lipolytic activity and elevated FFAs lead to increased insulin resistance and hypertension in hypertensive rats (Mauriege, et. al. J Physiol Biochem. 2009, 65, 33-41).

As HSL is a major hormone regulated lipase, it is known that during insulin resistant states, the ability of insulin to suppress lipolysis is reduced, and contributes to the increased FFA, ie. lipotoxicity. These fatty acids collect in the liver and lead to increased production of TAG, which are packaged into VLDLs which are secreted. There is also an accumulation of lipid in liver, leading to a fatty liver phenotype. Lipolysis is increased during diabetes and obesity which contributes to this phenotype. Therefore, reducing the activity of HSL would decrease the release of FFA to the blood, thus limiting the supply of FFA to the liver for TAG synthesis. Thus, HSL inhibitors could have beneficial effects as treatment of NAFLD (nonalkoholic fatty liver disease) and NASH (nonalkoholic steatohepatitis) (Jeffry R. Lewis et al, Dig Dis Sci 2010, 55: 560-578).

SUMMARY OF THE INVENTION

The present invention relates to a compound according to formula (I)

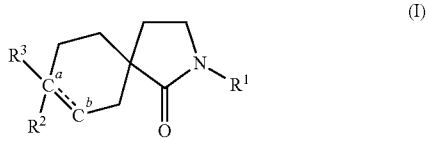

wherein $R^1$ is selected from the group consisting of: alkyl, phenyl, phenylalkyl, pyridinyl, pyridinylalkyl, pyridazinyl, pyridazinylalkyl, pyrazolyl, pyrazolylalkyl, imidazolyl, imidazolylalkyl, triazolyl, triazolylalkyl, 2,2-difluoro-benzo[1,3]dioxolyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl, wherein said substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, cycloalkyl, cycloalkylalkyl, alkylcycloalkyl, alkylcycloalkylalkyl, halocycloalkyl, halocycloalkylalkyl, hydroxy, hydroxyalkyl, hydroxyhaloalkyl, alkoxy, haloalkoxy, alkoxyalkyl, alkoxyalkoxy, alkoxyalkoxyalkyl, alkoxyhaloalkyl, haloalkoxyalkyl, alkenyl, alkylsulfonyl, cycloalkylsulfonyl, cycloalkylsulfonyloxy and alkylsulfonyloxy;

$R^2$ is selected from the group consisting of: hydrogen, alkyl, cycloalkyl, cycloalkylalkyl, cycloalkylalkoxyalkyl, oxetanylalkoxylalkyl, alkyloxetanylalkoxylalkyl, hydroxyalkyl, hydroxyhaloalkyl, dihydroxyhaloalkyl, alkoxyalkyl, alkoxyalkoxyalkyl, haloalkyl, haloalkoxyalkyl, haloalkylalkoxyalkyl, alkylsulfinylalkyl, alkylsulfanylalkyl, alkylsulfonylalkyl, alkylcarbonyl, alkenyl, hydroxyalkenyl, alkoxyalkenyl, alkynyl, hydroxyalkynyl, alkoxyalkynyl, carboxyalkyl, alkoxycarbonylalkyl, dialkylaminocarbonylalkyl, alkylaminocarbonylalkyl, oxopyrrolydinylalkyl, oxopiperidinylalkyl, triazolyl, pyrazolyl, isoxazolyl, thiophenyl, phenoxyalkyl, pyridinyloxyalkyl, oxopyridinylalkyl, (hydroxy)(pyrazolyealkyl, pyrazolylalkyl, benzyloxyalkyl, phenyl, phenylalkyl, substituted cycloalkyl, substituted cycloalkylalkyl, substituted phenyl and substituted phenylalkyl, wherein said substituted cycloalkyl, substituted cycloalkylalkyl, substituted triazolyl, substituted pyrazolyl, substituted isoxazolyl, substituted thiophenyl, substituted phenoxyalkyl, substituted pyridinyloxyalkyl, substituted oxopyridinylalkyl, substituted pyrazolylalkyl, substituted phenyl and substituted phenylalkyl are substituted with one to three substituents independently selected from the group consisting of: halogen, alkyl, haloalkyl, cycloalkyl, cycloalkylalkyl, alkylcycloalkyl, alkylcycloalkylalkyl, halocycloalkyl, halocycloalkylalkyl, hydroxy, hydroxyalkyl, hydroxyhaloalkyl, alkoxy, haloalkoxy, alkoxyalkyl, alkoxyalkoxy, alkoxyalkoxyalkyl, alkoxyhaloalkyl, haloalkoxyalkyl, alkenyl, alkylsulfonyl, cycloalkylsulfonyl, cycloalkylsulfonyloxy and alkylsulfonyloxy;

$R^3$ is $R^4$-A-, wherein in case the bond between carbon $C^a$ and carbon $C^b$ is a carbon-carbon double bond then $R^3$ is absent;

or $R^2$ and $R^3$ together with the carbon $C^a$ to which they are attached form a carbonyl group of formula —$C^a(O)$— and the bond between carbon $C^a$ and carbon $C^b$ is a carbon-carbon single bond;

A is selected from the group consisting of: a single bond, —O—, —$NR^5$—, —S—, —S(O)—, —S(O)$_2$—, —S(O)$_2$O— and —$NR^6C(O)O$—;

$R^4$ is selected from the group consisting of: hydrogen, alkyl, cycloalkyl, cycloalkylalkyl, hydroxyalkyl, alkoxyalkyl, alkenyl, phenyl, phenylalkyl, pyridinyl, pyridinylalkyl, pyridazinyl, pyridazinylalkyl, pyrimidinyl, pyrimidinylalkyl, pyrazinyl, pyrazinylalkyl, pyrazolyl, pyrazolylalkyl, imidazolyl, imidazolylalkyl, triazolyl, triazolylalkyl, substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl, wherein said substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, alkoxy, haloalkoxy, cycloalkyl, cycloalkylalkyl, hydroxy, alkoxyalkyl, haloalkoxyalkyl and hydroxyalkyl;

$R^5$ is selected from the group consisting of: hydrogen, alkyl and cycloalkyl;

$R^6$ is selected from the group consisting of: hydrogen, alkyl and cycloalkyl; and the bond between carbon $C^a$ and carbon $C^b$ is a carbon-carbon single bond or a carbon-carbon double bond, wherein, when $R^1$ is alkyl, the bond between carbon $C^a$ and carbon $C^b$ is a carbon-carbon single bond;

or a pharmaceutically acceptable salt thereof.

The present invention also relates to a pharmaceutical composition comprising a compound as described above and a therapeutically inert carrier.

DETAILED DESCRIPTION OF THE INVENTION

The term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl, isopropyl, butyl and isobutyl. Particularly preferred alkyl are methyl, ethyl, propyl, isopropyl and butyl.

The term "haloalkyl", alone or in combination, signifies an alkyl group as defined before, wherein one or more hydrogen atoms is replaced by a halogen atom. Examples of haloalkyl are fluoromethyl, difluoromethyl, trifluoromethyl, trifluoroethyl, trifluoromethylethyl or pentafluoroethyl. A preferred haloalkyl is trifluoroethyl.

The term "cycloalkyl", alone or in combination, signifies a cycloalkyl ring with 3 to 8 carbon atoms and preferably a cycloalkyl ring with 3 to 6 carbon atoms. Examples are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. A preferred cycloalkyl is cyclopropyl.

The term "cycloalkylalkyl", alone or in combination, signifies an alkyl, wherein one or more hydrogen atoms are replaced by a cycloalkyl. Examples are cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, cyclooctylmethyl and cyclooctylethyl. Preferred examples are cyclopropylmethyl, cyclopropylethyl, cyclobutylmethyl and cyclobutylethyl.

The term "alkylcycloalkyl", alone or in combination, signifies a cycloalkyl, wherein one or more hydrogen atoms are replaced by an alkyl. Examples are methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular examples are methyl-cyclopropyl and dimethyl-cyclopropyl.

The term "alkylcycloalkylalkyl", alone or in combination, signifies an alkyl, wherein one or more hydrogen atoms are replaced by an alkylcycloalkyl. Examples are methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "halocycloalkyl", alone or in combination, signifies a cycloalkyl as defined before, wherein one or more hydrogen atoms are replaced by a halogen, in particular fluorine. Examples of halocycloalkyl are fluorocyclopropyl, difluorocyclopropyl, fluorocyclobutyl or difluorocyclobutyl.

The term "halocycloalkylalkyl", alone or in combination, signifies an alkyl as defined before, wherein one or more hydrogen atoms are replaced by a halocycloalkyl. Examples of halocycloalkyl are fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl or difluorocyclobutylethyl.

The term "hydroxy", alone or in combination, signifies the —OH group.

The term "hydroxyalkyl", alone or in combination, signifies an alkyl group as defined before, wherein one or more hydrogen atoms is replaced by a hydroxy group. Examples of hydroxyalkyl are hydroxymethyl, hydroxyethyl, hydroxypropyl, hydroxymethypropyl and dihydroxypropyl. Preferred hydroxyalkyl are hydroxyethyl and hydroxymethylpropyl.

The term "hydroxyhaloalkyl", alone or in combination, signifies an alkyl as defined before, wherein one hydrogen atoms of the alkyl is replaced by a hydroxy and wherein one or more hydrogen atoms of the alkyl are replaced by a halogen, in which the terms hydroxy and halogen have the previously given significances. Examples of hydroxyhaloalkyl are hydroxytrifluoroethyl, hydroxytrifluoropropyl, hydroxyhexafluoropropyl.

The term "dihydroxyhaloalkyl", alone or in combination, signifies an alkyl as defined before, wherein two hydrogen atoms of the alkyl are replaced by a hydroxy and wherein one or more hydrogen atoms of the alkyl are replaced by a halogen, in which the terms hydroxy and halogen have the previously given significances. Examples of hydroxyhaloalkyl are hydroxytrifluoroethyl, hydroxytrifluoropropyl, hydroxyhexafluoropropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy. A particularly preferred alkoxy is methoxy.

The term "cycloalkylalkoxyalkyl", alone or in combination, signifies an alkyl, wherein one or more hydrogen atoms are replaced by a cycloalkylalkoxy. Examples are cyclopropylmethoxymethyl, cyclopropylmethoxyethyl, cyclobutylmethoxymethyl, cyclobutylmethoxyethyl, cyclopentylmethoxymethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "halogen", alone or in combination, signifies fluorine, chlorine, bromine or iodine and preferably fluorine or chlorine.

The term "haloalkyl", alone or in combination, signifies an alkyl group as defined before, wherein one or more hydrogen atoms is replaced by a halogen atom. Examples of haloalkyl are fluoromethyl, difluoromethyl, trifluoromethyl, trifluoroethyl, trifluoromethylethyl or pentafluoroethyl. A preferred haloalkyl is trifluoroethyl.

The term "haloalkoxy", alone or in combination, signifies an alkoxy group as defined before, wherein one or more hydrogen atoms is replaced by a halogen atom. Examples of haloalkyl are fluoromethoxy, difluoromethoxy, trifluoromethoxy, trifluoroethoxy, trifluoromethylethoxy, trifluorodimethylethoxy or pentafluoroethoxy. Preferred haloalkoxy are trifluoromethoxy and trifluoroethoxy.

The term "alkoxyalkyl", alone or in combination, signifies an alkyl as defined before, wherein one or more hydrogen atoms are replaced by an alkoxy. Examples are methoxymethyl, ethoxymethyl, methoxymethyl, ethoxyethyl, methoxypropyl and ethoxypropyl.

The term "alkoxyalkoxy", alone or in combination, signifies an alkoxy as defined before, wherein one or more hydrogen atoms are replaced by an alkoxy. Examples of methoxymethoxy, ethoxymethoxy, methoxymethoxy, ethoxyethoxy, methoxypropoxy and ethoxypropoxy.

The term "alkoxyalkoxyalkyl", alone or in combination, signifies an alkyl as defined before, wherein one or more hydrogen atoms are replaced by an alkoxyalkoxy. Examples of methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyhaloalkyl", alone or in combination, signifies an alkyl as defined before, wherein one or more hydrogen atoms of the alkyl are replaced by an alkoxy and wherein one or more hydrogen atoms of the alkyl are replaced by a halogen, in which the terms alkoxy and halogen have the previously given significances. Examples of hydroxyhaloalkyl are methoxytrifluoroethyl, methoxytrifluoropropyl, methoxyhexafluoropropyl.

The term "haloalkoxyalkyl", alone or in combination, signifies an alkyl as defined before, wherein one or more hydrogen atoms are replaced by a haloalkoxy. Examples of haloalkoxyalkyl are fluoromethoxymethyl, fluoromethoxyethyl, difluoromethoxymethyl, difluoromethoxyethyl, trifluoromethoxymethyl, trifluoromethoxyethyl, trifluoroethoxymethyl, trifluoroethoxyethyl, trifluoromethylethoxymethyl, trifluoromethylethoxyethyl, trifluorodimethylethoxymethyl, trifluorodimethylethoxyethyl, pentafluoroethoxymethyl or pentafluoroethoxymethyl.

The term "alkylsulfonyl", alone or in combination, signifies a signifies a group of the formula alkyl-S(O)$_2$— in which the term "alkyl" has the previously given significance, such as methanesulfonyl, ethanesulfonyl, n-propanesulfonyl, isopropanesulfonyl, n-butanesulfonyl, isobutanesulfonyl, sec-butanesulfonyl and tert-butanesulfonyl.

The term "cycloalkylsulfonyl", alone or in combination, signifies a signifies a group of the formula cycloalkyl-S(O)$_2$— in which the term "cycloalkyl" has the previously given significance, such as cyclopropanesulfonyl, cyclobutanesulfonyl, cyclopentanesulfonyl and cyclohexanesulfonyl.

The term "alkylsulfonyloxy", alone or in combination, signifies a signifies a group of the formula alkyl-S(O)$_2$O— in which the term "alkyl" has the previously given significance, such as methanesulfonyloxy, ethanesulfonyloxy, n-propanesulfonyloxy, isopropanesulfonyloxy, n-butanesulfonyloxy, isobutanesulfonyloxy, sec-butanesulfonyloxy and tert-butanesulfonyloxy.

The term "cycloalkylsulfonyl", alone or in combination, signifies a signifies a group of the formula cycloalkyl-S(O)$_2$O— in which the term "cycloalkyl" has the previously given significance, such as cyclopropanesulfonyloxy, cyclobutanesulfonyloxy, cyclopentanesulfonyloxy and cyclohexanesulfonyloxy.

The term "alkenyl", alone or in combination, signifies an alkyl group as defined above, wherein one or more carbon-carbon single bond is replaced by a carbon-carbon double bond. Examples of alkenyl are ethenyl, propenyl, n-butenyl or isobutenyl. Preferred alkenyl is butenyl.

The term "alkynyl", alone or in combination, signifies an alkyl group as defined above, wherein one or more carbon-carbon single bond is replaced by a carbon-carbon triple bond. Examples of alkenyl are ethynyl, propynyl, n-butynyl or isobutynyl. Preferred alkenyl is propynyl.

The term "carbonyl", alone or in combination, signifies the —C(O)— group.

The term "carboxy", alone or in combination, signifies the —COOH group.

The term "amino", alone or in combination, signifies the —NH$_2$ group.

The term "sulfanyl", alone or in combination, signifies the —S— group.

The term "sulfinyl", alone or in combination, signifies the —S(O)— group.

The term "sulfonyl", alone or in combination, signifies the —S(O)$_2$— group.

The term "sulfonyloxy", alone or in combination, signifies the —S(O)$_2$O— group.

The present invention relates to a compound according to formula (I)

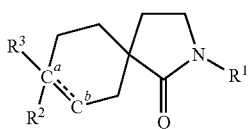

(I)

wherein

R$^1$ is selected from the group consisting of: alkyl, phenyl, phenylalkyl, pyridinyl, pyridinylalkyl, pyridazinyl, pyridazinylalkyl, pyrazolyl, pyrazolylalkyl, imidazolyl, imidazolylalkyl, triazolyl, triazolylalkyl, 2,2-difluoro-benzo[1,3]dioxolyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl, wherein said substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, cycloalkyl, cycloalkylalkyl, alkylcycloalkyl, alkylcycloalkylalkyl, halocycloalkyl, halocycloalkylalkyl, hydroxy, hydroxyalkyl, hydroxyhaloalkyl, alkoxy, haloalkoxy, alkoxyalkyl, alkoxyalkoxy, alkoxyalkoxyalkyl, alkoxyhaloalkyl, haloalkoxyalkyl, alkenyl, alkylsulfonyl, cycloalkylsulfonyl, cycloalkylsulfonyloxy and alkylsulfonyloxy;

R$^2$ is selected from the group consisting of: hydrogen, alkyl, cycloalkyl, cycloalkylalkyl, cycloalkylalkoxyalkyl, oxetanylalkoxylalkyl, alkyloxetanylalkoxylalkyl, hydroxyalkyl, hydroxyhaloalkyl, dihydroxyhaloalkyl, alkoxyalkyl, alkoxyalkoxyalkyl, haloalkyl, haloalkoxyalkyl, haloalkylalkoxyalkyl, alkylsulfinylalkyl, alkylsulfanylalkyl, alkylsulfonylalkyl, alkylcarbonyl, alkenyl, hydroxyalkenyl, alkoxyalkenyl, alkynyl, hydroxyalkynyl, alkoxyalkynyl, carboxyalkyl, alkoxycarbonylalkyl, dialkylaminocarbonylalkyl, alkylaminocarbonylalkyl, oxopyrrolydinylalkyl, oxopiperidinylalkyl, triazolyl, pyrazolyl, isoxazolyl, thiophenyl, phenoxyalkyl, pyridinyloxyalkyl, oxopyridinylalkyl, (hydroxy)(pyrazolyealkyl, pyrazolylalkyl, benzyloxyalkyl, phenyl, phenylalkyl, substituted cycloalkyl, substituted cycloalkylalkyl, substituted phenyl and substituted phenylalkyl, wherein said substituted cycloalkyl, substituted cycloalkylalkyl, substituted triazolyl, substituted pyrazolyl, substituted isoxazolyl, substituted thiophenyl, substituted phenoxyalkyl, substituted pyridinyloxyalkyl, substituted oxopyridinylalkyl, substituted pyrazolylalkyl, substituted phenyl and substituted phenylalkyl are substituted with one to three substituents independently selected from the group consisting of: halogen, alkyl, haloalkyl, cycloalkyl, cycloalkylalkyl, alkylcycloalkyl, alkylcycloalkylalkyl, halocycloalkyl, halocycloalkylalkyl, hydroxy, hydroxyalkyl, hydroxyhaloalkyl, alkoxy, haloalkoxy, alkoxyalkyl, alkoxyalkoxy, alkoxyalkoxyalkyl, alkoxyhaloalkyl, haloalkoxyalkyl, alkenyl, alkylsulfonyl, cycloalkylsulfonyl, cycloalkylsulfonyloxy and alkylsulfonyloxy;

R$^3$ is R$^4$-A-, wherein in case the bond between carbon C$^a$ and carbon C$^b$ is a carbon-carbon double bond then R$^3$ is absent;

or R$^2$ and R$^3$ together with the carbon C$^a$ to which they are attached form a carbonyl group of formula —C$^a$(O)— and the bond between carbon C$^a$ and carbon C$^b$ is a carbon-carbon single bond;

A is selected from the group consisting of: a single bond, —O—, —NR$^5$—, —S—, —S(O)—, —S(O)$_2$—, —S(O)$_2$O— and —NR$^6$C(O)O—;

R$^4$ is selected from the group consisting of: hydrogen, alkyl, cycloalkyl, cycloalkylalkyl, hydroxyalkyl, alkoxyalkyl, alkenyl, phenyl, phenylalkyl, pyridinyl, pyridinylalkyl, pyridazinyl, pyridazinylalkyl, pyrimidinyl, pyrimidinylalkyl, pyrazinyl, pyrazinylalkyl, pyrazolyl, pyrazolylalkyl, imidazolyl, imidazolylalkyl, triazolyl, triazolylalkyl, substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl, wherein said substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, alkoxy, haloalkoxy, cycloalkyl, cycloalkylalkyl, hydroxy, alkoxyalkyl, haloalkoxyalkyl and hydroxyalkyl;

$R^5$ is selected from the group consisting of: hydrogen, alkyl and cycloalkyl;

$R^6$ is selected from the group consisting of: hydrogen, alkyl and cycloalkyl; and the bond between carbon $C^a$ and carbon $C^b$ is a carbon-carbon single bond or a carbon-carbon double bond, wherein, when $R^1$ is alkyl, the bond between carbon $C^a$ and carbon $C^b$ is a carbon-carbon single bond;

or a pharmaceutically acceptable salt thereof.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particularly preferred pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred pharmaceutically acceptable esters of compounds of formula (I) are methyl and ethyl esters.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Preferred are compounds according to formula (I) as described above and pharmaceutically acceptable salts or esters thereof.

Further preferred are compounds according to formula (I) as described above and pharmaceutically acceptable salts thereof, particularly compounds according to formula (I) as described above.

Also an embodiment of the present invention are compounds according to formula (I), wherein $R^1$ is selected from the group consisting of: alkyl, phenyl, phenylalkyl, pyridinyl, pyridinylalkyl, pyridazinyl, pyridazinylalkyl, pyrazolyl, pyrazolylalkyl, imidazolyl, imidazolylalkyl, triazolyl, triazolylalkyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl, wherein said substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, cycloalkyl, cycloalkylalkyl, alkylcycloalkyl, hydroxy, hydroxyalkyl, alkoxy, haloalkoxy, alkoxyalkyl, haloalkoxyalkyl, alkylsulfonyl and alkylsulfonyloxy;

$R^2$ is selected from the group consisting of: hydrogen, alkyl, cycloalkyl, cycloalkylalkyl, hydroxyalkyl, alkoxyalkyl, alkenyl, hydroxyalkenyl, alkoxyalkenyl, alkynyl, hydroxyalkynyl, alkoxyalkynyl, phenyl, phenylalkyl, substituted cycloalkyl, substituted cycloalkylalkyl, substituted phenyl and substituted phenylalkyl, wherein substituted cycloalkyl, substituted cycloalkylalkyl, substituted phenyl and substituted phenylalkyl are substituted with one to three substituents independently selected from the group consisting of: halogen, alkyl, haloalkyl, cycloalkyl, cycloalkylalkyl, alkylcycloalkyl, hydroxy, hydroxyalkyl, alkoxy, haloalkoxy, alkoxyalkyl, haloalkoxyalkyl, alkylsulfonyl and alkylsulfonyloxy;

$R^3$ is $R^4$-A-, wherein in case the bond between carbon $C^a$ and carbon $C^b$ is a carbon-carbon double bond then $R^3$ is absent; or $R^2$ and $R^3$ together with the carbon $C^a$ to which they are attached form a carbonyl group of formula —$C^a(O)$— and the bond between carbon $C^a$ and carbon $C^b$ is a carbon-carbon single bond;

A is selected from the group consisting of: —O—, —$NR^6$—, —S—, —S(O)—, —$S(O)_2$—, —$S(O)_2O$— and —$NR^6C(O)O$—;

$R^4$ is selected from the group consisting of: hydrogen, alkyl, cycloalkyl, cycloalkylalkyl, hydroxyalkyl, alkoxyalkyl, alkenyl, phenyl, phenylalkyl, pyridinyl, pyridinylalkyl, pyridazinyl, pyridazinylalkyl, pyrimidinyl, pyrimidinylalkyl, pyrazinyl, pyrazinylalkyl, pyrazolyl, pyrazolylalkyl, imidazolyl, imidazolylalkyl, triazolyl, triazolylalkyl, substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl, wherein said substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, alkoxy, haloalkoxy, cycloalkyl, cycloalkylalkyl, hydroxy, alkoxyalkyl, haloalkoxyalkyl and hydroxyalkyl;

$R^5$ is selected from the group consisting of: hydrogen, alkyl and cycloalkyl;

$R^6$ is selected from the group consisting of: hydrogen, alkyl and cycloalkyl;

the bond between carbon $C^a$ and carbon $C^b$ is a carbon-carbon single bond or a carbon-carbon double bond, wherein, when $R^1$ is alkyl, the bond between carbon $C^a$ and carbon $C^b$ is a carbon-carbon single bond;

or a pharmaceutically acceptable salt thereof.

Also preferred are compounds according to formula (I) as described above, wherein $R^1$ is selected from the group consisting of: 2,2-difluoro-benzo[1,3]dioxolyl, substituted phenyl, substituted phenylalkyl, and substituted pyridinyl, wherein said substituted phenyl, substituted phenylalkyl, substituted pyridinyl are substituted with one to three substituents independently selected from the group consisting of: halogen, alkyl, haloalkyl, cycloalkyl, halocycloalkyl, hydroxyhaloalkyl, alkoxy, haloalkoxy, alkoxyalkyl, alkoxyalkoxy, alkoxyhaloalkyl, alkylsulfonyl, cycloalkylsulfonyloxy and alkylsulfonyloxy.

Also further preferred are compounds according to formula (I) as described above, wherein $R^1$ is selected from the group consisting of: substituted phenyl, substituted phenylalkyl and substituted pyridinyl, wherein said substituted phenyl, substituted phenyl alkyl and substituted pyridinyl are substituted with one to three substituents independently selected from the group consisting of: alkyl, haloalkyl, cycloalkyl, hydroxyhaloalkyl, alkoxy and haloalkoxy.

Also further preferred are compounds according to formula (I) as described above, wherein $R^1$ is selected from the group consisting of: alkyl, substituted phenyl and substituted phenylalkyl, wherein said substituted phenyl and substituted phenylalkyl are substituted with one to three substituents independently selected from the group consisting of: halogen, alkyl, haloalkyl, cycloalkyl, cycloalkylalkyl, alkoxy, haloalkoxy and alkoxyalkyl.

Furthermore preferred are compounds according to formula (I) as described above, wherein $R^1$ is substituted phenyl or substituted phenylalkyl, wherein substituted phenyl and substituted phenylalkyl are substituted with one to three substituents independently selected from the group consisting of: halogen, alkyl, haloalkyl, cycloalkyl, alkoxy and haloalkoxy.

Moreover preferred are compounds according to formula (I) as described above, wherein $R^1$ is substituted phenyl, wherein substituted phenyl is substituted with one to three substituents independently selected from the group consisting of: alkyl, haloalkyl, cycloalkyl and haloalkoxy.

Particularly preferred are compounds according to formula (I) as described above, wherein $R^1$ is substituted phenyl, wherein substituted phenyl is substituted with one to three substituents independently selected from the group consisting of: propyl, 2,2,2-trifluoroethyl, cyclopropyl and trifluoromethoxy.

Another preferred embodiment of the present invention are compounds according to formula (I) as described above, wherein $R^2$ is selected from the group consisting of: hydrogen, alkyl, cycloalkyl, cycloalkylalkoxyalkyl, oxetanylalkoxylalkyl, alkyloxetanylalkoxylalkyl, hydroxyalkyl, hydroxyhaloalkyl, dihydroxyhaloalkyl, alkoxyalkyl, alkoxyalkoxyalkyl, haloalkyl, haloalkoxyalkyl, haloalkylalkoxyalkyl, alkylsulfinylalkyl, alkylsulfanylalkyl, alkylsulfonylalkyl, alkenyl, alkynyl, alkoxyalkynyl, alkylcarbonyl, alkoxycarbonylalkyl, dialkylaminocarbonylalkyl, alkylaminocarbonylalkyl, oxopyrrolydinylalkyl, oxopiperidinylalkyl, triazolyl, thiophenyl, phenoxyalkyl, pyridinyloxyalkyl, oxopyridinylalkyl, (hydroxy)(pyrazolyl)alkyl, pyrazolylalkyl, benzyloxyalkyl, phenyl, phenylalkyl, substituted triazolyl, substituted pyrazolyl, substituted isoxazolyl and substituted phenoxyalkyl, wherein said substituted triazolyl, substituted pyrazolyl, substituted isoxazolyl and substituted phenoxyalkyl are substituted with one to three substituents independently selected from the group consisting of: halogen, alkyl and alkenyl.

Further preferred are compounds according to formula (I) as described above, wherein $R^2$ is selected from the group consisting of: hydrogen, alkyl, hydroxyhaloalkyl, alkoxyalkyl, haloalkyl, haloalkoxyalkyl, alkylsulfonylalkyl, alkoxyalkynyl, oxopyrrolydinylalkyl, oxopyridinylalkyl and substituted pyrazolyl, wherein said substituted pyrazolyl is substituted with one to three alkyl.

Another preferred embodiment of the present invention are compounds according to formula (I) as described above, wherein $R^2$ is selected from the group consisting of: hydrogen, alkyl, cycloalkyl, cycloalkylalkyl, alkoxyalkyl, alkenyl, alkoxyalkynyl and phenylalkyl.

Further preferred are compounds according to formula (I) as described above, wherein $R^2$ is selected from the group consisting of: hydrogen, alkyl, cycloalkyl, alkoxyalkyl, alkenyl, alkoxyalkynyl and phenylalkyl.

Moreover preferred are compounds according to formula (I) as described above, wherein $R^2$ is selected from the group consisting of: hydrogen, alkyl, alkoxyalkyl and alkoxyalkynyl.

Particularly preferred are compounds according to formula (I) as described above, wherein $R^2$ is selected from the group consisting of: hydrogen, methyl, ethyl, n-propyl, isopropyl, n-butyl, methoxypropyl and methoxypropynyl.

Another preferred embodiment of the present invention are compounds according to formula (I) as described above, wherein A is selected from the group consisting of: a single bond, —O—, —S—, —S(O)—, —S(O)$_2$—, —S(O)$_2$O— and —NR$^6$C(O)O—.

Preferred are compounds according to formula (I) as described above, wherein A is selected from the group consisting of: a single bond, —O—, —NR$^5$—, —S—, —S(O)—, —S(O)$_2$—, —S(O)$_2$O— and —NR$^6$C(O)O—, wherein, when A is —S—, —S(O)— or —S(O)$_2$—, $R^2$ is hydrogen;

Preferred are compounds according to formula (I) as described above, wherein A is selected from the group consisting of: —O—, —S—, —S(O)—, —S(O)$_2$—, —S(O)$_2$O— and —NR$^6$C(O)O—.

Also preferred are compounds according to formula (I) as described above, wherein A is selected from the group consisting of: —S—, —S(O)—, and —S(O)$_2$— and $R^2$ is hydrogen.

Also preferred are compounds according to formula (I) as described above, wherein A is selected from the group consisting of: a single bond, —O— and —NR$^6$C(O)O—.

Further preferred are compounds according to formula (I) as described above, wherein A is —O— or —NR$^6$C(O)O—.

Also further preferred are compounds according to formula (I) as described above, wherein A is —O—.

Also further preferred are compounds according to formula (I) as described above, wherein A is —NR$^6$C(O)O—.

Also further preferred are compounds according to formula (I) as described above, wherein A is a single bond.

Another preferred embodiment of the present invention are compounds according to formula (I) as described above, wherein R$^4$ is selected from the group consisting of: hydrogen, alkyl, cycloalkyl, cycloalkylalkyl, hydroxyalkyl, alkoxyalkyl, phenyl, phenylalkyl, pyrimidinyl, pyrazinyl, pyrazinylalkyl, substituted phenylalkyl, substituted pyridinylalkyl, substituted pyridazinyl and substituted pyrazinylalkyl, wherein said substituted phenylalkyl, substituted pyridinylalkyl, substituted pyridazinyl and substituted pyrazinylalkyl are substituted with one to three substituents independently selected from the group consisting of: halogen, alkyl and alkoxy.

Further preferred are compounds according to formula (I) as described above, wherein R$^4$ is selected from the group consisting of: hydrogen, alkyl, alkoxyalkyl and pyrimidinyl.

Moreover preferred are compounds according to formula (I) as described above, wherein R$^4$ is selected from the group consisting of: hydrogen, alkyl, methoxyethyl and pyrimidinyl.

Particularly preferred are compounds according to formula (I) as described above, wherein R$^4$ is hydrogen.

Also preferred are compounds according to formula (I) as described above, wherein the bond between carbon C$^a$ and carbon C$^b$ is a carbon-carbon double bond. Such compounds are compounds of formula (Ia).

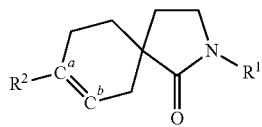

Further preferred are compounds according to formula (I) as described above, wherein the bond between carbon C$^a$ and carbon C$^b$ is a carbon-carbon single bond. Such compounds are compounds of formula (Ib).

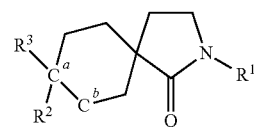

Another preferred embodiment of the present invention are compounds according to formula (I) as described above, wherein R$^6$ is hydrogen.

Also preferred are compounds according to formula (I) as described above of formula (Ic).

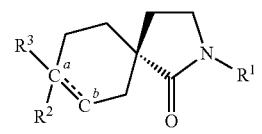

Also preferred are compounds according to formula (I) as described above of formula (Id).

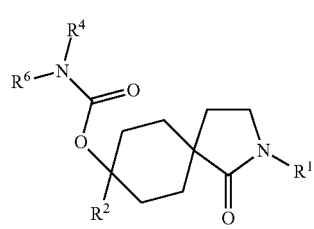

Also preferred are compounds according to formula (I) as described above, wherein R$^2$ and R$^3$ together with the carbon C$^a$ to which they are attached form a carbonyl group of formula —C$^a$(O)— and the bond between carbon C$^a$ and carbon C$^b$ is a carbon-carbon single bond and, wherein these compounds are of formula (Ie).

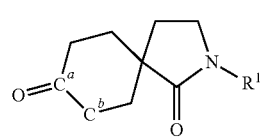

Examples of preferred compounds of formula (I) are selected from the group consisting of:

(5α,8β)-8-Hydroxy-2-(4-trifluoromethoxy-phenyl)-2-aza-spiro[4.5]decan-1-one;
(5α,8α)-8-Hydroxy-2-(4-trifluoromethoxy-phenyl)-2-aza-spiro[4.5]decan-1-one;
(5α,8β)-8-Benzyloxy-2-(4-methoxy-phenyl)-2-aza-spiro[4.5]decan-1-one;
(5α,8β)-8-Benzyloxy-2-(4-ethyl-phenyl)-2-aza-spiro[4.5]decan-1-one;
(5α,8β)-2-(4-Ethyl-phenyl)-8-hydroxy-2-aza-spiro[4.5]decan-1-one;
Propyl-carbamic acid [(5α,8β)-2-(4-ethyl-phenyl)-1-oxo-2-aza-spiro[4.5]dec-8-yl]ester;
(3-Fluoro-benzyl)-carbamic acid [(5α,8β)-2-(4-ethyl-phenyl)-1-oxo-2-aza-spiro[4.5]dec-8-yl]ester;
Phenyl-carbamic acid [(5α,8β)-2-(4-ethyl-phenyl)-1-oxo-2-aza-spiro[4.5]dec-8-yl]ester;
(5α,8β)-8-Benzyloxy-2-(4-trifluoromethoxy-phenyl)-2-aza-spiro[4.5]decan-1-one;
(3-Fluoro-benzyl)-carbamic acid [(5α,8β)-1-oxo-2-(4-trifluoromethoxy-phenyl)-2-aza-spiro[4.5]dec-8-yl]ester;
Propyl-carbamic acid [(5α,8β)-1-oxo-2-(4-trifluoromethoxy-phenyl)-2-aza-spiro[4.5]dec-8-yl]ester;
(3-Methoxy-benzyl)-carbamic acid [(5α,8β)-1-oxo-2-(4-trifluoromethoxy-phenyl)-2-aza-spiro[4.5]dec-8-yl]ester;
(4-Methoxy-benzyl)-carbamic acid [(5α,8β)-1-oxo-2-(4-trifluoromethoxy-phenyl)-2-aza-spiro[4.5]dec-8-yl]ester;
(2-Fluoro-benzyl)-carbamic acid [(5α,8β)-1-oxo-2-(4-trifluoromethoxy-phenyl)-2-aza-spiro[4.5]dec-8-yl]ester;
(4-Fluoro-benzyl)-carbamic acid [(5α,8β)-1-oxo-2-(4-trifluoromethoxy-phenyl)-2-aza-spiro[4.5]dec-8-yl]ester;
(5α,8β)-8-(6-Methyl-pyridin-2-ylmethoxy)-2-(4-trifluoromethoxy-phenyl)-2-aza-spiro[4.5]decan-1-one;
Methyl-carbamic acid [(5α,8β)-1-oxo-2-(4-trifluoromethoxy-phenyl)-2-aza-spiro[4.5]dec-8-yl]ester;
Phenethyl-carbamic acid [(5α,8β)-1-oxo-2-(4-trifluoromethoxy-phenyl)-2-aza-spiro[4.5]dec-8-yl]ester;

(5α,8β)-8-(Pyrazin-2-yloxy)-2-(4-trifluoromethoxy-phenyl)-2-aza-spiro[4.5]decan-1-one;
(5α,8β)-8-(Pyrimidin-2-yloxy)-2-(4-trifluoromethoxy-phenyl)-2-aza-spiro[4.5]decan-1-one;
(5α,8β)-8-(6-Methyl-pyridazin-3-yloxy)-2-(4-trifluoromethoxy-phenyl)-2-aza-spiro[4.5]decan-1-one;
(Cyclopropylmethyl)-carbamic acid [(5α,8β)-1-oxo-2-(4-trifluoromethoxy-phenyl)-2-aza-spiro[4.5]dec-8-yl]ester;
(5α,8β)-8-(2-Methoxy-ethoxy)-2-(4-trifluoromethoxy-phenyl)-2-aza-spiro[4.5]decan-1-one;
(5α,8β)-8-Ethoxy-2-(4-trifluoromethoxy-phenyl)-2-aza-spiro[4.5]decan-1-one;
(5-Methyl-pyrazin-2-ylmethyl)-carbamic acid [(5α,8β)-1-oxo-2-(4-trifluoromethoxy-phenyl)-2-aza-spiro[4.5]dec-8-yl]ester;
(2-Hydroxy-2-methyl-propyl)-carbamic acid [(5α,8β)-1-oxo-2-(4-trifluoromethoxy-phenyl)-2-aza-spiro[4.5]dec-8-yl]ester;
(2-Hydroxy-ethyl)-carbamic acid [(5α,8β)-1-oxo-2-(4-trifluoromethoxy-phenyl)-2-aza-spiro[4.5]dec-8-yl]ester;
(Pyrazin-2-ylmethyl)-carbamic acid [(5α,8β)-1-oxo-2-(4-trifluoromethoxy-phenyl)-2-aza-spiro[4.5]dec-8-yl]ester;
Cyclopropyl-carbamic acid [(5α,8β)-1-oxo-2-(4-trifluoromethoxy-phenyl)-2-aza-spiro[4.5]dec-8-yl]ester;
Carbamic acid [(5α,8β)-1-oxo-2-(4-trifluoromethoxy-phenyl)-2-aza-spiro[4.5]dec-8-yl]ester;
(5α,8α)-8-Hydroxy-2-(4-methoxy-phenyl)-2-aza-spiro[4.5]decan-1-one;
(5α,8α)-2-(4-Ethyl-phenyl)-8-hydroxy-2-aza-spiro[4.5]decan-1-one;
(5α,8α)-2-[2-(4-Fluoro-phenyl)-ethyl]-8-hydroxy-2-aza-spiro[4.5]decan-1-one;
(5α,8α)-2-[2-(4-Ethyl-phenyl)-ethyl]-8-hydroxy-2-aza-spiro[4.5]decan-1-one;
(5α,8α)-8-Hydroxy-2-[2-(4-methoxy-phenyl)-ethyl]-2-aza-spiro[4.5]decan-1-one;
(5α,8α)-2-(3-Chloro-benzyl)-8-hydroxy-2-aza-spiro[4.5]decan-1-one;
(5α,8α)-8-Hydroxy-2-(4-propyl-phenyl)-2-aza-spiro[4.5]decan-1-one;
(5α,8α)-8-Hydroxy-2-(4-isopropyl-phenyl)-2-aza-spiro[4.5]decan-1-one;
(5α,8α)-2-(4-Cyclopropyl-phenyl)-8-hydroxy-2-aza-spiro[4.5]decan-1-one;
(5α,8α)-8-Benzyloxy-2-(4-methoxy-phenyl)-2-aza-spiro[4.5]decan-1-one;
(5α,8α)-8-Ethoxy-2-(4-trifluoromethoxy-phenyl)-2-aza-spiro[4.5]decan-1-one;
(5α,8α)-8-Propoxy-2-(4-trifluoromethoxy-phenyl)-2-aza-spiro[4.5]decan-1-one;
(5α,8α)-8-Benzyloxy-2-(4-ethyl-phenyl)-2-aza-spiro[4.5]decan-1-one;
Propyl-carbamic acid [(5α,8α)-2-(4-ethyl-phenyl)-1-oxo-2-aza-spiro[4.5]dec-8-yl]ester;
(3-Fluoro-benzyl)-carbamic acid [(5α,8α)-2-(4-ethyl-phenyl)-1-oxo-2-aza-spiro[4.5]dec-8-yl]ester;
(5α,8α)-2-(4-Methoxy-phenyl)-8-phenoxy-2-aza-spiro[4.5]decan-1-one;
2-(4-Methoxy-phenyl)-2-aza-spiro[4.5]dec-7-en-1-one;
(5α,8β)-2-(4-Methoxy-phenyl)-8-phenoxy-2-aza-spiro[4.5]decan-1-one;
Methanesulfonic acid [(5α,8α)-1-oxo-2-(4-trifluoromethoxy-phenyl)-2-aza-spiro[4.5]dec-8-yl]ester;
2-(4-Trifluoromethoxy-phenyl)-2-aza-spiro[4.5]dec-7-en-1-one;
(5α,8β)-8-Benzenesulfinyl-2-(4-trifluoromethoxy-phenyl)-2-aza-spiro[4.5]decan-1-one;
(5α,8α)-8-Phenylsulfanyl-2-(4-trifluoromethoxy-phenyl)-2-aza-spiro[4.5]decan-1-one;
(5α,8β)-8-Benzenesulfonyl-2-(4-trifluoromethoxy-phenyl)-2-aza-spiro[4.5]decan-1-one;
2-(4-Trifluoromethoxy-phenyl)-2-aza-spiro[4.5]decane-1,8-dione;
(5α,8α)-8-Hydroxy-8-propyl-2-(4-trifluoromethoxy-phenyl)-2-aza-spiro[4.5]decan-1-one;
(5α,8β)-8-Hydroxy-8-propyl-2-(4-trifluoromethoxy-phenyl)-2-aza-spiro[4.5]decan-1-one;
(5α,8α)-8-Hydroxy-8-methyl-2-(4-trifluoromethoxy-phenyl)-2-aza-spiro[4.5]decan-1-one;
(5α,8β)-8-Hydroxy-8-methyl-2-(4-trifluoromethoxy-phenyl)-2-aza-spiro[4.5]decan-1-one;
8-Methyl-2-(4-trifluoromethoxy-phenyl)-2-aza-spiro[4.5]dec-7-en-1-one;
(5α,8α)-8-Ethyl-8-hydroxy-2-(4-trifluoromethoxy-phenyl)-2-aza-spiro[4.5]decan-1-one;
(5α,8β)-8-Ethyl-8-hydroxy-2-(4-trifluoromethoxy-phenyl)-2-aza-spiro[4.5]decan-1-one;
(5α,8α)-8-Benzyl-8-hydroxy-2-(4-trifluoromethoxy-phenyl)-2-aza-spiro[4.5]decan-1-one;
(5α,8β)-8-Benzyl-8-hydroxy-2-(4-trifluoromethoxy-phenyl)-2-aza-spiro[4.5]decan-1-one;
(5α,8α)-8-But-3-enyl-8-hydroxy-2-(4-trifluoromethoxy-phenyl)-2-aza-spiro[4.5]decan-1-one;
(5α,8β)-8-But-3-enyl-8-hydroxy-2-(4-trifluoromethoxy-phenyl)-2-aza-spiro[4.5]decan-1-one;
(5α,8α)-8-Butyl-8-hydroxy-2-(4-trifluoromethoxy-phenyl)-2-aza-spiro[4.5]decan-1-one;
(5α,8β)-8-Butyl-8-hydroxy-2-(4-trifluoromethoxy-phenyl)-2-aza-spiro[4.5]decan-1-one;
(5α,8α)-8-Hydroxy-8-isopropyl-2-(4-trifluoromethoxy-phenyl)-2-aza-spiro[4.5]decan-1-one;
(5α,8β)-8-Hydroxy-8-isopropyl-2-(4-trifluoromethoxy-phenyl)-2-aza-spiro[4.5]decan-1-one;
(5α,8α)-8-Cyclopropyl-8-hydroxy-2-(4-trifluoromethoxy-phenyl)-2-aza-spiro[4.5]decan-1-one;
(5α,8α)-8-Hydroxy-8-(3-methoxy-prop-1-ynyl)-2-(4-trifluoromethoxy-phenyl)-2-aza-spiro[4.5]decan-1-one;
(5α,8β)-8-Hydroxy-8-(3-methoxy-prop-1-ynyl)-2-(4-trifluoromethoxy-phenyl)-2-aza-spiro[4.5]decan-1-one;
(5α,8α)-2-(4-Cyclopropyl-phenyl)-8-hydroxy-8-methyl-2-aza-spiro[4.5]decan-1-one;
(5α,8β)-2-(4-Cyclopropyl-phenyl)-8-hydroxy-8-methyl-2-aza-spiro[4.5]decan-1-one;
(5α,8α)-2-(4-Cyclopropyl-phenyl)-8-hydroxy-8-propyl-2-aza-spiro[4.5]decan-1-one;
(5α,8β)-2-(4-Cyclopropyl-phenyl)-8-hydroxy-8-propyl-2-aza-spiro[4.5]decan-1-one;
(5α,8α)-8-Hydroxy-8-methyl-2-[4-(2,2,2-trifluoro-ethyl)-phenyl]-2-aza-spiro[4.5]decan-1-one;
(5α,8β)-8-Hydroxy-8-methyl-2-[4-(2,2,2-trifluoro-ethyl)-phenyl]-2-aza-spiro[4.5]decan-1-one;
(5α,8α)-8-Ethyl-8-hydroxy-2-[4-(2,2,2-trifluoro-ethyl)-phenyl]-2-aza-spiro[4.5]decan-1-one;
(5α,8β)-8-Ethyl-8-hydroxy-2-[4-(2,2,2-trifluoro-ethyl)-phenyl]-2-aza-spiro[4.5]decan-1-one;
(5α,8α)-8-Hydroxy-8-propyl-2-[4-(2,2,2-trifluoro-ethyl)-phenyl]-2-aza-spiro[4.5]decan-1-one;
(5α,8β)-8-Hydroxy-8-propyl-2-[4-(2,2,2-trifluoro-ethyl)-phenyl]-2-aza-spiro[4.5]decan-1-one;
(5α,8α)-8-Ethyl-8-hydroxy-2-(4-propyl-phenyl)-2-aza-spiro[4.5]decan-1-one;
(5α,8β)-8-Ethyl-8-hydroxy-2-(4-propyl-phenyl)-2-aza-spiro[4.5]decan-1-one;

(5α,8β)-8-Hydroxy-2-[4-(2,2,2-trifluoro-ethoxy)-phenyl]-2-aza-spiro[4.5]decan-1-one;
(5α,8α)-8-Hydroxy-8-methyl-2-[4-(2,2,2-trifluoro-ethoxy)-phenyl]-2-aza-spiro[4.5]decan-1-one;
(5α,8β)-8-Hydroxy-8-methyl-2-[4-(2,2,2-trifluoro-ethoxy)-phenyl]-2-aza-spiro[4.5]decan-1-one;
(5α,8α)-8-Ethyl-8-hydroxy-2-[4-(2,2,2-trifluoro-ethoxy)-phenyl]-2-aza-spiro[4.5]decan-1-one;
(5α,8β)-8-Ethyl-8-hydroxy-2-[4-(2,2,2-trifluoro-ethoxy)-phenyl]-2-aza-spiro[4.5]decan-1-one;
(5α,8α)-8-Hydroxy-8-(3-methoxy-propyl)-2-(4-trifluoromethoxy-phenyl)-2-aza-spiro[4.5]decan-1-one; and
(5α,8β)-8-Hydroxy-8-(3-methoxy-propyl)-2-(4-trifluoromethoxy-phenyl)-2-aza-spiro[4.5]decan-1-one.

Also preferred examples of compounds of formula (I) are selected from the group consisting of:
(5α,8α)-8-Hydroxy-8-(3-methoxy-prop-1-ynyl)-2-[4-(2,2,2-trifluoro-ethyl)-phenyl]-2-aza-spiro[4.5]decan-1-one;
(5α,8α)-8-Hydroxy-8-(3-methoxy-propyl)-2-[4-(2,2,2-trifluoro-ethyl)-phenyl]-2-aza-spiro[4.5]decan-1-one;
(5α,8α)-8-Hydroxy-2-[4-(3-methoxy-propoxy)-phenyl]-8-propyl-2-aza-spiro[4.5]decan-1-one;
(5α,8α)-8-Hydroxy-2-[4-(2-methoxy-ethoxy)-phenyl]-8-propyl-2-aza-spiro[4.5]decan-1-one;
(5α,8α)-8-Butyl-8-hydroxy-2-[4-(2-methoxy-ethoxy)-phenyl]-2-aza-spiro[4.5]decan-1-one;
(5α,8β)-8-Butyl-8-hydroxy-2-[4-(2-methoxy-ethoxy)-phenyl]-2-aza-spiro[4.5]decan-1-one;
(5α,8β)-8-Hydroxy-2-[4-(3,3,3-trifluoro-propoxy)-phenyl]-2-aza-spiro[4.5]decan-1-one;
(5α,8α)-8-Hydroxy-8-propyl-2-[4-(3,3,3-trifluoro-propoxy)-phenyl]-2-aza-spiro[4.5]decan-1-one;
(5α,8β)-8-Hydroxy-8-propyl-2-[4-(3,3,3-trifluoro-propoxy)-phenyl]-2-aza-spiro[4.5]decan-1-one;
(5α,8α)-8-hydroxy-2-(6-isopropylpyridin-3-yl)-8-propyl-2-aza-spiro[4.5]decan-1-one;
(5α,8α)-8-hydroxy-8-isopropyl-2-(6-isopropylpyridin-3-yl)-2-aza-spiro[4.5]decan-1-one;
(5α,8α)-8-Hydroxy-8-isopropyl-2-[4-(2,2,2-trifluoro-ethoxy)-phenyl]-2-aza-spiro[4.5]decan-1-one;
8-Hydroxy-8-propyl-2-[4-(2,2,2-trifluoro-ethoxy)-phenyl]-2-aza-spiro[4.5]decan-1-one;
(5α,8α)-8-hydroxy-8-(prop-1-en-2-yl)-2-(4-(2,2,2-trifluoroethoxy)phenyl)-2-aza-spiro[4.5]decan-1-one;
(5α,8β)-8-hydroxy-8-(prop-1-en-2-yl)-2-(4-(2,2,2-trifluoroethoxy)phenyl)-2-aza-spiro[4.5]decan-1-one;
(5α,8β)-8-hydroxy-8-isopropyl-2-(4-(2,2,2-trifluoroethoxy)phenyl)-2-aza-spiro[4.5]decan-1-one;
(5α,8α)-8-hydroxy-8-isopropyl-2-(6-(2,2,2-trifluoroethoxy)pyridin-3-yl)-2-aza-spiro[4.5]decan-1-one;
(5α,8β)-8-hydroxy-8-isopropyl-2-(6-(2,2,2-trifluoroethoxy)pyridin-3-yl)-2-aza-spiro[4.5]decan-1-one;
(5α,8α)-8-hydroxy-8-(methoxymethyl)-2-(6-(2,2,2-trifluoroethoxy)pyridin-3-yl)-2-aza-spiro[4.5]decan-1-one;
(5α,8α)-8-Hydroxy-8-prop-1-ynyl-2-[4-(2,2,2-trifluoro-ethoxy)-phenyl]-2-aza-spiro[4.5]decan-1-one;
(5α,8α)-8-Hydroxy-2-(4-trifluoromethoxy-phenyl)-8-trifluoromethyl-2-aza-spiro[4.5]decan-1-one;
(5α,8β)-8-Hydroxy-2-(4-trifluoromethoxy-phenyl)-8-trifluoromethyl-2-aza-spiro[4.5]decan-1-one;
(5α,8α)-8-Hydroxy-8-methoxymethyl-2-(4-trifluoromethoxy-phenyl)-2-aza-spiro[4.5]decan-1-one;
(5α,8β)-8-Hydroxy-8-methoxymethyl-2-(4-trifluoromethoxy-phenyl)-2-aza-spiro[4.5]decan-1-one;
[(5α,8α)-8-Hydroxy-1-oxo-2-(4-trifluoromethoxy-phenyl)-2-aza-spiro[4.5]dec-8-yl]-acetic acid ethyl ester;
(5α,8α)-8-Ethoxymethyl-8-hydroxy-2-(4-trifluoromethoxy-phenyl)-2-aza-spiro[4.5]decan-1-one;
(5α,8α)-8-Hydroxy-8-(2-hydroxy-ethyl)-2-(4-trifluoromethoxy-phenyl)-2-aza-spiro[4.5]decan-1-one;
(5α,8α)-8-Hydroxy-8-(2-methoxy-ethyl)-2-(4-trifluoromethoxy-phenyl)-2-aza-spiro[4.5]decan-1-one;
(5α,8α)-8-Methoxy-8-(2-methoxy-ethyl)-2-(4-trifluoromethoxy-phenyl)-2-aza-spiro[4.5]decan-1-one;
(5α,8α)-8-Hydroxy-8-methoxymethyl-2-(4-trifluoromethyl-phenyl)-2-aza-spiro[4.5]decan-1-one;
(5α,8α)-8-Hydroxy-2-[4-(2-methoxy-ethyl)-phenyl]-8-propyl-2-aza-spiro[4.5]decan-1-one;
(5α,8α)-8-Hydroxy-2-[4-(2-methoxy-ethyl)-phenyl]-8-trifluoromethyl-2-aza-spiro[4.5]decan-1-one;
(5α,8α)-8-Hydroxy-8-isobutyl-2-[4-(2-methoxy-ethyl)-phenyl]-2-aza-spiro[4.5]decan-1-one;
(5α,8β)-8-Hydroxy-8-isobutyl-2-[4-(2-methoxy-ethyl)-phenyl]-2-aza-spiro[4.5]decan-1-one;
(5α,8α)-8-(2,2-Dimethyl-propyl)-8-hydroxy-2-[4-(2-methoxy-ethyl)-phenyl]-2-aza-spiro[4.5]decan-1-one;
(5α,8α)-8-Hydroxy-8-isopropenyl-2-[4-(2-methoxy-ethyl)-phenyl]-2-aza-spiro[4.5]decan-1-one;
(5α,8α)-8-Hydroxy-8-isopropyl-2-[4-(2-methoxy-ethyl)-phenyl]-2-aza-spiro[4.5]decan-1-one;
(5α,8α)-8-Butyl-8-hydroxy-2-[4-(2-methoxy-ethyl)-phenyl]-2-aza-spiro[4.5]decan-1-one;
(5α,8α)-8-hydroxy-8-isopropyl-2-(4-(3-methoxypropyl)phenyl)-2-aza-spiro[4.5]decan-1-one;
(5α,8α)-8-Ethyl-8-hydroxy-2-[4-(2-methoxy-1,1-dimethyl-ethyl)-phenyl]-2-aza-spiro[4.5]decan-1-one;
(5α,8α)-8-Hydroxy-2-[4-(2-methoxy-1,1-dimethyl-ethyl)-phenyl]-8-propyl-2-aza-spiro[4.5]decan-1-one;
(5α,8α)-8-hydroxy-8-propyl-2-(4-(2,2,2-trifluoro-1-hydroxyethyl)phenyl)-2-aza-spiro[4.5]decan-1-one;
(5α,8α)-8-Hydroxy-8-propyl-2-[4-((S)-2,2,2-trifluoro-1-hydroxy-ethyl)-phenyl]-2-aza-spiro[4.5]decan-1-one;
(5α,8α)-8-Hydroxy-8-propyl-2-[4-((R)-2,2,2-trifluoro-1-hydroxy-ethyl)-phenyl]-2-aza-spiro[4.5]decan-1-one;
(5α,8β)-8-hydroxy-8-propyl-2-(4-(2,2,2-trifluoro-1-hydroxyethyl)phenyl)-2-aza-spiro[4.5]decan-1-one;
(5α,8α)-8-Hydroxy-8-isopropyl-2-[4-((R)-2,2,2-trifluoro-1-hydroxy-ethyl)-phenyl]-2-aza-spiro[4.5]decan-1-one;
(5α,8β)-8-hydroxy-8-isopropyl-2-(4-((R)-2,2,2-trifluoro-1-hydroxy-ethyl)-phenyl)-2-aza-spiro[4.5]decan-1-one;
(5α,8α)-8-hydroxy-8-isopropyl-2-(4-((R)-2,2,2-trifluoro-1-methoxyethyl)phenyl)-2-aza-spiro[4.5]decan-1-one;
(5α,8α)-8-hydroxy-8-(methoxymethyl)-2-(4-((R)-2,2,2-trifluoro-1-hydroxyethyl)phenyl)-2-aza-spiro[4.5]decan-1-one;
(5α,8α)-8-hydroxy-8-(methoxymethyl)-2-(4-((R)-2,2,2-trifluoro-1-methoxyethyl)phenyl)-2-aza-spiro[4.5]decan-1-one;
(5α,8α)-2-(4-((R)-1-ethoxy-2,2,2-trifluoroethyl)phenyl)-8-hydroxy-8-(methoxymethyl)-2-aza-spiro[4.5]decan-1-one;
(5α,8α)-8-hydroxy-8-(methoxymethyl)-2-(4-((R)-2,2,2-trifluoro-1-propoxyethyl)phenyl)-2-aza-spiro[4.5]decan-1-one;
(5α,8α)-8-Allyl-8-hydroxy-2-[4-((R)-2,2,2-trifluoro-1-methyl-ethoxy)-phenyl]-2-aza-spiro[4.5]decan-1-one;
(5α,8β)-8-Allyl-8-hydroxy-2-[4-((R)-2,2,2-trifluoro-1-methyl-ethoxy)-phenyl]-2-aza-spiro[4.5]decan-1-one;
(5α,8α)-8-Benzyloxymethyl-8-hydroxy-2-[4-((R)-2,2,2-trifluoro-1-methyl-ethoxy)-phenyl]-2-aza-spiro[4.5]decan-1-one;

(5α,8α)-8-Hydroxy-8-hydroxymethyl-2-[4-((R)-2,2,2-trifluoro-1-methyl-ethoxy)-phenyl]-2-aza-spiro[4.5]decan-1-one;
(5α,8α)-8-Hydroxy-8-methoxymethyl-2-[4-((S)-2,2,2-trifluoro-1-methyl-ethoxy)-phenyl]-2-aza-spiro[4.5]decan-1-one;
(5α,8α)-8-Hydroxy-8-methoxymethyl-2-[4-((R)-2,2,2-trifluoro-1-methyl-ethoxy)-phenyl]-2-aza-spiro[4.5]decan-1-one;
(5α,8α)-8-Hydroxy-8-isopropyl-2-[6-((S)-2,2,2-trifluoro-1-methyl-ethoxy)-pyridin-3-yl]-2-aza-spiro[4.5]decan-1-one;
(5α,8β)-8-Hydroxy-8-isopropyl-2-[6-((S)-2,2,2-trifluoro-1-methyl-ethoxy)-pyridin-3-yl]-2-aza-spiro[4.5]decan-1-one;
(5α,8α)-8-Hydroxy-8-isopropyl-2-[6-((R)-2,2,2-trifluoro-1-methyl-ethoxy)-pyridin-3-yl]-2-aza-spiro[4.5]decan-1-one;
(5α,8β)-8-Hydroxy-8-isopropyl-2-[6-((R)-2,2,2-trifluoro-1-methyl-ethoxy)-pyridin-3-yl]-2-aza-spiro[4.5]decan-1-one;
(5α,8α)-8-Hydroxy-8-methoxymethyl-2-[6-((R)-2,2,2-trifluoro-1-methyl-ethoxy)-pyridin-3-yl]-2-aza-spiro[4.5]decan-1-one;
(5α,8α)-8-Hydroxy-8-methoxymethyl-2-[6-((S)-2,2,2-trifluoro-1-methyl-ethoxy)-pyridin-3-yl]-2-aza-spiro[4.5]decan-1-one;
(5α,8α)-8-Hydroxy-8-methoxymethyl-2-[4-(2,2,2-trifluoro-ethyl)-phenyl]-2-aza-spiro[4.5]decan-1-one;
(5α,8α)-8-Hydroxy-8-(2,2,2-trifluoro-ethoxymethyl)-2-[4-((R)-2,2,2-trifluoro-1-hydroxy-ethyl)-phenyl]-2-aza-spiro[4.5]decan-1-one;
2-[(5α,8α)-8-Hydroxy-1-oxo-2-(4-trifluoromethoxy-phenyl)-2-aza-spiro[4.5]dec-8-yl]-N,N-dimethyl-acetamide;
2-[(5α,8α)-8-hydroxy-1-oxo-2-(4-(2,2,2-trifluoroethoxy)phenyl)-2-aza-spiro[4.5]decan-8-yl]-N,N-dimethylacetamide;
2-[(5α,8α)-8-hydroxy-1-oxo-2-(4-(2,2,2-trifluoroethoxy)phenyl)-2-aza-spiro[4.5]decan-8-yl]-N-methylacetamide;
(5α,8α)-8-Hydroxy-8-isopropoxymethyl-2-[4-((R)-2,2,2-trifluoro-1-hydroxy-ethyl)-phenyl]-2-aza-spiro[4.5]decan-1-one;
(5α,8α)-8-(2,2-Difluoro-ethoxymethyl)-8-hydroxy-2-[4-((R)-2,2,2-trifluoro-1-hydroxy-ethyl)-phenyl]-2-aza-spiro[4.5]decan-1-one;
(5α,8α)-2-(4-ethylphenethyl)-8-hydroxy-8-isopropyl-2-aza-spiro[4.5]decan-1-one;
8-Hydroxy-2-[4-(2,2,2-trifluoro-1-methyl-ethoxy)-phenyl]-2-aza-spiro[4.5]decan-1-one;
(5α,8β)-8-Hydroxy-8-propyl-2-[4-(2,2,2-trifluoro-1-methyl-ethoxy)-phenyl]-2-aza-spiro[4.5]decan-1-one;
(5α,8α)-8-Hydroxy-8-propyl-2-[4-(2,2,2-trifluoro-1-methyl-ethoxy)-phenyl]-2-aza-spiro[4.5]decan-1-one;
(5α,8α)-8-Hydroxy-8-propyl-2-[4-((S)-2,2,2-trifluoro-1-methyl-ethoxy)-phenyl]-2-aza-spiro[4.5]decan-1-one;
(5α,8α)-8-Hydroxy-8-propyl-2-[4-((R)-2,2,2-trifluoro-1-methyl-ethoxy)-phenyl]-2-aza-spiro[4.5]decan-1-one;
(5α,8α)-8-Ethyl-8-hydroxy-2-[4-(2,2,2-trifluoro-1-methyl-ethoxy)-phenyl]-2-aza-spiro[4.5]decan-1-one;
(5α,8α)-8-Ethyl-8-hydroxy-2-[4-((S)-2,2,2-trifluoro-1-methyl-ethoxy)-phenyl]-2-aza-spiro[4.5]decan-1-one;
(5α,8α)-8-Ethyl-8-hydroxy-2-[4-((R)-2,2,2-trifluoro-1-methyl-ethoxy)-phenyl]-2-aza-spiro[4.5]decan-1-one;
(5α,8α)-8-Hydroxy-2-[6-(2,2,2-trifluoro-ethoxy)-pyridin-3-yl]-8-(3,3,3-trifluoro-propyl)-2-aza-spiro[4.5]decan-1-one;
(5α,8α)-8-Hydroxy-8-propyl-2-[6-(2,2,2-trifluoro-ethoxy)-pyridin-3-yl]-2-aza-spiro[4.5]decan-1-one;
(5α,8α)-8-Ethyl-8-hydroxy-2-[6-(2,2,2-trifluoro-ethoxy)-pyridin-3-yl]-2-aza-spiro[4.5]decan-1-one;
(5α,8α)-8-Ethyl-8-hydroxy-2-[4-(3,3,3-trifluoro-propyl)-phenyl]-2-aza-spiro[4.5]decan-1-one;
(5α,8α)-8-Hydroxy-8-propyl-2-[4-(3,3,3-trifluoro-propyl)-phenyl]-2-aza-spiro[4.5]decan-1-one;
(5α,8α)-8-Ethyl-8-hydroxy-2-[6-((S)-2,2,2-trifluoro-1-methyl-ethoxy)-pyridin-3-yl]-2-aza-spiro[4.5]decan-1-one;
(5α,8α)-8-Hydroxy-8-propyl-2-[6-((S)-2,2,2-trifluoro-1-methyl-ethoxy)-pyridin-3-yl]-2-aza-spiro[4.5]decan-1-one;
(5α,8α)-8-Hydroxy-8-trifluoromethyl-2-[6-((S)-2,2,2-trifluoro-1-methyl-ethoxy)-pyridin-3-yl]-2-aza-spiro[4.5]decan-1-one;
(5α,8α)-8-Hydroxy-8-trifluoromethyl-2-[6-((R)-2,2,2-trifluoro-1-methyl-ethoxy)-pyridin-3-yl]-2-aza-spiro[4.5]decan-1-one;
(5α,8α)-8-Ethyl-8-hydroxy-2-[6-((R)-2,2,2-trifluoro-1-methyl-ethoxy)-pyridin-3-yl]-2-aza-spiro[4.5]decan-1-one;
(5α,8α)-8-Hydroxy-8-propyl-2-[6-((R)-2,2,2-trifluoro-1-methyl-ethoxy)-pyridin-3-yl]-2-aza-spiro[4.5]decan-1-one;
(5α,8α)-8-Hydroxy-8-trifluoromethyl-2-[4-(2,2,2-trifluoro-1-methyl-ethoxy)-phenyl]-2-aza-spiro[4.5]decan-1-one;
(5α,8α)-8-Hydroxy-8-trifluoromethyl-2-[4-((S)-2,2,2-trifluoro-1-methyl-ethoxy)-phenyl]-2-aza-spiro[4.5]decan-1-one;
(5α,8α)-8-Hydroxy-8-trifluoromethyl-2-[4-((R)-2,2,2-trifluoro-1-methyl-ethoxy)-phenyl]-2-aza-spiro[4.5]decan-1-one,
(5α,8α)-8-Hydroxy-2-[6-(2,2,2-trifluoro-ethoxy)-pyridin-3-yl]-8-trifluoromethyl-2-aza-spiro[4.5]decan-1-one;
(5α,8α)-8-Cyclopropyl-8-hydroxy-2-[6-((R)-2,2,2-trifluoro-1-methyl-ethoxy)-pyridin-3-yl]-2-aza-spiro[4.5]decan-1-one;
(5α,8α)-8-Cyclopropyl-8-hydroxy-2-[6-((S)-2,2,2-trifluoro-1-methyl-ethoxy)-pyridin-3-yl]-2-aza-spiro[4.5]decan-1-one;
(5α,8α)-8-Cyclopropyl-8-hydroxy-2-[4-(2,2,2-trifluoro-1-methyl-ethoxy)-phenyl]-2-aza-spiro[4.5]decan-1-one;
(5α,8α)-8-Cyclopropyl-8-hydroxy-2-[4-((R)-2,2,2-trifluoro-1-methyl-ethoxy)-phenyl]-2-aza-spiro[4.5]decan-1-one;
4-((5α,8α)-8-hydroxy-1-oxo-8-propyl-2-aza-spiro[4.5]decan-2-yl)phenyl cyclopropanesulfonate;
4-((5α,8α)-8-ethyl-8-hydroxy-1-oxo-2-aza-spiro[4.5]decan-2-yl)phenyl cyclopropanesulfonate;
(5α,8α)-8-hydroxy-2-(4-isopropoxyphenyl)-8-propyl-2-aza-spiro[4.5]decan-1-one;
4-((5α,8β)-8-hydroxy-1-oxo-8-propyl-2-aza-spiro[4.5]decan-2-yl)phenyl methanesulfonate;
(5α,8α)-8-Ethyl-8-hydroxy-2-(4-isopropoxy-phenyl)-2-aza-spiro[4.5]decan-1-one;
(5α,8α)-2-(4-Ethanesulfonyl-phenyl)-8-hydroxy-8-propyl-2-aza-spiro[4.5]decan-1-one;
(5α,8α)-8-hydroxy-8-propyl-2-(4-(trifluoromethoxy)benzyl)-2-aza-spiro[4.5]decan-1-one;
4-((5α,8α)-8-hydroxy-1-oxo-8-(trifluoromethyl)-2-aza-spiro[4.5]decan-2-yl)phenyl cyclopropanesulfonate;
(5α,8α)-8-butyl-8-hydroxy-2-(4-((R)-2,2,2-trifluoro-1-hydroxyethyl)phenyl)-2-aza-spiro[4.5]decan-1-one;
(5α,8α)-2-(4-(2,2-difluoro-1-hydroxypropyl)phenyl)-8-hydroxy-8-isopropyl-2-aza-spiro[4.5]decan-1-one;
(5α,8α)-2-(4-(2,2-difluoro-1-hydroxypropyl)phenyl)-8-hydroxy-8-propyl-2-aza-spiro[4.5]decan-1-one;

(5α,8α)-2-(4-(2,2-difluoro-1-hydroxypropyl)phenyl)-8-hydroxy-8-(3,3,3-trifluoropropyl)-2-aza-spiro[4.5]decan-1-one;

(5α,8α)-8-hydroxy-2-(4-((R)-2,2,2-trifluoro-1-hydroxyethyl)phenyl)-8-(3,3,3-trifluoropropyl)-2-aza-spiro[4.5]decan-1-one;

(5α,8α)-2-(4-(2,2-difluoro-1-hydroxyethyl)phenyl)-8-hydroxy-8-propyl-2-aza-spiro[4.5]decan-1-one;

(5α,8α)-8-hydroxy-2-(4-isopropoxyphenyl)-8-isopropyl-2-aza-spiro[4.5]decan-1-one;

(5α,8α)-8-cyclopropyl-8-hydroxy-2-(4-isopropoxyphenyl)-2-aza-spiro[4.5]decan-1-one;

(5α,8α)-8-cyclopentyl-8-hydroxy-2-(4-isopropoxyphenyl)-2-aza-spiro[4.5]decan-1-one;

(5α,8α)-8-hydroxy-8-isobutyl-2-(4-isopropoxyphenyl)-2-aza-spiro[4.5]decan-1-one (5α,8α)-8-cyclobutyl-8-hydroxy-2-(4-((R)-2,2,2-trifluoro-1-hydroxyethyl)phenyl)-2-aza-spiro[4.5]decan-1-one;

(5α,8α)-8-cyclopropyl-8-hydroxy-2-(4-((R)-2,2,2-trifluoro-1-hydroxyethyl)phenyl)-2-aza-spiro[4.5]decan-1-one;

(5α,8α)-8-cyclopentyl-8-hydroxy-2-(4-((R)-2,2,2-trifluoro-1-hydroxyethyl)phenyl)-2-aza-spiro[4.5]decan-1-one;

(5α,8α)-8-hydroxy-8-isopropyl-2-(4-isopropylphenyl)-2-aza-spiro[4.5]decan-1-one;

(5α,8α)-8-hydroxy-2-(4-isopropylphenyl)-8-propyl-2-aza-spiro[4.5]decan-1-one;

(5α,8α)-8-hydroxy-2-(4-isopropylphenyl)-8-phenyl-2-aza-spiro[4.5]decan-1-one;

(5α,8α)-8-hydroxy-2-(4-isopropoxyphenyl)-8-phenyl-2-aza-spiro[4.5]decan-1-one;

(5α,8α)-2-(4-(2,2-difluoro-1-hydroxyethyl)phenyl)-8-hydroxy-8-isopropyl-2-aza-spiro[4.5]decan-1-one;

(5α,8α)-8-hydroxy-8-propyl-2-(4-(trifluoromethyl)phenyl)-2-aza-spiro[4.5]decan-1-one;

(5α,8α)-8-hydroxy-8-isopropyl-2-(4-(trifluoromethyl)phenyl)-2-aza-spiro[4.5]decan-1-one;

(5α,8α)-8-hydroxy-2-(4-isopropoxyphenyl)-8-(methoxymethyl)-2-aza-spiro[4.5]decan-1-one;

(5α,8α)-8-hydroxy-2-(4-isopropoxyphenyl)-8-(thiophen-3-yl)-2-aza-spiro[4.5]decan-1-one;

(5α,8α)-8-(5-Bromo-3-methyl-3H-[1,2,3]triazol-4-yl)-8-hydroxy-2-(4-isopropoxy-phenyl)-2-aza-spiro[4.5]decan-1-one;

(5α,8α)-8-hydroxy-2-(4-isopropoxyphenyl)-8-(1-methyl-1H-1,2,3-triazol-4-yl)-2-aza-spiro[4.5]decan-1-one;

(5α,8α)-8-(5-Bromo-3-methyl-3H-[1,2,3]triazol-4-yl)-8-hydroxy-2-(4-trifluoromethyl-phenyl)-2-aza-spiro[4.5]decan-1-one;

(5α,8α)-8-Hydroxy-8-(3-methyl-3H-[1,2,3]triazol-4-yl)-2-(4-trifluoromethyl-phenyl)-2-aza-spiro[4.5]decan-1-one;

(5α,8α)-8-hydroxy-2-(4-isopropylphenyl)-8-((2,2,2-trifluoroethoxy)methyl)-2-aza-spiro[4.5]decan-1-one;

(5α,8α)-8-hydroxy-2-(4-isopropoxyphenyl)-8-(1-methyl-1H-pyrazol-3-yl)-2-aza-spiro[4.5]decan-1-one;

(5α,8α)-8-hydroxy-2-(4-isopropylphenyl)-8-(methoxymethyl)-2-aza-spiro[4.5]decan-1-one;

(5α,8α)-8-hydroxy-8-((2,2,2-trifluoroethoxy)methyl)-2-(4-(trifluoromethyl)phenyl)-2-aza-spiro[4.5]decan-1-one;

(5α,8α)-8-hydroxy-2-(4-isopropoxyphenyl)-8-((5-methyl-isoxazol-3-yl)methyl)-2-aza-spiro[4.5]decan-1-one;

(5α,8β)-8-hydroxy-2-(4-isopropoxyphenyl)-8-((5-methyl-isoxazol-3-yl)methyl)-2-aza-spiro[4.5]decan-1-one;

(5α,8α)-8-hydroxy-2-(4-isopropoxyphenyl)-8-(1-methyl-4-vinyl-1H-1,2,3-triazol-5-yl)-2-aza-spiro[4.5]decan-1-one;

(5α,8α)-2-(4-Cyclopropyl-phenyl)-8-hydroxy-8-methoxymethyl-2-aza-spiro[4.5]decan-1-one;

(5α,8α)-2-(4-Ethyl-phenyl)-8-hydroxy-8-methoxymethyl-2-aza-spiro[4.5]decan-1-one;

(5α,8α)-8-Ethoxymethyl-2-(4-ethyl-phenyl)-8-hydroxy-2-aza-spiro[4.5]decan-1-one;

(5α,8α)-2-(4-Ethyl-phenyl)-8-hydroxy-8-propoxymethyl-2-aza-spiro[4.5]decan-1-one;

(5α,8β)-2-(4-Ethyl-phenyl)-8-hydroxy-8-phenoxymethyl-2-aza-spiro[4.5]decan-1-one;

(5α,8α)-2-(4-Ethyl-phenyl)-8-hydroxy-8-phenoxymethyl-2-aza-spiro[4.5]decan-1-one;

(5α,8α)-2-(4-Ethyl-phenyl)-8-hydroxy-8-(2-methoxyethoxymethyl)-2-aza-spiro[4.5]decan-1-one;

(5α,8β)-2-(4-Ethyl-phenyl)-8-hydroxy-8-(2,2,2-trifluoroethoxymethyl)-2-aza-spiro[4.5]decan-1-one;

(5α,8α)-2-(4-Ethyl-phenyl)-8-hydroxy-8-(2,2,2-trifluoroethoxymethyl)-2-aza-spiro[4.5]decan-1-one;

(5α,8β)-8-Hydroxy-8-(2,2,2-trifluoro-ethoxymethyl)-2-[4-(2,2,2-trifluoro-ethoxy)-phenyl]-2-aza-spiro[4.5]decan-1-one;

(5α,8α)-8-Hydroxy-8-(2,2,2-trifluoro-ethoxymethyl)-2-[4-(2,2,2-trifluoro-ethoxy)-phenyl]-2-aza-spiro[4.5]decan-1-one;

(5α,8α)-8-Ethoxymethyl-8-hydroxy-2-[4-(2,2,2-trifluoro-ethoxy)-phenyl]-2-aza-spiro[4.5]decan-1-one;

(5α,8β)-8-Hydroxy-8-propoxymethyl-2-[4-(2,2,2-trifluoro-ethoxy)-phenyl]-2-aza-spiro[4.5]decan-1-one;

(5α,8α)-8-Hydroxy-8-propoxymethyl-2-[4-(2,2,2-trifluoro-ethoxy)-phenyl]-2-aza-spiro[4.5]decan-1-one, (5α,8β)-8-Butoxymethyl-8-hydroxy-2-[4-(2,2,2-trifluoro-ethoxy)-phenyl]-2-aza-spiro[4.5]decan-1-one, (5α,8α)-8-Butoxymethyl-8-hydroxy-2-[4-(2,2,2-trifluoro-ethoxy)-phenyl]-2-aza-spiro[4.5]decan-1-one, (5α,8β)-8-Hydroxy-8-phenoxymethyl-2-[4-(2,2,2-trifluoro-ethoxy)-phenyl]-2-aza-spiro[4.5]decan-1-one;

(5α,8α)-8-Hydroxy-8-phenoxymethyl-2-[4-(2,2,2-trifluoro-ethoxy)-phenyl]-2-aza-spiro[4.5]decan-1-one;

(5α,8β)-8-Benzyloxymethyl-8-hydroxy-2-[4-(2,2,2-trifluoro-ethoxy)-phenyl]-2-aza-spiro[4.5]decan-1-one, (5α,8α)-8-Benzyloxymethyl-8-hydroxy-2-[4-(2,2,2-trifluoro-ethoxy)-phenyl]-2-aza-spiro[4.5]decan-1-one, (5α,8β)-8-(2,2-Difluoro-ethoxymethyl)-8-hydroxy-2-[4-(2,2,2-trifluoro-ethoxy)-phenyl]-2-aza-spiro[4.5]decan-1-one, (5α,8α)-8-(2,2-Difluoro-ethoxymethyl)-8-hydroxy-2-[4-(2,2,2-trifluoro-ethoxy)-phenyl]-2-aza-spiro[4.5]decan-1-one, (5α,8β)-8-Hydroxy-8-isobutoxymethyl-2-[4-(2,2,2-trifluoro-ethoxy)-phenyl]-2-aza-spiro[4.5]decan-1-one;

(5α,8α)-8-Hydroxy-8-isobutoxymethyl-2-[4-(2,2,2-trifluoro-ethoxy)-phenyl]-2-aza-spiro[4.5]decan-1-one;

(5α,8α)-8-Ethoxymethyl-8-hydroxy-2-[6-(2,2,2-trifluoro-ethoxy)-pyridin-3-yl]-2-aza-spiro[4.5]decan-1-one;

(5α,8β)-8-Ethoxymethyl-8-hydroxy-2-[6-((S)-2,2,2-trifluoro-1-methyl-ethoxy)-pyridin-3-yl]-2-aza-spiro[4.5]decan-1-one, (5α,8α)-8-Ethoxymethyl-8-hydroxy-2-[6-((S)-2,2,2-trifluoro-1-methyl-ethoxy)-pyridin-3-yl]-2-aza-spiro[4.5]decan-1-one;

(5α,8β)-8-Ethoxymethyl-8-hydroxy-2-[4-((S)-2,2,2-trifluoro-1-methyl-ethoxy)-phenyl]-2-aza-spiro[4.5]decan-1-one;

(5α,8α)-8-Ethoxymethyl-8-hydroxy-2-[4-((S)-2,2,2-trifluoro-1-methyl-ethoxy)-phenyl]-2-aza-spiro[4.5]decan-1-one;

(5α,8β)-8-Ethoxymethyl-8-hydroxy-2-[4-((R)-2,2,2-trifluoro-1-methyl-ethoxy)-phenyl]-2-aza-spiro[4.5]decan-1-one;

(5α,8α)-8-Ethoxymethyl-8-hydroxy-2-[4-((R)-2,2,2-trifluoro-1-methyl-ethoxy)-phenyl]-2-aza-spiro[4.5]decan-1-one;
(5α,8β)-8-[(Cyclobutylmethoxy)methyl]-8-hydroxy-2-[4-(2,2,2-trifluoro-ethoxy)-phenyl]-2-aza-spiro[4.5]decan-1-one;
(5α,8α)-8-[(Cyclobutylmethoxy)methyl]-8-hydroxy-2-[4-(2,2,2-trifluoro-ethoxy)-phenyl]-2-aza-spiro[4.5]decan-1-one;
(5α,8β)-8-[(Cyclopropylmethoxy)methyl]-8-hydroxy-2-[4-(2,2,2-trifluoro-ethoxy)-phenyl]-2-aza-spiro[4.5]decan-1-one;
(5α,8α)-8-[(Cyclopropylmethoxy)methyl]-8-hydroxy-2-[4-(2,2,2-trifluoro-ethoxy)-phenyl]-2-aza-spiro[4.5]decan-1-one;
(5α,8α)-8-Hydroxy-8-methoxymethyl-2-[4-(2,2,2-trifluoro-ethoxy)-phenyl]-2-aza-spiro[4.5]decan-1-one;
(5α,8α)-8-Hydroxy-8-(oxetan-2-ylmethoxymethyl)-2-[4-(2,2,2-trifluoro-ethoxy)-phenyl]-2-aza-spiro[4.5]decan-1-one;
(5α,8α)-8-Hydroxy-8-(3-methyl-oxetan-3-ylmethoxymethyl)-2-[4-(2,2,2-trifluoro-ethoxy)-phenyl]-2-aza-spiro[4.5]decan-1-one;
(5α,8α)-8-Ethylsulfanylmethyl-8-hydroxy-2-[4-(2,2,2-trifluoro-ethoxy)-phenyl]-2-aza-spiro[4.5]decan-1-one;
(5α,8α)-8-(3-Fluoro-phenoxymethyl)-8-hydroxy-2-[4-(2,2,2-trifluoro-ethoxy)-phenyl]-2-aza-spiro[4.5]decan-1-one;
(5α,8α)-8-(4-Fluoro-phenoxymethyl)-8-hydroxy-2-[4-(2,2,2-trifluoro-ethoxy)-phenyl]-2-aza-spiro[4.5]decan-1-one;
(5α,8β)-8-(2,2-Difluoro-ethoxymethyl)-2-(4-ethyl-phenyl)-8-hydroxy-2-aza-spiro[4.5]decan-1-one;
(5α,8α)-8-(2,2-Difluoro-ethoxymethyl)-2-(4-ethyl-phenyl)-8-hydroxy-2-aza-spiro[4.5]decan-1-one;
(5α,8β)-8-Hydroxy-8-propoxymethyl-2-[6-(2,2,2-trifluoro-ethoxy)-pyridin-3-yl]-2-aza-spiro[4.5]decan-1-one;
(5α,8α)-8-Hydroxy-8-propoxymethyl-2-[6-(2,2,2-trifluoro-ethoxy)-pyridin-3-yl]-2-aza-spiro[4.5]decan-1-one;
(5α,8α)-8-Hydroxy-8-propoxymethyl-2-[6-((S)-2,2,2-trifluoro-1-methyl-ethoxy)-pyridin-3-yl]-2-aza-spiro[4.5]decan-1-one;
(5α,8α)-8-Hydroxy-8-propoxymethyl-2-[4-((S)-2,2,2-trifluoro-1-methyl-ethoxy)-phenyl]-2-aza-spiro[4.5]decan-1-one;
(5α,8α)-8-Hydroxy-8-propoxymethyl-2-[4-((R)-2,2,2-trifluoro-1-methyl-ethoxy)-phenyl]-2-aza-spiro[4.5]decan-1-one;
(5α,8α)-2-(4-Cyclopropyl-phenyl)-8-ethoxymethyl-8-hydroxy-2-aza-spiro[4.5]decan-1-one;
(5α,8α)-2-(4-Cyclopropyl-phenyl)-8-hydroxy-8-propoxymethyl-2-aza-spiro[4.5]decan-1-one;
(5α,8α)-8-[(Cyclopentylmethoxy)methyl]-8-hydroxy-2-[4-(2,2,2-trifluoro-ethoxy)-phenyl]-2-aza-spiro[4.5]decan-1-one;
(5α,8α)-8-(2,2-Dimethyl-propoxymethyl)-8-hydroxy-2-[4-(2,2,2-trifluoro-ethoxy)-phenyl]-2-aza-spiro[4.5]decan-1-one;
(5α,8α)-8-Ethanesulfonylmethyl-8-hydroxy-2-[4-(2,2,2-trifluoro-ethoxy)-phenyl]-2-aza-spiro[4.5]decan-1-one;
(5α,8α)-8-Hydroxy-8-isopropoxymethyl-2-[4-(2,2,2-trifluoro-ethoxy)-phenyl]-2-aza-spiro[4.5]decan-1-one;
(5α,8α)-8-Hydroxy-2-[4-(2,2,2-trifluoro-ethoxy)-phenyl]-8-(3,3,3-trifluoro-propoxymethyl)-2-aza-spiro[4.5]decan-1-one;
(5α,8β)-8-Hydroxy-8-(pyridin-2-yloxymethyl)-2-[4-(2,2,2-trifluoro-ethoxy)-phenyl]-2-aza-spiro[4.5]decan-1-one;
(5α,8α)-8-Hydroxy-8-(2,2,2-trifluoro-ethoxymethyl)-2-[6-(2,2,2-trifluoro-ethoxy)-pyridin-3-yl]-2-aza-spiro[4.5]decan-1-one;
(5α,8β)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one;
(5α,8α)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one;
(5α,8β)-8-Hydroxy-8-(2,2,2-trifluoro-ethoxymethyl)-2-[4-((S)-2,2,2-trifluoro-1-methyl-ethoxy)-phenyl]-2-aza-spiro[4.5]decan-1-one;
(5α,8α)-8-Hydroxy-8-(2,2,2-trifluoro-ethoxymethyl)-2-[4-((S)-2,2,2-trifluoro-1-methyl-ethoxy)-phenyl]-2-aza-spiro[4.5]decan-1-one;
(5α,8β)-8-Hydroxy-8-(2,2,2-trifluoro-ethoxymethyl)-2-[4-((R)-2,2,2-trifluoro-1-methyl-ethoxy)-phenyl]-2-aza-spiro[4.5]decan-1-one;
(5α,8α)-8-Hydroxy-8-(2,2,2-trifluoro-ethoxymethyl)-2-[4-((R)-2,2,2-trifluoro-1-methyl-ethoxy)-phenyl]-2-aza-spiro[4.5]decan-1-one;
(5α,8β)-8-Hydroxy-8-(2,2,2-trifluoro-ethoxymethyl)-2-[4-(2,2,2-trifluoro-ethyl)-phenyl]-2-aza-spiro[4.5]decan-1-one;
(5α,8α)-8-Hydroxy-8-(2,2,2-trifluoro-ethoxymethyl)-2-[4-(2,2,2-trifluoro-ethyl)-phenyl]-2-aza-spiro[4.5]decan-1-one;
(5α,8β)-2-(4-Cyclopropyl-phenyl)-8-hydroxy-8-(2,2,2-trifluoro-ethoxymethyl)-2-aza-spiro[4.5]decan-1-one;
(5α,8α)-2-(4-Cyclopropyl-phenyl)-8-hydroxy-8-(2,2,2-trifluoro-ethoxymethyl)-2-aza-spiro[4.5]decan-1-one;
(5α,8α)-8-(2-Cyclopropyl-ethoxymethyl)-8-hydroxy-2-[4-(2,2,2-trifluoro-ethoxy)-phenyl]-2-aza-spiro[4.5]decan-1-one;
(5α,8α)-8-Hydroxy-8-(3-methyl-butoxymethyl)-2-[4-(2,2,2-trifluoro-ethoxy)-phenyl]-2-aza-spiro[4.5]decan-1-one;
(5α,8α)-8-Hydroxy-2-[4-(2,2,2-trifluoro-ethoxy)-phenyl]-8-(2,2,2-trifluoro-1-methyl-ethoxymethyl)-2-aza-spiro[4.5]decan-1-one;
(5α,8α)-8-Hydroxy-8-methylsulfanylmethyl-2-[4-(2,2,2-trifluoro-ethoxy)-phenyl]-2-aza-spiro[4.5]decan-1-one;
(5α,8α)-8-Hydroxy-8-propylsulfanylmethyl-2-[4-(2,2,2-trifluoro-ethoxy)-phenyl]-2-aza-spiro[4.5]decan-1-one;
(5α,8α)-8-(2,2-Difluoro-ethoxymethyl)-8-hydroxy-2-[6-(2,2,2-trifluoro-ethoxy)-pyridin-3-yl]-2-aza-spiro[4.5]decan-1-one;
(5α,8β)-8-(2,2-Difluoro-ethoxymethyl)-8-hydroxy-2-[6-((S)-2,2,2-trifluoro-1-methyl-ethoxy)-pyridin-3-yl]-2-aza-spiro[4.5]decan-1-one;
(5α,8α)-8-(2,2-Difluoro-ethoxymethyl)-8-hydroxy-2-[6-((S)-2,2,2-trifluoro-1-methyl-ethoxy)-pyridin-3-yl]-2-aza-spiro[4.5]decan-1-one;
(5α,8β)-8-(2,2-Difluoro-ethoxymethyl)-8-hydroxy-2-[4-((S)-2,2,2-trifluoro-1-methyl-ethoxy)-phenyl]-2-aza-spiro[4.5]decan-1-one;
(5α,8α)-8-(2,2-Difluoro-ethoxymethyl)-8-hydroxy-2-[4-((S)-2,2,2-trifluoro-1-methyl-ethoxy)-phenyl]-2-aza-spiro[4.5]decan-1-one;
(5α,8β)-8-(2,2-Difluoro-ethoxymethyl)-8-hydroxy-2-[4-((R)-2,2,2-trifluoro-1-methyl-ethoxy)-phenyl]-2-aza-spiro[4.5]decan-1-one;
(5α,8α)-8-(2,2-Difluoro-ethoxymethyl)-8-hydroxy-2-[4-((R)-2,2,2-trifluoro-1-methyl-ethoxy)-phenyl]-2-aza-spiro[4.5]decan-1-one;
(5α,8β)-8-(2,2-Difluoro-ethoxymethyl)-8-hydroxy-2-[4-(2,2,2-trifluoro-ethyl)-phenyl]-2-aza-spiro[4.5]decan-1-one;

(5α,8α)-8-(2,2-Difluoro-ethoxymethyl)-8-hydroxy-2-[4-(2,2,2-trifluoro-ethyl)-phenyl]-2-aza-spiro[4.5]decan-1-one;
(5α,8α)-8-Hydroxy-8-methanesulfonylmethyl-2-[4-(2,2,2-trifluoro-ethoxy)-phenyl]-2-aza-spiro[4.5]decan-1-one;
(5α,8α)-8-Hydroxy-8-(propane-1-sulfonylmethyl)-2-[4-(2,2,2-trifluoro-ethoxy)-phenyl]-2-aza-spiro[4.5]decan-1-one;
(5α,8α)-8-Hydroxy-8-isopropylsulfanylmethyl-2-[4-(2,2,2-trifluoro-ethoxy)-phenyl]-2-aza-spiro[4.5]decan-1-one;
(5α,8β)-8-Hydroxy-8-isopropoxymethyl-2-[4-((S)-2,2,2-trifluoro-1-methyl-ethoxy)-phenyl]-2-aza-spiro[4.5]decan-1-one;
(5α,8α)-8-Hydroxy-8-isopropoxymethyl-2-[4-((S)-2,2,2-trifluoro-1-methyl-ethoxy)-phenyl]-2-aza-spiro[4.5]decan-1-one;
(5α,8α)-8-Hydroxy-8-isopropoxymethyl-2-[6-((S)-2,2,2-trifluoro-1-methyl-ethoxy)-pyridin-3-yl]-2-aza-spiro[4.5]decan-1-one;
(5α,8α)-8-Hydroxy-8-isopropoxymethyl-2-[4-((R)-2,2,2-trifluoro-1-methyl-ethoxy)-phenyl]-2-aza-spiro[4.5]decan-1-one;
(5α,8α)-8-Ethoxymethyl-8-hydroxy-2-[6-((R)-2,2,2-trifluoro-1-methyl-ethoxy)-pyridin-3-yl]-2-aza-spiro[4.5]decan-1-one;
(5α,8α)-8-Hydroxy-8-propoxymethyl-2-[6-((R)-2,2,2-trifluoro-1-methyl-ethoxy)-pyridin-3-yl]-2-aza-spiro[4.5]decan-1-one;
(5α,8β)-8-(2,2-Difluoro-ethoxymethyl)-8-hydroxy-2-[6-((R)-2,2,2-trifluoro-1-methyl-ethoxy)-pyridin-3-yl]-2-aza-spiro[4.5]decan-1-one;
(5α,8α)-8-(2,2-Difluoro-ethoxymethyl)-8-hydroxy-2-[6-((R)-2,2,2-trifluoro-1-methyl-ethoxy)-pyridin-3-yl]-2-aza-spiro[4.5]decan-1-one;
(5α,8β)-8-Hydroxy-8-isopropoxymethyl-2-[6-((R)-2,2,2-trifluoro-1-methyl-ethoxy)-pyridin-3-yl]-2-aza-spiro[4.5]decan-1-one;
(5α,8α)-8-Hydroxy-8-isopropoxymethyl-2-[6-((R)-2,2,2-trifluoro-1-methyl-ethoxy)-pyridin-3-yl]-2-aza-spiro[4.5]decan-1-one;
(5α,8α)-8-Hydroxy-8-(propane-2-sulfinylmethyl)-2-[4-(2,2,2-trifluoro-ethoxy)-phenyl]-2-aza-spiro[4.5]decan-1-one;
(5α,8α)-8-Hydroxy-8-(propane-2-sulfonylmethyl)-2-[4-(2,2,2-trifluoro-ethoxy)-phenyl]-2-aza-spiro[4.5]decan-1-one;
(5α,8α)-8-tert-Butylsulfanylmethyl-8-hydroxy-2-[4-(2,2,2-trifluoro-ethoxy)-phenyl]-2-aza-spiro[4.5]decan-1-one;
(5α,8α)-8-Hydroxy-8-isopropylsulfanylmethyl-2-[6-((S)-2,2,2-trifluoro-1-methyl-ethoxy)-pyridin-3-yl]-2-aza-spiro[4.5]decan-1-one;
(5α,8α)-8-Hydroxy-8-isopropylsulfanylmethyl-2-[6-((R)-2,2,2-trifluoro-1-methyl-ethoxy)-pyridin-3-yl]-2-aza-spiro[4.5]decan-1-one;
(5α,8α)-8-Hydroxy-8-(2-methyl-propane-2-sulfonylmethyl)-2-[4-(2,2,2-trifluoro-ethoxy)-phenyl]-2-aza-spiro[4.5]decan-1-one;
(5α,8α)-8-Hydroxy-8-(propane-2-sulfonylmethyl)-2-[6-((S)-2,2,2-trifluoro-1-methyl-ethoxy)-pyridin-3-yl]-2-aza-spiro[4.5]decan-1-one;
(5α,8α)-8-Hydroxy-8-(propane-2-sulfonylmethyl)-2-[6-((R)-2,2,2-trifluoro-1-methyl-ethoxy)-pyridin-3-yl]-2-aza-spiro[4.5]decan-1-one;
(5α,8α)-8-Hydroxy-8-(2-methyl-propane-2-sulfonylmethyl)-2-[6-((S)-2,2,2-trifluoro-1-methyl-ethoxy)-pyridin-3-yl]-2-aza-spiro[4.5]decan-1-one;
(5α,8α)-8-Hydroxy-8-(2-methyl-propane-2-sulfonylmethyl)-2-[6-((R)-2,2,2-trifluoro-1-methyl-ethoxy)-pyridin-3-yl]-2-aza-spiro[4.5]decan-1-one;
(5α,8α)-8-Hydroxy-8-(2,2,2-trifluoro-ethoxymethyl)-2-[6-((R)-2,2,2-trifluoro-1-methyl-ethoxy)-pyridin-3-yl]-2-aza-spiro[4.5]decan-1-one;
(5α,8α)-8-(1-Ethyl-propoxymethyl)-8-hydroxy-2-[6-((S)-2,2,2-trifluoro-1-methyl-ethoxy)-pyridin-3-yl]-2-aza-spiro[4.5]decan-1-one;
(5α,8α)-8-Hydroxy-2-(6-isopropoxy-pyridin-3-yl)-8-methoxymethyl-2-aza-spiro[4.5]decan-1-one;
(5α,8α)-8-Ethoxymethyl-8-hydroxy-2-(6-isopropoxy-pyridin-3-yl)-2-aza-spiro[4.5]decan-1-one;
(5α,8α)-2-(4-tert-Butyl-phenyl)-8-hydroxy-8-(propane-1-sulfonylmethyl)-2-aza-spiro[4.5]decan-1-one;
(5α,8α)-2-(4-tert-Butyl-phenyl)-8-hydroxy-8-(2-methyl-propane-1-sulfonylmethyl)-2-aza-spiro[4.5]decan-1-one;
(5α,8α)-2-(4-tert-Butyl-phenyl)-8-hydroxy-8-(propane-2-sulfonylmethyl)-2-aza-spiro[4.5]decan-1-one;
(5α,8α)-2-(4-tert-Butyl-phenyl)-8-hydroxy-8-(2-methyl-propane-2-sulfonylmethyl)-2-aza-spiro[4.5]decan-1-one;
(5α,8α)-8-Hydroxy-2-(6-isopropoxy-pyridin-3-yl)-8-(propane-1-sulfonylmethyl)-2-aza-spiro[4.5]decan-1-one;
(5α,8α)-2-(2,2-Difluoro-benzo[1,3]dioxol-5-yl)-8-hydroxy-8-trifluoromethyl-2-aza-spiro[4.5]decan-1-one;
(5α,8α)-2-(2,2-Difluoro-benzo[1,3]dioxol-5-yl)-8-ethyl-8-hydroxy-2-aza-spiro[4.5]decan-1-one;
(5α,8α)-8-Acetyl-8-hydroxy-2-[4-(2,2,2-trifluoro-ethoxy)-phenyl]-2-aza-spiro[4.5]decan-1-one;
(5α,8α)-8-Hydroxy-8-(1-hydroxy-1-methyl-ethyl)-2-[4-(2,2,2-trifluoro-ethoxy)-phenyl]-2-aza-spiro[4.5]decan-1-one;
(5α,8α)-2-[4-(3,3-Difluoro-cyclobutyl)-phenyl]-8-hydroxy-8-trifluoromethyl-2-aza-spiro[4.5]decan-1-one;
(5α,8β)-2-[4-(3,3-Difluoro-cyclobutyl)-phenyl]-8-hydroxy-8-trifluoromethyl-2-aza-spiro[4.5]decan-1-one;
(5α,8α)-2-[4-(3,3-Difluoro-cyclobutyl)-phenyl]-8-hydroxy-8-methoxymethyl-2-aza-spiro[4.5]decan-1-one;
(5α,8α)-2-(4-tert-Butyl-phenyl)-8-hydroxy-8-propyl-2-aza-spiro[4.5]decan-1-one;
(5α,8α)-2-(4-tert-Butyl-phenyl)-8-hydroxy-8-isopropyl-2-aza-spiro[4.5]decan-1-one;
(5α,8α)-2-(4-tert-Butyl-phenyl)-8-hydroxy-8-trifluoromethyl-2-aza-spiro[4.5]decan-1-one;
(5α,8α)-2-(4-tert-Butyl-phenyl)-8-hydroxy-8-methoxymethyl-2-aza-spiro[4.5]decan-1-one;
(5α,8α)-2-(4-tert-Butyl-phenyl)-8-hydroxy-8-(2,2,2-trifluoro-ethoxymethyl)-2-aza-spiro[4.5]decan-1-one;
(5α,8α)-2-(4-tert-Butyl-phenyl)-8-ethoxymethyl-8-hydroxy-2-aza-spiro[4.5]decan-1-one;
(5α,8α)-2-(4-tert-Butyl-phenyl)-8-hydroxy-8-isopropoxymethyl-2-aza-spiro[4.5]decan-1-one;
(5α,8α)-2-(4-tert-Butyl-phenyl)-8-hydroxy-8-(2-oxo-pyrrolidin-1-ylmethyl)-2-aza-spiro[4.5]decan-1-one;
(5α,8α)-2-(4-tert-Butyl-phenyl)-8-hydroxy-8-(2-oxo-piperidin-1-ylmethyl)-2-aza-spiro[4.5]decan-1-one;
(5α,8α)-2-(4-tert-Butyl-phenyl)-8-hydroxy-8-(pyridin-2-yloxymethyl)-2-aza-spiro[4.5]decan-1-one;
(5α,8α)-2-(4-tert-Butyl-phenyl)-8-hydroxy-8-(2-oxo-2H-pyridin-1-ylmethyl)-2-aza-spiro[4.5]decan-1-one;
(5α,8α)-2-(4-tert-Butyl-phenyl)-8-hydroxy-8-(pyridin-3-yloxymethyl)-2-aza-spiro[4.5]decan-1-one;
(5α,8β)-2-(4-tert-Butyl-phenyl)-8-hydroxy-8-(1-hydroxy-2-methyl-propyl)-2-aza-spiro[4.5]decan-1-one;
(5α,8α))-2-(4-tert-Butyl-phenyl)-8-(1-hydroxy-2-methyl-propyl)-2-aza-spiro[4.5]decan-1-one;

(5α,8β)-2-(4-tert-Butyl-phenyl)-8-(1-hydroxy-ethyl)-2-aza-spiro[4.5]decan-1-one;
(5α,8α)-2-(4-tert-Butyl-phenyl)-8-(1-hydroxy-ethyl)-2-aza-spiro[4.5]decan-1-one;
(5α,8β)-2-(4-tert-Butyl-phenyl)-8-(1-hydroxy-propyl)-2-aza-spiro[4.5]decan-1-one;
(5α,8β)-2-(4-tert-Butyl-phenyl)-8-(2,2,2-trifluoro-1-hydroxy-ethyl)-2-aza-spiro[4.5]decan-1-one;
(5α,8α)-2-(4-tert-Butyl-phenyl)-8-(2,2,2-trifluoro-1-hydroxy-ethyl)-2-aza-spiro[4.5]decan-1-one;
2-(4-tert-Butyl-phenyl)-8-(2,2,2-trifluoro-1,1-dihydroxy-ethyl)-2-aza-spiro[4.5]decan-1-one;
(5α,8β)-2-(4-tert-Butyl-phenyl)-8-[hydroxy-(2H-pyrazol-3-yl)-methyl]-2-aza-spiro[4.5]decan-1-one;
(5α,8β)-2-(4-tert-Butyl-phenyl)-8-(2H-pyrazol-3-ylmethyl)-2-aza-spiro[4.5]decan-1-one;
(5α,8β)-8-(1-Hydroxy-propyl)-2-[4-((R)-2,2,2-trifluoro-1-methyl-ethoxy)-phenyl]-2-aza-spiro[4.5]decan-1-one;
(5α,8α)-8-(1-Hydroxy-propyl)-2-[4-((R)-2,2,2-trifluoro-1-methyl-ethoxy)-phenyl]-2-aza-spiro[4.5]decan-1-one;
(5α,8α)-8-Hydroxy-8-(2-oxo-pyrrolidin-1-ylmethyl)-2-[4-(2,2,2-trifluoro-ethoxy)-phenyl]-2-aza-spiro[4.5]decan-1-one;
(5α,8α)-8-Hydroxy-8-(2-oxo-piperidin-1-ylmethyl)-2-[4-(2,2,2-trifluoro-ethoxy)-phenyl]-2-aza-spiro[4.5]decan-1-one;
(5α,8α)-8-Hydroxy-8-(2-oxo-2H-pyridin-1-ylmethyl)-2-[4-(2,2,2-trifluoro-ethoxy)-phenyl]-2-aza-spiro[4.5]decan-1-one;
(5α,8β)-8-Hydroxy-8-(2-oxo-2H-pyridin-1-ylmethyl)-2-[4-(2,2,2-trifluoro-ethoxy)-phenyl]-2-aza-spiro[4.5]decan-1-one;
(5α,8α)-8-Hydroxy-8-(pyridin-2-yloxymethyl)-2-[4-(2,2,2-trifluoro-ethoxy)-phenyl]-2-aza-spiro[4.5]decan-1-one;
(5α,8α)-8-Hydroxy-8-(2,2,2-trifluoro-ethoxymethyl)-2-[4-((R)-2,2,2-trifluoro-1-methoxy-ethyl)-phenyl]-2-aza-spiro[4.5]decan-1-one;
(5α,8α)-2-[2-(4-Ethyl-phenyl)-ethyl]-8-hydroxy-8-methoxymethyl-2-aza-spiro[4.5]decan-1-one;
(5α,8α)-8-hydroxy-2-(4-isopropoxyphenyl)-8-(1H-1,2,3-triazol-4-yl)-2-azaspiro[4.5]decan-1-one; and
(5α,8α)-2-[2-(4-Ethyl-phenyl)-ethyl]-8-hydroxy-8-isopropoxymethyl-2-aza-spiro[4.5]decan-1-one.

Further preferred examples of compounds of formula (I) are selected from the group consisting of:
Propyl-carbamic acid [(5α,8β)-1-oxo-2-(4-trifluoromethoxy-phenyl)-2-aza-spiro[4.5]dec-8-yl]ester;
Methyl-carbamic acid [(5α,8β)-1-oxo-2-(4-trifluoromethoxy-phenyl)-2-aza-spiro[4.5]dec-8-yl]ester;
(5α,8β)-8-(Pyrimidin-2-yloxy)-2-(4-trifluoromethoxy-phenyl)-2-aza-spiro[4.5]decan-1-one;
(5α,8β)-8-(2-Methoxy-ethoxy)-2-(4-trifluoromethoxy-phenyl)-2-aza-spiro[4.5]decan-1-one;
(5α,8α)-8-Hydroxy-8-propyl-2-(4-trifluoromethoxy-phenyl)-2-aza-spiro[4.5]decan-1-one;
(5α,8α)-8-Hydroxy-8-methyl-2-(4-trifluoromethoxy-phenyl)-2-aza-spiro[4.5]decan-1-one;
(5α,8α)-8-Ethyl-8-hydroxy-2-(4-trifluoromethoxy-phenyl)-2-aza-spiro[4.5]decan-1-one;
(5α,8α)-8-Butyl-8-hydroxy-2-(4-trifluoromethoxy-phenyl)-2-aza-spiro[4.5]decan-1-one;
(5α,8α)-8-Hydroxy-8-isopropyl-2-(4-trifluoromethoxy-phenyl)-2-aza-spiro[4.5]decan-1-one;
(5α,8α)-8-Hydroxy-8-(3-methoxy-prop-1-ynyl)-2-(4-trifluoromethoxy-phenyl)-2-aza-spiro[4.5]decan-1-one;
(5α,8α)-2-(4-Cyclopropyl-phenyl)-8-hydroxy-8-propyl-2-aza-spiro[4.5]decan-1-one;
(5α,8α)-8-Hydroxy-8-methyl-2-[4-(2,2,2-trifluoro-ethyl)-phenyl]-2-aza-spiro[4.5]decan-1-one;
(5α,8α)-8-Ethyl-8-hydroxy-2-[4-(2,2,2-trifluoro-ethyl)-phenyl]-2-aza-spiro[4.5]decan-1-one;
(5α,8α)-8-Ethyl-8-hydroxy-2-[4-(2,2,2-trifluoro-ethoxy)-phenyl]-2-aza-spiro[4.5]decan-1-one; and
(5α,8α)-8-Hydroxy-8-(3-methoxy-propyl)-2-(4-trifluoromethoxy-phenyl)-2-aza-spiro[4.5]decan-1-one.

Also further preferred examples of compounds of formula (I) are selected from the group consisting of:
(5α,8α)-8-Hydroxy-8-isopropyl-2-[4-(2,2,2-trifluoro-ethoxy)-phenyl]-2-aza-spiro[4.5]decan-1-one;
(5α,8α)-8-hydroxy-8-isopropyl-2-(6-(2,2,2-trifluoroethoxy)pyridin-3-yl)-2-aza-spiro[4.5]decan-1-one;
(5α,8α)-8-hydroxy-8-isopropyl-2-(4-((R)-2,2,2-trifluoro-1-methoxyethyl)phenyl)-2-aza-spiro[4.5]decan-1-one;
(5α,8α)-8-Hydroxy-8-methoxymethyl-2-[4-((R)-2,2,2-trifluoro-1-methyl-ethoxy)-phenyl]-2-aza-spiro[4.5]decan-1-one;
(5α,8α)-8-Hydroxy-8-propyl-2-[4-((R)-2,2,2-trifluoro-1-methyl-ethoxy)-phenyl]-2-aza-spiro[4.5]decan-1-one;
(5α,8α)-8-Hydroxy-2-[6-(2,2,2-trifluoro-ethoxy)-pyridin-3-yl]-8-(3,3,3-trifluoro-propyl)-2-aza-spiro[4.5]decan-1-one;
(5α,8α)-8-Hydroxy-8-trifluoromethyl-2-[4-((R)-2,2,2-trifluoro-1-methyl-ethoxy)-phenyl]-2-aza-spiro[4.5]decan-1-one;
(5α,8α)-8-hydroxy-2-(4-isopropoxyphenyl)-8-(1-methyl-1H-pyrazol-3-yl)-2-aza-spiro[4.5]decan-1-one;
(5α,8α)-8-(2,2-Difluoro-ethoxymethyl)-8-hydroxy-2-[4-(2,2,2-trifluoro-ethoxy)-phenyl]-2-aza-spiro[4.5]decan-1-one;
(5α,8α)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one;
(5α,8α)-8-Hydroxy-8-(2-methyl-propane-2-sulfonylmethyl)-2-[6-((R)-2,2,2-trifluoro-1-methyl-ethoxy)-pyridin-3-yl]-2-aza-spiro[4.5]decan-1-one;
(5α,8α)-2-(4-tert-Butyl-phenyl)-8-hydroxy-8-(2-oxo-2H-pyridin-1-ylmethyl)-2-aza-spiro[4.5]decan-1-one;
(5α,8β)-2-(4-tert-Butyl-phenyl)-8-(2H-pyrazol-3-ylmethyl)-2-aza-spiro[4.5]decan-1-one;
(5α,8β)-8-(1-Hydroxy-propyl)-2-[4-((R)-2,2,2-trifluoro-1-methyl-ethoxy)-phenyl]-2-aza-spiro[4.5]decan-1-one; and
(5α,8α)-8-Hydroxy-8-(2-oxo-pyrrolidin-1-ylmethyl)-2-[4-(2,2,2-trifluoro-ethoxy)-phenyl]-2-aza-spiro[4.5]decan-1-one.

Processes for the manufacture of compounds of formula (I) are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein. A relative configuration [5α,8α] on the 2-aza-spiro[4.5]decan-1-one backbone corresponds to cis configuration on the cyclohexane ring, whereas a relative configuration [5α,8β] corresponds to a trans configuration on the cyclohexane ring of compounds according to formula (I) as described above.

Scheme 1 describes the synthesis of intermediates used in reactions described therein.

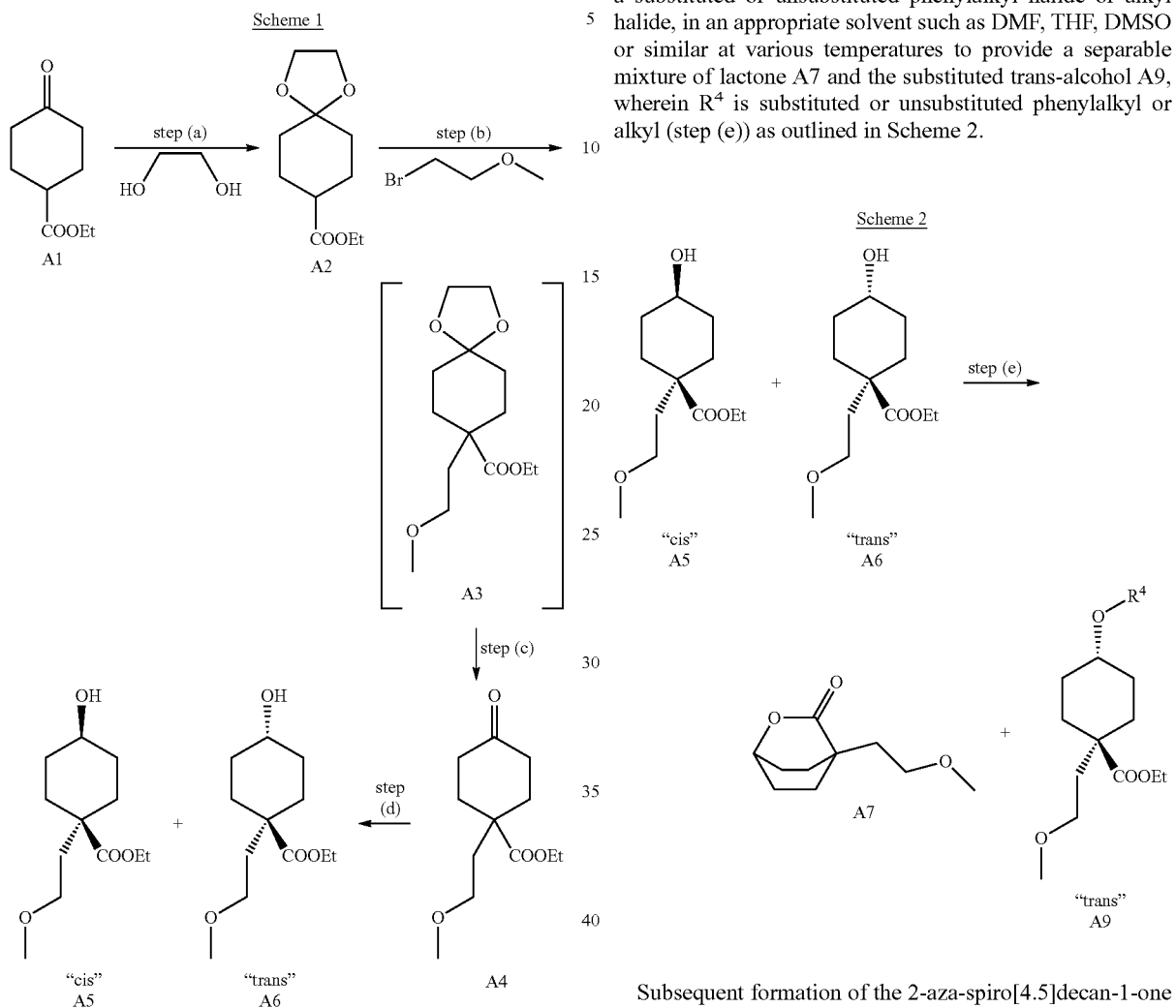

Commercially available ketone A1 can be protected for example as a ketal (step (a)) to give the compound A2 according to methods known in the literature. Ketal A2 is then alkylated at the appropriate position by treatment with a suitable base such as lithium diisopropylamide, lithium or sodium hexamethyldisilazane, potassium tert-butylate or the like in an appropriate solvent such as THF, DMF, diethylether or the like followed by addition of the appropriate electrophile such as 1-bromo-2-methoxyethane to give compound A3 (step (b)). A3 can be isolated if desired or the ketal group can be removed (step (c)) during the workup of reaction step (b). Treatment of crude A3 with a strong aqueous mineral acid such as HCl, $H_2SO_4$, HBr or the like at various temperatures ranging from −15° C. to 100° C. until hydrolysis of the ketal protecting group is completed (step (c)) gives compound A4.

From compound A4, mixtures of cis and trans alcohols A5 and A6, respectively, can be prepared via reduction of the carbonyl group (step (d)) with various reducing agents such as for example $NaBH_4$, $LiBH_4$, SMEAH, L-selectride or similar in an appropriate solvent such as MeOH, EtOH, THF, diethylether and the like and at various temperatures ranging from −78° C. to 100° C.

The mixture of alcohols A5 and A6 can be treated with a base such as sodium hydride, sodium hydroxide, potassium tert-butoxide or the like followed by an alkylating agent, e.g. a substituted or unsubstituted phenylalkyl halide or alkyl halide, in an appropriate solvent such as DMF, THF, DMSO or similar at various temperatures to provide a separable mixture of lactone A7 and the substituted trans-alcohol A9, wherein $R^4$ is substituted or unsubstituted phenylalkyl or alkyl (step (e)) as outlined in Scheme 2.

Subsequent formation of the 2-aza-spiro[4.5]decan-1-one backbone can be achieved as outlined in Scheme 3, step (f) by treatment of either A6, A7 or A9 with an appropriate compound of formula $R^1$—$NH_2$ and an appropriate organometallic reagent such as $(CH_3)_2AlCl$ or $Al(CH_3)_3$, in an appropriate solvent such as toluene, benzene, chloroform, dioxane or the like at a suitable temperature ranging from 0 to 150° C. to provide either compounds of formula A8 or A10, wherein $R^4$ is hydrogen, substituted or unsubstituted phenylalkyl or alkyl as outlined in Scheme 3.

In addition, A5 and A6 can be employed as a mixture (e.g. 1:1) in step (f), giving rise to a mixture of A8 and A10, accordingly.

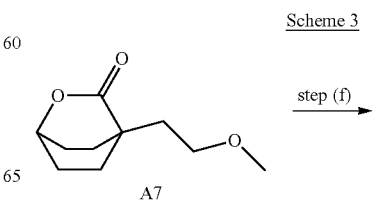

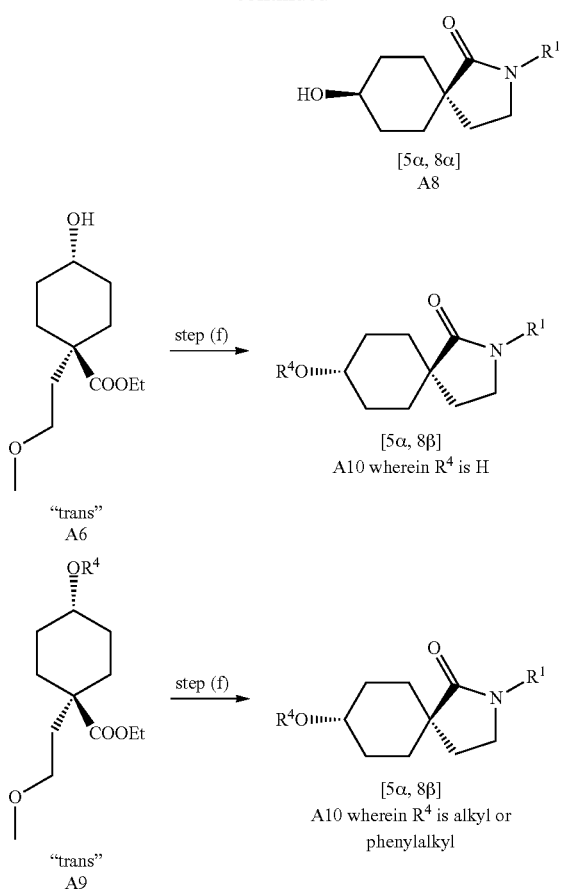

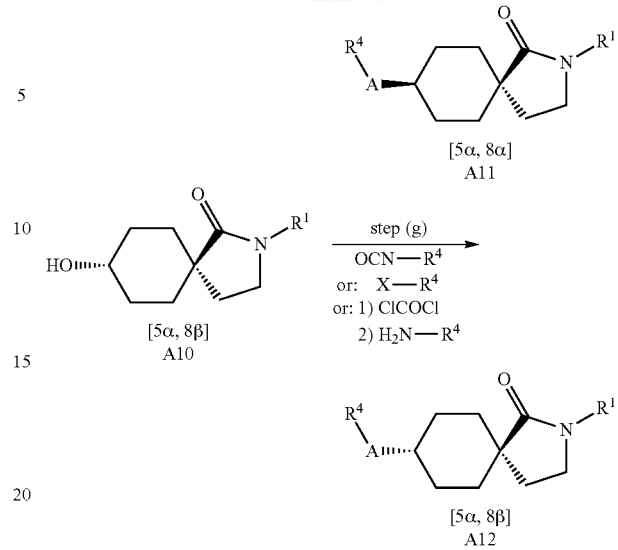

Scheme 4 outlines the functionalization of free spirocyclic alcohols A8 and A10, respectively. Both A8 or A10 can be treated with a suitable base such as sodium hydride, potassium tert-butoxide, sodium hydroxide, silver oxide or the like in an appropriate solvent such as DMF, THF, methanol, DMSO or the like at various temperatures followed by a suitable acylating agent (e.g. of formula $R^4$—NCO), alkylating or arylating agent of formula $R^4$—X to give A11 or A12, wherein A is —O— or —$NR^6C(O)O$—. As an alternative, acylation of either A8 or A10 can be achieved in a 2 step process by treatment with a phosgene derivative such as diphosgene or triphosgene followed by an appropriate amine $R^4$—$NH_2$ in a suitable solvent at various temperatures.

In addition, it is also possible to perform above transformations on a mixture of A8 and A10 (e.g., 1:1) and separate the products A11 and A12 for example by chromatographic methods.

Yet another way for functionalization of both alcohols A8 and A10 is outlined in Scheme 5. Oxidation of either A8 or A10 (step (h)) with various oxidizing agents such as oxalyl chloride/DMSO/amine base, TEMPO/NaOCl$_2$, TPAP/NMO, Jones reagent or many more under the appropriate conditions and temperatures will provide ketone A13. Intermediate A13 will allow addition of carbon nucleophiles to the carbonyl group (step (i)). Suitable carbon nucleophiles are, for example, Grignard reagents of formula $R^2MgX$, lithium alkyl or aryl derivatives of formula $R^2Li$, zinc reagents or metallated alkynides. The reactions are carried out in appropriate solvents under the proper conditions which are dependent on the nucleophilic reagent to be used for reaction step (i) and are known to the man skilled in the art. The [5α,8α] isomer A14 and the [5α,8β] isomer A15 can be separated by methods known to the man skilled in the art such as chromatography, chiral chromatography or crystallization.

Similarly, mixtures of A8 and A10 (e.g. 1:1), can be used to prepare intermediate A13 as described above.

Scheme 5

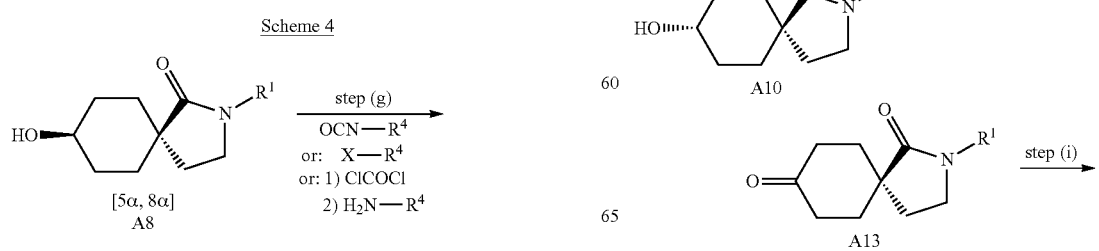

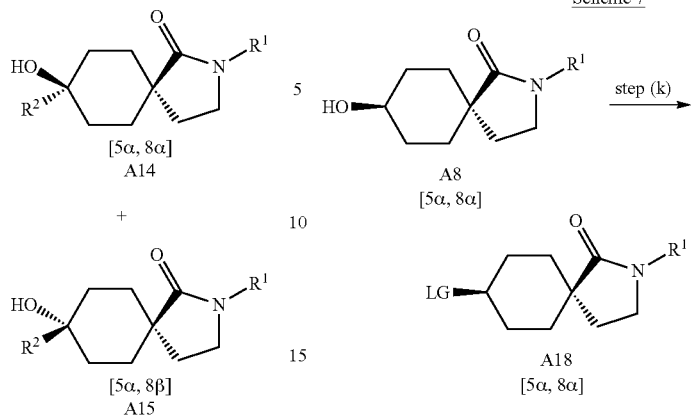

Free alcohol A14 and A15 can be functionalized as outlined in Scheme 6 according to methods described above to give compounds of formula A16 and A17, wherein A is —O— or —NR$^6$C(O)O—.

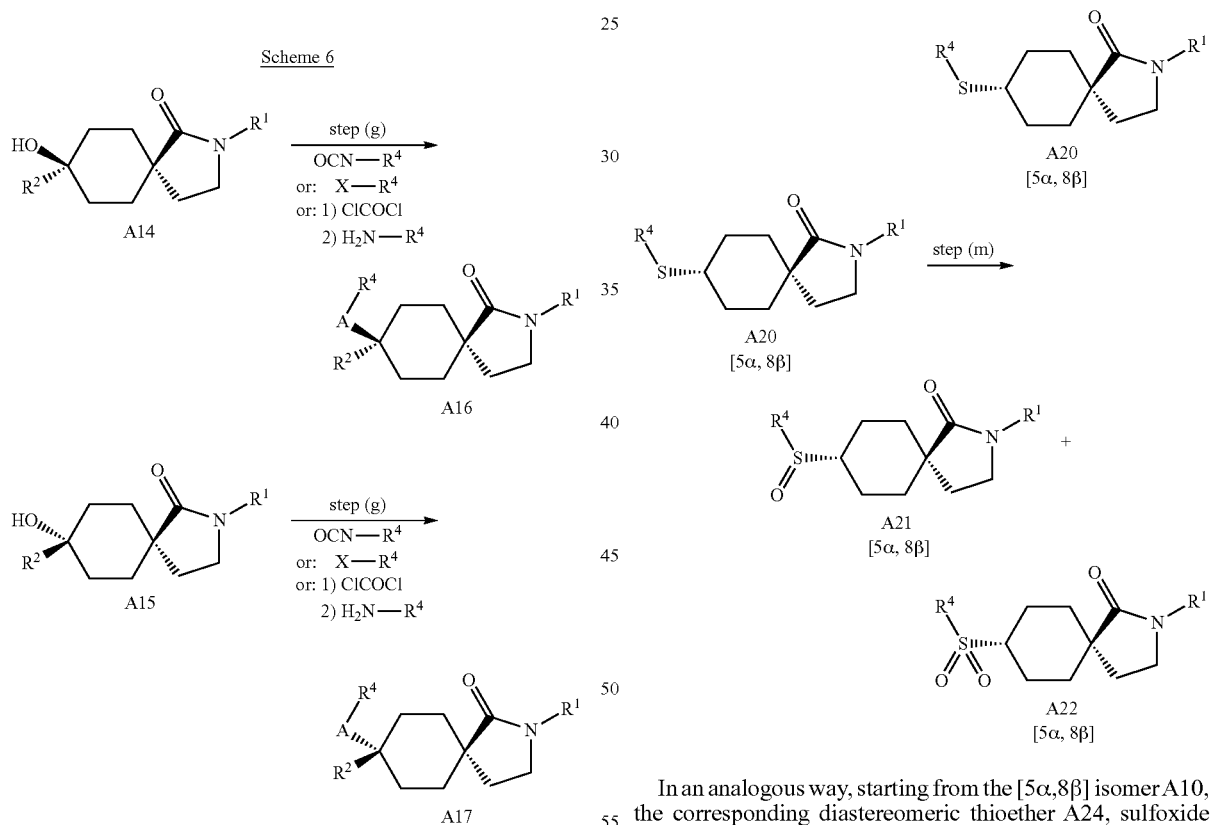

Another way for functionalization of alcohols A8 or A10 is outlined in Scheme 7. The hydroxy group of A8 or A10 can be converted to a leaving group for example by conversion to e.g. mesylate, tosylate or halogen (step (k)). The leaving group of A18 can be exchanged for example with a thiolate by nucleophilic substitution (step (l)) to give a thioether A20. Compound A19 can also be isolated from such a reaction, either as a side product or as the main product. Subsequent oxidation of a thioether A20 with various reagents such as mCPBA, H$_2$O$_2$ or others will provide sulfoxides A21 or sulfones A22.

In an analogous way, starting from the [5α,8β] isomer A10, the corresponding diastereomeric thioether A24, sulfoxide A25 and sulfone A26 with a [5α,8α] configuration can be prepared as outlined in Scheme 8.

Scheme 8

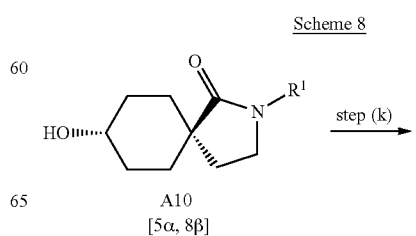

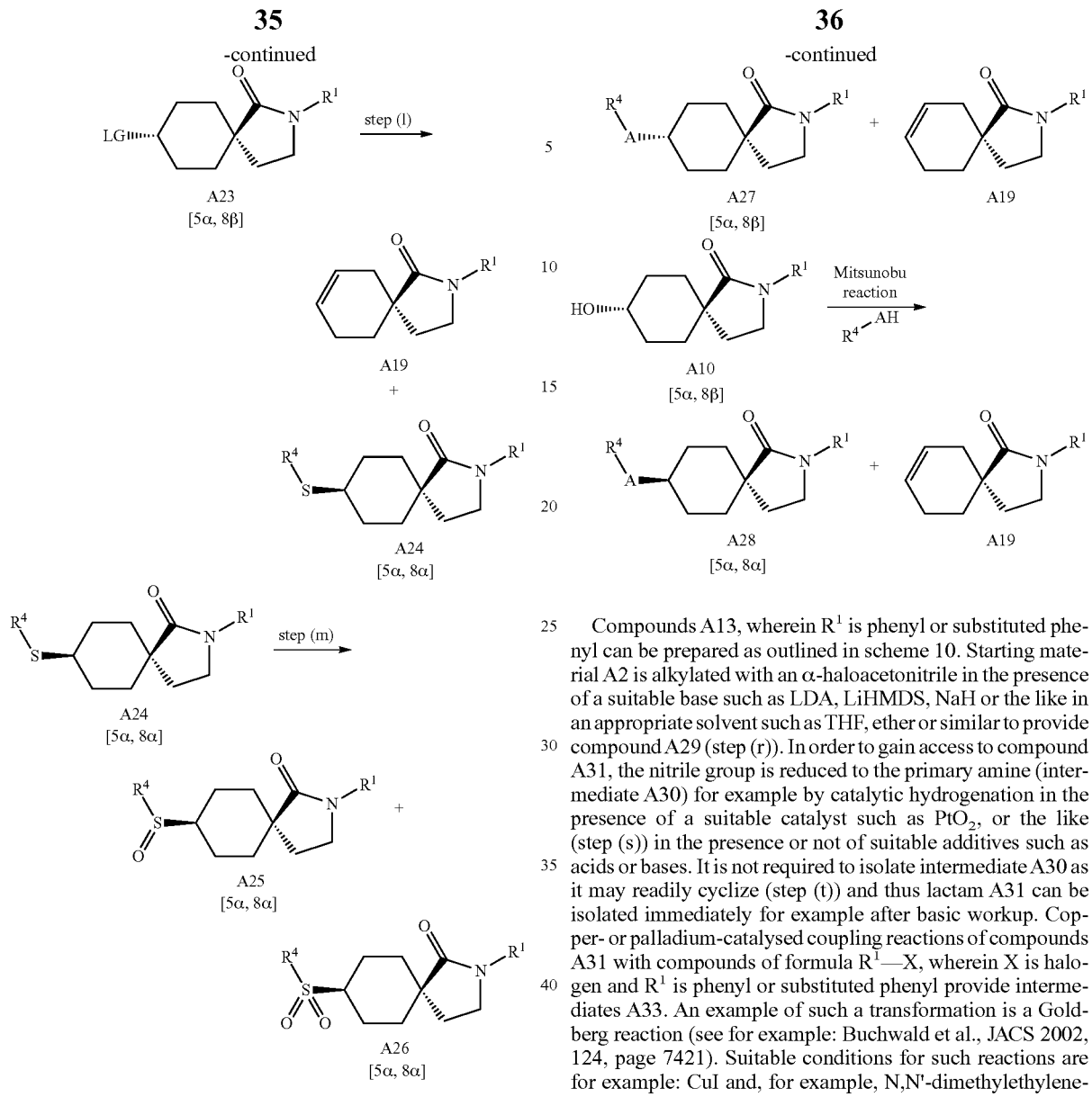

An alternative way of functionalization is the use of the Mitsunobu reaction which will convert for example alcohol A8 into compound A27, wherein A is —O— or —S— according to method known by the man skilled in the art or described in the literature as outlined in Scheme 9. Again, elimination product A19 may be isolated from such a reaction. In an exactly analogous way, A10 can be converted to compound A28, wherein A is —O— or —S— with a [5α,8α] configuration at the spirocyclic 2-aza-spiro[4.5]decan-1-one backbone as outlined in Scheme 9.

Compounds A13, wherein $R^1$ is phenyl or substituted phenyl can be prepared as outlined in scheme 10. Starting material A2 is alkylated with an α-haloacetonitrile in the presence of a suitable base such as LDA, LiHMDS, NaH or the like in an appropriate solvent such as THF, ether or similar to provide compound A29 (step (r)). In order to gain access to compound A31, the nitrile group is reduced to the primary amine (intermediate A30) for example by catalytic hydrogenation in the presence of a suitable catalyst such as $PtO_2$, or the like (step (s)) in the presence or not of suitable additives such as acids or bases. It is not required to isolate intermediate A30 as it may readily cyclize (step (t)) and thus lactam A31 can be isolated immediately for example after basic workup. Copper- or palladium-catalysed coupling reactions of compounds A31 with compounds of formula $R^1$—X, wherein X is halogen and $R^1$ is phenyl or substituted phenyl provide intermediates A33. An example of such a transformation is a Goldberg reaction (see for example: Buchwald et al., JACS 2002, 124, page 7421). Suitable conditions for such reactions are for example: CuI and, for example, N,N'-dimethylethylenediamine as ligand and $K_3PO_4$ as base in a solvent such as DMF or palladium(II) acetate as catalyst and, for example, bis(diphenylphosphino)-ferrocene (DPPF) as ligand, sodium tert-butoxide as a base in a solvent such as toluene. Subsequently, intermediate A33 can be converted to compounds A13, wherein $R^1$ is phenyl or substituted phenyl by acidic hydrolysis; for example by treatment with an aqueous mineral acid such as HCl, $H_2SO_4$ or the like (step (v)).

Scheme 9

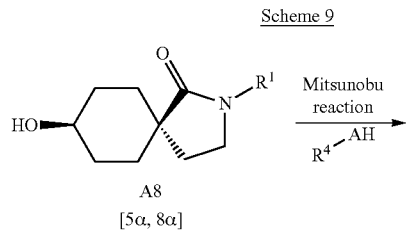

Scheme 10

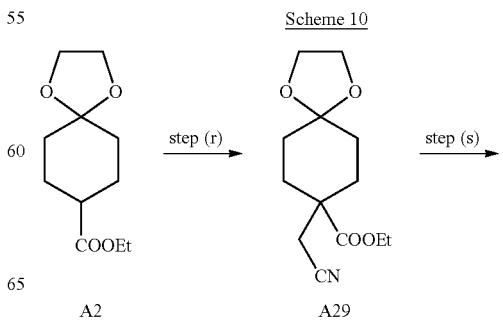

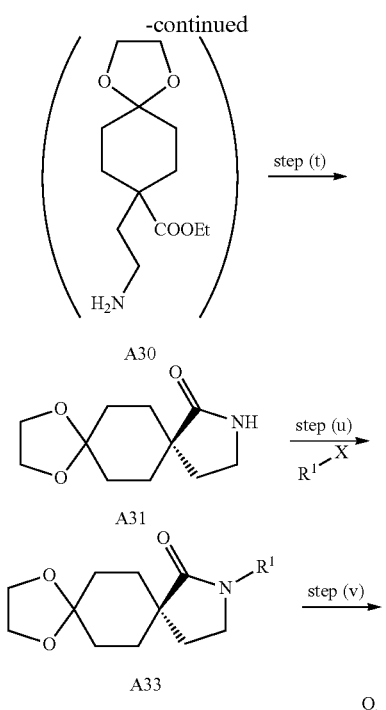

suitable carboxylic acid activation agents such as SOCl, PCl$_3$, carbonyldiimidazole, acetyl chloride, oxalyl chloride or the like as well as many other different reagents commonly used for peptide synthesis such as BOP, EDC, PyBOP or TBTU.

Compounds of formula (I), wherein A is O, R$^4$ is hydrogen and R$^2$ is carboxyalkyl or alkoxycarbonylalkyl can be reduced to compounds of formula (I), wherein A is O, R$^4$ is hydrogen and R$^2$ is hydroxyalkyl using suitable reducing agents such as DIBAL, NaBH$_4$, LiBH$_4$ or other agents (e.g. borane for carboxylic acids) in the appropriate solvents. Many different conditions for these transformations are described in the literature and are known to those skilled in the art. Subsequently, such primary alcohols can be further modified for example by alkylation with suitable alkyl halides such as alkyl chlorides, bromides or iodides in the presence of a suitable base such as NaH, Cs$_2$CO$_3$, Ag$_2$O, K$_2$CO$_3$ or the like to provide compounds of formula (I), wherein A is O, R$^4$ is hydrogen and R$^2$ is alkoxyalkyl.

Another way of functionalizing compounds A13 is via an epoxide intermediate A33 (Scheme 11). Such epoxides can be made directly from compounds A13 for example by treatment with trimethylsulfoxonium iodide or a related reagent in the presence of a base such as KOtBu, NaH or the like in a suitable solvent such as DMSO (step (w)).

Scheme 11

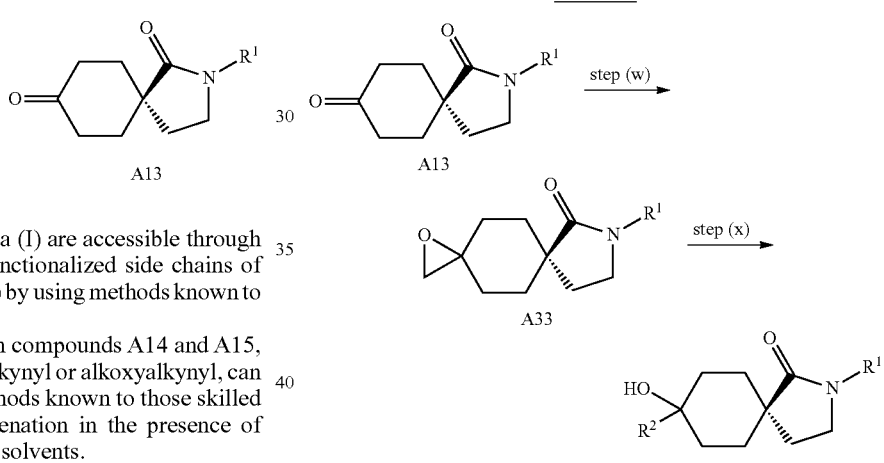

Compounds of general formula (I) are accessible through modification of appropriately functionalized side chains of compounds of general formula (I) by using methods known to the man skilled in the art.

For example, the triple bond in compounds A14 and A15, wherein R$^2$ is alkynyl, hydroxyalkynyl or alkoxyalkynyl, can be reduced using reductions methods known to those skilled in the art, for example, hydrogenation in the presence of various catalysts (e.g. Pd/C) and solvents.

Compounds A14 and A15, wherein R$^2$ is alkoxycarbonylalkyl, can be hydrolyzed to compounds of formula (I), wherein A is O, R$^4$ is hydrogen and R$^2$ is carboxyalkyl. Such compounds can be then used for the preparation of compounds of formula (I), wherein A is O, R$^4$ is hydrogen and R$^2$ is alkylaminocarbonylalkyl or dialkylaminocarbonylalkyl using methods known to those skilled in the art and like e.g. the treatment of the carboxylic acid with a vast variety of Compounds A33 are then readily reacted with suitable nucleophilic reagents, e.g alcoholate, thiolate or cuprates (step (x)) to provide compound of formula (I) using methods and conditions known to those skilled in the art.

An alternative route to compound A33 requires to carry out the sequence of steps (y), (z), (aa) and (ab) as disclosed in scheme 12:

Scheme 12

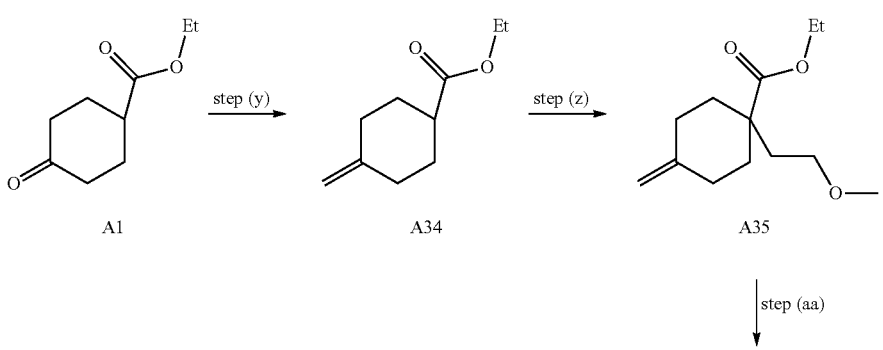

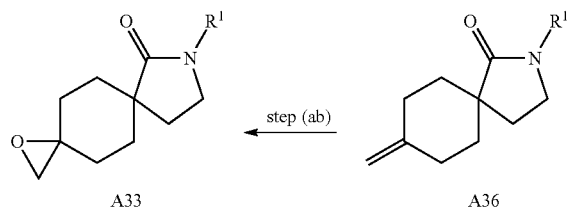

A33     step (ab)     A36

Step (y): Cyclohexane derivatives A1 are commercially available and can be transformed to A34 for example by a Wittig or Tebbe reaction.

Step (z): The methylene derivatives A34 can be deprotonated by suitable bases like LDA, HMDS and the like and reacted with 2-bromoethyl methyl ether to access the alkylated cyclohexane derivatives A35.

Step (aa): Cyclohexane derivatives A35 can be cyclized with adequate compounds of formula $R^1$—$NH_2$ as outlined previously in Scheme 3 in the presence of a metalorganic reagent such as $AlMe_2Cl$ and the like to afford the corresponding spirocycle A36 with the exo-methylene group.

Step (ab): Spirocycle A36 can be epoxidized for example with m-chloroperbenzoic acid to provide access to an epoxide A33.

Yet another set of possible modifications is shown in Scheme 13 below. Ketone intermediate A13 can be homologated to aldehyde A38 in a two step process: applying an alkenation methodology to intermediate A13 provides an enol ether A37 (step (af)), which can subsequently be converted to the corresponding aldehyde A38 (step (ag)). Step (af) requires ketone A13 to be treated with a suitable Wittig reagent such as (methoxymethyl)triphenyl phosphonium chloride in the presence of a suitable base such as potassium tert-butoxide in an appropriate solvent such as THF, ether or the like. Subsequently in step (ag), intermediate A37 can be deprotected under acidic conditions, such as aqueous 2N HCl solution or aqueous solutions of other mineral acids, to provide the corresponding aldehyde intermediate A38.

Intermediate A38 allows addition of various carbon nucleophiles (Nu) to the carbonyl group of the aldehyde (step (ah)) to provide compounds of formula (I). Suitable carbon nucleophiles are, for example, Grignard reagents, lithium derivatives, zinc reagents or metallated alkynides. The reactions are carried out in the appropriate solvents under the proper conditions which are dependent on the nucleophilic reagent to be used in the reaction step and which are known to those skilled in the art. The isomers formed during the reaction can be separated by methods known to those skilled in the art such as chromatography, chiral chromatography or crystallization.

Scheme 13

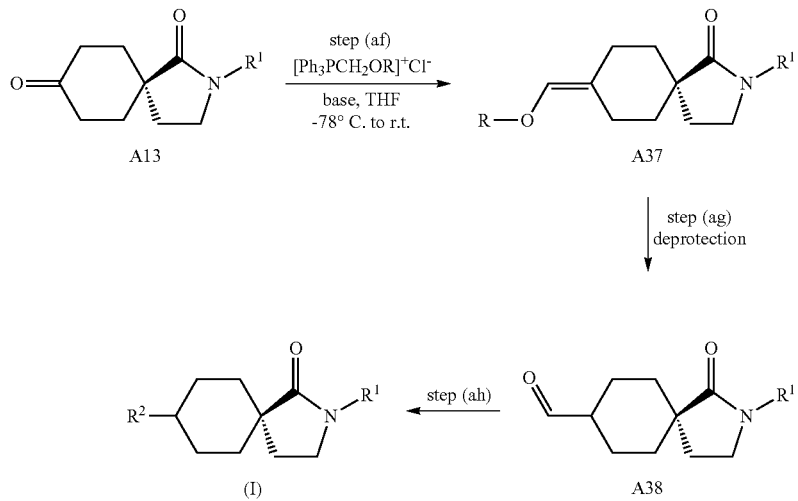

R is a protecting group, e.g. a methoxymethyl group (MOM)

$R^2 =$ 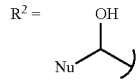

Compounds of formula (I), wherein $R^2$ is for example hydroxyalkyl or hydroxyhaloalkyl (A39 and/or A40, either in pure form or as a mixture), can be further converted into the corresponding deoxygenated analogues A41 and A42, respectively, for example via xanthate intermediates prepared is situ, by applying the well known Barton-McCombie procedure (step (ai)) (see for example W. Hartwig, Tetrahedron, 1983, 39, 2609) as exemplified in Scheme 14.

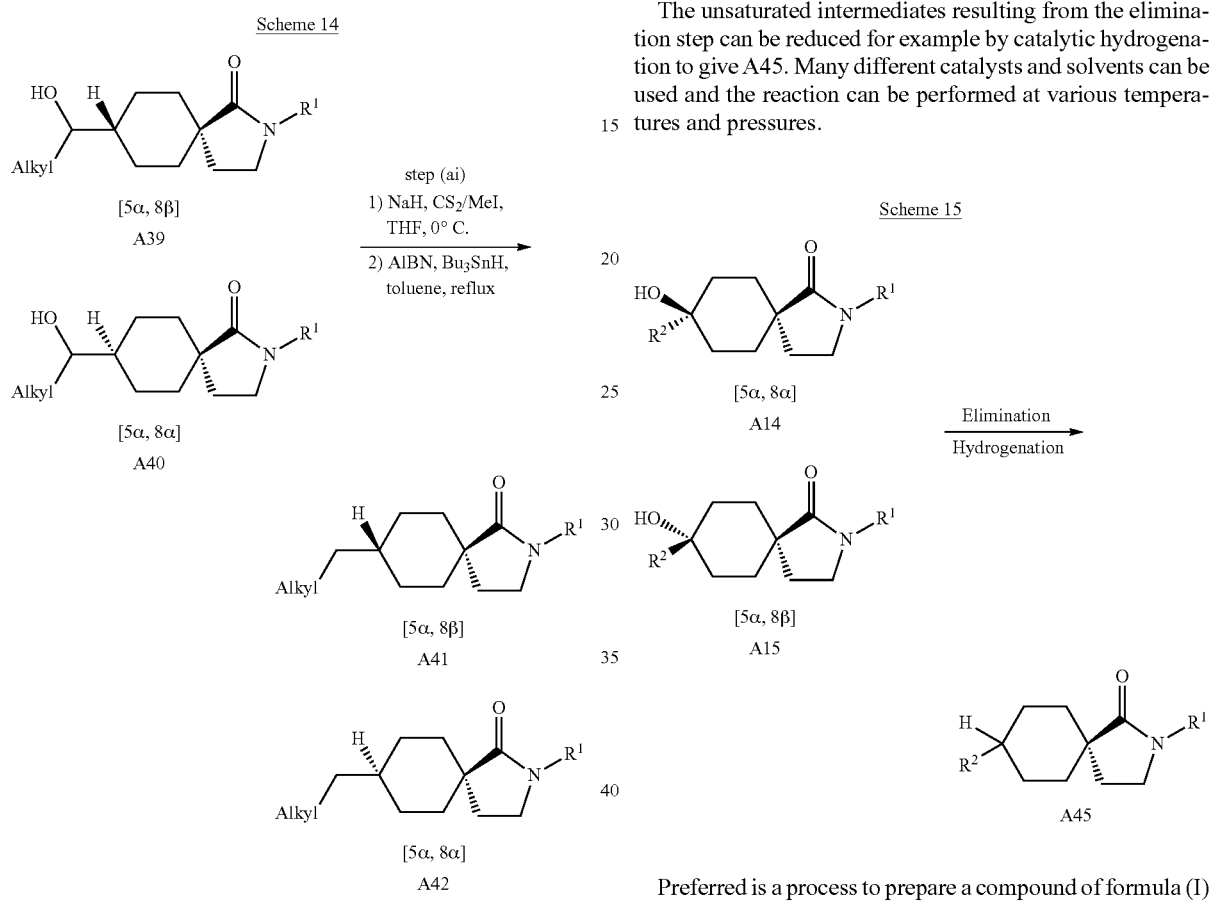

Compounds of formula (I), wherein A is a single bond and $R^4$ is hydrogen can be prepared in a similar way as described above. Both the [5α,8α] and [5α,8β] isomers (A14 and A15, respectively) can serve as a starting material in this transformation, either in pure form or as a mixture. Deoxygenation of A14 and/or A15 to obtain compound A45 can be achieved for example with a Barton-Mc Combie process as shown above in Scheme 14 or alternatively, for example when $R^2$ is e.g. phenyl, by reduction with a silane such as triethylsilane or the like in the presence of a Lewis acid such as $BF_3OEt_2$ or similar or a suitable organic acid such as trifluoroacetic acid or similar. Appropriate solvents have to be chosen which are dependent on the procedure to be used.

Alternatively, it is possible to use an elimination/hydrogenation process to obtain a compound of the structure A45 starting from compounds of formula (I), wherein A is O and $R^4$ is H, as exemplified in Scheme 15. The tertiary hydroxy group present in A14 and A15 can be eliminated under many different conditions. An example is treatment with a strong mineral acid such as HCl, HBr, $H_3PO_4$, $HClO_4$ or the like or with strong organic acids such as p-toluenesulfonic acid or trifluoroacetic acid and similar. Heating may be required and the process may or may not involve intermediates such as halides, depending on the acid or reagents that are being used. Alternatively, it is possible to achieve elimination by converting the tertiary hydroxy group of A14 and A15 into a distinct leaving group (for example an acetate, mesylate or others), followed by treatment with a base such as pyridine, DMAP, DBU, triethylamine and many others. Other conditions and reagents that may be used to achieve this transformation are described in the literature or known to those skilled in the art.

The unsaturated intermediates resulting from the elimination step can be reduced for example by catalytic hydrogenation to give A45. Many different catalysts and solvents can be used and the reaction can be performed at various temperatures and pressures.

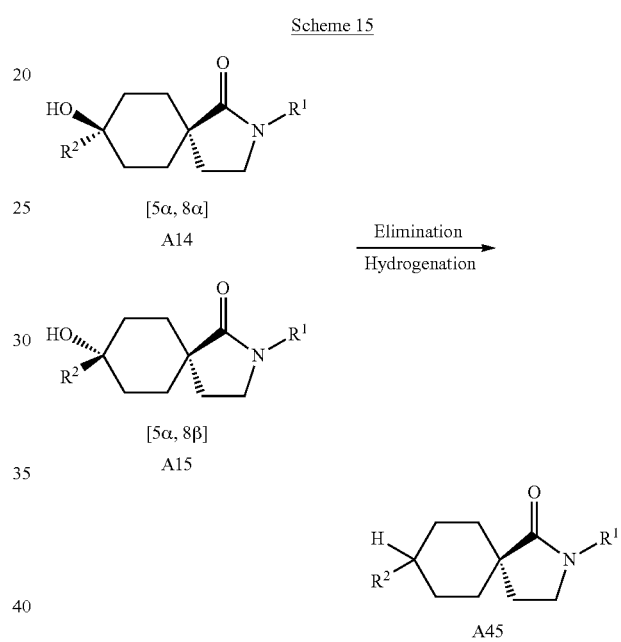

Preferred is a process to prepare a compound of formula (I) as defined above

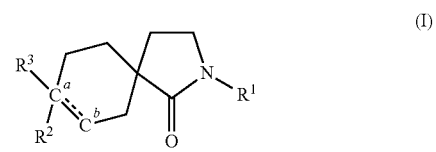

comprising a) reaction of a compound of formula (II) in the presence of a compound of formula (VI);

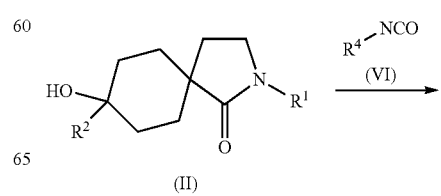

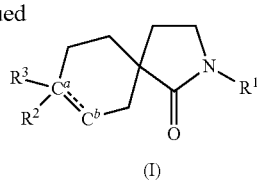

(I)

Preferably in the presence of a base, particularly triethylamine, in a solvent, particularly toluene, and at a temperature between RT and reflux of the solvent, particularly between 60° C. and reflux of the solvent, wherein $R^1$, $R^2$ and $R^4$ are as defined before, $R^3$ is $R^4$-A-, A is —$NR^6C(O)O$—, $R^6$ is hydrogen and the bond between carbon $C^a$ and carbon $C^b$ is a carbon-carbon single bond;

b) reaction of a compound of formula (III) in the presence of a compound of formula (VII);

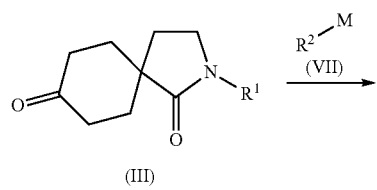

(I)

Preferably in a solvent, particularly diethyl ether, and at a temperature between −78° C. and reflux of the solvent, particularly between −10° C. and reflux of the solvent, wherein $R^1$ is as defined before, $R^3$ is $R^4$-A-, A is —O—, $R^4$ is hydrogen, $R^2$ is defined as before with the proviso that $R^2$ is not hydrogen and the bond between carbon $C^a$ and carbon $C^b$ is a carbon-carbon single bond, M is Li or MgX and X is halogen, particularly bromine or chlorine;

c) reaction of a compound of formula (II) in the presence of a compound of formula (VIII);

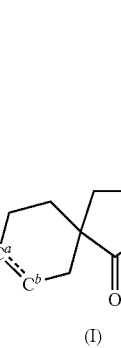

(I)

Preferably in the presence of a base, particularly sodium hydride, in a solvent, particularly DMF or THF, and at a temperature between −20° C. and reflux of the solvent, particularly between −10° C. and 70° C., wherein $R^1$ and $R^2$ are as defined before, $R^3$ is $R^4$-A-, A is —O—, $R^4$ is defined as before with the proviso that $R^4$ is not hydrogen and the bond between carbon $C^a$ and carbon $C^b$ is a carbon-carbon single bond and X is halogen, particularly bromine or chlorine;

d) reaction of a compound of formula (IV) in the presence of a compound of formula (IX);

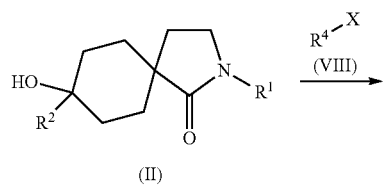

(I)

Preferably in the presence of a Lewis acid, particularly dimethylaluminium chloride, in a solvent, particularly toluene, and at a temperature between −10° C. and reflux of the solvent, particularly at reflux of the solvent, wherein $R^1$ and $R^4$ are as defined before, $R^3$ is $R^4$-A-, A is —O—, $R^2$ is hydrogen and the bond between carbon $C^a$ and carbon $C^b$ is a carbon-carbon single bond;

e) reaction of a compound of formula (V) in the presence of a compound of formula (IX);

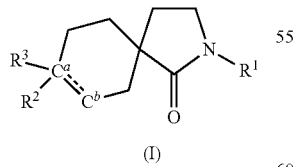

(I)

Preferably in the presence of a Lewis acid, particularly dimethylaluminium chloride, in a solvent, particularly toluene, and at a temperature between −10° C. and reflux of the solvent, particularly at reflux of the solvent, wherein $R^1$ is as defined before, $R^3$ is $R^4$-A-, A is —O—, $R^4$ is hydrogen, $R^2$ is hydrogen and the bond between carbon $C^a$ and carbon $C^b$ is a carbon-carbon single bond;

or f) reaction of a compound of formula (II) in the presence of a compound of formula (X);

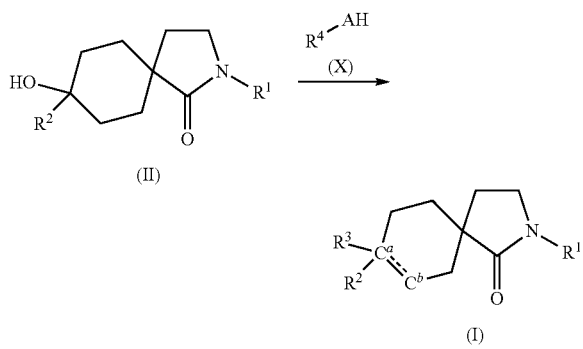

Preferably in the presence of triphenylphosphine and an azodicarboxylate compounds, particularly diethyl azodicarboxylate, in a solvent, particularly THF, and at a temperature between −10° C. and reflux of the solvent, particularly at reflux of the solvent, wherein $R^1$ is as defined before, $R^2$ is hydrogen, $R^3$ is $R^4$-A-, A is —O— or —S—, $R^4$ is defined as before with the proviso that $R^4$ is not hydrogen and the bond between carbon $C^a$ and carbon $C^b$ is a carbon-carbon single bond.

Preferred intermediates are selected from 1-(2-Methoxy-ethyl)-4-oxo-cyclohexanecarboxylic acid ethyl ester;

trans-4-Hydroxy-1-(2-methoxy-ethyl)-cyclohexanecarboxylic acid ethyl ester;

4-Hydroxy-1-(2-methoxy-ethyl)-cyclohexanecarboxylic acid ethyl ester;

4-(2-Methoxy-ethyl)-2-oxa-bicyclo[2.2.2]octan-3-one;

trans-4-Benzyloxy-1-(2-methoxy-ethyl)-cyclohexanecarboxylic acid ethyl ester;

[(5α,8β)-1-Oxo-2-(4-(trifluoromethoxy)phenyl)-2-azaspiro[4.5]decan-8-yl]carbonochloridate;

cis-Ethyl 1-(2-methoxyethyl)-4-phenoxycyclohexanecarboxylate;

trans-Ethyl 1-(2-methoxyethyl)-4-phenoxycyclohexanecarboxylate;

Methanesulfonic acid [(5α,8β)-1-oxo-2-(4-trifluoromethoxy-phenyl)-2-aza-spiro[4.5]dec-8-yl]ester;

(5α,8β)-8-Phenylsulfanyl-2-(4-trifluoromethoxy-phenyl)-2-aza-spiro[4.5]decan-1-one;

4-(2-Methoxy-ethyl)-1-methyl-2-oxa-bicyclo[2.2.2]octan-3-one;

(5α,8β)-2-(4-Cyclopropyl-phenyl)-8-hydroxy-2-aza-spiro[4.5]decan-1-one;

2-(4-Cyclopropyl-phenyl)-2-aza-spiro[4.5]decane-1,8-dione;

(5α,8β)-8-Hydroxy-2-[4-(2,2,2-trifluoro-ethyl)-phenyl]-2-aza-spiro[4.5]decan-1-one;

2-[4-(2,2,2-Trifluoro-ethyl)-phenyl]-2-aza-spiro[4.5]decane-1,8-dione;

2-(4-Propyl-phenyl)-2-aza-spiro[4.5]decane-1,8-dione; and

2-[4-(2,2,2-Trifluoro-ethoxy)-phenyl]-2-aza-spiro[4.5]decane-1,8-dione. A further object of the invention are compounds according to formula (I) as described above for use as therapeutically active substance.

Likewise an object of the present invention are pharmaceutical compositions comprising a compound according to formula (I) as described above, or a pharmaceutically acceptable salt thereof. and a therapeutically inert carrier.

Also an object of the present invention are compounds according to formula (I) as described above, or pharmaceutically acceptable salts thereof. for the preparation of a medicament for the treatment or prophylaxis of illnesses which are caused by disorders associated e.g. with the enzyme hormone-sensitive lipase.

Further preferred are compounds according to formula (I) as described above, or pharmaceutically acceptable salts thereof. for the preparation of a medicament for the treatment or prophylaxis of diabetes, metabolic syndrome, dyslipidemia, atherosclerosis or obesity.

Also further preferred are compounds according to formula (I) as described above, or pharmaceutically acceptable salts thereof. for the preparation of a medicament for the treatment or prophylaxis of cardiovascular diseases, myocardial dysfunction or inflammation.

Particularly preferred are compounds according to formula (I) as described above, or pharmaceutically acceptable salts thereof. for the preparation of medicaments for the treatment or prophylaxis of diabetes.

Moreover preferred are compounds according to formula (I) as described above, or pharmaceutically acceptable salts thereof. for the preparation of medicaments for the treatment or prophylaxis of diabetes Type II.

A further preferred embodiment of the present invention is the use of a compound according to formula (I) as described above, or a pharmaceutically acceptable salt thereof, for the preparation of a medicament for the treatment or prophylaxis of diabetes, metabolic syndrome, dyslipidemia, atherosclerosis or obesity.

Also a further preferred embodiment of the present invention is the use of a compound according to formula (I) as described above, or a pharmaceutically acceptable salt thereof. for the preparation of a medicament for the treatment or prophylaxis of cardiovascular diseases, myocardial dysfunction or inflammation.

Particularly preferred is the use of a compound according to formula (I) as described above, or a pharmaceutically acceptable salt thereof. for the preparation of medicaments for the treatment or prophylaxis of diabetes.

Moreover preferred is the use of a compound according to formula (I) as described above, or a pharmaceutically acceptable salt thereof. for the preparation of medicaments for the treatment or prophylaxis of diabetes Type II.

A further object of the present invention comprises a compound according to formula (I) as described above, or a pharmaceutically acceptable salt thereof. when manufactured according to any one of the described processes.

Also an object of the invention is a method for the treatment or prophylaxis of diabetes, metabolic syndrome, dyslipidemia, atherosclerosis or obesity, which method comprises administering an effective amount of a compound according to formula (I) as described above, or a pharmaceutically acceptable salt thereof.

Also preferred is a method for the treatment or prophylaxis of cardiovascular diseases, myocardial dysfunction or inflammation, which method comprises administering an effective amount of a compound according to formula (I) as described above, or a pharmaceutically acceptable salt thereof.

Particularly preferred is a method for the treatment or prophylaxis of diabetes, which method comprises administering an effective amount of a compound according to formula (I) as described above, or a pharmaceutically acceptable salt thereof.

Moreover preferred is a method for the treatment or prophylaxis of diabetes Type II, which method comprises administering an effective amount of a compound according to formula (I) as described above, or a pharmaceutically acceptable salt thereof.

Also an embodiment of the present invention is the use of a compound according to formula (I) as described above, or a pharmaceutically acceptable salt thereof, for the treatment or prophylaxis nonalkoholic fatty liver disease or nonalkoholic steatohepatitis.

Also an embodiment of the present invention is the use of a compound according to formula (I) as described above, or a pharmaceutically acceptable salt thereof, for the preparation of a medicament for the treatment or prophylaxis of nonalkoholic fatty liver disease or nonalkoholic steatohepatitis.

Also a particular embodiment of the present invention is a compound according to formula (I) as described above, or a pharmaceutically acceptable salt thereof, for the treatment or prophylaxis of nonalkoholic fatty liver disease or nonalkoholic steatohepatitis.

Also an embodiment of the present invention is a method for the treatment or prophylaxis of nonalkoholic fatty liver disease or nonalkoholic steatohepatitis, which method comprises administering an effective amount of a compound according to formula (I) as described above, or a pharmaceutically acceptable salt thereof.

Compounds as described above have $IC_{50}$ values between 0.005 uM and 1000 uM, preferred compounds have $IC_{50}$ values between 0.01 uM and 50 uM, particularly preferred compounds have $IC_{50}$ values between 0.01 uM and 0.5 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, the compounds of formula (I) and their pharmaceutically acceptable salts can be used for the prophylaxis or treatment of diabetes, metabolic syndrome, dyslipidemia, atherosclerosis and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

(5α,8β)-8-Hydroxy-2-(4-trifluoromethoxy-phenyl)-2-aza-spiro[4.5]decan-1-one

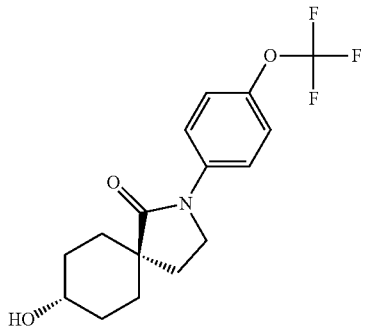 [SMILES: O=C1N(c2ccc(OC(F)(F)F)cc2)CC[C@]12CC[C@@H](O)CC2]

Step 1: 1,4-Dioxa-spiro[4.5]decane-8-carboxylic acid ethyl ester

Ethyl-cyclohexanone-4-carboxylate (54.8 g) was dissolved in toluene (120 mL). Then, ethylene glycol (24.8 mL) and toluene-4-sulfonic acid monohydrate (612 mg) were added to the reaction mixture. The mixture was refluxed over night and water was removed azeotropically with a Dean-Stark apparatus. The reaction mixture was cooled, poured into ice/water and basified with 2M aqueous NaOH to pH 9. The aqueous layer was extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title com pound as a light yellow liquid (39.5 g, 57%). MS (m/e)=215.3 [MH+].

Step 2:
1-(2-Methoxy-ethyl)-4-oxo-cyclohexanecarboxylic acid ethyl ester

A solution of 1,4-dioxa-spiro[4.5]decane-8-carboxylic acid ethyl ester (39.5 g) in THF (200 mL) was added dropwise over a period of 45 minutes at −5° C. (ice/methanol bath) to a solution of lithiumdiisopropylamide (2M in THF, 184.3 mL) in THF (300 mL). Stirring was continued for 2.5 hours at 0° C. The reaction mixture was cooled to −5° C. and 2-bromo-ethyl-methylether (34.6 mL) was added dropwise over a period of 30 minutes. Stirring was continued for 12 hours at r.t. The reaction mixture was cooled to 0° C. and aqueous HCl (25%, 300 mL) was added dropwise over a period of 45 minutes to pH 1. Stirring was continued for 2 hours at r.t. The reaction mixture was poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a yellow liquid (25.2 g, 60%). MS (EI)=288.0 [M+].

Step 3: trans-4-Hydroxy-1-(2-methoxy-ethyl)-cyclohexanecarboxylic acid ethyl ester 1-(2-Methoxy-ethyl)-4-oxo-cyclohexanecarboxylic acid ethyl ester (14 g) was dissolved in THF (200 mL). The mixture was cooled to −78° C. in a dry ice/acetone bath and LS-selectride (1M in THF, 49 mL) was added dropwise over a period of 30 minutes. Stirring was continued for 3 hours at −78° C. More LS-selectride (1M in THF, 49 mL) was added dropwise over a period of 30 minutes at −78° C. Stirring was continued for 3 hours at −78° C. The reaction mixture was warmed to 0° C. and 1M aqueous HCl (100 mL) was added. Stirring was continued for 1 hour at 0° C. The reaction mixture was poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a light yellow liquid (9.55 g, 68%). MS (m/e)= 231.2 [MH+].

Step 4: (5α,8β)-8-Hydroxy-2-(4-trifluoromethoxy-phenyl)-2-aza-spiro[4.5]decan-1-one 4-(Trifluoromethoxy)-aniline (3.05 mL, [CAS Reg. No. 461-82-5]) was added to a solution of trans-4-hydroxy-1-(2-methoxy-ethyl)-cyclohexanecarboxylic acid ethyl ester (3.49 g) in toluene (80 mL). The mixture was stirred for 10 minutes at r.t. Then, dimethylaluminiumchloride (1M in hexane, 30.3 mL) was added dropwise over a period of 20 minutes. The reaction mixture was stirred at reflux for 4.5 hours. The mixture was cooled, poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless solid (3.96 g, 79%). MS (m/e)=330.1 [MH+].

Example 2

(5α,8α)-8-Hydroxy-2-(4-trifluoromethoxy-phenyl)-2-aza-spiro[4.5]decan-1-one

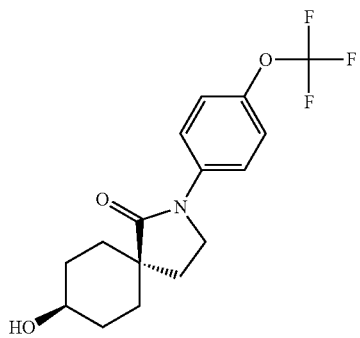 [SMILES: O=C1N(c2ccc(OC(F)(F)F)cc2)CC[C@]12CC[C@H](O)CC2]

Step 1: 1,4-Dioxa-spiro[4.5]decane-8-carboxylic acid ethyl ester

The title compound was prepared in analogy to example 1, step 1 from ethyl-cyclohexanone-4-carboxylate. MS (m/e)= 215.3 [MH+].

Step 2:
1-(2-Methoxy-ethyl)-4-oxo-cyclohexanecarboxylic acid ethyl ester

The title compound was prepared in analogy to example 1, step 2 from 1,4-dioxa-spiro[4.5]decane-8-carboxylic acid ethyl ester (obtained in example 2, step 1). MS (EI)=288.0 [M+].

Step 3: 4-Hydroxy-1-(2-methoxy-ethyl)-cyclohexanecarboxylic acid ethyl ester 1-(2-Methoxy-ethyl)-4-oxo-cyclohexanecarboxylic acid ethyl ester (1.60 g) was dissolved in 2-propanol (25 mL) The mixture was cooled to 0° C. and sodium borohydride (331 mg) was added in 3 portions over 10 minutes. Stirring was continued for 2 hours at 0° C. The reaction mixture was poured into ice/water and extracted two times with ethyl acetate. The combined organic layers were washed with brine, dried over Na₂SO₄, filtered and the solvent was evaporated. The title compound was obtained as an inseparable mixture of cis and trans diastereomeres (ratio: 3/1) as a light yellow liquid (1.58 g, 98%). This mixture was used without further purification. MS (EI)=230.0 [MH+].

Step 4: 4-(2-Methoxy-ethyl)-2-oxa-bicyclo[2.2.2]octan-3-one

A mixture of cis and trans 4-hydroxy-1-(2-methoxy-ethyl)-cyclohexanecarboxylic acid ethyl ester (1.58 g) was dissolved in DMF (25 mL). The solution was cooled to 0° C. and sodium hydride (60% in mineral oil, 549 mg) was added in four portions over a period of 15 minutes to the cold solution. The mixture was stirred for 1 hour at 0° C. Then benzylbromide (1.22 mL) was added dropwise over a period of 10 minutes to the reaction mixture. Stirring was continued for 10 minutes at 0° C. and then 3 hours at r.t. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a light yellow liquid (757 mg, 60%). MS (m/e)=185.1 [MH+].

From this reaction, trans-4-benzyloxy-1-(2-methoxyethyl)-cyclohexanecarboxylic acid ethyl ester was also isolated (originating from benzylation of trans-4-hydroxy-1-(2-methoxy-ethyl)-cyclohexanecarboxylic acid ethyl ester; see example 3, step 1).

Step 5: (5α,8α)-8-Hydroxy-2-(4-trifluoromethoxy-phenyl)-2-aza-spiro[4.5]decan-1-one The title compound was prepared in analogy to example 1, step 4 from 4-(2-methoxy-ethyl)-2-oxa-bicyclo[2.2.2]octan-3-one (obtained in example 2, step 4) with 4-(trifluoromethoxy)-aniline [CAS Reg. No. 461-82-5]. MS (m/e)= 330.3 [MH+].

Example 3

(5α,8β)-8-Benzyloxy-2-(4-methoxy-phenyl)-2-aza-spiro[4.5]decan-1-one

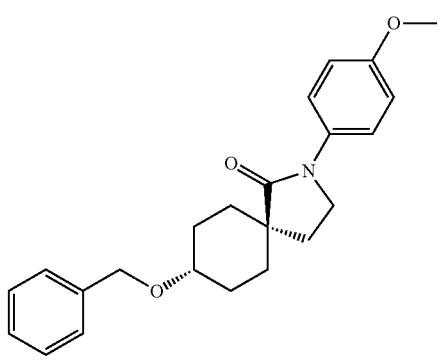 [SMILES: COc1ccc(N2CC[C@]3(CC[C@@H](OCc4ccccc4)CC3)C2=O)cc1]

Step 1: trans-4-Benzyloxy-1-(2-methoxy-ethyl)-cyclohexanecarboxylic acid ethyl ester A mixture of cis and trans-4-hydroxy-1-(2-methoxyethyl)-cyclohexanecarboxylic acid ethyl ester (500 mg, obtained in example 2, step 3) was dissolved in DMF (10 mL). The mixture was cooled to 0° C. and sodium hydride (60% in mineral oil, 174 mg) was added in two portions over a period of 5 minutes to the cold solution. The mixture was stirred for 1 hour at 0° C. Then benzylbromide (0.387 mL) was added dropwise over a period of 10 minutes to the reaction mixture. Stirring was continued for 10 minutes at 0° C. and then 3 hours at r.t. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a light yellow liquid (135 mg, 20%). MS (m/e)=321.3 [MH+].

From this reaction, 4-(2-methoxy-ethyl)-2-oxa-bicyclo [2.2.2]octan-3-one was also isolated (originating from lactonization of cis-4-hydroxy-1-(2-methoxy-ethyl)-cyclohexanecarboxylic acid ethyl ester; see example 2, step 4).

Step 2: (5α,8β)-8-Benzyloxy-2-(4-methoxy-phenyl)-2-aza-spiro[4.5]decan-1-one

The title compound was prepared in analogy to example 1, step 4 from trans-4-benzyloxy-1-(2-methoxy-ethyl)-cyclohexanecarboxylic acid ethyl ester (obtained in example 3, step 1) and 4-anisidine [CAS Reg. No. 104-94-9]. MS (m/e)= 366.2 [MH+].

Example 4

(5α,8β)-8-Benzyloxy-2-(4-ethyl-phenyl)-2-aza-spiro[4.5]decan-1-one

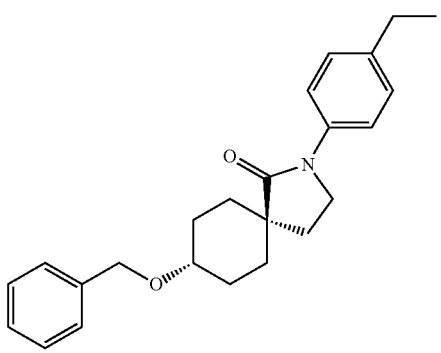 [SMILES: CCc1ccc(N2CC[C@]3(CC[C@@H](OCc4ccccc4)CC3)C2=O)cc1]

The title compound was prepared in analogy to example 1, step 4 from trans-4-benzyloxy-1-(2-methoxy-ethyl)-cyclohexanecarboxylic acid ethyl ester (obtained in example 3, step 1) and 4-ethylaniline [CAS Reg. No. 589-16-2]. MS (m/e)=364.4 [MH+].

Example 5

(5α,8β)-2-(4-Ethyl-phenyl)-8-hydroxy-2-aza-spiro[4.5]decan-1-one

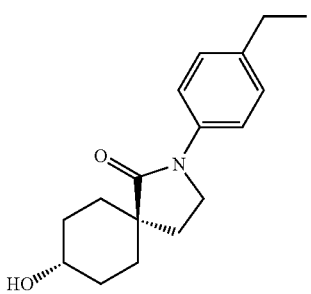 [SMILES: CCc1ccc(N2CC[C@]3(CC[C@@H](O)CC3)C2=O)cc1]

(5α,8β)-8-Benzyloxy-2-(4-ethyl-phenyl)-2-aza-spiro[4.5]decan-1-one (262 mg, obtained in example 4) was dissolved in ethanol (15 mL). Palladium on activated charcoal (77 mg, 10% Pd) was added and an atmosphere of hydrogen was introduced at r.t. The mixture was stirred under hydrogen at reflux for 4 hours. The reaction mixture was cooled and filtered over dicalite speed plus (Acros Organics) and the solvent was evaporated. The residue was purified by flash chromatography (silica gel, gradient of heptane in ethyl acetate) to give the title compound as a colorless foam (192 mg, 82%). MS (m/e)=274.4 [MH⁺].

Example 6

Propyl-carbamic acid [(5α,8β)-2-(4-ethyl-phenyl)-1-oxo-2-aza-spiro[4.5]dec-8-yl]ester

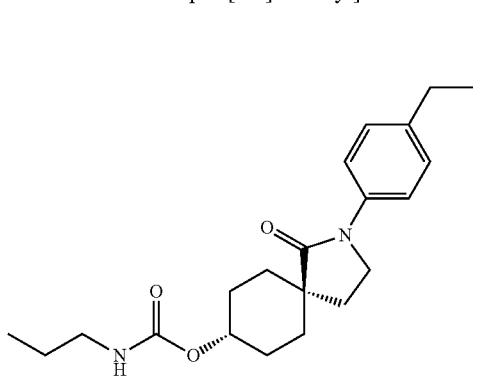

(5α,8β)-2-(4-Ethyl-phenyl)-8-hydroxy-2-aza-spiro[4.5]decan-1-one (55 mg, obtained in example 5), n-propyl isocyanate (0.06 mL, [CAS Reg. No. 110-78-1]) and triethylamine (0.03 mL) were dissolved in toluene (2 mL). The reaction mixture was stirred at 90° C. for 12 hours. The reaction mixture was cooled, poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless foam (65 mg, 90%). MS (m/e)=359.5 [MH⁺].

Example 7

(3-Fluoro-benzyl)-carbamic acid [(5α,8β)-2-(4-ethyl-phenyl)-1-oxo-2-aza-spiro[4.5]dec-8-yl]ester

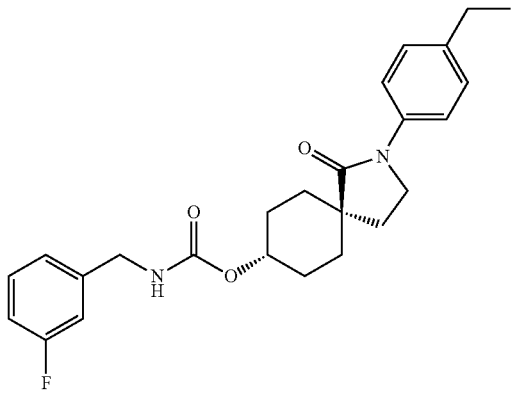 [SMILES: CCc1ccc(N2CC[C@]3(CC[C@@H](OC(=O)NCc4cccc(F)c4)CC3)C2=O)cc1]

The title compound was prepared in analogy to example 6 from (5α,8β)-2-(4-ethyl-phenyl)-8-hydroxy-2-aza-spiro[4.5]decan-1-one (obtained in example 5) and 3-fluorobenzyl isocyanate [CAS Reg. No. 102422-56-0]. MS (m/e)=425.2 [MH⁺].

Example 8

Phenyl-carbamic acid [(5α,8β)-2-(4-ethyl-phenyl)-1-oxo-2-aza-spiro[4.5]dec-8-yl]ester

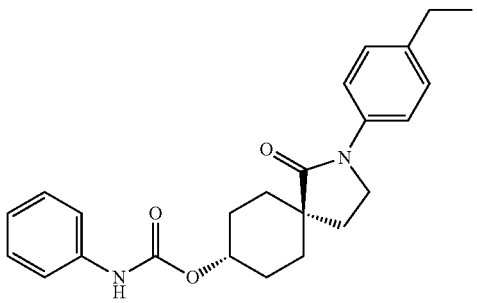 [SMILES: CCc1ccc(N2CC[C@]3(CC[C@@H](OC(=O)Nc4ccccc4)CC3)C2=O)cc1]

The title compound was prepared in analogy to example 6 from (5α,8β)-2-(4-ethyl-phenyl)-8-hydroxy-2-aza-spiro[4.5]decan-1-one (obtained in example 5) and phenyl isocyanate [CAS Reg. No. 103-71-9]. MS (m/e)=415.2 [MNa⁺].

Example 9

(5α,8β)-8-Benzyloxy-2-(4-trifluoromethoxy-phenyl)-2-aza-spiro[4.5]decan-1-one

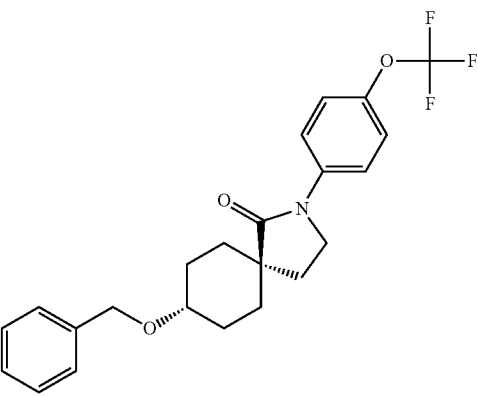 [SMILES: O=C1N(c2ccc(OC(F)(F)F)cc2)CC[C@]12CC[C@@H](OCc1ccccc1)CC2]

(5α,8β)-8-Hydroxy-2-(4-trifluoromethoxy-phenyl)-2-aza-spiro[4.5]decan-1-one (33 mg, obtained in example 1, step 4) was dissolved in THF (3 mL). The mixture was cooled to 0° C. and sodium hydride (60% in mineral oil, 18 mg) was added to the cold solution. The mixture was stirred for 1 hour at r.t. Then, benzylbromide (0.052 mL) was added dropwise over a period of 2 minutes to the reaction mixture. The mixture was stirred for 12 hours at r.t. and then heated to 45° C. for 2 hours. The reaction mixture was poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless foam (15 mg, 36%). MS (m/e)=420.2 [MH⁺].

Example 10

(3-Fluoro-benzyl)-carbamic acid [(5α,8β)-1-oxo-2-(4-trifluoromethoxy-phenyl)-2-aza-spiro[4.5]dec-8-yl]ester

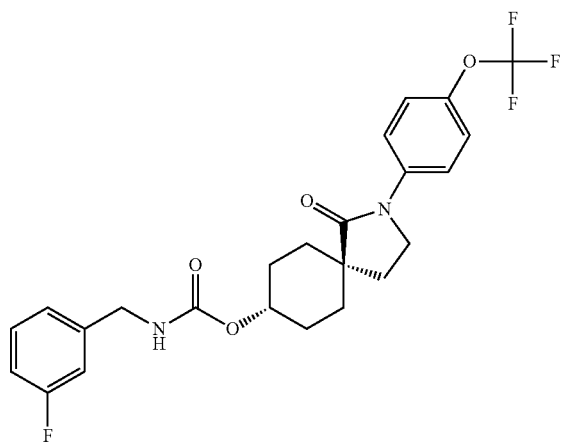 [SMILES: O=C(NCc1cccc(F)c1)O[C@H]1CC[C@@]2(CCN(c3ccc(OC(F)(F)F)cc3)C2=O)CC1]

The title compound was prepared in analogy to example 6 from (5α,8β)-8-hydroxy-2-(4-trifluoromethoxy-phenyl)-2-aza-spiro[4.5]decan-1-one (obtained in example 1, step 4) and 3-fluorobenzyl isocyanate [CAS Reg. No. 102422-56-0]. MS (m/e)=503.2 [MNa$^+$].

Example 11

Propyl-carbamic acid [(5α,8β)-1-oxo-2-(4-trifluoromethoxy-phenyl)-2-aza-spiro[4.5]dec-8-yl]ester

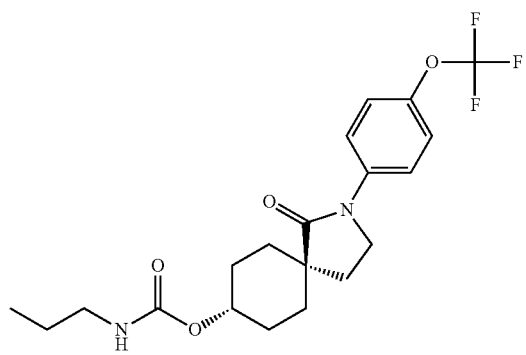 [SMILES: CCCNC(=O)O[C@H]1CC[C@@]2(CCN(c3ccc(OC(F)(F)F)cc3)C2=O)CC1]

The title compound was prepared in analogy to example 6 from (5α,8β)-8-hydroxy-2-(4-trifluoromethoxy-phenyl)-2-aza-spiro[4.5]decan-1-one (obtained in example 1, step 4) and n-propyl isocyanate [CAS Reg. No. 110-78-1]. MS (m/e)=415.2 [MH$^+$].

Example 12

(3-Methoxy-benzyl)-carbamic acid [(5α,8β)-1-oxo-2-(4-trifluoromethoxy-phenyl)-2-aza-spiro[4.5]dec-8-yl]ester

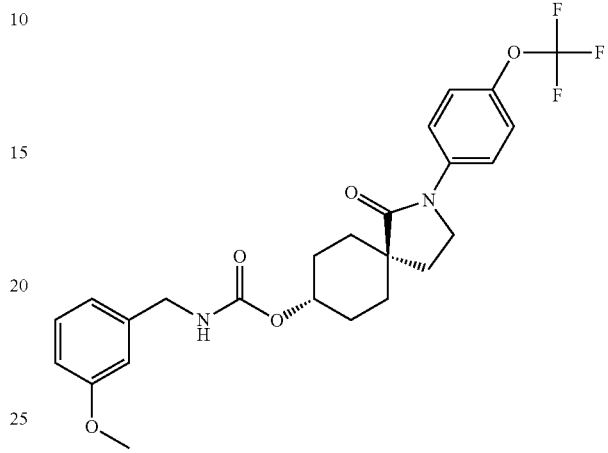

The title compound was prepared in analogy to example 6 from (5α,8β)-8-hydroxy-2-(4-trifluoromethoxy-phenyl)-2-aza-spiro[4.5]decan-1-one (obtained in example 1, step 4) and 3-methoxybenzyl isocyanate [CAS Reg. No. 57198-56-8]. MS (m/e)=515.2 [MNa$^+$].

Example 13

(4-Methoxy-benzyl)-carbamic acid [(5α,8β)-1-oxo-2-(4-trifluoromethoxy-phenyl)-2-aza-spiro[4.5]dec-8-yl]ester

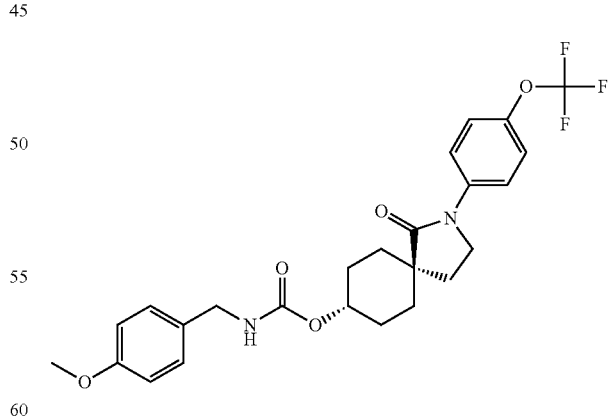

The title compound was prepared in analogy to example 6 from (5α,8β)-8-hydroxy-2-(4-trifluoromethoxy-phenyl)-2-aza-spiro[4.5]decan-1-one (obtained in example 1, step 4) and 4-methoxybenzyl isocyanate [CAS Reg. No. 56651-60-6]. MS (m/e)=515.2 [MNa$^+$].

Example 14

(2-Fluoro-benzyl)-carbamic acid [(5α,8β)-1-oxo-2-(4-trifluoromethoxy-phenyl)-2-aza-spiro[4.5]dec-8-yl]ester

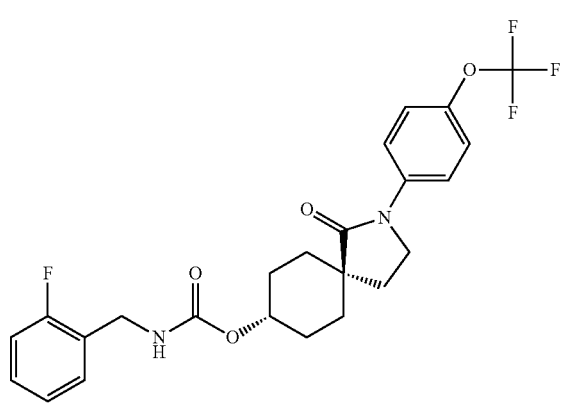 [SMILES: O=C(NCc1ccccc1F)O[C@H]1CC[C@@]2(CCN(c3ccc(OC(F)(F)F)cc3)C2=O)CC1]

The title compound was prepared in analogy to example 6 from (5α,8β)-8-hydroxy-2-(4-trifluoromethoxy-phenyl)-2-aza-spiro[4.5]decan-1-one (obtained in example 1, step 4) and 2-fluorobenzyl isocyanate [CAS Reg. No. 132740-44-4]. MS (m/e)=503.2 [MNa$^+$].

Example 15

(4-Fluoro-benzyl)-carbamic acid [(5α,8β)-1-oxo-2-(4-trifluoromethoxy-phenyl)-2-aza-spiro[4.5]dec-8-yl]ester

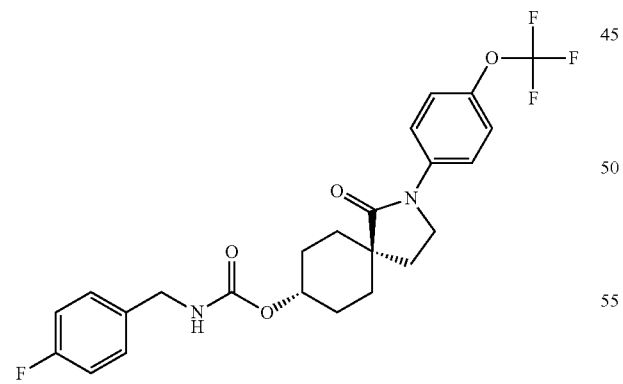

The title compound was prepared in analogy to example 6 from (5α,8β)-8-hydroxy-2-(4-trifluoromethoxy-phenyl)-2-aza-spiro[4.5]decan-1-one (obtained in example 1, step 4) and 4-fluorobenzyl isocyanate [CAS Reg. No. 132740-43-3]. MS (m/e)=503.2 [MNa$^+$].

Example 16

(5α,8β)-8-(6-Methyl-pyridin-2-ylmethoxy)-2-(4-trifluoromethoxy-phenyl)-2-aza-spiro[4.5]decan-1-one

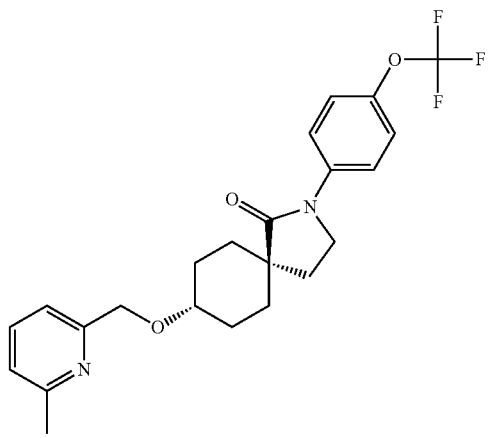 [SMILES: Cc1cccc(CO[C@H]2CC[C@@]3(CCN(c4ccc(OC(F)(F)F)cc4)C3=O)CC2)n1]

(5α,8β)-8-Hydroxy-2-(4-trifluoromethoxy-phenyl)-2-aza-spiro[4.5]decan-1-one (75 mg, obtained in example 1, step 4) was dissolved in THF (4.5 mL). The mixture was cooled to 0° C. and sodium hydride (60% in mineral oil, 46 mg) was added to the cold solution. The mixture was stirred for 1 hour at r.t. Then, 2-(bromomethyl)-6-methylpyridine (212 mg, [CAS Reg. No. 68470-59-7]) was added to the reaction mixture. The mixture was stirred for 2 hours at r.t. and then heated to 50° C. for 12 hours. The reaction mixture was cooled, poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless foam (71 mg, 72%). MS (m/e)=435.3 [MH$^+$].

Example 17

Methyl-carbamic acid [(5α,8β)-1-oxo-2-(4-trifluoromethoxy-phenyl)-2-aza-spiro[4.5]dec-8-yl]ester

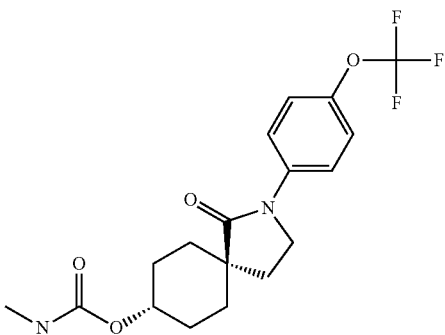

The title compound was prepared in analogy to example 6 from (5α,8β)-8-hydroxy-2-(4-trifluoromethoxy-phenyl)-2- aza-spiro[4.5]decan-1-one (obtained in example 1, step 4) and methyl isocyanate [CAS Reg. No. 624-83-9]. MS (m/e)= 409.1 [MNa⁺].

Example 18

Phenethyl-carbamic acid [(5α,8β)-1-oxo-2-(4-trifluoromethoxy-phenyl)-2-aza-spiro[4.5]dec-8-yl]ester

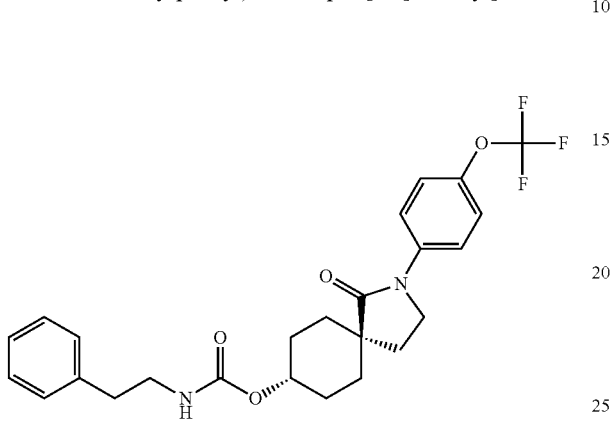

The title compound was prepared in analogy to example 6 from (5α,8β)-8-hydroxy-2-(4-trifluoromethoxy-phenyl)-2-aza-spiro[4.5]decan-1-one (obtained in example 1, step 4) and phenethyl isocyanate [CAS Reg. No. 1943-82-4]. MS (m/e)=499.2 [MNa⁺].

Example 19

(5α,8β)-8-(Pyrazin-2-yloxy)-2-(4-trifluoromethoxy-phenyl)-2-aza-spiro[4.5]decan-1-one

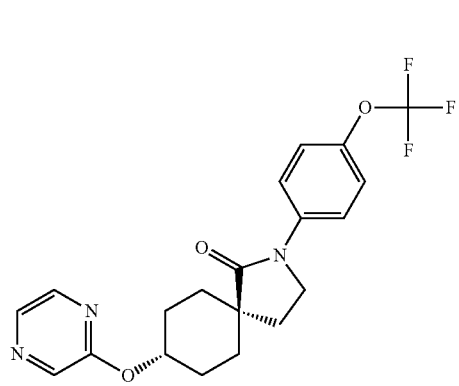 [SMILES: O=C1N(c2ccc(OC(F)(F)F)cc2)CC[C@]12CC[C@@H](Oc1cnccn1)CC2]

The title compound was prepared in analogy to example 16 from (5α,8β)-8-hydroxy-2-(4-trifluoromethoxy-phenyl)-2-aza-spiro[4.5]decan-1-one (obtained in example 1, step 4) and 2-iodopyrazine [CAS Reg. No. 32111-21-0]. MS (m/e)= 408.3 [MH⁺].

Example 20

(5α,8β)-8-(Pyrimidin-2-yloxy)-2-(4-trifluoromethoxy-phenyl)-2-aza-spiro[4.5]decan-1-one

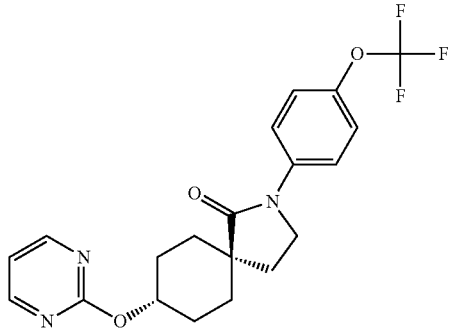 [SMILES: O=C1N(c2ccc(OC(F)(F)F)cc2)CC[C@]12CC[C@@H](Oc1ncccn1)CC2]

The title compound was prepared in analogy to example 16 from (5α,8β)-8-hydroxy-2-(4-trifluoromethoxy-phenyl)-2-aza-spiro[4.5]decan-1-one (obtained in example 1, step 4) and 2-bromopyrimidine [CAS Reg. No. 4595-60-2]. MS (m/e)=408.2 [MH⁺].

Example 21

(5α,8β)-8-(6-Methyl-pyridazin-3-yloxy)-2-(4-trifluoromethoxy-phenyl)-2-aza-spiro[4.5]decan-1-one

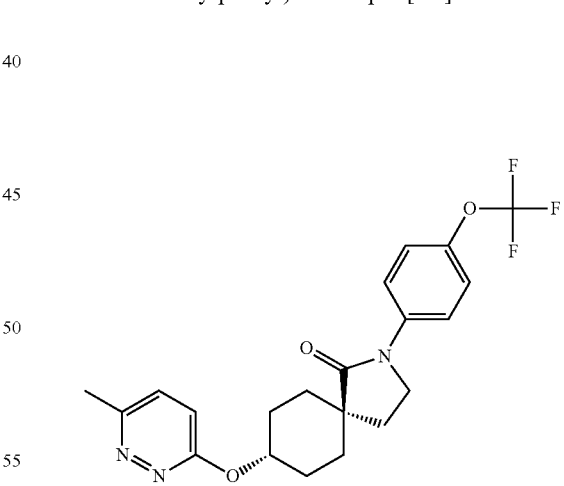

The title compound was prepared in analogy to example 16 from (5α,8β)-8-hydroxy-2-(4-trifluoromethoxy-phenyl)-2-aza-spiro[4.5]decan-1-one (obtained in example 1, step 4) and 3-chloro-6-methylpyridazine [CAS Reg. No. 1121-79-5] with the following modification: the reaction mixture was stirred at reflux for 12 hours (instead of 50° C.). MS (m/e)= 444.1 [MNa⁺].

Example 22

(Cyclopropylmethyl)-carbamic acid [(5α,8β)-1-oxo-2-(4-trifluoromethoxy-phenyl)-2-aza-spiro[4.5]dec-8-yl]ester

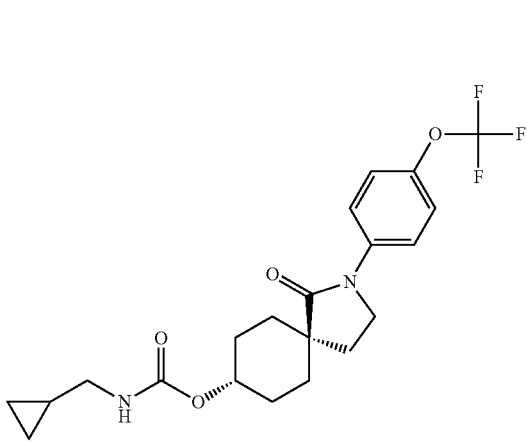 [SMILES: O=C(NCC1CC1)O[C@H]1CC[C@@]2(CCN(c3ccc(OC(F)(F)F)cc3)C2=O)CC1]

The title compound was prepared in analogy to example 6 from (5α,8β)-8-hydroxy-2-(4-trifluoromethoxy-phenyl)-2-aza-spiro[4.5]decan-1-one (obtained in example 1, step 4) and cyclopropylmethyl isocyanate [CAS Reg. No. 25694-89-7, which was prepared according to Journal of Medicinal Chemistry, 1996, Vol. 39, No. 5, 1157-1163]. MS (m/e)=449.2 [MNa$^+$].

Example 23

(5α,8β)-8-(2-Methoxy-ethoxy)-2-(4-trifluoromethoxy-phenyl)-2-aza-spiro[4.5]decan-1-one

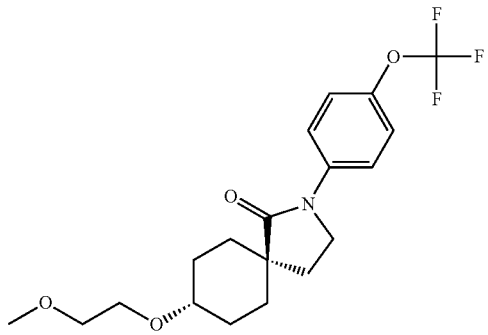 [SMILES: COCCO[C@H]1CC[C@@]2(CCN(c3ccc(OC(F)(F)F)cc3)C2=O)CC1]

The title compound was prepared in analogy to example 16 from (5α,8β)-8-hydroxy-2-(4-trifluoromethoxy-phenyl)-2-aza-spiro[4.5]decan-1-one (obtained in example 1, step 4) and 2-bromoethyl methyl ether [CAS Reg. No. 6482-24-2] with the following modification: the reaction mixture was stirred at 70° C. for 4 hours (instead of 50° C. for 12 hours). MS (m/e)=388.2 [MH$^+$].

Example 24

(5α,8β)-8-Ethoxy-2-(4-trifluoromethoxy-phenyl)-2-aza-spiro[4.5]decan-1-one

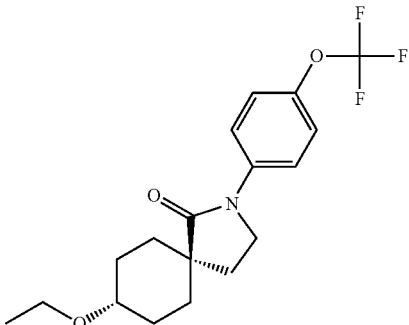

The title compound was prepared in analogy to example 16 from (5α,8β)-8-hydroxy-2-(4-trifluoromethoxy-phenyl)-2-aza-spiro[4.5]decan-1-one (obtained in example 1, step 4) by alkylation with iodoethane. MS (m/e)=358.3 [MH$^+$].

Example 25

(5-Methyl-pyrazin-2-ylmethyl)-carbamic acid [(5α,8β)-1-oxo-2-(4-trifluoromethoxy-phenyl)-2-aza-spiro[4.5]dec-8-yl]ester

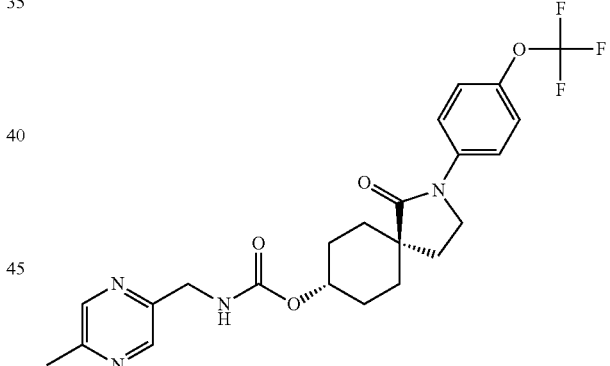

Step 1: [(5α,8β)-1-Oxo-2-(4-(trifluoromethoxy)phenyl)-2-azaspiro[4.5]decan-8-yl]carbonochloridate (5α,8β)-8-hydroxy-2-(4-trifluoromethoxy-phenyl)-2-aza-spiro[4.5]decan-1-one (500 mg, obtained in example 1, step 4) was dissolved in dichloromethane (9 mL) and cooled to −10° C. in an ice/methanol bath. A solution of triphosgene (180 mg) and pyridine (0.147 mL) in dichloromethane (9 mL) was added dropwise over a period of 5 minutes to the cold reaction mixture. Stirring was continued at 0° C. for 2 hours. The reaction mixture was poured into ice/water and extracted two times with ethyl acetate. The combined organic layers were washed with brine, dried over Na$_2$SO$_4$, filtered and the solvent was evaporated. The title compound was obtained as a light brown liquid (547 mg, 64%) and was used without further purification. MS (m/e)=392.2 [MH$^+$].

Step 2: (5-Methyl-pyrazin-2-ylmethyl)-carbamic acid [(5α,8β)-1-oxo-2-(4-trifluoromethoxy-phenyl)-2-aza-spiro[4.5]dec-8-yl]ester

[(5α,8β)-1-oxo-2-(4-(trifluoromethoxy)phenyl)-2-azaspiro[4.5]decan-8-yl]carbonochloridate (142 mg, obtained in example 25, step 1) was dissolved in THF (5 mL). Then N-ethyldiisopropylamine (0.12 mL) and 2-(aminomethyl)-5-methylpyrazine (54 mg, [CAS Reg. No. 132664-85-8]) were added to the reaction mixture. Stirring was continued at r.t. for 1.5 hours. The reaction mixture was poured into ice/water and acidified with sat. NH₄Cl. The aqueous phase was then extracted two times with ethyl acetate and the organic layers were washed with brine, dried over Na₂SO₄, filtered and the solvent was evaporated. The residue was purified by flash chromatography (silica gel, gradient of heptane in ethyl acetate) to give the title compound as a colorless solid (68 mg, 39%). MS (m/e)=479.2 [MH⁺].

Example 26

(2-Hydroxy-2-methyl-propyl)-carbamic acid [(5α,8β)-1-oxo-2-(4-trifluoromethoxy-phenyl)-2-aza-spiro[4.5]dec-8-yl]ester

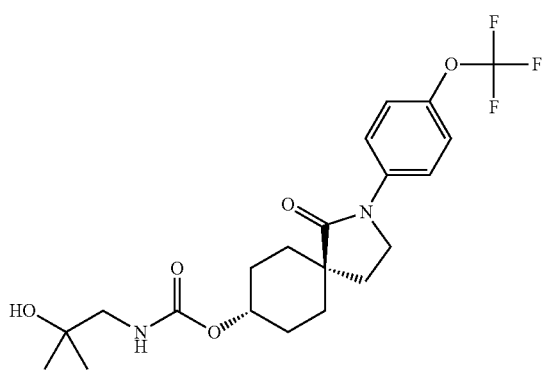 [SMILES: CC(C)(O)CNC(=O)O[C@H]1CC[C@@]2(CCN(c3ccc(OC(F)(F)F)cc3)C2=O)CC1]

The title compound was prepared in analogy to example 25, step 2 from [(5α,8β)-1-oxo-2-(4-(trifluoromethoxy)phenyl)-2-azaspiro[4.5]decan-8-yl]carbonochloridate (obtained in example 25, step 1) and 1-amino-2-methyl-2-propanol [CAS Reg. No. 2854-16-2]. MS (m/e)=445.2 [MH⁺].

Example 27

(2-Hydroxy-ethyl)-carbamic acid [(5α,8β)-1-oxo-2-(4-trifluoromethoxy-phenyl)-2-aza-spiro[4.5]dec-8-yl]ester

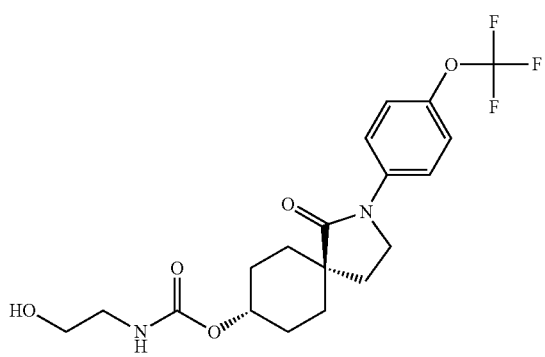 [SMILES: O=C(NCCO)O[C@H]1CC[C@@]2(CCN(c3ccc(OC(F)(F)F)cc3)C2=O)CC1]

The title compound was prepared in analogy to example 25, step 2 from [(5α,8β)-1-oxo-2-(4-(trifluoromethoxy)phenyl)-2-azaspiro[4.5]decan-8-yl]carbonochloridate (obtained in example 25, step 1) and ethanolamine [CAS Reg. No. 141-43-5]. MS (m/e)=417.3 [MH⁺].

Example 28

(Pyrazin-2-ylmethyl)-carbamic acid [(5α,8β)-1-oxo-2-(4-trifluoromethoxy-phenyl)-2-aza-spiro[4.5]dec-8-yl]ester

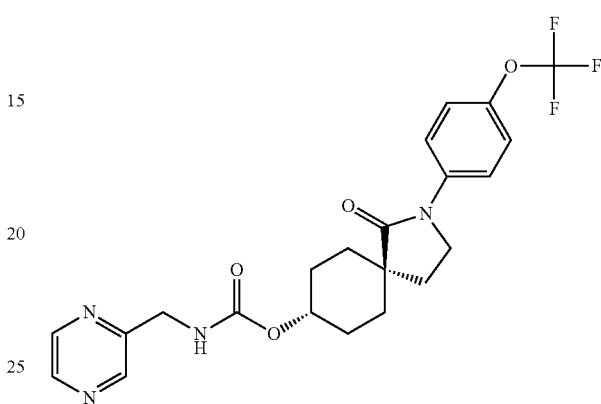

A solution of [(5α,8β)-1-oxo-2-(4-(trifluoromethoxy)phenyl)-2-azaspiro[4.5]decan-8-yl]carbonochloridate (135 mg, obtained in example 25, step 1) in DMF (3 mL) was added dropwise over a period of 5 minutes to a suspension of N-ethyldiisopropylamine (0.70 mL) and 2-aminomethylpyrazine hydrochloride (100 mg, [CAS Reg. No. 39204-49-4]) in DMF (5 mL). Stirring was continued at r.t. for 2 hours. The reaction mixture was poured into ice/water and acidified with saturated NH₄Cl. The aqueous phase was then extracted two times with ethyl acetate and the organic layers were washed with brine, dried over Na₂SO₄, filtered and the solvent was evaporated. The residue was purified by flash chromatography (silica gel, gradient of dichloromethane in acetonitrile) to give the title compound as a colorless solid (26 mg, 16%). MS (m/e)=465.3 [MH⁺].

Example 29

Cyclopropyl-carbamic acid [(5α,8β)-1-oxo-2-(4-trifluoromethoxy-phenyl)-2-aza-spiro[4.5]dec-8-yl]ester

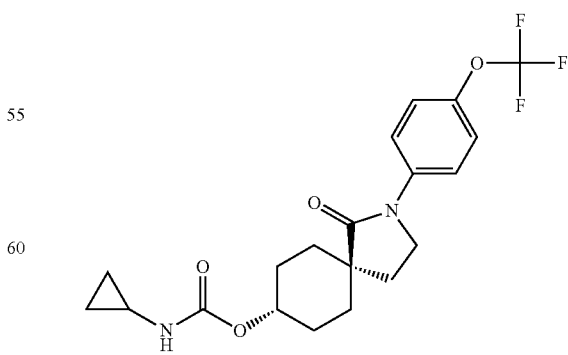

The title compound was prepared in analogy to example 25, step 2 from [(5α,8β)-1-oxo-2-(4-(trifluoromethoxy)phenyl)-2-azaspiro[4.5]decan-8-yl]carbonochloridate (obtained in example 25, step 1) and cyclopropylamine [CAS Reg. No. 765-30-0]. MS (m/e)=435.2 [MNa⁺].

Example 30

Carbamic acid [(5α,8β)-1-oxo-2-(4-trifluoromethoxy-phenyl)-2-aza-spiro[4.5]dec-8-yl]ester

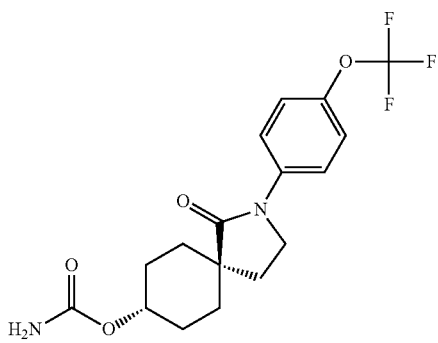 [SMILES: NC(=O)O[C@H]1CC[C@@]2(CCN(c3ccc(OC(F)(F)F)cc3)C2=O)CC1]

The title compound was prepared in analogy to example 25, step 2 from [(5α,8β)-1-oxo-2-(4-(trifluoromethoxy)phenyl)-2-azaspiro[4.5]decan-8-yl]carbonochloridate (obtained in example 25, step 1) and ammonium hydroxide solution (25%). MS (m/e)=395.1 [MNa⁺].

Example 31

(5α,8α)-8-Hydroxy-2-(4-methoxy-phenyl)-2-azaspiro[4.5]decan-1-one

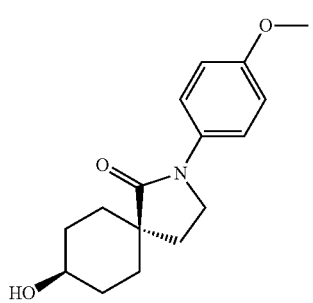 [SMILES: COc1ccc(N2CC[C@]3(CC[C@H](O)CC3)C2=O)cc1]

4-Anisidine (50 mg, [CAS Reg. No. 104-94-9]) was added to a solution of 4-(2-methoxy-ethyl)-2-oxa-bicyclo[2.2.2]octan-3-one (50 mg, obtained in example 2, step 4) in toluene (5 mL). The mixture was stirred for 10 minutes at r.t. Then, dimethylaluminiumchloride (1M in hexane, 0.54 mL) was added dropwise over a period of 2 minutes. The reaction mixture was stirred at reflux for 4 hours. The mixture was cooled, poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a off-white foam (74 mg, 99%). MS (m/e)=276.4 [MH⁺].

Example 32

(5α,8α)-2-(4-Ethyl-phenyl)-8-hydroxy-2-aza-spiro[4.5]decan-1-one

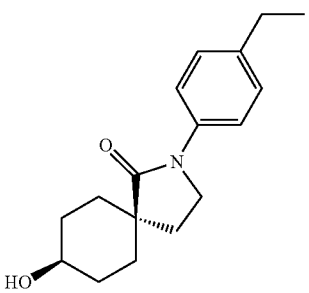 [SMILES: CCc1ccc(N2CC[C@]3(CC[C@H](O)CC3)C2=O)cc1]

The title compound was prepared in analogy to example 31 from 4-(2-methoxy-ethyl)-2-oxa-bicyclo[2.2.2]octan-3-one (obtained in example 2, step 4) and 4-ethylaniline [CAS Reg. No. 589-16-2]. MS (m/e)=274.3 [MH⁺].

Example 33

(5α,8α)-2-[2-(4-Fluoro-phenyl)-ethyl]-8-hydroxy-2-aza-spiro[4.5]decan-1-one

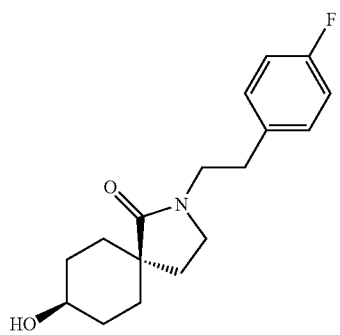 [SMILES: O=C1N(CCc2ccc(F)cc2)CC[C@]12CC[C@H](O)CC2]

The title compound was prepared in analogy to example 31 from 4-(2-methoxy-ethyl)-2-oxa-bicyclo[2.2.2]octan-3-one (obtained in example 2, step 4) and 4-fluorophenethylamine [CAS Reg. No. 1583-88-6]. MS (m/e)=292.3 [MH⁺].

Example 34

(5α,8α)-2-[2-(4-Ethyl-phenyl)-ethyl]-8-hydroxy-2-aza-spiro[4.5]decan-1-one

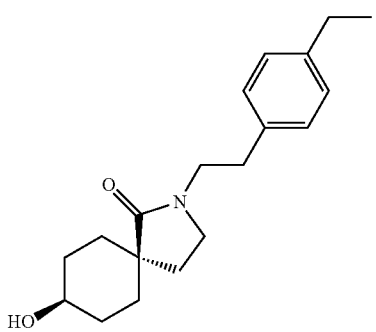 [SMILES: CCc1ccc(CCN2CC[C@]3(CC[C@H](O)CC3)C2=O)cc1]

The title compound was prepared in analogy to example 31 from 4-(2-methoxy-ethyl)-2-oxa-bicyclo[2.2.2]octan-3-one (obtained in example 2, step 4) and 4-ethylphenethylamine [CAS Reg. No. 64353-29-3]. MS (m/e)=302.5 [MH+].

Example 35

(5α,8α)-8-Hydroxy-2-[2-(4-methoxy-phenyl)-ethyl]-2-aza-spiro[4.5]decan-1-one

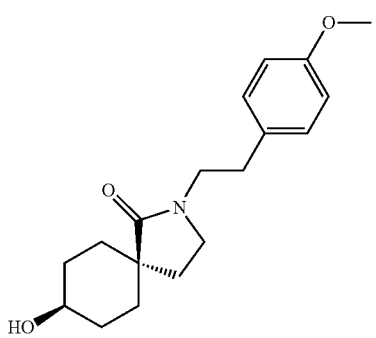 [SMILES: COc1ccc(CCN2CC[C@]3(CC[C@H](O)CC3)C2=O)cc1]

The title compound was prepared in analogy to example 31 from 4-(2-methoxy-ethyl)-2-oxa-bicyclo[2.2.2]octan-3-one (obtained in example 2, step 4) and 2-(4-methoxyphenyl)-ethylamine [CAS Reg. No. 55-81-2]. MS (m/e)=304.3 [MH+].

Example 36

(5α,8α)-2-(3-Chloro-benzyl)-8-hydroxy-2-aza-spiro[4.5]decan-1-one

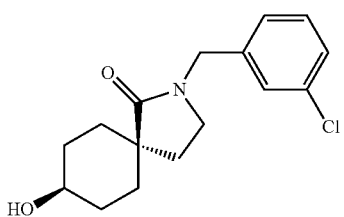 [SMILES: O=C1N(Cc2cccc(Cl)c2)CC[C@]12CC[C@H](O)CC2]

The title compound was prepared in analogy to example 31 from 4-(2-methoxy-ethyl)-2-oxa-bicyclo[2.2.2]octan-3-one (obtained in example 2, step 4) and 3-chlorobenzylamine [CAS Reg. No. 4152-90-3]. MS (m/e)=294.2 [MH+].

Example 37

(5α,8α)-8-Hydroxy-2-(4-propyl-phenyl)-2-aza-spiro[4.5]decan-1-one

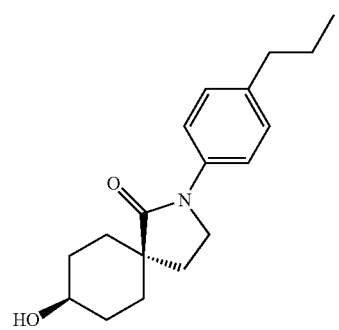 [SMILES: CCCc1ccc(N2CC[C@]3(CC[C@H](O)CC3)C2=O)cc1]

The title compound was prepared in analogy to example 31 from 4-(2-methoxy-ethyl)-2-oxa-bicyclo[2.2.2]octan-3-one (obtained in example 2, step 4) and 4-propylaniline [CAS Reg. No. 2696-84-6]. MS (m/e)=288.3 [MH+].

Example 38

(5α,8α)-8-Hydroxy-2-(4-isopropyl-phenyl)-2-aza-spiro[4.5]decan-1-one

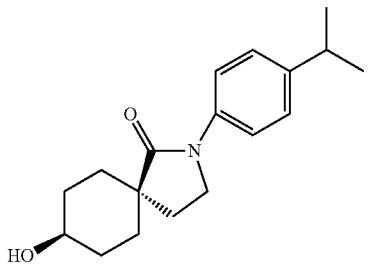 [SMILES: CC(C)c1ccc(N2CC[C@]3(CC[C@H](O)CC3)C2=O)cc1]

The title compound was prepared in analogy to example 31 from 4-(2-methoxy-ethyl)-2-oxa-bicyclo[2.2.2]octan-3-one (obtained in example 2, step 4) and 4-isopropylaniline [CAS Reg. No. 99-88-7]. MS (m/e)=288.1 [MH+].

Example 39

(5α,8α)-2-(4-Cyclopropyl-phenyl)-8-hydroxy-2-aza-spiro[4.5]decan-1-one

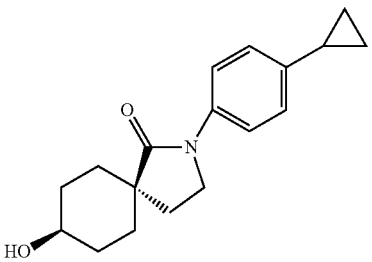 [SMILES: O=C1N(c2ccc(C3CC3)cc2)CC[C@]12CC[C@H](O)CC2]

The title compound was prepared in analogy to example 31 from 4-(2-methoxy-ethyl)-2-oxa-bicyclo[2.2.2]octan-3-one (obtained in example 2, step 4) and 4-cyclopropylaniline [CAS Reg. No. 3158-71-2]. MS (m/e)=286.3 [MH+].

Example 40

(5α,8α)-8-Benzyloxy-2-(4-methoxy-phenyl)-2-aza-spiro[4.5]decan-1-one

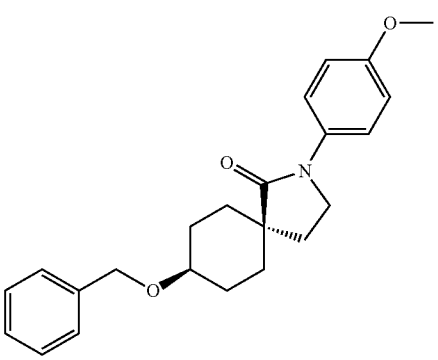 [SMILES: COc1ccc(N2CC[C@]3(CC[C@H](OCc4ccccc4)CC3)C2=O)cc1]

(5α,8α)-8-Hydroxy-2-(4-methoxy-phenyl)-2-aza-spiro[4.5]decan-1-one (54 mg, obtained in example 31) was dissolved in DMF (3 mL). The mixture was cooled to 0° C. and sodium hydride (60% in mineral oil, 16 mg) was added to the cold solution. The mixture was stirred for 1 hour at r.t. The reaction mixture was cooled to 0° C. and benzylbromide (0.035 mL) was added dropwise over a period of 2 minutes. The mixture was stirred at r.t. for 2 hours and then heated to 50° C. for 12 hours. The reaction mixture was cooled, poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless foam in low yield (4 mg, 5%). MS (m/e)=366.3 [MH$^+$].

Example 41

(5α,8α)-8-Ethoxy-2-(4-trifluoromethoxy-phenyl)-2-aza-spiro[4.5]decan-1-one

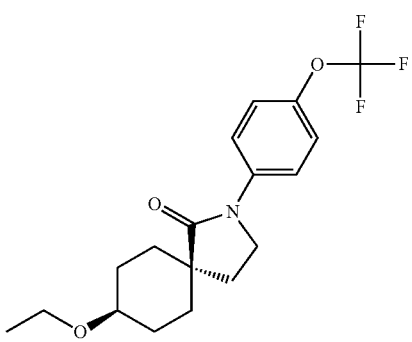 [SMILES: CCO[C@H]1CC[C@]2(CCN(c3ccc(OC(F)(F)F)cc3)C2=O)CC1]

Sodium hydride (60% in mineral oil, 46 mg) was added to a solution of (5α,8α)-8-hydroxy-2-(4-trifluoromethoxy-phenyl)-2-aza-spiro[4.5]decan-1-one (70 mg, obtained in example 2, step 5) in THF (4 mL). Stirring was continued for 1 hour at r.t. Then ethyliodide (0.074 mL) was added dropwise over a period of 2 minutes to the reaction mixture. The mixture was stirred at r.t. for 12 hours and then heated to 45° C. for 5 hours. The reaction mixture was cooled, poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless foam (60 mg, 79%). MS (m/e)=358.2 [MH$^+$].

Example 42

(5α,8α)-8-Propoxy-2-(4-trifluoromethoxy-phenyl)-2-aza-spiro[4.5]decan-1-one

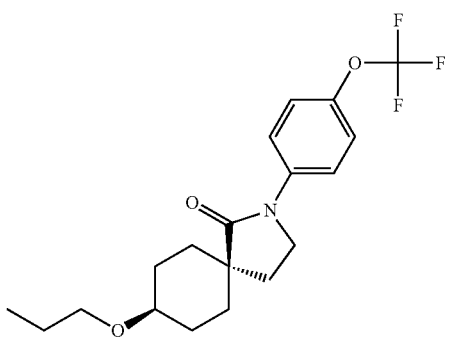 [SMILES: CCCO[C@H]1CC[C@]2(CCN(c3ccc(OC(F)(F)F)cc3)C2=O)CC1]

The title compound was prepared in analogy to example 41 from (5α,8α)-8-hydroxy-2-(4-trifluoromethoxy-phenyl)-2-aza-spiro[4.5]decan-1-one (obtained in example 2, step 5) and propyliodide. MS (m/e)=372.2 [MH$^+$].

Example 43

(5α,8α)-8-Benzyloxy-2-(4-ethyl-phenyl)-2-aza-spiro[4.5]decan-1-one

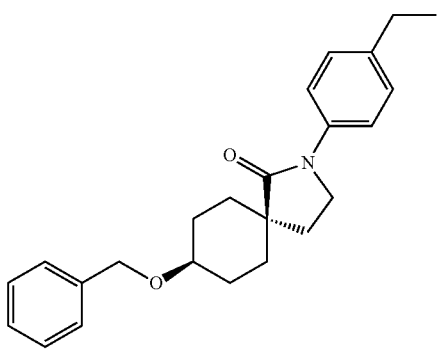 [SMILES: CCc1ccc(N2CC[C@]3(CC[C@H](OCc4ccccc4)CC3)C2=O)cc1]

The title compound was prepared in analogy to example 41 from (5α,8α)-2-(4-ethyl-phenyl)-8-hydroxy-2-aza-spiro[4.5]decan-1-one (obtained in example 32) and benzylbromide. MS (m/e)=364.3 [MH$^+$].

Example 44

Propyl-carbamic acid [(5α,8α)-2-(4-ethyl-phenyl)-1-oxo-2-aza-spiro[4.5]dec-8-yl]ester

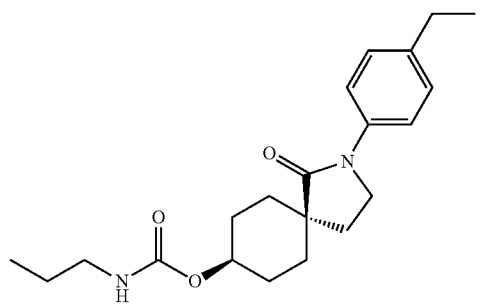 [SMILES: CCCNC(=O)O[C@H]1CC[C@]2(CCN(c3ccc(CC)cc3)C2=O)CC1]

The title compound was prepared in analogy to example 6 from (5α,8α)-2-(4-ethyl-phenyl)-8-hydroxy-2-aza-spiro[4.5]decan-1-one (obtained in example 32) and n-propyl isocyanate [CAS Reg. No. 110-78-1]. MS (m/e)=359.3 [MH$^+$].

Example 45

(3-Fluoro-benzyl)-carbamic acid [(5α,8α)-2-(4-ethyl-phenyl)-1-oxo-2-aza-spiro[4.5]dec-8-yl]ester

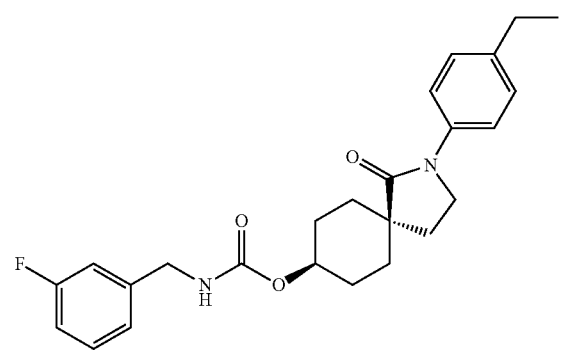 [SMILES: CCc1ccc(N2CC[C@]3(CC[C@H](OC(=O)NCc4cccc(F)c4)CC3)C2=O)cc1]

The title compound was prepared in analogy to example 6 from (5α,8α)-2-(4-ethyl-phenyl)-8-hydroxy-2-aza-spiro

[4.5]decan-1-one (obtained in example 32) and 3-fluorobenzyl isocyanate [CAS Reg. No. 102422-56-0]. MS (m/e)=425.2 [MH+].

Example 46

(5α,8α)-2-(4-Methoxy-phenyl)-8-phenoxy-2-aza-spiro[4.5]decan-1-one

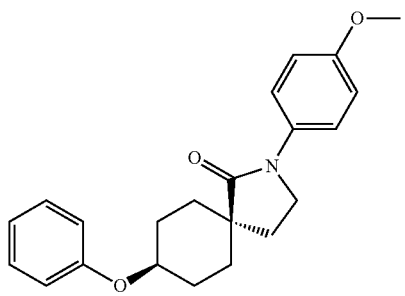 [SMILES: COc1ccc(N2CC[C@]3(CC[C@H](Oc4ccccc4)CC3)C2=O)cc1]

Step 1: cis-Ethyl 1-(2-methoxyethyl)-4-phenoxycyclohexanecarboxylate

Phenol (123 mg), triphenylphosphine (581 mg) and diethyl azodicarboxylate (40% in toluene, 1.0 mL) were added to a solution of a 3:1 mixture of cis and trans-4-hydroxy-1-(2-methoxy-ethyl)-cyclohexanecarboxylic acid ethyl ester (300 mg, obtained in example 2, step 3) in THF (8 mL). The mixture was stirred at r.t. for 30 minutes and then heated to 50° C. for 12 hours. The reaction mixture was cooled to r.t. and more triphenylphosphine (171 mg) and diethyl azodicarboxylate (40% in toluene, 0.30 mL) were added. The mixture was re-heated to 70° C. for another 12 hours. The reaction mixture was cooled, poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound with a cis configuration as a yellow liquid (53 mg, 13%). The title compound was used without further analysis.

Along with desired compound, trans-ethyl 1-(2-methoxy-ethyl)-4-phenoxycyclohexanecarboxylate originating from cis-4-hydroxy-1-(2-methoxy-ethyl)-cyclohexanecarboxylic acid ethyl ester was also isolated in the purification step (see example 48).

Step 2: (5α,8α)-2-(4-Methoxy-phenyl)-8-phenoxy-2-aza-spiro[4.5]decan-1-one

The title compound was prepared in analogy to example 1, step 4 from cis-ethyl 1-(2-methoxyethyl)-4-phenoxycyclohexanecarboxylate (obtained in example 46, step 1) and 4-anisidine [CAS Reg. No. 104-94-9]. MS (m/e)=352.2 [MH+].

Example 47

2-(4-Methoxy-phenyl)-2-aza-spiro[4.5]dec-7-en-1-one

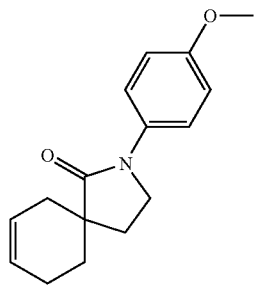 [SMILES: COc1ccc(N2CCC3(CC=CCC3)C2=O)cc1]

This material was obtained when an attempt was made to apply Mitsunobu conditions to the (5α,8α)-8-hydroxy-2-(4-methoxy-phenyl)-2-aza-spiro[4.5]decan-1-one system (obtained in example 31) in analogy to example 46, step. 1. However, these reaction conditions resulted in elimination and 2-(4-methoxy-phenyl)-2-aza-spiro[4.5]dec-7-en-1-one was obtained in 61% yield. MS (m/e)=258.3 [MH+].

Example 48

(5α,8β)-2-(4-Methoxy-phenyl)-8-phenoxy-2-aza-spiro[4.5]decan-1-one

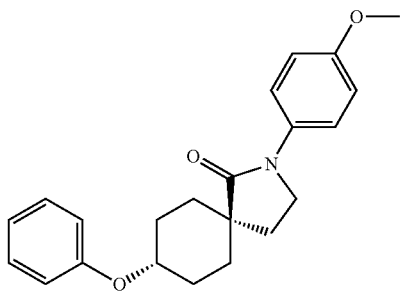 [SMILES: COc1ccc(N2CC[C@]3(CC[C@@H](Oc4ccccc4)CC3)C2=O)cc1]

Step 1: trans-Ethyl 1-(2-methoxyethyl)-4-phenoxycyclohexanecarboxylate

The title compound was obtained as described in example 46, step 1 from a mixture of cis and trans-4-hydroxy-1-(2-methoxy-ethyl)-cyclohexanecarboxylic acid ethyl ester (obtained in example 2, step 3) by treatment with phenol under Mitsunobu conditions. The title compound (178 mg, 42%) was used without further analysis.

Step 2: (5α,8β)-2-(4-Methoxy-phenyl)-8-phenoxy-2-aza-spiro[4.5]decan-1-one

The title compound was prepared in analogy to example 1, step 4 from trans-ethyl 1-(2-methoxyethyl)-4-phenoxycyclohexanecarboxylate (obtained in example 48, step 1) and 4-anisidine [CAS Reg. No. 104-94-9]. MS (m/e)=352.4 [MH⁺].

Example 49

Methanesulfonic acid [(5α,8α)-1-oxo-2-(4-trifluoromethoxy-phenyl)-2-aza-spiro[4.5]dec-8-yl]ester

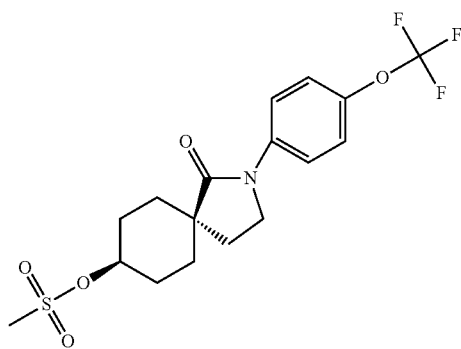 [SMILES: CS(=O)(=O)O[C@H]1CC[C@]2(CCN(c3ccc(OC(F)(F)F)cc3)C2=O)CC1]

Triethylamine (0.273 mL) was added to a solution of (5α, 8α)-8-hydroxy-2-(4-trifluoromethoxy-phenyl)-2-aza-spiro [4.5]decan-1-one (60 mg, obtained in example 2, step 5) in dichloromethane (6 mL). The mixture was cooled to 0° C. and methylsulfonyl chloride (0.021 mL) was added dropwise over a period of 1 minute. Stirring was continued for 3 hours at 0° C. The reaction mixture was poured into ice/water and extracted two times with ethyl acetate. The combined organic layers were washed with brine, dried over Na₂SO₄, filtered and the solvent was evaporated. The title compound was obtained as a colorless solid (74 mg, 100%) and was used without further purification. MS (m/e)=408.2 [MH⁺].

Example 50

2-(4-Trifluoromethoxy-phenyl)-2-aza-spiro[4.5]dec-7-en-1-one

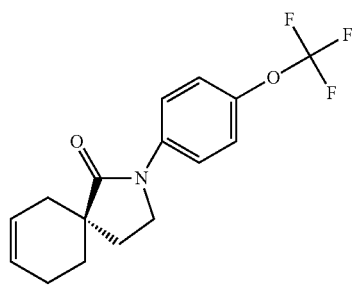 [SMILES: O=C1N(c2ccc(OC(F)(F)F)cc2)CC[C@]12CC=CCC2]

The title compound was isolated as the main product from a reaction where exchange of the mesylate of the starting material methanesulfonic acid [(5α,8α)-1-oxo-2-(4-trifluoromethoxy-phenyl)-2-aza-spiro[4.5]dec-8-yl]ester with a thiolate ion was attempted: Sodium thiophenolate (17 mg) was added to a solution of methanesulfonic acid [(5α,8α)-1-oxo-2-(4-trifluoromethoxy-phenyl)-2-aza-spiro[4.5]dec-8-yl]ester (35 mg, obtained in example 49) in DMF (5 mL). The mixture was heated to 100° C. for 24 hours. The reaction mixture was cooled, poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless amorphous solid (15 mg, 56%). MS (m/e)=312.3 [MH⁺].

Example 51

(5α,8β)-8-Benzenesulfinyl-2-(4-trifluoromethoxy-phenyl)-2-aza-spiro[4.5]decan-1-one

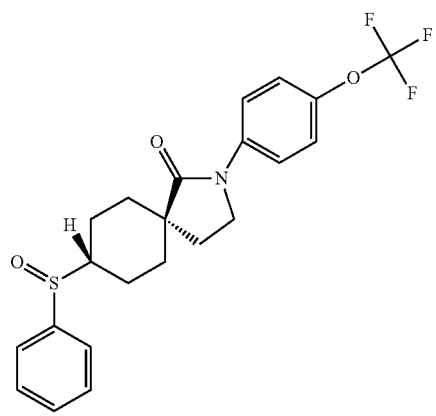 [SMILES: O=C1N(c2ccc(OC(F)(F)F)cc2)CC[C@]12CC[C@@H](S(=O)c1ccccc1)CC2]

The title compound was isolated as a side product from the reaction described in example 50 where exchange of the mesylate of the starting material methanesulfonic acid [(5α, 8α)-1-oxo-2-(4-trifluoromethoxy-phenyl)-2-aza-spiro[4.5] dec-8-yl]ester (obtained in example 49) with a thiolate ion was attempted. From this reaction, (5α,8β)-8-benzenesulfinyl-2-(4-trifluoromethoxy-phenyl)-2-aza-spiro[4.5]decan-1-one was isolated in a low yield of 13%. MS (m/e)=438.3 [MH⁺].

Example 52

(5α,8α)-8-Phenylsulfanyl-2-(4-trifluoromethoxy-phenyl)-2-aza-spiro[4.5]decan-1-one

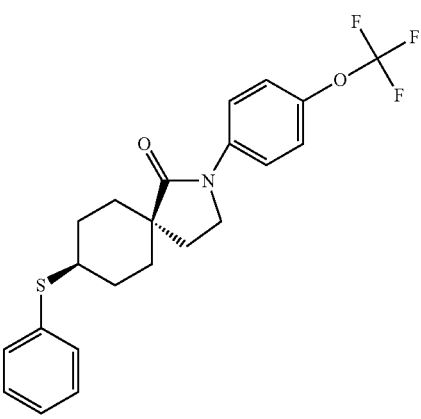 [SMILES: O=C1N(c2ccc(OC(F)(F)F)cc2)CC[C@]12CC[C@H](Sc1ccccc1)CC2]

Step 1: Methanesulfonic acid [(5α,8β)-1-oxo-2-(4-trifluoromethoxy-phenyl)-2-aza-spiro[4.5]dec-8-yl] ester The title compound was prepared in analogy to example 49 from (5α,8β)-8-hydroxy-2-(4-trifluoromethoxy-phenyl)-2-aza-spiro[4.5]decan-1-one (obtained in example 1, step 4) by treatment with methanesulfonyl chloride. MS (m/e)=408.2 [MH$^+$].

Step 2: (5α,8α)-8-Phenylsulfanyl-2-(4-trifluoromethoxy-phenyl)-2-aza-spiro[4.5]decan-1-one The title compound was prepared using similar reaction conditions as described in example 50 for the diastereomeric compound: Methanesulfonic acid [(5α,8β)-1-oxo-2-(4-trifluoromethoxy-phenyl)-2-aza-spiro[4.5]dec-8-yl]ester (42 mg, obtained in example 52, step 1) was dissolved in DMF (5 mL). To this solution, sodium thiophenolate (29 mg) was added and the mixture was heated to 100° C. for 16 hours. The mixture was cooled, diluted with water and extracted with ethyl acetate. The organic layer was washed with brine, dried over Na$_2$SO$_4$ and evaporated. The residue was purified by flash chromatography (silica gel, gradient of heptane/ethyl acetate 1:1) to give the title compound as a colorless s solid (28 mg, 62%) MS (m/e)=422.1 [MH$^+$].

Example 53

(5α,8β)-8-Benzenesulfonyl-2-(4-trifluoromethoxy-phenyl)-2-aza-spiro[4.5]decan-1-one

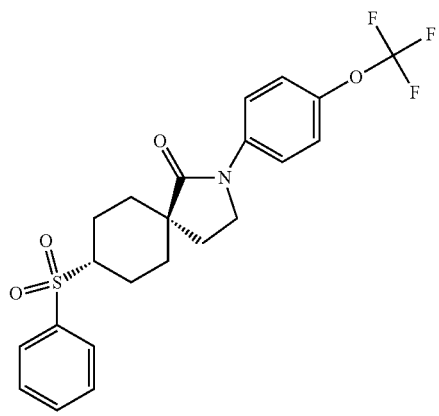 [SMILES: O=C1N(c2ccc(OC(F)(F)F)cc2)CC[C@]12CC[C@@H](S(=O)(=O)c1ccccc1)CC2]

Step 1: (5α,8β)-8-Phenylsulfanyl-2-(4-trifluoromethoxy-phenyl)-2-aza-spiro[4.5]decan-1-one Sodium thiophenolate (22 mg) was added to a solution of methanesulfonic acid [(5α,8α)-1-oxo-2-(4-trifluoromethoxy-phenyl)-2-aza-spiro[4.5]dec-8-yl]ester (34 mg, obtained in example 49) in DMF (5 mL). The mixture was heated to 100° C. for 12 hours. The reaction mixture was cooled, poured into ice/water and extracted two times with ethyl acetate. The combined organic layers were washed with brine, dried over Na$_2$SO$_4$, filtered and the solvent was evaporated. The title compound (5α,8β)-8-phenylsulfanyl-2-(4-trifluoromethoxy-phenyl)-2-aza-spiro[4.5]decan-1-one was obtained as an inseparable mixture together with 2-(4-trifluoromethoxy-phenyl)-2-aza-spiro[4.5]dec-7-en-1-one (ratio approx. 1/1) as a light yellow solid (15 mg, 22%). This mixture was used without further purification and analysis.

Step 2: (5α,8β)-8-Benzenesulfonyl-2-(4-trifluoromethoxy-phenyl)-2-aza-spiro[4.5]decan-1-one The mixture containing (5α,8β)-8-phenylsulfanyl-2-(4-trifluoromethoxy-phenyl)-2-aza-spiro[4.5]decan-1-one (15 mg, obtained in example 53, step 1) was dissolved in dichloromethane (2 mL). The mixture was cooled to 0° C. and 3-chloroperbenzoic acid (7 mg) was added to the cold solution. The mixture was stirred at 0° C. for 90 minutes. The reaction mixture was poured into ice/water and extracted two times with ethyl acetate. The combined organic layers were washed with brine, dried over Na$_2$SO$_4$, filtered and the solvent was evaporated. The residue was purified by flash chromatography (silica gel, heptane/ethyl acetate=6:4) to provide (5α,8β)-8-benzenesulfonyl-2-(4-trifluoromethoxy-phenyl)-2-aza-spiro[4.5]decan-1-one as a colorless solid (4.3 mg, 53%). MS (m/e)=454.2 [MH$^+$].

Example 54

2-(4-Trifluoromethoxy-phenyl)-2-aza-spiro[4.5]decane-1,8-dione

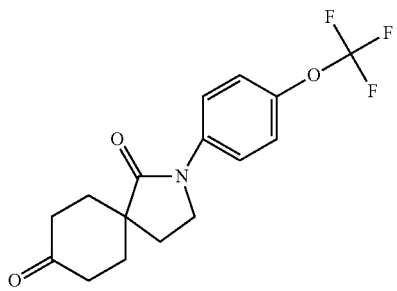 [SMILES: O=C1CCC2(CC1)CCN(c1ccc(OC(F)(F)F)cc1)C2=O]

To a solution of (5α,8β)-8-hydroxy-2-(4-trifluoromethoxy-phenyl)-2-aza-spiro[4.5]decan-1-one (1.29 g, obtained in example 1, step 4) and 2,2,6,6-tetramethylpiperidine-1-oxyl (102 mg) in dichloromethane (80 mL) was added a solution of potassium bromide (75 mg) in water (13 mL). Sodium hypochlorite (8.99 mL) and sodium bicarbonate (990 mg) were added to the reaction mixture. The mixture was stirred for 1 hour at r.t. The reaction mixture was poured into ice/water and extracted three times with CH$_2$Cl$_2$. The combined organic layers were washed with brine, dried over Na$_2$SO$_4$, filtered and the solvent was evaporated. The residue was purified by flash chromatography (silica gel, gradient of heptane in ethyl acetate) to give the title compound as an off-white solid (1.25 g, 97%). MS (m/e)=328.2 [MH$^+$].

Example 55

(5α,8α)-8-Hydroxy-8-propyl-2-(4-trifluoromethoxy-phenyl)-2-aza-spiro[4.5]decan-1-one

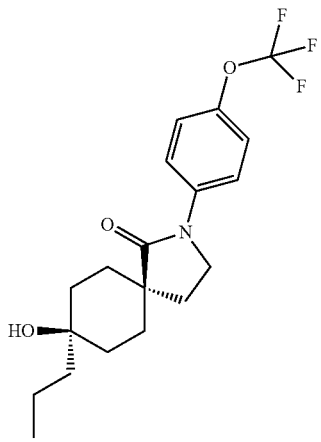 [SMILES: CCC[C@]1(O)CC[C@]2(CCN(c3ccc(OC(F)(F)F)cc3)C2=O)CC1]

Anhydrous cerous(III)-chloride (565 mg) in THF (12 mL) was cooled to 0° C. and propylmagnesium chloride (2.0M in diethyl ether, 1.15 mL) was added dropwise over a period of 5 minutes to the cold suspension. The mixture was stirred at 0° C. for 90 minutes. Then, 2-(4-trifluoromethoxy-phenyl)-2-aza-spiro[4.5]decane-1,8-dione (250 mg, obtained in example 54) was added in two portions over a period of 5 minutes to the reaction mixture. Stirring was continued at 0° C. for 2 hours. The reaction mixture was poured into ice/water and acidified with acetic acid (1 mL). The aqueous phase was then extracted two times with ethyl acetate and the organic layers were washed with saturated NaHCO₃ solution and brine, dried over Na₂SO₄, and filtered. The solvent was evaporated and the residue was purified by flash chromatography (silica gel, gradient of heptane in ethyl acetate) to give the title compound as a colorless solid (94 mg, 33%). MS (m/e)=394.2 [MNa⁺].

In the chromatographic purification step, the trans compound (5α,8β)-8-hydroxy-8-propyl-2-(4-trifluoromethoxy-phenyl)-2-aza-spiro[4.5]decan-1-one (116 mg, 41%) was also isolated (see example 56)

Example 56

(5α,8β)-8-Hydroxy-8-propyl-2-(4-trifluoromethoxy-phenyl)-2-aza-spiro[4.5]decan-1-one

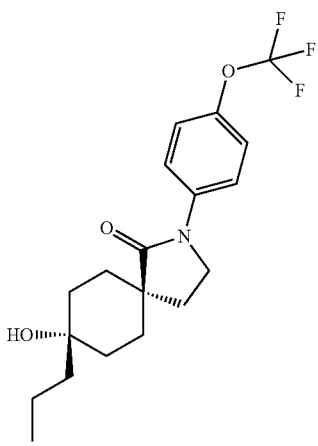 [SMILES: CCC[C@]1(O)CC[C@@]2(CCN(c3ccc(OC(F)(F)F)cc3)C2=O)CC1]

The title compound was isolated from the reaction providing example 55 as a colorless solid (116 mg, 41%). MS (m/e)=372.2 [MH⁺].

Example 57

(5α,8α)-8-Hydroxy-8-methyl-2-(4-trifluoromethoxy-phenyl)-2-aza-spiro[4.5]decan-1-one

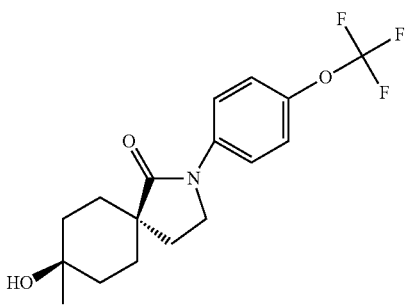 [SMILES: C[C@]1(O)CC[C@]2(CCN(c3ccc(OC(F)(F)F)cc3)C2=O)CC1]

The title compound was prepared in analogy to example 55 from 2-(4-trifluoromethoxy-phenyl)-2-aza-spiro[4.5]decane-1,8-dione (obtained in example 54) by reaction with methylmagnesium bromide (3M in diethyl ether). MS (m/e)= 344.3 [MH⁺].

Example 58

(5α,8β)-8-Hydroxy-8-methyl-2-(4-trifluoromethoxy-phenyl)-2-aza-spiro[4.5]decan-1-one

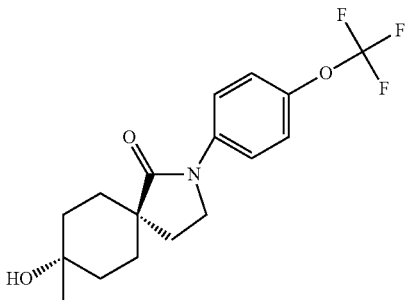 [SMILES: C[C@]1(O)CC[C@@]2(CCN(c3ccc(OC(F)(F)F)cc3)C2=O)CC1]

The title compound was prepared as described for example 56 from 2-(4-trifluoromethoxy-phenyl)-2-aza-spiro[4.5]decane-1,8-dione (obtained in example 54) by reaction with methylmagnesium bromide (3M in diethyl ether). MS (m/e)= 344.3 [MH⁺].

Example 59

8-Methyl-2-(4-trifluoromethoxy-phenyl)-2-aza-spiro[4.5]dec-7-en-1-one

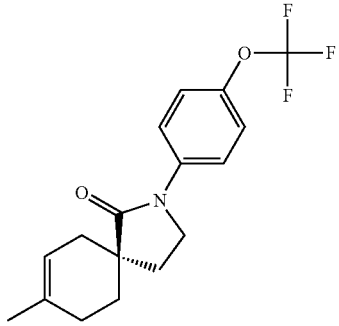 [SMILES: CC1=CC[C@@]2(CC1)CCN(c1ccc(OC(F)(F)F)cc1)C2=O]

Step 1: 4-(2-Methoxy-ethyl)-1-methyl-2-oxa-bicyclo[2.2.2]octan-3-one

Methylmagnesium bromide (3.0M in diethyl ether, 1.22 mL) was dissolved in THF (5 mL). The mixture was cooled to 0° C. and a solution of 1-(2-methoxy-ethyl)-4-oxo-cyclohexanecarboxylic acid ethyl ester (350 mg, obtained in example 1, step 2) in THF (5 mL) was added dropwise over a period of 5 minutes. The resulting mixture was stirred at 0° C. for 3 hours. The reaction mixture was poured into ice/water and acidified with sat. NH₄Cl. The aqueous phase was extracted two times with ethyl acetate and the organic layers were washed with brine, dried over Na₂SO₄, filtered and the solvent was evaporated. The residue was purified by flash chromatography (silica gel, gradient of heptane in ethyl acetate) to give the title compound as a colorless liquid (67 mg, 22%). ¹H-NMR (δ, CDCl₃): 3.55 (t, 2H); 3.31 (s, 3H); 1.86 (t, 2H); 1.84-1.73 (m, 8H); 1.39 (s, 3H).

Step 2: 8-Methyl-2-(4-trifluoromethoxy-phenyl)-2-aza-spiro[4.5]dec-7-en-1-one 4-(Trifluoromethoxy)-aniline (0.065 mL, [CAS Reg. No. 461-82-5]) was added to a solution of 4-(2-methoxy-ethyl)-1-methyl-2-oxa-bicyclo[2.2.2]octan-3-one (64 mg, obtained in example 59, step 1) in toluene (5 mL). The mixture was stirred for 10 minutes at r.t. Then, dimethylaluminiumchloride (1M in hexane, 0.65 mL) was added dropwise over a period of 5 minutes. The reaction mixture was stirred at reflux for 3 hours. The reaction mixture was cooled, poured into ice/water and extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give 8-methyl-2-(4-trifluoromethoxy-phenyl)-2-aza-spiro[4.5]dec-7-en-1-one as a light yellow solid as the main product (81 mg, 77%). MS (m/e)=326.4 [MH$^+$]. From this reaction, a small amount of (5α,8α)-8-hydroxy-8-methyl-2-(4-trifluoromethoxy-phenyl)-2-aza-spiro[4.5]decan-1-one (see example 57) was also isolated (6 mg, 5%).

Example 60

(5α,8α)-8-Ethyl-8-hydroxy-2-(4-trifluoromethoxy-phenyl)-2-aza-spiro[4.5]decan-1-one

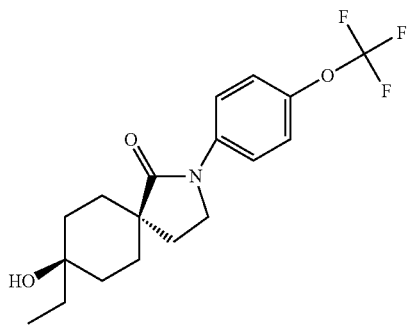 [SMILES: CC[C@]1(O)CC[C@]2(CCN(c3ccc(OC(F)(F)F)cc3)C2=O)CC1]

The title compound was prepared in analogy to example 55 from 2-(4-trifluoromethoxy-phenyl)-2-aza-spiro[4.5]decane-1,8-dione (obtained in example 54) by reaction with ethylmagnesium bromide (3M in diethyl ether). MS (m/e)= 358.2 [MH$^+$].

Example 61

(5α,8β)-8-Ethyl-8-hydroxy-2-(4-trifluoromethoxy-phenyl)-2-aza-spiro[4.5]decan-1-one

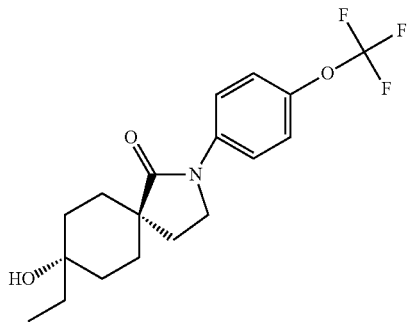 [SMILES: CC[C@]1(O)CC[C@@]2(CCN(c3ccc(OC(F)(F)F)cc3)C2=O)CC1]

The title compound was prepared as described for example 56 from 2-(4-trifluoromethoxy-phenyl)-2-aza-spiro[4.5]decane-1,8-dione (obtained in example 54) by reaction with ethylmagnesium bromide (3M in diethyl ether). MS (m/e)= 358.2 [MH$^+$].

Example 62

(5α,8α)-8-Benzyl-8-hydroxy-2-(4-trifluoromethoxy-phenyl)-2-aza-spiro[4.5]decan-1-one

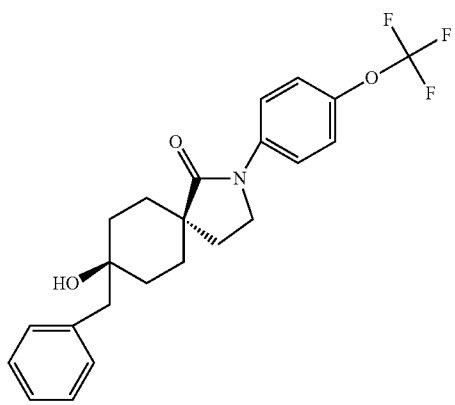 [SMILES: O=C1N(c2ccc(OC(F)(F)F)cc2)CC[C@]12CC[C@@](O)(Cc1ccccc1)CC2]

The title compound was prepared in analogy to example 55 from 2-(4-trifluoromethoxy-phenyl)-2-aza-spiro[4.5]decane-1,8-dione (obtained in example 54) by reaction with benzylmagnesium bromide (1M in THF). MS (m/e)=420.2 [MH$^+$].

Example 63

(5α,8β)-8-Benzyl-8-hydroxy-2-(4-trifluoromethoxy-phenyl)-2-aza-spiro[4.5]decan-1-one

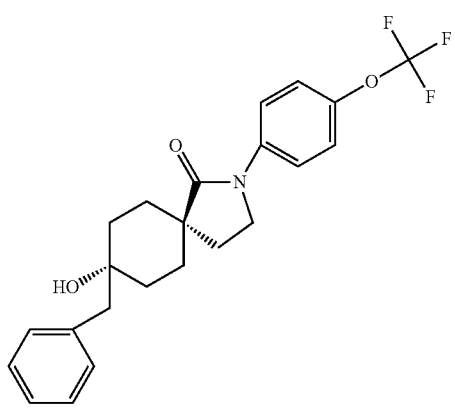 [SMILES: O=C1N(c2ccc(OC(F)(F)F)cc2)CC[C@]12CC[C@](O)(Cc1ccccc1)CC2]

The title compound was prepared as described for example 56 from 2-(4-trifluoromethoxy-phenyl)-2-aza-spiro[4.5]decane-1,8-dione (obtained in example 54) by reaction with benzylmagnesium bromide (1M in THF). MS (m/e)=420.2 [MH$^+$].

Example 64

(5α,8α)-8-But-3-enyl-8-hydroxy-2-(4-trifluoromethoxy-phenyl)-2-aza-spiro[4.5]decan-1-one

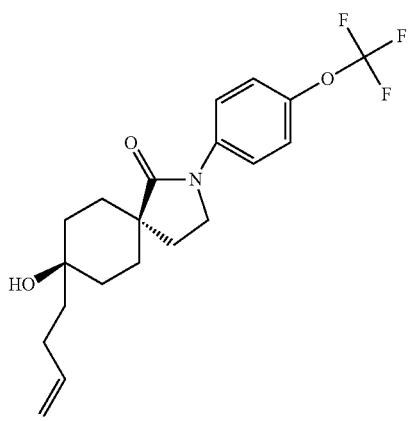 [SMILES: C=CCC[C@]1(O)CC[C@]2(CCN(c3ccc(OC(F)(F)F)cc3)C2=O)CC1]

Magnesium shavings (44 mg) were added to THF (10 mL), followed by five drops of a solution of bromomethylcyclopropane (0.20 mL, [CAS Reg. No. 7051-34-5]) in THF (5 mL). Three iodine crystals were added to the resulting red solution and the remainder of the bromomethylcyclopropane solution in THF was added dropwise over a period of 5 minutes. The mixture was heated to 60° C. and the mixture turned colorless. Stirring was continued for 1 hour at 45° C. The mixture was cooled to 0° C. and anhydrous cerous(III)-chloride (271 mg) was added. The mixture was stirred at 0° C. for 90 minutes. Then, a solution of 2-(4-trifluoromethoxy-phenyl)-2-aza-spiro[4.5]decane-1,8-dione (90 mg, obtained in example 54) in THF (3 mL) was added dropwise over a period of 5 minutes to the cold reaction mixture. The mixture was stirred for 1 hour at 0° C. and then for 45 minutes at r.t. The reaction mixture was poured into ice/water and acidified with acetic acid (0.30 mL). The aqueous phase was then extracted two times with ethyl acetate and the organic layers were washed with sat. NaHCO$_3$ solution and brine, dried over Na$_2$SO$_4$, filtered and the solvent was evaporated. The residue was purified by flash chromatography (silica gel, gradient of heptane in ethyl acetate). Instead of the expected compound (5α,8α)-8-cyclopropylmethyl-8-hydroxy-2-(4-trifluoromethoxy-phenyl)-2-aza-spiro[4.5]decan-1-one, (5α,8α)-8-but-3-enyl-8-hydroxy-2-(4-trifluoromethoxy-phenyl)-2-aza-spiro[4.5]decan-1-one was isolated as the main product as a colorless solid (34 mg, 32%). MS (m/e)=384.1 [MH$^+$].

In the chromatographic purification step, the trans compound (5α,8β)-8-but-3-enyl-8-hydroxy-2-(4-trifluoromethoxy-phenyl)-2-aza-spiro[4.5]decan-1-one (11 mg, 10%) was also isolated (see example 65).

Example 65

(5α,8β)-8-But-3-enyl-8-hydroxy-2-(4-trifluoromethoxy-phenyl)-2-aza-spiro[4.5]decan-1-one

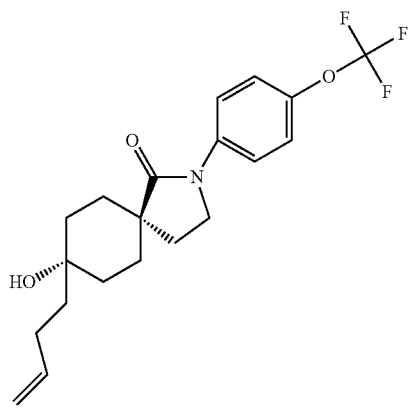 [SMILES: C=CCC[C@]1(O)CC[C@@]2(CCN(c3ccc(OC(F)(F)F)cc3)C2=O)CC1]

The title compound was isolated from the reaction providing example 64 where 2-(4-trifluoromethoxy-phenyl)-2-aza-spiro[4.5]decane-1,8-dione (obtained in example 54) was treated with cyclopropylmethylmagnesium bromide. (5α,8β)-8-But-3-enyl-8-hydroxy-2-(4-trifluoromethoxy-phenyl)-2-aza-spiro[4.5]decan-1-one was obtained in the form of a colorless solid (11 mg, 10%). MS (m/e)=384.1 [MH$^+$].

Example 66

(5α,8α)-8-Butyl-8-hydroxy-2-(4-trifluoromethoxy-phenyl)-2-aza-spiro[4.5]decan-1-one

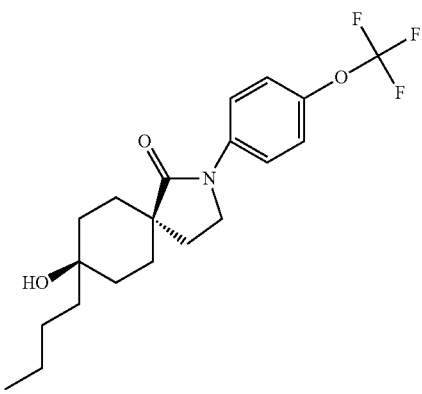 [SMILES: CCCC[C@]1(O)CC[C@]2(CCN(c3ccc(OC(F)(F)F)cc3)C2=O)CC1]

The title compound was prepared in analogy to example 55 from 2-(4-trifluoromethoxy-phenyl)-2-aza-spiro[4.5]decane-1,8-dione (obtained in example 54) and butylmagnesium chloride (2M in THF/toluene). MS (m/e)=386.4 [MH$^+$].

Example 67

(5α,8β)-8-Butyl-8-hydroxy-2-(4-trifluoromethoxy-phenyl)-2-aza-spiro[4.5]decan-1-one

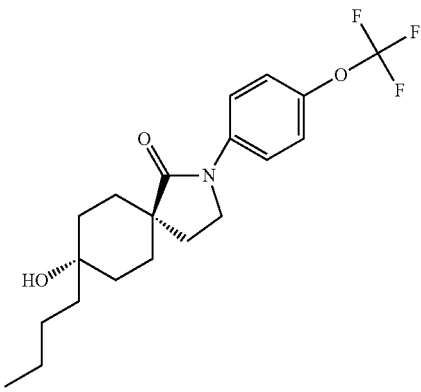 [SMILES: CCCC[C@]1(O)CC[C@@]2(CCN(c3ccc(OC(F)(F)F)cc3)C2=O)CC1]

The title compound was prepared as described in example 56 from 2-(4-trifluoromethoxy-phenyl)-2-aza-spiro[4.5]decane-1,8-dione (obtained in example 54) by reaction with butylmagnesium chloride (2M in THF/toluene). MS (m/e)= 386.4 [MH⁺].

Example 68

(5α,8α)-8-Hydroxy-8-isopropyl-2-(4-trifluoromethoxy-phenyl)-2-aza-spiro[4.5]decan-1-one

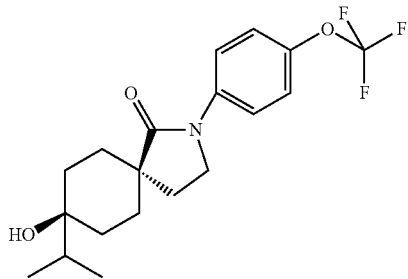 [SMILES: CC(C)[C@]1(O)CC[C@]2(CCN(c3ccc(OC(F)(F)F)cc3)C2=O)CC1]

The title compound was prepared in analogy to example 55 from 2-(4-trifluoromethoxy-phenyl)-2-aza-spiro[4.5]decane-1,8-dione (obtained in example 54) by reaction with isopropylmagnesium bromide (1M in THF). MS (m/e)=372.2 [MH⁺].

Example 69

(5α,8β)-8-Hydroxy-8-isopropyl-2-(4-trifluoromethoxy-phenyl)-2-aza-spiro[4.5]decan-1-one

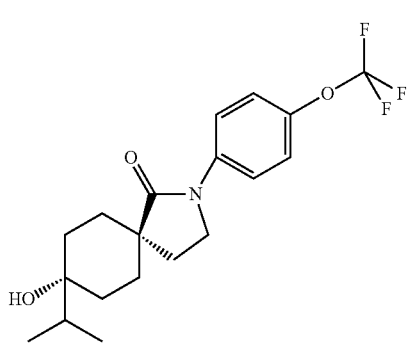 [SMILES: CC(C)[C@]1(O)CC[C@@]2(CCN(c3ccc(OC(F)(F)F)cc3)C2=O)CC1]

The title compound was prepared as described for example 56 from 2-(4-trifluoromethoxy-phenyl)-2-aza-spiro[4.5]decane-1,8-dione (obtained in example 54) by reaction with isopropylmagnesium bromide (1M in THF). MS (m/e)=372.2 [MH⁺].

Example 70

(5α,8α)-8-Cyclopropyl-8-hydroxy-2-(4-trifluoromethoxy-phenyl)-2-aza-spiro[4.5]decan-1-one

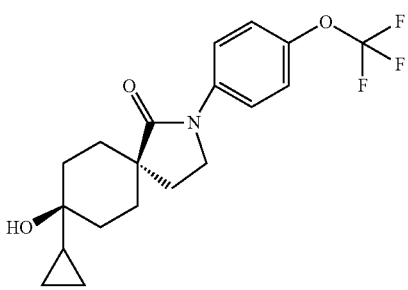 [SMILES: O=C1N(c2ccc(OC(F)(F)F)cc2)CC[C@]12CC[C@@](O)(C1CC1)CC2]

The title compound was prepared in analogy to example 55 from 2-(4-trifluoromethoxy-phenyl)-2-aza-spiro[4.5]decane-1,8-dione (obtained in example 54) by reaction with cyclopropylmagnesium bromide (0.5M in THF) in very low yield. MS (m/e)=370.4 [MH⁺].

Example 71

(5α,8α)-8-Hydroxy-8-(3-methoxy-prop-1-ynyl)-2-(4-trifluoromethoxy-phenyl)-2-aza-spiro[4.5]decan-1-one

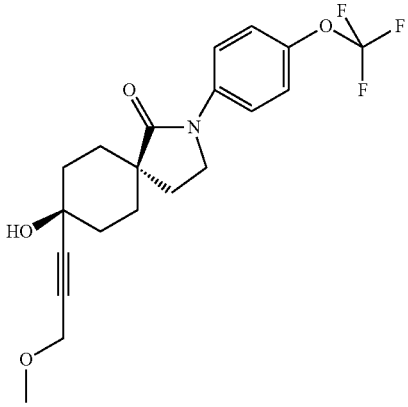 [SMILES: COCC#C[C@]1(O)CC[C@]2(CCN(c3ccc(OC(F)(F)F)cc3)C2=O)CC1]

Methylpropargyl ether (0.041 mL) was dissolved in diethyl ether (10 mL). The mixture was cooled to 0° C. and methyl-lithium (1.6M in diethyl ether, 0.51 mL) was added dropwise over a period of 5 minutes. Stirring was continued at 0° C. for 10 minutes. A solution of 2-(4-trifluoromethoxy-phenyl)-2-aza-spiro[4.5]decane-1,8-dione (200 mg, obtained in example 54) in diethyl ether (7 mL) was added dropwise over a period of 10 minutes. The mixture was then stirred at reflux for 18 hours. The reaction mixture was cooled, poured into ice/water and acidified with saturated NH₄Cl. The aqueous phase was extracted two times with diethyl ether and the organic layers were washed with brine, dried over Na₂SO₄, filtered and the solvent was evaporated. The residue was purified by flash chromatography (silica gel, dichloromethane/acetonitrile=95/5) to give the title compound as an off-white solid (29 mg, 12%). MS (m/e)=398.2 [MH⁺].

In the chromatographic purification step the trans compound (5α,8β)-8-hydroxy-8-(3-methoxy-prop-1-ynyl)-2-(4-trifluoromethoxy-phenyl)-2-aza-spiro[4.5]decan-1-one (32 mg, 13%) was also isolated (see example 72).

Example 72

(5α,8β)-8-Hydroxy-8-(3-methoxy-prop-1-ynyl)-2-(4-trifluoromethoxy-phenyl)-2-aza-spiro[4.5]decan-1-one

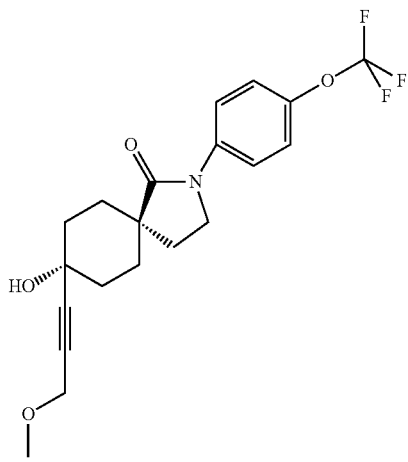 [SMILES: COCC#C[C@]1(O)CC[C@@]2(CCN(c3ccc(OC(F)(F)F)cc3)C2=O)CC1]

The title compound was isolated from the reaction providing example 71 (treatment of 2-(4-trifluoromethoxy-phenyl)-2-aza-spiro[4.5]decane-1,8-dione (obtained in example 54) with 3-methoxy-prop-1-yn-1-yl lithium). This material was obtained as an off-white solid (32 mg, 13%). MS (m/e)=398.2 [MH⁺].

Example 73

(5α,8α)-2-(4-Cyclopropyl-phenyl)-8-hydroxy-8-methyl-2-aza-spiro[4.5]decan-1-one

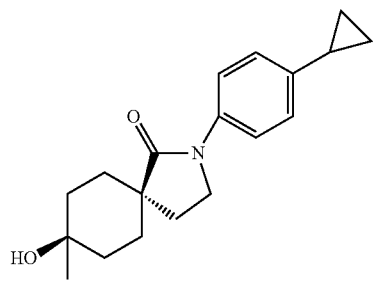 [SMILES: C[C@]1(O)CC[C@]2(CCN(c3ccc(C4CC4)cc3)C2=O)CC1]

Step 1: (5α,8β)-2-(4-Cyclopropyl-phenyl)-8-hydroxy-2-aza-spiro[4.5]decan-1-one

The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-cyclopropylaniline [CAS Reg. No. 3158-71-2]. MS (m/e)=286.4 [MH⁺].

Step 2: 2-(4-Cyclopropyl-phenyl)-2-aza-spiro[4.5]decan-1,8-dione

The title compound was prepared in analogy to example 54 by oxidation of (5α,8β)-2-(4-cyclopropyl-phenyl)-8-hydroxy-2-aza-spiro[4.5]decan-1-one (obtained in example 73, step 1). MS (m/e)=284.2 [MH⁺].

Step 3: (5α,8α)-2-(4-Cyclopropyl-phenyl)-8-hydroxy-8-methyl-2-aza-spiro[4.5]decan-1-one The title compound was prepared in analogy to example 55 from 2-(4-cyclopropyl-phenyl)-2-aza-spiro[4.5]decane-1,8-dione (obtained in example 73, step 2) by treatment with methylmagnesium bromide (3M in diethyl ether). MS (m/e)=300.1 [MH⁺].

Example 74

(5α,8β)-2-(4-Cyclopropyl-phenyl)-8-hydroxy-8-methyl-2-aza-spiro[4.5]decan-1-one

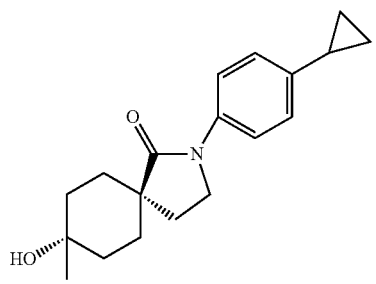 [SMILES: C[C@]1(O)CC[C@@]2(CCN(c3ccc(C4CC4)cc3)C2=O)CC1]

The title compound was prepared as described in example 56 from 2-(4-cyclopropyl-phenyl)-2-aza-spiro[4.5]decane-1,8-dione (obtained in example 73, step 2) by treatment with methylmagnesium bromide (3M in diethyl ether). MS (m/e)=300.1 [MH⁺].

Example 75

(5α,8α)-2-(4-Cyclopropyl-phenyl)-8-hydroxy-8-propyl-2-aza-spiro[4.5]decan-1-one

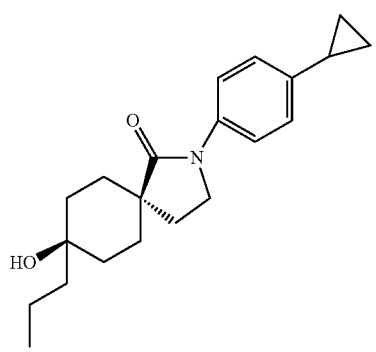 [SMILES: CCC[C@]1(O)CC[C@]2(CCN(c3ccc(C4CC4)cc3)C2=O)CC1]

The title compound was prepared in analogy to example 55 from 2-(4-cyclopropyl-phenyl)-2-aza-spiro[4.5]decane-1,8- dione (obtained in example 73, step 2) and propylmagnesium chloride (2M in diethyl ether). MS (m/e)=328.2 [MH⁺].

Example 76

(5α,8β)-2-(4-Cyclopropyl-phenyl)-8-hydroxy-8-propyl-2-aza-spiro[4.5]decan-1-one

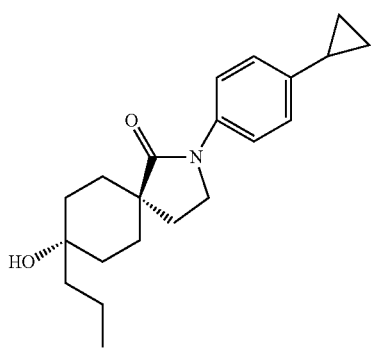 [SMILES: CCC[C@]1(O)CC[C@@]2(CCN(c3ccc(C4CC4)cc3)C2=O)CC1]

The title compound was prepared as described in example 56 from 2-(4-cyclopropyl-phenyl)-2-aza-spiro[4.5]decane-1,8-dione (obtained in example 73, step 2) by treatment with propylmagnesium chloride (2M in diethyl ether). MS (m/e)=328.2 [MH⁺].

Example 77

(5α,8α)-8-Hydroxy-8-methyl-2-[4-(2,2,2-trifluoro-ethyl)-phenyl]-2-aza-spiro[4.5]decan-1-one

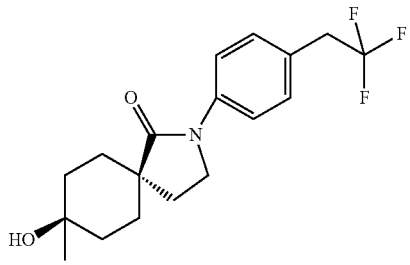 [SMILES: C[C@]1(O)CC[C@]2(CCN(c3ccc(CC(F)(F)F)cc3)C2=O)CC1]

Step 1: (5α,8β)-8-Hydroxy-2-[4-(2,2,2-trifluoro-ethyl)-phenyl]-2-aza-spiro[4.5]decan-1-one The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(2,2,2-trifluoromethyl)-aniline [CAS Reg. No. 131395-17-0]. MS (m/e)=328.3 [MH⁺].

Step 2: 2-[4-(2,2,2-Trifluoro-ethyl)-phenyl]-2-aza-spiro[4.5]decane-1,8-dione

The title compound was prepared in analogy to example 54 by oxidation of (5α,8β)-8-hydroxy-2-[4-(2,2,2-trifluoro-ethyl)-phenyl]-2-aza-spiro[4.5]decan-1-one (obtained in example 77, step 1). MS (m/e)=326.2 [MH⁺].

Step 3: (5α,8α)-8-Hydroxy-8-methyl-2-[4-(2,2,2-trifluoro-ethyl)-phenyl]-2-aza-spiro[4.5]decan-1-one The title compound was prepared in analogy to example 55 from 2-[4-(2,2,2-trifluoro-ethyl)-phenyl]-2-aza-spiro[4.5]decane-1,8-dione (obtained in example 77, step 2) by treatment with methylmagnesium bromide (3M in diethyl ether). MS (m/e)=342.1 [MH⁺].

Example 78

(5α,8β)-8-Hydroxy-8-methyl-2-[4-(2,2,2-trifluoro-ethyl)-phenyl]-2-aza-spiro[4.5]decan-1-one

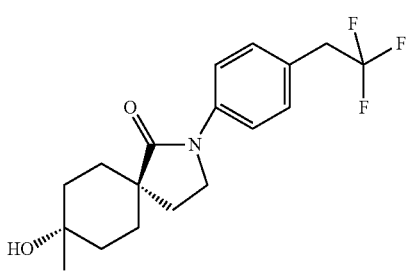 [SMILES: C[C@]1(O)CC[C@@]2(CCN(c3ccc(CC(F)(F)F)cc3)C2=O)CC1]

The title compound was prepared as described in example 56 from 2-[4-(2,2,2-trifluoro-ethyl)-phenyl]-2-aza-spiro[4.5]decane-1,8-dione (obtained in example 77, step 2) by treatment with methylmagnesium bromide (3M in diethyl ether). MS (m/e)=342.1 [MH⁺].

Example 79

(5α,8α)-8-Ethyl-8-hydroxy-2-[4-(2,2,2-trifluoro-ethyl)-phenyl]-2-aza-spiro[4.5]decan-1-one

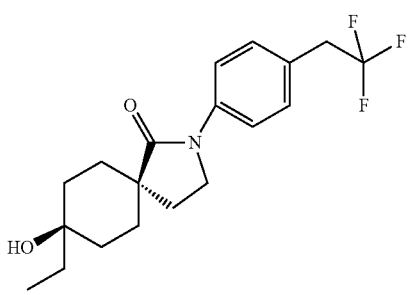 [SMILES: CC[C@]1(O)CC[C@]2(CCN(c3ccc(CC(F)(F)F)cc3)C2=O)CC1]

The title compound was prepared in analogy to example 55 from 2-[4-(2,2,2-trifluoro-ethyl)-phenyl]-2-aza-spiro[4.5]decane-1,8-dione (obtained in example 77, step 2) by treatment with ethylmagnesium bromide (3M in diethyl ether). MS (m/e)=356.4 [MH⁺].

Example 80

(5α,8β)-8-Ethyl-8-hydroxy-2-[4-(2,2,2-trifluoro-ethyl)-phenyl]-2-aza-spiro[4.5]decan-1-one

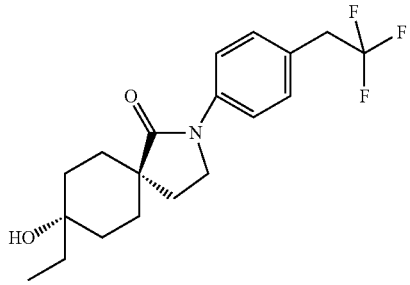 [SMILES: CC[C@]1(O)CC[C@@]2(CCN(c3ccc(CC(F)(F)F)cc3)C2=O)CC1]

The title compound was prepared as described in example 56 from 2-[4-(2,2,2-trifluoro-ethyl)-phenyl]-2-aza-spiro[4.5]decane-1,8-dione (obtained in example 77, step 2) by treatment with ethylmagnesium bromide (3M in diethyl ether). MS (m/e)=356.4 [MH$^+$].

Example 81

(5α,8α)-8-Hydroxy-8-propyl-2-[4-(2,2,2-trifluoro-ethyl)-phenyl]-2-aza-spiro[4.5]decan-1-one

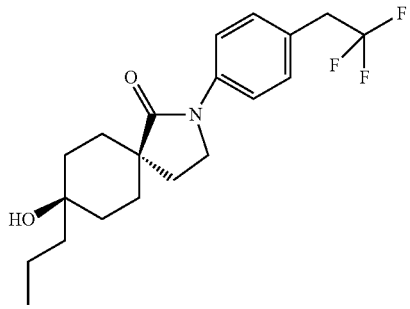 [SMILES: CCC[C@]1(O)CC[C@]2(CCN(c3ccc(CC(F)(F)F)cc3)C2=O)CC1]

The title compound was prepared in analogy to example 55 from 2-[4-(2,2,2-trifluoro-ethyl)-phenyl]-2-aza-spiro[4.5]decane-1,8-dione (obtained in example 77, step 2) by treatment with propylmagnesium chloride (2M in diethyl ether). MS (m/e)=370.1 [MH$^+$].

Example 82

(5α,8β)-8-Hydroxy-8-propyl-2-[4-(2,2,2-trifluoro-ethyl)-phenyl]-2-aza-spiro[4.5]decan-1-one

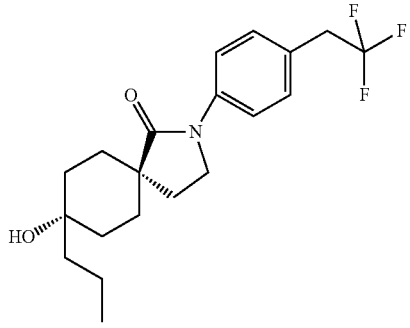 [SMILES: CCC[C@]1(O)CC[C@@]2(CCN(c3ccc(CC(F)(F)F)cc3)C2=O)CC1]

The title compound was prepared as described in example 56 from 2-[4-(2,2,2-trifluoro-ethyl)-phenyl]-2-aza-spiro[4.5]decane-1,8-dione (obtained in example 77, step 2) by treatment with propylmagnesium chloride (2M in diethyl ether). MS (m/e)=370.1 [MH$^+$].

Example 83

(5α,8α)-8-Ethyl-8-hydroxy-2-(4-propyl-phenyl)-2-aza-spiro[4.5]decan-1-one

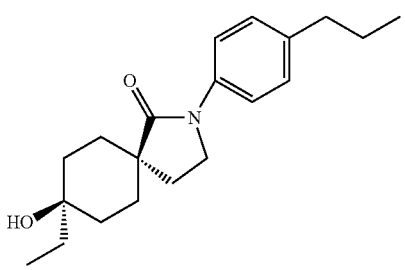 [SMILES: CCCc1ccc(N2CC[C@]3(CC[C@@](O)(CC)CC3)C2=O)cc1]

Step 1: 2-(4-Propyl-phenyl)-2-aza-spiro[4.5]decane-1,8-dione

The title compound was prepared in analogy to example 54 by oxidation of (5α,8α)-8-hydroxy-2-(4-propyl-phenyl)-2-aza-spiro[4.5]decan-1-one (obtained in example 37). MS (m/e)=286.2 [MH$^+$].

Step 2: (5α,8α)-8-Ethyl-8-hydroxy-2-(4-propyl-phenyl)-2-aza-spiro[4.5]decan-1-one The title compound was prepared in analogy to example 55 from 2-(4-propyl-phenyl)-2-aza-spiro[4.5]decane-1,8-dione (obtained in example 83, step 1) by treatment with ethylmagnesium bromide (3M in diethyl ether). MS (m/e)=298.5 [(M-H$_2$O)H$^+$].

Example 84

(5α,8β)-8-Ethyl-8-hydroxy-2-(4-propyl-phenyl)-2-aza-spiro[4.5]decan-1-one

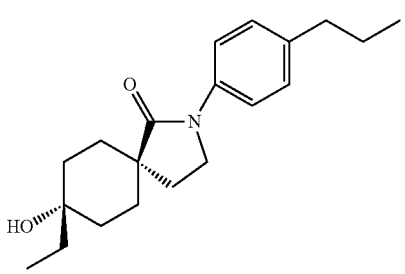 [SMILES: CCCc1ccc(N2CC[C@]3(CC[C@](O)(CC)CC3)C2=O)cc1]

The title compound was prepared as described in example 56 from 2-(4-propyl-phenyl)-2-aza-spiro[4.5]decane-1,8-dione (obtained in example 83, step 1) by treatment with ethylmagnesium bromide (3M in diethyl ether). MS (m/e)=316.3 [MH$^+$].

Example 85

(5α,8β)-8-Hydroxy-2-[4-(2,2,2-trifluoro-ethoxy)-phenyl]-2-aza-spiro[4.5]decan-1-one

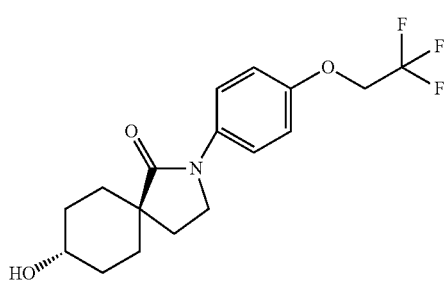 [SMILES: O=C1N(c2ccc(OCC(F)(F)F)cc2)CC[C@]12CC[C@@H](O)CC2]

The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(2,2,2-trifluoroethoxy)-aniline [CAS Reg. No. 57946-61-9]. MS (m/e)=344.4 [MH$^+$].

Example 86

(5α,8α)-8-Hydroxy-8-methyl-2-[4-(2,2,2-trifluoro-ethoxy)-phenyl]-2-aza-spiro[4.5]decan-1-one

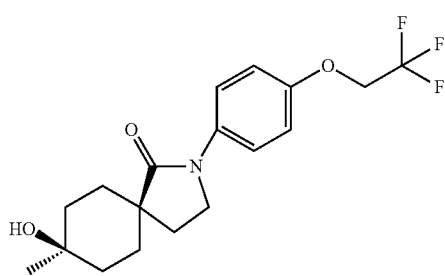 [SMILES: C[C@]1(O)CC[C@]2(CCN(c3ccc(OCC(F)(F)F)cc3)C2=O)CC1]

Step 1: 2-[4-(2,2,2-Trifluoro-ethoxy)-phenyl]-2-aza-spiro[4.5]decane-1,8-dione

The title compound was prepared in analogy to example 54 by oxidation of (5α,8β)-8-hydroxy-2-[4-(2,2,2-trifluoro-ethoxy)-phenyl]-2-aza-spiro[4.5]decan-1-one (obtained in example 85). MS (m/e)=342.1 [MH$^+$].

Step 2: (5α,8α)-8-Hydroxy-8-methyl-2-[4-(2,2,2-trifluoro-ethoxy)-phenyl]-2-aza-spiro[4.5]decan-1-one The title compound was prepared in analogy to example 55 from 2-[4-(2,2,2-trifluoro-ethoxy)-phenyl]-2-aza-spiro[4.5]decane-1,8-dione (obtained in example 86, step 1) by treatment with methylmagnesium bromide (3M in diethyl ether). MS (m/e)=340.2 [(M-H$_2$O)H$^+$].

Example 87

(5α,8β)-8-Hydroxy-8-methyl-2-[4-(2,2,2-trifluoro-ethoxy)-phenyl]-2-aza-spiro[4.5]decan-1-one

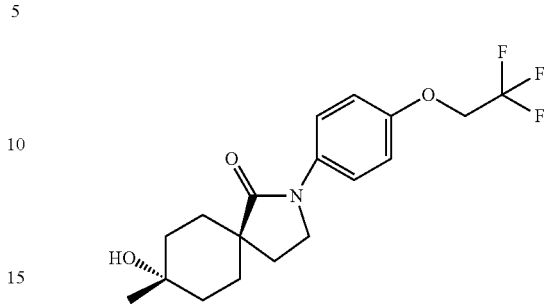

The title compound was prepared as described in example 56 from 2-[4-(2,2,2-trifluoro-ethoxy)-phenyl]-2-aza-spiro[4.5]decane-1,8-dione (obtained in example 86, step 1) by treatment with methylmagnesium bromide (3M in diethyl ether). MS (m/e)=358.3 [MH$^+$].

Example 88

(5α,8α)-8-Ethyl-8-hydroxy-2-[4-(2,2,2-trifluoro-ethoxy)-phenyl]-2-aza-spiro[4.5]decan-1-one

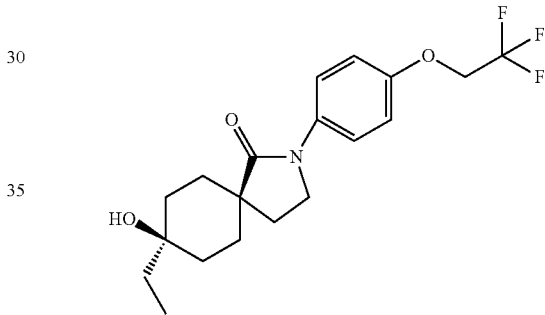

The title compound was prepared in analogy to example 55 from 2-[4-(2,2,2-trifluoro-ethoxy)-phenyl]-2-aza-spiro[4.5]decane-1,8-dione (obtained in example 86, step 1) by treatment with ethylmagnesium bromide (3M in diethyl ether). MS (m/e)=372.2 [MH$^+$].

Example 89

(5α,8β)-8-Ethyl-8-hydroxy-2-[4-(2,2,2-trifluoro-ethoxy)-phenyl]-2-aza-spiro[4.5]decan-1-one

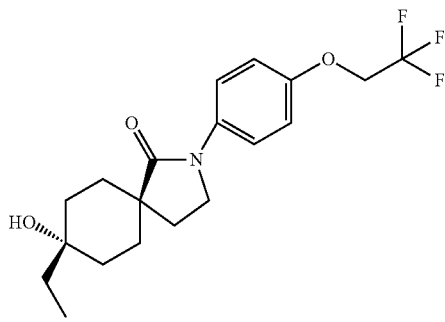 [SMILES: CC[C@]1(O)CC[C@@]2(CCN(c3ccc(OCC(F)(F)F)cc3)C2=O)CC1]

The title compound was prepared as described in example 56 from 2-[4-(2,2,2-trifluoro-ethoxy)-phenyl]-2-aza-spiro[4.5]decane-1,8-dione (obtained in example 86, step 1) by

Example 90

(5α,8α)-8-Hydroxy-8-(3-methoxy-propyl)-2-(4-trifluoromethoxy-phenyl)-2-aza-spiro[4.5]decan-1-one

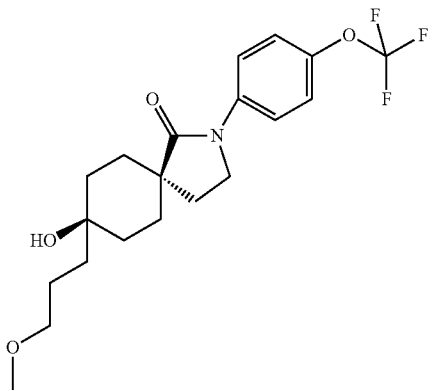 [SMILES: COCCC[C@]1(O)CC[C@]2(CCN(c3ccc(OC(F)(F)F)cc3)C2=O)CC1]

(5α,8α)-8-Hydroxy-8-(3-methoxy-prop-1-ynyl)-2-(4-trifluoromethoxy-phenyl)-2-aza-spiro[4.5]decan-1-one (29 mg, obtained in example 71) was dissolved in ethanol (5 mL). Palladium on activated charcoal (10 mg, 10% Pd) was added and an atmosphere of hydrogen was introduced at r.t. The mixture was stirred under hydrogen for 3 hours at r.t. The reaction mixture was filtered over dicalite speed plus (Acros Organics) and the solvent was evaporated. The residue was purified by flash chromatography (silica gel, gradient of heptane in ethyl acetate) to give the title compound as a colorless solid (12 mg, 41%). MS (m/e)=402.4 [MH$^+$].

Example 91

(5α,8β)-8-Hydroxy-8-(3-methoxy-propyl)-2-(4-trifluoromethoxy-phenyl)-2-aza-spiro[4.5]decan-1-one

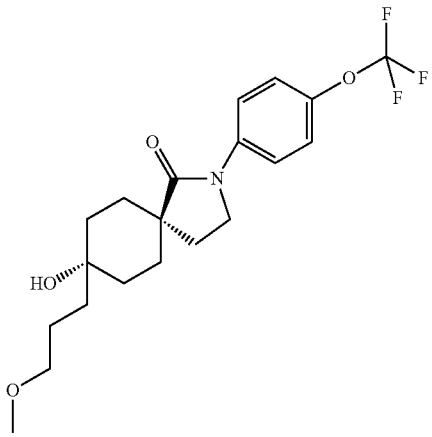 [SMILES: COCCC[C@]1(O)CC[C@@]2(CCN(c3ccc(OC(F)(F)F)cc3)C2=O)CC1]

The title compound was prepared in analogy to example 90 from (5α,8β)-8-hydroxy-8-(3-methoxy-prop-1-ynyl)-2-(4-trifluoromethoxy-phenyl)-2-aza-spiro[4.5]decan-1-one (obtained in example 72) by hydrogenation. MS (m/e)=402.4 [MH$^+$].

Example 92

(5α,8α)-8-Hydroxy-8-(3-methoxy-prop-1-ynyl)-2-[4-(2,2,2-trifluoro-ethyl)-phenyl]-2-aza-spiro[4.5]decan-1-one

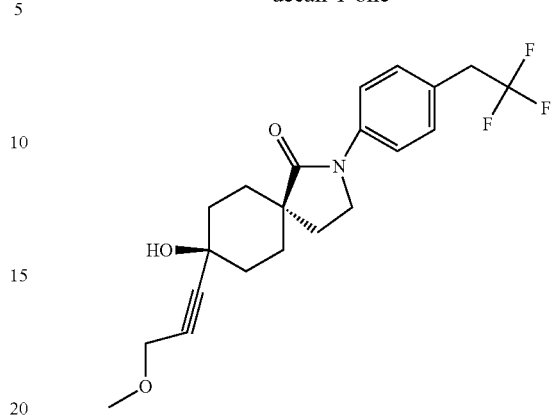

Lithiumdiisopropylamide (2M in THF/heptane/ethyl benzene, 0.42 mL) was dissolved in THF (13 mL) and cooled down to −78° C. in an acetone/CO$_2$-bath. A solution of methylpropargyl ether (42 µL) in THF (3 mL) was added dropwise over a period of 2 minutes to the cold mixture. Stirring was continued for 10 minutes at −78° C. Then, a solution of 2-[4-(2,2,2-trifluoro-ethyl)-phenyl]-2-aza-spiro[4.5]decane-1,8-dione (250 mg, obtained in example 77, step 2) in THF (4 mL) was added dropwise over a period of 5 minutes at −78° C. The mixture was warmed up to −30° C. and stirring was continued for 45 minutes at this temperature. The reaction mixture was poured into ice/water and acidified with saturated NH$_4$Cl solution. The aqueous phase was then extracted three times with ethyl acetate and the organic layers were washed brine, dried over Na$_2$SO$_4$, filtered and the solvent was evaporated. The residue was purified by flash chromatography (silica gel, gradient of dichloromethane in acetonitrile) to give the title compound as a colorless solid (67 mg, 22%). MS (m/e): 396.2 [MH$^+$].

In the chromatographic purification step, the trans compound (5α,8β)-8-hydroxy-8-(3-methoxy-prop-1-ynyl)-2-[4-(2,2,2-trifluoro-ethyl)-phenyl]-2-aza-spiro[4.5]decan-1-one was also isolated as a colorless solid (53 mg, 18%). MS (m/e): 396.2 [MH$^+$].

Example 93

(5α,8α)-8-Hydroxy-8-(3-methoxy-propyl)-2-[4-(2,2,2-trifluoro-ethyl)-phenyl]-2-aza-spiro[4.5]decan-1-one

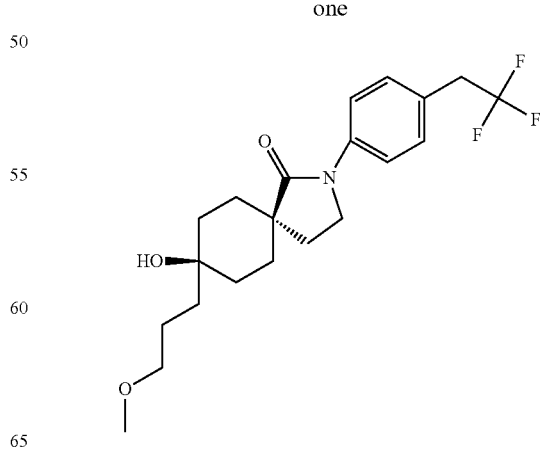

The title compound was prepared in analogy to example 90 from (5α,8α)-8-hydroxy-8-(3-methoxy-prop-1-ynyl)-2-[4-

(2,2,2-trifluoro-ethyl)-phenyl]-2-aza-spiro[4.5]decan-1-one (obtained in example 92) by hydrogenation. MS (m/e): 400.3 [MH$^+$].

Example 94

(5α,8α)-8-Hydroxy-2-[4-(3-methoxy-propoxy)-phenyl]-8-propyl-2-aza-spiro[4.5]decan-1-one

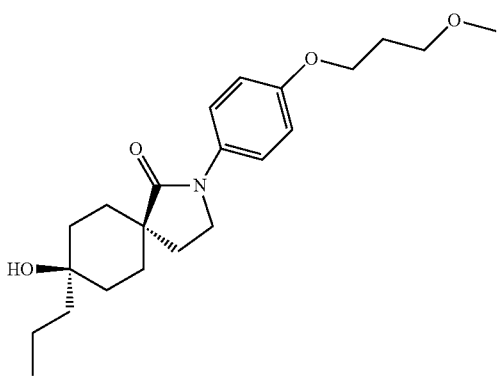 [SMILES: CCC[C@]1(O)CC[C@]2(CCN(c3ccc(OCCCOC)cc3)C2=O)CC1]

Step 1: 8-Hydroxy-2-[4-(3-methoxy-propoxy)-phenyl]-2-aza-spiro[4.5]decan-1-one

The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(3-methoxy-propoxy)-phenylamine (CAS Reg. No. 100131-95-1; see for example: Collins et al.; British Journal of Pharmacology and Chemotherapy 1958, 13, 238-43). MS (m/e): 334.3 [MH$^+$].

Step 2: 2-[4-(3-Methoxy-propoxy)-phenyl]-2-aza-spiro[4.5]decane-1,8-dione

The title compound was prepared in analogy to example 54 by oxidation of 8-hydroxy-2-[4-(3-methoxy-propoxy)-phenyl]-2-aza-spiro[4.5]decan-1-one (obtained in example 94, step 1). MS (m/e): 332.2 [MH$^+$].

Step 3: (5α,8α)-8-Hydroxy-2-[4-(3-methoxy-propoxy)-phenyl]-8-propyl-2-aza-spiro[4.5]decan-1-one The title compound was prepared in analogy to example 55 from 2-[4-(3-methoxy-propoxy)-phenyl]-2-aza-spiro[4.5]decane-1,8-dione (obtained in example 94, step 2) by reaction with propylmagnesium chloride (2M in diethyl ether). MS (m/e): 358.4 [(M-H$_2$O)H$^+$].

Example 95

(5α,8α)-8-Hydroxy-2-[4-(2-methoxy-ethoxy)-phenyl]-8-propyl-2-aza-spiro[4.5]decan-1-one

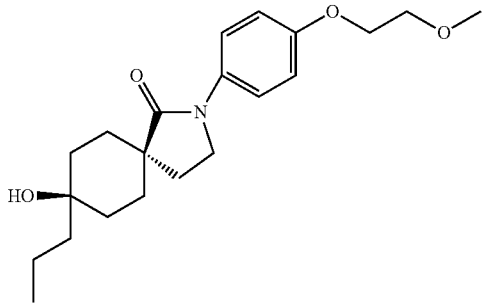 [SMILES: CCC[C@]1(O)CC[C@]2(CCN(c3ccc(OCCOC)cc3)C2=O)CC1]

Step 1: 8-Hydroxy-2-[4-(2-methoxy-ethoxy)-phenyl]-2-aza-spiro[4.5]decan-1-one

The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(2-methoxy-ethoxy)-phenylamine (CAS Reg. No. 33311-29-4, commercially available). MS (m/e): 320.2 [MH$^+$].

Step 2: 2-[4-(2-Methoxy-ethoxy)-phenyl]-2-aza-spiro[4.5]decane-1,8-dione

The title compound was prepared in analogy to example 54 by oxidation of 8-hydroxy-2-[4-(2-methoxy-ethoxy)-phenyl]-2-aza-spiro[4.5]decan-1-one (obtained in example 95, step 1). MS (m/e): 318.3 [MH$^+$].

Step 3: (5α,8α)-8-Hydroxy-2-[4-(2-methoxy-ethoxy)-phenyl]-8-propyl-2-aza-spiro[4.5]decan-1-one The title compound was prepared in analogy to example 55 from 2-[4-(2-methoxy-ethoxy)-phenyl]-2-aza-spiro[4.5]decane-1,8-dione (obtained in example 95, step 2) by reaction with propylmagnesium chloride (2M in diethyl ether). MS (m/e): 362.3 [MH$^+$].

Example 96

(5α,8α)-8-Butyl-8-hydroxy-2-[4-(2-methoxy-ethoxy)-phenyl]-2-aza-spiro[4.5]decan-1-one

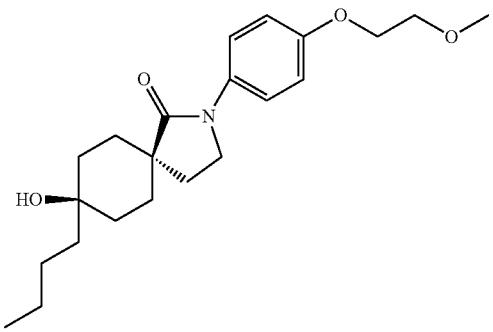 [SMILES: CCCC[C@]1(O)CC[C@]2(CCN(c3ccc(OCCOC)cc3)C2=O)CC1]

The title compound was prepared in analogy to example 55 from 2-[4-(2-methoxy-ethoxy)-phenyl]-2-aza-spiro[4.5]decane-1,8-dione (obtained in example 95, step 2) by reaction with butylmagnesium chloride (2M in THF/toluene). MS (m/e): 376.4 [MH$^+$].

Example 97

(5α,8β)-8-Butyl-8-hydroxy-2-[4-(2-methoxy-ethoxy)-phenyl]-2-aza-spiro[4.5]decan-1-one

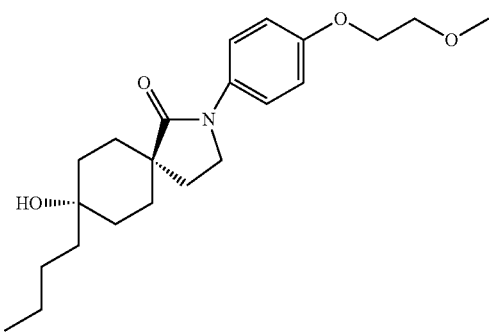 [SMILES: CCCC[C@]1(O)CC[C@@]2(CCN(c3ccc(OCCOC)cc3)C2=O)CC1]

The title compound was prepared as described for example 56 from 2-[4-(2-methoxy-ethoxy)-phenyl]-2-aza-spiro[4.5]decane-1,8-dione (obtained in example 95, step 2) by reaction with butylmagnesium chloride (2M in THF/toluene). MS (m/e): 376.4 [MH$^+$].

Example 98

(5α,8β)-8-Hydroxy-2-[4-(3,3,3-trifluoro-propoxy)-phenyl]-2-aza-spiro[4.5]decan-1-one

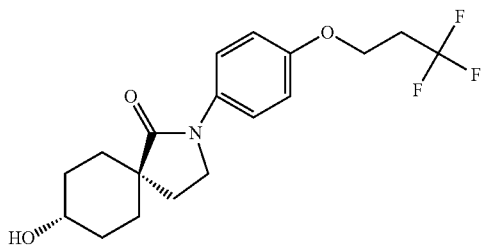 [SMILES: O=C1N(c2ccc(OCCC(F)(F)F)cc2)CC[C@]12CC[C@@H](O)CC2]

Step 1: 1-Nitro-4-(3,3,3-trifluoro-propoxy)-benzene

To a solution of a 3,3,3-trifluoro-propan-1-ol (6.22 g) in acetonitrile (200 ml) kept at RT under an argon atmosphere were added 1-fluoro-4-nitro-benzene (10.1 g) and Cs$_2$CO$_3$ (28.7 g) and the mixture was heated to 100° C. for 18 h. The reaction mixture was cooled to RT and partitioned between AcOEt and ice water. The layers were separated, dried, over Na$_2$SO$_4$ and the solvent was evaporated. The residue was purified by flash chromatography (silica gel; eluent: AcOEt/heptane:gradient 3 to 5%) to afford 1-nitro-4-(3,3,3-trifluoro-propoxy)-benzene as light yellow liquid (3.5 g). MS (EI, m/e): 235.0 (M$^+$).

Step 2: 4-(3,3,3-Trifluoro-propoxy)-phenylamine nitro-4-(3,3,3-trifluoro-propoxy)-benzene (1.4 g) in methanol (50 ml) was hydrogenated over Pd/C at RT and at atmospheric pressure for 12 h. The catalyst was filtered off and the solvent was removed in vacuo to give the desired 4-(3,3,3-trifluoro-propoxy)-phenylamine (0.45 g) as a light brown solid. MS (ESI, m/e): 206.1 (MH$^+$).

Step 3: (5α,8β)-8-Hydroxy-2-[4-(3,3,3-trifluoro-propoxy)-phenyl]-2-aza-spiro[4.5]decan-1-one The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(3,3,3-trifluoro-propoxy)-phenylamine MS (m/e): 358.2 [MH$^+$].

Example 99

(5α,8α)-8-Hydroxy-8-propyl-2-[4-(3,3,3-trifluoro-propoxy)-phenyl]-2-aza-spiro[4.5]decan-1-one

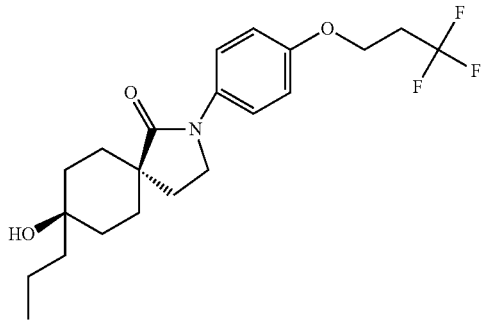 [SMILES: CCC[C@]1(O)CC[C@]2(CCN(c3ccc(OCCC(F)(F)F)cc3)C2=O)CC1]

Step 1: 2-[4-(3,3,3-Trifluoro-propoxy)-phenyl]-2-aza-spiro[4.5]decane-1,8-dione The title compound was prepared in analogy to example 54 by oxidation of (5α,8β)-8-hydroxy-2-[4-(3,3,3-trifluoro-propoxy)-phenyl]-2-aza-spiro[4.5]decan-1-one (obtained in example 98, step 3). MS (m/e): 356.1 [MH$^+$].

Step 2: (5α,8α)-8-Hydroxy-8-propyl-2-[4-(3,3,3-trifluoro-propoxy)-phenyl]-2-aza-spiro[4.5]decan-1-one The title compound was prepared in analogy to example 55 from 2-[4-(3,3,3-trifluoro-propoxy)-phenyl]-2-aza-spiro[4.5]decane-1,8-dione (obtained in example 99, step 1) by reaction with propylmagnesium chloride (2M in diethyl ether). MS (m/e): 400.3 [MH$^+$].

Example 100

(5α,8β)-8-Hydroxy-8-propyl-2-[4-(3,3,3-trifluoro-propoxy)-phenyl]-2-aza-spiro[4.5]decan-1-one

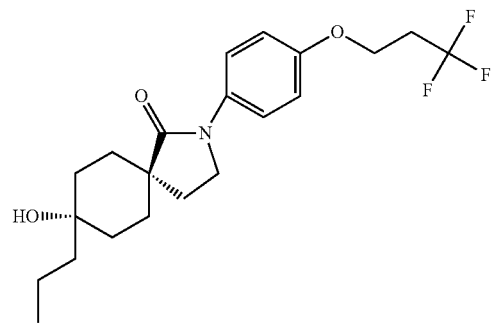 [SMILES: CCC[C@]1(O)CC[C@@]2(CCN(c3ccc(OCCC(F)(F)F)cc3)C2=O)CC1]

The title compound was prepared as described for example 56 from 2-[4-(3,3,3-trifluoro-propoxy)-phenyl]-2-aza-spiro[4.5]decane-1,8-dione (obtained in example 99, step 1) by reaction with propylmagnesium chloride (2M in diethyl ether). MS (m/e): 400.2 [MH$^+$].

Example 101

(5α,8α)-8-Hydroxy-2-(6-isopropylpyridin-3-yl)-8-propyl-2-aza-spiro[4.5]decan-1-one

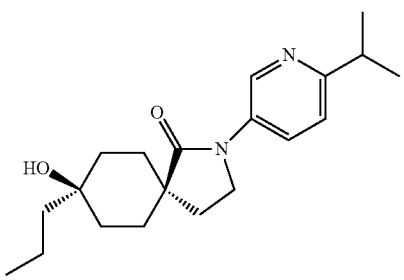 [SMILES: CCC[C@]1(O)CC[C@]2(CCN(c3ccc(C(C)C)nc3)C2=O)CC1]

Step 1: 8-Hydroxy-2-(6-isopropyl-pyridin-3-yl)-2-aza-spiro[4.5]decan-1-one

The title compound was prepared in analogy to example 1, step 4 from 4-hydroxy-1-(2-methoxy-ethyl)-cyclohexanecarboxylic acid ethyl ester (obtained in example 2, step 3) by treatment with 6-isopropylpyridin-3-amine [CAS Reg. No. 405103-O$_2$-8]. MS (m/e): 289.1 [MH$^+$].

Step 2: 2-(6-Isopropyl-pyridin-3-yl)-2-aza-spiro[4.5]decane-1,8-dione

The title compound was prepared in analogy to example 54 by oxidation of 8-hydroxy-2-(6-isopropyl-pyridin-3-yl)-2-aza-spiro[4.5]decan-1-one (obtained in example 101, step 1). MS (m/e): 287.1 [MH$^+$].

Step 3: (5α,8α)-8-Hydroxy-2-(6-isopropylpyridin-3-yl)-8-propyl-2-aza-spiro[4.5]decan-1-one Anhydrous cerous(III)-chloride (310 mg) in tetrahydrofuran (8.0 mL) was stirred for 1 hour at r.t. Then, 2-(6-isopropyl-pyridin-3-yl)-2-aza-spiro[4.5]decane-1,8-dione (200 mg, obtained in example 101, step 2) was added to the reaction mixture and stirring was continued for 1 hour. Next, propylmagnesium chloride (2M in diethyl ether, 0.63 mL) was added dropwise over a period of 5 minutes. Stirring was continued for 1 hour at RT. More propylmagnesium chloride (2M in diethyl ether, 0.17 mL) was added dropwise over a period of 5 minutes to the reaction mixture and stirring was continued for 20 hours at RT. The reaction mixture was poured into ice/water and was then acidified with saturated NH$_4$Cl solution. The aqueous phase was extracted two times with ethyl acetate and the organic layers were washed with brine, dried over Na$_2$SO$_4$ and filtered. The solvent was evaporated and the residue was purified by flash chromatography (silica gel, gradient of heptane in ethyl acetate) to give the title compound as a colorless solid (48 mg, 21%). MS (m/e): 331.3 [MH$^+$].

In the chromatographic purification step, the trans compound (5α,8β)-8-hydroxy-2-(6-isopropylpyridin-3-yl)-8-propyl-2-aza-spiro[4.5]decan-1-one was also isolated as a light yellow oil (45 mg, 19%). MS (m/e): 331.3 [MH$^+$].

Example 102

(5α,8α)-8-Hydroxy-8-isopropyl-2-(6-isopropylpyridin-3-yl)-2-aza-spiro[4.5]decan-1-one

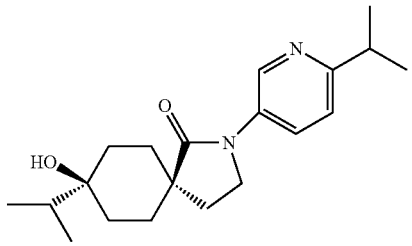 [SMILES: CC(C)c1ccc(N2CC[C@]3(CC[C@@](O)(C(C)C)CC3)C2=O)cn1]

The title compound was prepared in analogy to example 101, step 3 from 2-(6-isopropyl-pyridin-3-yl)-2-aza-spiro[4.5]decane-1,8-dione (obtained in example 101, step 2) by reaction with isopropylmagnesium chloride (2M in THF). MS (m/e): 331.2 [MH$^+$].

Example 103

(5α,8α)-8-Hydroxy-8-isopropyl-2-[4-(2,2,2-trifluoro-ethoxy)-phenyl]-2-aza-spiro[4.5]decan-1-one

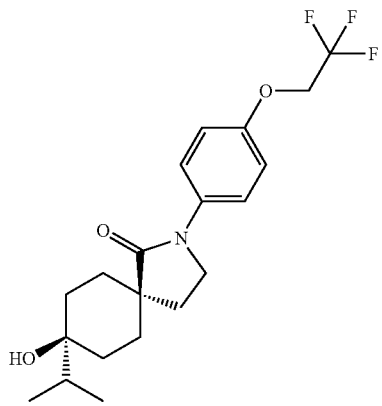 [SMILES: CC(C)[C@]1(O)CC[C@]2(CCN(c3ccc(OCC(F)(F)F)cc3)C2=O)CC1]

Anhydrous cerous(III)-chloride (260 mg, [CAS Reg. No. 7790-86-5]) in tetrahydrofuran (9 mL) was stirred for 60 minutes at RT. Then, 2-[4-(2,2,2-trifluoro-ethoxy)-phenyl]-2-aza-spiro[4.5]decane-1,8-dione (200 mg, obtained in example 86, step 1) was added to the reaction mixture and stirring was continued for 90 minutes. Isopropylmagnesiumchloride (2.0M in THF, 0.53 mL) was added dropwise over a period of 5 minutes to the reaction mixture and stirring was continued for another 2 hours. The reaction mixture was poured into ice/water and was acidified with saturated NH$_4$Cl solution. The aqueous phase was then extracted two times with ethyl acetate and the organic layers were washed brine, dried over Na$_2$SO$_4$ and filtered. The solvent was evaporated and the residue was purified by flash chromatography (silica gel, gradient of dichloromethane in acetonitrile) to give the title compound as a colorless solid (137 mg, 59%). MS (m/e): 368.2 [(M-H$_2$O)H$^+$].

In the chromatographic purification step, the trans compound (5α,8β)-8-hydroxy-8-isopropyl-2-[4-(2,2,2-trifluoro-ethoxy)-phenyl]-2-aza-spiro[4.5]decan-1-one (71 mg, 31%) was also isolated (see example 107).

Example 104

8-Hydroxy-8-propyl-2-[4-(2,2,2-trifluoro-ethoxy)-phenyl]-2-aza-spiro[4.5]decan-1-one

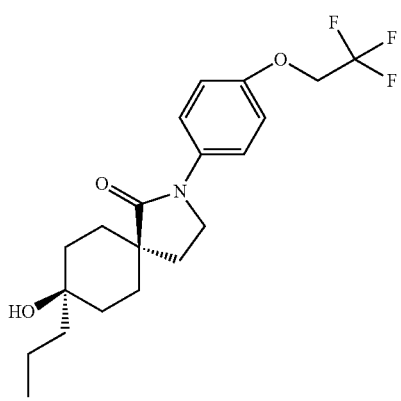 [SMILES: CCC[C@]1(O)CC[C@]2(CCN(c3ccc(OCC(F)(F)F)cc3)C2=O)CC1]

The title compound was prepared in analogy to example 55 from 2-[4-(2,2,2-trifluoro-ethoxy)-phenyl]-2-aza-spiro[4.5]

decane-1,8-dione (obtained in example 86, step 1) by reaction with propylmagnesium chloride (2M in diethyl ether). MS (m/e): 368.2 [(M-H$_2$O)H$^+$].

Example 105

(5α,8α)-8-Hydroxy-8-(prop-1-en-2-yl)-2-(4-(2,2,2-trifluoroethoxy)phenyl)-2-aza-spiro[4.5]decan-1-one

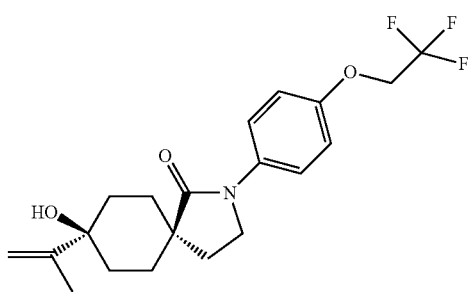 [SMILES: C=C(C)[C@]1(O)CC[C@]2(CCN(c3ccc(OCC(F)(F)F)cc3)C2=O)CC1]

The title compound was prepared in analogy to example 103 from 2-[4-(2,2,2-trifluoro-ethoxy)-phenyl]-2-aza-spiro[4.5]decane-1,8-dione (obtained in example 86, step 1) with the following modification: addition of isopropenylmagnesium bromide (0.5M in THF) was done at −78° C. (acetone/CO$_2$-bath). MS (m/e): 366.2 [(M-H$_2$O)H$^+$].

In the chromatographic purification step, the trans compound (5α,8β)-8-hydroxy-8-(prop-1-en-2-yl)-2-(4-(2,2,2-trifluoroethoxy)phenyl)-2-aza-spiro[4.5]decan-1-one was also isolated (see example 106).

Example 106

(5α,8β)-8-Hydroxy-8-(prop-1-en-2-yl)-2-(4-(2,2,2-trifluoroethoxy)phenyl)-2-aza-spiro[4.5]decan-1-one

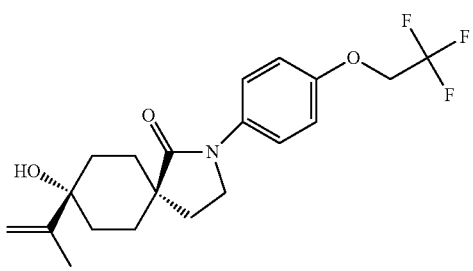 [SMILES: C=C(C)[C@]1(O)CC[C@@]2(CCN(c3ccc(OCC(F)(F)F)cc3)C2=O)CC1]

The title compound was isolated from the reaction providing example 105 (treatment of 2-[4-(2,2,2-trifluoro-ethoxy)-phenyl]-2-aza-spiro[4.5]decane-1,8-dione (obtained in example 86, step 1) with isopropenylmagnesium bromide). MS (m/e): 384.2 [MH$^+$].

Example 107

(5α,8β)-8-Hydroxy-8-isopropyl-2-(4-(2,2,2-trifluoroethoxy)phenyl)-2-aza-spiro[4.5]decan-1-one

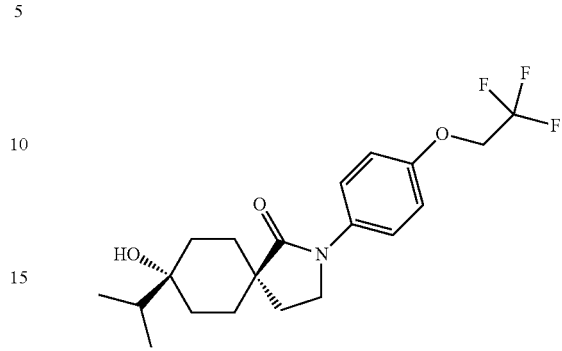

The title compound was isolated from the reaction providing example (treatment of 2-[4-(2,2,2-trifluoro-ethoxy)-phenyl]-2-aza-spiro[4.5]decane-1,8-dione (obtained in example 86, step 1) with isopropylmagnesiumchloride) as a colorless solid (71 mg, 31%). MS (m/e): 386.2 [MH$^+$].

Example 108

(5α,8α)-8-Hydroxy-8-isopropyl-2-(6-(2,2,2-trifluoroethoxy)pyridin-3-yl)-2-aza-spiro[4.5]decan-1-one

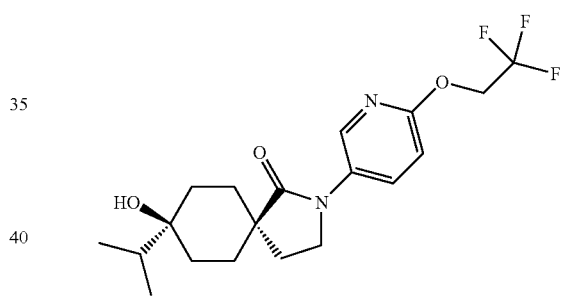

Step 1: 5-Nitro-2-(2,2,2-trifluoro-ethoxy)-pyridine

In a 250 mL four-necked flask, sodiumhydride (60% in mineral oil, 4.16 g) was combined with DMF (60 mL). The suspension was cooled to 0° C. and 2,2,2-trifluoroethanol (10.4 g, [CAS Reg. No. 75-89-8]) was added dropwise over a period of 20 minutes to the cold suspension. The mixture was stirred for 1 hour at 0° C. Then, a solution of 2-chloro-5-nitropyridine (15 g, [CAS Reg. No. 4548-45-2]) in DMF (70 mL) was added dropwise over a period of 20 minutes to the cold reaction mixture. Stirring was continued for 10 minutes at 0° C. and for 2 hours at r.t. The reaction mixture was poured into ice/water and was then extracted two times with ethyl acetate. The combined organic layers were washed with brine, dried over Na$_2$SO$_4$, and filtered. The solvent was evaporated and the residue was purified by flash chromatography (silica gel, gradient of heptane in ethyl acetate) to give the title compound as a yellow solid (20.52 g, 93%). MS (EI, m/e): 222.0 [M$^+$].

Step 2: 6-(2,2,2-Trifluoro-ethoxy)-pyridin-3-ylamine

5-Nitro-2-(2,2,2-trifluoro-ethoxy)-pyridine (20.5 g, obtained in example 108, step 1) was dissolved in methanol (160 mL). Palladium on activated charcoal (1.96 g, 10% Pd) was added and an atmosphere of hydrogen was introduced at RT. The mixture was stirred under hydrogen for 72 hours. The reaction mixture was filtered over dicalite speed plus (Acros Organics), washed with ethyl acetate and the solvent was evaporated. The residue was purified by flash chromatography (silica gel, gradient of heptane in ethyl acetate) to give the title compound as a brown liquid (16.49 g, 91%). MS (m/e): 193.1 [MH$^+$].

Step 3: 8-Hydroxy-2-[6-(2,2,2-trifluoro-ethoxy)-pyridin-3-yl]-2-aza-spiro[4.5]decan-1-one 6-(2,2,2-Trifluoro-ethoxy)-pyridin-3-ylamine (5.11 g, obtained in example 108, step 2) was added to a solution of 4-hydroxy-1-(2-methoxy-ethyl)-cyclohexanecarboxylic acid ethyl ester (5.10 g, obtained in example 2, step 3) in toluene (160 mL). The mixture was stirred for 10 minutes at RT. Then, dimethylaluminiumchloride (1M in hexane, 66.4 mL) was added dropwise over a period of 30 minutes. The reaction mixture was heated to reflux for 2 hours and then at 95° C. for 16 hours. The mixture was cooled, poured into ice/water and extracted two times with ethyl acetate. The combined organic layers were washed with brine, dried over Na$_2$SO$_4$, filtered and the solvent was evaporated. The title compound was obtained as an inseparable mixture of cis and trans diastereomeres as a brown oil (9.56 g, 100%). This mixture was used without further purification. MS (m/e): 345.1 [MH$^+$].

Step 4: 2-[6-(2,2,2-Trifluoro-ethoxy)-pyridin-3-yl]-2-aza-spiro[4.5]decane-1,8-dione DMSO (5.19 mL) was added dropwise over a period of 5 minutes to a solution of 8-hydroxy-2-[6-(2,2,2-trifluoro-ethoxy)-pyridin-3-yl]-2-aza-spiro[4.5]decan-1-one (9.53 g, obtained in example 108, step 3) in dichloromethane (100 mL) that was cooled down to –78° C. in a CO$_2$/acetone-bath. After 5 minutes, oxalylchloride (3.04 mL) was added dropwise over a period of 10 minutes and stirring was continued for 30 minutes at –78° C. Then, triethylamine (17 mL) was added dropwise over a period of 10 minutes to the reaction mixture and after 5 minutes, the mixture was allowed to warm to 20° C. The reaction mixture was poured into ice/water and was acidified with 2M aqueous HCl solution (150 mL) to pH 3. The aqueous phase was extracted two times with dichloromethane and the combined organic layers were washed with brine, dried over Na$_2$SO$_4$ and filtered. The solvent was evaporated and the residue was purified by flash chromatography (silica gel, gradient of dichloromethane in acetonitrile) to give the title compound as a light yellow solid (6.19 g, 80%). MS (m/e): 343.2 [MH$^+$].

Step 5: (5α,8α)-8-Hydroxy-8-isopropyl-2-(6-(2,2,2-trifluoroethoxy)pyridin-3-yl)-2-aza-spiro[4.5]decan-1-one The title compound was prepared in analogy to example 55 from 2-[6-(2,2,2-trifluoro-ethoxy)-pyridin-3-yl]-2-aza-spiro[4.5]decane-1,8-dione (obtained in example 108, step 4) by reaction with isopropylmagnesium bromide (1M in THF). MS (m/e): 369.2 [(M-H$_2$O)H$^+$].

Example 109

(5α,8β)-8-Hydroxy-8-isopropyl-2-(6-(2,2,2-trifluoroethoxy)pyridin-3-yl)-2-aza-spiro[4.5]decan-1-one

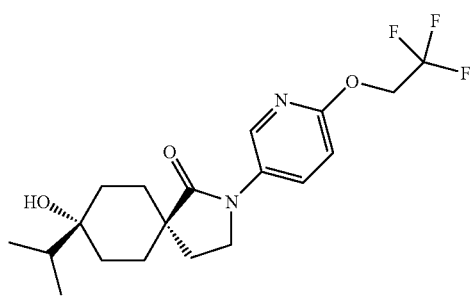 [SMILES: CC(C)[C@]1(O)CC[C@@]2(CCN(c3ccc(OCC(F)(F)F)nc3)C2=O)CC1]

The title compound was prepared as described for example 56 from 2-[6-(2,2,2-trifluoro-ethoxy)-pyridin-3-yl]-2-aza-spiro[4.5]decane-1,8-dione (obtained in example 108, step 4) by reaction with isopropylmagnesium bromide (1M in THF). MS (m/e): 387.3 [MH$^+$].

Example 110

(5α,8α)-8-Hydroxy-8-(methoxymethyl)-2-(6-(2,2,2-trifluoroethoxy)pyridin-3-yl)-2-aza-spiro[4.5]decan-1-one

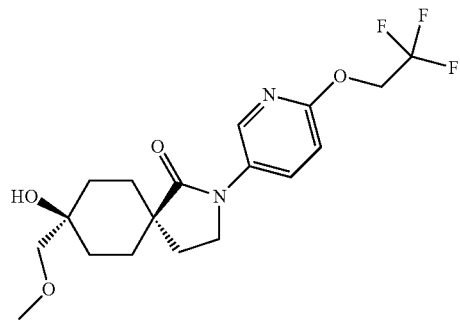 [SMILES: COC[C@]1(O)CC[C@]2(CCN(c3ccc(OCC(F)(F)F)nc3)C2=O)CC1]

Step 1: (3α,6α)-8-[6-(2,2,2-Trifluoro-ethoxy)-pyridin-3-yl]-1-oxa-8-aza-dispiro[2.2.4.2]dodecan-7-one 2-[6-(2,2,2-Trifluoro-ethoxy)-pyridin-3-yl]-2-aza-spiro [4.5]decane-1,8-dione (250 mg, obtained in example 108, step 4) and trimethylsulfoxonium iodide (249 mg) were dissolved in DMSO (6.0 mL). A solution of potassium tert-butoxide (127 mg) in DMSO (6.0 mL) was added dropwise over a period of 5 minutes and the mixture was stirred at RT for 4 hours. The reaction mixture was poured into ice/water and was extracted two times with ethyl acetate. The combined organic layers were washed with brine, dried over Na$_2$SO$_4$ and filtered. The solvent was evaporated and the residue was purified by flash chromatography (silica gel, gradient of heptane in ethyl acetate) to give the title compound as a colorless solid (200 mg, 76%). MS (m/e): 357.2 [MH$^+$].

In the chromatographic purification step, the trans compound (3α,6β)-8-[6-(2,2,2-trifluoro-ethoxy)-pyridin-3-yl]-1-oxa-8-aza-dispiro[2.2.4.2]dodecan-7-one was also isolated as a colorless solid (28 mg, 11%). MS (m/e): 357.2 [MH$^+$].

Step 2: (5α,8α)-8-Hydroxy-8-(methoxymethyl)-2-(6-(2,2,2-trifluoroethoxy)pyridin-3-yl)-2-aza-spiro[4.5]decan-1-one (3α,6α)-8-[6-(2,2,2-Trifluoro-ethoxy)-pyridin-3-yl]-1-oxa-8-aza-dispiro[2.2.4.2]dodecan-7-one (196 mg, obtained in example 110, step 1) was dissolved in THF (10 mL). Then, sodium methylate (5.4M in methanol, 1.53 mL) was added dropwise over a period of 5 minutes. The mixture was stirred at reflux for 1.5 hours. The reaction mixture was cooled, poured into ice/water and extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless solid (197 mg, 91%). MS (m/e): 389.3 [MH⁺].

Example 111

(5α,8α)-8-Hydroxy-8-prop-1-ynyl-2-[4-(2,2,2-trifluoro-ethoxy)phenyl]-2-aza-spiro[4.5]decan-1-one

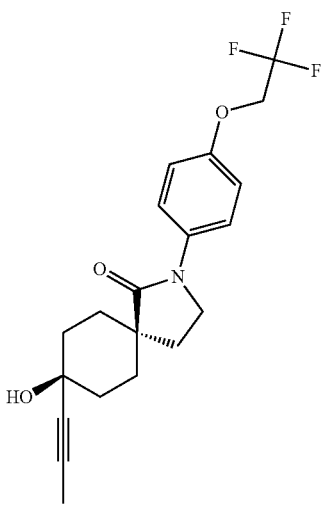 [SMILES: CC#C[C@]1(O)CC[C@]2(CCN(c3ccc(OCC(F)(F)F)cc3)C2=O)CC1]

A 25 mL three-necked-flask was cooled down to −78° C. (in an acetone/CO₂-bath) and propyne (excess) was condensed into the flask. Next, cold THF (10 mL) was added. At −78° C., lithiumdiisopropylamide (2.0M in THF/heptane/ethylbenzene, 0.29 mL) was added dropwise over a period of 5 minutes to the cold mixture and stirring was continued for 10 minutes. A solution of 2-[4-(2,2,2-trifluoro-ethoxy)-phenyl]-2-aza-spiro[4.5]decane-1,8-dione (100 mg, obtained in example 86, step 1) in THF (4 mL) was added dropwise over a period of 5 minutes. Stirring was continued at −70° C. for another hour and then the mixture was allowed to warm to room temperature over a period of 16 hours. The reaction mixture was poured into ice/water and was acidified with saturated NH₄Cl solution. The aqueous phase was extracted two times with ethyl acetate and the organic layers were washed with saturated NaHCO₃ solution and brine, dried over Na₂SO₄ and filtered. The solvent was evaporated and the residue was purified by flash chromatography (silica gel, gradient of dichloromethane in acetonitrile) to give the title compound as a light yellow solid (30 mg, 27%). MS (m/e): 364.1 [MH⁺].

Example 112

(5α,8α)-8-Hydroxy-2-(4-trifluoromethoxy-phenyl)-8-trifluoromethyl-2-aza-spiro[4.5]decan-1-one

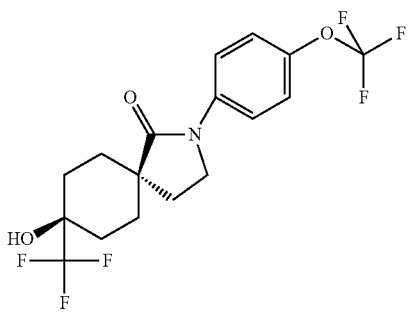 [SMILES: O=C1N(c2ccc(OC(F)(F)F)cc2)CC[C@]12CC[C@@](O)(C(F)(F)F)CC2]

(Trifluoromethyl)-trimethylsilane (2M in THF, 0.67 mL) was added dropwise over a period of 10 minutes to a solution of 2-(4-trifluoromethoxy-phenyl)-2-aza-spiro[4.5]decane-1,8-dione (200 mg, obtained in example 54) in THF (26 mL) at 0° C. Then, tetrabutylammoniumfluoride trihydrate (231 mg) was added to the cold mixture and stirring was continued at 0° C. for 30 minutes and then at room temperature for 16 hours. The reaction mixture was poured into ice/water and was extracted two times with ethyl acetate. The combined organic layers were washed with brine, dried over Na₂SO₄ and filtered. The solvent was evaporated and the residue was purified by flash chromatography (silica gel, gradient of heptane in ethyl acetate) to give the title compound as a colorless solid (92 mg, 38%). MS (m/e): 398.2 [MH⁺].

In the chromatographic purification step, the trans compound (5α,8β)-8-hydroxy-2-(4-trifluoromethoxy-phenyl)-8-trifluoromethyl-2-aza-spiro[4.5]decan-1-one (31 mg, 13%) was also isolated (see example 113).

Example 113

(5α,8β)-8-Hydroxy-2-(4-trifluoromethoxy-phenyl)-8-trifluoromethyl-2-aza-spiro[4.5]decan-1-one

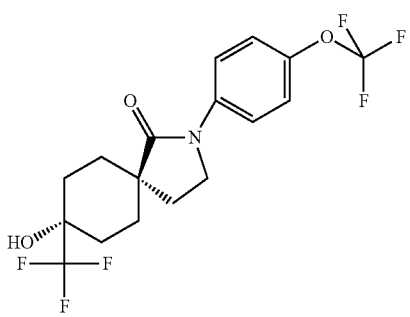 [SMILES: O=C1N(c2ccc(OC(F)(F)F)cc2)CC[C@]12CC[C@](O)(C(F)(F)F)CC2]

The title compound was isolated from the reaction providing example 112 (treatment of 2-(4-trifluoromethoxy-phenyl)-2-aza-spiro[4.5]decane-1,8-dione (obtained in example 54) with (trifluoromethyl)-trimethylsilane) as a colorless solid (31 mg, 13%). MS (m/e): 398.2 [MH⁺].

Example 114

(5α,8α)-8-Hydroxy-8-methoxymethyl-2-(4-trifluoromethoxy-phenyl)-2-aza-spiro[4.5]decan-1-one

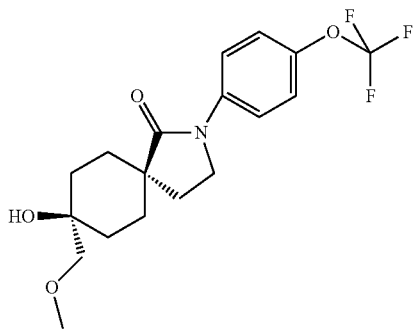 [SMILES: COC[C@]1(O)CC[C@]2(CCN(c3ccc(OC(F)(F)F)cc3)C2=O)CC1]

Step 1: (3α,6α)-8-(4-Trifluoromethoxy-phenyl)-1-oxa-8-aza-dispiro[2.2.4.2]dodecan-7-one The title compound was prepared in analogy to example 110, step 1 from 2-(4-trifluoromethoxy-phenyl)-2-aza-spiro[4.5]decane-1,8-dione (obtained in example 54). MS (m/e): 342.1 [MH$^+$].

Step 2: (5α,8α)-8-Hydroxy-8-methoxymethyl-2-(4-trifluoromethoxy-phenyl)-2-aza-spiro[4.5]decan-1-one The title compound was prepared in analogy to example 110, step 2 from (3α,6α)-8-(4-trifluoromethoxy-phenyl)-1-oxa-8-aza-dispiro[2.2.4.2]dodecan-7-one (obtained in example 114, step 1) by treatment with sodium methylate. MS (m/e): 374.2 [MH$^+$].

Example 115

(5α,8β)-8-Hydroxy-8-methoxymethyl-2-(4-trifluoromethoxy-phenyl)-2-aza-spiro[4.5]decan-1-one

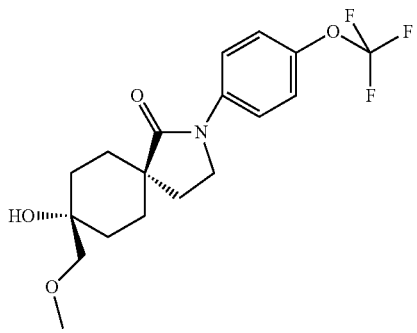 [SMILES: COC[C@]1(O)CC[C@@]2(CCN(c3ccc(OC(F)(F)F)cc3)C2=O)CC1]

Step 1: (3α,6β)-8-(4-Trifluoromethoxy-phenyl)-1-oxa-8-aza-dispiro[2.2.4.2]dodecan-7-one The title compound can be obtained from the reaction described in example 110, step 1 from 2-(4-trifluoromethoxy-phenyl)-2-aza-spiro[4.5]decane-1,8-dione (obtained in example 54) as a side product. MS (m/e): 342.1 [MH$^+$].

Step 2: (5α,8β)-8-Hydroxy-8-methoxymethyl-2-(4-trifluoromethoxy-phenyl)-2-aza-spiro[4.5]decan-1-one The title compound was prepared in analogy to example 110, step 2 from (3α,6β)-8-(4-trifluoromethoxy-phenyl)-1-oxa-8-aza-dispiro[2.2.4.2]dodecan-7-one (obtained in example 115, step 1). MS (m/e): 374.2 [MH$^+$].

Example 116

[(5α,8α)-8-Hydroxy-1-oxo-2-(4-trifluoromethoxy-phenyl)-2-aza-spiro[4.5]dec-8-yl]-acetic acid ethyl ester

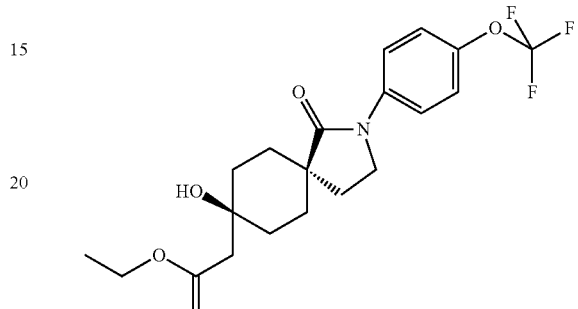

Ethyl-bromoacetate (0.11 mL, [CAS Reg. No. 105-36-2]) was added dropwise over a period of 5 minutes to a solution of tris-(triphenylphosphine)-ruthenium-(II)-chloride (44 mg) in THF (30 mL) at 0° C. Then, 2-(4-trifluoromethoxy-phenyl)-2-aza-spiro[4.5]decane-1,8-dione (300 mg, obtained in example 54) was added to the cold mixture and stirring was continued for 10 minutes. Next, diethylzinc (1M in hexanes, 2.0 mL) was added dropwise over a period of 10 minutes. Stirring was continued for 30 minutes at 0° C. and then for 5 hours at room temperature. The reaction mixture was poured into ice/water and was basified with saturated NaHCO$_3$ solution. The aqueous layer was extracted two times with ethyl acetate. The combined organic layers were washed with brine, dried over Na$_2$SO$_4$, filtered and the solvent was evaporated. The residue was purified by flash chromatography (silica gel, gradient of dichloromethane in acetonitrile) to give the title compound as a colorless solid (106 mg, 28%). MS (m/e): 416.3 [MH$^+$].

In the chromatographic purification step, the trans compound [(5α,8β)-8-hydroxy-1-oxo-2-(4-trifluoromethoxy-phenyl)-2-aza-spiro[4.5]dec-8-yl]-acetic acid ethyl ester was also isolated as a colorless solid (122 mg, 32%). MS (m/e): 416.3 [MH$^+$].

Example 117

(5α,8α)-8-Ethoxymethyl-8-hydroxy-2-(4-trifluoromethoxy-phenyl)-2-aza-spiro[4.5]decan-1-one

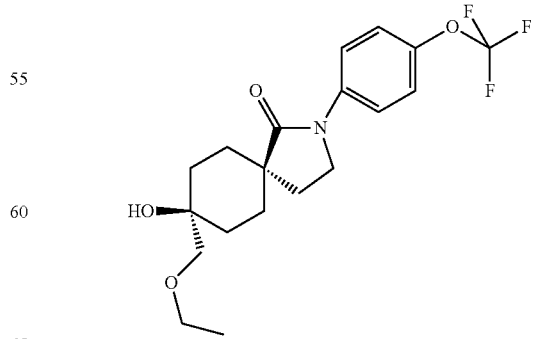

The title compound was prepared in analogy to example 110, step 2 from (3α,6α)-8-(4-trifluoromethoxy-phenyl)-1- oxa-8-aza-dispiro[2.2.4.2]dodecan-7-one (obtained in example 114, step 1) by reaction with sodium ethylate (3M in ethanol). MS (m/e): 388.3 [MH⁺].

Example 118

(5α,8α)-8-Hydroxy-8-(2-hydroxy-ethyl)-2-(4-trifluoromethoxy-phenyl)-2-aza-spiro[4.5]decan-1-one

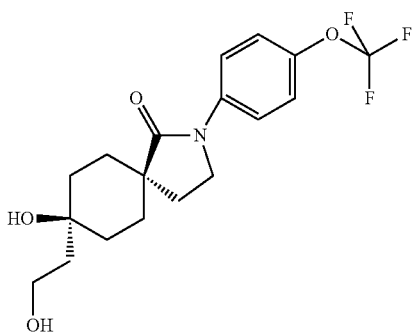 [SMILES: O=C1N(c2ccc(OC(F)(F)F)cc2)CC[C@]12CC[C@@](O)(CCO)CC2]

[(5α,8α)-8-Hydroxy-1-oxo-2-(4-trifluoromethoxy-phenyl)-2-aza-spiro[4.5]dec-8-yl]-acetic acid ethyl ester (207 mg, obtained in example 116) was dissolved in THF (10 mL). The mixture was cooled to 0° C. and lithium borohydride (22 mg) was added. Stirring was continued for 10 minutes at 0° C. and then for 3 hours at room temperature. The reaction mixture was poured into ice/water and was extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless solid (139 mg, 75%). MS (m/e): 374.2 [MH⁺].

Example 119

(5α,8α)-8-Hydroxy-8-(2-methoxy-ethyl)-2-(4-trifluoromethoxy-phenyl)-2-aza-spiro[4.5]decan-1-one

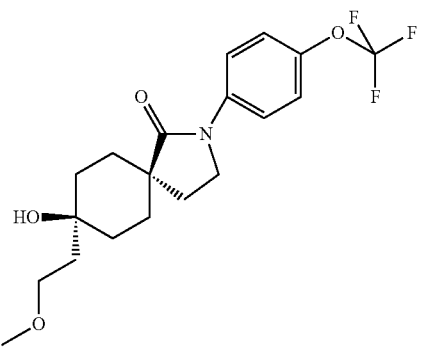 [SMILES: COCC[C@]1(O)CC[C@]2(CCN(c3ccc(OC(F)(F)F)cc3)C2=O)CC1]

Sodium hydride (60% in mineral oil, 32 mg) was added to a solution of (5α,8α)-8-hydroxy-8-(2-hydroxy-ethyl)-2-(4-trifluoromethoxy-phenyl)-2-aza-spiro[4.5]decan-1-one (100 mg, obtained in example 118) in DMF (5 mL) at 0° C. and the mixture was stirred for 45 minutes. Then, iodomethane (18 µL) was added dropwise over a period of 1 minute and stirring was continued for 90 minutes at 0° C. The reaction mixture was poured into ice/water and was then extracted two times with ethyl acetate. The combined organic layers were washed with brine, dried over Na₂SO₄ and filtered. The solvent was evaporated and the residue was purified by flash chromatography (silica gel, gradient of heptane in ethyl acetate) to give the title compound as a colorless solid (65 mg, 63%). MS (m/e): 388.2 [MH⁺].

In the chromatographic purification step, the "di-methylated compound" (5α,8α)-8-methoxy-8-(2-methoxy-ethyl)-2-(4-trifluoromethoxy-phenyl)-2-aza-spiro[4.5]decan-1-one (36 mg, 33%) was also isolated (see example 120).

Example 120

(5α,8α)-8-Methoxy-8-(2-methoxy-ethyl)-2-(4-trifluoromethoxy-phenyl)-2-aza-spiro[4.5]decan-1-one

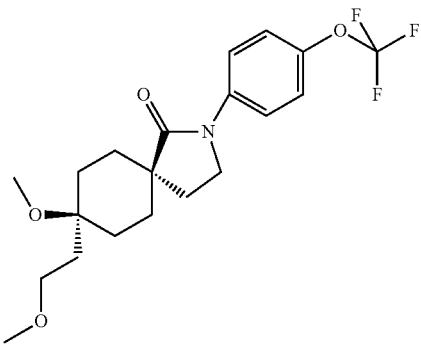 [SMILES: COCC[C@]1(OC)CC[C@]2(CCN(c3ccc(OC(F)(F)F)cc3)C2=O)CC1]

The title compound was isolated from the reaction providing example 119 (from (5α,8α)-8-hydroxy-8-(2-hydroxy-ethyl)-2-(4-trifluoromethoxy-phenyl)-2-aza-spiro[4.5]decan-1-one (obtained in example 118) by alkylation with iododmethane) as a colorless solid (36 mg, 33%). MS (m/e): 402.3 [MH⁺].

Example 121

(5α,8α)-8-Hydroxy-8-methoxymethyl-2-(4-trifluoromethyl-phenyl)-2-aza-spiro[4.5]decan-1-one

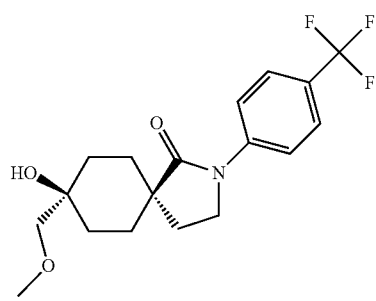 [SMILES: COC[C@]1(O)CC[C@]2(CCN(c3ccc(C(F)(F)F)cc3)C2=O)CC1]

Step 1: Step 1:
1,4-Dioxa-spiro[4.5]decane-8-carboxylic acid ethyl ester

The title compound was prepared in analogy to example 1, step 1 from ethyl-cyclohexanone-4-carboxylate [CAS Reg. No. 17159-79-4]. MS (m/e): 215.3 [MH⁺].

Step 2: 8-Cyanomethyl-1,4-dioxa-spiro[4.5]decane-8-carboxylic acid ethyl ester A solution of 1,4-dioxa-spiro[4.5]decane-8-carboxylic acid ethyl ester (1.0 g, obtained in example 121, step 1) in THF (8 mL) was added dropwise over a period of 10 minutes at −5° C. (ice/methanol bath) to a solution of lithiumdiisopropylamide (2M in THF/heptane/ethyl benzene, 4.67 mL) in THF (12 mL) and the mixture was stirred for 1 hour at 0° C. The reaction mixture was re-cooled to −5° C. and a solution of bromoacetonitrile (0.65 mL, [CAS Reg. No. 590-17-0]) in THF (4 mL) was added dropwise over a period of 10 minutes. The mixture was allowed to warm to RT and stirring was continued for 16 hours. The reaction was poured into ice/water and was acidified with 1M aqueous HCl solution (50 mL). The aqueous layer was extracted two times with ethyl acetate and the combined organic layers were washed with brine, dried over $Na_2SO_4$ and filtered. The solvent was evaporated and the residue was purified by flash chromatography (silica gel, gradient of heptane in ethyl acetate) to give the title compound as a brown liquid (528 mg, 45%). MS (m/e): 254.2 [$MH^+$].

Step 3: 1,4-Dioxa-10-aza-dispiro[4.2.4.2]tetradecan-9-one

8-Cyanomethyl-1,4-dioxa-spiro[4.5]decane-8-carboxylic acid ethyl ester (525 mg, obtained in example 121, step 2) was dissolved in methanol (10 mL) and acetic acid (5 mL). Platinum (IV) oxide (235 mg) was added and an atmosphere of hydrogen was introduced at RT. The mixture was stirred under hydrogen at room temperature for 18 hours. The reaction mixture was filtered over dicalite speed plus (Acros Organics) and the solvent was evaporated. The residue was poured into ice/water and was basified with 2M aqueous NaOH solution. The aqueous layer was extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a colorless solid (169 mg, 39%). MS (m/e): 212.2 [$MH^+$].

Step 4: 2-(4-Trifluoromethyl-phenyl)-2-aza-spiro[4.5]decane-1,8-dione 1,4-Dioxa-10-aza-dispiro[4.2.4.2]tetradecan-9-one (60 mg, obtained in example 121, step 3) was dissolved in DMF (5 mL) at r.t. Then, 4-iodobenzotrifluoride (155 mg, [CAS Reg. No. 455-13-0]), N,N'-dimethylethylenediamine (sym) (50 mg), Cuprous iodide (81 mg) and $K_3PO_4$ (181 mg) were added to the reaction mixture. The mixture was heated at 70° C. for 16 hours and at reflux for 2 hours. The reaction mixture was cooled, poured into ice/water and HCl (2M, 50 mL) was added to the mixture. Stirring was continued for 1 hour at room temperature. The mixture was then extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a colorless solid (51 mg, 58%). MS (m/e): 312.3 [$MH^+$].

Step 5: (3α,6α)-8-(4-Trifluoromethyl-phenyl)-1-oxa-8-aza-dispiro[2.2.4.2]dodecan-7-one The title compound was prepared in analogy to example 110, step 1 from 2-(4-trifluoromethyl-phenyl)-2-aza-spiro[4.5]decane-1,8-dione (obtained in example 121, step 4). MS (m/e): 326.2 [$MH^+$].

Step 6: (5α,8α)-8-Hydroxy-8-methoxymethyl-2-(4-trifluoromethyl-phenyl)-2-aza-spiro[4.5]decan-1-one The title compound was prepared in analogy to example 110, step 2 from (3α,6α)-8-(4-trifluoromethyl-phenyl)-1-oxa-8-aza-dispiro[2.2.4.2]dodecan-7-one (obtained in example 121, step 5) by treatment with sodium methylate. MS (m/e): 358.2 [$MH^+$].

Example 122

(5α,8α)-8-Hydroxy-2-[4-(2-methoxy-ethyl)-phenyl]-8-propyl-2-aza-spiro[4.5]decan-1-one

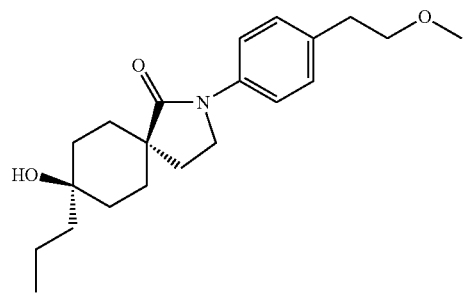 [SMILES: CCC[C@]1(O)CC[C@]2(CCN(c3ccc(CCOC)cc3)C2=O)CC1]

Step 1: 8-Hydroxy-2-[4-(2-methoxy-ethyl)-phenyl]-2-aza-spiro[4.5]decan-1-one The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(2-methoxyethyl)-aniline [CAS Reg. No. 84803-56-5, commercially available]. MS (m/e): 304.3 [$MH^+$].

Step 2: 2-[4-(2-Methoxy-ethyl)-phenyl]-2-aza-spiro[4.5]decane-1,8-dione

The title compound was prepared in analogy to example 54 by oxidation of 8-hydroxy-2-[4-(2-methoxy-ethyl)-phenyl]-2-aza-spiro[4.5]decan-1-one (obtained in example 122, step 1). MS (m/e): 302.4 [$MH^+$].

Step 3: (5α,8α)-8-Hydroxy-2-[4-(2-methoxy-ethyl)-phenyl]-8-propyl-2-aza-spiro[4.5]decan-1-one The title compound was prepared in analogy to example 55 from 2-[4-(2-methoxy-ethyl)-phenyl]-2-aza-spiro[4.5]decane-1,8-dione (obtained in example 122, step 2) by reaction with propylmagnesium chloride (2M in diethyl ether). MS (m/e): 346.2 [MH+].

Example 123

(5α,8α)-8-Hydroxy-2-[4-(2-methoxy-ethyl)-phenyl]-8-trifluoromethyl-2-aza-spiro[4.5]decan-1-one

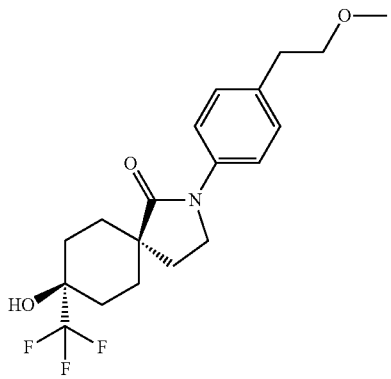 [SMILES: COCCc1ccc(N2CC[C@]3(CC[C@@](O)(C(F)(F)F)CC3)C2=O)cc1]

Step 1: 8-Hydroxy-2-[4-(2-methoxy-ethyl)-phenyl]-2-aza-spiro[4.5]decan-1-one

The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(2-methoxyethyl)-aniline [CAS Reg. No. 84803-56-5]. MS (m/e): 304.3 [MH+].

Step 2: 2-[4-(2-Methoxy-ethyl)-phenyl]-2-aza-spiro[4.5]decane-1,8-dione

The title compound was prepared in analogy to example 54 by oxidation of 8-hydroxy-2-[4-(2-methoxy-ethyl)-phenyl]-2-aza-spiro[4.5]decan-1-one (obtained in example 123, step 1). MS (m/e): 302.2 [MH+].

Step 3: (5α,8α)-8-Hydroxy-2-[4-(2-methoxy-ethyl)-phenyl]-8-trifluoromethyl-2-aza-spiro[4.5]decan-1-one (Trifluoromethyl)-trimethylsilane (2M in THF, 1.04 mL) was added dropwise over a period of 5 minutes to a solution of 2-[4-(2-methoxy-ethyl)-phenyl]-2-aza-spiro[4.5]decane-1,8-dione (250 mg, obtained in example 123, step 2) in THF (12 mL) at 0° C. Then, tetrabutylammoniumfluoride trihydrate (262 mg) was added to the cold mixture. Stirring was continued at 0° C. for 30 minutes and then at room temperature for 4 hours. The reaction mixture was poured into ice/water and was extracted two times with ethyl acetate. The combined organic layers were washed with brine, dried over Na2SO4, filtered and the solvent was evaporated. The residue was purified by flash chromatography (silica gel, gradient of dichloromethane in acetonitrile) to give the title compound as a colorless solid (140 mg, 45%). MS (m/e): 372.2 [MH+].

In the chromatographic purification step, the trans compound (5α,8β)-8-hydroxy-2-[4-(2-methoxy-ethyl)-phenyl]-8-trifluoromethyl-2-aza-spiro[4.5]decan-1-one was also isolated as a colorless solid (147 mg, 48%). MS (m/e): 372.2 [MH+].

Example 124

(5α,8α)-8-Hydroxy-8-isobutyl-2-[4-(2-methoxy-ethyl)-phenyl]-2-aza-spiro[4.5]decan-1-one

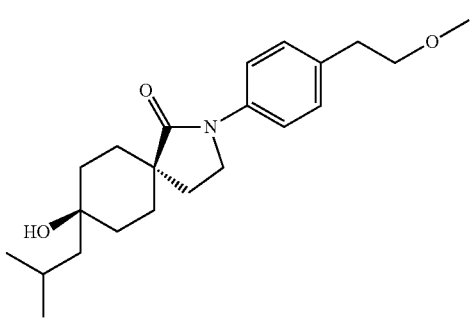 [SMILES: COCCc1ccc(N2CC[C@]3(CC[C@@](O)(CC(C)C)CC3)C2=O)cc1]

The title compound was prepared in low yield (9%) in analogy to example 55 from 2-[4-(2-methoxy-ethyl)-phenyl]-2-aza-spiro[4.5]decane-1,8-dione (obtained in example 123, step 2) by reaction with isobutylmagnesium chloride (2M in diethyl ether). MS (m/e): 360.4 [MH+].

Example 125

(5α,8β)-8-Hydroxy-8-isobutyl-2-[4-(2-methoxy-ethyl)-phenyl]-2-aza-spiro[4.5]decan-1-one

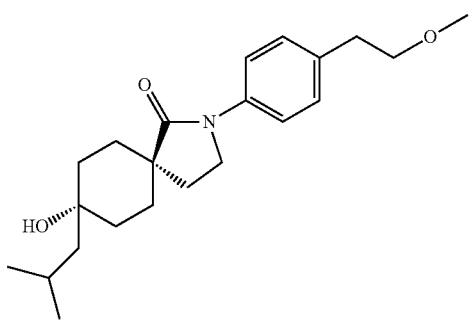 [SMILES: COCCc1ccc(N2CC[C@]3(CC[C@](O)(CC(C)C)CC3)C2=O)cc1]

The title compound was prepared in low yield (6%) as described for example 56 from 2-[4-(2-methoxy-ethyl)-phenyl]-2-aza-spiro[4.5]decane-1,8-dione (obtained in example 123, step 2) by reaction with isobutylmagnesium chloride (2M in diethyl ether). MS (m/e): 360.4 [MH+].

Example 126

(5α,8α)-8-(2,2-Dimethyl-propyl)-8-hydroxy-2-[4-(2-methoxy-ethyl)-phenyl]-2-aza-spiro[4.5]decan-1-one

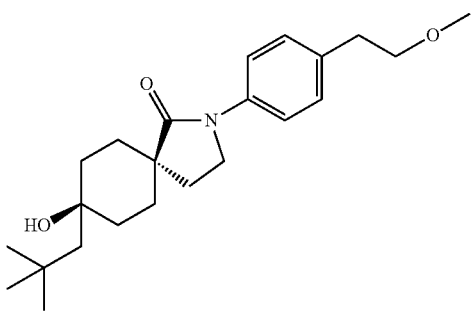 [SMILES: COCCc1ccc(N2CC[C@]3(CC[C@@](O)(CC(C)(C)C)CC3)C2=O)cc1]

The title compound was prepared in low yield (6%) in analogy to example 55 from 2-[4-(2-methoxy-ethyl)phenyl]-2-aza-spiro[4.5]decane-1,8-dione (obtained in example 123, step 2) by reaction with neopentylmagnesium chloride (1M in diethyl ether). MS (m/e): 374.3 [MH$^+$].

Example 127

(5α,8α)-8-Hydroxy-8-isopropenyl-2-[4-(2-methoxy-ethyl)-phenyl]-2-aza-spiro[4.5]decan-1-one

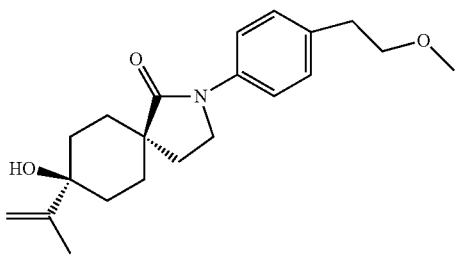 [SMILES: C=C(C)[C@]1(O)CC[C@]2(CCN(c3ccc(CCOC)cc3)C2=O)CC1]

The title compound was prepared in analogy to example 55 from 2-[4-(2-methoxy-ethyl)-phenyl]2-aza-spiro[4.5]decane-1,8-dione (obtained in example 123, step 2) by reaction with isopropenylmagnesium bromide (0.5M in THF). MS (m/e): 344.4 [MH$^+$].

Example 128

(5α,8α)-8-Hydroxy-8-isopropyl-2-[4-(2-methoxy-ethyl)-phenyl]-2-aza-spiro[4.5]decan-1-one

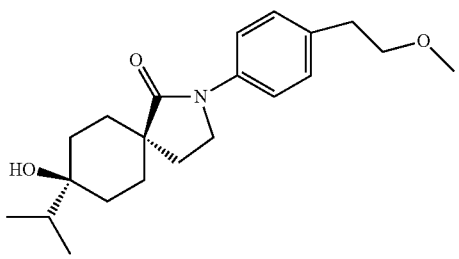 [SMILES: COCCc1ccc(N2CC[C@]3(CC[C@@](O)(C(C)C)CC3)C2=O)cc1]

(5α,8α)-8-Hydroxy-8-isopropenyl-2-[4-(2-methoxy-ethyl)-phenyl]-2-aza-spiro[4.5]decan-1-one (100 mg, obtained in example 127) was dissolved in ethanol (18 mL). Palladium on activated charcoal (38 mg, 10% Pd) was added and an atmosphere of hydrogen was introduced at RT. The mixture was stirred under hydrogen for 2 hours. The reaction mixture was then filtered over dicalite speed plus (Acros Organics) and the solvent was evaporated. The residue was purified by flash chromatography (silica gel, gradient of dichloromethane in acetonitrile) to give the title compound as a colorless foam (18 mg, 18%). MS (m/e): 346.2 [MH$^+$].

Example 129

(5α,8α)-8-Butyl-8-hydroxy-2-[4-(2-methoxy-ethyl)-phenyl]-2-aza-spiro[4.5]decan-1-one

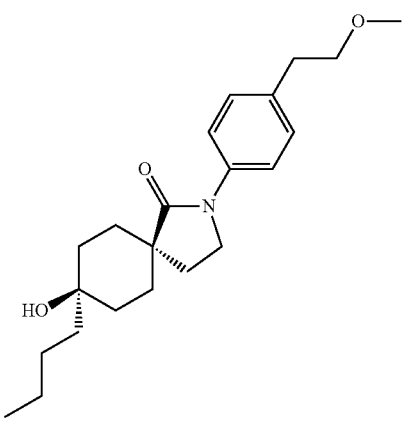 [SMILES: CCCC[C@]1(O)CC[C@]2(CCN(c3ccc(CCOC)cc3)C2=O)CC1]

The title compound was prepared in analogy to example 55 from 2-[4-(2-methoxy-ethyl)-phenyl]-2-aza-spiro[4.5]decane-1,8-dione (obtained in example 123, step 2) by reaction with n-butylmagnesium chloride (20 wt % in THF/toluene). MS (m/e): 342.3 [(M-H$_2$O)H$^+$].

Example 130

(5α,8α)-8-Hydroxy-8-isopropyl-2-(4-(3-methoxypropyl)phenyl)-2-aza-spiro[4.5]decan-1-one

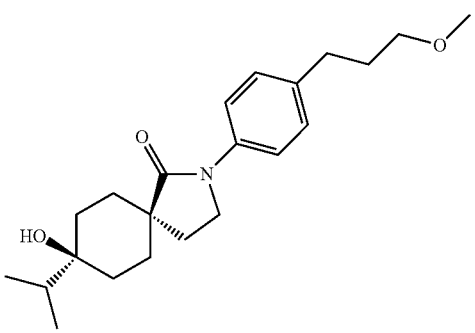 [SMILES: COCCCc1ccc(N2CC[C@]3(CC[C@@](O)(C(C)C)CC3)C2=O)cc1]

Step 1: 3-(4-Bromo-phenyl)-propan-1-ol

To a suspension of 3-(4-bromophenyl)-propionic acid (3.0 g, [CAS Reg. No. 1643-30-7]) in diethyl ether (50 mL) was added lithium aluminium hydride (746 mg) in three portions. The mixture was then heated to reflux for 16 hours. The mixture was cooled to room temperature and saturated sodium sulfate solution (3 mL) was added dropwise over a period of 5 minutes. Stirring was continued for 30 minutes at RT. A white precipitation was obtained. The solid was filtered off, washed with diethyl ether and the filtrate was concentrated in vacuo to afford the title compound as a colorless liquid (2.62 g, 93%) that was used without further purification. MS (EI): 215.0 [MH$^+$].

Step 2: 1-Bromo-4-(3-methoxy-propyl)-benzene 3-(4-Bromo-phenyl)-propan-1-ol (2.60 g, obtained in example 130, step 1) was dissolved in THF (35 mL). The mixture was cooled to 0° C. and sodium hydride (60% in mineral oil, 967 mg) was added in four portions to the cold mixture. Stirring was continued at 0° C. for 1 hour. Then, iodomethane (1.13 mL) was added dropwise over a period of 15 minutes to the reaction mixture. The mixture was warmed to room temperature over a period of 1 hour. The reaction mixture was poured into ice/water and was extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a light yellow liquid (2.61 g, 94%). MS (EI): 229.0 [M$^-$].

Step 3: 10-[4-(3-Methoxy-propyl)-phenyl]-1,4-dioxa-10-aza-dispiro[4.2.4.2]tetradecan-9-one 1,4-Dioxa-10-aza-dispiro[4.2.4.2]tetradecan-9-one (276 mg, obtained in example 121, step 3) was dissolved in DMF (18 mL) at r.t. Then, 1-bromo-4-(3-methoxy-propyl)-benzene (599 mg, obtained in example 130, step 2), N,N'-dimethylethylenediamine (sym) (230 mg), Cuprous iodide (373 mg) and K$_3$PO$_4$ (832 mg) were added to the reaction mixture and the mixture was heated to 80° C. for 3 hours. The reaction mixture was cooled, poured into ice/water and was extracted two times with ethyl acetate. The combined organic layers were washed with brine, dried over Na$_2$SO$_4$, filtered and the solvent was evaporated. The title compound was obtained as a yellow liquid (460 mg, 93%) and was used without further purification. MS (m/e): 360.2. [MH$^+$].

Step 4: 2-[4-(3-Methoxy-propyl)-phenyl]-2-aza-spiro[4.5]decane-1,8-dione

10-[4-(3-Methoxy-propyl)-phenyl]-1,4-dioxa-10-aza-dispiro[4.2.4.2]tetradecan-9-one (460 mg, obtained in example 130, step 3) was dissolved in tetrahydrofuran (12 mL). Then hydrochloric acid (2M, 6.40 mL) was added dropwise over a period of 10 minutes and the mixture was stirred for 3 hours at RT. The reaction mixture was poured into ice/water and was extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless solid (128 mg, 32%). MS (m/e): 316.2 [MH$^+$].

Step 5: (5α,8α)-8-Hydroxy-8-isopropyl-2-(4-(3-methoxypropyl)phenyl)-2-aza-spiro[4.5]decan-1-one The title compound was prepared in analogy to example 55 from 2-[4-(3-methoxy-propyl)-phenyl]-2-aza-spiro[4.5]decane-1,8-dione (obtained in example 130, step 4) by reaction with isopropylmagnesium bromide (1M in THF). MS (m/e): 342.3 [(M-H$_2$O)H$^+$].

Example 131

(5α,8α)-8-Ethyl-8-hydroxy-2-[4-(2-methoxy-1,1-dimethyl-ethyl)-phenyl]-2-aza-spiro[4.5]decan-1-one

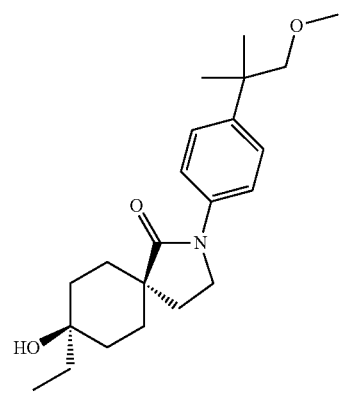 [SMILES: CC[C@]1(O)CC[C@]2(CCN(c3ccc(C(C)(C)COC)cc3)C2=O)CC1]

Step 1: 8-Hydroxy-2-[4-(2-methoxy-1,1-dimethyl-ethyl)-phenyl]-2-aza-spiro[4.5]decan-1-one The title compound was prepared in analogy to example 1, step 4 from trans-4-hydroxy-1-(2-methoxy-ethyl)-cyclohexanecarboxylic acid ethyl ester (obtained in example 1, step 3) by treatment with 4-(2-methoxy-1,1-dimethyl-ethyl)-phenylamine [CAS Reg. No. 1021439-70-2; for synthesis see: Tegley et al., PCT Int. Appl. 2005, WO 2005021532 or Bonnet et al., PCT Int. Appl. 2008, WO 2008117175 A2]. MS (m/e): 332.4 [MH$^+$].

Step 2: 2-[4-(2-Methoxy-1,1-dimethyl-ethyl)-phenyl]-2-aza-spiro[4.5]decane-1,8-dione The title compound was prepared in analogy to example 54 by oxidation of 8-hydroxy-2-[4-(2-methoxy-1,1-dimethyl-ethyl)-phenyl]-2-aza-spiro[4.5]decan-1-one (obtained in example 131, step 1). MS (m/e): 330.2 [MH$^+$].

Step 3: (5α,8α)-8-Ethyl-8-hydroxy-2-[4-(2-methoxy-1,1-dimethyl-ethyl)-phenyl]-2-aza-spiro[4.5]decan-1-one The title compound was prepared in analogy to example 55 from 2-[4-(2-methoxy-1,1-dimethyl-ethyl)-phenyl]-2-aza-spiro[4.5]decane-1,8-dione (obtained in example 131, step 2) by reaction with ethylmagnesium bromide (3M in diethyl ether). MS (m/e): 342.3 [(M-H$_2$O)H$^+$].

Example 132

(5α,8α)-8-Hydroxy-2-[4-(2-methoxy-1,1-dimethyl-ethyl)-phenyl]-8-propyl-2-aza-spiro[4.5]decan-1-one

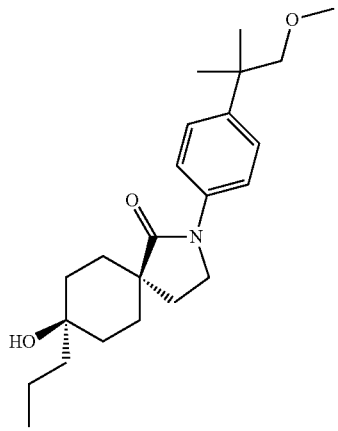 [SMILES: CCC[C@]1(O)CC[C@]2(CCN(c3ccc(C(C)(C)COC)cc3)C2=O)CC1]

The title compound was prepared in analogy to example 55 from 2-[4-(2-methoxy-1,1-dimethyl-ethyl)-phenyl]-2-aza-spiro[4.5]decane-1,8-dione (obtained in example 131, step 2) by reaction with propylmagnesium chloride (2M in diethyl ether). MS (m/e): 356.4 [(M-H$_2$O)H$^+$].

Example 133

(5α,8α)-8-Hydroxy-8-propyl-2-(4-(2,2,2-trifluoro-1-hydroxyethyl)phenyl)-2-aza-spiro[4.5]decan-1-one

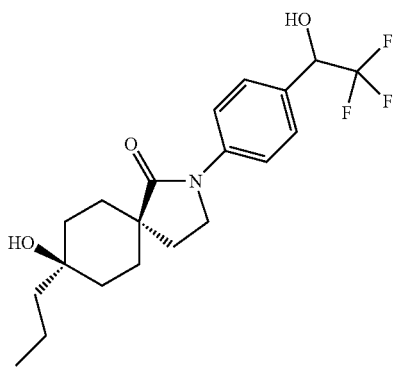 [SMILES: CCC[C@]1(O)CC[C@]2(CCN(c3ccc(C(O)C(F)(F)F)cc3)C2=O)CC1]

Step 1: 1,4-Dioxa-spiro[4.5]decane-8-carboxylic acid ethyl ester

The title compound was prepared in analogy to example 1, step 1 from ethyl-cyclohexanone-4-carboxylate [CAS Reg. No. 17159-79-4]. MS (m/e): 215.3 [MH$^+$].

Step 2: 8-Cyanomethyl-1,4-dioxa-spiro[4.5]decane-8-carboxylic acid ethyl ester A solution of 1,4-dioxa-spiro[4.5]decane-8-carboxylic acid ethyl ester (1.0 g, obtained in example 133, step 1) in THF (8 mL) was added dropwise over a period of 10 minutes to a solution of lithiumdiisopropylamide (2M in THF/heptane/ethyl benzene, 4.67 mL) in THF (12 mL) kept at −5° C. (ice/methanol bath). Stirring was continued for 1 hour at 0° C. The reaction mixture was re-cooled to −5° C. and a solution of bromoacetonitrile (0.65 mL, [CAS Reg. No. 590-17-0]) in THF (4 mL) was added dropwise over a period of 10 minutes. Stirring was then continued for 16 hours at RT. The reaction mixture was poured into ice/water and was acidified with 1M aqueous HCl solution (50 mL). The aqueous layer was extracted two times with ethyl acetate and the combined organic layers were washed with brine, dried over Na$_2$SO$_4$ and filtered. The solvent was evaporated and the residue was purified by flash chromatography (silica gel, gradient of heptane in ethyl acetate) to give the title compound as a brown liquid (528 mg, 45%). MS (m/e): 254.2 [MH$^+$].

Step 3: 1,4-Dioxa-10-aza-dispiro[4.2.4.2]tetradecan-9-one

8-Cyanomethyl-1,4-dioxa-spiro[4.5]decane-8-carboxylic acid ethyl ester (525 mg, obtained in example 133, step 2) was dissolved in methanol (10 mL) and acetic acid (5 mL). Platinum (IV) oxide (235 mg) was added and an atmosphere of hydrogen was introduced at r.t. The mixture was stirred under hydrogen at room temperature for 18 hours. The reaction was filtered over dicalite speed plus (Acros Organics) and the filtrate was concentrated in vacuo. The residue was poured into ice/water and was basified with 2M aqueous NaOH solution. The aqueous layer was extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless solid (169 mg, 39%). MS (m/e): 212.2 [MH$^+$].

Step 4: 10-[4-(2,2,2-Trifluoro-1-hydroxy-ethyl)-phenyl]-1,4-dioxa-10-aza-dispiro[4.2.4.2]tetradecan-9-one 1,4-Dioxa-10-aza-dispiro[4.2.4.2]tetradecan-9-one (352 mg, obtained in example 133, step 3) was dissolved in DMF (22 mL) at r.t. Then, 2,2,2-trifluoro-1-(4-iodophenyl)ethanol (755 mg, [CAS Reg. No. 857521-44-9; for synthesis see: Beyer et al., PCT Int. Appl. (2005), WO 2005061497 A1], N,N'-dimethylethylenediamine (sym) (294 mg), cuprous iodide (476 mg) and K$_3$PO$_4$ (1.06 g) were added to the reaction mixture. The mixture was heated to 80° C. for 4.5 hours. The reaction mixture was cooled down to 30° C. and more 2,2,2-trifluoro-1-(4-iodophenyl)ethanol (252 mg) was added. The mixture was re-heated to 80° C. for 2 hours. The reaction mixture was cooled, poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless solid (415 mg, 62%). MS (m/e): 386.4 [MH$^+$].

Step 5: 2-[4-(2,2,2-Trifluoro-1-hydroxy-ethyl)-phenyl]-2-aza-spiro[4.5]decane-1,8-dione 10-[4-(2,2,2-Trifluoro-1-hydroxy-ethyl)-phenyl]-1,4-dioxa-10-aza-dispiro[4.2.4.2]tetradecan-9-one (402 mg, obtained in example 133, step 4) was dissolved in tetrahydrofuran (10 mL). Then, hydrochloric acid (2M, 5.22 mL) was added dropwise over a period of 10 minutes to the reaction mixture. The mixture was stirred for 3 hours at RT. The reaction mixture was poured into ice/water and was extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a colorless foam (265 mg, 73%). MS (m/e): 342.1 [MH⁺].

Step 6: (5α,8α)-8-Hydroxy-8-propyl-2-(4-(2,2,2-trifluoro-1-hydroxyethyl)phenyl)-2-aza-spiro[4.5]decan-1-one The title compound was prepared in analogy to example 55 from 2-[4-(2,2,2-trifluoro-1-hydroxy-ethyl)-phenyl]-2-aza-spiro[4.5]decane-1,8-dione (obtained in example 133, step 5) by reaction with propylmagnesium chloride (2M in diethyl ether). MS (m/e): 368.2 [(M-H$_2$O)H⁺].

Example 133a (5α,8α)-8-Hydroxy-8-propyl-2-[4-((S)-2,2,2-trifluoro-1-hydroxy-ethyl)-phenyl]-2-aza-spiro[4.5]decan-1-one

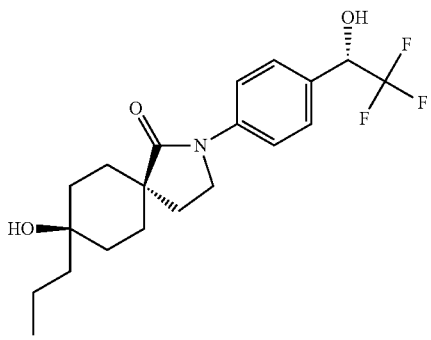 [SMILES: CCC[C@]1(O)CC[C@]2(CCN(c3ccc([C@H](O)C(F)(F)F)cc3)C2=O)CC1]

The racemic mixture (5α,8α)-8-hydroxy-8-propyl-2-(4-(2,2,2-trifluoro-1-hydroxyethyl)phenyl)-2-aza-spiro[4.5]decan-1-one (57 mg, obtained in example 133, step 6) was separated by chiral prep. HPLC (Chiralpack AD, 40% ethanol in heptane) to afford the title compound as a light brown solid (23 mg, 40%).

Alternatively, this compound can be made by following the sequence outlined in example 133, steps 1 to 6, whereby the appropriate enantiomerically pure 2,2,2-trifluoro-1-(4-iodophenyl)ethanol (for synthesis see: J. Org. Chem. 2009, 74, 1605-1610) is used in step 4. MS (m/e): 386.2 [MH⁺].

Example 133b (5α,8α)-8-Hydroxy-8-propyl-2-[4-((R)-2,2,2-trifluoro-1-hydroxy-ethyl)-phenyl]-2-aza-spiro[4.5]decan-1-one

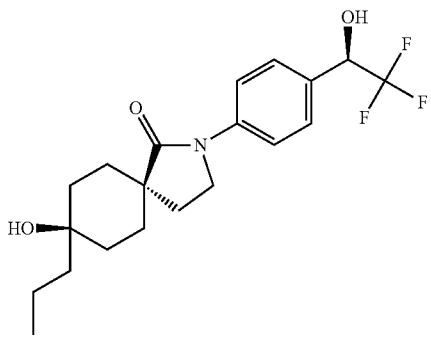 [SMILES: CCC[C@]1(O)CC[C@]2(CCN(c3ccc([C@@H](O)C(F)(F)F)cc3)C2=O)CC1]

The racemic mixture (5α,8α)-8-hydroxy-8-propyl-2-(4-(2,2,2-trifluoro-1-hydroxyethyl)phenyl)-2-aza-spiro[4.5]decan-1-one (57 mg, obtained in example 133, step 6) was separated by chiral prep. HPLC (Chiralpack AD, 40% ethanol in heptane) to afford the title compound as a light brown solid (22 mg, 35%).

Alternatively, this compound can be made by following the sequence outlined in example 133, steps 1 to 6, whereby the appropriate enantiomerically pure 2,2,2-trifluoro-1-(4-iodophenyl)ethanol (for synthesis see: J. Org. Chem. 2009, 74, 1605-1610) is used in step 4. MS (m/e): 386.2 [MH⁺].

Example 134

(5α,8β)-8-Hydroxy-8-propyl-2-(4-(2,2,2-trifluoro-1-hydroxyethyl)phenyl)-2-aza-spiro[4.5]decan-1-one

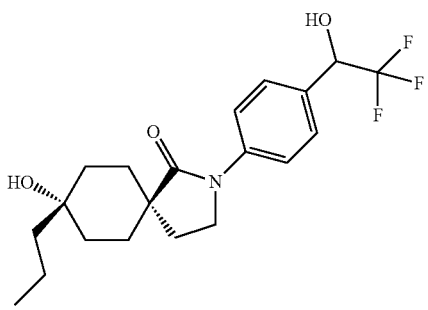 [SMILES: CCC[C@]1(O)CC[C@@]2(CCN(c3ccc(C(O)C(F)(F)F)cc3)C2=O)CC1]

The title compound was prepared as described in example 56 from 2-[4-(2,2,2-trifluoro-1-hydroxy-ethyl)-phenyl]-2-aza-spiro[4.5]decane-1,8-dione (obtained in example 133, step 5) by reaction with propylmagnesium chloride (2M in diethyl ether). MS (m/e): 386.4 [MH⁺].

Example 135

(5α,8α)-8-Hydroxy-8-isopropyl-2-[4-((R)-2,2,2-trifluoro-1-hydroxy-ethyl)-phenyl]-2-aza-spiro[4.5]decan-1-one

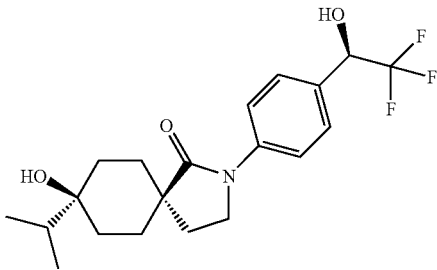 [SMILES: CC(C)[C@]1(O)CC[C@]2(CCN(c3ccc([C@@H](O)C(F)(F)F)cc3)C2=O)CC1]

Step 1: 10-[4-((R)-2,2,2-Trifluoro-1-hydroxy-ethyl)-phenyl]-1,4-dioxa-10-aza-dispiro[4.2.4.2]tetradecan-9-one

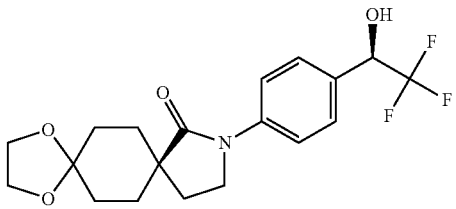

The title compound was prepared in analogy to example 133, step 4 from 1,4-dioxa-10-aza-dispiro[4.2.4.2]tetradecan-9-one (5.01 g) (described in example 133, step 3) and (1R)-1-(4-bromophenyl)-2,2,2-trifluoroethanol (9.07 g) (synthesis described in J. Org. Chem. 2009, 74, 1605-1610) as a white solid (4.9 g). MS (m/e): 386.1[MH⁺].

Step 2: 2-(4-((R)-2,2,2-trifluoro-1-hydroxy-ethyl) phenyl)-2-aza-spiro[4.5]decane-1,8-dione

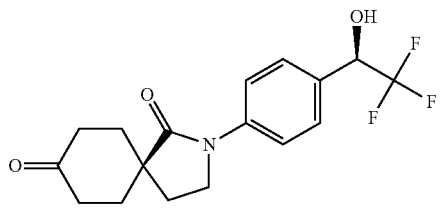

The title compound was prepared in analogy to example 133, step 5 from 10-[4-((R)-2,2,2-trifluoro-1-hydroxy-ethyl)-phenyl]-1,4-dioxa-10-aza-dispiro[4.2.4.2]tetradecan-9-one (4.09 g) by treatment with 2 M HCl (64 ml) in THF (127 ml) as a white solid. (4.06 g). MS (m/e): 342.130 [MH⁺].

Step 3: (5α,8α)-8-Hydroxy-8-isopropyl-2-[4-((R)-2, 2,2-trifluoro-1-hydroxy-ethyl)-phenyl]-2-aza-spiro [4.5]decan-1-one The title compound was prepared in analogy to example 103 from 2-[4-((R)-2,2,2-trifluoro-1-hydroxy-ethyl)-phenyl]-2-aza-spiro[4.5]decane-1,8-dione by reaction with isopropylmagnesium chloride (2M in THF). MS (m/e): 368.2 [(M-H₂O)H⁺].

In the chromatographic purification step, the trans compound (5α,8β)-8-hydroxy-8-isopropyl-2-(4-((R)-2,2,2-trifluoro-1-hydroxy-ethyl)-phenyl)-2-aza-spiro[4.5]decan-1-one was also isolated (see example 136).

Example 136

(5α,8β)-8-Hydroxy-8-isopropyl-2-(4-((R)-2,2,2-trifluoro-1-hydroxy-ethyl)-phenyl)-2-aza-spiro[4.5] decan-1-one

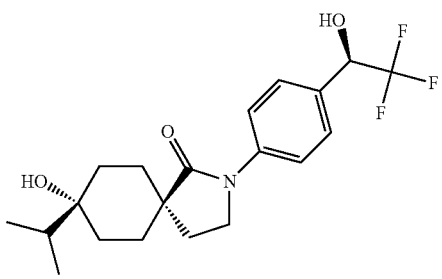 [SMILES: CC(C)[C@]1(O)CC[C@@]2(CCN(c3ccc([C@@H](O)C(F)(F)F)cc3)C2=O)CC1]

The title compound was isolated from the final reaction providing example 135 (treatment of 2-[4-((R)-2,2,2-trifluoro-1-hydroxy-ethyl)-phenyl]-2-aza-spiro[4.5]decane-1, 8-dione (obtained in Example 135, Step 2) with isopropylmagnesium chloride). MS (m/e): 386.2 [MH⁺].

Example 137

(5α,8α)-8-Hydroxy-8-isopropyl-2-(4-((R)-2,2,2-trifluoro-1-methoxyethyl)phenyl)-2-aza-spiro[4.5] decan-1-one

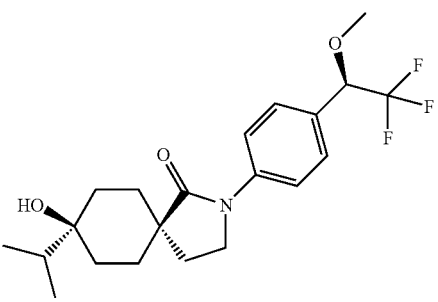 [SMILES: CO[C@H](c1ccc(N2CC[C@]3(CC[C@@](O)(C(C)C)CC3)C2=O)cc1)C(F)(F)F]

Sodium hydride (60% in mineral oil, 7 mg) was added to a solution of (5α,8α)-8-hydroxy-8-isopropyl-2-[4-((R)-2,2,2-trifluoro-1-hydroxy-ethyl)-phenyl]-2-aza-spiro[4.5]decan-1-one (45 mg, obtained in example 135) in DMF (3.0 mL) and the mixture was stirred for 40 minutes at RT. Then, iodomethane (8.0 µL) was added dropwise over a period of 1 minute and stirring was continued for 1 hour. The reaction mixture was poured into ice/water and was extracted two times with ethyl acetate. The combined organic layers were washed with brine, dried over Na₂SO₄, filtered and the solvent was evaporated. The residue was purified by flash chromatography (silica gel, gradient of heptane in ethyl acetate) to give the title compound as a colorless solid (38 mg, 82%). MS (m/e): 382.2 [MH⁺].

Example 138

(5α,8α)-8-Hydroxy-8-(methoxymethyl)-2-(4-((R)-2, 2,2-trifluoro-1-hydroxyethyl)phenyl)-2-aza-spiro [4.5]decan-1-one

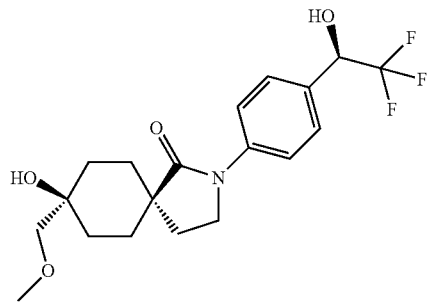 [SMILES: COC[C@]1(O)CC[C@]2(CCN(c3ccc([C@@H](O)C(F)(F)F)cc3)C2=O)CC1]

Step 1: (3α,6α)-8-[4-((R)-2,2,2-Trifluoro-1-hydroxy-ethyl)-phenyl]-1-oxa-8-aza-dispiro[2.2.4.2] dodecan-7-one The title compound was prepared in analogy to example 110, step 1 from 2-[4-((R)-2,2,2-trifluoro-1-hydroxy-ethyl)- phenyl]-2-aza-spiro[4.5]decane-1,8-dione (obtained in Example 135, Step 2). MS (m/e): 338.4 [(M-H$_2$O)H$^+$].

Step 2: (5α,8α)-8-Hydroxy-8-(methoxymethyl)-2-(4-((R)-2,2,2-trifluoro-1-hydroxyethyl)phenyl)-2-aza-spiro[4.5]decan-1-one The title compound was prepared in analogy to example 110, step 2 from (3α,6α)-8-[4-((R)-2,2,2-trifluoro-1-hydroxy-ethyl)-phenyl]-1-oxa-8-aza-dispiro[2.2.4.2]dodecan-7-one (obtained in example 138, step 1) by treatment with sodium methylate. MS (m/e): 388.3 [MH$^+$].

Example 139

(5α,8α)-8-Hydroxy-8-(methoxymethyl)-2-(4-((R)-2,2,2-trifluoro-1-methoxyethyl)phenyl)-2-aza-spiro[4.5]decan-1-one

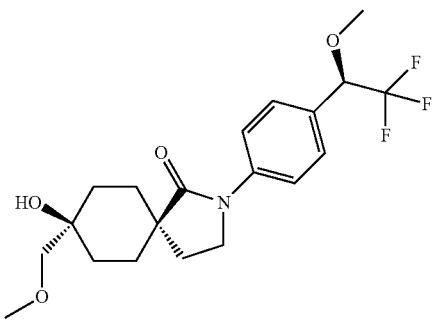 [SMILES: COC[C@]1(O)CC[C@]2(CCN(c3ccc([C@@H](OC)C(F)(F)F)cc3)C2=O)CC1]

The title compound was prepared in analogy to example 137 from (5α,8α)-8-hydroxy-8-(methoxymethyl)-2-(4-((R)-2,2,2-trifluoro-1-hydroxyethyl)phenyl)-2-aza-spiro[4.5]decan-1-one (obtained in example 138, step 2) by alkylation with iodomethane [CAS Reg. No. 74-88-4]. MS (m/e): 402.4 [MH$^+$].

Example 140

(5α,8α)-2-(4-((R)-1-Ethoxy-2,2,2-trifluoroethyl)phenyl)-8-hydroxy-8-(methoxymethyl)-2-aza-spiro[4.5]decan-1-one

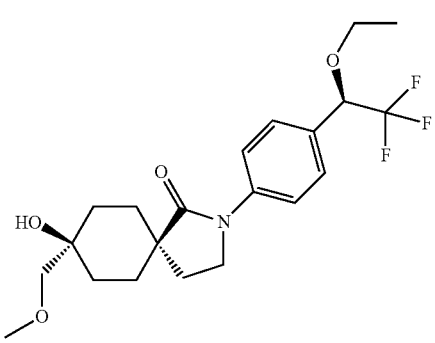 [SMILES: CCO[C@H](c1ccc(N2CC[C@]3(CC[C@@](O)(COC)CC3)C2=O)cc1)C(F)(F)F]

The title compound was prepared in analogy to example 137 from (5α,8α)-8-hydroxy-8-(methoxymethyl)-2-(4-((R)-2,2,2-trifluoro-1-hydroxyethyl)phenyl)-2-aza-spiro[4.5]decan-1-one (obtained in example 138, step 2) by alkylation with 1-iodoethane [CAS Reg. No. 75-03-6]. MS (m/e): 416.4 [MH$^+$].

Example 141

(5α,8α)-8-Hydroxy-8-(methoxymethyl)-2-(4-((R)-2,2,2-trifluoro-1-propoxyethyl)phenyl)-2-aza-spiro[4.5]decan-1-one

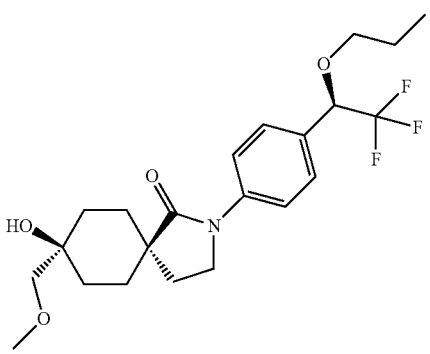 [SMILES: CCCO[C@H](c1ccc(N2CC[C@]3(CC[C@@](O)(COC)CC3)C2=O)cc1)C(F)(F)F]

The title compound was prepared in analogy to example 137 from (5α,8α)-8-hydroxy-8-(methoxymethyl)-2-(4-((R)-2,2,2-trifluoro-1-hydroxyethyl)phenyl)-2-aza-spiro[4.5]decan-1-one (obtained in example 138, step 2) by alkylation with 1-iodopropane [CAS Reg. No. 107-08-4]. MS (m/e): 430.4 [MH$^+$].

Example 142

(5α,8α)-8-Allyl-8-hydroxy-2-[4-((R)-2,2,2-trifluoro-1-methyl-ethoxy)-phenyl]-2-aza-spiro[4.5]decan-1-one

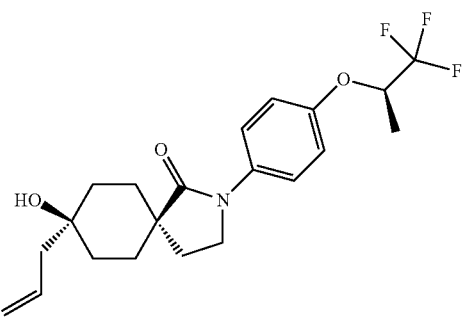 [SMILES: C=CC[C@]1(O)CC[C@]2(CCN(c3ccc(O[C@H](C)C(F)(F)F)cc3)C2=O)CC1]

Step 1: 4-((R)-2,2,2-Trifluoro-1-methyl-ethoxy)-phenylamine

Sodium hydride (55%, 3.22 g) was added to DMF (20 mL) and the mixture was cooled to 0° C. Then, (R)-1,1,1-trifluoro-2-propanol (8.5 g) [CAS 17628-73-8] was added over a period of 1 hour and stirring was continued for 30 minutes at 0° C. A solution of 1-fluoro-4-nitro-benzene [CAS 350-46-9] (10 g) in DMF (15 mL) was added over a period of 1.5 hours while the internal temperature was kept between 5 to 15° C. Following addition, the mixture was allowed to warm to RT and stirring was continued for another 12 hours. The reaction mixture was acidified and partitioned between ethyl acetate and water. The organic layer was separated, dried over $Na_2SO_4$ and evaporated to dryness. The residue was dissolved in methanol (150 mL) and Pd on carbon (10% Pd, 1 g) was added. The mixture was then hydrogenated at RT for 12 hours. The catalyst was removed by filtration and the filtrate was concentrated in vacuo to provide crude 4-((R)-2,2,2-trifluoro-1-methyl-ethoxy)-phenylamine as a dark liquid (14.5 g). MS (m/e): 206.1 (MH$^+$).

Step 2: 8-Hydroxy-2-[4-((R)-2,2,2-trifluoro-1-methyl-ethoxy)-phenyl]-2-aza-spiro[4.5]decan-1-one (mixture of cis and trans diastereomers)

4-((R)-2,2,2-Trifluoro-1-methyl-ethoxy)-phenylamine (7.57 g,) was added to a solution of 4-hydroxy-1-(2-methoxy-ethyl)-cyclohexanecarboxylic acid ethyl ester (5.0 g, obtained in example 2, step 3) in toluene (150 mL). The mixture was stirred for 10 minutes at RT. Then, dimethylalu-miniumchloride (1M in hexane, 65.1 mL) was added dropwise over a period of 45 minutes. The reaction mixture was heated to reflux for 2 hours and was then kept at 95° C. for 16 hours. The mixture was cooled, poured into ice/water and extracted two times with ethyl acetate. The combined organic layers were washed with brine, dried over $Na_2SO_4$, filtered and the solvent was evaporated. The title compound was obtained as an inseparable mixture of cis and trans diastereomers as a light brown solid (5.79 g). This mixture was used without further purification. MS (m/e): 358.3 [MH$^+$].

Step 3: 2-[4-((R)-2,2,2-trifluoro-1-methyl-ethoxy)-phenyl]-2-aza-spiro[4.5]decane-1,8-dione To a solution of 8-hydroxy-2-[4-((R)-2,2,2-trifluoro-1-methyl-ethoxy)-phenyl]-2-aza-spiro[4.5]decan-1-one (5.79 g) and 2,2,6,6-tetramethylpiperidine-1-oxyl radical (TEMPO) (506 mg) in $CH_2Cl_2$ (85 mL) was added a solution of potassium bromide (482 mg) in water (16 mL). Then, sodiumhypochlorite (13%, 42.5 mL) was added dropwise over a period of 10 minutes followed by sodium bicarbonate (NaHCO$_3$) (4.08 g). The mixture was stirred for 1.5 hours at RT. TLC showed a remainder of starting material. More TEMPO (125 mg) and sodiumhypochlorite solution (10 mL) were added to the reaction mixture and the mixture was stirred for additional 2 hours at RT. The reaction mixture was poured into ice/water and was extracted three times with $CH_2Cl_2$. The combined organic layers were washed with brine, dried over $Na_2SO_4$, filtered and the solvent was evaporated. The crude material was purified by flash chromatography (silica gel, gradient of heptane in ethyl acetate) to provide the title compound as a light brown solid (5.47 g). MS (m/e): 356.1 (MH$^+$).

Step 4: (5α,8α)-8-Allyl-8-hydroxy-2-[4-((R)-2,2,2-trifluoro-1-methyl-ethoxy)-phenyl]-2-aza-spiro[4.5]decan-1-one Anhydrous cerous(III)-chloride (166 mg) in THF (7.0 mL) was cooled to 0° C. in an ice bath and the mixture was stirred at 0° C. for 40 minutes. A solution of 2-[4-((R)-2,2,2-trifluoro-1-methyl-ethoxy)-phenyl]-2-aza-spiro[4.5]decane-1,8-dione (150 mg) in THF (3.0 mL) was added dropwise over a period of 5 minutes to the cold reaction mixture and stirring was continued for 35 minutes. The reaction mixture was then cooled to −78° C. in an acetone/$CO_2$ bath and allylmagnesium bromide (1.0M in diethyl ether, 0.68 mL) was added dropwise over a period of 5 minutes. Stirring was continued at −78° C. for 30 minutes. The reaction mixture was warmed up to 0° C., poured into ice/water and was acidified with saturated NH$_4$Cl solution. The aqueous phase was then extracted two times with ethyl acetate and the organic layers were washed brine, dried over $Na_2SO_4$ and filtered The solvent was evaporated and the residue was purified by flash chromatography (silica gel, gradient of dichloromethane in acetonitrile) to give the title compound as a light yellow solid (66 mg, 39%). MS (m/e): 380.3 [(M-H$_2$O)H$^+$].

In the chromatographic purification step, the trans compound (5α,8β)-8-allyl-8-hydroxy-2-[4-((R)-2,2,2-trifluoro-1-methyl-ethoxy)-phenyl]-2-aza-spiro[4.5]decan-1-one was also isolated (see example 143).

Example 143

(5α,8β)-8-Allyl-8-hydroxy-2-[4-((R)-2,2,2-trifluoro-1-methyl-ethoxy)-phenyl]-2-aza-spiro[4.5]decan-1-one

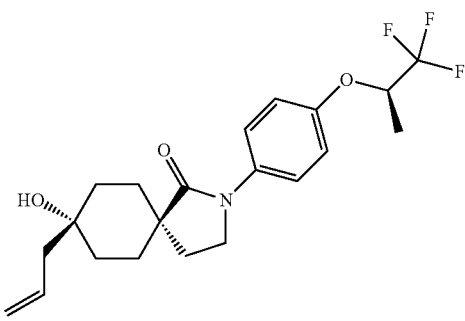 [SMILES: C=CC[C@]1(O)CC[C@@]2(CCN(c3ccc(O[C@H](C)C(F)(F)F)cc3)C2=O)CC1]

The title compound was isolated from the final reaction step providing example 142 (treatment of 2-[4-((R)-2,2,2-trifluoro-1-methyl-ethoxy)-phenyl]-2-aza-spiro[4.5]decane-1,8-dione (obtained in Example 142, Step 3) with allylmagnesium bromide) as a light brown solid (66 mg, 32%). MS (m/e): 398.2 [MH$^+$].

Example 144

(5α,8α)-8-(Benzyloxymethyl)-8-hydroxy-2-[4-((R)-2,2,2-trifluoro-1-methyl-ethoxy)-phenyl]-2-aza-spiro[4.5]decan-1-one

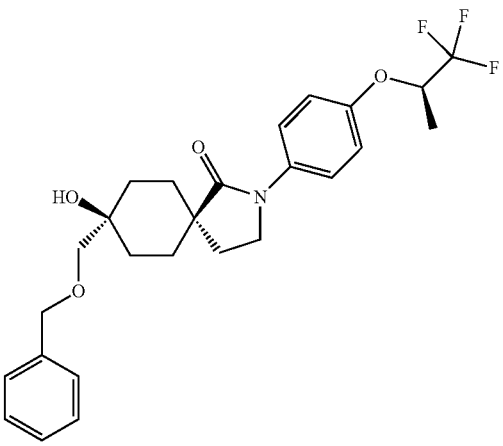 [SMILES: C[C@@H](Oc1ccc(N2CC[C@]3(CC[C@@](O)(COCc4ccccc4)CC3)C2=O)cc1)C(F)(F)F]

Step 1: (3α,6α)-8-[4-((R)-2,2,2-Trifluoro-1-methyl-ethoxy)-phenyl]-1-oxa-8-aza-dispiro[2.2.4.2]dodecan-7-one The title compound was prepared in analogy to example 110, step 1 from 2-[4-((R)-2,2,2-trifluoro-1-methyl-ethoxy)-phenyl]-2-aza-spiro[4.5]decane-1,8-dione (obtained in example 142, step 3). MS (m/e): 370.2 [MH⁺].

Step 2: (5α,8α)-8-(Benzyloxymethyl)-8-hydroxy-2-[4-((R)-2,2,2-trifluoro-1-methyl-ethoxy)-phenyl]-2-aza-spiro[4.5]decan-1-one The title compound was prepared in analogy to example 110, step 2 from (3α,6α)-8-[4-((R)-2,2,2-trifluoro-1-methyl-ethoxy)-phenyl]-1-oxa-8-aza-dispiro[2.2.4.2]dodecan-7-one (obtained in example 144, step 1) by reaction with sodium phenyl-methanolate (1.0M in benzyl alcohol). MS (m/e): 478.3 [MH⁺].

Example 145

(5α,8α)-8-Hydroxy-8-(hydroxymethyl)-2-[4-((R)-2,2,2-trifluoro-1-methyl-ethoxy)-phenyl]-2-aza-spiro[4.5]decan-1-one

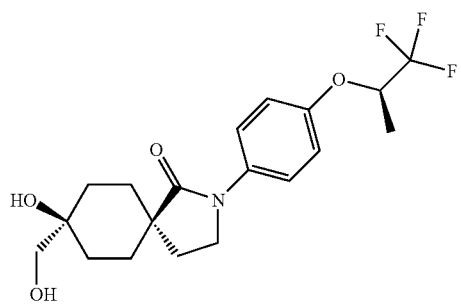 [SMILES: C[C@@H](Oc1ccc(N2CC[C@]3(CC[C@@](O)(CO)CC3)C2=O)cc1)C(F)(F)F]

The title compound was prepared in analogy to example 5 from (5α,8α)-8-(benzyloxymethyl)-8-hydroxy-2-[4-((R)-2,2,2-trifluoro-1-methyl-ethoxy)-phenyl]-2-aza-spiro[4.5]decan-1-one (obtained in example 144, step 2) by hydrogenation. MS (m/e): 388.3 [MH⁺].

Example 146

(5α,8α)-8-Hydroxy-8-methoxymethyl-2-[4-((S)-2,2,2-trifluoro-1-methyl-ethoxy)-phenyl]-2-aza-spiro[4.5]decan-1-one

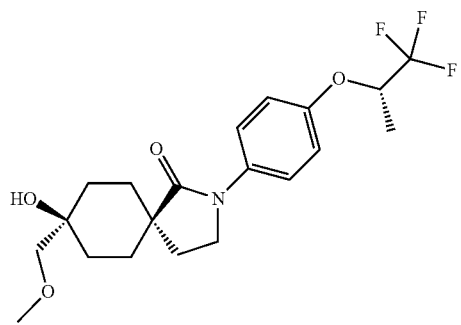 [SMILES: COC[C@]1(O)CC[C@]2(CCN(c3ccc(O[C@@H](C)C(F)(F)F)cc3)C2=O)CC1]

Step 1: 4-((S)-2,2,2-Trifluoro-1-methyl-ethoxy)-phenylamine

This material was made in analogy to example 142, step 1 from (S)-1,1,1-trifluoro-2-propanol [CAS 17628-73-8] and 1-fluoro-4-nitro-benzene [CAS 350-46-9]. MS (m/e): 206.1 (MH⁺).

Step 2: 8-Hydroxy-2-[4-((S)-2,2,2-trifluoro-1-methyl-ethoxy)-phenyl]-2-aza-spiro[4.5]decan-1-one (Mixture of Cis and Trans Diastereomers)

The title compound was made in analogy to example 142, step 2 and was used crude without further analysis in the subsequent reaction step.

Step 3: 2-[4-((S)-2,2,2-trifluoro-1-methyl-ethoxy)-phenyl]-2-aza-spiro[4.5]decane-1,8-dione To a solution of 8-hydroxy-2-[4-((S)-2,2,2-trifluoro-1-methyl-ethoxy)-phenyl]-2-aza-spiro[4.5]decan-1-one (5.79 g) and 2,2,6,6-tetramethylpiperidine-1-oxyl radical (TEMPO) (506 mg) in CH₂Cl₂ (85 mL) was added a solution of potassium bromide (482 mg) in water (16 mL). Then, sodiumhypochlorite (13%, 42.5 mL) was added dropwise over a period of 10 minutes, followed by sodium bicarbonate (NaHCO₃) (4.08 g). The mixture was stirred for 1.5 hours at RT. TLC showed a remainder of starting material. More TEMPO (125 mg) and sodiumhypochlorite solution (10 mL) were added and the mixture was stirred for an additional 2 hours at RT. The reaction was poured into ice/water and was extracted three times with CH₂Cl₂. The combined organic layers were washed with brine, dried over Na₂SO₄ and filtered. The solvent was evaporated and the crude material was purified by flash chromatography (silica gel, gradient of heptane in ethyl acetate) to provide the title compound as a light brown solid (5.47 g). MS (m/e): 356.1 (MH⁺).

Step 4: (3α,6α)-8-[4-((S)-2,2,2-Trifluoro-1-methyl-ethoxy)-phenyl]-1-oxa-8-aza-dispiro[2.2.4.2]dodecan-7-one The title compound was prepared in analogy to example 110, step 1 from 2-[4-((S)-2,2,2-trifluoro-1-methyl-ethoxy)-phenyl]-2-aza-spiro[4.5]decane-1,8-dione. MS (m/e): 352.3 [(M-H₂O)H⁺].

Step 5: (5α,8α)-8-Hydroxy-8-methoxymethyl-2-[4-((S)-2,2,2-trifluoro-1-methyl-ethoxy)-phenyl]-2-aza-spiro[4.5]decan-1-one The title compound was prepared in analogy to example 110, step 2 from (3α,6α)-8-[4-((S)-2,2,2-trifluoro-1-methyl-ethoxy)-phenyl]-1-oxa-8-aza-dispiro[2.2.4.2]dodecan-7-one (obtained in example 146, step 4) by treatment with sodium methylate. MS (m/e): 402.3 [MH⁺].

Example 147

(5α,8α)-8-Hydroxy-8-(methoxymethyl)-2-[4-((R)-2,2,2-trifluoro-1-methyl-ethoxy)-phenyl]-2-aza-spiro[4.5]decan-1-one

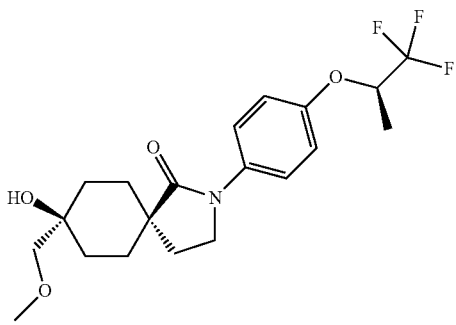 [SMILES: COC[C@]1(O)CC[C@]2(CCN(c3ccc(O[C@H](C)C(F)(F)F)cc3)C2=O)CC1]

The title compound was prepared in analogy to example 110, step 2 from (3α,6α)-8-[4-((R)-2,2,2-trifluoro-1-methyl-ethoxy)-phenyl]-1-oxa-8-aza-dispiro[2.2.4.2]dodecan-7-one (obtained in example 144, step 1) by treatment with sodium methylate. MS (m/e): 402.4 [MH⁺].

Example 148

(5α,8α)-8-Hydroxy-8-isopropyl-2-[6-((S)-2,2,2-trifluoro-1-methyl-ethoxy)pyridin-3-yl]-2-aza-spiro[4.5]decan-1-one

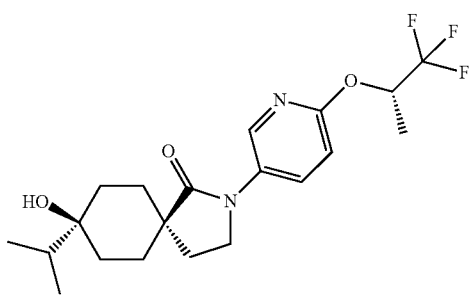 [SMILES: CC(C)[C@]1(O)CC[C@]2(CCN(c3ccc(O[C@@H](C)C(F)(F)F)nc3)C2=O)CC1]

Step 1: 5-Nitro-2-((S)-2,2,2-trifluoro-1-methyl-ethoxy)-pyridine

In a 4-neck flask, commercially available 2-chloro-5-nitropyridine (71.9 g) and (S)-1,1,1-trifluoropropan-2-ol (54.3 g) were dissolved in DMF (610 mL) and sodium hydride (20 g, 55%) was added at a temperature of 16 to 18° C. (ice cooling). Following addition, the mixture was allowed to stir for 1 hour. The mixture was poured into ice and was allowed to hydrolyze. The suspension was warmed to RT over a period of 12 hours and the solid was filtered and washed with additional water and then with a small amount of hexanes (50 mL). The brown solid was further dried in vacuo to provide the title compound. (81.9 g). ¹H-NMR (δ, CDCl₃): 9.06 (m, 1H), 8.43 (dd, 1H), 6.93 (d, 1H), 5.87 (m, 1H); 1.54 (m, 3H).

Step 2: 6-((S)-2,2,2-Trifluoro-1-methyl-ethoxy)-pyridin-3-ylamine

5-Nitro-2-((S)-2,2,2-trifluoro-1-methyl-ethoxy)-pyridine (81.9 g) and palladium on carbon (10% Pd, 0.0065 mol-eq) were added to MeOH and the mixture was hydrogenated until uptake of hydrogen was ceasing. The catalyst was removed by filtration and the filtrate was concentrated and further dried in vacuo to provide the title compound as a dark oil. MS (m/e): 207.0 (MH⁺).

Step 3: 8-Hydroxy-2-[6-((S)-2,2,2-trifluoro-1-methyl-ethoxy)-pyridin-3-yl]-2-aza-spiro[4.5]decan-1-one This material was obtained in analogy to example 108, step 3 from 6-((S)-2,2,2-trifluoro-1-methyl-ethoxy)-pyridin-3-ylamine (23.3 g) and 4-hydroxy-1-(2-methoxy-ethyl)-cyclohexanecarboxylic acid ethyl ester (20 g, obtained in example 2, step-3) as a brown oil (39.3 g). MS (m/e): 359.3 (MH⁺).

Step 4: 2-[6-((S)-2,2,2-Trifluoro-1-methyl-ethoxy)-pyridin-3-yl]-2-aza-spiro[4.5]decane-1,8-dione This material was obtained in analogy to example 108, step 4 from 8-hydroxy-2-[6-((S)-2,2,2-trifluoro-1-methyl-ethoxy)-pyridin-3-yl]-2-aza-spiro[4.5]decan-1-one (39.3 g) by Swern oxidation as an off-white solid (27.4 g). MS (m/e): 357.2 (MH⁺).

Step 5: (5α,8α)-8-Hydroxy-8-isopropyl-2-[6-((S)-2,2,2-trifluoro-1-methyl-ethoxy)pyridin-3-yl]-2-aza-spiro[4.5]decan-1-one The title compound was prepared in analogy to example 55 from 2-[6-((S)-2,2,2-trifluoro-1-methyl-ethoxy)-pyridin-3-yl]-2-aza-spiro[4.5]decane-1,8-dione by reaction with isopropylmagnesium chloride (2M in THF). MS (m/e): 383.2 [(M-H₂O)H⁺].

Example 149

(5α,8β)-8-Hydroxy-8-isopropyl-2-[6-((S)-2,2,2-trifluoro-1-methyl-ethoxy)pyridin-3-yl]-2-aza-spiro[4.5]decan-1-one

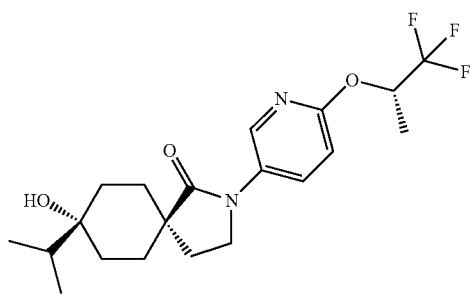 [SMILES: CC(C)[C@]1(O)CC[C@@]2(CCN(c3ccc(O[C@@H](C)C(F)(F)F)nc3)C2=O)CC1]

The title compound was prepared as described for example 56 from 2-[6-((S)-2,2,2-trifluoro-1-methyl-ethoxy)-pyridin-3-yl]-2-aza-spiro[4.5]decane-1,8-dione (obtained in example 148, step 4) by reaction with isopropylmagnesium chloride (2M in THF). MS (m/e): 401.3 [MH⁺].

Example 150

(5α,8α)-8-Hydroxy-8-isopropyl-2-[6-((R)-2,2,2-trifluoro-1-methyl-ethoxy)-pyridin-3-yl]-2-aza-spiro[4.5]decan-1-one

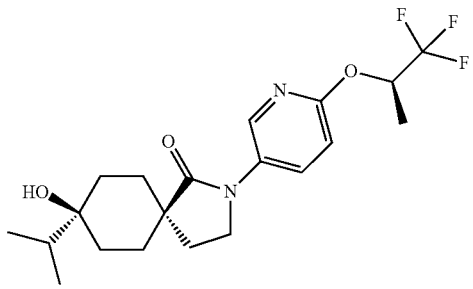 [SMILES: CC(C)[C@]1(O)CC[C@]2(CCN(c3ccc(O[C@H](C)C(F)(F)F)nc3)C2=O)CC1]

Step 1: 6-((R)-2,2,2-Trifluoro-1-methyl-ethoxy)-pyridin-3-ylamine

This material was obtained in analogy to example 148, steps 1 and 2 from 2-chloro-5-nitropyridine and (R)-1,1,1-trifluoropropan-2-ol as a dark oil. Rf: 0.43 (ether/heptane 2:1).

Step 2: 8-Hydroxy-2-[6-((R)-2,2,2-trifluoro-1-methyl-ethoxy)-pyridin-3-yl]-2-aza-spiro[4.5]decan-1-one This material was obtained in analogy to example 108, step 3 from 6-((R)-2,2,2-trifluoro-1-methyl-ethoxy)-pyridin-3-ylamine and 4-hydroxy-1-(2-methoxy-ethyl)-cyclohexanecarboxylic acid ethyl ester (obtained in example 2, step 3) and was used crude without further analysis.

Step 3: 2-[6-((R)-2,2,2-Trifluoro-1-methyl-ethoxy)-pyridin-3-yl]-2-aza-spiro[4.5]decane-1,8-dione This material was obtained in analogy to example 108, step 4 from 8-hydroxy-2-[6-((R)-2,2,2-trifluoro-1-methyl-ethoxy)-pyridin-3-yl]-2-aza-spiro[4.5]decan-1-one (39.3 g) by Swern oxidation as an off-white solid (27.4 g). MS (m/e): 357.1 (MH$^+$).

Step 4: (5α,8α)-8-Hydroxy-8-isopropyl-2-[6-((R)-2,2,2-trifluoro-1-methyl-ethoxy)-pyridin-3-yl]-2-aza-spiro[4.5]decan-1-one The title compound was prepared in analogy to example 55 from 2-[6-((R)-2,2,2-trifluoro-1-methyl-ethoxy)-pyridin-3-yl]-2-aza-spiro[4.5]decane-1,8-dione by reaction with isopropylmagnesium chloride (2M in THF). MS (m/e): 383.2 [(M-H$_2$O)H$^+$].

Example 151

(5α,8β)-8-Hydroxy-8-isopropyl-2-[6-((R)-2,2,2-trifluoro-1-methyl-ethoxy)pyridin-3-yl]-2-aza-spiro[4.5]decan-1-one

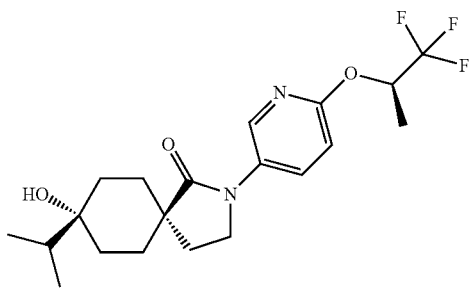 [SMILES: CC(C)[C@]1(O)CC[C@@]2(CCN(c3ccc(O[C@H](C)C(F)(F)F)nc3)C2=O)CC1]

The title compound was prepared as described for example 56 from 2-[6-((R)-2,2,2-trifluoro-1-methyl-ethoxy)-pyridin-3-yl]-2-aza-spiro[4.5]decane-1,8-dione (obtained in example 150, step 3) by reaction with isopropylmagnesium chloride (2M in THF). MS (m/e): 401.3 [MH$^+$].

Example 152

(5α,8α)-8-Hydroxy-8-methoxymethyl-2-[6-((R)-2,2,2-trifluoro-1-methyl-ethoxy)-pyridin-3-yl]-2-aza-spiro[4.5]decan-1-one

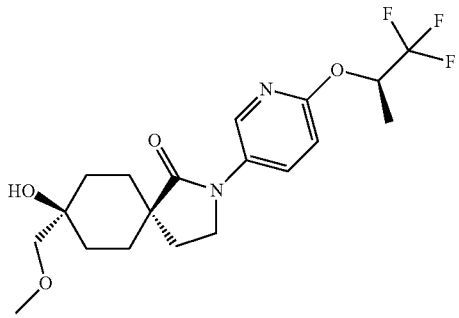 [SMILES: COC[C@]1(O)CC[C@]2(CCN(c3ccc(O[C@H](C)C(F)(F)F)nc3)C2=O)CC1]

Step 1: (3α,6α)-8-[6-((R)-2,2,2-Trifluoro-1-methyl-ethoxy)-pyridin-3-yl]-1-oxa-8-aza-dispiro[2.2.4.2]dodecan-7-one The title compound was prepared in analogy to example 110, step 1 from 2-[6-((R)-2,2,2-trifluoro-1-methyl-ethoxy)-pyridin-3-yl]-2-aza-spiro[4.5]decane-1,8-dione (obtained in example 150, step 3). MS (m/e): 371.1 [MH$^+$].

Step 2: (5α,8α)-8-Hydroxy-8-methoxymethyl-2-[6-((R)-2,2,2-trifluoro-1-methyl-ethoxy)pyridin-3-yl]-2-aza spiro[4.5]decan-1-one The title compound was prepared in analogy to example 110, step 2 from (3α,6α)-8-[6-((R)-2,2,2-trifluoro-1-methyl-ethoxy)-pyridin-3-yl]-1-oxa-8-aza-dispiro[2.2.4.2]dodecan-7-one (obtained in example 152, step 1) by treatment with sodium methylate. MS (m/e): 403.4 [MH$^+$].

Example 153

(5α,8α)-8-Hydroxy-8-methoxymethyl-2-[6-((S)-2,2,2-trifluoro-1-methyl-ethoxy)-pyridin-3-yl]-2-aza-spiro[4.5]decan-1-one

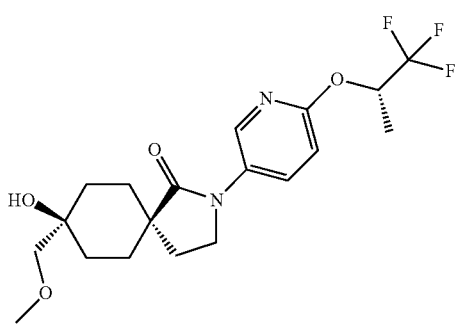 [SMILES: COC[C@]1(O)CC[C@]2(CCN(c3ccc(O[C@@H](C)C(F)(F)F)nc3)C2=O)CC1]

Step 1: (3α,6α)-8-[6-((S)-2,2,2-Trifluoro-1-methyl-ethoxy)-pyridin-3-yl]-1-oxa-8-aza-dispiro[2.2.4.2]dodecan-7-one The title compound was prepared in analogy to example 110, step 1 from 2-[6-((S)-2,2,2-trifluoro-1-methyl-ethoxy)-pyridin-3-yl]-2-aza-spiro[4.5]decane-1,8-dione (obtained in example 148, step 4). MS (m/e): 371.1 [MH$^+$].

Step 2: (5α,8α)-8-Hydroxy-8-methoxymethyl-2-[6-((S)-2,2,2-trifluoro-1-methyl-ethoxy)-pyridin-3-yl]-2-aza-spiro[4.5]decan-1-one The title compound was prepared in analogy to example 110, step 2 from (3α,6α)-8-[6-((S)-2,2,2-trifluoro-1-methyl-ethoxy)-pyridin-3-yl]-1-oxa-8-aza-dispiro[2.2.4.2]dodecan-7-one (obtained in example 153, step 1) by treatment with sodium methylate. MS (m/e): 403.4 [MH$^+$].

Example 154

(5α,8α)-8-Hydroxy-8-methoxymethyl-2-[4-(2,2,2-trifluoro-ethyl)-phenyl]-2-aza-spiro[4.5]decan-1-one

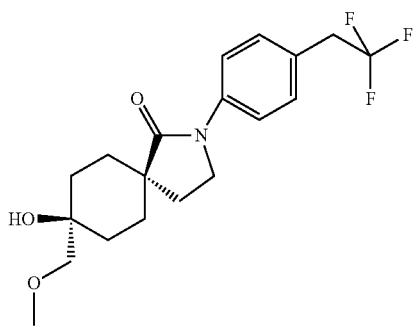 [SMILES: COC[C@]1(O)CC[C@]2(CCN(c3ccc(CC(F)(F)F)cc3)C2=O)CC1]

Step 1: (3α,6α)-8-[4-(2,2,2-Trifluoro-ethyl)-phenyl]-1-oxa-8-aza-dispiro[2.2.4.2]dodecan-7-one The title compound was prepared in analogy to example 110, step 1 from 2-[4-(2,2,2-trifluoro-ethyl)-phenyl]-2-aza-spiro[4.5]decane-1,8-dione (obtained in example 77, step 2). MS (m/e): 340.1 [MH$^+$].

Step 2: (5α,8α)-8-Hydroxy-8-methoxymethyl-2-[4-(2,2,2-trifluoro-ethyl)-phenyl]-2-aza-spiro[4.5]decan-1-one The title compound was prepared in analogy to example 110, step 2 from (3α,6α)-8-[4-(2,2,2-trifluoro-ethyl)-phenyl]-1-oxa-8-aza-dispiro[2.2.4.2]dodecan-7-one (obtained in example 154, step 1) by treatment with sodium methylate. MS (m/e): 372.2 [MH$^+$].

Example 155

(5α,8α)-8-Hydroxy-8-(2,2,2-trifluoro-ethoxymethyl)-2-[4-((R)-2,2,2-trifluoro-1-hydroxy-ethyl)-phenyl]-2-aza-spiro[4.5]decan-1-one

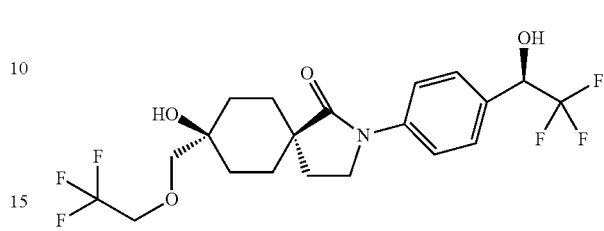

DMF (5 mL) was added to sodium hydride (60% in mineral oil, 49.5 mg). The suspension was cooled down to 0° C. and 2,2,2-trifluoroethanol (0.082 mL) was added dropwise over a period of 2 minutes to the cold mixture. Stirring was continued for 30 minutes at 0° C. Then, (3α,6α)-8-[4-((R)-2,2,2-trifluoro-1-hydroxy-ethyl)-phenyl]-1-oxa-8-aza-dispiro[2.2.4.2]dodecan-7-one (80 mg, obtained in example 138, step 1) was added to the reaction mixture. Stirring was continued for 10 minutes at 0° C. and then the reaction was heated to 70° C. for 20 hours. The mixture was poured into ice/water and was extracted two times with ethyl acetate. The combined organic layers were washed with brine, dried over Na$_2$SO$_4$ and filtered. The solvent was evaporated and the residue was purified by flash chromatography (silica gel, gradient of heptane in ethyl acetate) to give the title compound as a colorless solid (34 mg, 33%). MS (m/e): 456.3 [MH$^+$].

Example 156

2-[(5α,8α)-8-Hydroxy-1-oxo-2-(4-trifluoromethoxy-phenyl)-2-aza-spiro[4.5]dec-8-yl]-N,N-dimethyl-acetamide

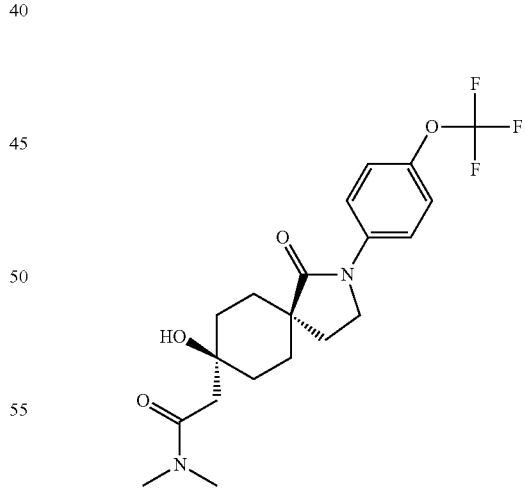

Step 1: [(5α,8α)-8-Hydroxy-1-oxo-2-(4-trifluoromethoxy-phenyl)-2-aza-spiro[4.5]dec-8-yl]-acetic acid Lithiumhydroxide (15 mg) was added to a solution of [(5α,8α)-8-hydroxy-1-oxo-2-(4-trifluoromethoxy-phenyl)-2-aza-spiro[4.5]dec-8-yl]-acetic acid ethyl ester (130 mg, obtained in example 116) in methanol (13 mL) and the reaction was stirred for 3 hours at room temperature. The reaction mixture was poured into ice/water and was acidified with 1M aqueous HCl solution to pH 1. The aqueous layer was extracted two times with ethyl acetate and the combined organic layers were washed with brine, dried over $Na_2SO_4$ and filtered. The solvent was evaporated and the residue was purified by flash chromatography (silica gel, gradient of heptane in ethyl acetate) to give the title compound as a colorless solid (90 mg, 74%). MS (m/e): 388.2 [MH$^+$].

Step 2: 2-[(5α,8α)-8-Hydroxy-1-oxo-2-(4-trifluoromethoxy-phenyl)-2-aza-spiro[4.5]dec-8-yl]-N,N-dimethyl-acetamide

[(5α,8α)-8-Hydroxy-1-oxo-2-(4-trifluoromethoxy-phenyl)-2-aza-spiro[4.5]dec-8-yl]-acetic acid (80 mg, obtained in example 156, step 1) was dissolved in THF (6 mL). Then, diisopropylethylamine (0.14 mL), 1-(3-dimethylaminopropy)-3-ethylcarbodiimide hydrochloride (79 mg), 1-hydroxy-7-azabenzotriazole (56 mg) and dimethylamine hydrochloride (35 mg) were added to the reaction mixture and stirring was continued for 40 minutes at room temperature. The reaction mixture was poured into ice/water and was acidified with 1M aqueous HCl solution. The aqueous phase was then extracted two times with ethyl acetate and the organic layers were washed with 1M aqueous NaOH and with brine, dried over $Na_2SO_4$ and filtered. The solvent was evaporated and the residue was purified by flash chromatography (silica gel, ethyl acetate) to give the title compound as a colorless solid (46 mg, 54%). MS (m/e): 415.2 [MH$^+$].

Example 157

2-((5α,8α)-8-Hydroxy-1-oxo-2-(4-(2,2,2-trifluoroethoxy)phenyl)-2-aza-spiro[4.5]decan-8-yl)-N,N-dimethylacetamide

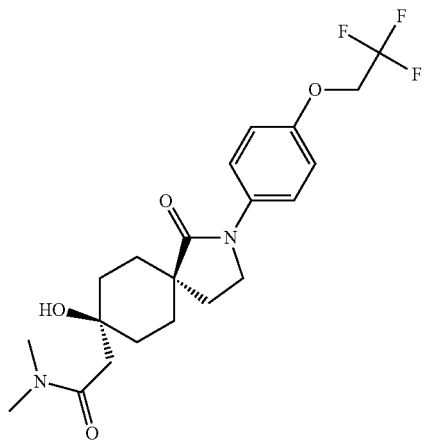 [SMILES: CN(C)C(=O)C[C@]1(O)CC[C@]2(CCN(c3ccc(OCC(F)(F)F)cc3)C2=O)CC1]

Step 1: {(5α,8α)-8-Hydroxy-1-oxo-2-[4-(2,2,2-trifluoro-ethoxy)-phenyl]-2-aza-spiro[4.5]dec-8-yl}-acetic acid ethyl ester The title compound was prepared in analogy to example 116 from 2-[4-(2,2,2-trifluoro-ethoxy)-phenyl]-2-aza-spiro[4.5]decane-1,8-dione (obtained in example 86, step 1). MS (m/e): 430.3 [MH$^+$].

Step 2: {(5α,8α)-8-Hydroxy-1-oxo-2-[4-(2,2,2-trifluoro-ethoxy)-phenyl]-2-aza-spiro[4.5]dec-8-yl}-acetic acid Lithiumhydroxide (35 mg) was added to a solution of {(5α,8α)-8-hydroxy-1-oxo-2-[4-(2,2,2-trifluoro-ethoxy)-phenyl]-2-aza-spiro[4.5]dec-8-yl}-acetic acid ethyl ester (300 mg, obtained in example 157, step 1 [or the corresponding "methyl ester"]) in THF (5 mL) and water (5 mL) and the reaction was stirred for 2 hours at room temperature. The mixture was poured into ice/water and was acidified with 1M aqueous HCl solution to pH 1. The aqueous layer was extracted two times with ethyl acetate. The combined organic layers were washed with brine, dried over $Na_2SO_4$ and filtered. The solvent was evaporated and the residue was purified by flash chromatography (silica gel, gradient of heptane in ethyl acetate) to give the title compound as a colorless solid (274 mg, 94%). MS (m/e): 402.3 [MH$^+$].

Step 3: 2-((5α,8α)-8-Hydroxy-1-oxo-2-(4-(2,2,2-trifluoroethoxy)phenyl)-2-aza-spiro[4.5]decan-8-yl)-N,N-dimethylacetamide The title compound was prepared in analogy to example 156, step 2 from {(5α,8α)-8-hydroxy-1-oxo-2-[4-(2,2,2-trifluoro-ethoxy)-phenyl]-2-aza-spiro[4.5]dec-8-yl}-acetic acid (obtained in example 157, step 2) by coupling with dimethylamine. MS (m/e): 429.3 [MH$^+$].

Example 158

2-((5α,8α)-8-Hydroxy-1-oxo-2-(4-(2,2,2-trifluoroethoxy)phenyl)-2-aza-spiro[4.5]decan-8-yl)-N-methylacetamide

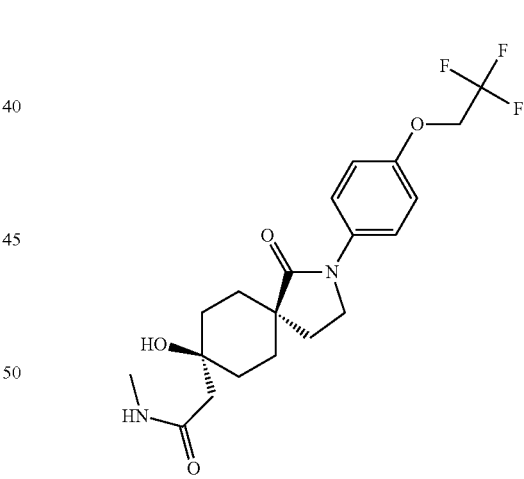

{(5α,8α)-8-Hydroxy-1-oxo-2-[4-(2,2,2-trifluoro-ethoxy)-phenyl]-2-aza-spiro[4.5]dec-8-yl}-acetic acid (135 mg, obtained in example 157, step 2) was dissolved in THF (9 mL). Then, diisopropylethylamine (0.23 mL), 1-(3-dimethylaminopropy)-3-ethylcarbodiimide hydrochloride (129 mg), 1-hydroxy-7-azabenzotriazole (92 mg) and methylamine hydrochloride (57 mg) were added to the reaction mixture and the reaction was stirred for 3 hours at room temperature. The mixture was poured into ice/water and was acidified with 1M aqueous HCl solution. The aqueous phase was then extracted two times with ethyl acetate and the combined organic layers were washed with 1M aqueous NaOH and with brine, dried

Example 159

(5α,8α)-8-Hydroxy-8-isopropoxymethyl-2-[4-((R)-2,2,2-trifluoro-1-hydroxy-ethyl)-phenyl]-2-aza-spiro[4.5]decan-1-one

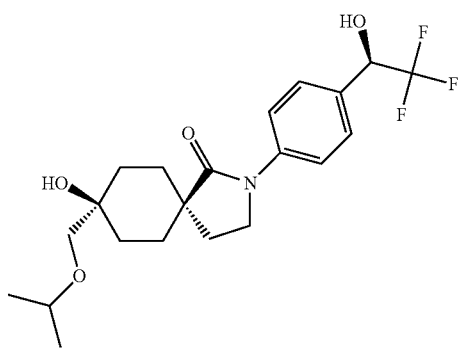 [SMILES: CC(C)OC[C@]1(O)CC[C@]2(CCN(c3ccc([C@@H](O)C(F)(F)F)cc3)C2=O)CC1]

The title compound was prepared in analogy to example 110, step 2 from (3α,6α)-8-[4-((R)-2,2,2-trifluoro-1-hydroxy-ethyl)-phenyl]-1-oxa-8-aza-dispiro[2.2.4.2]dodecan-7-one (obtained in example 138, step 1) by reaction with sodium isopropoxide [CAS Reg. No. 683-60-3]. MS (m/e): 416.4 [MH+].

Example 160

(5α,8α)-8-(2,2-Difluoro-ethoxymethyl)-8-hydroxy-2-[4-((R)-2,2,2-trifluoro-1-hydroxy-ethyl)-phenyl]-2-aza-spiro[4.5]decan-1-one

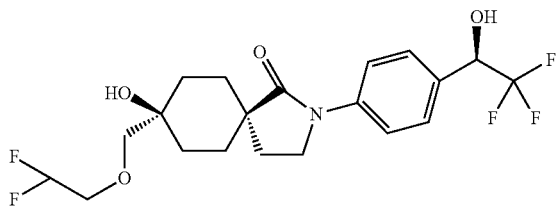 [SMILES: O=C1N(c2ccc([C@@H](O)C(F)(F)F)cc2)CC[C@]12CC[C@@](O)(COCC(F)F)CC2]

The title compound was prepared in analogy to example 155 from (3α,6α)-8-[4-((R)-2,2,2-trifluoro-1-hydroxy-ethyl)-phenyl]-1-oxa-8-aza-dispiro[2.2.4.2]dodecan-7-one (obtained in example 138, step 1) by reaction with sodium 2,2-difluoroethoxide. MS (m/e): 438.3 [MH+].

Example 161

(5α,8α)-2-(4-Ethylphenethyl)-8-hydroxy-8-isopropyl-2-aza-spiro[4.5]decan-1-one

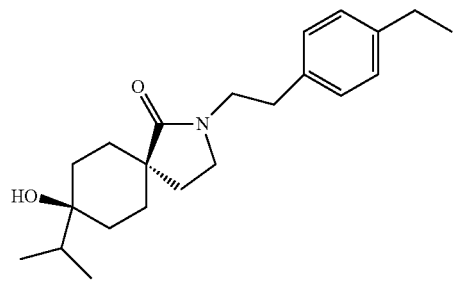 [SMILES: CCc1ccc(CCN2CC[C@]3(CC[C@@](O)(C(C)C)CC3)C2=O)cc1]

Step 1: 2-[2-(4-Ethyl-phenyl)-ethyl]-8-hydroxy-2-aza-spiro[4.5]decan-1-one

The title compound was prepared in analogy to example 1, step 4 from 4-hydroxy-1-(2-methoxy-ethyl)-cyclohexanecarboxylic acid ethyl ester (obtained in example 2, step 3) by treatment with 2-(4-ethylphenyl)-ethylamine [CAS Reg. No. 64353-29-3]. MS (m/e): 302.3 [MH+].

Step 2: 2-[2-(4-Ethyl-phenyl)-ethyl]-2-aza-spiro[4.5]decane-1,8-dione

The title compound was prepared in analogy to example 54 by oxidation of 2-[2-(4-ethyl-phenyl)-ethyl]-8-hydroxy-2-aza-spiro[4.5]decan-1-one (obtained in example 161, step 1). MS (m/e): 300.3 [MH+].

Step 3: (5α,8α)-2-(4-Ethylphenethyl)-8-hydroxy-8-isopropyl-2-aza-spiro[4.5]decan-1-one The title compound was prepared in low yield (6%) in analogy to example 103 from 2-(obtained in example 161, step 2) by reaction with isopropylmagnesium chloride (2M in THF). MS (m/e): 344.2 [MH+].

Example 162

8-Hydroxy-2-[4-(2,2,2-trifluoro-1-methyl-ethoxy)-phenyl]-2-aza-spiro[4.5]decan-1-one

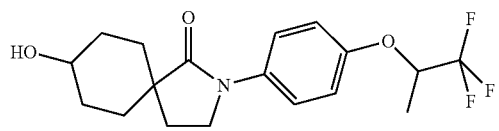 [SMILES: CC(Oc1ccc(N2CCC3(CCC(O)CC3)C2=O)cc1)C(F)(F)F]

Step 1: 1-Nitro-4-(2,2,2-trifluoro-1-methyl-ethoxy)-benzene

A mixture of 1-fluoro-4-nitrobenzene (4.24 g, CAS Reg. No. 350-46-9), 1,1,1-trifluoro-propan-2-ol (4.56 g, CAS Reg. No. 374-01-6) and cesium carbonate (13.04 g) in CH₃CN (50 mL) was heated to reflux for 10 hours. Then, the reaction mixture was cooled, acidified with conc. HCl and then distributed between ethyl acetate and water. The organic layer was separated, washed with brine and evaporated to provide the title compound (6.74 g) that was used without further purification. Rf: 0.38 (silica gel, ether/heptane 1:4).

Step 2: 4-(2,2,2-Trifluoro-1-methyl-ethoxy)-phenylamine

Nitro-4-(2,2,2-trifluoro-1-methyl-ethoxy)-benzene (6.74 g) was dissolved in MeOH (70 mL). Pd on carbon (10% Pd, 500 mg) was added and the mixture was hydrogenated at RT for 12 hours. The suspension was filtered and the filtrate was concentrated in vacuo to provide the title compound as a brown liquid (5.8 g). Rf: 0.38 (silica gel, ether/heptane 1:1). MS (m/e): 206.1 (MH$^+$).

Step 3: 8-Hydroxy-2-[4-(2,2,2-trifluoro-1-methyl-ethoxy)-phenyl]-2-aza-spiro[4.5]decan-1-one This material was obtained in analogy to example 1, step 4 from 4-hydroxy-1-(2-methoxy-ethyl)-cyclohexanecarboxylic acid ethyl ester (210 mg, obtained in example 2, step 3) and 4-(2,2,2-trifluoro-1-methyl-ethoxy)-phenylamine (308 mg) as a mixture of cis and trans diastereomers (230 mg). MS (m/e): 358.2 (MH$^+$).

Example 163

(5α,8β)-8-Hydroxy-8-propyl-2-[4-(2,2,2-trifluoro-1-methyl-ethoxy)-phenyl]-2-aza-spiro[4.5]decan-1-one

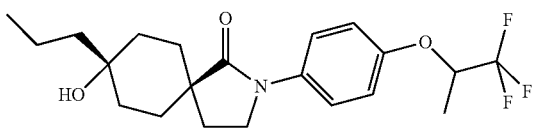 [SMILES: CCC[C@]1(O)CC[C@@]2(CCN(c3ccc(OC(C)C(F)(F)F)cc3)C2=O)CC1]

Step 1: 2-[4-(2,2,2-Trifluoro-1-methyl-ethoxy)-phenyl]-2-aza-spiro[4.5]decane-1,8-dione This material was obtained in analogy to example 108, step 4 by Swern oxidation of 8-hydroxy-2-[4-(2,2,2-trifluoro-1-methyl-ethoxy)-phenyl]-2-aza-spiro[4.5]decan-1-one (230 mg, obtained in example 162, step 3) as a colorless solid (230 mg). Rf: 0.3 (silica gel, ether/heptane 1:1).

Step 2: (5α,8β)-8-Hydroxy-8-propyl-2-[4-(2,2,2-trifluoro-1-methyl-ethoxy)-phenyl]-2-aza-spiro[4.5]decan-1-one The title compound was obtained in analogy to example 55 from 2-[4-(2,2,2-trifluoro-1-methyl-ethoxy)-phenyl]-2-aza-spiro[4.5]decane-1,8-dione (230 mg) by treatment with propylmagnesium chloride as a colorless solid (66 mg): MS (m/e): 400.2 (NH$^+$).

Example 164

(5α,8α)-8-Hydroxy-8-propyl-2-[4-(2,2,2-trifluoro-1-methyl-ethoxy)-phenyl]-2-aza-spiro[4.5]decan-1-one

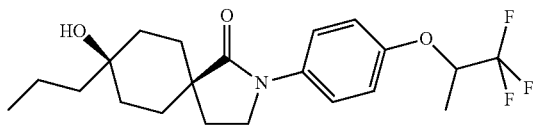 [SMILES: CCC[C@]1(O)CC[C@]2(CCN(c3ccc(OC(C)C(F)(F)F)cc3)C2=O)CC1]

This material was isolated from the reaction performed in example 163, step 2 as a colorless solid (77 mg). MS (m/e): 400.2 (NH$^+$).

Example 164a (5α,8α)-8-Hydroxy-8-propyl-2-[4-((S)-2,2,2-trifluoro-1-methyl-ethoxy)-phenyl]-2-aza-spiro[4.5]decan-1-one

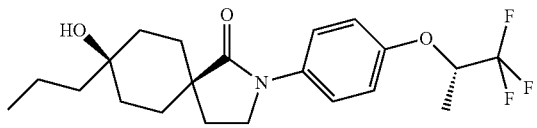 [SMILES: CCC[C@]1(O)CC[C@]2(CCN(c3ccc(O[C@@H](C)C(F)(F)F)cc3)C2=O)CC1]

The title compound (5α,8α)-8-hydroxy-8-propyl-2-[4-((S)-2,2,2-trifluoro-1-methyl-ethoxy)-phenyl]-2-aza-spiro [4.5]decan-1-one was made in analogy to example 55 from 2-[4-((S)-2,2,2-trifluoro-1-methyl-ethoxy)-phenyl]-2-aza-spiro[4.5]decane-1,8-dione (obtained in example 146, step 3) by treatment with propylmagnesium chloride. MS (m/e): 400.2 (MH$^+$).

Example 164b (5α,8α)-8-Hydroxy-8-propyl-2-[4-((R)-2,2,2-trifluoro-1-methyl-ethoxy)-phenyl]-2-aza-spiro[4.5]decan-1-one

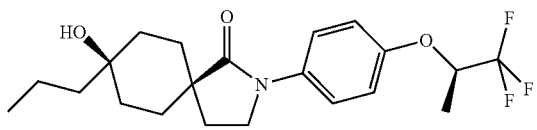 [SMILES: CCC[C@]1(O)CC[C@]2(CCN(c3ccc(O[C@H](C)C(F)(F)F)cc3)C2=O)CC1]

The title compound (5α,8α)-8-hydroxy-8-propyl-2-[4-((R)-2,2,2-trifluoro-1-methyl-ethoxy)-phenyl]-2-aza-spiro [4.5]decan-1-one was made in analogy to example 55 from 2-[4-((R)-2,2,2-trifluoro-1-methyl-ethoxy)-phenyl]-2-aza-spiro[4.5]decane-1,8-dione (obtained in example 142, step 3) by treatment with propylmagnesium chloride. MS (m/e): 400.2 (MH$^+$).

Example 165

(5α,8α)-8-Ethyl-8-hydroxy-2-[4-(2,2,2-trifluoro-1-methyl-ethoxy)-phenyl]-2-aza-spiro[4.5]decan-1-one

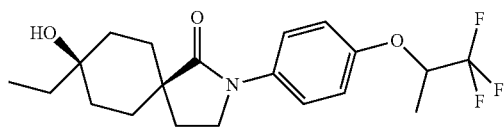 [SMILES: CC[C@]1(O)CC[C@]2(CCN(c3ccc(OC(C)C(F)(F)F)cc3)C2=O)CC1]

The title compound was obtained in analogy to example 55 from 2-[4-(2,2,2-trifluoro-1-methyl-ethoxy)-phenyl]-2-aza-spiro[4.5]decane-1,8-dione (200 mg, obtained in example 163, step 1) by treatment with ethylmagnesium bromide as a colorless solid (57 mg): MS (m/e): 386.2 (MH+).

Example 165a (5α,8α)-8-Ethyl-8-hydroxy-2-[4-((S)-2,2,2-trifluoro-1-methyl-ethoxy)-phenyl]-2-aza-spiro[4.5]decan-1-one

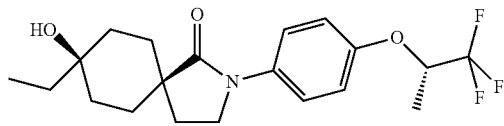 [SMILES: CC[C@]1(O)CC[C@]2(CCN(c3ccc(O[C@@H](C)C(F)(F)F)cc3)C2=O)CC1]

The title compound (5α,8α)-8-ethyl-8-hydroxy-2-[4-((S)-2,2,2-trifluoro-1-methyl-ethoxy)-phenyl]-2-aza-spiro[4.5]decan-1-one can be obtained in analogy to example 55 from 2-[4-((S)-2,2,2-trifluoro-1-methyl-ethoxy)-phenyl]-2-aza-spiro[4.5]decane-1,8-dione (obtained in example 146, step 3) by treatment with ethylmagnesium bromide. MS (m/e): 386.4 (MH+).

Example 165b (5α,8α)-8-Ethyl-8-hydroxy-2-[4-((R)-2,2,2-trifluoro-1-methyl-ethoxy)-phenyl]-2-aza-spiro[4.5]decan-1-one

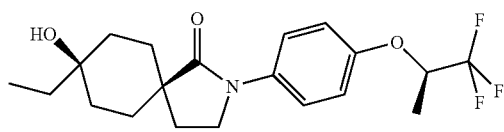 [SMILES: CC[C@]1(O)CC[C@]2(CCN(c3ccc(O[C@H](C)C(F)(F)F)cc3)C2=O)CC1]

The title compound (5α,8α)-8-ethyl-8-hydroxy-2-[4-((R)-2,2,2-trifluoro-1-methyl-ethoxy)-phenyl]-2-aza-spiro[4.5]decan-1-one can be obtained in analogy to example 55 from 2-[4-((R)-2,2,2-trifluoro-1-methyl-ethoxy)-phenyl]-2-aza-spiro[4.5]decane-1,8-dione (obtained in example 142, step 3) by treatment with ethylmagnesium bromide. MS (m/e): 386.4 (MH+).

Example 166

(5α,8α)-8-Hydroxy-2-[6-(2,2,2-trifluoro-ethoxy)-pyridin-3-yl]-8-(3,3,3-trifluoro-propyl)-2-aza-spiro[4.5]decan-1-one

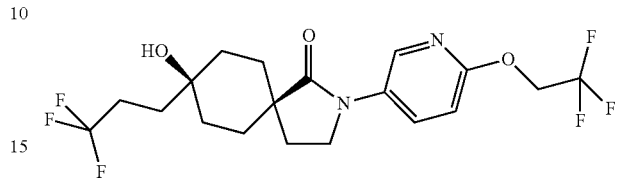

Step 1: (3,3,3-trifluoropropyl)magnesium iodide solution

Magnesium shavings (57 mg) were added to a 2-neck round bottom flask. The flask was heated and evacuated and then flushed with argon. Dry THF (1 mL) was added and then 1/10th of a solution of 1,1,1-trifluoro-3-iodopropane in THF (total of 525 mg 1,1,1-trifluoro-3-iodopropane in 0.5 mL THF) was added. The reaction was initiated by heating with a heat gun. Following initiation, the rest of the solution of the halide was added dropwise and heating was continued for one hour.

The Grignard solution was decanted from residual solids and was used immediately in the following reaction step.

Step 2: (5α,8α)-8-Hydroxy-2-[6-(2,2,2-trifluoro-ethoxy)-pyridin-3-yl]-8-(3,3,3-trifluoro-propyl)-2-aza-spiro[4.5]decan-1-one The title compound was obtained in analogy to example 55 from 2-[6-(2,2,2-trifluoro-ethoxy)-pyridin-3-yl]-2-aza-spiro[4.5]decane-1,8-dione (obtained in example 108, step 4) and freshly prepared (3,3,3-trifluoropropyl)magnesium iodide solution. MS (m/e): 441.3 (MH+).

Example 167

(5α,8α)-8-Hydroxy-8-propyl-2-[6-(2,2,2-trifluoro-ethoxy)-pyridin-3-yl]-2-aza-spiro[4.5]decan-1-one

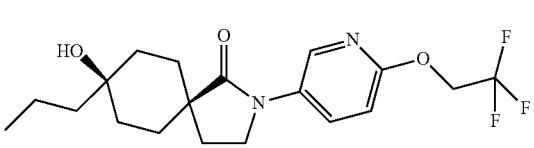 [SMILES: CCC[C@]1(O)CC[C@]2(CCN(c3ccc(OCC(F)(F)F)nc3)C2=O)CC1]

The title compound was obtained in analogy to example 55 from 2-[6-(2,2,2-trifluoro-ethoxy)-pyridin-3-yl]-2-aza-spiro[4.5]decane-1,8-dione (obtained in example 108, step 4 and commercial n-propylmagnesium chloride solution. MS (m/e): 387.3 (MH+).

Example 168

(5α,8α)-8-Ethyl-8-hydroxy-2-[6-(2,2,2-trifluoro-ethoxy)-pyridin-3-yl]-2-aza-spiro[4.5]decan-1-one

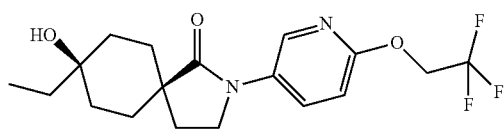 [SMILES: CC[C@]1(O)CC[C@]2(CCN(c3ccc(OCC(F)(F)F)nc3)C2=O)CC1]

The title compound was obtained in analogy to example 55 from 2-[6-(2,2,2-trifluoro-ethoxy)-pyridin-3-yl]-2-aza-spiro[4.5]decane-1,8-dione (obtained in example 108, step 4) and commercial ethylmagnesium bromide solution. MS (m/e): 373.1 (MH$^+$).

Example 169

(5α,8α)-8-Ethyl-8-hydroxy-2-[4-(3,3,3-trifluoro-propyl)-phenyl]-2-aza-spiro[4.5]decan-1-one

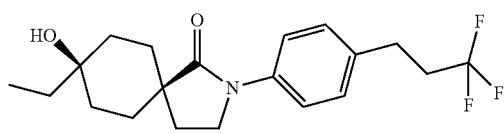 [SMILES: CC[C@]1(O)CC[C@]2(CCN(c3ccc(CCC(F)(F)F)cc3)C2=O)CC1]

Step 1: 8-Hydroxy-2-[4-(3,3,3-trifluoro-propyl)-phenyl]-2-aza-spiro[4.5]decan-1-one This material was obtained in analogy to example 1, step 4 from 4-hydroxy-1-(2-methoxy-ethyl)-cyclohexanecarboxylic acid ethyl ester (1.58 g, obtained in example 2, step 3) and 4-(3,3,3-trifluoro-propyl)-phenylamine (1.71 g, accessible according to procedures outlined in the Literature: Meazza G. et al., Pestic. Sci. 1992, 35, 137-144). 8-Hydroxy-2-[4-(3,3,3-trifluoro-propyl)-phenyl]-2-aza-spiro[4.5]decan-1-one was used without further characterization.

Step 2: 2-[4-(3,3,3-Trifluoro-propyl)-phenyl]-2-aza-spiro[4.5]decane-1,8-dione

Oxidation of crude 8-hydroxy-2-[4-(3,3,3-trifluoro-propyl)-phenyl]-2-aza-spiro[4.5]decan-1-one was performed as described in example 108, step 4 to provide the title compound as a colorless solid (1.77 g over 2 steps). Rf: 0.23 (silica gel, ether/dichloromethane 1:19).

Step 3: (5α,8α)-8-Ethyl-8-hydroxy-2-[4-(3,3,3-trifluoro-propyl)-phenyl]-2-aza-spiro[4.5]decan-1-one The title compound was obtained in analogy to example 55 from 2-[4-(3,3,3-trifluoro-propyl)-phenyl]-2-aza-spiro[4.5]decane-1,8-dione (200 mg) and commercial ethylmagnesium bromide solution (0.65 mL, 3M in diethylether) as a colorless solid (60 mg). MS (m/e): 370.2 (MH$^+$).

Example 170

(5α,8α)-8-Hydroxy-8-propyl-2-[4-(3,3,3-trifluoro-propyl)-phenyl]-2-aza-spiro[4.5]decan-1-one

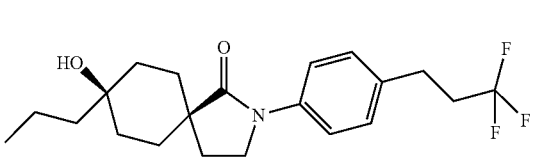 [SMILES: CCC[C@]1(O)CC[C@]2(CCN(c3ccc(CCC(F)(F)F)cc3)C2=O)CC1]

The title compound was obtained in analogy to example 55 from 2-[4-(3,3,3-trifluoro-propyl)-phenyl]-2-aza-spiro[4.5]decane-1,8-dione (200 mg, obtained in example 169, step 2) and commercial propylmagnesium chloride solution (0.65 mL, 2M in diethylether) as a colorless solid (50 mg). MS (m/e): 384.3 (MH$^+$).

Example 171

(5α,8α)-8-Ethyl-8-hydroxy-2-[6-((S)-2,2,2-trifluoro-1-methyl-ethoxy)-pyridin-3-yl]-2-aza-spiro[4.5]decan-1-one

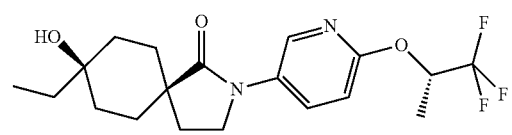 [SMILES: CC[C@]1(O)CC[C@]2(CCN(c3ccc(O[C@@H](C)C(F)(F)F)nc3)C2=O)CC1]

This material was obtained in analogy to example 55 from 2-[6-((S)-2,2,2-trifluoro-1-methyl-ethoxy)-pyridin-3-yl]-2-aza-spiro[4.5]decane-1,8-dione (250 mg, obtained in example 148, step 4) by treatment with ethylmagnesium bromide solution (1.4 mL, 3M in diethylether,) as a solid (87 mg). MS (m/e): 387.3 (MH$^+$).

Example 172

(5α,8α)-8-Hydroxy-8-propyl-2-[6-((S)-2,2,2-trifluoro-1-methyl-ethoxy)-pyridin-3-yl]-2-aza-spiro[4.5]decan-1-one

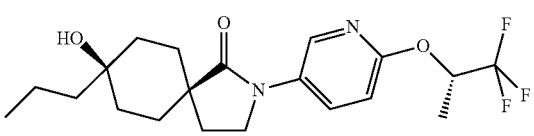 [SMILES: CCC[C@]1(O)CC[C@]2(CCN(c3ccc(O[C@@H](C)C(F)(F)F)nc3)C2=O)CC1]

This material was obtained in analogy to example 55 from 2-[6-((S)-2,2,2-trifluoro-1-methyl-ethoxy)-pyridin-3-yl]-2-aza-spiro[4.5]decane-1,8-dione (250 mg, obtained in example 148, step 4) by treatment with propylmagnesium chloride solution (1.4 mL; 2M in diethylether) as a solid (92 mg). MS (m/e): 401.3 (MH+).

Example 173

(5α,8α)-8-Hydroxy-8-trifluoromethyl-2-[6-((S)-2,2,2-trifluoro-1-methyl-ethoxy)-pyridin-3-yl]-2-aza-spiro[4.5]decan-1-one

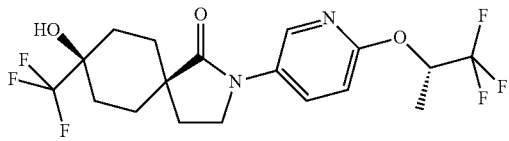 [SMILES: C[C@H](Oc1ccc(N2CC[C@]3(CC[C@@](O)(C(F)(F)F)CC3)C2=O)cn1)C(F)(F)F]

This material was obtained in analogy to example 112 from 2-[6-((S)-2,2,2-trifluoro-1-methyl-ethoxy)-pyridin-3-yl]-2-aza-spiro[4.5]decane-1,8-dione (250 mg, obtained in example 148, step 4) by treatment with (trifluoromethyl)-trimethylsilane and tetrabutylammoniumfluoride as a solid (130 mg). MS (m/e): 427.2 (MH+).

Example 174

(5α,8α)-8-Hydroxy-8-trifluoromethyl-2-[6-((R)-2,2,2-trifluoro-1-methyl-ethoxy)-pyridin-3-yl]-2-aza-spiro[4.5]decan-1-one

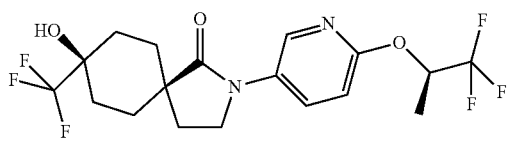 [SMILES: C[C@@H](Oc1ccc(N2CC[C@]3(CC[C@@](O)(C(F)(F)F)CC3)C2=O)cn1)C(F)(F)F]

This material was obtained in analogy to example 112 from 2-[6-((R)-2,2,2-trifluoro-1-methyl-ethoxy)-pyridin-3-yl]-2-aza-spiro[4.5]decane-1,8-dione (250 mg, obtained in example 150, step 3) by treatment with (trifluoromethyl)-trimethylsilane and tetrabutylammoniumfluoride as a solid (110 mg). MS (m/e): 427.2 (MH+).

Example 175

(5α,8α)-8-Ethyl-8-hydroxy-2-[6-((R)-2,2,2-trifluoro-1-methyl-ethoxy)-pyridin-3-yl]-2-aza-spiro[4.5]decan-1-one

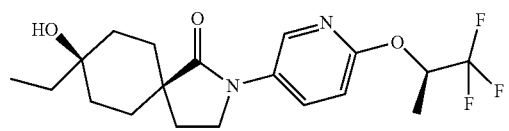 [SMILES: CC[C@]1(O)CC[C@]2(CCN(c3ccc(O[C@H](C)C(F)(F)F)nc3)C2=O)CC1]

This material was obtained in analogy to example 55 from 2-[6-((R)-2,2,2-trifluoro-1-methyl-ethoxy)-pyridin-3-yl]-2-aza-spiro[4.5]decane-1,8-dione (250 mg, obtained in example 150, step 3) by treatment with ethylmagnesium bromide solution (1.4 mL, 3M in diethylether) as a solid (128 mg). MS (m/e): 387.2 (MH+).

Example 176

(5α,8α)-8-Hydroxy-8-propyl-2-[6-((R)-2,2,2-trifluoro-1-methyl-ethoxy)-pyridin-3-yl]-2-aza-spiro[4.5]decan-1-one

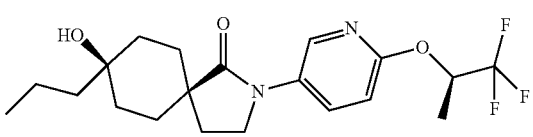 [SMILES: CCC[C@]1(O)CC[C@]2(CCN(c3ccc(O[C@H](C)C(F)(F)F)nc3)C2=O)CC1]

This material was obtained in analogy to example 55 from 2-[6-((R)-2,2,2-trifluoro-1-methyl-ethoxy)-pyridin-3-yl]-2-aza-spiro[4.5]decane-1,8-dione (250 mg, obtained in example 150, step 3) by treatment with propylmagnesium chloride solution (0.7 mL, 2M, in diethylether) as a solid (68 mg). MS (m/e): 401.3 (MH+).

Example 177

(5α,8α)-8-Hydroxy-8-trifluoromethyl-2-[4-(2,2,2-trifluoro-1-methyl-ethoxy)-phenyl]-2-aza-spiro[4.5]decan-1-one

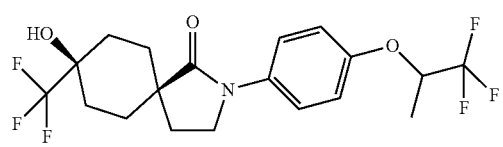 [SMILES: CC(Oc1ccc(N2CC[C@]3(CC[C@@](O)(C(F)(F)F)CC3)C2=O)cc1)C(F)(F)F]

This material was obtained in analogy to example 112 from 2-[4-(2,2,2-trifluoro-1-methyl-ethoxy)-phenyl]-2-aza-spiro[4.5]decane-1,8-dione (200 mg, obtained in example 163, step 1) by treatment with (trifluoromethyl)-trimethylsilane and tetrabutylammoniumfluoride as a solid (36 mg). MS (m/e): 426.2 (MH+).

Example 177a (5α,8α)-8-Hydroxy-8-trifluoromethyl-2-[4-((S)-2,2,2-trifluoro-1-methyl-ethoxy)-phenyl]-2-aza-spiro[4.5]decan-1-one

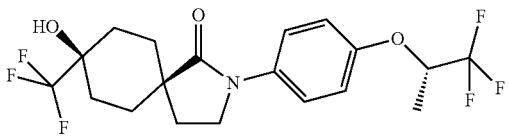 [SMILES: C[C@H](Oc1ccc(N2CC[C@]3(CC[C@@](O)(C(F)(F)F)CC3)C2=O)cc1)C(F)(F)F]

This material was obtained in analogy to example 112 from 2-[4-((S)-2,2,2-trifluoro-1-methyl-ethoxy)-phenyl]-2-aza-spiro[4.5]decane-1,8-dione (200 mg, obtained in example 146, step 3) by treatment with (trifluoromethyl)-trimethylsilane and tetrabutylammoniumfluoride as a solid (93 mg). MS (m/e): 426.2 (MH⁺).

Example 177b (5α,8α)-8-Hydroxy-8-trifluoromethyl-2-[4-((R)-2,2,2-trifluoro-1-methyl-ethoxy)-phenyl]-2-aza-spiro[4.5]decan-1-one

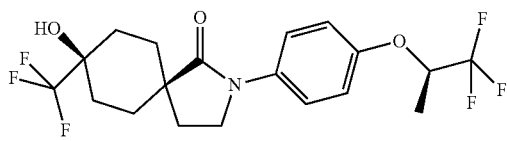 [SMILES: C[C@@H](Oc1ccc(N2CC[C@]3(CC[C@@](O)(C(F)(F)F)CC3)C2=O)cc1)C(F)(F)F]

This material was obtained in analogy to example 112 from 2-[4-((R)-2,2,2-trifluoro-1-methyl-ethoxy)-phenyl]-2-aza-spiro[4.5]decane-1,8-dione (200 mg, obtained in example 142, step 3) by treatment with (trifluoromethyl)-trimethylsilane and tetrabutylammoniumfluoride as a solid (74 mg). MS (m/e): 426.2 (MH⁺).

Example 178

(5α,8α)-8-Hydroxy-2-[6-(2,2,2-trifluoro-ethoxy)-pyridin-3-yl]-8-trifluoromethyl-2-aza-spiro[4.5]decan-1-one

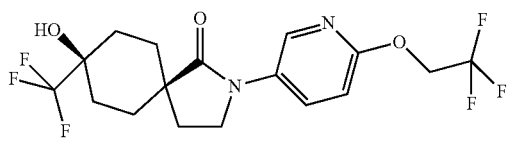 [SMILES: O=C1N(c2ccc(OCC(F)(F)F)nc2)CC[C@]12CC[C@@](O)(C(F)(F)F)CC2]

This material was obtained in analogy to example 112 from 2-[6-(2,2,2-trifluoro-ethoxy)-pyridin-3-yl]-2-aza-spiro[4.5]decane-1,8-dione (110 mg, obtained in example 108, step 4) by treatment with (trifluoromethyl)-trimethylsilane and tetrabutylammoniumfluoride as a solid (25 mg). MS (m/e): 413.2 (MH⁺).

Example 179

(5α,8α)-8-Cyclopropyl-8-hydroxy-2-[6-((R)-2,2,2-trifluoro-1-methyl-ethoxy)-pyridin-3-yl]-2-aza-spiro[4.5]decan-1-one

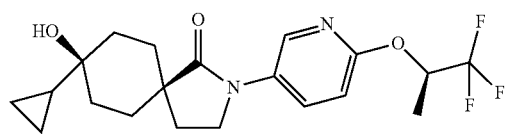 [SMILES: C[C@@H](Oc1ccc(N2CC[C@]3(CC[C@@](O)(C4CC4)CC3)C2=O)cn1)C(F)(F)F]

This material was obtained in analogy to example 55 from 2-[6-((R)-2,2,2-trifluoro-1-methyl-ethoxy)-pyridin-3-yl]-2-aza-spiro[4.5]decane-1,8-dione (200 mg, obtained in example 150, step 3) by treatment with cyclopropylmagnesium bromide solution (0.7 mL, 0.5M in THF) as a solid (113 mg). MS (m/e): 399.1 (MH⁺).

Example 180

(5α,8α)-8-Cyclopropyl-8-hydroxy-2-[6-((S)-2,2,2-trifluoro-1-methyl-ethoxy)-pyridin-3-yl]-2-aza-spiro[4.5]decan-1-one

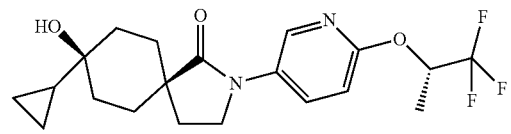 [SMILES: C[C@H](Oc1ccc(N2CC[C@]3(CC[C@@](O)(C4CC4)CC3)C2=O)cn1)C(F)(F)F]

This material was obtained in analogy to example 55 from 2-[6-((S)-2,2,2-trifluoro-1-methyl-ethoxy)-pyridin-3-yl]-2-aza-spiro[4.5]decane-1,8-dione (200 mg, obtained in example 148, step 4) by treatment with cyclopropylmagnesium bromide solution (0.7 mL, 0.5 M in THF) as a solid (68 mg). MS (m/e): 399.1 (MH⁺).

Example 181

(5α,8α)-8-Cyclopropyl-8-hydroxy-2-[4-(2,2,2-trifluoro-1-methyl-ethoxy)-phenyl]-2-aza-spiro[4.5]decan-1-one

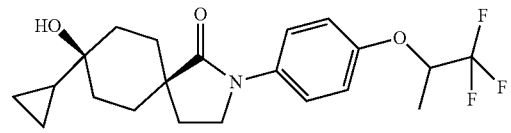 [SMILES: CC(Oc1ccc(N2CC[C@]3(CC[C@@](O)(C4CC4)CC3)C2=O)cc1)C(F)(F)F]

This material was obtained in analogy to example 55 from 2-[4-(2,2,2-trifluoro-1-methyl-ethoxy)-phenyl]-2-aza-spiro[4.5]decane-1,8-dione (235 mg, obtained in example 163, step 1) by treatment with ethylmagnesium bromide solution (0.8 mL, 3M in diethylether) as a solid (51 mg). MS (m/e): 398.3 (MH⁺).

Example 181a (5α,8α)-8-Cyclopropyl-8-hydroxy-2-[4-((R)-2,2,2-trifluoro-1-methyl-ethoxy)-phenyl]-2-aza-spiro[4.5]decan-1-one

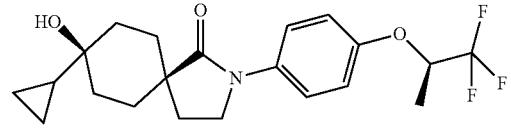 [SMILES: C[C@@H](Oc1ccc(N2CC[C@]3(CC[C@@](O)(C4CC4)CC3)C2=O)cc1)C(F)(F)F]

The title compound (5α,8α)-8-cyclopropyl-8-hydroxy-2-[4-((R)-2,2,2-trifluoro-1-methyl-ethoxy)-phenyl]-2-aza-spiro[4.5]decan-1-one can be obtained in analogy to example 55 from 2-[4-((R)-2,2,2-trifluoro-1-methyl-ethoxy)-phenyl]-2-aza-spiro[4.5]decane-1,8-dione (obtained in example 142, step 3) by treatment with cyclopropylmagnesium bromide. MS (m/e): 398.2 (MH⁺).

Example 182

4-((5α,8α)-8-hydroxy-1-oxo-8-propyl-2-aza-spiro[4.5]decan-2-yl)phenyl cyclopropanesulfonate

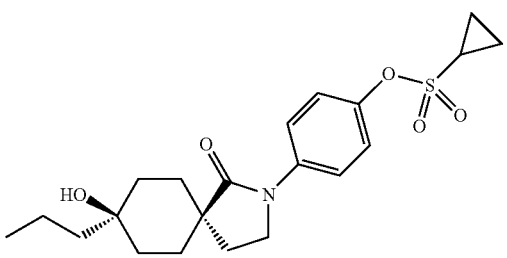 [SMILES: CCC[C@]1(O)CC[C@]2(CCN(c3ccc(OS(=O)(=O)C4CC4)cc3)C2=O)CC1]

Step 1: Cyclopropanesulfonic acid 4-amino-phenyl ester

This material was prepared from cyclopropanesulfonic acid 4-nitro-phenyl ester (J. F. King et al; Phosphorus, Sulfur and Silicon and the Related Elements; 1-4; 1993; p 445) (1.096 g) by hydrogenation over 10% Pd/C as catalyst, in ethanol/AcOEt as solvent (10 ml/15 ml) for 16 h, and at atmospheric pressure and RT. Yellow oil (0.55 g). MS (m/e): 214.2 [MH$^+$].

Step 2: Cyclopropanesulfonic acid 4-(8-hydroxy-1-oxo-2-aza-spiro[4.5]dec-2-yl)-phenyl ester The title compound was prepared in analogy to example 108, step 3 from 4-hydroxy-1-(2-methoxy-ethyl)-cyclohexanecarboxylic acid ethyl ester (obtained in example 2, step 3) by treatment with cyclopropanesulfonic acid 4-amino-phenyl ester as a mixture of cis and trans diastereomers. MS (m/e): 366.137 [MH$^+$].

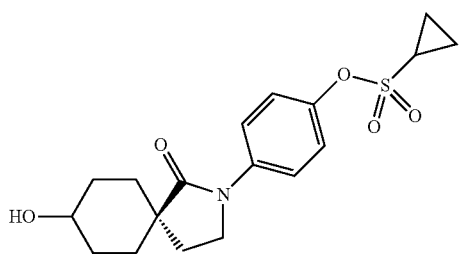

Step 3: 4-(1,8-dioxo-2-aza-spiro[4.5]decan-2-yl)phenyl cyclopropanesulfonate

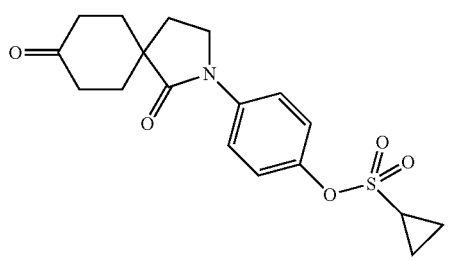 [SMILES: O=C1CCC2(CC1)CCN(c1ccc(OS(=O)(=O)C3CC3)cc1)C2=O]

The title compound was prepared in analogy to example 54 by oxidation of cyclopropanesulfonic acid 4-(8-hydroxy-1-oxo-2-aza-spiro[4.5]dec-2-yl)-phenyl ester (obtained in example 182, step 2) as off-white solid. MS (m/e): 364.121 [MH$^+$].

Step 4: 4-((5α,8α)-8-hydroxy-1-oxo-8-propyl-2-aza-spiro[4.5]decan-2-yl)phenyl cyclopropanesulfonate The title compound was prepared in analogy to example 55 from 4-(1,8-dioxo-2-aza-spiro[4.5]decan-2-yl)phenyl cyclopropanesulfonate by reaction with propylmagnesium chloride (2M in diethyl ether), but without use of anhydrous cerous(III)-chloride in the reaction, as a white solid. MS (m/e): 408.184 [MH$^+$].

Example 183

4-((5α,8α)-8-ethyl-8-hydroxy-1-oxo-2-aza-spiro[4.5]decan-2-yl)phenyl cyclopropanesulfonate

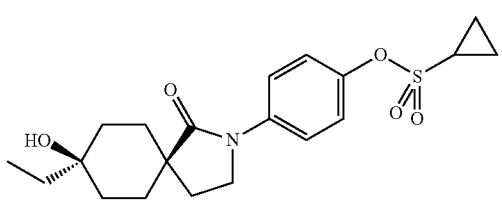 [SMILES: CC[C@]1(O)CC[C@]2(CCN(c3ccc(OS(=O)(=O)C4CC4)cc3)C2=O)CC1]

The title compound was prepared in analogy to example 55 from 4-(1,8-dioxo-2-aza-spiro[4.5]decan-2-yl)phenyl cyclopropanesulfonate (obtained in example 182, step 3) by reaction with ethylmagnesium chloride (3M in diethyl ether), but without use of anhydrous cerous (III)-chloride in the reaction, as a white solid.

Example 184

(5α,8α)-8-Hydroxy-2-(4-isopropoxyphenyl)-8-propyl-2-aza-spiro[4.5]decan-1-one

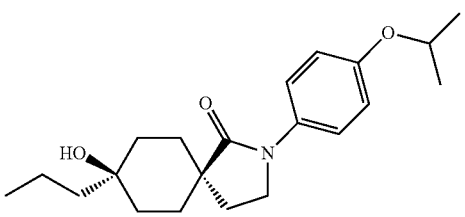 [SMILES: CCC[C@]1(O)CC[C@]2(CCN(c3ccc(OC(C)C)cc3)C2=O)CC1]

Step 1: 8-Hydroxy-2-(4-isopropoxy-phenyl)-2-aza-spiro[4.5]decan-1-one

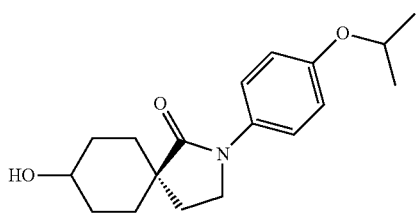

The title compound was prepared in analogy to example 108, step 3 from 4-hydroxy-1-(2-methoxy-ethyl)-cyclohexanecarboxylic acid ethyl ester (obtained in example 2, step 3) by treatment with 4-isopropoxy-phenylamine as a mixture of cis and trans diastereomers. White solid. MS (m/e): 304.190 [MH$^+$].

Step 2: 2-(4-Isopropoxy-phenyl)-2-aza-spiro[4.5]decane-1,8-dione

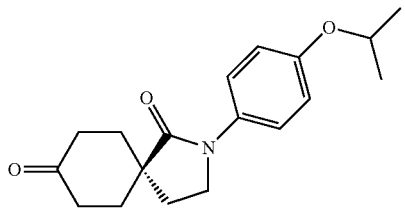

The title compound was prepared in analogy to example 54 by oxidation of 8-hydroxy-2-(4-isopropoxy-phenyl)-2-aza-spiro[4.5]decan-1-one as off-white solid. MS (m/e): 302.174 [MH$^+$].

Step 3: (5α,8α)-8-Hydroxy-2-(4-isopropoxyphenyl)-8-propyl-2-aza-spiro[4.5]decan-1-one The title compound was prepared in analogy to example 55 from 2-(4-isopropoxy-phenyl)-2-aza-spiro[4.5]decane-1,8-dione by reaction with propylmagnesium chloride (2M in diethyl ether), but without use of anhydrous cerous(III)-chloride in the reaction, as a white solid. MS (m/e): 346.238 [(MH$^+$].

Example 185

4-((5α,8β))-8-hydroxy-1-oxo-8-propyl-2-aza-spiro[4.5]decan-2-yl)phenyl methanesulfonate

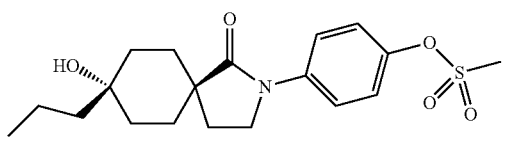 [SMILES: CCC[C@]1(O)CC[C@@]2(CCN(c3ccc(OS(C)(=O)=O)cc3)C2=O)CC1]

Step 1: Methanesulfonic acid 4-(8-hydroxy-1-oxo-2-aza-spiro[4.5]dec-2-yl)-phenyl ester

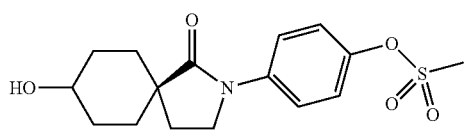

The title compound was prepared in analogy to example 108, step 3 from 4-hydroxy-1-(2-methoxy-ethyl)-cyclohexanecarboxylic acid ethyl ester (obtained in example 2, step 3) by treatment with methanesulfonic acid 4-amino-phenyl ester (synthesis: S. Kobayashi, et al.; Synlett. 2000, p 883) as a mixture of cis and trans diastereomers. MS (m/e): 340.121 [MH$^+$].

Step 2: Methanesulfonic acid 4-(1,8-dioxo-2-aza-spiro[4.5]dec-2-yl)-phenyl ester

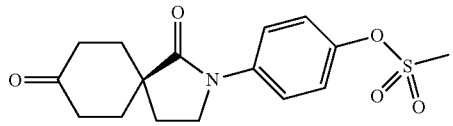

The title compound was prepared in analogy to example 54 by oxidation of methanesulfonic acid 4-(8-hydroxy-1-oxo-2-aza-spiro[4.5]dec-2-yl)-phenyl ester as light brown solid. MS (m/e): 338.105 [MH$^+$].

Step 3: 4-((5α,8β))-8-hydroxy-1-oxo-8-propyl-2-aza-spiro[4.5]decan-2-yl)phenyl methanesulfonate The title compound was prepared in analogy to example 55 from methanesulfonic acid 4-(1,8-dioxo-2-aza-spiro[4.5]dec-2-yl)-phenyl ester by reaction with propylmagnesium chloride (2M in diethyl ether), but without use of anhydrous cerous (III)-chloride in the reaction, and was isolated from the reaction mixtures as a white solid. Rf: 0.6 (thin layer plate, silica gel; methylene chloride/acetonitrile 4/1 as eluent).

Example 186

(5α,8α)-8-Ethyl-8-hydroxy-2-(4-isopropoxy-phenyl)-2-aza-spiro[4.5]decan-1-one

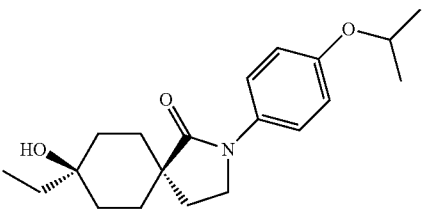 [SMILES: CC[C@]1(O)CC[C@]2(CCN(c3ccc(OC(C)C)cc3)C2=O)CC1]

The title compound was prepared in analogy to example 55 from 2-(4-isopropoxy-phenyl)-2-aza-spiro[4.5]decane-1,8-dione (obtained in example 184, step 2) by reaction with reaction with ethylmagnesium chloride (3M in diethyl ether), but without use of anhydrous cerous(III)-chloride in the reaction, as a white solid. MS (m/e): 332.222 [MH$^+$].

Example 187

(5α,8α)-2-(4-Ethanesulfonyl-phenyl)-8-hydroxy-8-propyl-2-aza-spiro[4.5]decan-1-one

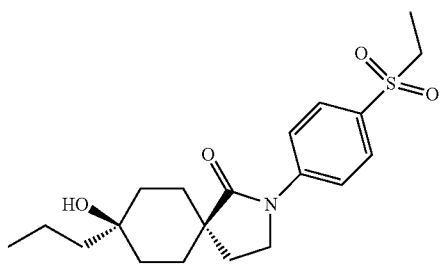 [SMILES: CCC[C@]1(O)CC[C@]2(CCN(c3ccc(S(=O)(=O)CC)cc3)C2=O)CC1]

Step 1: 10-(4-Ethanesulfonyl-phenyl)-1,4-dioxa-10-aza-dispiro[4.2.4.2]tetradecan-9-one

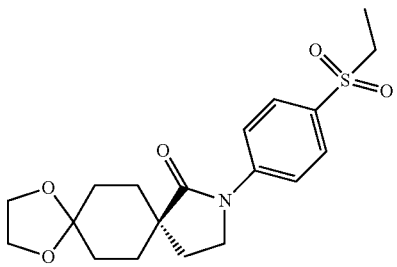

The title compound was prepared in analogy to example 133, step 4 from 1,4-dioxa-10-aza-dispiro[4.2.4.2]tetradecan-9-one (described in example 133 step 3) and 1-bromo-4-ethylsulfonylbenzene as light yellow solid. MS (m/e): 380.153 [MH$^+$].

Step 2: 2-(4-Ethanesulfonyl-phenyl)-2-aza-spiro[4.5]decane-1,8-dione

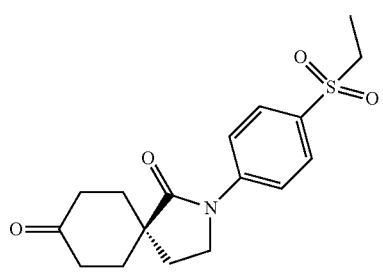

The title compound was prepared in analogy to example 133 step 5 from 10-(4-ethanesulfonyl-phenyl)-1,4-dioxa-10-aza-dispiro[4.2.4.2]tetradecan-9-one as off white crystalline solid. MS (m/e): 336.126 [MH$^+$].

Step 3: (5α,8α)-2-(4-Ethanesulfonyl-phenyl)-8-hydroxy-8-propyl-2-aza-spiro[4.5]decan-1-one The title compound was prepared in analogy to example 55 from 2-(4-ethanesulfonyl-phenyl)-2-aza-spiro[4.5]decane-1,8-dione by reaction with reaction with propylmagnesium chloride (2M in diethyl ether), but without use of anhydrous cerous (III)-chloride in the reaction, as an off white solid. MS (m/e): 380.187 [MH$^+$].

Example 188

(5α,8α)-8-hydroxy-8-propyl-2-(4-(trifluoromethoxy)benzyl)-2-aza-spiro[4.5]decan-1-one

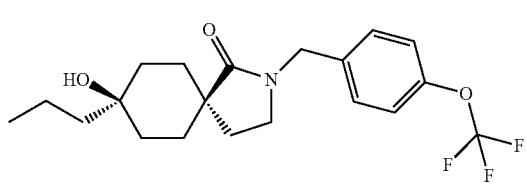 [SMILES: CCC[C@]1(O)CC[C@]2(CCN(Cc3ccc(OC(F)(F)F)cc3)C2=O)CC1]

Step 1: 8-Hydroxy-2-(4-trifluoromethoxy-benzyl)-2-aza-spiro[4.5]decan-1-one

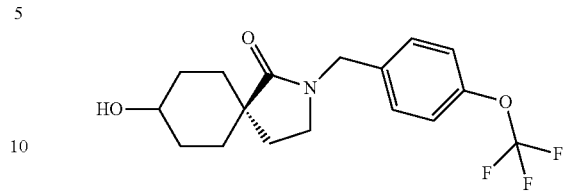

The title compound was prepared in analogy to example 108, step 3 from 4-hydroxy-1-(2-methoxy-ethyl)-cyclohexanecarboxylic acid ethyl ester (obtained in example 2, step 3) by treatment with 4-trifluoromethoxybenzylamine as a mixture of cis and trans diastereomers. Light yellow viscous oil. MS (m/e): 344.147 [MH$^+$].

Step 2: 2-(4-Trifluoromethoxy-benzyl)-2-aza-spiro[4.5]decane-1,8-dione

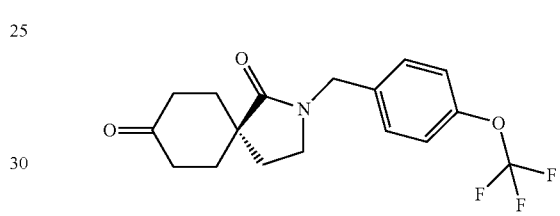

The title compound was prepared in analogy to example 54 by oxidation of 8-hydroxy-2-(4-trifluoromethoxy-benzyl)-2-aza-spiro[4.5]decan-1-one as light brown viscous oil. MS (m/e): 342.131 [(MH$^+$].

Step 3: (5α,8α)-8-allyl-8-hydroxy-2-(4-(trifluoromethoxy)benzyl)-2-aza-spiro[4.5]decan-1-one

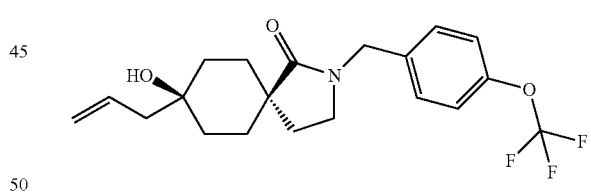

The title compound was prepared in analogy to example 55 from 2-(4-trifluoromethoxy-benzyl)-2-aza-spiro[4.5]decane-1,8-dione by reaction with reaction with allylmagnesium bromide (1M in diethyl ether), but without use of anhydrous cerous(III)-chloride in the reaction, as a light yellow gum. MS (m/e): 384.176 [MH$^+$].

Step 4: (5α,8α)-8-hydroxy-8-propyl-2-(4-(trifluoromethoxy)benzyl)-2-aza-spiro[4.5]decan-1-one (5α,8α)-8-allyl-8-hydroxy-2-(4-(trifluoromethoxy)benzyl)-2-aza-spiro[4.5]decan-1-one (100 mg) in methanol (10 ml) was hydrogenated over Pd on charcoal (10 mg, 10% Pd)) at RT and atmospheric pressure for 2 h until the reaction was complete. The catalyst was filtered off and the solvent removed in vacuo to give the title compound (87 mg) as a gum. MS (m/e): 386.2 [MH⁺].

Example 189

4-((5α,8α)-8-hydroxy-1-oxo-8-(trifluoromethyl)-2-aza-spiro[4.5]decan-2-yl)phenyl cyclopropanesulfonate

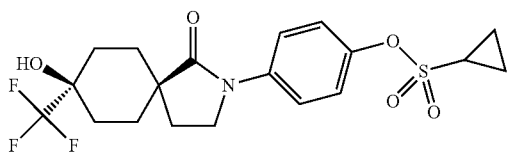 [SMILES: O=C1N(c2ccc(OS(=O)(=O)C3CC3)cc2)CC[C@]12CC[C@@](O)(C(F)(F)F)CC2]

The title compound was prepared in analogy to example 112 from 4-(1,8-dioxo-2-aza-spiro[4.5]decan-2-yl)phenyl cyclopropanesulfonate (obtained in example 182 step 3) and (trifluoromethyl)-trimethylsilane as a white solid. MS (m/e): 434.124 [MH⁺].

Example 190

(5α,8α)-8-butyl-8-hydroxy-2-(4-((R)-2,2,2-trifluoro-1-hydroxyethyl)phenyl)-2-aza-spiro[4.5]decan-1-one

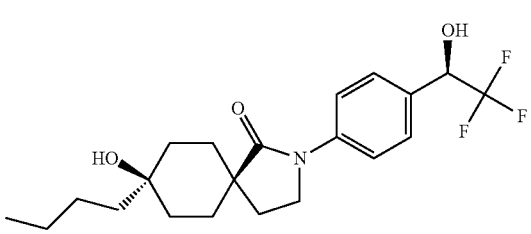 [SMILES: CCCC[C@]1(O)CC[C@]2(CCN(c3ccc([C@@H](O)C(F)(F)F)cc3)C2=O)CC1]

The title compound was prepared in analogy to example 55 from (R)-2-(4-(2,2,2-trifluoro-1-hydroxyethyl)phenyl)-2-aza-spiro[4.5]decane-1,8-dione (product of example 135, step 2) by reaction with butylmagnesium chloride (2M in THF) as a white solid. MS (m/e): 401.212 [MH⁺].

Example 191

(5α,8α)-2-(4-(2,2-difluoro-1-hydroxypropyl)phenyl)-8-hydroxy-8-isopropyl-2-aza-spiro[4.5]decan-1-one

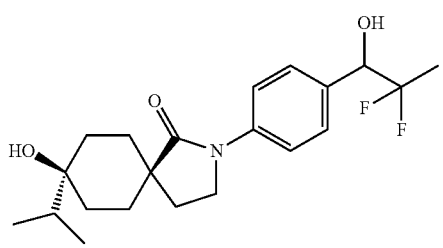 [SMILES: CC(C)[C@]1(O)CC[C@]2(CCN(c3ccc(C(O)C(C)(F)F)cc3)C2=O)CC1]

Step 1: 10-[4-(2,2-Difluoro-1-hydroxy-propyl)-phenyl]-1,4-dioxa-10-aza-dispiro[4.2.4.2]tetradecan-9-one

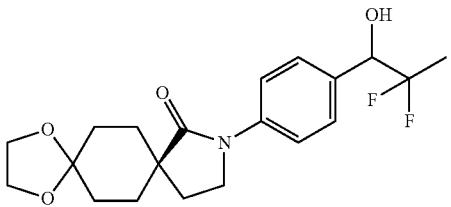

The title compound was prepared in analogy to example 133, step 4 from 1,4-dioxa-10-aza-dispiro[4.2.4.2]tetradecan-9-one (0.8 g) (described in example 133 step 3) and 1-(4-bromo-phenyl)-2,2-difluoro-propan-1-ol (1.14 g) (synthesis: R. Mogi, et al, Journal of Fluorine Chemistry; 10; 2007; p 1098) and the crude product was directly used in the next step.

Step 2: 2-(4-(2,2-difluoro-1-hydroxypropyl) phenyl)-2-aza-spiro[4.5]decane-1,8-dione

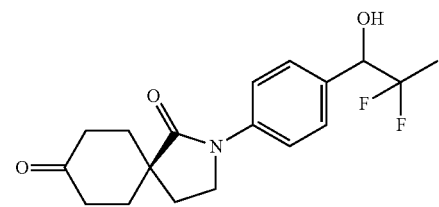

The title compound was prepared in analogy to example 133 step 5 from 10-[4-(2,2-difluoro-1-hydroxy-propyl)-phenyl]-1,4-dioxa-10-aza-dispiro[4.2.4.2]tetradecan-9-one as a white solid. MS (m/e): 338.156 [MH⁺].

Step 3: (5α,8α)-)-2-(4-(2,2-difluoro-1-hydroxypropyl)phenyl)-8-hydroxy-8-(prop-1-en-2-yl)-2-aza-spiro[4.5]decan-1-one

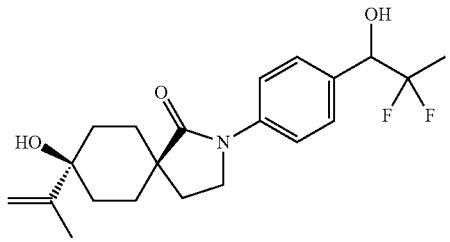 [SMILES: C=C(C)[C@]1(O)CC[C@]2(CCN(c3ccc(C(O)C(C)(F)F)cc3)C2=O)CC1]

The title compound was prepared in analogy to example 55 from (2-(4-(2,2-difluoro-1-hydroxypropyl)phenyl)-2-aza-spiro[4.5]decane-1,8-dione by reaction with isopropenyl-magnesium bromide (0.5 M in THF) as a white solid. MS (m/e): 379[M⁺].

Step 4: (5α,8α)-2-(4-(2,2-difluoro-1-hydroxypropyl)phenyl)-8-hydroxy-8-isopropyl-2-aza-spiro[4.5]decan-1-one The title compound was prepared in analogy to example 188 step 4 by hydrogenation of (5α,8α)-2-(4-(2,2-difluoro-1-hydroxypropyl)phenyl)-8-hydroxy-8-(prop-1-en-2-yl)-2-aza-spiro[4.5]decan-1-one as a white solid. MS (m/e): 382.218 [MH+].

Example 192

(5α,8α)-2-(4-(2,2-difluoro-1-hydroxypropyl)phenyl)-8-hydroxy-8-propyl-2-aza-spiro[4.5]decan-1-one

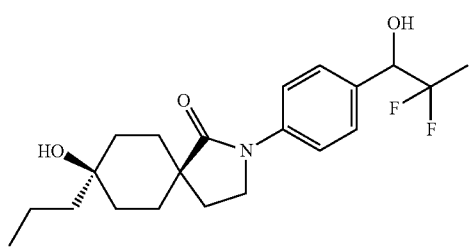 [SMILES: CCC[C@]1(O)CC[C@]2(CCN(c3ccc(C(O)C(C)(F)F)cc3)C2=O)CC1]

Step 1: (5α,8α)-8-allyl-2-(4-(2,2-difluoro-1-hydroxypropyl)phenyl)-8-hydroxy-2-aza-spiro[4.5]decan-1-one

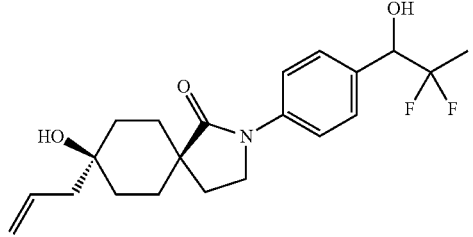 [SMILES: C=CC[C@]1(O)CC[C@]2(CCN(c3ccc(C(O)C(C)(F)F)cc3)C2=O)CC1]

The title compound was prepared in analogy to example 55 from 2-(4-(2,2-difluoro-1-hydroxypropyl)phenyl)-2-aza-spiro[4.5]decane-1,8-dione (described in example 191 step 2) by reaction with allylmagnesium chloride (2M in diethyl ether) as a white solid. MS (m/e): 380.202 [MH+].

Step 2: (5α,8α)-2-(4-(2,2-difluoro-1-hydroxypropyl)phenyl)-8-hydroxy-8-propyl-2-aza-spiro[4.5]decan-1-one The title compound was prepared in analogy to example 188 step 4 by hydrogenation of (5α,8α)-8-allyl-2-(4-(2,2-difluoro-1-hydroxypropyl)phenyl)-8-hydroxy-2-aza-spiro[4.5]decan-1-one as a white solid. MS (m/e): 382.218 [MH+].

Example 193

(5α,8α)-2-(4-(2,2-difluoro-1-hydroxypropyl)phenyl)-8-hydroxy-8-(3,3,3-trifluoropropyl)-2-aza-spiro[4.5]decan-1-one

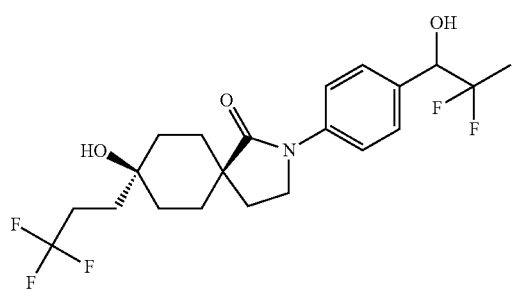 [SMILES: CC(F)(F)C(O)c1ccc(N2CC[C@]3(CC[C@@](O)(CCC(F)(F)F)CC3)C2=O)cc1]

The title compound was prepared in analogy to example 55 from 2-(4-(2,2-difluoro-1-hydroxypropyl)phenyl)-2-aza-spiro[4.5]decane-1,8-dione (described in example 191 step 2) by reaction with (3,3,3-trifluoro-propyl)-magnesium bromide as a white solid. MS (m/e): 436.190 [MH+].

Example 194

(5α,8α)-8-hydroxy-2-(4-((R)-2,2,2-trifluoro-1-hydroxyethyl)phenyl)-8-(3,3,3-trifluoropropyl)-2-aza-spiro[4.5]decan-1-one

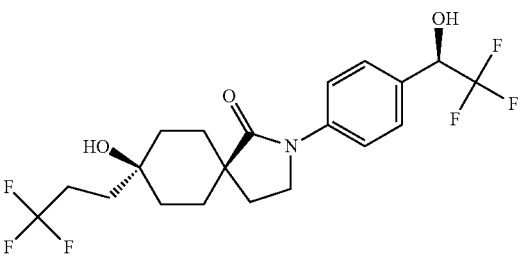 [SMILES: O=C1N(c2ccc([C@@H](O)C(F)(F)F)cc2)CC[C@]12CC[C@@](O)(CCC(F)(F)F)CC2]

The title compound was prepared in analogy to example 55 from (R)-2-(4-(2,2,2-trifluoro-1-hydroxyethyl)phenyl)-2-aza-spiro[4.5]decane-1,8-dione (described in Example 135, Step 2) by reaction with (3,3,3-trifluoro-propyl)-magnesium bromide as a white solid. MS (m/e): 440.3 [MH+].

Example 195

(5α,8α)-2-(4-(2,2-difluoro-1-hydroxyethyl)phenyl)-8-hydroxy-8-propyl-2-aza-spiro[4.5]decan-1-one

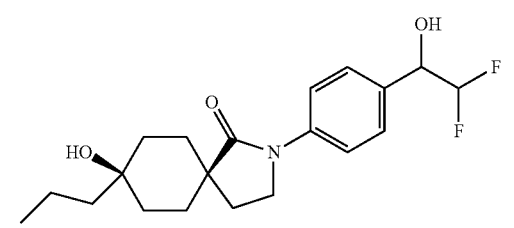 [SMILES: CCC[C@]1(O)CC[C@]2(CCN(c3ccc(C(O)C(F)F)cc3)C2=O)CC1]

Step 1: 1-(4-bromo-phenyl)-2,2-difluoro-ethanol

The title compound was prepared from 1-(4-bromo-phenyl)-2,2-difluoro-ethanone (1.6 g) (for synthesis, e.g.: G. K. Prakash et al; Journal of Fluorine Chemistry; 112; 2001; p 357) by standard reduction with NaBH$_4$ (0.515 g) in THF (20 ml) at RT and 2 h reaction time as colorless oil (1.23 g). MS (m/e)=236 [MH$^+$].

Step 2: 10-[4-(2,2-Difluoro-1-hydroxy-ethyl)-phenyl]-1,4-dioxa-10-aza-dispiro[4.2.4.2]tetradecan-9-one

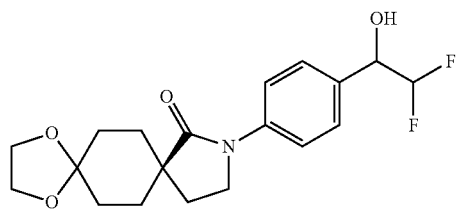

The title compound was prepared in analogy to example 133, step 4 from 1,4-dioxa-10-aza-dispiro[4.2.4.2]tetradecan-9-one (described in example 133, step 3) and 1-(4-bromo-phenyl)-2,2-difluoro-ethanol as yellow solid. MS (m/e): 368.166 [MH$^+$].

Step 3: 2-[4-(2,2-Difluoro-1-hydroxy-ethyl)-phenyl]-2-aza-spiro[4.5]decane-1,8-dione

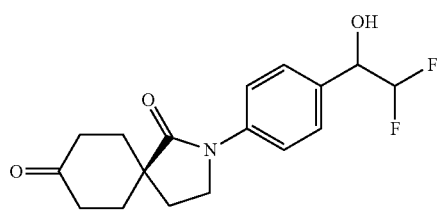

The title compound was prepared in analogy to example 133 step 5 from 10-[4-(2,2-Difluoro-1-hydroxy-ethyl)-phenyl]-1,4-dioxa-10-aza-dispiro[4.2.4.2]tetradecan-9-one as a light yellow oil. MS (m/e):324.140 [MH$^+$].

Step 4: (5α,8α)-2-(4-(2,2-difluoro-1-hydroxyethyl)phenyl)-8-hydroxy-8-propyl-2-aza-spiro[4.5]decan-1-one The title compound was prepared in analogy to example 55 from (2-[4-(2,2-difluoro-1-hydroxy-ethyl)-phenyl]-2-aza-spiro[4.5]decane-1,8-dione by reaction with propylmagnesium chloride (2M in diethyl ether), but without use of anhydrous cerous(III)-chloride in the reaction, as a white solid. MS (m/e): 368.202 [MH$^+$].

Example 196

(5α,8α)-8-hydroxy-2-(4-isopropoxyphenyl)-8-isopropyl-2-aza-spiro[4.5]decan-1-one

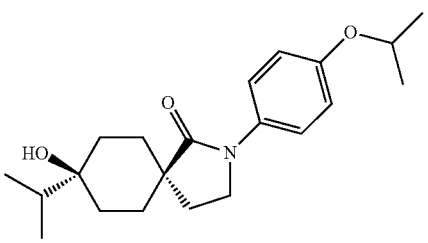 [SMILES: CC(C)Oc1ccc(N2CC[C@]3(CC[C@@](O)(C(C)C)CC3)C2=O)cc1]

Step 1: (5α,8α)-8-hydroxy-2-(4-isopropoxyphenyl)-8-(prop-1-en-2-yl)-2-aza-spiro[4.5]decan-1-one

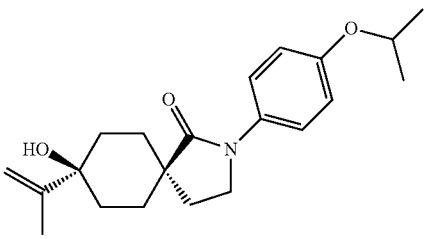 [SMILES: C=C(C)[C@]1(O)CC[C@]2(CCN(c3ccc(OC(C)C)cc3)C2=O)CC1]

The title compound was prepared in analogy to example 55 from 2-(4-isopropoxy-phenyl)-2-aza-spiro[4.5]decane-1,8-dione (obtained in example 184, step 2) by reaction with isopropenylmagnesium bromide (0.5 M in THF) as off white solid. MS (m/e): 344.221 [MH$^+$].

Step 2: (5α,8α)-8-hydroxy-2-(4-isopropoxyphenyl)-8-isopropyl-2-aza-spiro[4.5]decan-1-one The title compound was prepared in analogy to example 188, step 4 by hydrogenation of (5α,8α)-8-hydroxy-2-(4-isopropoxyphenyl)-8-(prop-1-en-2-yl)-2-aza-spiro[4.5]decan-1-one as a white solid. MS (m/e): 346.237 [MH$^+$].

Example 197

(5α,8α)-8-cyclopropyl-8-hydroxy-2-(4-isopropoxyphenyl)-2-aza-spiro[4.5]decan-1-one

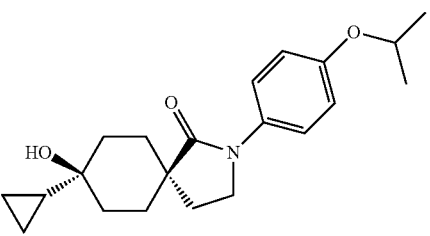 [SMILES: CC(C)Oc1ccc(N2CC[C@]3(CC[C@@](O)(C4CC4)CC3)C2=O)cc1]

The title compound was prepared in analogy to example 55 from 2-(4-isopropoxy-phenyl)-2-aza-spiro[4.5]decane-1,8-dione (obtained in example 184, step 2) by reaction with cyclopropylmagnesium bromide (0.5 M in THF) as white solid. MS (m/e): 343 [M$^+$].

Example 198

(5α,8α)-8-cyclopentyl-8-hydroxy-2-(4-isopropoxyphenyl)-2-aza-spiro[4.5]decan-1-one

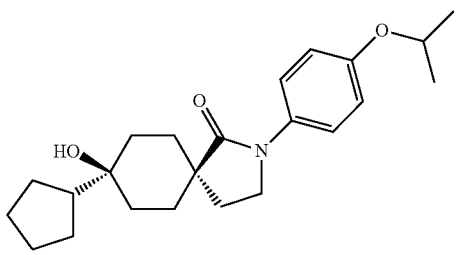 [SMILES: CC(C)Oc1ccc(N2CC[C@]3(CC[C@@](O)(C4CCCC4)CC3)C2=O)cc1]

The title compound was prepared in analogy to example 55 from 2-(4-isopropoxy-phenyl)-2-aza-spiro[4.5]decane-1,8-dione (obtained in example 184, step 2) by reaction with cyclopentylmagnesium bromide (2 M in THF) as white solid. MS (m/e): 372.25 [MH$^+$].

Example 199

(5α,8α)-8-hydroxy-8-isobutyl-2-(4-isopropoxyphenyl)-2-aza-spiro[4.5]decan-1-one

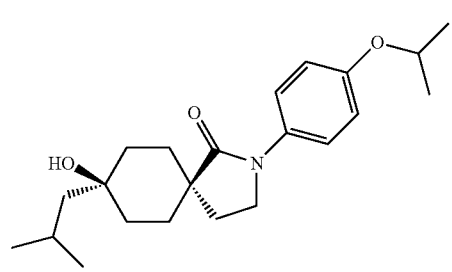 [SMILES: CC(C)C[C@]1(O)CC[C@]2(CCN(c3ccc(OC(C)C)cc3)C2=O)CC1]

The title compound was prepared in analogy to example 55 from 2-(4-isopropoxy-phenyl)-2-aza-spiro[4.5]decane-1,8-dione (obtained in example 184, step 2) by reaction with isobuylmagnesium chloride (2 M in THF) as white solid. MS (m/e): 360.252 [MH$^+$].

Example 200

(5α,8α)-8-cyclobutyl-8-hydroxy-2-(4-((R)-2,2,2-trifluoro-1-hydroxyethyl)phenyl)-2-aza-spiro[4.5]decan-1-one

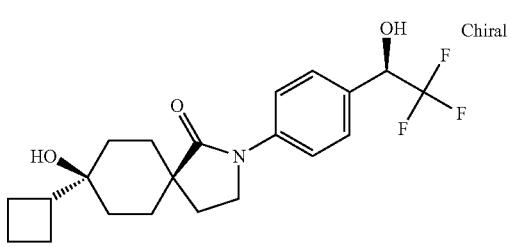 [SMILES: O=C1N(c2ccc([C@@H](O)C(F)(F)F)cc2)CC[C@]12CC[C@@](O)(C1CCC1)CC2]

The title compound was prepared in analogy to example 55 from (R)-2-(4-(2,2,2-trifluoro-1-hydroxyethyl)phenyl)-2-aza-spiro[4.5]decane-1,8-dione (obtained in example 135, step 2) by reaction with cyclobutylmagnesium chloride (1.6 M in THF) as white solid. MS (m/e): 398.194 [MH$^+$].

Example 201

(5α,8α)-8-cyclopropyl-8-hydroxy-2-(4-((R)-2,2,2-trifluoro-1-hydroxyethyl)phenyl)-2-aza-spiro[4.5]decan-1-one

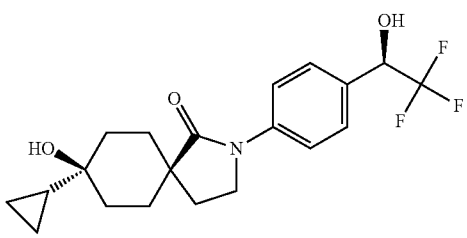 [SMILES: O=C1N(c2ccc([C@@H](O)C(F)(F)F)cc2)CC[C@]12CC[C@@](O)(C1CC1)CC2]

The title compound was prepared in analogy to example 55 from (R)-2-(4-(2,2,2-trifluoro-1-hydroxyethyl)phenyl)-2-aza-spiro[4.5]decane-1,8-dione (obtained in example 135 step 2) by reaction with cyclopropylmagnesium chloride (0.5 M in THF) as white solid. MS (m/e): 384.2 [MH$^+$].

Example 202

(5α,8α)-8-cyclopentyl-8-hydroxy-2-(4-((R)-2,2,2-trifluoro-1-hydroxyethyl)phenyl)-2-aza-spiro[4.5]decan-1-one

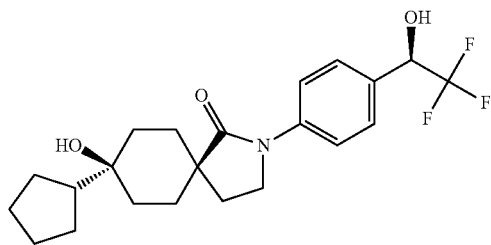 [SMILES: O=C1N(c2ccc([C@@H](O)C(F)(F)F)cc2)CC[C@]12CC[C@@](O)(C1CCCC1)CC2]

The title compound was prepared in analogy to example 55 from (R)-2-(4-(2,2,2-trifluoro-1-hydroxyethyl)phenyl)-2-aza-spiro[4.5]decane-1,8-dione (obtained in example 135 step 2) by reaction with cyclopentylmagnesium chloride (2 M in THF) as white solid. MS (m/e): 411 [M$^+$].

Example 203

(5α,8α)-8-hydroxy-8-isopropyl-2-(4-isopropylphenyl)-2-aza-spiro[4.5]decan-1-one

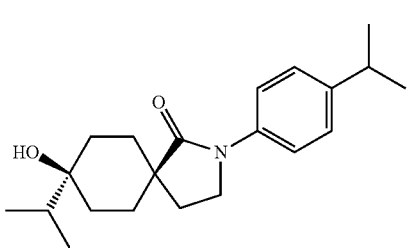 [SMILES: CC(C)c1ccc(N2CC[C@]3(CC[C@@](O)(C(C)C)CC3)C2=O)cc1]

Step 1: 8-hydroxy-2-(4-isopropylphenyl)-2-aza-spiro[4.5]decan-1-one

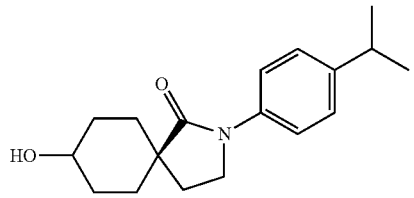

The title compound was prepared in analogy to example 108, step 3 from 4-hydroxy-1-(2-methoxy-ethyl)-cyclohexanecarboxylic acid ethyl ester (obtained in example 2, step 3) by treatment with 4-isopropylaniline as a mixture of cis and trans diastereomers. Light brown solid. MS (m/e): 288.1 [MH$^+$].

Step 2: 2-(4-isopropylphenyl)-2-aza-spiro[4.5]decane-1,8-dione

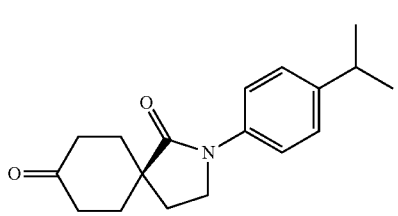

The title compound was prepared in analogy to example 54 by oxidation of 8-hydroxy-2-(4-isopropylphenyl)-2-azaspiro[4.5]decan-1-one as light red solid. MS (m/e): 286.18 [MH$^+$].

Step 3: (5α,8α)-8-hydroxy-2-(4-isopropylphenyl)-8-(prop-1-en-2-yl)-2-aza-spiro[4.5]decan-1-one

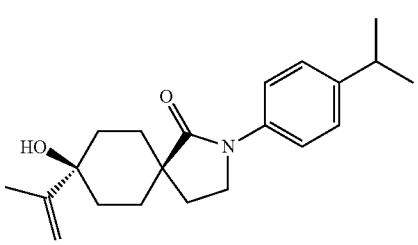 [SMILES: C=C(C)[C@]1(O)CC[C@]2(CCN(c3ccc(C(C)C)cc3)C2=O)CC1]

The title compound was prepared in analogy to example 55 from 2-(4-isopropylphenyl)-2-aza-spiro[4.5]decane-1,8-dione by reaction with isopropenylmagnesium bromide (0.5 M in diethyl ether) as a white solid. MS (m/e): 329.228 [MH$^+$].

Step 4: (5α,8α)-8-hydroxy-8-isopropyl-2-(4-isopropylphenyl)-2-aza-spiro[4.5]decan-1-one The title compound was prepared in analogy to example 188, step 4 by hydrogenation of (5α,8α)-8-hydroxy-2-(4-isopropylphenyl)-8-(prop-1-en-2-yl)-2-aza-spiro[4.5]decan-1-one as a white solid. MS (m/e) 330.243 [MH$^+$].

Example 204

(5α,8α)-8-hydroxy-2-(4-isopropylphenyl)-8-propyl-2-aza-spiro[4.5]decan-1-one

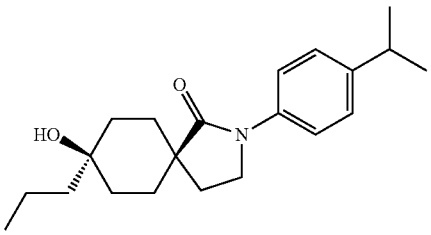 [SMILES: CCC[C@]1(O)CC[C@]2(CCN(c3ccc(C(C)C)cc3)C2=O)CC1]

Step 1: (5α,8α)-8-allyl-8-hydroxy-2-(4-isopropylphenyl)-2-aza-spiro[4.5]decan-1-one

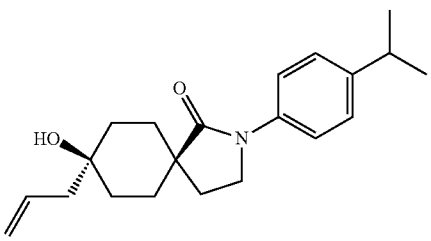 [SMILES: C=CC[C@]1(O)CC[C@]2(CCN(c3ccc(C(C)C)cc3)C2=O)CC1]

The title compound was prepared in analogy to example 55 from 2-(4-isopropylphenyl)-2-aza-spiro[4.5]decane-1,8-dione (product of example 203, step 2) by reaction with allylmagnesium bromide (1 M in diethyl ether), but without use of anhydrous cerous(III)-chloride in the reaction, as a white solid. MS (m/e): 328.227 [MH$^+$].

Step 2: (5α,8α)-8-hydroxy-2-(4-isopropylphenyl)-8-propyl-2-aza-spiro[4.5]decan-1-one The title compound was prepared in analogy to example 188, step 4 by hydrogenation of (5α,8α)-8-allyl-8-hydroxy-2-(4-isopropylphenyl)-2-aza-spiro[4.5]decan-1-one as a white solid. MS (m/e) 330.243 [MH$^+$].

Example 205

(5α,8α)-8-hydroxy-2-(4-isopropylphenyl)-8-phenyl-2-aza-spiro[4.5]decan-1-one

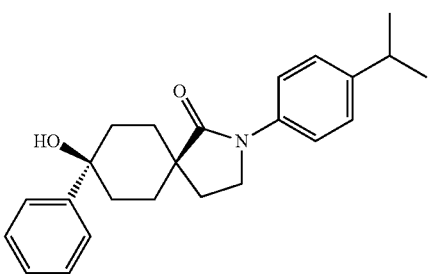 [SMILES: CC(C)c1ccc(N2CC[C@]3(CC[C@@](O)(c4ccccc4)CC3)C2=O)cc1]

The title compound was prepared in analogy to example 55 from 2-(4-isopropylphenyl)-2-aza-spiro[4.5]decane-1,8-dione (product of example 203 step 2) by reaction with phenylmagnesium bromide (2.8 M in diethyl ether), but without use of anhydrous cerous(III)-chloride in the reaction, as colorless crystals. MS (m/e): 346.215 [(M-H$_2$O)H$^+$].

Example 206

(5α,8α)-8-hydroxy-2-(4-isopropoxyphenyl)-8-phenyl-2-aza-spiro[4.5]decan-1-one

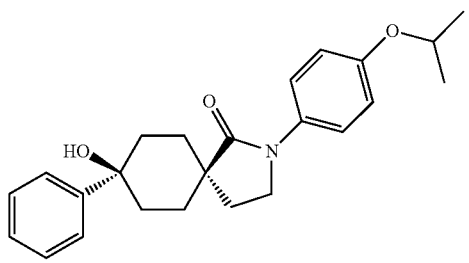 [SMILES: CC(C)Oc1ccc(N2CC[C@]3(CC[C@@](O)(c4ccccc4)CC3)C2=O)cc1]

The title compound was prepared in analogy to example 55 from 2-(4-isopropoxy-phenyl)-2-aza-spiro[4.5]decane-1,8-dione (obtained in example 184, step 2) by reaction with reaction with phenylmagnesium bromide (2.8 M in diethyl ether), but without use of anhydrous cerous (III)-chloride in the reaction, as an off white solid. MS (m/e): 379 [M$^+$].

Example 207

(5α,8α)-2-(4-(2,2-difluoro-1-hydroxyethyl)phenyl)-8-hydroxy-8-isopropyl-2-aza-spiro[4.5]decan-1-one

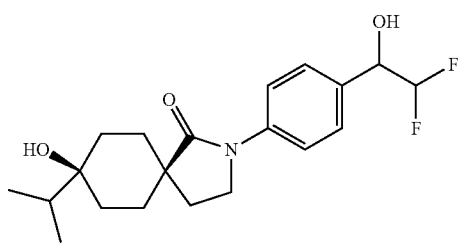 [SMILES: CC(C)[C@]1(O)CC[C@]2(CCN(c3ccc(C(O)C(F)F)cc3)C2=O)CC1]

The title compound was prepared in analogy to example 55 from (R)-2-(4-(2,2,2-trifluoro-1-hydroxyethyl)phenyl)-2-aza-spiro[4.5]decane-1,8-dione (product of example 195, step 3) by reaction with isopropylmagnesium chloride (2M in THF) as a white solid. MS (m/e): 368.202 [(M-H$_2$O)H$^+$].

Example 208

(5α,8α)-8-hydroxy-8-propyl-2-(4-(trifluoromethyl)phenyl)-2-aza-spiro[4.5]decan-1-one

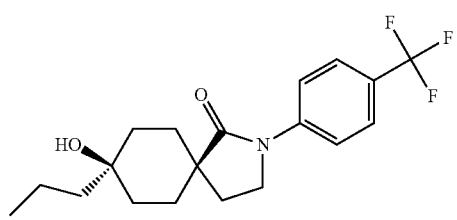 [SMILES: CCC[C@]1(O)CC[C@]2(CCN(c3ccc(C(F)(F)F)cc3)C2=O)CC1]

Step 1: 10-(4-Trifluoromethyl-phenyl)-1,4-dioxa-10-aza-dispiro[4.2.4.2]tetradecan-9-one

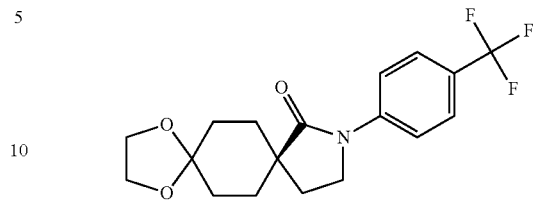

The title compound was prepared in analogy to example 133, step 4 from 1,4-dioxa-10-aza-dispiro[4.2.4.2]tetradecan-9-one (described in example 133 step 3) and 1-bromo-4-(trifluoromethyl)benzene as white crystalline solid. MS (m/e): 356.146 [(M-H$_2$O)H$^+$].

Step 2: 2-(4-Trifluoromethyl-phenyl)-2-aza-spiro[4.5]decane-1,8-dione

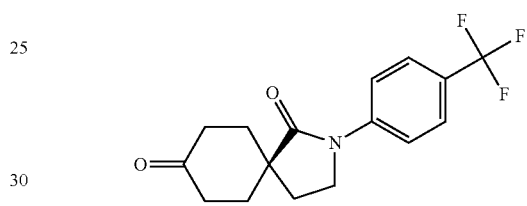

The title compound was prepared in analogy to example 133 step 5 from 10-(4-trifluoromethyl-phenyl)-1,4-dioxa-10-aza-dispiro[4.2.4.2]tetradecan-9-one as a white solid. MS (m/e): 311 [M$^+$].

Step 3: (5α,8α)-8-allyl-8-hydroxy-2-(4-(trifluoromethyl)phenyl)-2-aza-spiro[4.5]decan-1-one

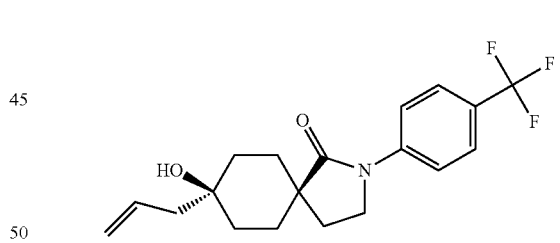

The title compound was prepared in analogy to example 55 from 2-(4-trifluoromethyl-phenyl)-2-aza-spiro[4.5]decane-1,8-dione by reaction with allylmagnesium bromide (1 M in diethyl ether), but without use of anhydrous cerous(III)-chloride in the reaction, as a white solid. MS (m/e): 354.168 [MH$^+$].

Step 4: (5α,8α)-8-hydroxy-8-propyl-2-(4-(trifluoromethyl)phenyl)-2-aza-spiro[4.5]decan-1-one The title compound was prepared in analogy to example 188 step 4 by hydrogenation of (5α,8α)-8-allyl-8-hydroxy-2-(4-(trifluoromethyl)phenyl)-2-aza-spiro[4.5]decan-1-one as a white solid. MS (m/e): 356.183 [MH$^+$].

Example 209

(5α,8α)-8-hydroxy-8-isopropyl-2-(4-(trifluoromethyl)phenyl)-2-aza-spiro[4.5]decan-1-one

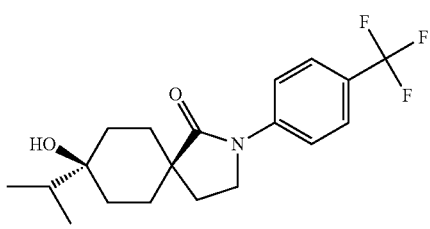 [SMILES: CC(C)[C@]1(O)CC[C@]2(CCN(c3ccc(C(F)(F)F)cc3)C2=O)CC1]

Step 1: (5α,8α)-)-8-hydroxy-8-(prop-1-en-2-yl)-2-(4-(trifluoromethyl)phenyl)-2-aza-spiro[4.5]decan-1-one

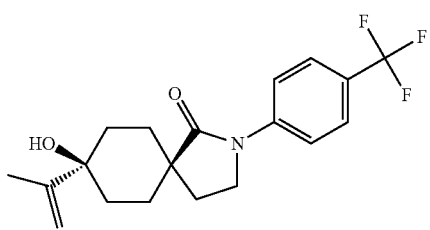 [SMILES: C=C(C)[C@]1(O)CC[C@]2(CCN(c3ccc(C(F)(F)F)cc3)C2=O)CC1]

The title compound was prepared in analogy to example 55 from 2-(4-trifluoromethyl-phenyl)-2-aza-spiro[4.5]decane-1,8-dione (product of example 208, step 2) by reaction with isopropenylmagnesium bromide (0.5 M in THF), but without use of anhydrous cerous(III)-chloride in the reaction, as a light yellow solid. MS (m/e): 353 [M F].

Step 2 (5α,8α)-8-hydroxy-8-isopropyl-2-(4-(trifluoromethyl)phenyl)-2-aza-spiro[4.5]decan-1-one The title compound was prepared in analogy to example 188 step 4 by hydrogenation of (5α,8α)-8-hydroxy-8-(prop-1-en-2-yl)-2-(4-(trifluoromethyl)phenyl)-2-aza-spiro[4.5]decan-1-one as a white solid. MS (m/e): 356.188 [MH+].

Example 210

(5α,8α)-8-hydroxy-2-(4-isopropoxyphenyl)-8-(methoxymethyl)-2-aza-spiro[4.5]decan-1-one

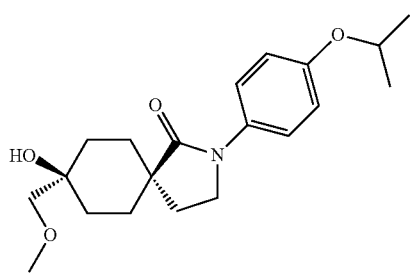 [SMILES: COC[C@]1(O)CC[C@]2(CCN(c3ccc(OC(C)C)cc3)C2=O)CC1]

Step 1: (3α,6α)-8-(4-Isopropoxy-phenyl)-1-oxa-8-aza-dispiro[2.2.4.2]dodecan-7-one

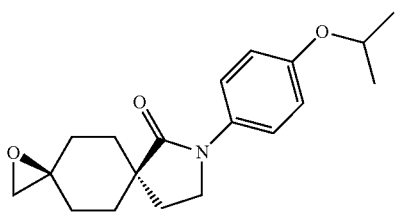 [SMILES: CC(C)Oc1ccc(N2CC[C@]3(CC[C@]4(CC3)CO4)C2=O)cc1]

The title compound was prepared in analogy to example 110, step 1 from 2-(4-isopropoxy-phenyl)-2-aza-spiro[4.5]decane-1,8-dione (product of example 184, step 2) as a white solid. MS (m/e): 316.190 [MH+].

Step 2: (5α,8α)-8-hydroxy-2-(4-isopropoxyphenyl)-8-(methoxymethyl)-2-aza-spiro[4.5]decan-1-one The title compound was prepared in analogy to example 110 step 2 from (3α,6α)-8-(4-isopropoxy-phenyl)-1-oxa-8-aza-dispiro[2.2.4.2]dodecan-7-one and sodium methylate as white solid. MS (m/e): 348.216 [MH+].

Example 211

(5α,8α)-8-hydroxy-2-(4-isopropoxyphenyl)-8-(thiophen-3-yl)-2-aza-spiro[4.5]decan-1-one

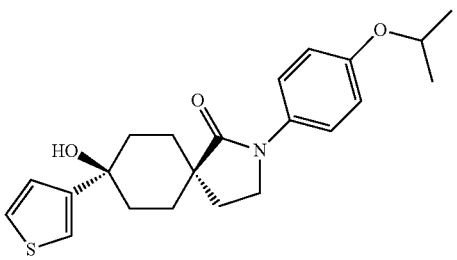 [SMILES: CC(C)Oc1ccc(N2CC[C@]3(CC[C@@](O)(c4ccsc4)CC3)C2=O)cc1]

The title compound was prepared in analogy to example 55 from 2-(4-isopropoxy-phenyl)-2-aza-spiro[4.5]decane-1,8-dione (product of example 184, step 2) by reaction with 3-thienylmagnesium iodide (0.5 M in THF), but without use of anhydrous cerous(III)-chloride in the reaction, as a white solid. MS (m/e): 385 [M+].

Example 212

(5α,8α)-8-(5-Bromo-3-methyl-3H-[1,2,3]triazol-4-yl)-8-hydroxy-2-(4-isopropoxy-phenyl)-2-aza-spiro[4.5]decan-1-one

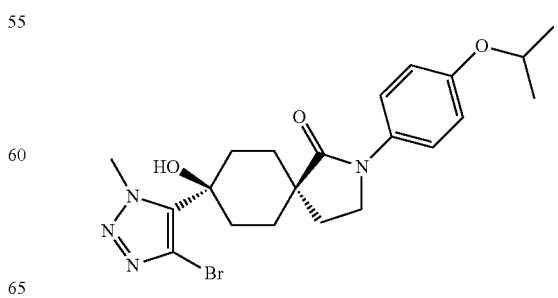

A solution of 4-bromo-1-methyl-1H-1,2,3-triazole (108 mg) in tetrahyrofurane (5 mL) was cooled to −78° C. under an argon atmosphere and then treated dropwise with n-butyllithium (415 μl, 1.6 M in hexanes) over 10 minutes. The reaction mixture was stirred 15 min at −78° C., then treated dropwise with 2-(4-isopropoxyphenyl)-2-aza-spiro[4.5]decane-1,8-dione (200 mg in 3 ml tetrahydrofuran, product of example 184, step 2). The mixture was stirred further 1 h at −78° C. then warmed slowly to RT. It was then partitioned between AcOEt and saturated aqueous NH₄Cl, the layers were separated, the organic layer washes with 1M aqueous HCL then brine and dried over Na₂SO₄. The solvent was evaporated off the residue purified by flash chromatography (silica gel, gradient of methylene chloride and AcOEt) to give the title compound (102 mg, 31%) as a white solid. MS (m/e): 465.131 [MH⁺].

Example 213

5α,8α)-8-hydroxy-2-(4-isopropoxyphenyl)-8-(1-methyl-1H-1,2,3-triazol-4-yl)-2-aza-spiro[4.5]decan-1-one

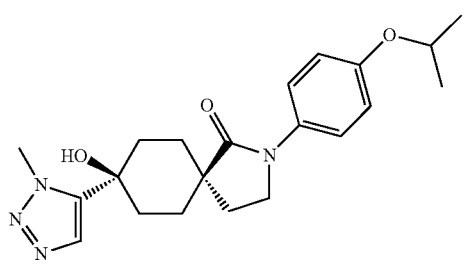 [SMILES: CC(C)Oc1ccc(N2CC[C@]3(CC[C@@](O)(c4cnnn4C)CC3)C2=O)cc1]

The title compound was obtained from (5α,8α)-8-(5-bromo-3-methyl-3H-[1,2,3]triazol-4-yl)-8-hydroxy-2-(4-isopropoxy-phenyl)-2-aza-spiro[4.5]decan-1-one (product of example 212) by hydrogenation over Pd as catalyst (10% on charcoal) in methanol as solvent, at atmospheric pressure and RT, as white solid: MS (m/e): 385.223 [MH⁺].

Example 214

(5α,8α)-8-(5-Bromo-3-methyl-3H-[1,2,3]triazol-4-yl)-8-hydroxy-2-(4-trifluoromethyl-phenyl)-2-aza-spiro[4.5]decan-1-one

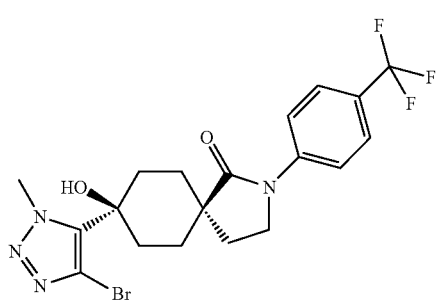 [SMILES: Cn1nnc(Br)c1[C@]1(O)CC[C@]2(CCN(c3ccc(C(F)(F)F)cc3)C2=O)CC1]

The title compound was obtained in analogy to example 212 from 2-(4-trifluoromethyl-phenyl)-2-aza-spiro[4.5]decane-1,8-dione (product of example 208, step 2) and 4-bromo-1-methyl-1H-1,2,3-triazole as white solid. MS (m/e): 475.078 [MH⁺].

Example 215

(5α,8α)-8-Hydroxy-8-(3-methyl-3H-[1,2,3]triazol-4-yl)-2-(4-trifluoromethyl-phenyl)-2-aza-spiro[4.5]decan-1-one

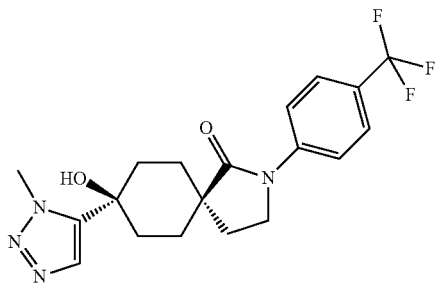 [SMILES: Cn1nncc1[C@]1(O)CC[C@]2(CCN(c3ccc(C(F)(F)F)cc3)C2=O)CC1]

The title compound was prepared in analogy to example 213 by hydrogenation of (5α,8α)-8-(5-bromo-3-methyl-3H-[1,2,3]triazol-4-yl)-8-hydroxy-2-(4-trifluoromethyl-phenyl)-2-aza-spiro[4.5]decan-1-one (product of example 214) as white solid. MS (m/e): 395.169 [MH⁺].

Example 216

(5α,8α)-8-hydroxy-2-(4-isopropylphenyl)-8-((2,2,2-trifluoroethoxy)methyl)-2-aza-spiro[4.5]decan-1-one

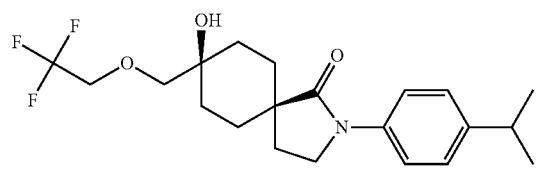 [SMILES: CC(C)c1ccc(N2CC[C@]3(CC[C@@](O)(COCC(F)(F)F)CC3)C2=O)cc1]

Step 1: (3α,6α)-8-(4-isopropyl-phenyl)-1-oxa-8-aza-dispiro[2.2.4.2]dodecan-7-one

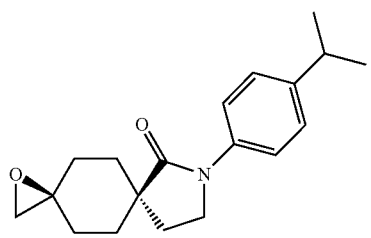 [SMILES: CC(C)c1ccc(N2CC[C@]3(CC[C@]4(CC3)CO4)C2=O)cc1]

The title compound was prepared in analogy to example 110, step 1 from 2-(4-isopropylphenyl)-2-aza-spiro[4.5]decane-1,8-dione (product of example 203, step 2) as a white solid.

Step 2: 5α,8α)-8-hydroxy-2-(4-isopropylphenyl)-8-((2,2,2-trifluoroethoxy)methyl)-2-aza-spiro[4.5]decan-1-one The title compound was prepared in analogy to example 155 from (3α,6α)-8-(4-isopropyl-phenyl)-1-oxa-8-aza-dispiro[2.2.4.2]dodecan-7-one and 2,2,2-trifluoroethanol as white solid. MS (m/e): 399 [M⁺].

Example 217

(5α,8α)-8-hydroxy-2-(4-isopropoxyphenyl)-8-(1-methyl-1H-pyrazol-3-yl)-2-aza-spiro[4.5]decan-1-one

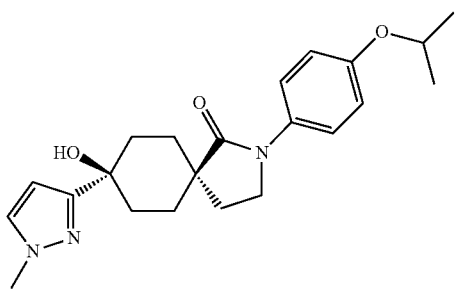 [SMILES: CC(C)Oc1ccc(N2CC[C@]3(CC[C@@](O)(c4ccn(C)n4)CC3)C2=O)cc1]

The title compound was obtained in analogy to example 212 from 2-(4-isopropoxyphenyl)-2-aza-spiro[4.5]decane-1,8-dione (product of example 184, step 2), 3-iodo-1-methyl-1H-pyrazole and n-butyllithium, whereby iodo-lithium exchange occurred under the reaction conditions, as white solid. MS (m/e): 366.2 [(M-H$_2$O)H$^+$].

Example 218

(5α,8α)-8-hydroxy-2-(4-isopropylphenyl)-8-(methoxymethyl)-2-aza-spiro[4.5]decan-1-one

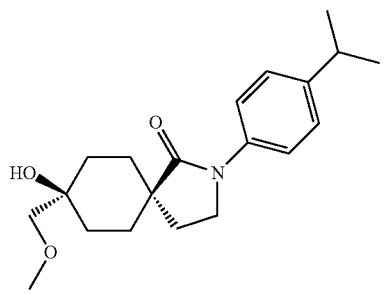 [SMILES: COC[C@]1(O)CC[C@]2(CCN(c3ccc(C(C)C)cc3)C2=O)CC1]

The title compound was prepared in analogy to example 110 step 2 from (3α,6α)-8-(4-isopropyl-phenyl)-1-oxa-8-aza-dispiro[2.2.4.2]dodecan-7-one (product of example 216, step 1) and sodium methylate as white solid. MS (m/e): 332.222 [MH$^+$].

Example 219

(5α,8α)-8-hydroxy-8-((2,2,2-trifluoroethoxy)methyl)-2-(4-(trifluoromethyl)phenyl)-2-aza-spiro[4.5]decan-1-one

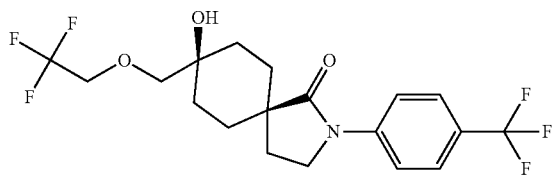 [SMILES: O=C1N(c2ccc(C(F)(F)F)cc2)CC[C@]12CC[C@@](O)(COCC(F)(F)F)CC2]

Step 1: (3α,6α)-8-(4-Trifluoromethyl-phenyl)-1-oxa-8-aza-dispiro[2.2.4.2]dodecan-7-one The title compound was prepared in analogy to example 110, step 1 from 2-(4-trifluoromethyl-phenyl)-2-aza-spiro[4.5]decane-1,8-dione (product of example 208 step 1) as a white solid. MS (m/e): 326.2 [MH$^+$]

Step 2: (5α,8α)-8-hydroxy-8-((2,2,2-trifluoroethoxy)methyl)-2-(4-(trifluoromethyl) phenyl)-2-aza-spiro[4.5]decan-1-one The title compound was prepared in analogy to example 155 from (3α,6α)-8-(4-trifluoromethyl-phenyl)-1-oxa-8-aza-dispiro[2.2.4.2]dodecan-7-one and 2,2,2-trifluoroethanol as white solid. MS (m/e): 426.149 [MH$^+$].

Example 220

(5α,8α)-8-hydroxy-2-(4-isopropoxyphenyl)-84 (5-methylisoxazol-3-yl)methyl)-2-aza-spiro[4.5]decan-1-one

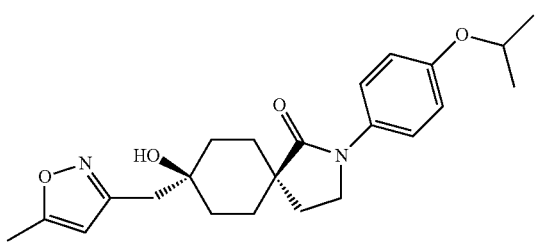 [SMILES: Cc1cc(C[C@]2(O)CC[C@]3(CCN(c4ccc(OC(C)C)cc4)C3=O)CC2)no1]

The title compound was obtained in analogy to example 212 from 2-(4-isopropoxyphenyl)-2-aza-spiro[4.5]decane-1,8-dione (80 mg) product of example 184, step 2), 3,5-dimethylisoxazole (103 mg) and n-butyllithium (332 μl, 1.6 molar in hexanes) through selective deprotonation as a major product, isolated by flash chromatography on silica gel, gradients of methylene chloride and AcOEt. Light yellow solid (25 mg, 24%). MS (m/e): 399.228 [(MH$^+$].

Example 221

(5α,8β)-8-hydroxy-2-(4-isopropoxyphenyl)-8-((5-methylisoxazol-3-yl)methyl)-2-aza-spiro[4.5]decan-1-one

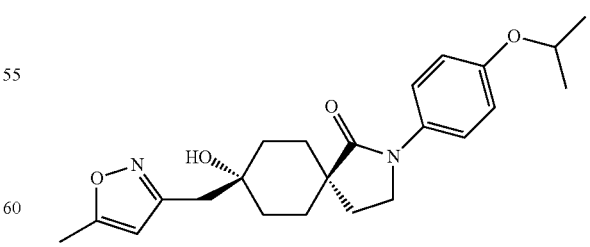

The title compound was isolated by flash chromatography (silica gel gradients of methylene chloride and AcOEt) as second major product from the mixture of products obtained in the reaction described in example 220 (27 mg, 26%). White powder. MS (m/e): 399.228 [(MH$^+$].

Example 222

(5α,8α)-8-hydroxy-2-(4-isopropoxyphenyl)-8-(1-methyl-4-vinyl-1H-1,2,3-triazol-5-yl)-2-aza-spiro[4.5]decan-1-one

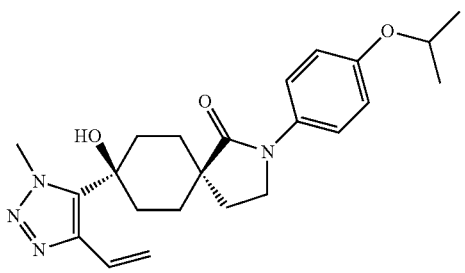 [SMILES: C=Cc1nnn(C)c1[C@]1(O)CC[C@]2(CCN(c3ccc(OC(C)C)cc3)C2=O)CC1]

(5α,8α)-8-(5-Bromo-3-methyl-3H-[1,2,3]triazol-4-yl)-8-hydroxy-2-(4-isopropoxy-phenyl)-2-aza-spiro[4.5]decan-1-one (20 mg, product of example 212) dissolved in a mixture of water and dioxane (1:2, 6 ml) was treated at RT under an argon atmosphere sequentially with 4,4,5,5-tetramethyl-2-vinyl-1,3,2-dioxaborolane (6.65 mg), tetrakis(triphenylphosphan)palladium (0.5 mg) and potassium carbonate (5.6 mg) and the reaction mixture was then heated at 100° C. for 12 h. It was then cooled to RT and partitioned between water (5 ml) and AcOEt (10 ml). The layers were separated, the aqueous layer extracted again with AcOEt (10 ml), the combined organic layers were dried over MgSO₄ filtered and concentrated in vacuo. The title compound was isolated by flash chromatography (silica gel gradients of methylene chloride and AcOEt) as a white solid (4 mg, 23%). MS (m/e): 411.3 [MH$^+$].

Example 223

(5α,8α)-2-(4-Cyclopropyl-phenyl)-8-hydroxy-8-methoxymethyl-2-aza-spiro[4.5]decan-1-one

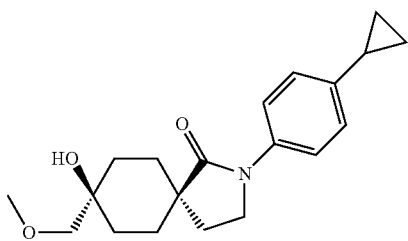 [SMILES: COC[C@]1(O)CC[C@]2(CCN(c3ccc(C4CC4)cc3)C2=O)CC1]

Step 1: 1-(2-Methoxy-ethyl)-4-methylene-cyclohexanecarboxylic acid ethyl ester

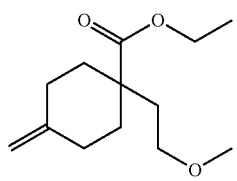

A solution of 5 g (30 mmol) 4-methylene-cyclohexanecarboxylic acid ethyl ester (commercially available) in 19 mL THF was added to 59 mmol LDA in 75 mL THF at −5° C. and stirred for 3 h. 8.2 g (59 mmol) 2-bromoethyl methyl ether in 10 mL THF was added and the mixture was allowed to stir to room temperature and stirred additionally over night. Water and 2M Na₂CO₃ aq. was added and the mixture was evaporated to dryness. The residue was taken up in ethyl acetate washed with water and brine, dried with MgSO₄, filtered and evaporated. The residue was purified by flash column chromatography over silica eluting with a gradient formed from hexane and ethyl acetate to yield after evaporation of the product containing fractions 4.98 g (74%) of the title compound as yellow liquid.

Step 2: 2-(4-Cyclopropyl-phenyl)-8-methylene-2-aza-spiro[4.5]decan-1-one

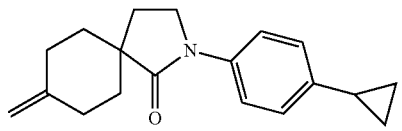 [SMILES: C=C1CCC2(CC1)CCN(c1ccc(C3CC3)cc1)C2=O]

A mixture of 0.3 g (1.3 mmol) 1-(2-methoxy-ethyl)-4-methylene-cyclohexanecarboxylic acid ethyl ester and 0.264 g (1.98 mmol) 4-cyclopropylaniline in 6 mL toluene was treated with 2.65 mL (2.65 mmol) dimethylaluminium chloride (1M in toluol) and stirred for 4 h at 100° C. After cooling to room temperature water and 1N HCl aq. was carefully added and the mixture poured onto water and extracted with ethyl acetate. The combined organic layers were washed with water, dried with MgSO₄, filtered and evaporated to dryness. The residue was purified by flash column chromatography over silica eluting with a gradient formed from hexane and ethyl acetate to yield after evaporation of the product containing fractions 0.264 g (71%) of the title compound as yellow crystals. MS (m/e): 282.4 [MH$^+$].

Step 3: 8-(4-Cyclopropyl-phenyl)-1-oxa-8-aza-dispiro[2.2.4.2]dodecan-7-one

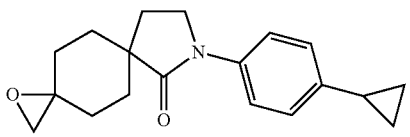 [SMILES: O=C1N(c2ccc(C3CC3)cc2)CCC12CCC1(CC2)CO1]

A solution of 0.251 g (0.89 mmol) 2-(4-cyclopropyl-phenyl)-8-methylene-2-aza-spiro[4.5]decan-1-one in 3 mL DCM was added at 0° C. to a solution of 0.157 g (0.91 mmol) m-chloroperbenzoic acid and 0.098 mg (1.1 mmol) NaHCO₃ in 3 mL DCM and allowed to stir to room temperature and continued for another hour at room temperature. The mixture was poured onto water and extracted with DCM. The combined organic phases were dried with MgSO₄, filtered and evaporated. The title compound (0.312 g) was used in the consecutive step without further purification. MS (m/e): 298.8 [MH$^+$].

Step 4: (5α,8α)-2-(4-Cyclopropyl-phenyl)-8-hydroxy-8-methoxymethyl-2-aza-spiro[4.5]decan-1-one A solution of 0.265 g 8-(4-cyclopropyl-phenyl)-1-oxa-8-aza-dispiro[2.2.4.2]dodecan-7-one (crude) in 6 mL THF was treated with 0.4 mL NaOMe (5.4 M in methanol) and heated to reflux temperature for 8 h and stirred at room temperature over night. The mixture was filtered over silica and washed with THF. The organic fraction was evaporated to dryness and the residue was purified by preparative HPLC on reversed phase eluting with a gradient formed from acetonitrile, water and NEt$_3$. The product containing fractions were evaporated to yield 60 mg of the title compound as with crystals. MS (m/e): 330.2 [MH$^+$].

Example 224

(5α,8α)-2-(4-Ethyl-phenyl)-8-hydroxy-8-methoxymethyl-2-aza-spiro[4.5]decan-1-one

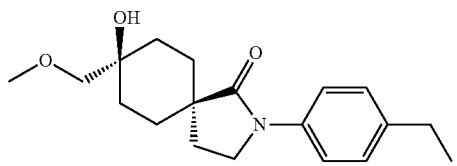

Step 1: 2-(4-Ethyl-phenyl)-8-methylene-2-aza-spiro[4.5]decan-1-one

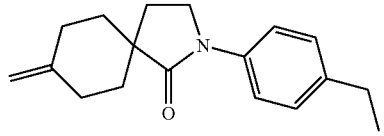 [SMILES: C=C1CCC2(CC1)CCN(c1ccc(CC)cc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 4-ethyl-phenylamine. MS (m/e): 270.2 [MH$^+$].

Step 2: 8-(4-Ethyl-phenyl)-1-oxa-8-aza-dispiro[2.2.4.2]dodecan-7-one

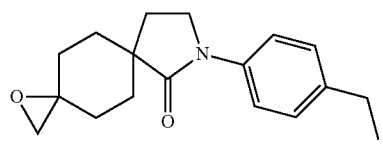 [SMILES: CCc1ccc(N2CCC3(CCC4(CC3)CO4)C2=O)cc1]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 2-(4-ethyl-phenyl)-8-methylene-2-aza-spiro[4.5]decan-1-one and m-chloroperbenzoic acid.

Step 3: (5α,8α)-2-(4-Ethyl-phenyl)-8-hydroxy-8-methoxymethyl-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and methanol. MS (m/e): 318.3 [MH$^+$].

Example 225

(5α,8α)-8-Ethoxymethyl-2-(4-ethyl-phenyl)-8-hydroxy-2-aza-spiro[4.5]decan-1-one

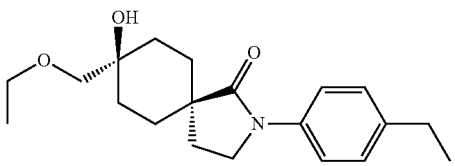 [SMILES: CCOC[C@]1(O)CC[C@]2(CCN(c3ccc(CC)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and ethanol. MS (m/e): 332.4 [MH$^+$].

Example 226

(5α,8α)-2-(4-Ethyl-phenyl)-8-hydroxy-8-propoxymethyl-2-aza-spiro[4.5]decan-1-one

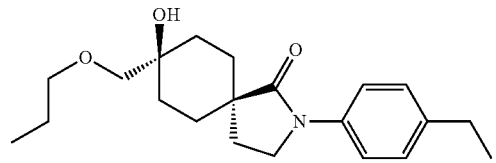 [SMILES: CCCOC[C@]1(O)CC[C@]2(CCN(c3ccc(CC)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and propanol. MS (m/e): 346.2 [MH$^+$].

Example 227

(5α,8β)-2-(4-Ethyl-phenyl)-8-hydroxy-8-phenoxymethyl-2-aza-spiro[4.5]decan-1-one

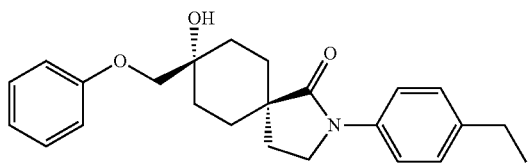 [SMILES: CCc1ccc(N2CC[C@]3(CC[C@](O)(COc4ccccc4)CC3)C2=O)cc1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and phenol. MS (m/e): 380.4 [MH⁺].

Example 228

(5α,8α)-2-(4-Ethyl-phenyl)-8-hydroxy-8-phenoxymethyl-2-aza-spiro[4.5]decan-1-one

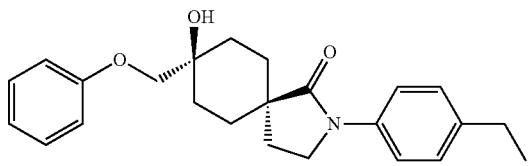 [SMILES: CCc1ccc(N2CC[C@]3(CC[C@@](O)(COc4ccccc4)CC3)C2=O)cc1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and phenol. MS (m/e): 380.4 [MH⁺].

Example 229

(5α,8α)-2-(4-Ethyl-phenyl)-8-hydroxy-8-(2-methoxy-ethoxymethyl)-2-aza-spiro[4.5]decan-1-one

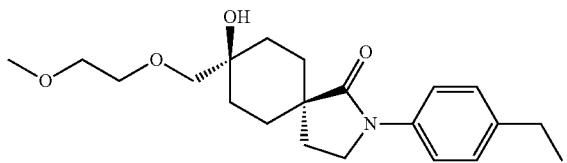 [SMILES: CCc1ccc(N2CC[C@]3(CC[C@@](O)(COCCOC)CC3)C2=O)cc1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and 2-methoxy-ethanol. MS (m/e): 362.3 [MH⁺].

Example 230

(5α,8β)-2-(4-Ethyl-phenyl)-8-hydroxy-8-(2,2,2-trifluoro-ethoxymethyl)-2-aza-spiro[4.5]decan-1-one

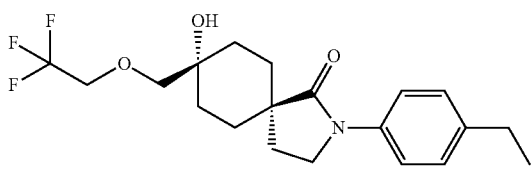 [SMILES: CCc1ccc(N2CC[C@]3(CC[C@](O)(COCC(F)(F)F)CC3)C2=O)cc1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and 2,2,2-trifluoro-ethanol. MS (m/e): 386.4 [MH⁺].

Example 231

(5α,8α)-2-(4-Ethyl-phenyl)-8-hydroxy-8-(2,2,2-trifluoro-ethoxymethyl)-2-aza-spiro[4.5]decan-1-one

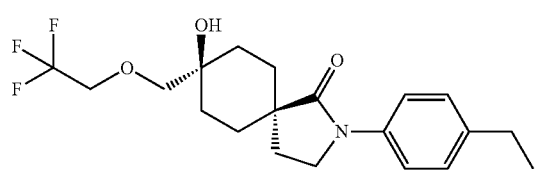 [SMILES: CCc1ccc(N2CC[C@]3(CC[C@@](O)(COCC(F)(F)F)CC3)C2=O)cc1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and 2,2,2-trifluoro-ethanol. MS (m/e): 386.4 [MH⁺].

Example 232

(5α,8β)-8-Hydroxy-8-(2,2,2-trifluoro-ethoxymethyl)-2-[4-(2,2,2-trifluoro-ethoxy)-phenyl]-2-aza-spiro[4.5]decan-1-one

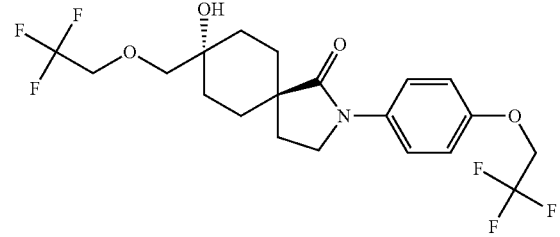 [SMILES: O=C1N(c2ccc(OCC(F)(F)F)cc2)CC[C@]12CC[C@](O)(COCC(F)(F)F)CC2]

Step 1: 8-Methylene-2-[4-(2,2,2-trifluoro-ethoxy)-phenyl]-2-aza-spiro[4.5]decan-1-one

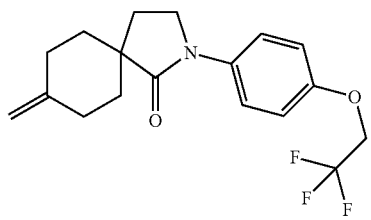 [SMILES: C=C1CCC2(CC1)CCN(c1ccc(OCC(F)(F)F)cc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 4-(2,2,2-trifluoro-ethoxy)-phenylamine. MS (m/e): 340.2 [MH+].

Step 2: 8-[4-(2,2,2-Trifluoro-ethoxy)-phenyl]-1-oxa-8-aza-dispiro[2.2.4.2]dodecan-7-one

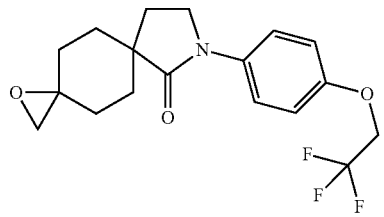 [SMILES: O=C1N(c2ccc(OCC(F)(F)F)cc2)CCC12CCC1(CC2)CO1]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 8-methylene-2-[4-(2,2,2-trifluoro-ethoxy)-phenyl]-2-aza-spiro[4.5]decan-1-one and m-chloroperbenzoic acid. MS (m/e): 356.2 [MH+].

Step 3: (5α,8β)-8-Hydroxy-8-(2,2,2-trifluoro-ethoxymethyl)-2-[4-(2,2,2-trifluoro-ethoxy)-phenyl]-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 2,2,2-Trifluoro-ethanol. MS (m/e): 456.2 [MH+].

Example 233

(5α,8α)-8-Hydroxy-8-(2,2,2-trifluoro-ethoxymethyl)-2-[4-(2,2,2-trifluoro-ethoxy)-phenyl]-2-aza-spiro[4.5]decan-1-one

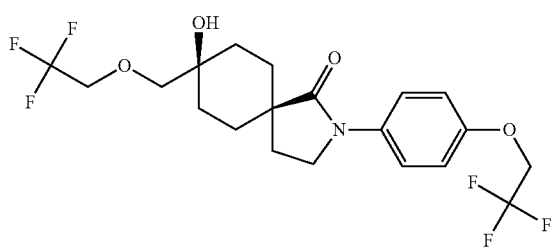 [SMILES: O=C1N(c2ccc(OCC(F)(F)F)cc2)CC[C@]12CC[C@@](O)(COCC(F)(F)F)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 2,2,2-trifluoro-ethanol. MS (m/e): 456.2 [MH+].

Example 234

(5α,8α)-8-Ethoxymethyl-8-hydroxy-2-[4-(2,2,2-trifluoro-ethoxy)phenyl]-2-aza-spiro[4.5]decan-1-one

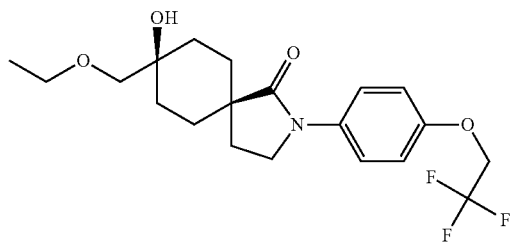 [SMILES: CCOC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and ethanol. MS (m/e): 402.3 [MH+].

Example 235

(5α,8β)-8-Hydroxy-8-propoxymethyl-2-[4-(2,2,2-trifluoro-ethoxy)-phenyl]-2-aza-spiro[4.5]decan-1-one

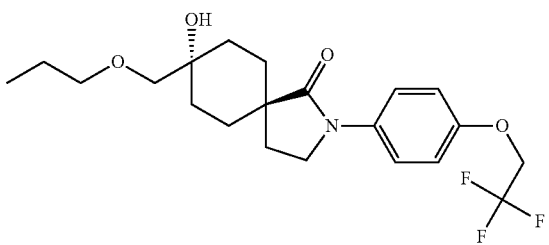

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and propanol. MS (m/e): 416.3 [MH+].

Example 236

(5α,8α)-8-Hydroxy-8-propoxymethyl-2-[4-(2,2,2-trifluoro-ethoxy)-phenyl]-2-aza-spiro[4.5]decan-1-one

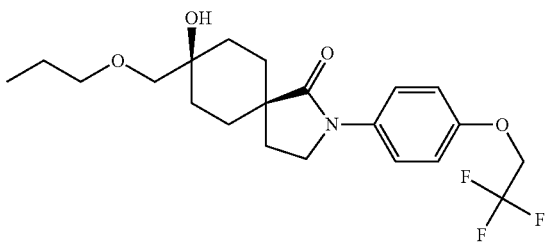 [SMILES: CCCOC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and propanol. MS (m/e): 416.3 [MH⁺].

Example 237

(5α,8β)-8-Butoxymethyl-8-hydroxy-2-[4-(2,2,2-trifluoro-ethoxy)-phenyl]-2-aza-spiro[4.5]decan-1-one

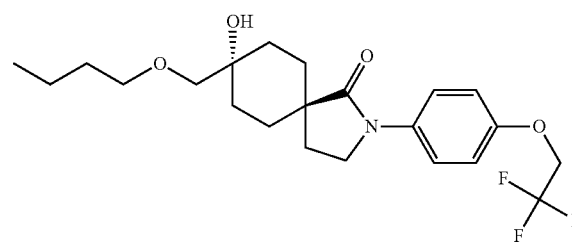

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and butanol. MS (m/e): 430.3 [MH⁺].

Example 238

(5α,8α)-8-Butoxymethyl-8-hydroxy-2-[4-(2,2,2-trifluoro-ethoxy)-phenyl]-2-aza-spiro[4.5]decan-1-one

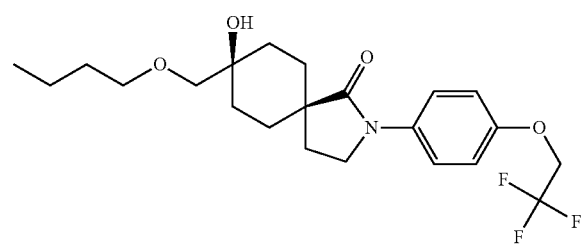 [SMILES: CCCCOC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and butanol. MS (m/e): 488.3 ((M+59)-H)⁻.

Example 239

(5α,8β)-8-Hydroxy-8-phenoxymethyl-2-[4-(2,2,2-trifluoro-ethoxy)-phenyl]-2-aza-spiro[4.5]decan-1-one

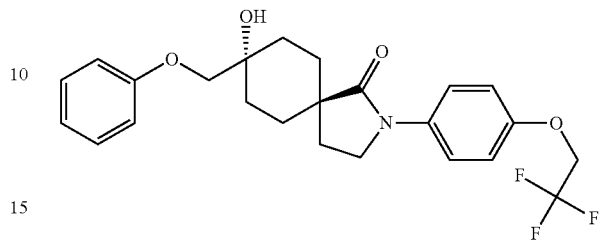

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and phenol. MS (m/e): 450.2 [MH⁺].

Example 240

(5α,8α)-8-Hydroxy-8-phenoxymethyl-2-[4-(2,2,2-trifluoro-ethoxy)-phenyl]-2-aza-spiro[4.5]decan-1-one

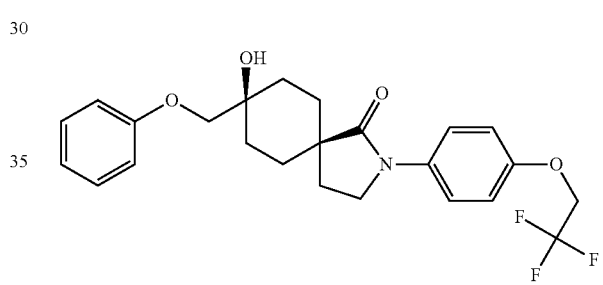

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and phenol. MS (m/e): 450.2 [MH⁺].

Example 241

(5α,8β)-8-Benzyloxymethyl-8-hydroxy-2-[4-(2,2,2-trifluoro-ethoxy)-phenyl]-2-aza-spiro[4.5]decan-1-one

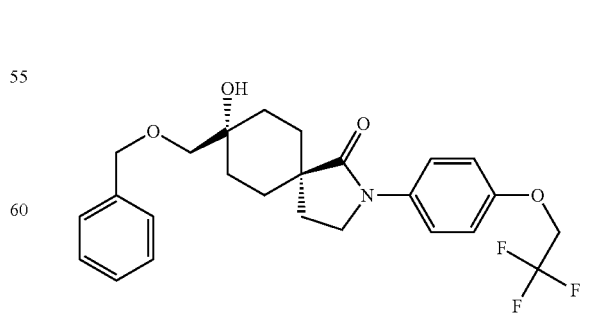

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and phenyl-methanol. MS (m/e): 464.3 [MH+].

Example 242

(5α,8α)-8-Benzyloxymethyl-8-hydroxy-2-[4-(2,2,2-trifluoro-ethoxy)-phenyl]-2-aza-spiro[4.5]decan-1-one

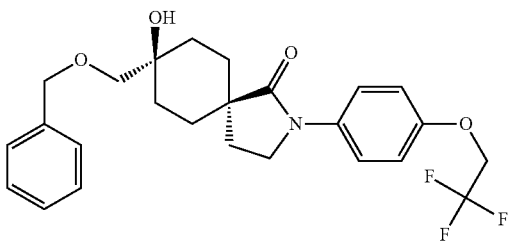 [SMILES: O=C1N(c2ccc(OCC(F)(F)F)cc2)CC[C@]12CC[C@@](O)(COCc1ccccc1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and phenyl-methanol. MS (m/e): 464.3 [MH+].

Example 243

(5α,8β)-8-(2,2-Difluoro-ethoxymethyl)-8-hydroxy-2-[4-(2,2,2-trifluoro-ethoxy)-phenyl]-2-aza-spiro[4.5]decan-1-one

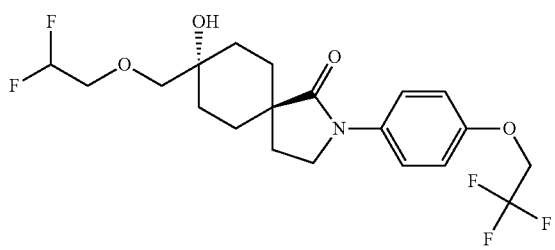 [SMILES: O=C1N(c2ccc(OCC(F)(F)F)cc2)CC[C@]12CC[C@](O)(COCC(F)F)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 2,2-difluoro-ethanol. MS (m/e): 438.2 [MH+].

Example 244

(5α,8α)-8-(2,2-Difluoro-ethoxymethyl)-8-hydroxy-2-[4-(2,2,2-trifluoro-ethoxy)-phenyl]-2-aza-spiro[4.5]decan-1-one

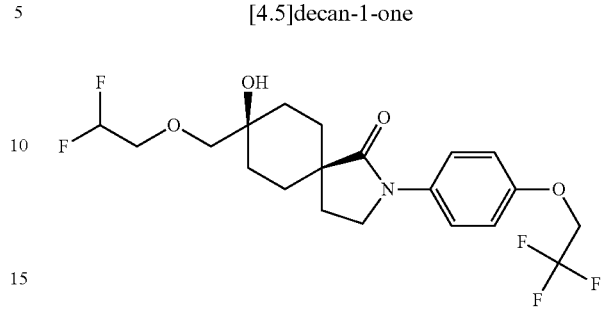

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 2,2-difluoro-ethanol. MS (m/e): 438.2 [MH+].

Example 245

(5α,8β)-8-Hydroxy-8-isobutoxymethyl-2-[4-(2,2,2-trifluoro-ethoxy)-phenyl]-2-aza-spiro[4.5]decan-1-one

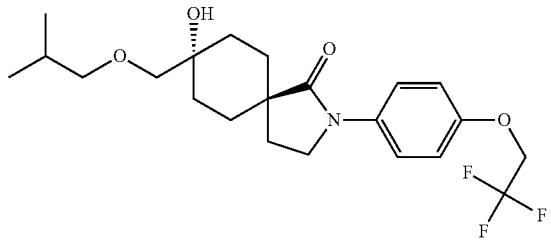 [SMILES: CC(C)COC[C@]1(O)CC[C@@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 2-methyl-propan-1-ol. MS (m/e): 430.3 [MH+].

Example 246

(5α,8α)-8-Hydroxy-8-isobutoxymethyl-2-[4-(2,2,2-trifluoro-ethoxy)-phenyl]-2-aza-spiro[4.5]decan-1-one

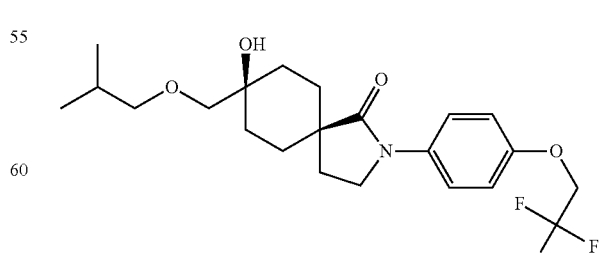

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 2-methyl-propan-1-ol. MS (m/e): 430.3 [MH⁺].

Example 247

(5α,8α)-8-Ethoxymethyl-8-hydroxy-2-[6-(2,2,2-trifluoro-ethoxy)-pyridin-3-yl]-2-aza-spiro[4.5]decan-1-one

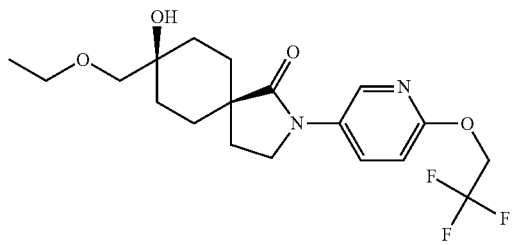 [SMILES: CCOC[C@]1(O)CC[C@]2(CCN(c3ccc(OCC(F)(F)F)nc3)C2=O)CC1]

Step 1: 8-Methylene-2-[6-(2,2,2-trifluoro-ethoxy)-pyridin-3-yl]-2-aza-spiro[4.5]decan-1-one

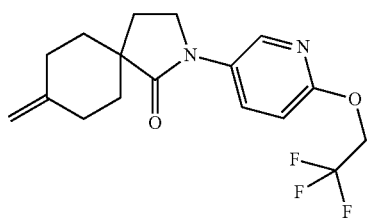 [SMILES: C=C1CCC2(CC1)CCN(c1ccc(OCC(F)(F)F)nc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 6-(2,2,2-trifluoro-ethoxy)-pyridin-3-ylamine (commercially available). MS (m/e): 341.1 [MH⁺].

Step 2: 8-[6-(2,2,2-Trifluoro-ethoxy)-pyridin-3-yl]-1-oxa-8-aza-dispiro[2.2.4.2]dodecan-7-one

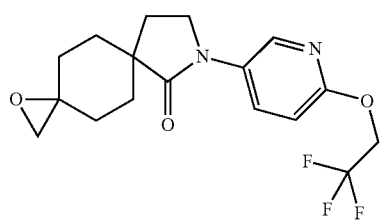 [SMILES: O=C1N(c2ccc(OCC(F)(F)F)nc2)CCC12CCC1(CC2)CO1]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 8-methylene-2-[6-(2,2,2-trifluoro-ethoxy)-pyridin-3-yl]-2-aza-spiro[4.5]decan-1-one and m-chloroperbenzoic acid. MS (m/e): 357.1 [MH⁺].

Step 3: (5α,8α)-8-Ethoxymethyl-8-hydroxy-2-[6-(2,2,2-trifluoro-ethoxy)-pyridin-3-yl]-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-(2,2,2-trifluoro-ethoxy)-pyridin-3-yl]-1-oxa-8-aza-dispiro[2.2.4.2]dodecan-7-one and ethanol. MS (m/e): 403.3 [MH⁺].

Example 248

(5α,8β)-8-Ethoxymethyl-8-hydroxy-2-[6-((S)-2,2,2-trifluoro-1-methyl-ethoxy)-pyridin-3-yl]-2-aza-spiro[4.5]decan-1-one

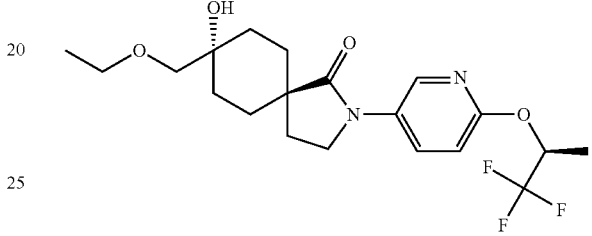

Step 1: 8-Methylene-2-[6-((S)-2,2,2-trifluoro-1-methyl-ethoxy)-pyridin-3-yl]-2-aza-spiro[4.5]decan-1-one

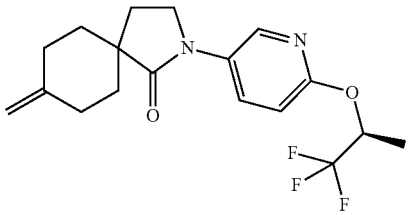 [SMILES: C=C1CCC2(CC1)CCN(c1ccc(O[C@@H](C)C(F)(F)F)nc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 6-((S)-2,2,2-trifluoro-1-methyl-ethoxy)-pyridin-3-ylamine. MS (m/e): 355.2 [MH⁺].

Step 2: 8-[6-((S)-2,2,2-Trifluoro-1-methyl-ethoxy)-pyridin-3-yl]-1-oxa-8-aza-dispiro[2.2.4.2]dodecan-7-one

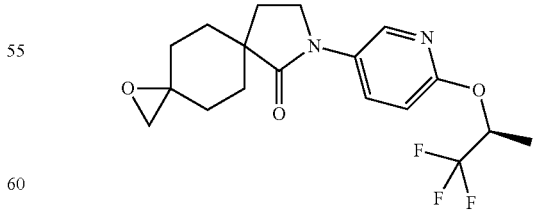

In analogy to the procedure described for the synthesis of 8-(4-cyclopropyl-phenyl)-1-oxa-8-aza-dispiro[2.2.4.2]dodecan-7-one (example 223, step 3) the title compound was prepared from 8-methylene-2-[6-((S)-2,2,2-trifluoro-1-methyl-ethoxy)-pyridin-3-yl]-2-aza-spiro[4.5]decan-1-one and m-chloroperbenzoic acid. MS (m/e): 371.2 [MH⁺].

Step 3: (5α,8β)-8-Ethoxymethyl-8-hydroxy-2-[6-((S)-2,2,2-trifluoro-1-methyl-ethoxy)-pyridin-3-yl]-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and ethanol. MS (m/e): 417.3 [MH+].

Example 249

(5α,8α)-8-Ethoxymethyl-8-hydroxy-2-[6-((S)-2,2,2-trifluoro-1-methyl-ethoxy)-pyridin-3-yl]-2-aza-spiro[4.5]decan-1-one

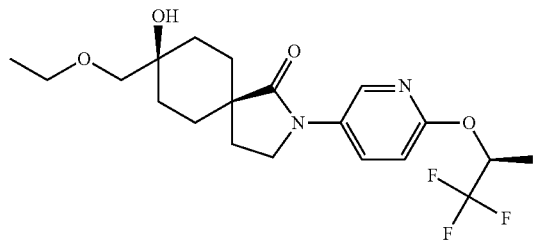

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and ethanol. MS (m/e): 417.3 [MH+].

Example 250

(5α,8β)-8-Ethoxymethyl-8-hydroxy-2-[4-((S)-2,2,2-trifluoro-1-methyl-ethoxy)-phenyl]-2-aza-spiro[4.5]decan-1-one

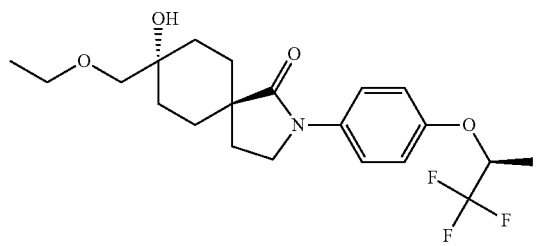 [SMILES: CCOC[C@]1(O)CC[C@@]2(CCN(c3ccc(O[C@@H](C)C(F)(F)F)cc3)C2=O)CC1]

Step 1: 8-Methylene-2-[4-((S)-2,2,2-trifluoro-1-methyl-ethoxy)-phenyl]-2-aza-spiro[4.5]decan-1-one

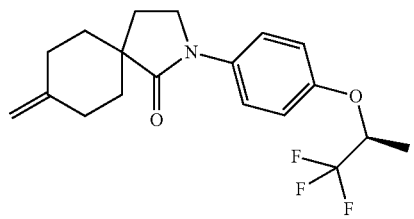 [SMILES: C=C1CCC2(CC1)CCN(c1ccc(O[C@@H](C)C(F)(F)F)cc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 4-((S)-2,2,2-trifluoro-1-methyl-ethoxy)-phenylamine. MS (m/e): 354.2 [MH+].

Step 2: 8-[4-((S)-2,2,2-Trifluoro-1-methyl-ethoxy)-phenyl]-1-oxa-8-aza-dispiro[2.2.4.2]dodecan-7-one

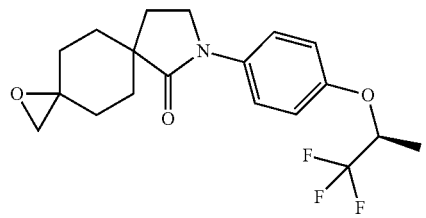 [SMILES: C[C@H](Oc1ccc(N2CCC3(CCC4(CC3)CO4)C2=O)cc1)C(F)(F)F]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 8-methylene-2-[4-((S)-2,2,2-trifluoro-1-methyl-ethoxy)-phenyl]-2-aza-spiro[4.5]decan-1-one and m-chloroperbenzoic acid. MS (m/e): 370.2 [MH+].

Step 3: (5α,8β)-8-Ethoxymethyl-8-hydroxy-2-[4-((S)-2,2,2-trifluoro-1-methyl-ethoxy)-phenyl]-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and ethanol. MS (m/e): 416.3 [MH+].

Example 251

(5α,8α)-8-Ethoxymethyl-8-hydroxy-2-[4-((S)-2,2,2-trifluoro-1-methyl-ethoxy)-phenyl]-2-aza-spiro[4.5]decan-1-one

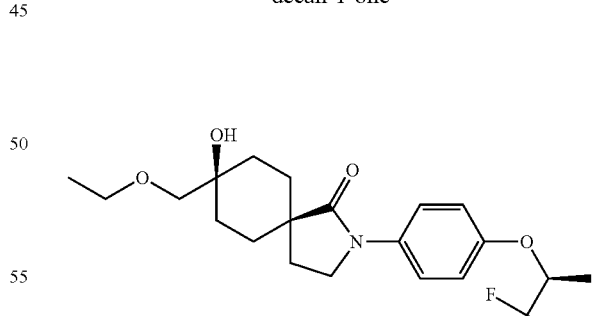

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and ethanol. MS (m/e): 416.3 [MH+].

Example 252

(5α,8β)-8-Ethoxymethyl-8-hydroxy-2-[4-((R)-2,2,2-trifluoro-1-methyl-ethoxy)-phenyl]-2-aza-spiro[4.5]decan-1-one

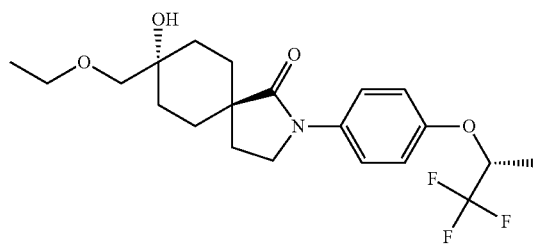 [SMILES: CCOC[C@]1(O)CC[C@@]2(CCN(c3ccc(O[C@H](C)C(F)(F)F)cc3)C2=O)CC1]

Step 1: 8-Methylene-2-[4-((R)-2,2,2-trifluoro-1-methyl-ethoxy)-phenyl]-2-aza-spiro[4.5]decan-1-one

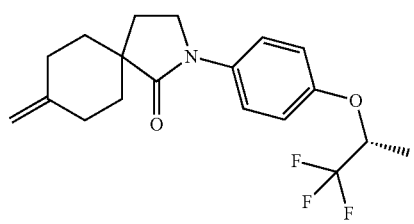 [SMILES: C=C1CCC2(CC1)CCN(c1ccc(O[C@H](C)C(F)(F)F)cc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 4-((R)-2,2,2-Trifluoro-1-methyl-ethoxy)-phenylamine. MS (m/e): 354.2 [MH⁺].

Step 2: 8-[4-((R)-2,2,2-Trifluoro-1-methyl-ethoxy)-phenyl]-1-oxa-8-aza-dispiro[2.2.4.2]dodecan-7-one

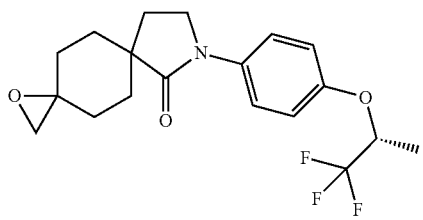 [SMILES: C[C@@H](Oc1ccc(N2CCC3(CCC4(CC3)CO4)C2=O)cc1)C(F)(F)F]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 8-methylene-2-[4-((R)-2,2,2-trifluoro-1-methyl-ethoxy)-phenyl]-2-aza-spiro[4.5]decan-1-one and m-chloroperbenzoic acid. MS (m/e): 370.2 [MH⁺].

Step 3: (5α,8β)-8-Ethoxymethyl-8-hydroxy-2-[4-((R)-2,2,2-trifluoro-1-methyl-ethoxy)-phenyl]-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and ethanol. MS (m/e): 416.3 [MH⁺].

Example 253

(5α,8α)-8-Ethoxymethyl-8-hydroxy-2-[4-((R)-2,2,2-trifluoro-1-methyl-ethoxy)-phenyl]-2-aza-spiro[4.5]decan-1-one

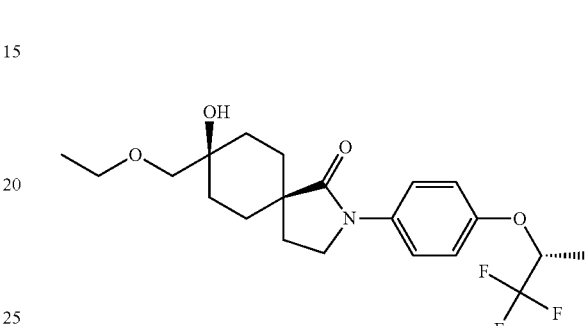

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and ethanol. MS (m/e): 416.3 [MH⁺].

Example 254

(5α,8β)-8-[(Cyclobutylmethoxy)methyl]-8-hydroxy-2-[4-(2,2,2-trifluoro-ethoxy)-phenyl]-2-aza-spiro[4.5]decan-1-one

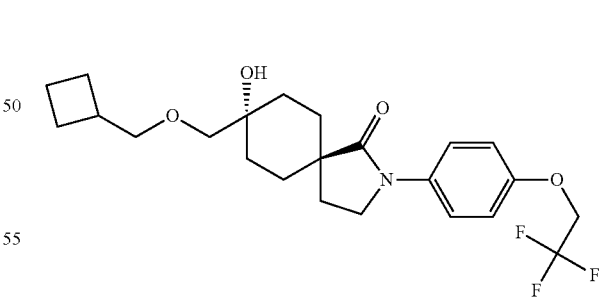

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and cyclobutyl-methanol. MS (m/e): 442.2 [MH⁺].

Example 255

(5α,8α)-8-[(Cyclobutylmethoxy)methyl]-8-hydroxy-2-[4-(2,2,2-trifluoro-ethoxy)-phenyl]-2-aza-spiro[4.5]decan-1-one

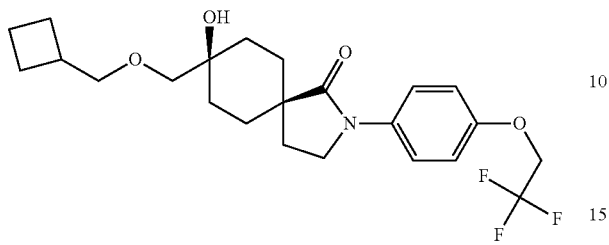

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and cyclobutyl-methanol. MS (m/e): 442.2 [MH+].

Example 256

(5α,8β)-8-[(Cyclopropylmethoxy)methyl]-8-hydroxy-2-[4-(2,2,2-trifluoro-ethoxy)-phenyl]-2-aza-spiro[4.5]decan-1-one

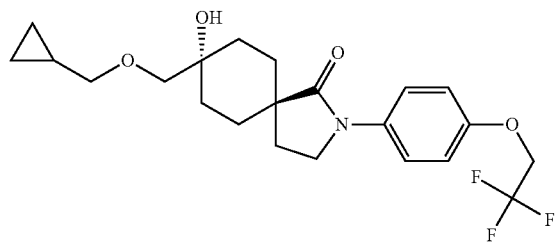 [SMILES: O=C1N(c2ccc(OCC(F)(F)F)cc2)CC[C@]12CC[C@](O)(COCC1CC1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and cyclopropyl-methanol. MS (m/e): 428.3 [MH+].

Example 257

(5α,8α)-8-[(Cyclopropylmethoxy)methyl]-8-hydroxy-2-[4-(2,2,2-trifluoro-ethoxy)-phenyl]-2-aza-spiro[4.5]decan-1-one

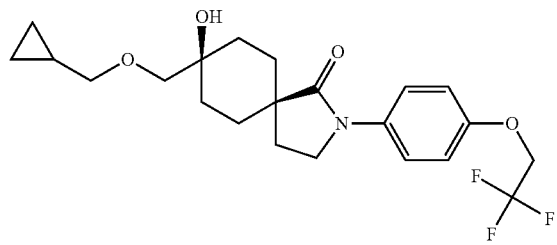 [SMILES: O=C1N(c2ccc(OCC(F)(F)F)cc2)CC[C@]12CC[C@@](O)(COCC1CC1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and cyclopropyl-methanol. MS (m/e): 428.3 [MH+].

Example 258

(5α,8α)-8-Hydroxy-8-methoxymethyl-2-[4-(2,2,2-trifluoro-ethoxy)-phenyl]-2-aza-spiro[4.5]decan-1-one

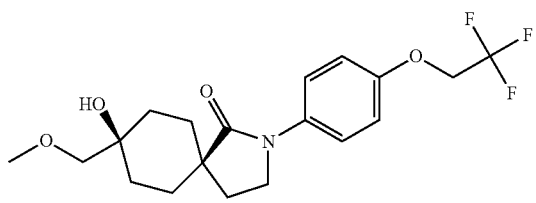 [SMILES: COC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and methanol. MS (m/e): 388.2 [MH+].

Example 259

(5α,8α)-8-Hydroxy-8-(oxetan-2-ylmethoxymethyl)-2-[4-(2,2,2-trifluoro-ethoxy)-phenyl]-2-aza-spiro[4.5]decan-1-one

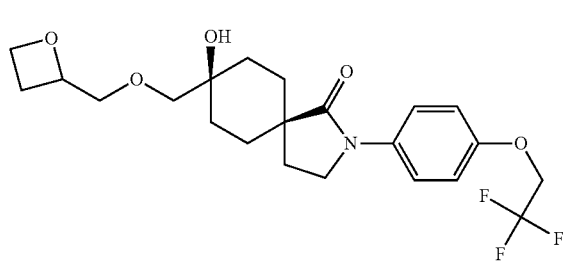 [SMILES: O=C1N(c2ccc(OCC(F)(F)F)cc2)CC[C@]12CC[C@@](O)(COCC1CCO1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and oxetan-2-yl-methanol. MS (m/e): 444.3 [MH+].

Example 260

(5α,8α)-8-Hydroxy-8-(3-methyl-oxetan-3-yl-methoxymethyl)-2-[4-(2,2,2-trifluoro-ethoxy)-phenyl]-2-aza-spiro[4.5]decan-1-one

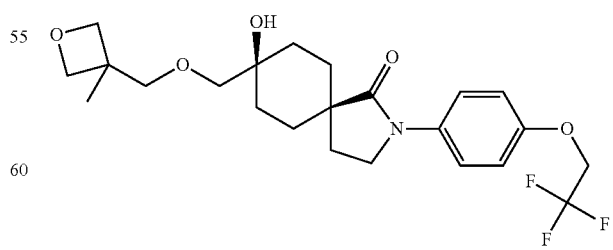

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoroethoxy)-phenyl]-1-oxa-8-aza-dispiro[2.2.4.2]dodecan-7-one and (3-methyl-oxetan-3-yl)-methanol. MS (m/e): 458.3 [MH⁺].

Example 261

(5α,8α)-8-Ethylsulfanylmethyl-8-hydroxy-2-[4-(2,2,2-trifluoro-ethoxy)-phenyl]-2-aza-spiro[4.5]decan-1-one

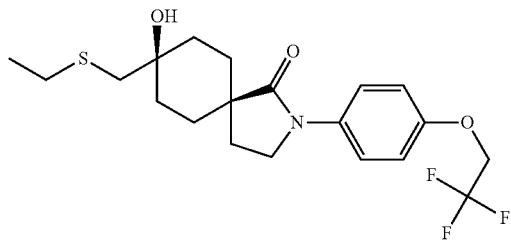

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and ethanethiol. MS (m/e): 418.3 [MH⁺].

Example 262

(5α,8α)-8-(3-Fluoro-phenoxymethyl)-8-hydroxy-2-[4-(2,2,2-trifluoro-ethoxy)-phenyl]-2-aza-spiro[4.5]decan-1-one

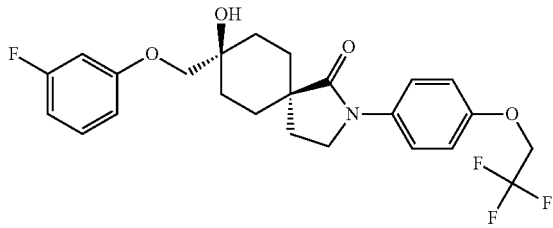 [SMILES: O=C1N(c2ccc(OCC(F)(F)F)cc2)CC[C@]12CC[C@@](O)(COc1cccc(F)c1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 3-fluoro-phenol. MS (m/e): 468.2 [MH⁺].

Example 263

(5α,8α)-8-(4-Fluoro-phenoxymethyl)-8-hydroxy-2-[4-(2,2,2-trifluoro-ethoxy)-phenyl]-2-aza-spiro[4.5]decan-1-one

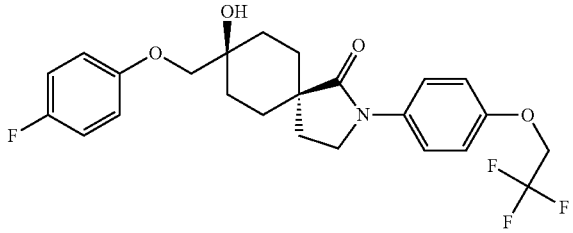 [SMILES: O=C1N(c2ccc(OCC(F)(F)F)cc2)CC[C@]12CC[C@@](O)(COc1ccc(F)cc1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 3-fluoro-phenol. MS (m/e): 468.2 [MH⁺].

Example 264

(5α,8β)-8-(2,2-Difluoro-ethoxymethyl)-2-(4-ethyl-phenyl)-8-hydroxy-2-aza-spiro[4.5]decan-1-one

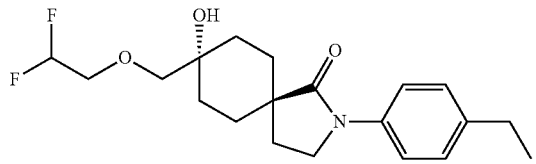 [SMILES: CCc1ccc(N2CC[C@]3(CC[C@](O)(COCC(F)F)CC3)C2=O)cc1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and 2,2-Difluoro-ethanol. MS (m/e): 368.3 [MH⁺].

Example 265

(5α,8α)-8-(2,2-Difluoro-ethoxymethyl)-2-(4-ethyl-phenyl)-8-hydroxy-2-aza-spiro[4.5]decan-1-one

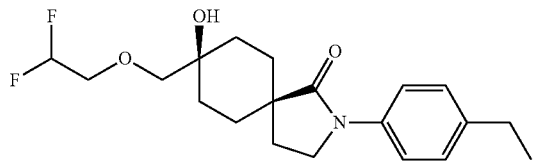 [SMILES: CCc1ccc(N2CC[C@]3(CC[C@@](O)(COCC(F)F)CC3)C2=O)cc1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-ethyl-phenyl)-1-oxa-8-aza-dispiro[2.2.4.2]dodecan-7-one and 2,2-Difluoro-ethanol. MS (m/e): 368.3 [MH⁺].

Example 266

(5α,8β)-8-Hydroxy-8-propoxymethyl-2-[6-(2,2,2-trifluoro-ethoxy)-pyridin-3-yl]-2-aza-spiro[4.5]decan-1-one

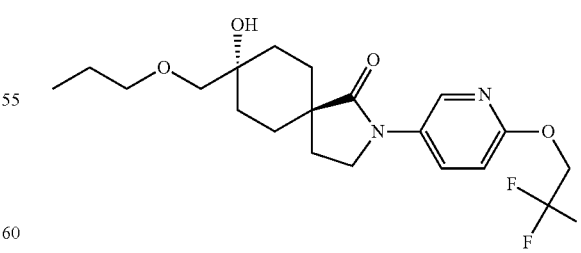

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-(2,2,2-trifluoro-ethoxy)-pyridin-3-yl]-1-oxa-8-aza-dispiro[2.2.4.2]dodecan-7-one and propanol. MS (m/e): 417.3 [MH⁺].

Example 267

(5α,8α)-8-Hydroxy-8-propoxymethyl-2-[6-(2,2,2-trifluoro-ethoxy)-pyridin-3-yl]-2-aza-spiro[4.5]decan-1-one

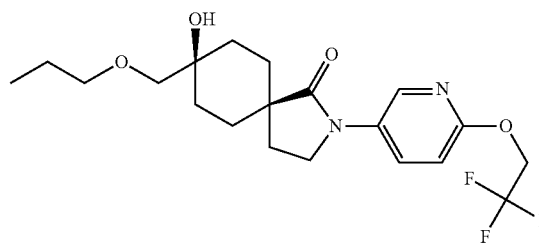

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-(2,2,2-trifluoroethoxy)-pyridin-3-yl]-1-oxa-8-aza-dispiro[2.2.4.2]dodecan-7-one and propanol. MS (m/e): 417.3 [MH+].

Example 268

(5α,8α)-8-Hydroxy-8-propoxymethyl-2-[6-((S)-2,2,2-trifluoro-1-methyl-ethoxy)-pyridin-3-yl]-2-aza-spiro[4.5]decan-1-one

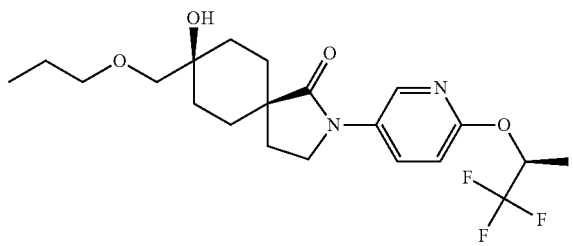 [SMILES: CCCOC[C@]1(O)CC[C@]2(CCN(c3ccc(O[C@@H](C)C(F)(F)F)nc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and propanol. MS (m/e): 431.3 [MH+].

Example 269

(5α,8α)-8-Hydroxy-8-propoxymethyl-2-[4-((S)-2,2,2-trifluoro-1-methyl-ethoxy)-phenyl]-2-aza-spiro[4.5]decan-1-one

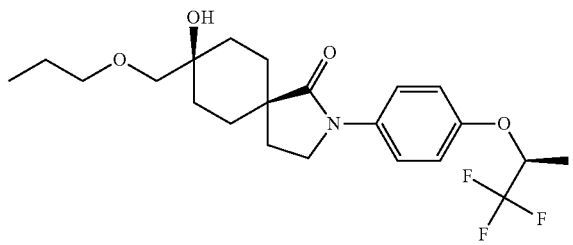 [SMILES: CCCOC[C@]1(O)CC[C@]2(CCN(c3ccc(O[C@@H](C)C(F)(F)F)cc3)C2=O)CC1]

In analogy to the procedure described for the synthesis of (5α,8α)-2-(4-Cyclopropyl-phenyl)-8-hydroxy-8-methoxymethyl-2-aza-spiro[4.5]decan-1-one (example 223, step 4) the title compound was prepared from 8-[4-((S)-2,2,2-Trifluoro-1-methyl-ethoxy)-phenyl]-1-oxa-8-aza-dispiro[2.2.4.2]dodecan-7-one and propanol. MS (m/e): 430.3 [MH+].

Example 270

(5α,8α)-8-Hydroxy-8-propoxymethyl-2-[4-((R)-2,2,2-trifluoro-1-methyl-ethoxy)-phenyl]-2-aza-spiro[4.5]decan-1-one

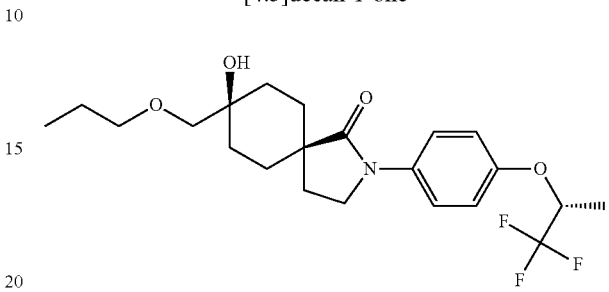

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and propanol. MS (m/e): 430.3 [MH+].

Example 271

(5α,8α)-2-(4-Cyclopropyl-phenyl)-8-ethoxymethyl-8-hydroxy-2-aza-spiro[4.5]decan-1-one

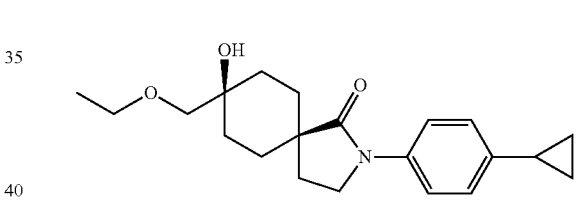

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-cyclopropyl-phenyl)-1-oxa-8-aza-dispiro[2.2.4.2]dodecan-7-one and ethanol. MS (m/e): 344.3 [MH+].

Example 272

(5α,8α)-2-(4-Cyclopropyl-phenyl)-8-hydroxy-8-propoxymethyl-2-aza-spiro[4.5]decan-1-one

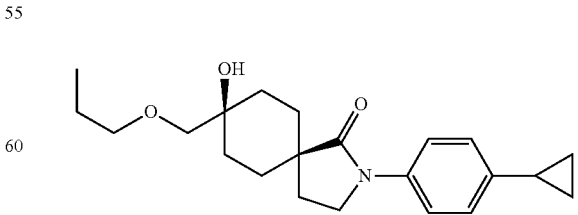

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-cyclopropyl-phenyl)-1-oxa-8-aza-dispiro[2.2.4.2]dodecan-7-one and propanol. MS (m/e): 358.3 [MH+].

Example 273

(5α,8α)-8-[(Cyclopentylmethoxy)methyl]-8-hydroxy-2-[4-(2,2,2-trifluoro-ethoxy)-phenyl]-2-aza-spiro[4.5]decan-1-one

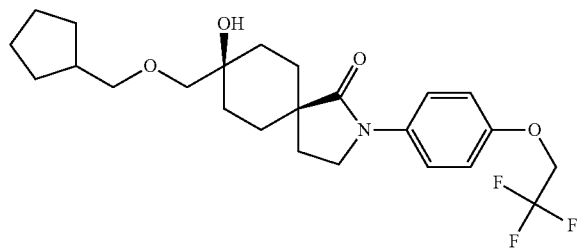 [SMILES: O=C1N(c2ccc(OCC(F)(F)F)cc2)CC[C@]12CC[C@@](O)(COCC1CCCC1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and cyclopentyl-methanol. MS (m/e): 456.3 [MH+].

Example 274

(5α,8α)-8-(2,2-Dimethyl-propoxymethyl)-8-hydroxy-2-[4-(2,2,2-trifluoro-ethoxy)-phenyl]-2-aza-spiro[4.5]decan-1-one

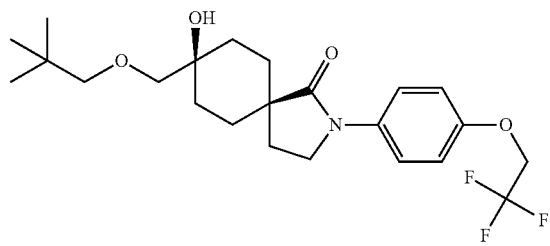 [SMILES: CC(C)(C)COC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 2,2-dimethyl-propan-1-ol. MS (m/e): 444.4 [MH+].

Example 275

(5α,8α)-8-Ethanesulfonylmethyl-8-hydroxy-2-[4-(2,2,2-trifluoro-ethoxy)-phenyl]-2-aza-spiro[4.5]decan-1-one

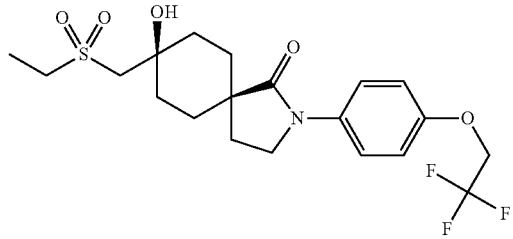 [SMILES: CCS(=O)(=O)C[C@]1(O)CC[C@]2(CCN(c3ccc(OCC(F)(F)F)cc3)C2=O)CC1]

A mixture of 0.1 g (0.24 mmol) (5α,8α)-8-ethylsulfanylmethyl-8-hydroxy-2-[4-(2,2,2-trifluoro-ethoxy)-phenyl]-2-aza-spiro[4.5]decan-1-one (obtained in example 261) and 0.1 g (0.6 mmol) m-chloroperbenzoic acid in 3 mL DCM was stirred for 45 min at room temperature. NaHCO₃ aq. was added and the mixture was extracted with DCM and the combined organic fraction were treated with silica and MgSO₄, filtered and evaporated. The residue was purified by preparative HPLC on reversed phase eluting with a gradient formed from acetonitrile, water and NEt₃. The product containing fractions were evaporated to yield 32.9 mg (30%) of the title compound. MS (m/e): 450.3 [MH+].

Example 276

(5α,8α)-8-Hydroxy-8-isopropoxymethyl-2-[4-(2,2,2-trifluoro-ethoxy)-phenyl]-2-aza-spiro[4.5]decan-1-one

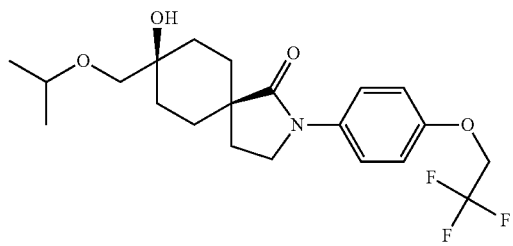 [SMILES: CC(C)OC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and isopropanol. MS (m/e): 416.1 [MH+].

Example 277

(5α,8α)-8-Hydroxy-2-[4-(2,2,2-trifluoro-ethoxy)-phenyl]-8-(3,3,3-trifluoro-propoxymethyl)-2-aza-spiro[4.5]decan-1-one

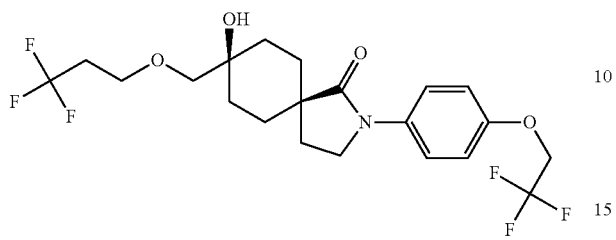

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 3,3,3-trifluoro-propan-1-ol. MS (m/e): 470.1 [MH$^+$].

Example 278

(5α,8β)-8-Hydroxy-8-(pyridin-2-yloxymethyl)-2-[4-(2,2,2-trifluoro-ethoxy)-phenyl]-2-aza-spiro[4.5]decan-1-one

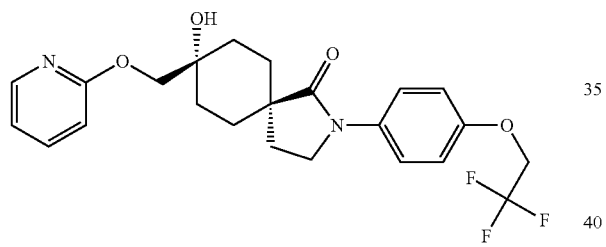

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and pyridin-2-ol. MS (m/e): 451.2 [MH$^+$].

Example 279

(5α,8α)-8-Hydroxy-8-(2,2,2-trifluoro-ethoxymethyl)-2-[6-(2,2,2-trifluoro-ethoxy)-pyridin-3-yl]-2-aza-spiro[4.5]decan-1-one

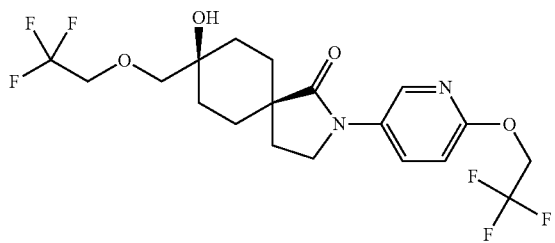 [SMILES: O=C1N(c2ccc(OCC(F)(F)F)nc2)CC[C@]12CC[C@@](O)(COCC(F)(F)F)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-(2,2,2-trifluoro-ethoxy)-pyridin-3-yl]-1-oxa-8-aza-dispiro[2.2.4.2]dodecan-7-one and 2,2,2-trifluoro-ethanol. MS (m/e): 457.3 [MH$^+$].

Example 280

(5α,8β)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one

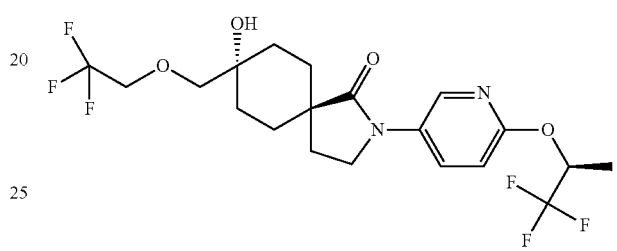

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and 2,2,2-trifluoro-ethanol. MS (m/e): 471.3 [MH$^+$].

Example 281

(5α,8α)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one

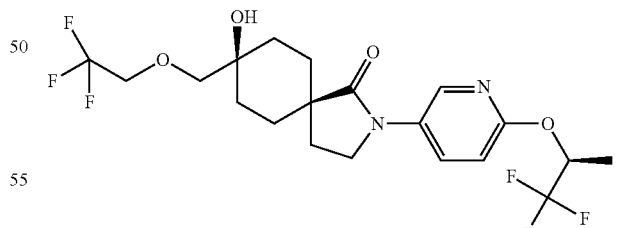

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and 2,2,2-trifluoro-ethanol. MS (m/e): 471.3 [MH$^+$].

Example 282

(5α,8β)-8-Hydroxy-8-(2,2,2-trifluoro-ethoxymethyl)-2-[4-((S)-2,2,2-trifluoro-1-methyl-ethoxy)-phenyl]-2-aza-spiro[4.5]decan-1-one

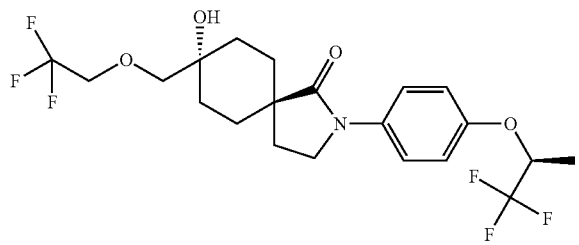 [SMILES: C[C@H](Oc1ccc(N2CC[C@]3(CC[C@](O)(COCC(F)(F)F)CC3)C2=O)cc1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and 2,2,2-trifluoro-ethanol. MS (m/e): 470.3 [MH+].

Example 283

(5α,8α)-8-Hydroxy-8-(2,2,2-trifluoro-ethoxymethyl)-2-[4-((S)-2,2,2-trifluoro-1-methyl-ethoxy)-phenyl]-2-aza-spiro[4.5]decan-1-one

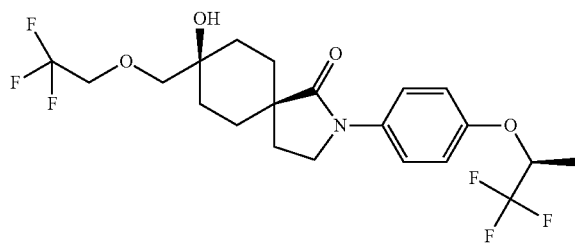 [SMILES: C[C@H](Oc1ccc(N2CC[C@]3(CC[C@@](O)(COCC(F)(F)F)CC3)C2=O)cc1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and 2,2,2-trifluoro-ethanol. MS (m/e): 470.3 [MH+].

Example 284

(5α,8β)-8-Hydroxy-8-(2,2,2-trifluoro-ethoxymethyl)-2-[4-((R)-2,2,2-trifluoro-1-methyl-ethoxy)-phenyl]-2-aza-spiro[4.5]decan-1-one

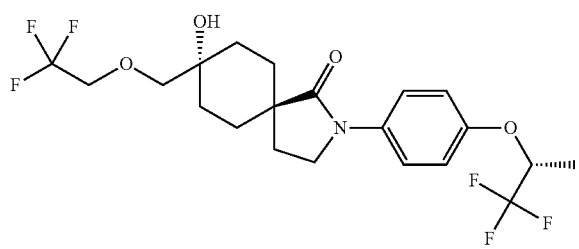 [SMILES: C[C@@H](Oc1ccc(N2CC[C@]3(CC[C@](O)(COCC(F)(F)F)CC3)C2=O)cc1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and 2,2,2-trifluoro-ethanol. MS (m/e): 470.3 [MH+].

Example 285

(5α,8α)-8-Hydroxy-8-(2,2,2-trifluoro-ethoxymethyl)-2-[4-((R)-2,2,2-trifluoro-1-methyl-ethoxy)-phenyl]-2-aza-spiro[4.5]decan-1-one

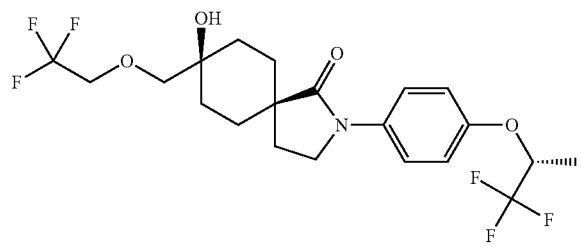 [SMILES: C[C@@H](Oc1ccc(N2CC[C@]3(CC[C@@](O)(COCC(F)(F)F)CC3)C2=O)cc1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and 2,2,2-trifluoro-ethanol. MS (m/e): 470.3 [MH+].

Example 286

(5α,8β)-8-Hydroxy-8-(2,2,2-trifluoro-ethoxymethyl)-2-[4-(2,2,2-trifluoro-ethyl)-phenyl]-2-aza-spiro[4.5]decan-1-one

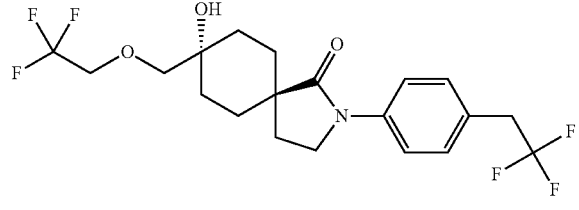

Step 1: 8-Methylene-2-[4-(2,2,2-trifluoro-ethyl)-phenyl]-2-aza-spiro[4.5]decan-1-one

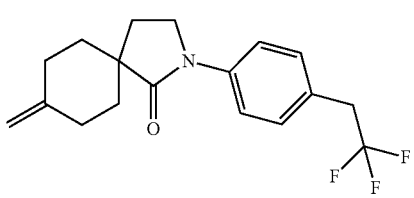 [SMILES: C=C1CCC2(CC1)CCN(c1ccc(CC(F)(F)F)cc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 4-(2,2,2-trifluoro-ethyl)-phenylamine. MS (m/e): 324.2 [MH+].

Step 2: 8-[4-(2,2,2-Trifluoro-ethyl)-phenyl]-1-oxa-8-aza-dispiro[2.2.4.2]dodecan-7-one

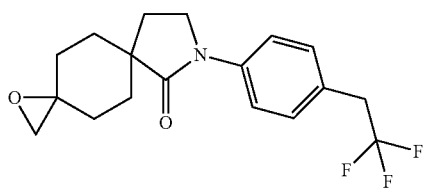 [SMILES: O=C1N(c2ccc(CC(F)(F)F)cc2)CCC12CCC1(CC2)CO1]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 8-methylene-2-[4-(2,2,2-trifluoro-ethyl)-phenyl]-2-aza-spiro[4.5]decan-1-one and m-chloroperbenzoic acid. MS (m/e): 340.2 [MH+].

Step 3: (5α,8β)-8-Hydroxy-8-(2,2,2-trifluoro-ethoxymethyl)-2-[4-(2,2,2-trifluoro-ethyl)-phenyl]-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethyl)-phenyl]-1-oxa-8-aza-dispiro[2.2.4.2]dodecan-7-one and 2,2,2-trifluoro-ethanol. MS (m/e): 440.2 [MH+].

Example 287

(5α,8α)-8-Hydroxy-8-(2,2,2-trifluoro-ethoxymethyl)-2-[4-(2,2,2-trifluoro-ethyl)-phenyl]-2-aza-spiro[4.5]decan-1-one

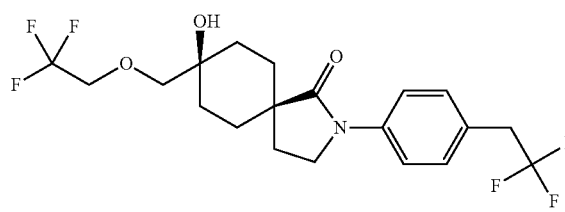

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethyl)-phenyl]-1-oxa-8-aza-dispiro[2.2.4.2]dodecan-7-one and 2,2,2-trifluoro-ethanol. MS (m/e): 440.2 [MH+].

Example 288

(5α,8β)-2-(4-Cyclopropyl-phenyl)-8-hydroxy-8-(2,2,2-trifluoro-ethoxymethyl)-2-aza-spiro[4.5]decan-1-one

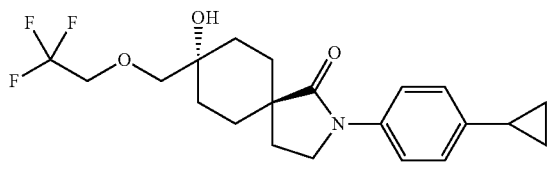 [SMILES: O=C1N(c2ccc(C3CC3)cc2)CC[C@]12CC[C@](O)(COCC(F)(F)F)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-cyclopropyl-phenyl)-1-oxa-8-aza-dispiro[2.2.4.2]dodecan-7-one and 2,2,2-trifluoro-ethanol. MS (m/e): 398.3 [MH+].

Example 289

(5α,8α)-2-(4-Cyclopropyl-phenyl)-8-hydroxy-8-(2,2,2-trifluoro-ethoxymethyl)-2-aza-spiro[4.5]decan-1-one

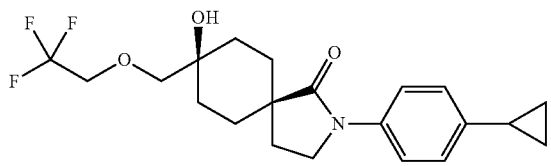 [SMILES: O=C1N(c2ccc(C3CC3)cc2)CC[C@]12CC[C@@](O)(COCC(F)(F)F)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-cyclopropyl-phenyl)-1-oxa-8-aza-dispiro[2.2.4.2]dodecan-7-one and 2,2,2-trifluoro-ethanol. MS (m/e): 398.3 [MH+].

Example 290

(5α,8α)-8-(2-Cyclopropyl-ethoxymethyl)-8-hydroxy-2-[4-(2,2,2-trifluoro-ethoxy)-phenyl]-2-aza-spiro[4.5]decan-1-one

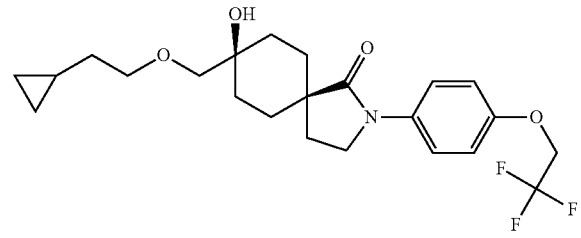 [SMILES: O=C1N(c2ccc(OCC(F)(F)F)cc2)CC[C@]12CC[C@@](O)(COCCC1CC1)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoroethoxy)-phenyl]-1-oxa-8-aza-dispiro[2.2.4.2]dodecan-7-one and 2-Cyclopropyl-ethanol. MS (m/e): 442.3 [MH⁺].

Example 291

(5α,8α)-8-Hydroxy-8-(3-methyl-butoxymethyl)-2-[4-(2,2,2-trifluoro-ethoxy)-phenyl]-2-aza-spiro[4.5]decan-1-one

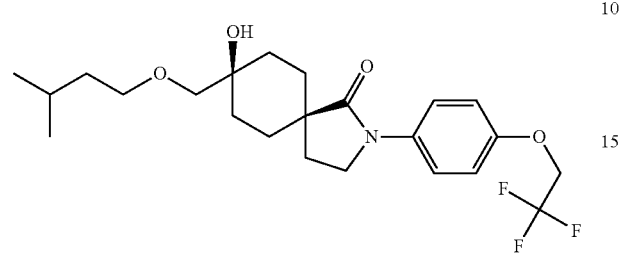

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 3-Methyl-butan-1-ol. MS (m/e): 444.3 [MH⁺].

Example 292

(5α,8α)-8-Hydroxy-2-[4-(2,2,2-trifluoro-ethoxy)-phenyl]-8-(2,2,2-trifluoro-1-methyl-ethoxymethyl)-2-aza-spiro[4.5]decan-1-one

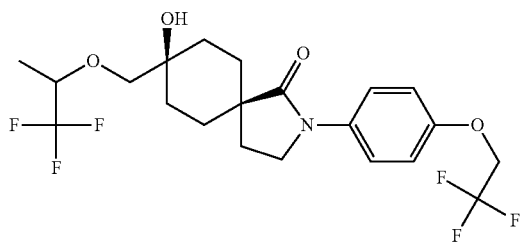 [SMILES: CC(OC[C@]1(O)CC[C@]2(CCN(c3ccc(OCC(F)(F)F)cc3)C2=O)CC1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and 1,1,1-trifluoro-propan-2-ol. MS (m/e): 470.3 [MH⁺].

Example 293

(5α,8α)-8-Hydroxy-8-methylsulfanylmethyl-2-[4-(2,2,2-trifluoro-ethoxy)-phenyl]-2-aza-spiro[4.5]decan-1-one

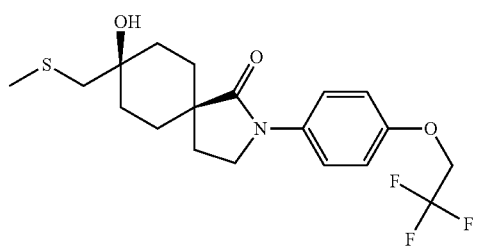 [SMILES: CSC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and methanethiol. MS (m/e): 404.4 [MH⁺].

Example 294

(5α,8α)-8-Hydroxy-8-propylsulfanylmethyl-2-[4-(2,2,2-trifluoro-ethoxy)-phenyl]-2-aza-spiro[4.5]decan-1-one

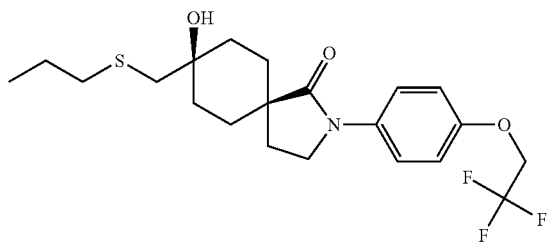

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethoxy)-phenyl]-1-oxa-8-aza-dispiro[2.2.4.2]dodecan-7-one and propanethiol. MS (m/e): 432.3 [MH⁺].

Example 295

(5α,8α)-8-(2,2-Difluoro-ethoxymethyl)-8-hydroxy-2-[6-(2,2,2-trifluoro-ethoxy)-pyridin-3-yl]-2-aza-spiro[4.5]decan-1-one

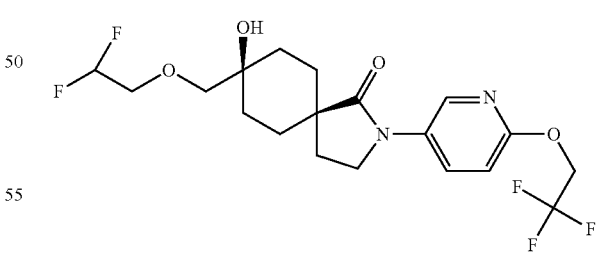

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-(2,2,2-trifluoro-ethoxy)-pyridin-3-yl]-1-oxa-8-aza-dispiro[2.2.4.2]dodecan-7-one and 2,2-difluoro-ethanol. MS (m/e): 439.3 [MH⁺].

Example 296

(5α,8β)-8-(2,2-Difluoro-ethoxymethyl)-8-hydroxy-2-[6-((S)-2,2,2-trifluoro-1-methyl-ethoxy)-pyridin-3-yl]-2-aza-spiro[4.5]decan-1-one

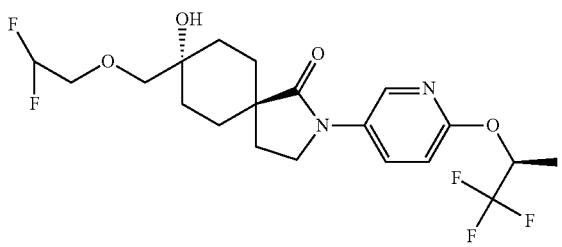 [SMILES: C[C@H](Oc1ccc(N2CC[C@]3(CC[C@](O)(COCC(F)F)CC3)C2=O)cn1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and 2,2-difluoro-ethanol. MS (m/e): 453.3 [MH+].

Example 297

(5α,8α)-8-(2,2-Difluoro-ethoxymethyl)-8-hydroxy-2-[6-((S)-2,2,2-trifluoro-1-methyl-ethoxy)-pyridin-3-yl]-2-aza-spiro[4.5]decan-1-one

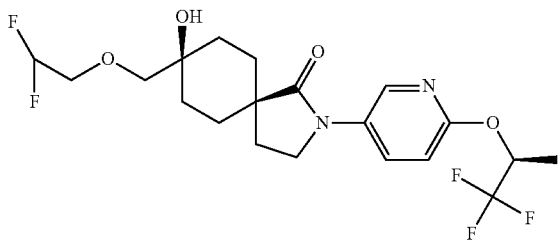 [SMILES: C[C@H](Oc1ccc(N2CC[C@]3(CC[C@@](O)(COCC(F)F)CC3)C2=O)cn1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and 2,2-Difluoro-ethanol. MS (m/e): 453.3 [MH+].

Example 298

(5α,8β)-8-(2,2-Difluoro-ethoxymethyl)-8-hydroxy-2-[4-((S)-2,2,2-trifluoro-1-methyl-ethoxy)-phenyl]-2-aza-spiro[4.5]decan-1-one

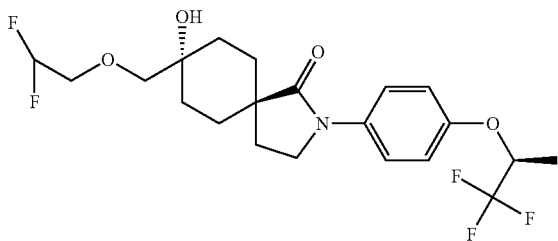 [SMILES: C[C@H](Oc1ccc(N2CC[C@]3(CC[C@](O)(COCC(F)F)CC3)C2=O)cc1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and 2,2-difluoro-ethanol. MS (m/e): 452.3 [MH+].

Example 299

(5α,8α)-8-(2,2-Difluoro-ethoxymethyl)-8-hydroxy-2-[4-((S)-2,2,2-trifluoro-1-methyl-ethoxy)-phenyl]-2-aza-spiro[4.5]decan-1-one

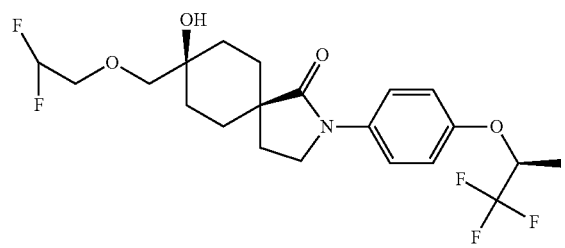 [SMILES: C[C@H](Oc1ccc(N2CC[C@]3(CC[C@@](O)(COCC(F)F)CC3)C2=O)cc1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and 2,2-difluoro-ethanol. MS (m/e): 452.3 [MH+].

Example 300

(5α,8β)-8-(2,2-Difluoro-ethoxymethyl)-8-hydroxy-2-[4-((R)-2,2,2-trifluoro-1-methyl-ethoxy)-phenyl]-2-aza-spiro[4.5]decan-1-one

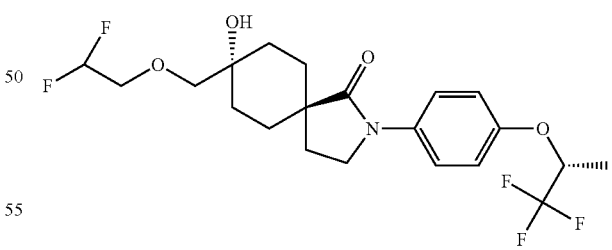

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and 2,2-difluoro-ethanol. MS (m/e): 452.3 [MH+].

Example 301

(5α,8α)-8-(2,2-Difluoro-ethoxymethyl)-8-hydroxy-2-[4-((R)-2,2,2-trifluoro-1-methyl-ethoxy)-phenyl]-2-aza-spiro[4.5]decan-1-one

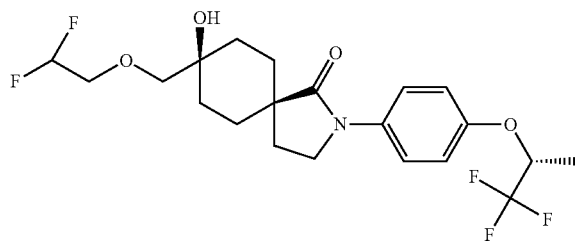 [SMILES: C[C@@H](Oc1ccc(N2CC[C@]3(CC[C@@](O)(COCC(F)F)CC3)C2=O)cc1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and 2,2-difluoro-ethanol. MS (m/e): 452.3 [MH⁺].

Example 302

(5α,8β)-8-(2,2-Difluoro-ethoxymethyl)-8-hydroxy-2-[4-(2,2,2-trifluoro-ethyl)-phenyl]-2-aza-spiro[4.5]decan-1-one

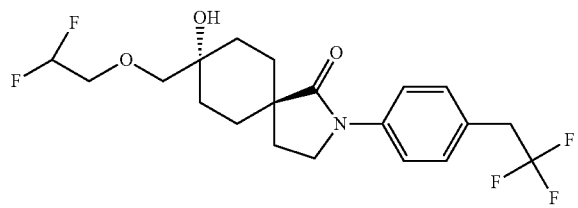 [SMILES: O=C1N(c2ccc(CC(F)(F)F)cc2)CC[C@]12CC[C@](O)(COCC(F)F)CC2]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethyl)-phenyl]-1-oxa-8-aza-dispiro[2.2.4.2]dodecan-7-one and 2,2-difluoro-ethanol. MS (m/e): 422.3 [MH⁺].

Example 303

(5α,8α)-8-(2,2-Difluoro-ethoxymethyl)-8-hydroxy-2-[4-(2,2,2-trifluoro-ethyl)-phenyl]-2-aza-spiro[4.5]decan-1-one

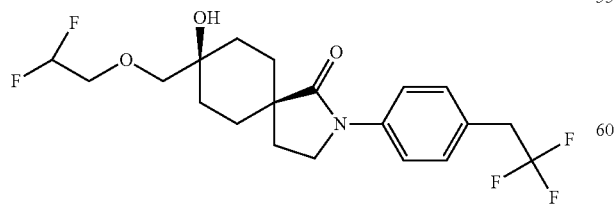

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethyl)-phenyl]-1-oxa-8-aza-dispiro[2.2.4.2]dodecan-7-one and 2,2-difluoro-ethanol. MS (m/e): 422.3 [MH⁺].

Example 304

(5α,8α)-8-Hydroxy-8-methanesulfonylmethyl-2-[4-(2,2,2-trifluoro-ethoxy)-phenyl]-2-aza-spiro[4.5]decan-1-one

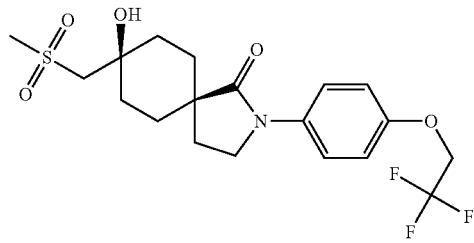 [SMILES: CS(=O)(=O)C[C@]1(O)CC[C@]2(CCN(c3ccc(OCC(F)(F)F)cc3)C2=O)CC1]

In analogy to the procedure described for the synthesis of (5α,8α)-8-ethanesulfonylmethyl-8-hydroxy-2-[4-(2,2,2-trifluoro-ethoxy)-phenyl]-2-aza-spiro[4.5]decan-1-one (example 275) the title compound was prepared from (5α,8α)-8-hydroxy-8-methylsulfanylmethyl-2-[4-(2,2,2-trifluoro-ethoxy)-phenyl]-2-aza-spiro[4.5]decan-1-one. MS (m/e): 436.2 [MH⁺].

Example 305

(5α,8α)-8-Hydroxy-8-(propane-1-sulfonylmethyl)-2-[4-(2,2,2-trifluoro-ethoxy)-phenyl]-2-aza-spiro[4.5]decan-1-one

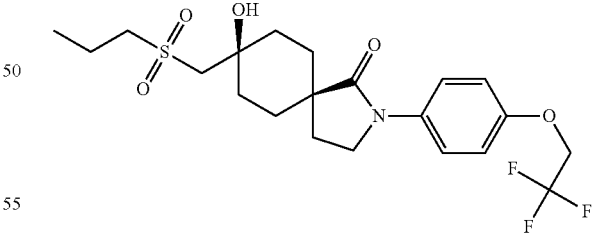

In analogy to the procedure described for the synthesis of (5α,8α)-8-ethanesulfonylmethyl-8-hydroxy-2-[4-(2,2,2-trifluoro-ethoxy)-phenyl]-2-aza-spiro[4.5]decan-1-one (example 275) the title compound was prepared from (5α,8α)-8-hydroxy-8-propylsulfanylmethyl-2-[4-(2,2,2-trifluoro-ethoxy)-phenyl]-2-aza-spiro[4.5]decan-1-one. MS (m/e): 464.2 [MH⁺].

Example 306

(5α,8α)-8-Hydroxy-8-isopropylsulfanylmethyl-2-[4-(2,2,2-trifluoro-ethoxy)-phenyl]-2-aza-spiro[4.5]decan-1-one

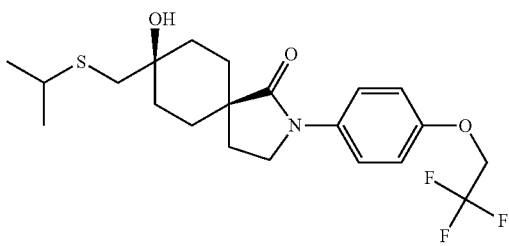

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethyl)-phenyl]-1-oxa-8-aza-dispiro[2.2.4.2]dodecan-7-one and propane-2-thiol. MS (m/e): 432.2 [MH$^+$].

Example 307

(5α,8β)-8-Hydroxy-8-isopropoxymethyl-2-[4-((S)-2,2,2-trifluoro-1-methyl-ethoxy)-phenyl]-2-aza-spiro[4.5]decan-1-one

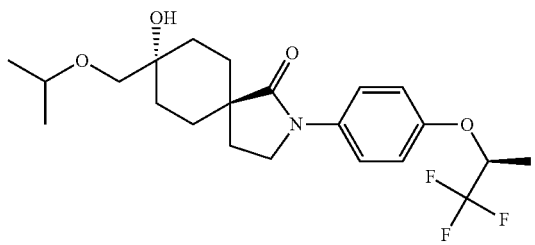 [SMILES: CC(C)OC[C@]1(O)CC[C@@]2(CCN(c3ccc(O[C@@H](C)C(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and propan-2-ol. MS (m/e): 430.3 [MH$^+$].

Example 308

(5α,8α)-8-Hydroxy-8-isopropoxymethyl-2-[4-((S)-2,2,2-trifluoro-1-methyl-ethoxy)-phenyl]-2-aza-spiro[4.5]decan-1-one

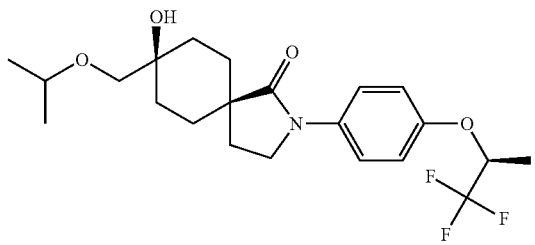 [SMILES: CC(C)OC[C@]1(O)CC[C@]2(CCN(c3ccc(O[C@@H](C)C(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((S)-2,2,2-trifluoro-1-methyl-ethoxy)-phenyl]-1-oxa-8-aza-dispiro[2.2.4.2]dodecan-7-one and propan-2-ol. MS (m/e): 430.3 [MH$^+$].

Example 309

(5α,8α)-8-Hydroxy-8-isopropoxymethyl-2-[6-((S)-2,2,2-trifluoro-1-methyl-ethoxy)-pyridin-3-yl]-2-aza-spiro[4.5]decan-1-one

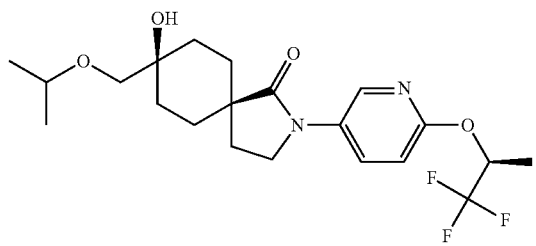 [SMILES: CC(C)OC[C@]1(O)CC[C@]2(CCN(c3ccc(O[C@@H](C)C(F)(F)F)nc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and propan-2-ol. MS (m/e): 431.3 [MH$^+$].

Example 310

(5α,8α)-8-Hydroxy-8-isopropoxymethyl-2-[4-((R)-2,2,2-trifluoro-1-methyl-ethoxy)-phenyl]-2-aza-spiro[4.5]decan-1-one

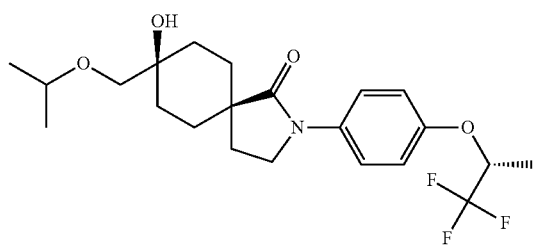 [SMILES: CC(C)OC[C@]1(O)CC[C@]2(CCN(c3ccc(O[C@H](C)C(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-((R)-2,2,2-trifluoro-1-methyl-ethoxy)-phenyl]-1-oxa-8-aza-dispiro[2.2.4.2]dodecan-7-one and propan-2-ol. MS (m/e): 430.3 [MH$^+$].

Example 311

(5α,8α)-8-Ethoxymethyl-8-hydroxy-2-[6-((R)-2,2,2-trifluoro-1-methyl-ethoxy)-pyridin-3-yl]-2-aza-spiro[4.5]decan-1-one

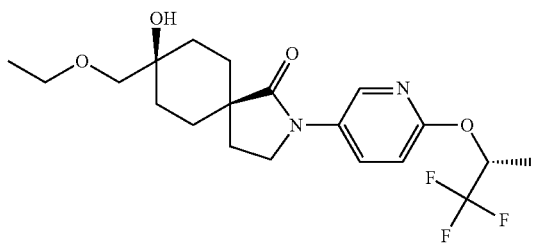 [SMILES: CCOC[C@]1(O)CC[C@]2(CCN(c3ccc(O[C@H](C)C(F)(F)F)nc3)C2=O)CC1]

Step 1: 8-Methylene-2-[6-((R)-2,2,2-trifluoro-1-methyl-ethoxy)-pyridin-3-yl]-2-aza-spiro[4.5]decan-1-one

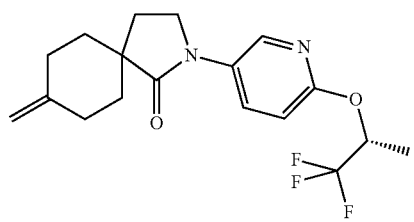 [SMILES: C=C1CCC2(CC1)CCN(c1ccc(O[C@H](C)C(F)(F)F)nc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 6-((R)-2,2,2-trifluoro-1-methyl-ethoxy)-pyridin-3-ylamine. MS (m/e): 355.2 [MH$^+$].

Step 2: 8-[6-((R)-2,2,2-Trifluoro-1-methyl-ethoxy)-pyridin-3-yl]-1-oxa-8-aza-dispiro[2.2.4.2]dodecan-7-one

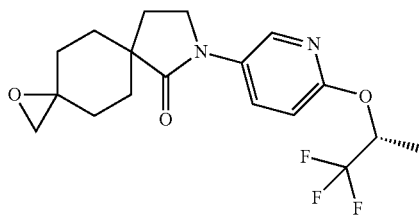 [SMILES: C[C@@H](Oc1ccc(N2CCC3(CCC4(CC3)CO4)C2=O)cn1)C(F)(F)F]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 8-methylene-2-[6-((R)-2,2,2-trifluoro-1-methyl-ethoxy)-pyridin-3-yl]-2-aza-spiro[4.5]decan-1-one and m-chloroperbenzoic acid.

Step 3: (5α,8β)-8-Ethoxymethyl-8-hydroxy-2-[6-((R)-2,2,2-trifluoro-1-methyl-ethoxy)-pyridin-3-yl]-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and ethanol. MS (m/e): 417.3 [MH$^+$].

Example 312

(5α,8α)-8-Hydroxy-8-propoxymethyl-2-[6-((R)-2,2,2-trifluoro-1-methyl-ethoxy)-pyridin-3-yl]-2-aza-spiro[4.5]decan-1-one

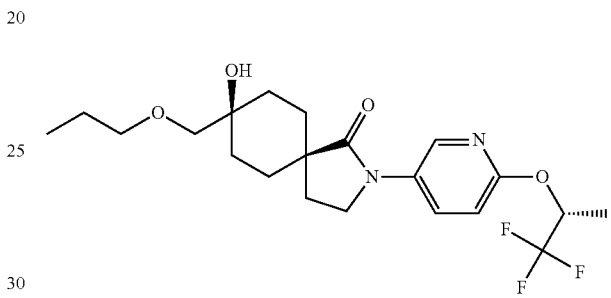

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and propanol. MS (m/e): 431.3 [MH$^+$].

Example 313

(5α,8β)-8-(2,2-Difluoro-ethoxymethyl)-8-hydroxy-2-[6-((R)-2,2,2-trifluoro-1-methyl-ethoxy)-pyridin-3-yl]-2-aza-spiro[4.5]decan-1-one

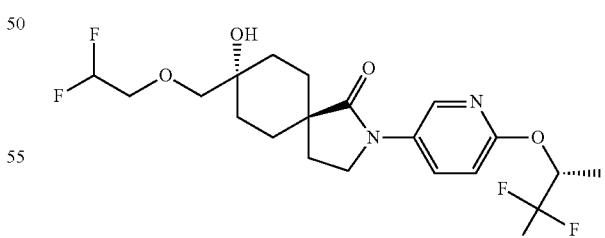

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and 2,2-difluoro-ethanol. MS (m/e): 453.3 [MH$^+$].

Example 314

(5α,8α)-8-(2,2-Difluoro-ethoxymethyl)-8-hydroxy-2-[6-((R)-2,2,2-trifluoro-1-methyl-ethoxy)-pyridin-3-yl]-2-aza-spiro[4.5]decan-1-one

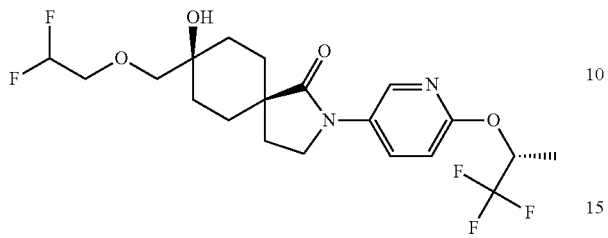

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and 2,2-difluoro-ethanol. MS (m/e): 453.3 [MH$^+$].

Example 315

(5α,8β)-8-Hydroxy-8-isopropoxymethyl-2-[6-((R)-2,2,2-trifluoro-1-methyl-ethoxy)-pyridin-3-yl]-2-aza-spiro[4.5]decan-1-one

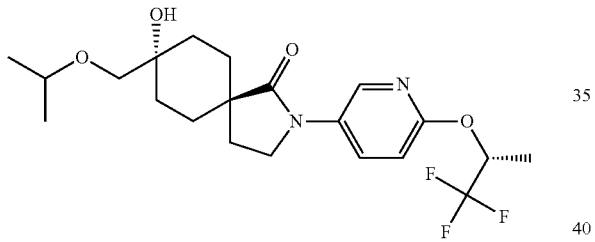

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and propan-2-ol. MS (m/e): 431.3 [MH$^+$].

Example 316

(5α,8α)-8-Hydroxy-8-isopropoxymethyl-2-[6-((R)-2,2,2-trifluoro-1-methyl-ethoxy)-pyridin-3-yl]-2-aza-spiro[4.5]decan-1-one

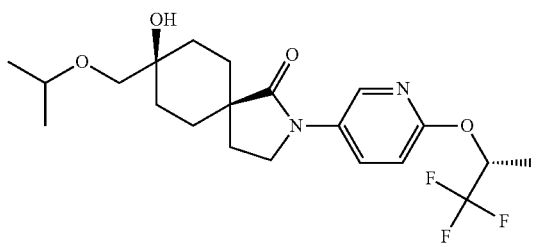 [SMILES: CC(C)OC[C@]1(O)CC[C@]2(CCN(c3ccc(O[C@H](C)C(F)(F)F)nc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and propan-2-ol. MS (m/e): 431.3 [MH$^+$].

Example 317

(5α,8α)-8-Hydroxy-8-(propane-2-sulfinylmethyl)-2-[4-(2,2,2-trifluoro-ethoxy)-phenyl]-2-aza-spiro[4.5]decan-1-one

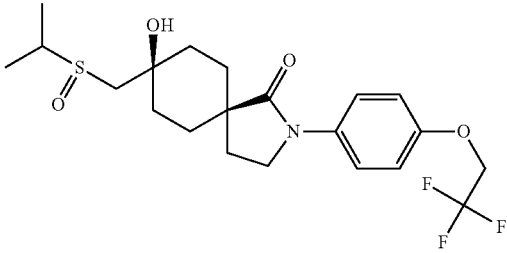 [SMILES: CC(C)S(=O)C[C@]1(O)CC[C@]2(CCN(c3ccc(OCC(F)(F)F)cc3)C2=O)CC1]

A mixture of 41.6 mg (0.096 mmol) (5α,8α)-8-hydroxy-8-isopropylsulfanylmethyl-2-[4-(2,2,2-trifluoro-ethoxy)-phenyl]-2-aza-spiro[4.5]decan-1-one (example 306), 16.6 mg (0.096 mmol) m-chloroperbenzoic acid and 24.3 mg (0.28 mmol) sodium bicarbonate in 10 mL DCM was stirred at room temperature over night. The mixture was filtered over isolute HM-N, washed with ethyl acetate and evaporated. The residue was purified by preparative HPLC on reversed phase eluting with a gradient formed from acetonitrile, water and NEt$_3$. The product containing fractions were evaporated to yield 37.4 mg (87%) of the title compound as white solid. MS (m/e): 448.2 [MH$^+$].

Example 318

(5α,8α)-8-Hydroxy-8-(propane-2-sulfonylmethyl)-2-[4-(2,2,2-trifluoro-ethoxy)-phenyl]-2-aza-spiro[4.5]decan-1-one

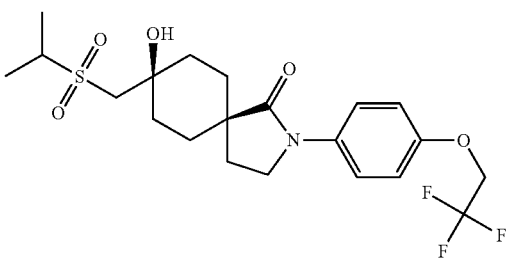 [SMILES: CC(C)S(=O)(=O)C[C@]1(O)CC[C@]2(CCN(c3ccc(OCC(F)(F)F)cc3)C2=O)CC1]

A mixture of 25.3 mg (0.056 mmol) (5α,8α)-8-hydroxy-8-(propane-2-sulfinylmethyl)-2-[4-(2,2,2-trifluoro-ethoxy)-phenyl]-2-aza-spiro[4.5]decan-1-one, 19.5 mg (0.11 mmol) m-chloroperbenzoic acid and 14.2 mg (0.17 mmol) sodium bicarbonate in 10 mL DCM was stirred at room temperature over night. NaHCO$_3$ aq. was added and the organic phase was evaporated. The residue was purified by preparative HPLC on reversed phase eluting with a gradient formed from acetonitrile, water and NEt$_3$. The product containing fractions were evaporated to yield 20 mg (76%) of the title compound as white solid. MS (m/e): 464.3 [MH+].

Example 319

(5α,8α)-8-tert-Butylsulfanylmethyl-8-hydroxy-2-[4-(2,2,2-trifluoro-ethoxy)-phenyl]-2-aza-spiro[4.5]decan-1-one

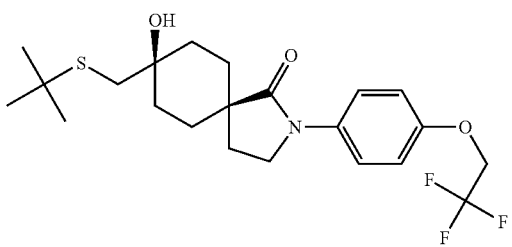 [SMILES: CC(C)(C)SC[C@]1(O)CC[C@]2(CCN(c3ccc(OCC(F)(F)F)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[4-(2,2,2-trifluoro-ethyl)-phenyl]-1-oxa-8-aza-dispiro[2.2.4.2]dodecan-7-one and 2-methyl-propane-2-thiol. MS (m/e): 446.3 [MH+].

Example 320

(5α,8α)-8-Hydroxy-8-isopropylsulfanylmethyl-2-[6-((S)-2,2,2-trifluoro-1-methyl-ethoxy)-pyridin-3-yl]-2-aza-spiro[4.5]decan-1-one

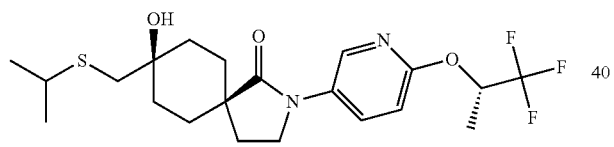

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and propane-2-thiol. MS (m/e): 447.3 [MH+].

Example 321

(5α,8α)-8-Hydroxy-8-isopropylsulfanylmethyl-2-[6-((R)-2,2,2-trifluoro-1-methyl-ethoxy)-pyridin-3-yl]-2-aza-spiro[4.5]decan-1-one

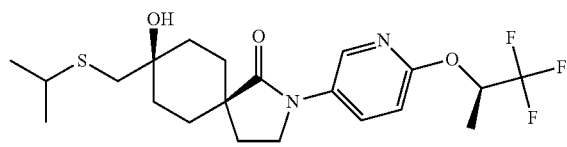 [SMILES: CC(C)SC[C@]1(O)CC[C@]2(CCN(c3ccc(O[C@H](C)C(F)(F)F)nc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and propane-2-thiol. MS (m/e): 447.3 [MH+].

Example 322

(5α,8α)-8-Hydroxy-8-(2-methyl-propane-2-sulfonyl-methyl)-2-[4-(2,2,2-trifluoro-ethoxy)-phenyl]-2-aza-spiro[4.5]decan-1-one

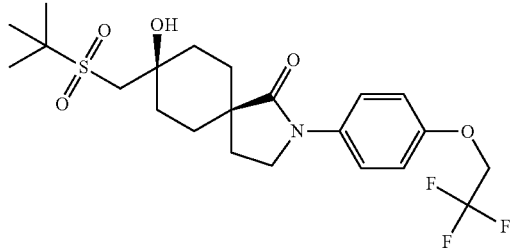 [SMILES: CC(C)(C)S(=O)(=O)C[C@]1(O)CC[C@]2(CCN(c3ccc(OCC(F)(F)F)cc3)C2=O)CC1]

In analogy to the procedure described for the synthesis of (5α,8α)-8-ethanesulfonylmethyl-8-hydroxy-2-[4-(2,2,2-trifluoro-ethoxy)-phenyl]-2-aza-spiro[4.5]decan-1-one (example 275) the title compound was prepared from (5α,8α)-8-tert-butylsulfanylmethyl-8-hydroxy-2-[4-(2,2,2-trifluoro-ethoxy)-phenyl]-2-aza-spiro[4.5]decan-1-one. MS (m/e): 478.2 [MH+].

Example 323

(5α,8α)-8-Hydroxy-8-(propane-2-sulfonylmethyl)-2-[6-((S)-2,2,2-trifluoro-1-methyl-ethoxy)-pyridin-3-yl]-2-aza-spiro[4.5]decan-1-one

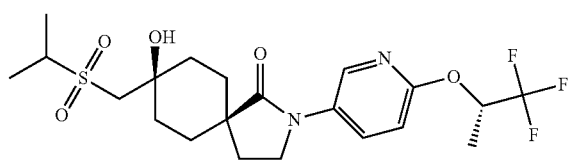 [SMILES: CC(C)S(=O)(=O)C[C@]1(O)CC[C@]2(CCN(c3ccc(O[C@@H](C)C(F)(F)F)nc3)C2=O)CC1]

In analogy to the procedure described for the synthesis of (5α,8α)-8-ethanesulfonylmethyl-8-hydroxy-2-[4-(2,2,2-trifluoro-ethoxy)-phenyl]-2-aza-spiro[4.5]decan-1-one (example 275) the title compound was prepared from (5α,8α)-8-hydroxy-8-isopropylsulfanylmethyl-2-[6-((S)-2,2,2-trifluoro-1-methyl-ethoxy)-pyridin-3-yl]-2-aza-spiro[4.5]decan-1-one. MS (m/e): 479.2 [MH+].

Example 324

(5α,8α)-8-Hydroxy-8-(propane-2-sulfonylmethyl)-2-[6-((R)-2,2,2-trifluoro-1-methyl-ethoxy)-pyridin-3-yl]-2-aza-spiro[4.5]decan-1-one

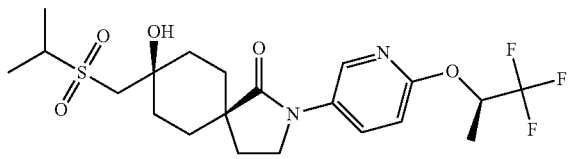 [SMILES: CC(C)S(=O)(=O)C[C@]1(O)CC[C@]2(CCN(c3ccc(O[C@H](C)C(F)(F)F)nc3)C2=O)CC1]

In analogy to the procedure described for the synthesis of (5α,8α)-8-ethanesulfonylmethyl-8-hydroxy-2-[4-(2,2,2-trifluoro-ethoxy)-phenyl]-2-aza-spiro[4.5]decan-1-one (example 275) the title compound was prepared from (5α,8α)-8-hydroxy-8-isopropylsulfanylmethyl-2-[6-((R)-2,2,2-trifluoro-1-methyl-ethoxy)-pyridin-3-yl]-2-aza-spiro[4.5]decan-1-one. MS (m/e): 479.2 [MH+].

Example 325

(5α,8α)-8-Hydroxy-8-(2-methyl-propane-2-sulfonyl-methyl)-2-[6-((S)-2,2,2-trifluoro-1-methyl-ethoxy)pyridin-3-yl]-2-aza-spiro[4.5]decan-1-one

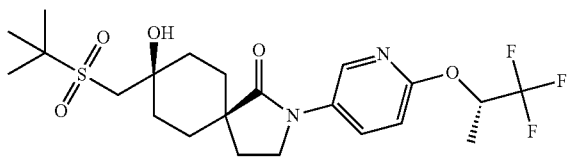 [SMILES: C[C@H](Oc1ccc(N2CC[C@]3(CC[C@@](O)(CS(=O)(=O)C(C)(C)C)CC3)C2=O)cn1)C(F)(F)F]

Step 1: (5α,8α)-8-(tert-butylthiomethyl)-8-hydroxy-2-[6-((S)-2,2,2-trifluoro-1-methyl-ethoxy)-pyridin-3-yl]-2-aza-spiro[4.5]decan-1-one

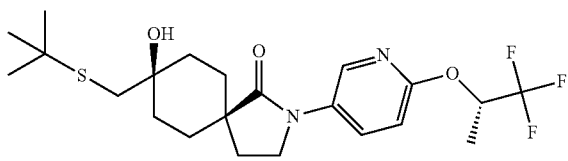 [SMILES: C[C@H](Oc1ccc(N2CC[C@]3(CC[C@@](O)(CSC(C)(C)C)CC3)C2=O)cn1)C(F)(F)F]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and 2-methyl-propane-2-thiol. MS (m/e): 461.3 [MH+].

Step 2: (5α,8α)-8-Hydroxy-8-(2-methyl-propane-2-sulfonylmethyl)-2-[6-((S)-2,2,2-trifluoro-1-methyl-ethoxy)-pyridin-3-yl]-2-aza-spiro[4.5]decan-1-one In analogy to the procedure described for the synthesis of (5α,8α)-8-ethanesulfonylmethyl-8-hydroxy-2-[4-(2,2,2-trifluoro-ethoxy)-phenyl]-2-aza-spiro[4.5]decan-1-one (example 275) the title compound was prepared from (5α,8α)-8-(tert-butylthiomethyl)-8-hydroxy-2-[6-((S)-2,2,2-trifluoro-1-methyl-ethoxy)-pyridin-3-yl]-2-aza-spiro[4.5]decan-1-one. MS (m/e): 493.3 [MH+].

Example 326

(5α,8α)-8-Hydroxy-8-(2-methyl-propane-2-sulfonyl-methyl)-2-[6-((R)-2,2,2-trifluoro-1-methyl-ethoxy)-pyridin-3-yl]-2-aza-spiro[4.5]decan-1-one

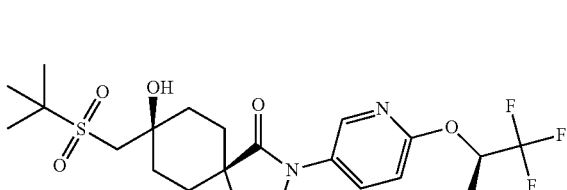

In analogy to the procedure described for the synthesis of (5α,8α)-8-hydroxy-8-(2-methyl-propane-2-sulfonylmethyl)-2-[6-((S)-2,2,2-trifluoro-1-methyl-ethoxy)-pyridin-3-yl]-2-aza-spiro[4.5]decan-1-one (example 325, steps 1 to 2) the title compound was prepared from 8-[6-((R)-2,2,2-trifluoro-1-methyl-ethoxy)-pyridin-3-yl]-1-oxa-8-aza-dispiro[2.2.4.2]dodecan-7-one. MS (m/e): 493.3 [MH+].

Example 327

(5α,8α)-8-Hydroxy-8-(2,2,2-trifluoro-ethoxymethyl)-2-[6-((R)-2,2,2-trifluoro-1-methyl-ethoxy)-pyridin-3-yl]-2-aza-spiro[4.5]decan-1-one

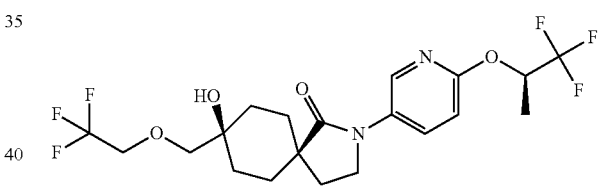

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((R)-2,2,2-trifluoro-1-methyl-ethoxy)-pyridin-3-yl]-1-oxa-8-aza-dispiro[2.2.4.2]dodecan-7-one and 2,2,2-trifluoro-ethanol. MS (m/e): 471.4 [MH+].

Example 328

(5α,8α)-8-(1-Ethyl-propoxymethyl)-8-hydroxy-2-[6-((S)-2,2,2-trifluoro-1-methyl-ethoxy)-pyridin-3-yl]-2-aza-spiro[4.5]decan-1-one

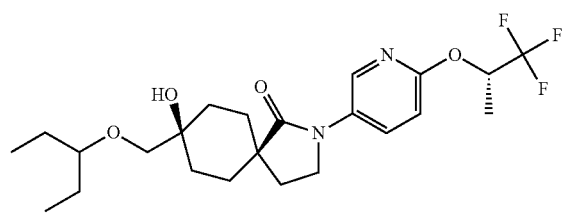 [SMILES: CCC(CC)OC[C@]1(O)CC[C@]2(CCN(c3ccc(O[C@@H](C)C(F)(F)F)nc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-[6-((S)-2,2,2-trifluoro-1-methyl-ethoxy)-pyridin-3-yl]-1-oxa-8-aza-dispiro[2.2.4.2]dodecan-7-one and pentan-3-ol. MS (m/e): 459.4 [MH⁺].

Example 329

(5α,8α)-8-Hydroxy-2-(6-isopropoxy-pyridin-3-yl)-8-methoxymethyl-2-aza-spiro[4.5]decan-1-one

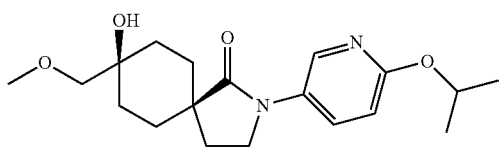 [SMILES: COC[C@]1(O)CC[C@]2(CCN(c3ccc(OC(C)C)nc3)C2=O)CC1]

Step 1: 2-(6-Isopropoxy-pyridin-3-yl)-8-methylene-2-aza-spiro[4.5]decan-1-one

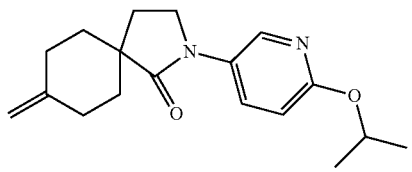 [SMILES: C=C1CCC2(CC1)CCN(c1ccc(OC(C)C)nc1)C2=O]

In analogy to the procedure described for the synthesis of 2-(4-cyclopropyl-phenyl)-8-methylene-2-aza-spiro[4.5]decan-1-one (example 223, step 2) the title compound was prepared from 1-(2-methoxy-ethyl)-4-methylene-cyclohexanecarboxylic acid ethyl ester and 6-isopropoxy-pyridin-3-ylamine. MS (m/e): 301.2 [MH⁺].

Step 2: 8-(6-Isopropoxy-pyridin-3-yl)-1-oxa-8-aza-dispiro[2.2.4.2]dodecan-7-one

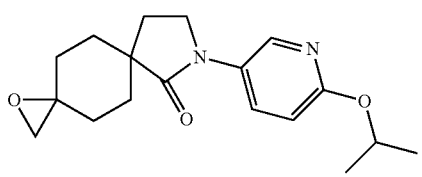 [SMILES: CC(C)Oc1ccc(N2CCC3(CCC4(CC3)CO4)C2=O)cn1]

In analogy to the procedure described for the synthesis of 8-(4-cyclopropyl-phenyl)-1-oxa-8-aza-dispiro[2.2.4.2]dodecan-7-one (example 223, step 3) the title compound was prepared from 2-(6-isopropoxy-pyridin-3-yl)-8-methylene-2-aza-spiro[4.5]decan-1-one and m-chloroperbenzoic acid. MS (m/e): 317.2 [MH⁺].

Step 3: (5α,8α)-8-Hydroxy-2-(6-isopropoxy-pyridin-3-yl)-8-methoxymethyl-2-aza-spiro[4.5]decan-1-one In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(6-isopropoxy-pyridin-3-yl)-1-oxa-8-azadispiro[2.2.4.2]dodecan-7-one and methanol. MS (m/e): 417.3 [MH⁺].

Example 330

(5α,8α)-8-Ethoxymethyl-8-hydroxy-2-(6-isopropoxy-pyridin-3-yl)-2-aza-spiro[4.5]decan-1-one

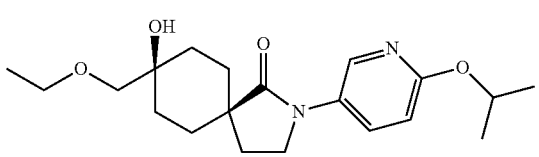 [SMILES: CCOC[C@]1(O)CC[C@]2(CCN(c3ccc(OC(C)C)nc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(6-isopropoxy-pyridin-3-yl)-1-oxa-8-azadispiro[2.2.4.2]dodecan-7-one and ethanol. MS (m/e): 363.2 [MH⁺].

Example 331

(5α,8α)-2-(4-tert-Butyl-phenyl)-8-hydroxy-8-(propane-1-sulfonylmethyl)-2-aza-spiro[4.5]decan-1-one

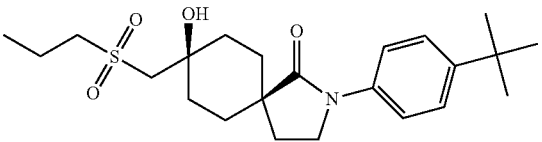 [SMILES: CCCS(=O)(=O)C[C@]1(O)CC[C@]2(CCN(c3ccc(C(C)(C)C)cc3)C2=O)CC1]

Step 1: (3α,6α)-8-(4-tert-Butyl-phenyl)-1-oxa-8-aza-dispiro[2.2.4.2]dodecan-7-one

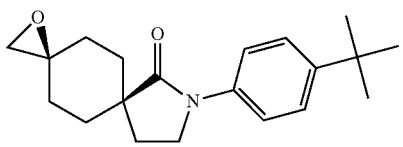 [SMILES: CC(C)(C)c1ccc(N2CC[C@]3(CC[C@]4(CC3)CO4)C2=O)cc1]

A mixture of 510 mg (1.7 mmol) 2-(4-tert-butylphenyl)-2-aza-spiro[4.5]decane-1,8-dione (obtained in example 343, step 2) and 581 mg (2.64 mmol) trimethylsulfoxonium iodide in 7 mL DMSO was treated with 296 mg (2.64 mmol) KOtBu in 7 mL DMSO and stirred for 1 h at room temperature. The mixture was poured on ice and the precipitate collected and washed with water. The residue was dried and purified by flash column chromatography on silica eluting with a gradient formed from ethyl acetate and hexane. The product con- Step 2: 2-(4-tert-Butyl-phenyl)-8-hydroxy-8-propyl-sulfanylmethyl-2-aza-spiro[4.5]decan-1-one

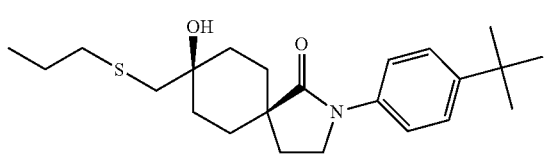 [SMILES: CCCSC[C@]1(O)CC[C@]2(CCN(c3ccc(C(C)(C)C)cc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(4-tert-butyl-phenyl)-1-oxa-8-aza-dispiro[2.2.4.2]dodecan-7-one and propane-1-thiol. MS (m/e): 390.4 [MH$^+$].

Step 3: (5α,8α)-2-(4-tert-Butyl-phenyl)-8-hydroxy-8-(propane-1-sulfonylmethyl)-2-aza-spiro[4.5]decan-1-one In analogy to the procedure described for the synthesis of (5α,8α)-8-hydroxy-8-(2-methyl-propane-2-sulfonylmethyl)-2-[6-((S)-2,2,2-trifluoro-1-methyl-ethoxy)-pyridin-3-yl]-2-aza-spiro[4.5]decan-1-one the title compound was prepared from 2-(4-tert-butyl-phenyl)-8-hydroxy-8-propylsulfanylmethyl-2-aza-spiro[4.5]decan-1-one. MS (m/e): 422.4 [MH$^+$].

Example 332

(5α,8α)-2-(4-tert-Butyl-phenyl)-8-hydroxy-8-(2-methyl-propane-1-sulfonylmethyl)-2-aza-spiro[4.5]decan-1-one

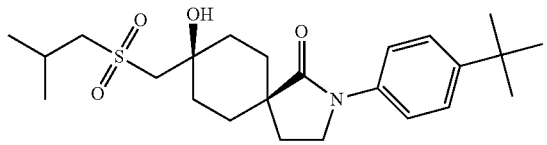 [SMILES: CC(C)CS(=O)(=O)C[C@]1(O)CC[C@]2(CCN(c3ccc(C(C)(C)C)cc3)C2=O)CC1]

In analogy to the procedure described for the synthesis of (5α,8α)-2-(4-tert-butyl-phenyl)-8-hydroxy-8-(propane-1-sulfonylmethyl)-2-aza-spiro[4.5]decan-1-one (example 331) the title compound was prepared from 8-(4-tert-butyl-phenyl)-1-oxa-8-aza-dispiro[2.2.4.2]dodecan-7-one, 2-methyl-propane-1-thiol and subsequent oxidation with m-chloroperbenzoic acid. MS (m/e): 436.4 [MH$^+$].

Example 333

(5α,8α)-2-(4-tert-Butyl-phenyl)-8-hydroxy-8-(propane-2-sulfonylmethyl)-2-aza-spiro[4.5]decan-1-one

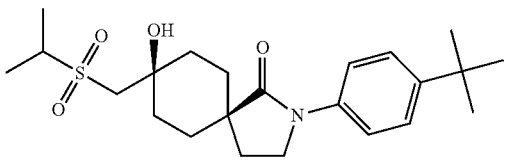 [SMILES: CC(C)S(=O)(=O)C[C@]1(O)CC[C@]2(CCN(c3ccc(C(C)(C)C)cc3)C2=O)CC1]

In analogy to the procedure described for the synthesis of (5α,8α)-2-(4-tert-butyl-phenyl)-8-hydroxy-8-(propane-1-sulfonylmethyl)-2-aza-spiro[4.5]decan-1-one (example 331) the title compound was prepared from 8-(4-tert-butyl-phenyl)-1-oxa-8-aza-dispiro[2.2.4.2]dodecan-7-one, propane-2-thiol and subsequent oxidation with m-chloroperbenzoic acid. MS (m/e): 422.4 [MH$^+$].

Example 334

(5α,8α)-2-(4-tert-Butyl-phenyl)-8-hydroxy-8-(2-methyl-propane-2-sulfonylmethyl)-2-aza-spiro[4.5]decan-1-one

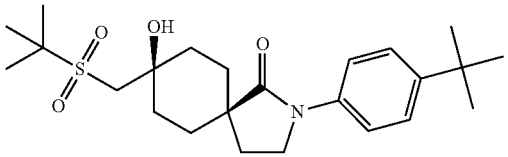 [SMILES: CC(C)(C)c1ccc(N2CC[C@]3(CC[C@@](O)(CS(=O)(=O)C(C)(C)C)CC3)C2=O)cc1]

In analogy to the procedure described for the synthesis of (5α,8α)-2-(4-tert-butyl-phenyl)-8-hydroxy-8-(propane-1-sulfonylmethyl)-2-aza-spiro[4.5]decan-1-one (example 331) the title compound was prepared from 8-(4-tert-butyl-phenyl)-1-oxa-8-aza-dispiro[2.2.4.2]dodecan-7-one, 2-methyl-propane-2-thiol and subsequent oxidation with m-chloroperbenzoic acid. MS (m/e): 436.4 [MH$^+$].

Example 335

(5α,8α)-8-Hydroxy-2-(6-isopropoxy-pyridin-3-yl)-8-(propane-1-sulfonylmethyl)-2-aza-spiro[4.5]decan-1-one

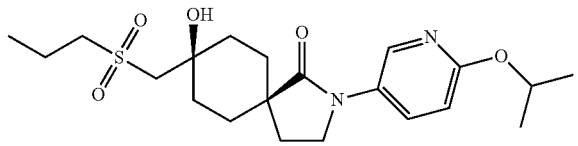 [SMILES: CCCS(=O)(=O)C[C@]1(O)CC[C@]2(CCN(c3ccc(OC(C)C)nc3)C2=O)CC1]

In analogy to the procedure described for the synthesis of (5α,8α)-2-(4-cyclopropyl-phenyl)-8-hydroxy-8-methoxymethyl-2-aza-spiro[4.5]decan-1-one (example 223, step 4) the title compound was prepared from 8-(6-isopropoxy-pyridin-3-yl)-1-oxa-8-azadispiro[2.2.4.2]dodecan-7-one, propane-1- thiol and subsequent oxidation with m-chloroperbenzoic acid. MS (m/e): 425.3 [MH+].

Example 336

(5α,8α)-2-(2,2-Difluoro-benzo[1,3]dioxol-5-yl)-8-hydroxy-8-trifluoromethyl-2-aza-spiro[4.5]decan-1-one

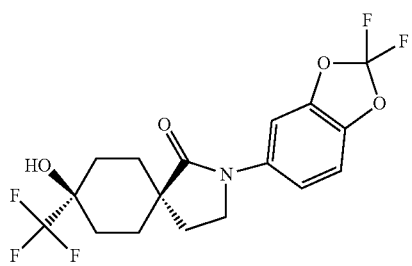 [SMILES: O=C1N(c2ccc3c(c2)OC(F)(F)O3)CC[C@]12CC[C@@](O)(C(F)(F)F)CC2]

Step 1: 10-(2,2-Difluoro-benzo[1,3]dioxol-5-yl)-1,4-dioxa-10-aza-dispiro[4.2.4.2]tetradecan-9-one To a mixture of 1,4-dioxa-10-aza-dispiro[4.2.4.2]tetradecan-9-one (262 mg, 1.24 mmol, obtained in example 133, step 3), potassium carbonate (790 mg, 3.72 mmol) and cuprous iodide (354 mg, 1.86 mmol) was added a solution of 5-bromo-2,2-difluoro-benzo[1,3]dioxole (588 mg, 2.48 mmol) in 5 ml toluene under argon. The solution was then degassed by bubbling argon through the mixture for 2 mins after which N—N'-dimethylethylenediamine (266 uL, 2.48 mmol) was added. The sealed tube was closed and the mixture was heated to 110° C. overnight. The reaction mixture was then cooled to room temperature and filtered through a short pad of Celite® using ethyl acetate to wash the mixture through. The solution was then concentrated in vacuo to give a residue which was purified by flash column chromatography (3:7 ethyl acetate heptane) to give the title compound as white solid (350 mg, 75%). MS (m/e): 368.0 [MH+].

Step 2: 2-(2,2-Difluoro-benzo[1,3]dioxol-5-yl)-2-aza-spiro[4.5]decane-1,8-dione

The title compound was prepared in analogy to example 133 step 5 from 10-(2,2-difluoro-benzo[1,3]dioxol-5-yl)-1,4-dioxa-10-aza-dispiro[4.2.4.2]tetradecan-9-one (described in example 336, step 1) by treatment with 2M HCl. White solid. MS (m/e): 324.2 [MH+].

Step 3: (5α,8α)-2-(2,2-Difluoro-benzo[1,3]dioxol-5-yl)-8-hydroxy-8-trifluoromethyl-2-aza-spiro[4.5]decan-1-one The title compound was prepared in analogy to example 112 from 2-(2,2-difluoro-benzo[1,3]dioxol-5-yl)-2-aza-spiro[4.5]decane-1,8-dione (obtained in Example 336, Step 2) by treatment with (trifluoromethyl)-trimethylsilane and tetrabutylammoniumfluoride. White solid. MS (m/e): 394.0 (MH+).

Example 337

(5α,8α)-2-(2,2-Difluoro-benzo[1,3]dioxol-5-yl)-8-ethyl-8-hydroxy-2-aza-spiro[4.5]decan-1-one

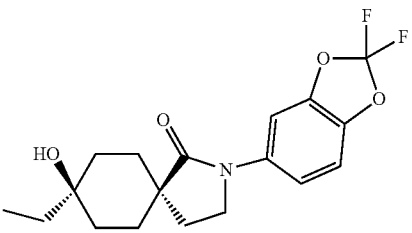 [SMILES: CC[C@]1(O)CC[C@]2(CCN(c3ccc4c(c3)OC(F)(F)O4)C2=O)CC1]

The title compound was prepared in analogy to example 55 from 2-(2,2-difluoro-benzo[1,3]dioxol-5-yl)-2-aza-spiro[4.5]decane-1,8-dione (described in example 336, Step 2) by treatment with ethylmagnesium bromide solution. White solid (54 mg). MS (m/e): 354.2 (MH+).

Example 338

(5α,8α)-8-Acetyl-8-hydroxy-2-[4-(2,2,2-trifluoro-ethoxy)-phenyl]-2-aza-spiro[4.5]decan-1-one

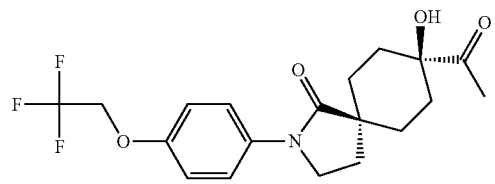 [SMILES: CC(=O)[C@]1(O)CC[C@]2(CCN(c3ccc(OCC(F)(F)F)cc3)C2=O)CC1]

Step 1: (5α,8α)-8-Hydroxy-8-(2-methyl-[1,3]dithian-2-yl)-2-[4-(2,2,2-trifluoro-ethoxy)-phenyl]-2-aza-spiro[4.5]decan-1-one To a solution of 2-methyl-1,3-dithiane (168 uL, 1.37 mmol) in THF (4 mL) at −78° C. was added nBuLi (1.6M, 857 uL, 1.37 mmol) dropwise. The flask was warmed to −10° C., stirred for 2 h, re-cooled to −78° C. and a solution of 2-(4-(2,2,2-trifluoroethoxy)phenyl)-2-aza-spiro[4.5]decane-1,8-dione (390 mg, 1.14 mmol, prepared as described in example 86 step 1) in THF (1 mL) was added dropwise and the reaction mixture was stirred over night at room temperature. The reaction mixture was quenched with sat. NH4Cl(aq) (1 mL) and extracted with EtOAc. The combined organic layers were washed with brine, dried (Na2SO4), filtered and concentrated in vacuo to give a crude residue which was purified by flash column chromatography (heptane/EtOAc) to yield the title compound as a light yellow solid (190 mg, 35%). MS (m/e): 476.2 (MH+).

Step 2: (5α,8α)-8-Acetyl-8-hydroxy-2-[4-(2,2,2-trifluoro-ethoxy)-phenyl]-2-aza-spiro[4.5]decan-1-one To a solution of (5α,8α)-8-hydroxy-8-(2-methyl-1,3-dithian-2-yl)-2-(4-(2,2,2-trifluoroethoxy)phenyl)-2-aza-spiro[4.5]decan-1-one (190 mg, 0.400 mmol) in methanol (4 mL) was added mercury(II)-perchlorate hydrate (362 mg, 0.800 mmol) to give a light yellow suspension. The reaction mixture was stirred for 2 h and then filtered through Celite®. The filtrate was concentrated in vacuo and the crude residue was partitioned between ethyl acetate and water. The organic layers were combined washed with brine, dried ($Na_2SO_4$), filtered and concentrated in vacuo to give a crude residue which was purified by flash column chromatography (0% to 100% EtOAc in heptane) to yield the title compound as a light yellow solid (150 mg, 97%). MS (m/e): 386.4 ($MH^+$).

Example 339

(5α,8α)-8-Hydroxy-8-(1-hydroxy-1-methyl-ethyl)-2-[4-(2,2,2-trifluoro-ethoxy)-phenyl]-2-aza-spiro[4.5]decan-1-one

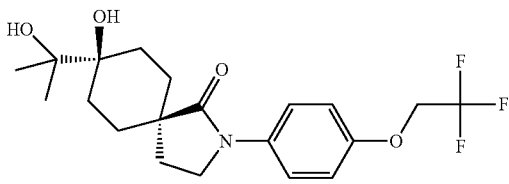 [SMILES: CC(C)(O)[C@]1(O)CC[C@]2(CCN(c3ccc(OCC(F)(F)F)cc3)C2=O)CC1]

To a light yellow suspension of (5α,8α)-8-acetyl-8-hydroxy-2-[4-(2,2,2-trifluoro-ethoxy)-phenyl]-2-aza-spiro[4.5]decan-1-one (91.5 mg, 0.237 mmol, prepared as described in example 338) in diethyl ether (2 mL) at 0° C. was added methyl magnesium iodide (3M, 119 µl, 0.356 mmol) dropwise. The reaction mixture was warmed to room temperature and stirred for 2 h. The reaction mixture was poured into 10 mL sat $NH_4Cl$ and extracted with diethyl ether (4×20 mL). The organic layers were combined washed with brine, dried ($Na_2SO_4$), filtered and concentrated in vacuo to give a crude residue which was purified by flash column chromatography (0% to 80% EtOAc in heptane) to yield the title compound as an off white solid (29 mg, 31%). MS (m/e): 402.3 ($MH^+$).

Example 340

(5α,8α)-2-[4-(3,3-Difluoro-cyclobutyl)-phenyl]-8-hydroxy-8-trifluoromethyl-2-aza-spiro[4.5]decan-1-one

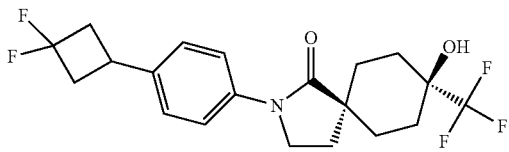 [SMILES: O=C1N(c2ccc(C3CC(F)(F)C3)cc2)CC[C@]12CC[C@@](O)(C(F)(F)F)CC2]

Step 1: 1-Bromo-4-(3,3-difluoro-cyclobutyl)-benzene

To a solution of 3-(4-bromophenyl)cyclobutanone (512 mg, 2.27 mmol) in dichloromethane (15 mL) at −78° C. was added DAST (751 uL, 5.69 mmol) dropwise. The reaction mixture was stirred overnight and then diluted with dichloromethane and washed with sat. $NaHCO_{3(aq)}$ and brine. The organic layers were dried over $Na_2SO_4$ and concentrated in vacuo to give a crude residue which was purified by flash chromatography (0% to 80% EtOAc in heptane) to give the title compound as a brown oil (211 mg, 38%). $^1H$ NMR (300 MHz, $CDCl_3$) δ 2.54-2.72 (m, 2H), 2.93-3.07 (m, 2H), 3.36 (m, 1H), 7.11 (d, 2H, J=9 Hz), 7.46 (d, 2H, J=9 Hz)

Step 2: 10-[4-(3,3-Difluoro-cyclobutyl)-phenyl]-1,4-dioxa-10-aza-dispiro[4.2.4.2]tetradecan-9-one The title compound was prepared in analogy to example 336, step 1 from 1,4-dioxa-10-aza-dispiro[4.2.4.2]tetradecan-9-one (described in example 133, step 3, 165 mg) and 1-bromo-4-(3,3-difluoro-cyclobutyl)-benzene (193 mg, described above). White solid (270 mg, 70%). MS (m/e): 378.3 [$MH^+$].

Step 3: 2-[4-(3,3-Difluoro-cyclobutyl)-phenyl]-2-aza-spiro[4.5]decane-1,8-dione

The title compound was prepared in analogy to example 133 step 5 from 10-[4-(3,3-Difluoro-cyclobutyl)-phenyl]-1,4-dioxa-10-aza-dispiro[4.2.4.2]tetradecan-9-one (described in example 340, step 2) by treatment with 2M HCl. White solid (89%). $R_f$ 0.53 (4:1 AcOEt:heptane)

Step 4: (5α,8α)-2-[4-(3,3-Difluoro-cyclobutyl)-phenyl]-8-hydroxy-8-trifluoromethyl-2-aza-spiro[4.5]decan-1-one The title compound was prepared in analogy to Example 112 from 2-(2,2-difluoro-benzo[1,3]dioxol-5-yl)-2-aza-spiro[4.5]decane-1,8-dione (50 mg, described in example 340, Step 3) by treatment with (trifluoromethyl)-trimethylsilane and tetrabutylammoniumfluoride. White solid (31 mg, 51%). MS (m/e): 404.2 ($MH^+$).

In the chromatographic purification step, the trans compound (5α,8β)-2-[4-(3,3-difluoro-cyclobutyl)-phenyl]-8-hydroxy-8-trifluoromethyl-2-aza-spiro[4.5]decan-1-one was also isolated (see example 341).

Example 341

(5α,8β)-2-[4-(3,3-Difluoro-cyclobutyl)-phenyl]-8-hydroxy-8-trifluoromethyl-2-aza-spiro[4.5]decan-1-one

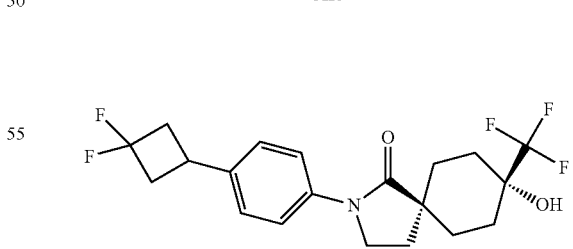

The title compound was isolated from the reaction described in example 340 step 4 from 2-(2,2-difluoro-benzo[1,3]dioxol-5-yl)-2-aza-spiro[4.5]decane-1,8-dione (50 mg, described in example 340, Step 3) by treatment with (trifluoromethyl)-trimethylsilane and tetrabutylammoniumfluoride. White solid (18 mg, 30%). MS (m/e): 404.2 ($MH^+$).

Example 342

(5α,8α)-2-[4-(3,3-Difluoro-cyclobutyl)-phenyl]-8-hydroxy-8-methoxymethyl-2-aza-spiro[4.5]decan-1-one

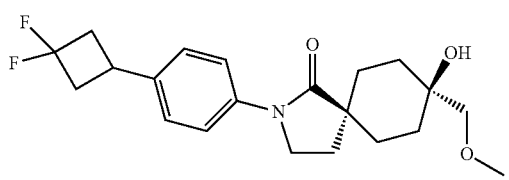 [SMILES: COC[C@]1(O)CC[C@]2(CCN(c3ccc(C4CC(F)(F)C4)cc3)C2=O)CC1]

Step 1: (3α,6α)-8-[4-(3,3-Difluoro-cyclobutyl)-phenyl]-1-oxa-8-aza-dispiro[2.2.4.2]dodecan-7-one The title compound was prepared in analogy to example 110 step 1 from 2-(described in example 340 step 3) and trimethylsulfoxonium iodide. White solid (41%). MS (m/e): 348.2 [MH+].

Step 2: (5α,8α)-2-[4-(3,3-Difluoro-cyclobutyl)-phenyl]-8-hydroxy-8-methoxymethyl-2-aza-spiro[4.5]decan-1-one The title compound was prepared in analogy to example 110 step 2 from (3α,6α)-8-[4-(3,3-Difluoro-cyclobutyl)-phenyl]-1-oxa-8-aza-dispiro[2.2.4.2]dodecan-7-one (described in example 342 step 1) and sodium methoxide (5.4M solution in methanol). White solid (37 mg, 78%). MS (m/e): 380.3 (MH+).

Example 343

(5α,8α)-2-(4-tert-Butyl-phenyl)-8-hydroxy-8-propyl-2-aza-spiro[4.5]decan-1-one

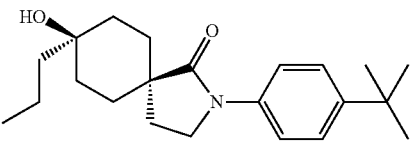 [SMILES: CCC[C@]1(O)CC[C@]2(CCN(c3ccc(C(C)(C)C)cc3)C2=O)CC1]

Step 1: 10-(4-tert-Butyl-phenyl)-1,4-dioxa-10-aza-dispiro[4.2.4.2]tetradecan-9-one The title compound was prepared in analogy to example 336, step 1 from 1,4-dioxa-10-aza-dispiro[4.2.4.2]tetradecan-9-one (described in example 133, step 3) and 1-bromo-4-tert-butyl-benzene. White solid (84%). MS (m/e): 344.2 [MH+].

Step 2: 2-(4-tert-Butyl-phenyl)-2-aza-spiro[4.5]decane-1,8-dione

The title compound was prepared in analogy to example 133 step 5 from 10-(4-tert-butyl-phenyl)-1,4-dioxa-10-aza-dispiro[4.2.4.2]tetradecan-9-one (described in example 343, step 1) by treatment with 2M HCl. Off-white solid (90%). MS (m/e): 300.4 [MH+].

Step 3: (5α,8α)-2-(4-tert-Butyl-phenyl)-8-hydroxy-8-propyl-2-aza-spiro[4.5]decan-1-one The title compound was prepared in analogy to example 55 from 2-(4-tert-butyl-phenyl)-2-aza-spiro[4.5]decane-1,8-dione (obtained in example 343, step 2) by reaction with n-propylmagnesium chloride (2M in diethyl ether). White solid. MS (m/e): 344.2 [MH+].

Example 344

(5α,8α)-2-(4-tert-Butyl-phenyl)-8-hydroxy-8-isopropyl-2-aza-spiro[4.5]decan-1-one

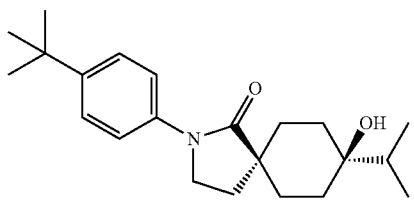 [SMILES: CC(C)[C@]1(O)CC[C@]2(CCN(c3ccc(C(C)(C)C)cc3)C2=O)CC1]

The title compound was prepared in analogy to example 55 from 2-(4-tert-butyl-phenyl)-2-aza-spiro[4.5]decane-1,8-dione (obtained in example 343, step 2) by reaction with isopropylmagnesium chloride (2M in diethyl ether). White solid (41%). MS (m/e): 344.3 [MH+].

Example 345

(5α,8α)-2-(4-tert-Butyl-phenyl)-8-hydroxy-8-trifluoromethyl-2-aza-spiro[4.5]decan-1-one

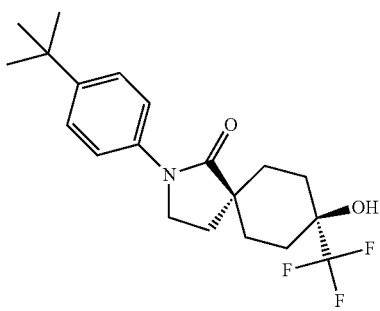 [SMILES: CC(C)(C)c1ccc(N2CC[C@]3(CC[C@@](O)(C(F)(F)F)CC3)C2=O)cc1]

The title compound was prepared in analogy to Example 112 from 2-(4-tert-butyl-phenyl)-2-aza-spiro[4.5]decane-1,8-dione (described in example 343, Step 2) by treatment with (trifluoromethyl)-trimethylsilane and tetrabutylammonium-fluoride. White solid (15%). MS (m/e): 370.2 (MH+).

Example 346

(5α,8α)-2-(4-tert-Butyl-phenyl)-8-hydroxy-8-methoxymethyl-2-aza-spiro[4.5]decan-1-one

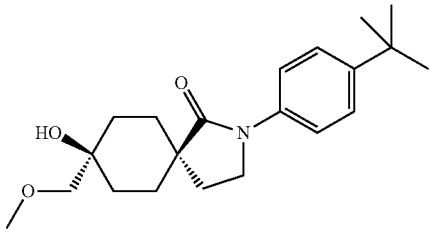 [SMILES: COC[C@]1(O)CC[C@]2(CCN(c3ccc(C(C)(C)C)cc3)C2=O)CC1]

Step 1: (3α,6α)-8-(4-tert-Butyl-phenyl)-1-oxa-8-aza-dispiro[2.2.4.2]dodecan-7-one 2-(4-tert-Butylphenyl)-2-aza-spiro[4.5]decane-1,8-dione (300 mg, 1.00 mmol) and trimethylsulfoxonium iodide (342 mg, 1.55 mmol) were dissolved in DMSO (8.35 ml) at rt. A solution of potassium tert-butoxide (174 mg, 1.55 mmol) in DMSO was added drop-wise over a period of 5 minutes to the reaction mixture. The reaction mixture was stirred at r.t. overnight and subsequently poured into ice/water and extracted two times with ethyl acetate. The combined organic layers were washed with brine, dried over Na₂SO₄, filtered and the solvent was concentrated in vacuo to give a crude residue which was purified by flash chromatography (EtOAc: heptane) to give the title compound as a colourless solid (200 mg, 64%). MS (m/e): 314.2 [MH$^+$].

Step 2: (5α,8α)-2-(4-tert-Butyl-phenyl)-8-hydroxy-8-methoxymethyl-2-aza-spiro[4.5]decan-1-one The title compound was prepared in analogy to example 110 step 2 from 8-(4-tert-Butyl-phenyl)-1-oxa-8-aza-dispiro[2.2.4.2]dodecan-7-one (described in example 346, step 1) and sodium methoxide (5.4M solution in methanol). White solid (79%). MS (m/e): 346.2 (MH$^+$).

Example 347

(5α,8α)-2-(4-tert-Butyl-phenyl)-8-hydroxy-8-(2,2,2-trifluoro-ethoxymethyl)-2-aza-spiro[4.5]decan-1-one

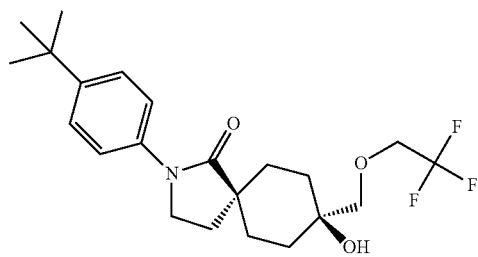 [SMILES: CC(C)(C)c1ccc(N2CC[C@]3(CC[C@@](O)(COCC(F)(F)F)CC3)C2=O)cc1]

To a suspension of sodium hydride (24.5 mg, 1.02 mmol) in DMF (5 mL) at 0° C. was added 2,2,2 trifluoroethanol (95.8 mg, 0.96 mmol) and the reaction mixture was stirred for 10 mins. A solution of (3α,6α)-8-(4-tert-butyl-phenyl)-1-oxa-8-aza-dispiro[2.2.4.2]dodecan-7-one (100 mg, 0.32 mmol, described in example 346 step 1) in DMF (1 mL) was added and the reaction mixture was slowly warmed to room temperature and stirring was continued over night. The reaction mixture was poured into ice/water, extracted with EtOAc, washed with brine and dried over Na₂SO₄ and concentrated in vacuo to give a crude residue which was purified by flash column chromatography (0% to 50% EtOAc in Heptane) to yield the title compound as a white solid (111 mg, 84%). MS (m/e): 414.2 (MH$^+$).

Example 348

(5α,8α)-2-(4-tert-Butyl-phenyl)-8-ethoxymethyl-8-hydroxy-2-aza-spiro[4.5]decan-1-one

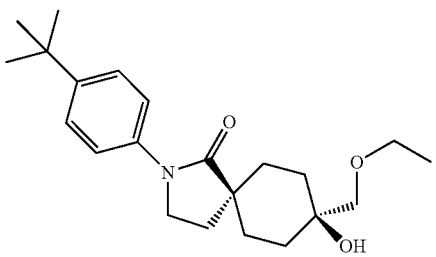 [SMILES: CCOC[C@]1(O)CC[C@]2(CCN(c3ccc(C(C)(C)C)cc3)C2=O)CC1]

The title compound was prepared in analogy to example 110 step 2 from (3α,6α)-8-(4-tert-butyl-phenyl)-1-oxa-8-aza-dispiro[2.2.4.2]dodecan-7-one (described in example 346 step 1) and sodium ethoxide (21% solution in ethanol). White solid (99%). MS (m/e): 360.2 (MH$^+$).

Example 349

(5α,8α)-2-(4-tert-Butyl-phenyl)-8-hydroxy-8-isopropoxymethyl-2-aza-spiro[4.5]decan-1-one

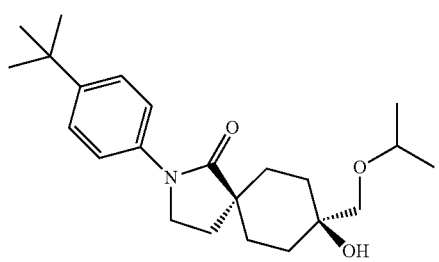 [SMILES: CC(C)OC[C@]1(O)CC[C@]2(CCN(c3ccc(C(C)(C)C)cc3)C2=O)CC1]

The title compound was prepared in analogy to example 347 from (3α,6α)-8-(4-tert-butyl-phenyl)-1-oxa-8-aza-dispiro[2.2.4.2]dodecan-7-one (described in example 346 step 1) and propan-2-ol. White solid (40%). MS (m/e): 374.3 (MH$^+$).

Example 350

(5α,8α)-2-(4-tert-Butyl-phenyl)-8-hydroxy-8-(2-oxo-pyrrolidin-1-ylmethyl)-2-aza-spiro[4.5]decan-1-one

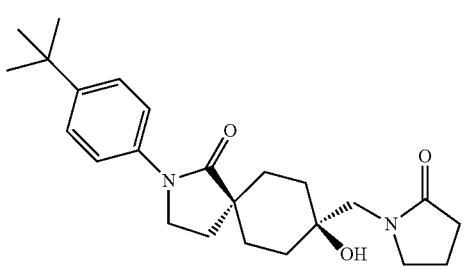 [SMILES: CC(C)(C)c1ccc(N2CC[C@]3(CC[C@@](O)(CN4CCCC4=O)CC3)C2=O)cc1]

The title compound was prepared in analogy to example 347 from (3α,6α)-8-(4-tert-butyl-phenyl)-1-oxa-8-azadispiro[2.2.4.2]dodecan-7-one (described in example 346 step 1) and pyrrolidin-2-one at 80° C. overnight. White solid (64%). MS (m/e): 399.2 (MH⁺).

Example 351

(5α,8α)-2-(4-tert-Butyl-phenyl)-8-hydroxy-8-(2-oxo-piperidin-1-ylmethyl)-2-aza-spiro[4.5]decan-1-one

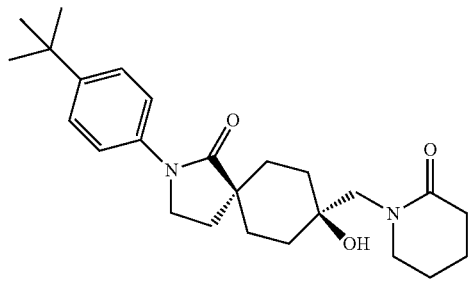 [SMILES: CC(C)(C)c1ccc(N2CC[C@]3(CC[C@@](O)(CN4CCCCC4=O)CC3)C2=O)cc1]

The title compound was prepared in analogy to example 347 from (3α,6α)-8-(4-tert-butyl-phenyl)-1-oxa-8-aza-dispiro[2.2.4.2]dodecan-7-one (described in example 346 step 1) and piperidin-2-one at 80° C. overnight. White solid (20%). MS (m/e): 413.3 (MH⁺).

Examples 352 and 353

(5α,8α)-2-(4-tert-Butyl-phenyl)-8-hydroxy-8-(pyridin-2-yloxymethyl)-2-aza-spiro[4.5]decan-1-one and (5α,8α)-2-(4-tert-Butyl-phenyl)-8-hydroxy-8-(2-oxo-2H-pyridin-1-ylmethyl)-2-aza-spiro[4.5]decan-1-one

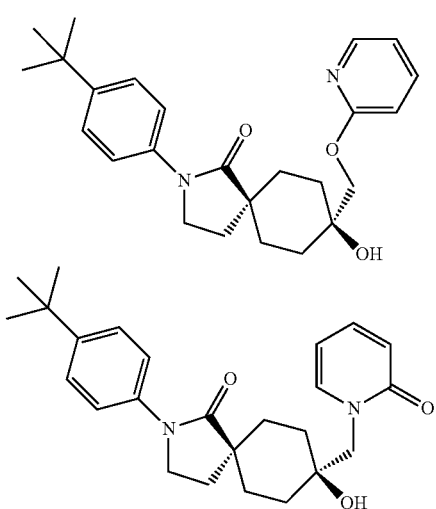

The title compounds were prepared in analogy to example 347 from (3α,6α)-8-(4-tert-butyl-phenyl)-1-oxa-8-aza-dispiro[2.2.4.2]dodecan-7-one (described in example 346 step 1) and pyridin-2-ol at 110° C. overnight. The reaction yielded a mixture of regioisomers which were separated by flash column chromatography (10% MeOH in DCM) to give (5α,8α)-2-(4-tert-butyl-phenyl)-8-hydroxy-8-(pyridin-2-yloxymethyl)-2-aza-spiro[4.5]decan-1-one as a white solid (6%). MS (m/e): 409.3 (MH⁺) and (5α,8α)-2-(4-tert-butyl-phenyl)-8-hydroxy-8-(2-oxo-2H-pyridin-1-ylmethyl)-2-aza-spiro[4.5]decan-1-one as a white solid (48%), MS (m/e): 409.3 (MH⁺)

Example 354

(5α,8α)-2-(4-tert-Butyl-phenyl)-8-hydroxy-8-(pyridin-3-yloxymethyl)-2-aza-spiro[4.5]decan-1-one

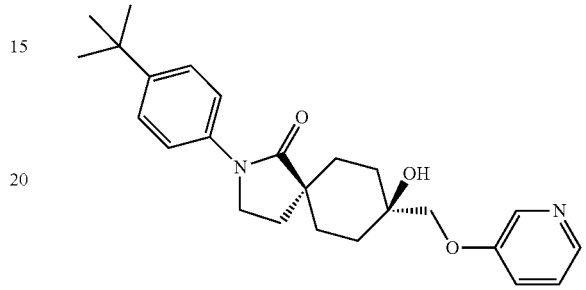

To a solution of (3α,6α)-8-(4-tert-butyl-phenyl)-1-oxa-8-aza-dispiro[2.2.4.2]dodecan-7-one (described in example 346 step 1, 24 mg, 0.08 mmol) in DMF (2 mL) was added hydroxypyridine sodium salt (26.9 mg, 0.23 mmol) and the reaction mixture was heated to 110° C. overnight. The reaction mixture was cooled to room temperature and poured into ice/water, extracted with EtOAc, washed with brine and dried over Na₂SO₄ and concentrated in vacuo to give a crude residue which was purified by flash column chromatography (0% to 10% MeOH in DCM) to yield the title compound as a white solid (11 mg, 34%). MS (m/e): 409.3 (MH⁺).

Example 355

(5α,8β)-2-(4-tert-Butyl-phenyl)-8-(1-hydroxy-2-methyl-propyl)-2-aza-spiro[4.5]decan-1-one

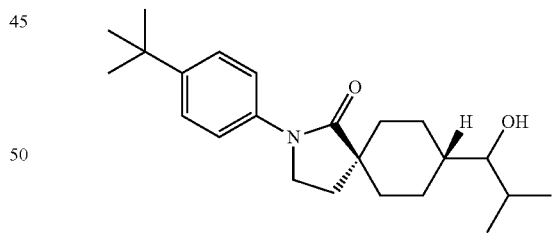

Step 1: 2-(4-tert-Butyl-phenyl)-8-methoxymethylene-2-aza-spiro[4.5]decan-1-one (Methoxymethyl)triphenyl phosphonium chloride (3.05 g, 8.9 mmol) in THF was cooled to −78° C. under argon and a solution of potassium tert-butoxide (832 mg, 7.41 mmol) in THF was added at −78° C. To the resulting red solution was added a solution of 2-(4-tert-butyl-phenyl)-2-aza-spiro[4.5]decane-1,8-dione (described in example 343 step 2, 888 mg, 2.97 mmol) in THF was added dropwise at −78° C. The reaction was allowed to warm to room temperature and the reaction was monitored by TLC. After disappearance of starting material, the reaction was quenched with sat NaHCO₃ (aq), and extracted with EtOAc. The organic layers were combined washed with brine, dried (Na₂SO₄), filtered and concentrated in vacuo to give a crude residue which was purified by flash column chromatography (0% to 50% EtOAc in heptane) to yield the title compound as a white solid (793 mg, 82%). MS (m/e): 328.3 (MH⁺).

Step 2: 2-(4-tert-Butyl-phenyl)-1-oxo-2-aza-spiro [4.5]decane-8-carbaldehyde

To a solution of 2-(4-tert-butylphenyl)-8-(methoxymethylene)-2-aza-spiro[4.5]decan-1-one (793 mg, 2.42 mmol,) in THF (10 mL) was added 2N HCl (12.1 mL, 24.2 mmol). The reaction mixture was stirred at room temperature overnight and then quenched with sat NaHCO₃ (aq), and extracted with EtOAc. The organic layers were combined washed with brine, dried (Na₂SO₄), filtered and concentrated in vacuo to give the desired product as a white solid (750 mg, 98%) which did not require any further purification. MS (m/e): 314.2 (MH⁺).

Step 3: (5α,8β)-2-(4-tert-Butyl-phenyl)-8-(1-hydroxy-2-methyl-propyl)-2-aza-spiro[4.5]decan-1-one To a solution of 2-(4-tert-butyl-phenyl)-1-oxo-2-aza-spiro [4.5]decane-8-carbaldehyde (33.4 mg, 107 mol) in THF (2 mL) at 0° C. was added isopropylmagnesium chloride (160 µl, 320 µmol). The reaction was warmed to room temperature and stirred for 1 hour. The reaction mixture was quenched with aqueous sat. NH₄Cl and exctracted with EtOAc. The organic layers were combined washed with brine, dried (Na₂SO₄), filtered and concentrated in vacuo to give a crude residue which was purified by flash column chromatography (0 to 50% AcOEt in heptane) to yield the title compound as a white solid (25 mg, 66%). MS (m/e): 358.3 (MH⁺).

In the chromatographic purification step, the cis compound (5α,8α))-2-(4-tert-butyl-phenyl)-8-((rac)-1-hydroxy-2-methyl-propyl)-2-aza-spiro[4.5]decan-1-one was also isolated (see example 356).

Example 356

(5α,8α))-2-(4-tert-Butyl-phenyl)-8-(1-hydroxy-2-methyl-propyl)-2-aza-spiro[4.5]decan-1-one

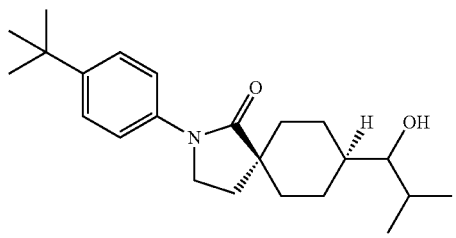 [SMILES: CC(C)C(O)[C@H]1CC[C@]2(CCN(c3ccc(C(C)(C)C)cc3)C2=O)CC1]

The title compound was isolated from the reaction described in example 355 step 3 from 2-(4-tert-butyl-phenyl)-1-oxo-2-aza-spiro[4.5]decane-8-carbaldehyde (described in example 355 step 2) by treatment with isopropylmagnesium chloride. White solid (14%). MS (m/e): 358.3 (MH⁺).

Examples 357 and 358

(5α,8β)-2-(4-tert-Butyl-phenyl)-8-(1-hydroxy-ethyl)-2-aza-spiro[4.5]decan-1-one and (5α,8α)-2-(4-tert-Butyl-phenyl)-8-(1-hydroxy-ethyl)-2-aza-spiro[4.5]decan-1-one

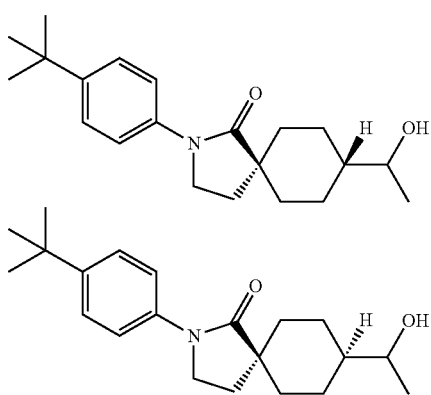

The title compounds were prepared in analogy to example 355 step 3 from 2-(4-tert-butyl-phenyl)-1-oxo-2-aza-spiro [4.5]decane-8-carbaldehyde (described in example 355, step 2) by treatment with methyl magnesiumchloride. The reaction gave a mixture of diastereomers which were separated by flash column chromatography to give (5α,8β)-2-(4-tert-butyl-phenyl)-8-(1-hydroxy-ethyl)-2-aza-spiro[4.5]decan-1-one (64%) as a white solid, MS (m/e): 330.3 (MH⁺) and (5α,8α)-2-(4-tert-butyl-phenyl)-8-(1-hydroxy-ethyl)-2-aza-spiro[4.5]decan-1-one (20%) as a white solid, MS (m/e): 330.3 (MH⁺).

Example 359

(5α,8β)-2-(4-tert-Butyl-phenyl)-8-(1-hydroxy-propyl)-2-aza-spiro[4.5]decan-1-one

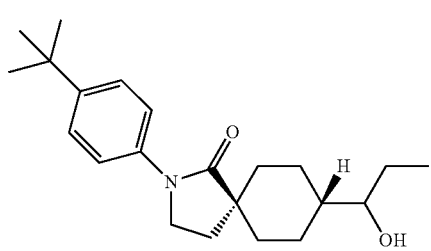 [SMILES: CCC(O)[C@H]1CC[C@@]2(CCN(c3ccc(C(C)(C)C)cc3)C2=O)CC1]

The title compound was prepared in analogy to example 355 step 3 from 2-(4-tert-butyl-phenyl)-1-oxo-2-aza-spiro [4.5]decane-8-carbaldehyde (described in example 355 step 2) by treatment with ethyl magnesium bromide. White solid (56%). MS (m/e): 344.3 (MH⁺).

Examples 360 and 361

(5α,8β)-2-(4-tert-Butyl-phenyl)-8-(2,2,2-trifluoro-1-hydroxy-ethyl)-2-aza-spiro[4.5]decan-1-one and (5α,8α)-2-(4-tert-Butyl-phenyl)-8-(2,2,2-trifluoro-1-hydroxy-ethyl)-2-aza-spiro[4.5]decan-1-one

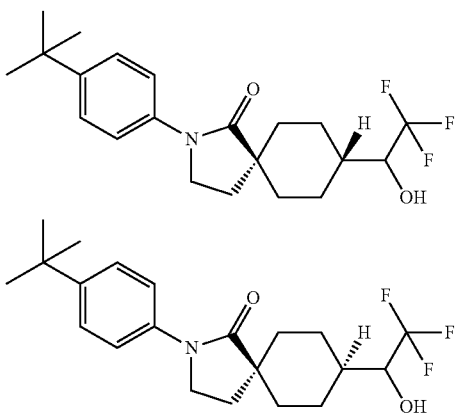

The title compounds were prepared in analogy to example 355 step 3 from 2-(4-tert-butyl-phenyl)-1-oxo-2-aza-spiro[4.5]decane-8-carbaldehyde (described in example 355 step 2) by treatment with (trifluoromethyl)-trimethylsilane and tetrabutylammoniumfluoride. The reaction gave a mixture of diastereomers which were separated by flash column chromatography to give (5α,8β)-2-(4-tert-butyl-phenyl)-8-(2,2,2-trifluoro-1-hydroxy-ethyl)-2-aza-spiro[4.5]decan-1-one (45%) as a white solid, MS (m/e): 384.2 (MH$^+$) and (5α,8α)-2-(4-tert-butyl-phenyl)-8-(2,2,2-trifluoro-1-hydroxy-ethyl)-2-aza-spiro[4.5]decan-1-one (13%) as a white solid, MS (m/e): 384.2 (MH$^+$).

Example 362

2-(4-tert-Butyl-phenyl)-8-(2,2,2-trifluoro-1,1-dihydroxy-ethyl)-2-aza-spiro[4.5]decan-1-one

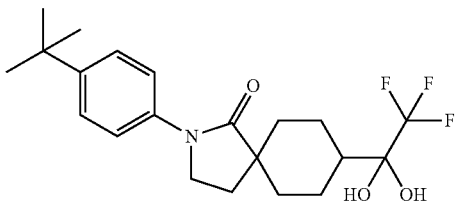 [SMILES: CC(C)(C)c1ccc(N2CCC3(CCC(C(O)(O)C(F)(F)F)CC3)C2=O)cc1]

A solution of 2-(4-tert-butyl-phenyl)-8-(2,2,2-trifluoro-1-hydroxy-ethyl)-2-aza-spiro[4.5]decan-1-one (100 mg, 319 μmol, described in example 360 and 361) in DCM (1 mL) was added to a stirred suspension of Dess-Martin periodinane (501 mg, 1.18 mmol) in DCM (2.5 mL) and the reaction mixture was stirred overnight at room temperature. The reaction mixture was diluted with EtOAc and poured into a 1:7 mixture of aqueous sat. NaHCO$_3$ and Na$_2$S$_2$O$_3$ and the mixture was stirred for 10 min. The organic phase was separated and washed with brine, dried (Na$_2$SO$_4$), filtered and concentrated in vacuo to give a crude residue which was purified by reverse phase prep HPLC to give the title compound as a white solid (94%). MS (m/e): 400.3 (MH$^+$).

Example 363

(5α,8β)-2-(4-tert-Butyl-phenyl)-8-[hydroxy-(2H-pyrazol-3-yl)-methyl]-2-aza-spiro[4.5]decan-1-one

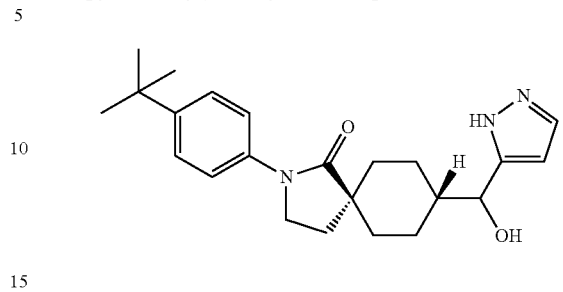

Step 1: (5α,8β)-2-(4-tert-Butyl-phenyl)-8-{hydroxy-[2-(2-trimethylsilanyl-ethoxymethyl)-2H-pyrazol-3-yl]-methyl}-2-aza-spiro[4.5]decan-1-one To a solution of 1-((2-(trimethylsilyl)ethoxy)methyl)-1H-pyrazole (69.6 mg, 351 μmol; CAS Reg. No. 133560-57-3) in THF (5 mL) at −78° C. was added nBuLi (1.6M, 229 μl, 367 μmol) dropwise. The reaction was stirred for 30 min at −78° C. followed by the addition of a solution of 2-(4-tert-butylphenyl)-1-oxo-2-aza-spiro[4.5]decane-8-carbaldehyde (prepared as described in example 355 step 2, 100 mg, 319 mol) in THF (1 mL). The reaction mixture was stirred at −78° C. for 90 min and then allowed to warm to room temperature. After 3 h, the reaction mixture was quenched with ice and sat. NH$_4$Cl (aq) and extracted with EtOAc (3 times). The organic layers were combined washed with brine, dried (Na$_2$SO$_4$), filtered and concentrated in vacuo to give a crude residue which was purified by flash column chromatography (0 to 50% AcOEt in heptane) to yield the title compound as a white solid (53 mg, 32%). MS (m/e): 512.5 (MH$^+$).

Step 2: (5α,8β)-2-(4-tert-Butyl-phenyl)-8-[hydroxy-(2H-pyrazol-3-yl)-methyl]-2-aza-spiro[4.5]decan-1-one To a solution of (5α,8β)-2-(4-tert-butyl-phenyl)-8-{hydroxy-[2-(2-trimethylsilanyl-ethoxymethyl)-2H-pyrazol-3-yl]-methyl}-2-aza-spiro[4.5]decan-1-one (16 mg, 31.9 umol) in THF was added TBAF (1M, 159 uL, 159 umol) and the reaction mixture was refluxed for 5 hours. The reaction mixture was cooled to room temperature and quenched with sat. NH$_4$Cl (aq) and extracted with EtOAc (3 times). The organic layers were combined washed with brine, dried (Na$_2$SO$_4$), filtered and concentrated in vacuo to give a crude residue which was purified by flash column chromatography to yield the title compound as a colourless oil (10 mg, 82%). MS (m/e): 382.3 (MH$^+$).

Example 364

(5α,8β)-2-(4-tert-Butyl-phenyl)-8-(2H-pyrazol-3-ylmethyl)-2-aza-spiro[4.5]decan-1-one

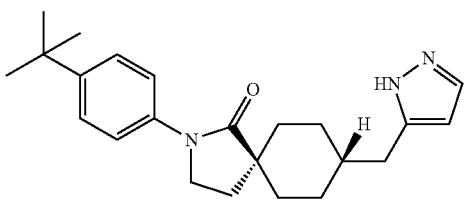 [SMILES: CC(C)(C)c1ccc(N2CC[C@]3(CC[C@@H](Cc4ccn[nH]4)CC3)C2=O)cc1]

Step 1: (5α,8β)-2-(4-tert-Butyl-phenyl)-8-[2-(2-trimethylsilanyl-ethoxymethyl)-2H-pyrazol-3-ylmethyl]-2-aza-spiro[4.5]decan-1-one To a suspension of NaH (60%, 5 mg, 131 umol) in THF (4 mL) at 0° C. was added a solution of (5α,8β)-2-(4-tert-butyl-phenyl)-8-{hydroxy-[2-(2-trimethylsilanyl-ethoxymethyl)-2H-pyrazol-3-yl]-methyl}-2-aza-spiro[4.5]decan-1-one (described in example 363 step 1, 22 mg, 43.6 umol) in THF (1 mL). The reaction mixture was stirred at 0° C. for 10 min and a further 15 min at room temperature and then re-cooled to 0° C. Carbon disulfide (21 uL, 349 umol) was added dropwise, and the reaction mixture was warmed to room temperature and stirred for 30 min. Subsequently the reaction mixture was re-cooled to 0° C. and methyl iodide 43.6 uL, 697 umol) was added dropwise. The reaction mixture was stirred at room temperature for 5 h. The reaction mixture was quenched with sat. NH$_4$Cl(aq) and extracted with EtOAc (3 times). The organic layers were combined washed with brine, dried (Na$_2$SO$_4$), filtered and concentrated in vacuo to give a crude residue of dithiocarbonic acid {[2-(4-tert-butyl-phenyl)-1-oxo-2-aza-spiro[4.5]dec-8-yl]-[2-(2-trimethylsilanyl-ethoxymethyl)-2H-pyrazol-3-yl]-methyl}ester methyl ester which was reacted on without further purification.

To a mixture of AIBN (6.4 mg, 39.2 umol) and tri-n-butyltin hydride (93.1 uL, 349 umol) in toluene (4 mL) was added a solution of the crude dithiocarbonic acid {[2-(4-tert-butyl-phenyl)-1-oxo-2-aza-spiro[4.5]dec-8-yl]-[2-(2-trimethylsilanyl-ethoxymethyl)-2H-pyrazol-3-yl]-methyl}ester methyl ester in toluene (1 mL) and the reaction mixture was refluxed overnight. The reaction mixture was cooled to room temperature, filtered on a short pad of silica and directly purified by flash column chromatography (0% to 100% AcOEt in heptane) to give the title compound as a white solid (20 mg, 93%). MS (m/e): 496.5 (MH$^+$).

Step 2: (5α,8β)-2-(4-tert-Butyl-phenyl)-8-(2H-pyrazol-3-ylmethyl)-2-aza-spiro[4.5]decan-1-one To a solution of (5α,8β)-2-(4-tert-Butyl-phenyl)-8-[2-(2-trimethylsilanyl-ethoxymethyl)-2H-pyrazol-3-ylmethyl]-2-aza-spiro[4.5]decan-1-one (described in 364 step 1, 20 mg, 40 umol) in ethanol (1 mL) was added 3M HCl (aq) (605 uL, 1.82 mmol) solution and the reaction mixture was refluxed for 3 h. The reaction mixture was quenched with NaHCO$_3$ and extracted with EtOAc (3×). The organic layers were combined washed with brine, dried (Na$_2$SO$_4$), filtered and concentrated in vacuo to give a crude residue which was purified by flash column chromatography to give the title compound as a white solid (13 mg, 88%). MS (m/e): 366.3 (MH$^+$).

Example 365

(5α,8β)-8-(1-Hydroxy-propyl)-2-[4-((R)-2,2,2-trifluoro-1-methyl-ethoxy)-phenyl]-2-aza-spiro[4.5]decan-1-one

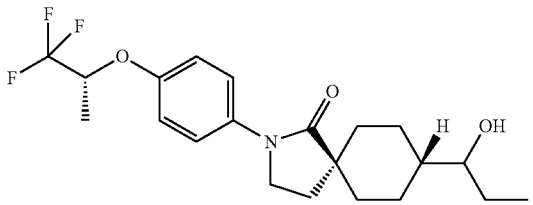 [SMILES: CCC(O)[C@H]1CC[C@@]2(CCN(c3ccc(O[C@H](C)C(F)(F)F)cc3)C2=O)CC1]

Step 1: 1-oxo-2-[4-((R)-2,2,2-trifluoro-1-methyl-ethoxy)-phenyl]-2-aza-spiro[4.5]decane-8-carbaldehyde To a solution of 8-[4-((R)-2,2,2-trifluoro-1-methyl-ethoxy)-phenyl]-1-oxa-8-aza-dispiro[2.2.4.2]dodecan-7-one (50 mg, 135 umol, obtained in example 252, Step 2) in chloroform was added tosic acid (26 mg, 135 umol) and the reaction mixture was stirred overnight at room temperature and then diluted with ethyl acetate. The organic layer was washed with brine, dried (Na$_2$SO$_4$), filtered and concentrated in vacuo to give a crude residue which was purified by flash column chromatography (grad 0% to 80% EtOAc in heptane) to yield the title compound as a white solid (7 mg, 14%). MS (m/e): 370.1 (MH$^+$).

Step 2: (5α,8β)-8-(1-Hydroxy-propyl)-2-[4-((R)-2,2,2-trifluoro-1-methyl-ethoxy)-phenyl]-2-aza-spiro[4.5]decan-1-one The title compound was prepared in analogy to example 355 from 1-oxo-2-[4-((R)-2,2,2-trifluoro-1-methyl-ethoxy)-phenyl]-2-aza-spiro[4.5]decane-8-carbaldehyde (described in example 365 step 1) by treatment with ethyl magnesium bromide. White solid (50%). MS (m/e): 400.1 (MH$^+$).

In the chromatographic purification step, the cis compound (5α,8α)-8-(1-hydroxy-propyl)-2-[4-((R)-2,2,2-trifluoro-1-methyl-ethoxy)-phenyl]-2-aza-spiro[4.5]decan-1-one was also isolated (see example 366).

Example 366

(5α,8α)-8-(1-Hydroxy-propyl)-2-[4-((R)-2,2,2-trifluoro-1-methyl-ethoxy)-phenyl]-2-aza-spiro[4.5]decan-1-one

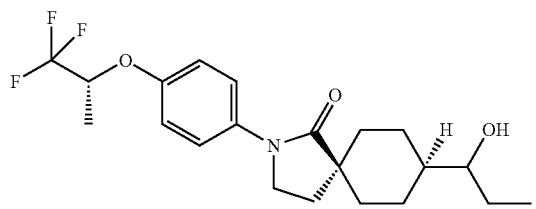 [SMILES: CCC(O)[C@H]1CC[C@]2(CCN(c3ccc(O[C@H](C)C(F)(F)F)cc3)C2=O)CC1]

The title compound was isolated from the reaction described in example 365 step 2 from 1-oxo-2-[4-((R)-2,2,2-trifluoro-1-methyl-ethoxy)-phenyl]-2-aza-spiro[4.5]decane-8-carbaldehyde (described in example 365, step 1) by treatment with ethyl magnesium bromide. White solid (30%). MS (m/e): 400.1 (MH$^+$).

Example 367

(5α,8α)-8-Hydroxy-8-(2-oxo-pyrrolidin-1-ylmethyl)-2-[4-(2,2,2-trifluoro-ethoxy)-phenyl]-2-azaspiro[4.5]decan-1-one

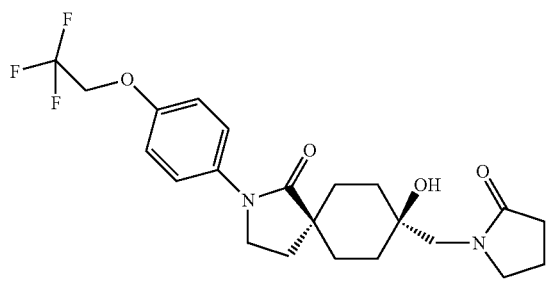 [SMILES: O=C1CCCN1C[C@]1(O)CC[C@]2(CCN(c3ccc(OCC(F)(F)F)cc3)C2=O)CC1]

Step 1: 8-[4-(2,2,2-Trifluoro-ethoxy)-phenyl]-1-oxa-8-aza-dispiro[2.2.4.2]dodecan-7-one The title compound was prepared in analogy to example 346 step 1 from 2-[4.5]decane-1,8-dione (described in example 86 step 1) and trimethylsulfoxonium iodide. White solid (87%). MS (m/e): 356.1 [MH$^+$].

Step 2: (5α,8α)-8-Hydroxy-8-(2-oxo-pyrrolidin-1-ylmethyl)-2-[4-(2,2,2-trifluoro-ethoxy)-phenyl]-2-aza-spiro[4.5]decan-1-one The title compound was prepared in analogy to example 347 from 8-[4-(2,2,2-trifluoro-ethoxy)-phenyl]-1-oxa-8-aza-dispiro[2.2.4.2]dodecan-7-one (described in example 367 step 1) and pyrrolidin-2-one at 110° C. overnight. White solid (33%). MS (m/e): 441.3 (MH$^+$).

Example 368

(5α,8α)-8-Hydroxy-8-(2-oxo-piperidin-1-ylmethyl)-2-[4-(2,2,2-trifluoro-ethoxy)-phenyl]-2-aza-spiro[4.5]decan-1-one

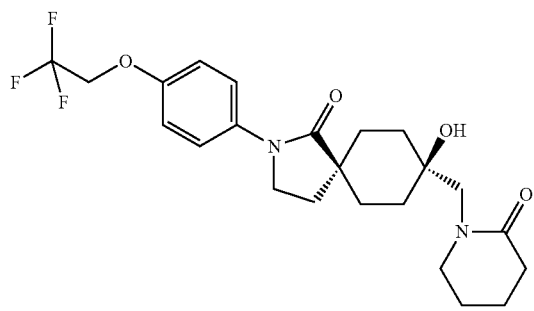 [SMILES: O=C1CCCCN1C[C@]1(O)CC[C@]2(CCN(c3ccc(OCC(F)(F)F)cc3)C2=O)CC1]

The title compound was prepared in analogy to example 347 from 8-[4-(2,2,2-trifluoro-ethoxy)-phenyl]-1-oxa-8-aza-dispiro[2.2.4.2]dodecan-7-one (described in example 367 step 1) and piperidin-2-one at 110° C. overnight. White solid (6%). MS (m/e): 455.3 (MH$^+$).

Example 369

(5α,8α)-8-Hydroxy-8-(2-oxo-2H-pyridin-1-ylmethyl)-2-[4-(2,2,2-trifluoro-ethoxy)-phenyl]-2-azaspiro[4.5]decan-1-one

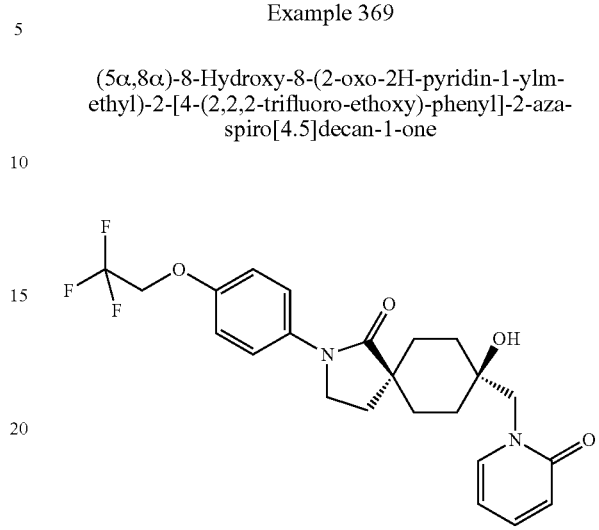

The title compound was prepared in analogy to example 347 from 8-[4-(2,2,2-trifluoro-ethoxy)-phenyl]-1-oxa-8-aza-dispiro[2.2.4.2]dodecan-7-one (described in example 367 step 1) and pyridin-2-ol at 110° C. overnight. White solid (48%). MS (m/e): 451.2 (MH$^+$).

In the chromatographic purification step, the trans compound (5α,8β))-8-hydroxy-8-(2-oxo-2H-pyridin-1-ylmethyl)-2-[4-(2,2,2-trifluoro-ethoxy)-phenyl]-2-aza-spiro[4.5]decan-1-one and the cis regioisomer (5α,8α)-8-hydroxy-8-(pyridin-2-yloxymethyl)-2-[4-(2,2,2-trifluoro-ethoxy)-phenyl]-2-aza-spiro[4.5]decan-1-one were also isolated (see example 370 and 371).

Example 370

(5α,8β)-8-Hydroxy-8-(2-oxo-2H-pyridin-1-ylmethyl)-2-[4-(2,2,2-trifluoro-ethoxy)-phenyl]-2-azaspiro[4.5]decan-1-one

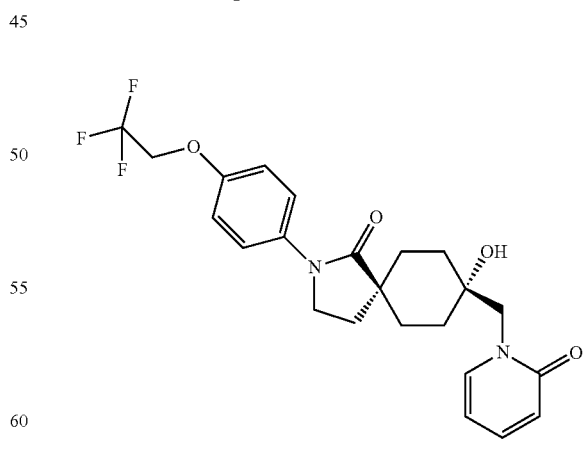

The title compound was isolated from the reaction described in example 369, from 8-[4-(2,2,2-trifluoro-ethoxy)-phenyl]-1-oxa-8-aza-dispiro[2.2.4.2]dodecan-7-one (described in example 367 step 1) and pyridin-2-ol at 110° C. overnight. White solid (3%). MS (m/e): 451.2 (MH$^+$).

Example 371

(5α,8α)-8-Hydroxy-8-(pyridin-2-yloxymethyl)-2-[4-(2,2,2-trifluoro-ethoxy)-phenyl]-2-aza-spiro[4.5]decan-1-one

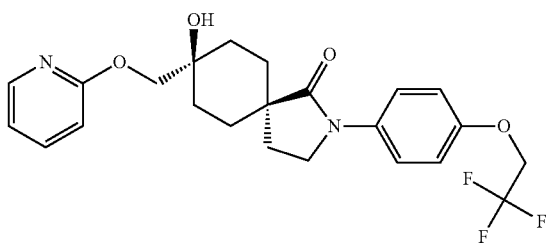 [SMILES: O=C1N(c2ccc(OCC(F)(F)F)cc2)CC[C@]12CC[C@@](O)(COc1ccccn1)CC2]

The title compound was isolated from the reaction described in example 369, from 8-[4-(2,2,2-trifluoro-ethoxy)-phenyl]-1-oxa-8-aza-dispiro[2.2.4.2]dodecan-7-one (described in example 367 step 1) and pyridin-2-ol at 110° C. overnight. White solid (5%). MS (m/e): 451.2 (MH+).

Example 372

(5α,8α)-8-Hydroxy-8-(2,2,2-trifluoro-ethoxymethyl)-2-[4-((R)-2,2,2-trifluoro-1-methoxy-ethyl)-phenyl]-2-aza-spiro[4.5]decan-1-one

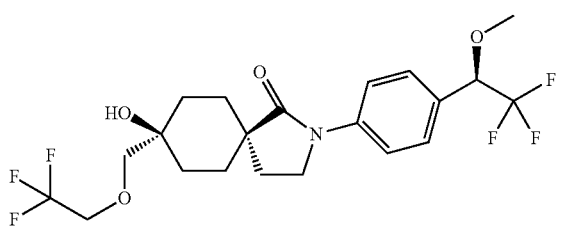 [SMILES: CO[C@H](c1ccc(N2CC[C@]3(CC[C@@](O)(COCC(F)(F)F)CC3)C2=O)cc1)C(F)(F)F]

The title compound was obtained in analogy to example 137 from (5α,8α)-8-hydroxy-8-(2,2,2-trifluoro-ethoxymethyl)-2-[4-((R)-2,2,2-trifluoro-1-hydroxy-ethyl)-phenyl]-2-aza-spiro[4.5]decan-1-one (78 mg, obtained in example 155) by alkylation with iodomethane as a colorless oil (19 mg). MS (m/e): 470.3 (MH+).

Example 373

(5α,8α)-2-[2-(4-Ethyl-phenyl)-ethyl]-8-hydroxy-8-methoxymethyl-2-aza-spiro[4.5]decan-1-one

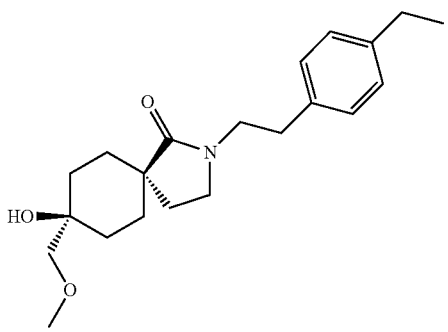 [SMILES: CCc1ccc(CCN2CC[C@]3(CC[C@@](O)(COC)CC3)C2=O)cc1]

Step 1: (3α,6α)-8-[2-(4-Ethyl-phenyl)-ethyl]-1-oxa-8-aza-dispiro[2.2.4.2]dodecan-7-one This material was obtained in analogy to example 110, step 1 from 2-[2-(4-ethyl-phenyl)-ethyl]-2-aza-spiro[4.5]decane-1,8-dione (1.0 g, obtained in example 161, step 2) by treatment with trimethylsulfoxonium iodide as a colorless solid (560 mg). MS (m/e): 314.2 (MH+).

Step 2: (5α,8α)-2-[2-(4-Ethyl-phenyl)-ethyl]-8-hydroxy-8-methoxymethyl-2-aza-spiro[4.5]decan-1-one The title compound was obtained in analogy to example 110, step 2 from (3α,6α)-8-[2-(4-ethyl-phenyl)-ethyl]-1-oxa-8-aza-dispiro[2.2.4.2]dodecan-7-one (100 mg) by treatment with sodium methylate as a colorless solid (100 mg). MS (m/e): 346.2 (MH+).

Example 374

(5α,8α)-8-hydroxy-2-(4-isopropoxyphenyl)-8-(1H-1,2,3-triazol-4-yl)-2-azaspiro[4.5]decan-1-one

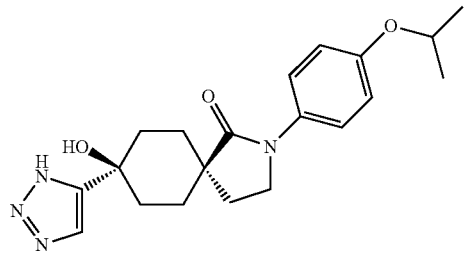 [SMILES: CC(C)Oc1ccc(N2CC[C@]3(CC[C@@](O)(c4cnn[nH]4)CC3)C2=O)cc1]

Step 1: 1-((2-(trimethylsilyl)ethoxy)methyl)-1H-1,2,3-triazole

Sodium hydride (289 mg; 60% suspension in paraffin oil) in THF (10 ml) was treated under an argon atmosphere at RT dropwise with a solution of 1,2,3-triazole (500 mg) in THF (10 ml). The mixture was stirred at RT for 1 hour and was then treated at 0° C. dropwise with (2-(chloromethoxy)ethyl)trimethylsilane (1.21 g). Stirring was continued for 2 h. The reaction was quenched with water (10 ml), the layers were separated and the aqueous layer once extracted with AcOEt (15 ml). The combined organic layers were dried over MgSO4, filtered and the solvent was removed in vacuo to give the title compound as a crude product that was used without further purification. Colorless liquid (1.5 g). MS (m/e): 198.204 (M-H+).

Step 2: (5α,8α)-8-hydroxy-2-(4-isopropoxyphenyl)-8-(1H-1,2,3-triazol-4-yl)-2-azaspiro[4.5]decan-1-one A protected intermediate of (5α,8α)-8-hydroxy-2-(4-isopropoxyphenyl)-8-(1H-1,2,3-triazol-4-yl)-2-azaspiro[4.5]decan-1-one was prepared in analogy to example 212 from 1-((2-(trimethylsilyl)ethoxy)methyl)-1H-1,2,3-triazole, 2-(4-isopropoxyphenyl)-2-aza-spiro[4.5]decane-1,8-dione (obtained in example 184, step 2) and n-butyllithium as a colorless solid. MS (m/e): 501.2 (MH+).

For deprotection, the intermediate (73 mg) was dissolved in dichloromethane (4 mL) and ethanol (0.2 mL) and trifluoroacetic acid (1.12 mL) was added. The mixture was allowed to stir at RT for 6 hours. The reaction was poured into water and ethyl acetate and the organic layer was separated, dried over MgSO$_4$ and evaporated. The residue was purified by flash chromatography (silica gel, gradient of dichloromethane and AcOEt) to provide the title compound as a colorless solid (27 mg). MS (m/e): 371.2 (MH$^+$).

Example 375

(5α,8α)-2-[2-(4-Ethyl-phenyl)-ethyl]-8-hydroxy-8-isopropoxymethyl-2-aza-spiro[4.5]decan-1-one

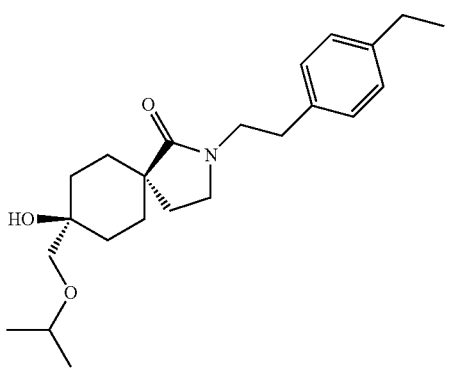 [SMILES: CCc1ccc(CCN2CC[C@]3(CC[C@@](O)(COC(C)C)CC3)C2=O)cc1]

The title compound was obtained in analogy to example 110, step 2 from (3α,6α)-8-[2-(4-ethyl-phenyl)-ethyl]-1-oxa-8-aza-dispiro[2.2.4.2]dodecan-7-one (200 mg, obtained in example 373, step 1) by treatment with sodium isopropoxide as a colorless solid (119 mg). MS (m/e): 374.4 (MH$^+$).

Example 376

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 377

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Example 378

Assay Procedures

Production of Human Full Length Hormone Sensitive Lipase-His$^6$:

1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His$^6$, 48 hr., containing 25 μM E-64. Cell count: 1.78×10$^{10}$ cells/ml, 90% viable. Cells were thawed. On ice, cells were suspended in Base Buffer containing 10% glycerol, 25 mM Tris-Cl, 300 mM NaCl, 10 mM imidazole, 10 mM 2-mercaptoethanol, 2 μg pepstatin/ml, 2 μg leupeptin/ml, 2 μg antipain/ml, pH 8.0 at 4° C. in a final volume of 475 ml with 3.75×10$^7$ cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 μm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 μm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 μm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes). 3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows: The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 µM). Each compound was then diluted 200-fold into KRBH/3% BSA (0.5% DMSO final). The resulting solutions range from 25 uM to 1.6 µM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC$_{50}$ (uM) |
|---|---|
| 1 | 0.47 |
| 2 | 0.15 |
| 3 | 0.61 |
| 4 | 0.24 |
| 5 | 2.37 |
| 6 | 0.1 |
| 7 | 0.07 |
| 8 | 0.27 |
| 9 | 0.19 |
| 10 | 0.06 |
| 11 | 0.04 |
| 12 | 0.06 |
| 13 | 0.09 |
| 14 | 0.02 |
| 15 | 0.07 |
| 16 | 0.1 |
| 17 | 0.08 |
| 18 | 0.06 |
| 19 | 0.14 |
| 20 | 0.1 |
| 21 | 0.1 |
| 22 | 0.06 |
| 23 | 0.19 |
| 24 | 0.37 |
| 25 | 0.08 |
| 26 | 0.11 |
| 27 | 0.18 |
| 28 | 0.08 |
| 29 | 0.08 |
| 30 | 0.25 |
| 31 | 23.75 |
| 32 | 0.9 |
| 33 | 6 |
| 34 | 0.8 |
| 35 | 16.5 |
| 37 | 0.21 |
| 38 | 0.24 |
| 39 | 0.56 |
| 40 | 4.59 |
| 41 | 0.39 |
| 42 | 0.32 |
| 43 | 0.74 |
| 44 | 1.48 |
| 45 | 1.11 |
| 46 | 4.24 |
| 47 | 6.75 |
| 48 | 1.71 |
| 50 | 0.2 |
| 51 | 0.02 |
| 52 | 2.27 |
| 53 | 0.03 |
| 54 | 0.64 |
| 55 | 0.02 |
| 56 | 0.57 |
| 57 | 0.07 |
| 58 | 0.95 |
| 59 | 1.6 |
| 60 | 0.03 |
| 61 | 2.09 |
| 62 | 0.02 |
| 63 | 0.6 |
| 64 | 0.03 |
| 65 | 0.44 |
| 66 | 0.03 |
| 67 | 11.11 |
| 68 | 0.03 |
| 69 | 0.56 |
| 70 | 0.13 |
| 71 | 0.04 |
| 72 | 0.71 |
| 73 | 0.15 |
| 74 | 0.8 |
| 75 | 0.03 |
| 76 | 0.19 |
| 77 | 0.05 |
| 78 | 0.9 |
| 79 | 0.03 |
| 80 | 0.91 |
| 81 | 0.02 |
| 82 | 0.46 |
| 83 | 0.07 |
| 84 | 4.3 |
| 85 | 2.29 |
| 86 | 0.13 |
| 87 | 3.82 |
| 88 | 0.042 |
| 89 | 3.19 |
| 90 | 0.023 |
| 91 | 0.896 |
| 92 | 0.03 |
| 93 | 0.02 |
| 94 | 0.08 |
| 95 | 0.24 |
| 96 | 0.06 |
| 97 | 1.82 |
| 98 | 2.5 |
| 99 | 0.03 |
| 100 | 0.36 |
| 101 | 0.11 |
| 102 | 0.1 |

| Examples | HSL hum IC$_{50}$ (uM) |
|---|---|
| 103 | 0.02 |
| 104 | 0.02 |
| 105 | 0.03 |
| 106 | 1.35 |
| 107 | 2.03 |
| 108 | 0.02 |
| 109 | 2.22 |
| 110 | 0.19 |
| 111 | 0.1 |
| 112 | 0.02 |
| 113 | 2.18 |
| 114 | 0.03 |
| 115 | 0.68 |
| 116 | 0.01 |
| 117 | 0.02 |
| 118 | 0.1 |
| 119 | 0.03 |
| 120 | 0.1 |
| 121 | 0.1 |
| 122 | 0.05 |
| 123 | 0.42 |
| 124 | 0.02 |
| 125 | 1.81 |
| 126 | 0.01 |
| 127 | 0.12 |
| 128 | 0.05 |
| 129 | 0.02 |
| 130 | 0.05 |
| 131 | 0.09 |
| 132 | 0.02 |
| 133 | 0.03 |
| 133a | 0.05 |
| 133b | 0.03 |
| 134 | 1.18 |
| 135 | 0.02 |
| 136 | 2.76 |
| 137 | 0.01 |
| 138 | 0.1 |
| 139 | 0.04 |
| 140 | 0.16 |
| 141 | 0.03 |
| 142 | 0.01 |
| 143 | 1.48 |
| 144 | 0.01 |
| 145 | 0.39 |
| 146 | 0.02 |
| 147 | 0.03 |
| 148 | 0.02 |
| 149 | 1.65 |
| 150 | 0.02 |
| 151 | 1.85 |
| 152 | 0.05 |
| 153 | 0.05 |
| 154 | 0.03 |
| 155 | 0.009 |
| 156 | 0.06 |
| 157 | 0.25 |
| 158 | 0.34 |
| 159 | 0.02 |
| 160 | 0.3 |
| 161 | 0.01 |
| 162 | 0.22 |
| 163 | 0.79 |
| 164 | 0.02 |
| 164a | 0.02 |
| 164b | 0.02 |
| 165 | 0.02 |
| 165a | 0.02 |
| 165b | 0.03 |
| 166 | 0.04 |
| 167 | 0.04 |
| 168 | 0.07 |
| 169 | 0.05 |
| 170 | 0.05 |
| 171 | 0.03 |
| 172 | 0.02 |
| 173 | 0.05 |
| 174 | 0.06 |
| 175 | 0.04 |
| 176 | 0.02 |
| 177 | 0.03 |
| 177a | 0.04 |
| 177b | 0.04 |
| 178 | 0.15 |
| 179 | 0.03 |
| 180 | 0.03 |
| 181 | 0.02 |
| 181a | 0.02 |
| 182 | 0.03 |
| 183 | 0.07 |
| 184 | 0.02 |
| 185 | 0.05 |
| 186 | 0.02 |
| 187 | 0.65 |
| 188 | 0.08 |
| 189 | 0.1 |
| 190 | 0.01 |
| 191 | 0.05 |
| 192 | 0.05 |
| 193 | 0.03 |
| 194 | 0.02 |
| 195 | 0.11 |
| 196 | 0.01 |
| 197 | 0.02 |
| 198 | 0.01 |
| 199 | 0.01 |
| 200 | 0.02 |
| 201 | 0.05 |
| 202 | 0.01 |
| 203 | 0.01 |
| 204 | 0.02 |
| 205 | 0.01 |
| 206 | 0.01 |
| 207 | 0.09 |
| 208 | 0.03 |
| 209 | 0.03 |
| 210 | 0.05 |
| 211 | 0.01 |
| 212 | 0.01 |
| 213 | 0.39 |
| 214 | 0.05 |
| 215 | 0.59 |
| 216 | 0.01 |
| 217 | 0.05 |
| 218 | 0.04 |
| 219 | 0.011 |
| 220 | 0.02 |
| 221 | 1.16 |
| 222 | 0.103 |
| 223 | 0.05 |
| 224 | 0.15 |
| 225 | 0.06 |
| 226 | 0.02 |
| 227 | 0.7 |
| 228 | 0.02 |
| 229 | 0.13 |
| 230 | 0.4 |
| 231 | 0.02 |
| 232 | 0.29 |
| 233 | 0.02 |
| 234 | 0.04 |
| 235 | 0.63 |
| 236 | 0.02 |
| 237 | 0.27 |
| 238 | 0.02 |
| 239 | 0.14 |
| 240 | 0.02 |
| 241 | 0.09 |
| 242 | 0.01 |
| 243 | 0.3 |
| 244 | 0.03 |
| 245 | 0.28 |
| 246 | 0.64 |
| 247 | 0.07 |

| Examples | HSL hum IC$_{50}$ (uM) |
|---|---|
| 248 | 0.34 |
| 249 | 0.02 |
| 250 | 0.6 |
| 251 | 0.01 |
| 252 | 0.23 |
| 253 | 0.02 |
| 254 | 0.41 |
| 255 | 0.01 |
| 256 | 0.69 |
| 257 | 0.01 |
| 258 | 0.07 |
| 259 | 0.08 |
| 260 | 0.06 |
| 261 | 0.01 |
| 262 | 0.07 |
| 263 | 0.02 |
| 264 | 0.2 |
| 265 | 0.04 |
| 266 | 0.37 |
| 267 | 0.03 |
| 268 | 0.02 |
| 269 | 0.01 |
| 270 | 0.01 |
| 271 | 0.03 |
| 272 | 0.02 |
| 273 | 0.02 |
| 274 | 0.02 |
| 275 | 0.08 |
| 276 | 0.01 |
| 277 | 0.04 |
| 278 | 0.02 |
| 279 | 0.02 |
| 280 | 0.98 |
| 281 | 0.01 |
| 282 | 0.4 |
| 283 | 0.01 |
| 284 | 0.36 |
| 285 | 0.01 |
| 286 | 0.19 |
| 287 | 0.01 |
| 288 | 0.8 |
| 289 | 0.02 |
| 290 | 0.02 |
| 291 | 0.02 |
| 292 | 0.01 |
| 293 | 0.02 |
| 294 | 0.02 |
| 295 | 0.04 |
| 296 | 0.55 |
| 297 | 0.02 |
| 298 | 0.59 |
| 299 | 0.01 |
| 300 | 0.3 |
| 301 | 0.01 |
| 302 | 0.51 |
| 303 | 0.01 |
| 304 | 0.33 |
| 305 | 0.03 |
| 306 | 0.01 |
| 307 | 0.2 |
| 308 | 0.01 |
| 309 | 0.01 |
| 310 | 0.01 |
| 311 | 0.03 |
| 312 | 0.01 |
| 313 | 0.28 |
| 314 | 0.02 |
| 315 | 0.18 |
| 316 | 0.02 |
| 317 | 0.2 |
| 318 | 0.03 |
| 319 | 0.01 |
| 320 | 0.01 |
| 321 | 0.01 |
| 322 | 0.02 |
| 323 | 0.01 |
| 324 | 0.02 |
| 325 | 0.01 |
| 326 | 0.01 |
| 327 | 0.03 |
| 328 | 0.01 |
| 329 | 0.17 |
| 330 | 0.04 |
| 331 | 0.012 |
| 332 | 0.007 |
| 333 | 0.008 |
| 334 | 0.008 |
| 335 | 0.05 |
| 336 | 0.21 |
| 337 | 0.08 |
| 338 | 0.25 |
| 339 | 0.12 |
| 340 | 0.04 |
| 341 | 1.35 |
| 342 | 0.03 |
| 343 | 0.02 |
| 344 | 0.01 |
| 345 | 0.02 |
| 346 | 0.02 |
| 347 | 0.01 |
| 348 | 0.01 |
| 349 | 0.01 |
| 350 | 0.01 |
| 351 | 0.01 |
| 352 | 0.03 |
| 353 | 0.01 |
| 354 | 0.05 |
| 355 | 0.05 |
| 356 | 0.1 |
| 357 | 0.05 |
| 358 | 0.05 |
| 359 | 0.03 |
| 360 | 0.01 |
| 361 | 0.11 |
| 362 | 0.01 |
| 363 | 0.03 |
| 364 | 0.01 |
| 365 | 0.05 |
| 366 | 0.29 |
| 367 | 0.08 |
| 368 | 0.08 |
| 369 | 0.02 |
| 370 | 0.08 |
| 371 | 0.02 |
| 372 | 0.017 |
| 373 | 0.07 |
| 374 | 0.4 |
| 375 | 0.0142 |

The invention claimed is:
1. A compound according to formula (I)

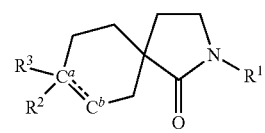

wherein
R$^1$ is selected from the group consisting of: alkyl, phenyl, phenylalkyl, pyridinyl, pyridinylalkyl, pyridazinyl, pyridazinylalkyl, pyrazolyl, pyrazolylalkyl, imidazolyl, imidazolylalkyl, triazolyl, triazolylalkyl, 2,2-difluoro-benzo[1,3]dioxolyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl, wherein said substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, cycloalkyl, cycloalkylalkyl, alkylcycloalkyl, alkylcycloalkylalkyl, halocycloalkyl, halocycloalkylalkyl, hydroxy, hydroxyalkyl, hydroxyhaloalkyl, alkoxy, haloalkoxy, alkoxyalkyl, alkoxyalkoxy, alkoxyalkoxyalkyl, alkoxyhaloalkyl, haloalkoxyalkyl, alkenyl, alkylsulfonyl, cycloalkylsulfonyl, cycloalkylsulfonyloxy and alkylsulfonyloxy;

$R^2$ is selected from the group consisting of: hydrogen, alkyl, cycloalkyl, cycloalkylalkyl, cycloalkylalkoxyalkyl, oxetanylalkoxylalkyl, alkyloxetanylalkoxylalkyl, hydroxyalkyl, hydroxyhaloalkyl, dihydroxyhaloalkyl, alkoxyalkyl, alkoxyalkoxyalkyl, haloalkyl, haloalkoxyalkyl, haloalkylalkoxyalkyl, alkylsulfinylalkyl, alkylsulfanylalkyl, alkylsulfonylalkyl, alkylcarbonyl, alkenyl, hydroxyalkenyl, alkoxyalkenyl, alkynyl, hydroxyalkynyl, alkoxyalkynyl, carboxyalkyl, alkoxycarbonylalkyl, dialkylaminocarbonylalkyl, alkylaminocarbonylalkyl, oxopyrrolydinylalkyl, oxopiperidinylalkyl, triazolyl, pyrazolyl, isoxazolyl, thiophenyl, phenoxyalkyl, pyridinyloxyalkyl, oxopyridinylalkyl, (hydroxy)(pyrazolyl)alkyl, pyrazolylalkyl, benzyloxyalkyl, phenyl, phenylalkyl, substituted cycloalkyl, substituted cycloalkylalkyl, substituted phenyl and substituted phenylalkyl, wherein said substituted cycloalkyl, substituted cycloalkylalkyl, substituted triazolyl, substituted pyrazolyl, substituted isoxazolyl, substituted thiophenyl, substituted phenoxyalkyl, substituted pyridinyloxyalkyl, substituted oxopyridinylalkyl, substituted pyrazolylalkyl, substituted phenyl and substituted phenylalkyl are substituted with one to three substituents independently selected from the group consisting of: halogen, alkyl, haloalkyl, cycloalkyl, cycloalkylalkyl, alkylcycloalkyl, alkylcycloalkylalkyl, halocycloalkyl, halocycloalkylalkyl, hydroxy, hydroxyalkyl, hydroxyhaloalkyl, alkoxy, haloalkoxy, alkoxyalkyl, alkoxyalkoxy, alkoxyalkoxyalkyl, alkoxyhaloalkyl, haloalkoxyalkyl, alkenyl, alkylsulfonyl, cycloalkylsulfonyl, cycloalkylsulfonyloxy and alkylsulfonyloxy;

$R^3$ is $R^4$-A-, wherein in case the bond between carbon $C^a$ and carbon $C^b$ is a carbon-carbon double bond then $R^3$ is absent;

or $R^2$ and $R^3$ together with the carbon $C^a$ to which they are attached form a carbonyl group of formula —$C^a(O)$— and the bond between carbon $C^a$ and carbon $C^b$ is a carbon-carbon single bond;

A is selected from the group consisting of: —O—, —S—, —S(O)—, —S(O)$_2$—, —S(O)$_2$O— and —NR$^6$C(O)O—;

$R^4$ is selected from the group consisting of: hydrogen, alkyl, cycloalkyl, cycloalkylalkyl, hydroxyalkyl, alkoxyalkyl, alkenyl, phenyl, phenylalkyl, pyridinyl, pyridinylalkyl, pyridazinyl, pyridazinylalkyl, pyrimidinyl, pyrimidinylalkyl, pyrazinyl, pyrazinylalkyl, pyrazolyl, pyrazolylalkyl, imidazolyl, imidazolylalkyl, triazolyl, triazolylalkyl, substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl, wherein said substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, alkoxy, haloalkoxy, cycloalkyl, cycloalkylalkyl, hydroxy, alkoxyalkyl, haloalkoxyalkyl and hydroxyalkyl;

$R^5$ is selected from the group consisting of: hydrogen, alkyl and cycloalkyl;

$R^6$ is selected from the group consisting of: hydrogen, alkyl and cycloalkyl; and the bond between carbon $C^a$ and carbon $C^b$ is a carbon-carbon single bond or a carbon-carbon double bond, wherein, when $R^1$ is alkyl, the bond between carbon $C^a$ and carbon $C^b$ is a carbon-carbon single bond;

or a pharmaceutically acceptable salt thereof.

2. A compound according to claim 1, wherein $R^1$ is selected from the group consisting of: alkyl, phenyl, phenylalkyl, pyridinyl, pyridinylalkyl, pyridazinyl, pyridazinylalkyl, pyrazolyl, pyrazolylalkyl, imidazolyl, imidazolylalkyl, triazolyl, triazolylalkyl, substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl, wherein said substituted phenyl, substituted phenylalkyl, substituted pyridinyl, substituted pyridinylalkyl, substituted pyridazinyl, substituted pyridazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, cycloalkyl, cycloalkylalkyl, alkylcycloalkyl, hydroxy, hydroxyalkyl, alkoxy, haloalkoxy, alkoxyalkyl, haloalkoxyalkyl, alkylsulfonyl and alkylsulfonyloxy;

$R^2$ is selected from the group consisting of: hydrogen, alkyl, cycloalkyl, cycloalkylalkyl, hydroxyalkyl, alkoxyalkyl, alkenyl, hydroxyalkenyl, alkoxyalkenyl, alkynyl, hydroxyalkynyl, alkoxyalkynyl, phenyl, phenylalkyl, substituted cycloalkyl, substituted cycloalkylalkyl, substituted phenyl and substituted phenylalkyl, wherein substituted cycloalkyl, substituted cycloalkylalkyl, substituted phenyl and substituted phenylalkyl are substituted with one to three substituents independently selected from the group consisting of: halogen, alkyl, haloalkyl, cycloalkyl, cycloalkylalkyl, alkylcycloalkyl, hydroxy, hydroxyalkyl, alkoxy, haloalkoxy, alkoxyalkyl, haloalkoxyalkyl, alkylsulfonyl and alkylsulfonyloxy;

R³ is R⁴-A-, wherein in case the bond between carbon Cᵃ and carbon Cᵇ is a carbon-carbon double bond then R³ is absent;

or R² and R³ together with the carbon Cᵃ to which they are attached form a carbonyl group of formula —Cᵃ(O)— and the bond between carbon Cᵃ and carbon Cᵇ is a carbon-carbon single bond;

A is selected from the group consisting of: —O—, —S—, —S(O)—, —S(O)₂—, —S(O)₂O— and —NR⁶C(O)O—;

R⁴ is selected from the group consisting of: hydrogen, alkyl, cycloalkyl, cycloalkylalkyl, hydroxyalkyl, alkoxyalkyl, alkenyl, phenyl, phenylalkyl, pyridinyl, pyridinylalkyl, pyridazinyl, pyridazinylalkyl, pyrimidinyl, pyrimidinylalkyl, pyrazinyl, pyrazinylalkyl, pyrazolyl, pyrazolylalkyl, imidazolyl, imidazolylalkyl, triazolyl, triazolylalkyl, substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl, wherein said substituted cycloalkyl, substituted cycloalkylalkyl, substituted phenyl, substituted phenylalkyl, substituted pyridinyl, substituted pyridinylalkyl, substituted pyridazinyl, substituted pyridazinylalkyl, substituted pyrimidinyl, substituted pyrimidinylalkyl, substituted pyrazinyl, substituted pyrazinylalkyl, substituted pyrazolyl, substituted pyrazolylalkyl, substituted imidazolyl, substituted imidazolylalkyl, substituted triazolyl and substituted triazolylalkyl are substituted with one to three substituents independently selected from the group consisting of: halogen, alkyl, haloalkyl, alkoxy, haloalkoxy, cycloalkyl, cycloalkylalkyl, hydroxy, alkoxyalkyl, haloalkoxyalkyl and hydroxyalkyl;

R⁵ is selected from the group consisting of: hydrogen, alkyl and cycloalkyl;

R⁶ is selected from the group consisting of: hydrogen, alkyl and cycloalkyl; and the bond between carbon Cᵃ and carbon Cᵇ is a carbon-carbon single bond or a carbon-carbon double bond, wherein, when R¹ is alkyl, the bond between carbon Cᵃ and carbon Cᵇ is a carbon-carbon single bond;

or a pharmaceutically acceptable salt thereof.

3. A compound according to claim 1, wherein R¹ is selected from the group consisting of: 2,2-difluoro-benzo[1,3]dioxolyl, substituted phenyl, substituted phenylalkyl, and substituted pyridinyl, wherein said substituted phenyl, substituted phenylalkyl, substituted pyridinyl are substituted with one to three substituents independently selected from the group consisting of: halogen, alkyl, haloalkyl, cycloalkyl, halocycloalkyl, hydroxyhaloalkyl, alkoxy, haloalkoxy, alkoxyalkyl, alkoxyalkoxy, alkoxyhaloalkyl, alkylsulfonyl, cycloalkylsulfonyloxy and alkylsulfonyloxy.

4. A compound according to claim 1, wherein R¹ is selected from the group consisting of: substituted phenyl, substituted phenylalkyl and substituted pyridinyl, wherein said substituted phenyl, substituted phenylalkyl and substituted pyridinyl are substituted with one to three substituents independently selected from the group consisting of: alkyl, haloalkyl, cycloalkyl, hydroxyhaloalkyl, alkoxy and haloalkoxy.

5. A compound according to claim 1, wherein R¹ is substituted phenyl or substituted phenylalkyl, wherein substituted phenyl and substituted phenylalkyl are substituted with one to three substituents independently selected from the group consisting of: halogen, alkyl, haloalkyl, cycloalkyl, alkoxy and haloalkoxy.

6. A compound according to claim 1, wherein R¹ is substituted phenyl, wherein substituted phenyl is substituted with one to three substituents independently selected from the group consisting of: alkyl, haloalkyl, cycloalkyl and haloalkoxy.

7. A compound according to claim 1, wherein R² is selected from the group consisting of: hydrogen, alkyl, cycloalkyl, cycloalkylalkoxyalkyl, oxetanylalkoxyalkyl, alkyloxetanylalkoxyalkyl, hydroxyalkyl, hydroxyhaloalkyl, dihydroxyhaloalkyl, alkoxyalkyl, alkoxyalkoxyalkyl, haloalkyl, haloalkoxyalkyl, haloalkylalkoxyalkyl, alkylsulfinylalkyl, alkylsulfanylalkyl, alkylsulfonylalkyl, alkenyl, alkynyl, alkoxyalkynyl, alkylcarbonyl, alkoxycarbonylalkyl, dialkylaminocarbonylalkyl, alkylaminocarbonylalkyl, oxopyrrolydinylalkyl, oxopiperidinylalkyl, triazolyl, thiophenyl, phenoxyalkyl, pyridinyloxyalkyl, oxopyridinylalkyl, (hydroxy)(pyrazolyl)alkyl, pyrazolylalkyl, benzyloxyalkyl, phenyl, phenylalkyl, substituted triazolyl, substituted pyrazolyl, substituted isoxazolyl and substituted phenoxyalkyl, wherein said substituted triazolyl, substituted pyrazolyl, substituted isoxazolyl and substituted phenoxyalkyl are substituted with one to three substituents independently selected from the group consisting of: halogen, alkyl and alkenyl.

8. A compound according to claim 1, wherein R² is selected from the group consisting of: hydrogen, alkyl, hydroxyhaloalkyl, alkoxyalkyl, haloalkyl, haloalkoxyalkyl, alkylsulfonylalkyl, alkoxyalkynyl, oxopyrrolydinylalkyl, oxopyridinylalkyl and substituted pyrazolyl, wherein said substituted pyrazolyl is substituted with one to three alkyls.

9. A compound according to claim 1, wherein R² is selected from the group consisting of: hydrogen, alkyl, cycloalkyl, alkoxyalkyl, alkenyl, alkoxyalkynyl and phenylalkyl.

10. A compound according to claim 1, wherein R² is selected from the group consisting of: hydrogen, alkyl, alkoxyalkyl and alkoxyalkynyl.

11. A compound according to claim 1, wherein A is —O— or —NR⁶C(O)O—.

12. A compound according to claim 1, wherein R⁴ is selected from the group consisting of: hydrogen, alkyl, cycloalkyl, cycloalkylalkyl, hydroxyalkyl, alkoxyalkyl, phenyl, phenylalkyl, pyrimidinyl, pyrazinyl, pyrazinylalkyl, substituted phenylalkyl, substituted pyridinylalkyl, substituted pyridazinyl and substituted pyrazinylalkyl, wherein said substituted phenylalkyl, substituted pyridinylalkyl, substituted pyridazinyl and substituted pyrazinylalkyl are substituted with one to three substituents independently selected from the group consisting of: halogen, alkyl and alkoxy.

13. A compound according to claim 1, wherein R⁴ is selected from the group consisting of: hydrogen, alkyl, alkoxyalkyl and pyrimidinyl.

14. A compound according to claim 1, wherein R⁴ is hydrogen.

15. A compound according to claim 1, wherein the bond between carbon Cᵃ and carbon Cᵇ is a carbon-carbon single bond.

16. A compound according to claim 1 selected from the group consisting of:
 (5α,8β)-8-Hydroxy-2-(4-trifluoromethoxy-phenyl)-2-aza-spiro[4.5]decan-1-one;
 (5α,8α)-8-Hydroxy-2-(4-trifluoromethoxy-phenyl)-2-aza-spiro[4.5]decan-1-one;
 (5α,8β)-8-Benzyloxy-2-(4-methoxy-phenyl)-2-aza-spiro[4.5]decan-1-one;

(5α,8β)-8-Benzyloxy-2-(4-ethyl-phenyl)-2-aza-spiro [4.5]decan-1-one;
(5α,8β)-2-(4-Ethyl-phenyl)-8-hydroxy-2-aza-spiro[4.5] decan-1-one;
Propyl-carbamic acid [(5α,8β)-2-(4-ethyl-phenyl)-1-oxo-2-aza-spiro[4.5]dec-8-yl]ester;
(3-Fluoro-benzyl)-carbamic acid [(5α,8β)-2-(4-ethyl-phenyl)-1-oxo-2-aza-spiro[4.5]dec-8-yl]ester;
Phenyl-carbamic acid [(5α,8β)-2-(4-ethyl-phenyl)-1-oxo-2-aza-spiro[4.5]dec-8-yl]ester;
(5α,8β)-8-Benzyloxy-2-(4-trifluoromethoxy-phenyl)-2-aza-spiro[4.5]decan-1-one; and
(3-Fluoro-benzyl)-carbamic acid [(5α,8β)-1-oxo-2-(4-trifluoromethoxy-phenyl)-2-aza-spiro[4.5]dec-8-yl]ester.

17. A compound according to claim 1 selected from the group consisting of:
Propyl-carbamic acid [(5α,8β)-1-oxo-2-(4-trifluoromethoxy-phenyl)-2-aza-spiro[4.5]dec-8-yl]ester;
Methyl-carbamic acid [(5α,8β)-1-oxo-2-(4-trifluoromethoxy-phenyl)-2-aza-spiro[4.5]dec-8-yl]ester;
(5α,8β)-8-(Pyrimidin-2-yloxy)-2-(4-trifluoromethoxy-phenyl)-2-aza-spiro[4.5]decan-1-one;
(5α,8β)-8-(2-Methoxy-ethoxy)-2-(4-trifluoromethoxy-phenyl)-2-aza-spiro[4.5]decan-1-one;
(5α,8α)-8-Ethyl-8-hydroxy-2-(4-trifluoromethoxy-phenyl)-2-aza-spiro[4.5]decan-1-one;
(5α,8α)-8-Butyl-8-hydroxy-2-(4-trifluoromethoxy-phenyl)-2-aza-spiro[4.5]decan-1-one;
(5α,8α)-8-Hydroxy-8-isopropyl-2-(4-trifluoromethoxy-phenyl)-2-aza-spiro[4.5]decan-1-one;
(5α,8α)-8-Hydroxy-8-(3-methoxy-prop-1-ynyl)-2-(4-trifluoromethoxy-phenyl)-2-aza-spiro[4.5]decan-1-one;
(5α,8α)-2-(4-Cyclopropyl-phenyl)-8-hydroxy-8-propyl-2-aza-spiro[4.5]decan-1-one;
(5α,8α)-8-Hydroxy-8-methyl-2-[4-(2,2,2-trifluoro-ethyl)-phenyl]-2-aza-spiro[4.5]decan-1-one;
(5α,8α)-8-Ethyl-8-hydroxy-2-[4-(2,2,2-trifluoro-ethyl)-phenyl]-2-aza-spiro[4.5]decan-1-one;
(5α,8α)-8-Ethyl-8-hydroxy-2-[4-(2,2,2-trifluoro-ethoxy)-phenyl]-2-aza-spiro[4.5]decan-1-one; and
(5α,8α)-8-Hydroxy-8-(3-methoxy-propyl)-2-(4-trifluoromethoxy-phenyl)-2-aza-spiro[4.5]decan-1-one.

18. A compound according to claim 1 selected from the group consisting of:
(5α,8α)-8-Hydroxy-8-(3-methoxy-prop-1-ynyl)-2-[4-(2,2,2-trifluoro-ethyl)-phenyl]-2-aza-spiro[4.5]decan-1-one;
(5α,8α)-8-Hydroxy-8-(3-methoxy-propyl)-2-[4-(2,2,2-trifluoro-ethyl)-phenyl]-2-aza-spiro[4.5]decan-1-one;
(5α,8α)-8-Hydroxy-2-[4-(3-methoxy-propoxy)-phenyl]-8-propyl-2-aza-spiro[4.5]decan-1-one;
(5α,8α)-8-Hydroxy-2-[4-(2-methoxy-ethoxy)-phenyl]-8-propyl-2-aza-spiro[4.5]decan-1-one;
(5α,8α)-8-Butyl-8-hydroxy-2-[4-(2-methoxy-ethoxy)-phenyl]-2-aza-spiro[4.5]decan-1-one;
(5α,8β)-8-Butyl-8-hydroxy-2-[4-(2-methoxy-ethoxy)-phenyl]-2-aza-spiro[4.5]decan-1-one;
(5α,8β)-8-Hydroxy-2-[4-(3,3,3-trifluoro-propoxy)-phenyl]-2-aza-spiro[4.5]decan-1-one;
(5α,8α)-8-Hydroxy-8-propyl-2-[4-(3,3,3-trifluoro-propoxy)-phenyl]-2-aza-spiro[4.5]decan-1-one;
(5α,8β)-8-Hydroxy-8-propyl-2-[4-(3,3,3-trifluoro-propoxy)-phenyl]-2-aza-spiro[4.5]decan-1-one; and
(5α,8α)-8-hydroxy-2-(6-isopropylpyridin-3-yl)-8-propyl-2-aza-spiro[4.5]decan-1-one.

19. A compound according to claim 1 selected from the group consisting of:
(5α,8α)-8-Hydroxy-8-isopropyl-2-[4-(2,2,2-trifluoro-ethoxy)-phenyl]-2-aza-spiro[4.5]decan-1-one;
(5α,8α)-8-hydroxy-8-isopropyl-2-(6-(2,2,2-trifluoroethoxy)pyridin-3-yl)-2-aza-spiro[4.5]decan-1-one;
(5α,8α)-8-hydroxy-8-isopropyl-2-(4-((R)-2,2,2-trifluoro-1-methoxyethyl)phenyl)-2-aza-spiro[4.5]decan-1-one;
(5α,8α)-8-Hydroxy-8-methoxymethyl-2-[4-((R)-2,2,2-trifluoro-1-methyl-ethoxy)-phenyl]-2-aza-spiro[4.5] decan-1-one;
(5α,8α)-8-Hydroxy-8-propyl-2-[4-((R)-2,2,2-trifluoro-1-methyl-ethoxy)-phenyl]-2-aza-spiro[4.5]decan-1-one;
(5α,8α)-8-Hydroxy-2-[6-(2,2,2-trifluoro-ethoxy)-pyridin-3-yl]-8-(3,3,3-trifluoro-propyl)-2-aza-spiro[4.5] decan-1-one;
(5α,8α)-8-Hydroxy-8-trifluoromethyl-2-[4-((R)-2,2,2-trifluoro-1-methyl-ethoxy)-phenyl]-2-aza-spiro[4.5] decan-1-one;
(5α,8α)-8-hydroxy-2-(4-isopropoxyphenyl)-8-(1-methyl-1H-pyrazol-3-yl)-2-aza-spiro[4.5]decan-1-one;
(5α,8α)-8-(2,2-Difluoro-ethoxymethyl)-8-hydroxy-2-[4-(2,2,2-trifluoro-ethoxy)-phenyl]-2-aza-spiro[4.5]decan-1-one;
(5α,8α)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one;
(5α,8α)-8-Hydroxy-8-(2-methyl-propane-2-sulfonylmethyl)-2-[6-((R)-2,2,2-trifluoro-1-methyl-ethoxy)-pyridin-3-yl]-2-aza-spiro[4.5]decan-1-one;
(5α,8α)-2-(4-tert-Butyl-phenyl)-8-hydroxy-8-(2-oxo-2H-pyridin-1-ylmethyl)-2-aza-spiro[4.5]decan-1-one;
(5α,8β)-2-(4-tert-Butyl-phenyl)-8-(2H-pyrazol-3-ylmethyl)-2-aza-spiro[4.5]decan-1-one;
(5α,8β)-8-(1-Hydroxy-propyl)-2-[4-((R)-2,2,2-trifluoro-1-methyl-ethoxy)-phenyl]-2-aza-spiro[4.5]decan-1-one; and
(5α,8α)-8-Hydroxy-8-(2-oxo-pyrrolidin-1-ylmethyl)-2-[4-(2,2,2-trifluoro-ethoxy)-phenyl]-2-aza-spiro[4.5]decan-1-one.

20. A pharmaceutical composition comprising a compound according to claim 1 and a therapeutically inert carrier.

21. A compound according to claim 1 selected from the group consisting of:
Propyl-carbamic acid [(5α,8β)-1-oxo-2-(4-trifluoromethoxy-phenyl)-2-aza-spiro[4.5]dec-8-yl]ester;
(3-Methoxy-benzyl)-carbamic acid [(5α,8β)-1-oxo-2-(4-trifluoromethoxy-phenyl)-2-aza-spiro[4.5]dec-8-yl]ester;
(4-Methoxy-benzyl)-carbamic acid [(5α,8β)-1-oxo-2-(4-trifluoromethoxy-phenyl)-2-aza-spiro[4.5]dec-8-yl]ester;
(2-Fluoro-benzyl)-carbamic acid [(5α,8β)-1-oxo-2-(4-trifluoromethoxy-phenyl)-2-aza-spiro[4.5]dec-8-yl]ester;
(4-Fluoro-benzyl)-carbamic acid [(5α,8β)-1-oxo-2-(4-trifluoromethoxy-phenyl)-2-aza-spiro[4.5]dec-8-yl]ester;
(5α,8β)-8-(6-Methyl-pyridin-2-ylmethoxy)-2-(4-trifluoromethoxy-phenyl)-2-aza-spiro[4.5]decan-1-one;
Methyl-carbamic acid [(5α,8β)-1-oxo-2-(4-trifluoromethoxy-phenyl)-2-aza-spiro[4.5]dec-8-yl]ester;
Phenethyl-carbamic acid [(5α,8β)-1-oxo-2-(4-trifluoromethoxy-phenyl)-2-aza-spiro[4.5]dec-8-yl]ester;
(5α,8β)-8-(Pyrazin-2-yloxy)-2-(4-trifluoromethoxy-phenyl)-2-aza-spiro[4.5]decan-1-one; and
(5α,8β)-8-(Pyrimidin-2-yloxy)-2-(4-trifluoromethoxy-phenyl)-2-aza-spiro[4.5]decan-1-one.

22. A compound according to claim 1 selected from the group consisting of:
- (5α,8β)-8-(6-Methyl-pyridazin-3-yloxy)-2-(4-trifluoromethoxy-phenyl)-2-aza-spiro[4.5]decan-1-one;
- (Cyclopropylmethyl)-carbamic acid [(5α,8β)-1-oxo-2-(4-trifluoromethoxy-phenyl)-2-aza-spiro[4.5]dec-8-yl]ester;
- (5α,8β)-8-(2-Methoxy-ethoxy)-2-(4-trifluoromethoxy-phenyl)-2-aza-spiro[4.5]decan-1-one;
- (5α,8β)-8-Ethoxy-2-(4-trifluoromethoxy-phenyl)-2-aza-spiro[4.5]decan-1-one;
- (5-Methyl-pyrazin-2-ylmethyl)-carbamic acid [(5α,8β)-1-oxo-2-(4-trifluoromethoxy-phenyl)-2-aza-spiro[4.5]dec-8-yl]ester;
- (2-Hydroxy-2-methyl-propyl)-carbamic acid [(5α,8β)-1-oxo-2-(4-trifluoromethoxy-phenyl)-2-aza-spiro[4.5]dec-8-yl]ester;
- (2-Hydroxy-ethyl)-carbamic acid [(5α,8β)-1-oxo-2-(4-trifluoromethoxy-phenyl)-2-aza-spiro[4.5]dec-8-yl]ester;
- (Pyrazin-2-ylmethyl)-carbamic acid [(5α,8β)-1-oxo-2-(4-trifluoromethoxy-phenyl)-2-aza-spiro[4.5]dec-8-yl]ester;
- Cyclopropyl-carbamic acid [(5α,8β)-1-oxo-2-(4-trifluoromethoxy-phenyl)-2-aza-spiro[4.5]dec-8-yl]ester; and
- Carbamic acid [(5α,8β)-1-oxo-2-(4-trifluoromethoxy-phenyl)-2-aza-spiro[4.5]dec-8-yl]ester.

23. A compound according to claim 1 selected from the group consisting of:
- (5α,8α)-8-Hydroxy-2-(4-methoxy-phenyl)-2-aza-spiro[4.5]decan-1-one;
- (5α,8α)-2-(4-Ethyl-phenyl)-8-hydroxy-2-aza-spiro[4.5]decan-1-one;
- (5α,8β)-2-[2-(4-Fluoro-phenyl)-ethyl]-8-hydroxy-2-aza-spiro[4.5]decan-1-one;
- (5α,8α)-2-[2-(4-Ethyl-phenyl)-ethyl]-8-hydroxy-2-aza-spiro[4.5]decan-1-one;
- (5α,8α)-8-Hydroxy-2-[2-(4-methoxy-phenyl)-ethyl]-2-aza-spiro[4.5]decan-1-one;
- (5α,8α)-2-(3-Chloro-benzyl)-8-hydroxy-2-aza-spiro[4.5]decan-1-one;
- (5α,8α)-8-Hydroxy-2-(4-propyl-phenyl)-2-aza-spiro[4.5]decan-1-one;
- (5α,8α)-8-Hydroxy-2-(4-isopropyl-phenyl)-2-aza-spiro[4.5]decan-1-one;
- (5α,8β)-2-(4-Cyclopropyl-phenyl)-8-hydroxy-2-aza-spiro[4.5]decan-1-one; and
- (5α,8β)-8-Benzyloxy-2-(4-methoxy-phenyl)-2-aza-spiro[4.5]decan-1-one.

24. A compound according to claim 1 selected from the group consisting of:
- (5α,8β)-8-Ethoxy-2-(4-trifluoromethoxy-phenyl)-2-aza-spiro[4.5]decan-1-one;
- (5α,8β)-8-Propoxy-2-(4-trifluoromethoxy-phenyl)-2-aza-spiro[4.5]decan-1-one;
- (5α,8β)-8-Benzyloxy-2-(4-ethyl-phenyl)-2-aza-spiro[4.5]decan-1-one;
- Propyl-carbamic acid [(5α,8β)-2-(4-ethyl-phenyl)-1-oxo-2-aza-spiro[4.5]dec-8-yl]ester;
- (3-Fluoro-benzyl)-carbamic acid [(5α,8β)-2-(4-ethyl-phenyl)-1-oxo-2-aza-spiro[4.5]dec-8-yl]ester;
- (5α,8β)-2-(4-Methoxy-phenyl)-8-phenoxy-2-aza-spiro[4.5]decan-1-one;
- 2-(4-Methoxy-phenyl)-2-aza-spiro[4.5]dec-7-en-1-one;
- (5α,8β)-2-(4-Methoxy-phenyl)-8-phenoxy-2-aza-spiro[4.5]decan-1-one;
- Methanesulfonic acid [(5α,8α)-1-oxo-2-(4-trifluoromethoxy-phenyl)-2-aza-spiro[4.5]dec-8-yl]ester; and
- 2-(4-Trifluoromethoxy-phenyl)-2-aza-spiro[4.5]dec-7-en-1-one.

25. A compound according to claim 1 selected from the group consisting of:
- (5α,8β)-8-Benzenesulfinyl-2-(4-trifluoromethoxy-phenyl)-2-aza-spiro[4.5]decan-1-one;
- (5α,8β)-8-Phenylsulfanyl-2-(4-trifluoromethoxy-phenyl)-2-aza-spiro[4.5]decan-1-one;
- (5α,8β)-8-Benzenesulfonyl-2-(4-trifluoromethoxy-phenyl)-2-aza-spiro[4.5]decan-1-one;
- 2-(4-Trifluoromethoxy-phenyl)-2-aza-spiro[4.5]decane-1,8-dione;
- (5α,8β)-8-Hydroxy-8-methyl-2-(4-trifluoromethoxy-phenyl)-2-aza-spiro[4.5]decan-1-one;
- (5α,8β)-8-Hydroxy-8-methyl-2-(4-trifluoromethoxy-phenyl)-2-aza-spiro[4.5]decan-1-one;
- 8-Methyl-2-(4-trifluoromethoxy-phenyl)-2-aza-spiro[4.5]dec-7-en-1-one;
- (5α,8α)-8-Ethyl-8-hydroxy-2-(4-trifluoromethoxy-phenyl)-2-aza-spiro[4.5]decan-1-one;
- (5α,8β)-8-Ethyl-8-hydroxy-2-(4-trifluoromethoxy-phenyl)-2-aza-spiro[4.5]decan-1-one; and
- (5α,8α)-8-Benzyl-8-hydroxy-2-(4-trifluoromethoxy-phenyl)-2-aza-spiro[4.5]decan-1-one.

26. A compound according to claim 1 selected from the group consisting of:
- (5α,8β)-8-Benzyl-8-hydroxy-2-(4-trifluoromethoxy-phenyl)-2-aza-spiro[4.5]decan-1-one;
- (5α,8α)-8-But-3-enyl-8-hydroxy-2-(4-trifluoromethoxy-phenyl)-2-aza-spiro[4.5]decan-1-one;
- (5α,8β)-8-But-3-enyl-8-hydroxy-2-(4-trifluoromethoxy-phenyl)-2-aza-spiro[4.5]decan-1-one;
- (5α,8α)-8-Butyl-8-hydroxy-2-(4-trifluoromethoxy-phenyl)-2-aza-spiro[4.5]decan-1-one;
- (5α,8β)-8-Butyl-8-hydroxy-2-(4-trifluoromethoxy-phenyl)-2-aza-spiro[4.5]decan-1-one;
- (5α,8α)-8-Hydroxy-8-isopropyl-2-(4-trifluoromethoxy-phenyl)-2-aza-spiro[4.5]decan-1-one;
- (5α,8β)-8-Hydroxy-8-isopropyl-2-(4-trifluoromethoxy-phenyl)-2-aza-spiro[4.5]decan-1-one;
- (5α,8α)-8-Cyclopropyl-8-hydroxy-2-(4-trifluoromethoxy-phenyl)-2-aza-spiro[4.5]decan-1-one;
- (5α,8β)-8-Hydroxy-8-(3-methoxy-prop-1-ynyl)-2-(4-trifluoromethoxy-phenyl)-2-aza-spiro [4.5]decan-1-one; and
- (5α,8β)-8-Hydroxy-8-(3-methoxy-prop-1-ynyl)-2-(4-trifluoromethoxy-phenyl)-2-aza-spiro[4.5]decan-1-one.

27. A compound according to claim 1 selected from the group consisting of:
- (5α,8α)-2-(4-Cyclopropyl-phenyl)-8-hydroxy-8-methyl-2-aza-spiro[4.5]decan-1-one;
- (5α,8β)-2-(4-Cyclopropyl-phenyl)-8-hydroxy-8-methyl-2-aza-spiro[4.5]decan-1-one;
- (5α,8α)-2-(4-Cyclopropyl-phenyl)-8-hydroxy-8-propyl-2-aza-spiro[4.5]decan-1-one;
- (5α,8β)-2-(4-Cyclopropyl-phenyl)-8-hydroxy-8-propyl-2-aza-spiro[4.5]decan-1-one;
- (5α,8α)-8-Hydroxy-8-methyl-2-[4-(2,2,2-trifluoro-ethyl)-phenyl]-2-aza-spiro[4.5]decan-1-one;
- (5α,8β)-8-Hydroxy-8-methyl-2-[4-(2,2,2-trifluoro-ethyl)-phenyl]-2-aza-spiro[4.5]decan-1-one;
- (5α,8α)-8-Ethyl-8-hydroxy-2-[4-(2,2,2-trifluoro-ethyl)-phenyl]-2-aza-spiro[4.5]decan-1-one;
- (5α,8β)-8-Ethyl-8-hydroxy-2-[4-(2,2,2-trifluoro-ethyl)-phenyl]-2-aza-spiro[4.5]decan-1-one;
- (5α,8α)-8-Hydroxy-8-propyl-2-[4-(2,2,2-trifluoro-ethyl)-phenyl]-2-aza-spiro[4.5]decan-1-one; and (5α,8β)-8-Hydroxy-8-propyl-2-[4-(2,2,2-trifluoro-ethyl)-phenyl]-2-aza-spiro[4.5]decan-1-one.

28. A compound according to claim 1 selected from the group consisting of:
   (5α,8α)-8-Ethyl-8-hydroxy-2-(4-propyl-phenyl)-2-aza-spiro[4.5]decan-1-one;
   (5α,8β)-8-Ethyl-8-hydroxy-2-(4-propyl-phenyl)-2-aza-spiro[4.5]decan-1-one;
   (5α,8β)-8-Hydroxy-2-[4-(2,2,2-trifluoro-ethoxy)-phenyl]-2-aza-spiro[4.5]decan-1-one;
   (5α,8α)-8-Hydroxy-8-methyl-2-[4-(2,2,2-trifluoro-ethoxy)-phenyl]-2-aza-spiro[4.5]decan-1-one;
   (5α,8β)-8-Hydroxy-8-methyl-2-[4-(2,2,2-trifluoro-ethoxy)-phenyl]-2-aza-spiro[4.5]decan-1-one;
   (5α,8α)-8-Ethyl-8-hydroxy-2-[4-(2,2,2-trifluoro-ethoxy)-phenyl]-2-aza-spiro[4.5]decan-1-one;
   (5α,8β)-8-Ethyl-8-hydroxy-2-[4-(2,2,2-trifluoro-ethoxy)-phenyl]-2-aza-spiro[4.5]decan-1-one;
   (5α,8α)-8-Hydroxy-8-(3-methoxy-propyl)-2-(4-trifluoromethoxy-phenyl)-2-aza-spiro[4.5]decan-1-one; and
   (5α,8β)-8-Hydroxy-8-(3-methoxy-propyl)-2-(4-trifluoromethoxy-phenyl)-2-aza-spiro[4.5]decan-1-one.

29. A compound according to claim 1 selected from the group consisting of:
   (5α,8α)-8-hydroxy-8-isopropyl-2-(6-isopropylpyridin-3-yl)-2-aza-spiro[4.5]decan-1-one;
   (5α,8α)-8-Hydroxy-8-isopropyl-2-[4-(2,2,2-trifluoro-ethoxy)-phenyl]-2-aza-spiro[4.5]decan-1-one;
   8-Hydroxy-8-propyl-2-[4-(2,2,2-trifluoro-ethoxy)-phenyl]-2-aza-spiro[4.5]decan-1-one;
   (5α,8α)-8-hydroxy-8-(prop-1-en-2-yl)-2-(4-(2,2,2-trifluoroethoxy)phenyl)-2-aza-spiro[4.5]decan-1-one;
   (5α,8β)-8-hydroxy-8-(prop-1-en-2-yl)-2-(4-(2,2,2-trifluoroethoxy)phenyl)-2-aza-spiro[4.5]decan-1-one;
   (5α,8β)-8-hydroxy-8-isopropyl-2-(4-(2,2,2-trifluoroethoxy)phenyl)-2-aza-spiro[4.5]decan-1-one;
   (5α,8α)-8-hydroxy-8-isopropyl-2-(6-(2,2,2-trifluoroethoxy)pyridin-3-yl)-2-aza-spiro[4.5]decan-1-one;
   (5α,8β)-8-hydroxy-8-isopropyl-2-(6-(2,2,2-trifluoroethoxy)pyridin-3-yl)-2-aza-spiro[4.5]decan-1-one; and
   (5α,8α)-8-hydroxy-8-(methoxymethyl)-2-(6-(2,2,2-trifluoroethoxy)pyridin-3-yl)-2-aza-spiro[4.5]decan-1-one.

30. A compound according to claim 1 selected from the group consisting of:
   (5α,8α)-8-Hydroxy-8-prop-1-ynyl-2-[4-(2,2,2-trifluoroethoxy)-phenyl]-2-aza-spiro[4.5]decan-1-one;
   (5α,8α)-8-Hydroxy-2-(4-trifluoromethoxy-phenyl)-8-trifluoromethyl-2-aza-spiro[4.5]decan-1-one;
   (5α,8β)-8-Hydroxy-2-(4-trifluoromethoxy-phenyl)-8-trifluoromethyl-2-aza-spiro[4.5]decan-1-one;
   (5α,8α)-8-Hydroxy-8-methoxymethyl-2-(4-trifluoromethoxy-phenyl)-2-aza-spiro[4.5]decan-1-one;
   (5α,8β)-8-Hydroxy-8-methoxymethyl-2-(4-trifluoromethoxy-phenyl)-2-aza-spiro[4.5]decan-1-one;
   [(5α,8α)-8-Hydroxy-1-oxo-2-(4-trifluoromethoxy-phenyl)-2-aza-spiro[4.5]dec-8-yl]-acetic acid ethyl ester;
   (5α,8α)-8-Ethoxymethyl-8-hydroxy-2-(4-trifluoromethoxy-phenyl)-2-aza-spiro[4.5]decan-1-one;
   (5α,8α)-8-Hydroxy-8-(2-hydroxy-ethyl)-2-(4-trifluoromethoxy-phenyl)-2-aza-spiro[4.5]decan-1-one;
   (5α,8α)-8-Hydroxy-8-(2-methoxy-ethyl)-2-(4-trifluoromethoxy-phenyl)-2-aza-spiro[4.5]decan-1-one; and
   (5α,8α)-8-Methoxy-8-(2-methoxy-ethyl)-2-(4-trifluoromethoxy-phenyl)-2-aza-spiro[4.5]decan-1-one.

31. A compound according to claim 1 selected from the group consisting of:
   (5α,8α)-8-Hydroxy-8-methoxymethyl-2-(4-trifluoromethyl-phenyl)-2-aza-spiro[4.5]decan-1-one;
   (5α,8α)-8-Hydroxy-2-[4-(2-methoxy-ethyl)-phenyl]-8-propyl-2-aza-spiro[4.5]decan-1-one;
   (5α,8α)-8-Hydroxy-2-[4-(2-methoxy-ethyl)-phenyl]-8-trifluoromethyl-2-aza-spiro[4.5]decan-1-one;
   (5α,8α)-8-Hydroxy-8-isobutyl-2-[4-(2-methoxy-ethyl)-phenyl]-2-aza-spiro[4.5]decan-1-one;
   (5α,8β)-8-Hydroxy-8-isobutyl-2-[4-(2-methoxy-ethyl)-phenyl]-2-aza-spiro[4.5]decan-1-one;
   (5α,8α)-8-(2,2-Dimethyl-propyl)-8-hydroxy-2-[4-(2-methoxy-ethyl)-phenyl]-2-aza-spiro[4.5]decan-1-one;
   (5α,8α)-8-Hydroxy-8-isopropenyl-2-[4-(2-methoxy-ethyl)-phenyl]-2-aza-spiro[4.5]decan-1-one;
   (5α,8α)-8-Hydroxy-8-isopropyl-2-[4-(2-methoxy-ethyl)-phenyl]-2-aza-spiro[4.5]decan-1-one;
   (5α,8α)-8-Butyl-8-hydroxy-2-[4-(2-methoxy-ethyl)-phenyl]-2-aza-spiro[4.5]decan-1-one; and
   (5α,8α)-8-hydroxy-8-isopropyl-2-(4-(3-methoxypropyl)phenyl)-2-aza-spiro[4.5]decan-1-one.

32. A compound according to claim 1 selected from the group consisting of:
   (5α,8α)-8-Ethyl-8-hydroxy-2-[4-(2-methoxy-1,1-dimethyl-ethyl)-phenyl]-2-aza-spiro[4.5]decan-1-one;
   (5α,8α)-8-Hydroxy-2-[4-(2-methoxy-1,1-dimethyl-ethyl)-phenyl]-8-propyl-2-aza-spiro[4.5]decan-1-one;
   (5α,8α)-8-hydroxy-8-propyl-2-(4-(2,2,2-trifluoro-1-hydroxyethyl)phenyl)-2-aza-spiro[4.5]decan-1-one;
   (5α,8α)-8-Hydroxy-8-propyl-2-[4-((S)-2,2,2-trifluoro-1-hydroxy-ethyl)-phenyl]-2-aza-spiro[4.5]decan-1-one;
   (5α,8α)-8-Hydroxy-8-propyl-2-[4-((R)-2,2,2-trifluoro-1-hydroxy-ethyl)-phenyl]-2-aza-spiro[4.5]decan-1-one;
   (5α,8β)-8-hydroxy-8-propyl-2-(4-(2,2,2-trifluoro-1-hydroxyethyl)phenyl)-2-aza-spiro[4.5]decan-1-one;
   (5α,8α)-8-Hydroxy-8-isopropyl-2-[4-((R)-2,2,2-trifluoro-1-hydroxy-ethyl)-phenyl]-2-aza-spiro[4.5]decan-1-one;
   (5α,8β)-8-hydroxy-8-isopropyl-2-(4-((R)-2,2,2-trifluoro-1-hydroxy-ethyl)-phenyl)-2-aza-spiro[4.5]decan-1-one;
   (5α,8α)-8-hydroxy-8-isopropyl-2-(4-((R)-2,2,2-trifluoro-1-methoxyethyl)phenyl)-2-aza-spiro[4.5]decan-1-one; and
   (5α,8α)-8-hydroxy-8-(methoxymethyl)-2-(4-((R)-2,2,2-trifluoro-1-hydroxyethyl)phenyl)-2-aza-spiro[4.5]decan-1-one.

33. A compound according to claim 1 selected from the group consisting of:
   (5α,8α)-8-hydroxy-8-(methoxymethyl)-2-(4-((R)-2,2,2-trifluoro-1-methoxyethyl)phenyl)-2-aza-spiro[4.5]decan-1-one;
   (5α,8α)-2-(4-((R)-1-ethoxy-2,2,2-trifluoroethyl)phenyl)-8-hydroxy-8-(methoxymethyl)-2-aza-spiro[4.5]decan-1-one;
   (5α,8α)-8-hydroxy-8-(methoxymethyl)-2-(4-((R)-2,2,2-trifluoro-1-propoxyethyl)phenyl)-2-aza-spiro[4.5]decan-1-one;
   (5α,8α)-8-Allyl-8-hydroxy-2-[4-((R)-2,2,2-trifluoro-1-methyl-ethoxy)-phenyl]-2-aza-spiro[4.5]decan-1-one;
   (5α,8β)-8-Allyl-8-hydroxy-2-[4-((R)-2,2,2-trifluoro-1-methyl-ethoxy)-phenyl]-2-aza-spiro[4.5]decan-1-one;
   (5α,8α)-8-Benzyloxymethyl-8-hydroxy-2-[4-((R)-2,2,2-trifluoro-1-methyl-ethoxy)-phenyl]-2-aza-spiro[4.5]decan-1-one;

(5α,8α)-8-Hydroxy-8-hydroxymethyl-2-[4-((R)-2,2,2-trifluoro-1-methyl-ethoxy)-phenyl]-2-aza-spiro[4.5]decan-1-one;
(5α,8α)-8-Hydroxy-8-methoxymethyl-2-[4-((S)-2,2,2-trifluoro-1-methyl-ethoxy)-phenyl]-2-aza-spiro[4.5]decan-1-one;
(5α,8α)-8-Hydroxy-8-methoxymethyl-2-[4-((R)-2,2,2-trifluoro-1-methyl-ethoxy)-phenyl]-2-aza-spiro[4.5]decan-1-one; and
(5α,8α)-8-Hydroxy-8-isopropyl-2-[6-((S)-2,2,2-trifluoro-1-methyl-ethoxy)-pyridin-3-yl]-2-aza-spiro[4.5]decan-1-one.

34. A compound according to claim 1 selected from the group consisting of:
(5α,8β)-8-Hydroxy-8-isopropyl-2-[6-((S)-2,2,2-trifluoro-1-methyl-ethoxy)-pyridin-3-yl]-2-aza-spiro[4.5]decan-1-one;
(5α,8α)-8-Hydroxy-8-isopropyl-2-[6-((R)-2,2,2-trifluoro-1-methyl-ethoxy)-pyridin-3-yl]-2-aza-spiro[4.5]decan-1-one;
(5α,8β)-8-Hydroxy-8-isopropyl-2-[6-((R)-2,2,2-trifluoro-1-methyl-ethoxy)-pyridin-3-yl]-2-aza-spiro[4.5]decan-1-one;
(5α,8α)-8-Hydroxy-8-m ethoxymethyl-2-[6-((R)-2,2,2-trifluoro-1-m ethyl-ethoxy)-pyridin-3-yl]-2-aza-spiro[4.5]decan-1-one;
(5α,8α)-8-Hydroxy-8-methoxymethyl-2-[6-((S)-2,2,2-trifluoro-1-methyl-ethoxy)-pyridin-3-yl]-2-aza-spiro[4.5]decan-1-one;
(5α,8α)-8-Hydroxy-8-methoxymethyl-2-[4-(2,2,2-trifluoro-ethyl)-phenyl]-2-aza-spiro[4.5]decan-1-one;
(5α,8α)-8-Hydroxy-8-(2,2,2-trifluoro-ethoxymethyl)-2-[4-((R)-2,2,2-trifluoro-1-hydroxy-ethyl)-phenyl]-2-aza-spiro[4.5]decan-1-one;
2-[(5α,8α)-8-Hydroxy-1-oxo-2-(4-trifluoromethoxy-phenyl)-2-aza-spiro[4.5]dec-8-yl]-N,N-dimethyl-acetamide;
2-((5α,8α)-8-hydroxy-1-oxo-2-(4-(2,2,2-trifluoroethoxy)phenyl)-2-aza-spiro[4.5]decan-8-yl)-N,N-dimethylacetamide; and
2-((5α,8α)-8-hydroxy-1-oxo-2-(4-(2,2,2-trifluoroethoxy)phenyl)-2-aza-spiro[4.5]decan-8-yl)-N-methylacetamide.

35. A compound according to claim 1 selected from the group consisting of:
(5α,8α)-8-Hydroxy-8-isopropoxymethyl-2-[4-((R)-2,2,2-trifluoro-1-hydroxy-ethyl)-phenyl]-2-aza-spiro[4.5]decan-1-one;
(5α,8α)-8-(2,2-Difluoro-ethoxymethyl)-8-hydroxy-2-[4-((R)-2,2,2-trifluoro-1-hydroxy-ethyl)-phenyl]-2-aza-spiro[4.5]decan-1-one;
(5α,8α)-2-(4-ethylphenethyl)-8-hydroxy-8-isopropyl-2-aza-spiro[4.5]decan-1-one;
8-Hydroxy-2-[4-(2,2,2-trifluoro-1-methyl-ethoxy)-phenyl]-2-aza-spiro[4.5]decan-1-one;
(5α,8β)-8-Hydroxy-8-propyl-2-[4-(2,2,2-trifluoro-1-methyl-ethoxy)-phenyl]-2-aza-spiro[4.5]decan-1-one;
(5α,8α)-8-Hydroxy-8-propyl-2-[4-(2,2,2-trifluoro-1-methyl-ethoxy)-phenyl]-2-aza-spiro[4.5]decan-1-one;
(5α,8α)-8-Hydroxy-8-propyl-2-[4-((S)-2,2,2-trifluoro-1-methyl-ethoxy)-phenyl]-2-aza-spiro[4.5]decan-1-one;
(5α,8α)-8-Hydroxy-8-propyl-2-[4-((R)-2,2,2-trifluoro-1-methyl-ethoxy)-phenyl]-2-aza-spiro[4.5]decan-1-one;
(5α,8α)-8-Ethyl-8-hydroxy-2-[4-(2,2,2-trifluoro-1-methyl-ethoxy)-phenyl]-2-aza-spiro[4.5]decan-1-one; and
(5α,8α)-8-Ethyl-8-hydroxy-2-[4-((S)-2,2,2-trifluoro-1-methyl-ethoxy)-phenyl]-2-aza-spiro[4.5]decan-1-one.

36. A compound according to claim 1 selected from the group consisting of:
(5α,8α)-8-Ethyl-8-hydroxy-2-[4-((R)-2,2,2-trifluoro-1-methyl-ethoxy)-phenyl]-2-aza-spiro[4.5]decan-1-one;
(5α,8α)-8-Hydroxy-2-[6-(2,2,2-trifluoro-ethoxy)-pyridin-3-yl]-8-(3,3,3-trifluoro-propyl)-2-aza-spiro[4.5]decan-1-one;
(5α,8α)-8-Hydroxy-8-propyl-2-[6-(2,2,2-trifluoro-ethoxy)-pyridin-3-yl]-2-aza-spiro[4.5]decan-1-one;
(5α,8α)-8-Ethyl-8-hydroxy-2-[6-(2,2,2-trifluoro-ethoxy)-pyridin-3-yl]-2-aza-spiro[4.5]decan-1-one;
(5α,8α)-8-Ethyl-8-hydroxy-2-[4-(3,3,3-trifluoro-propyl)-phenyl]-2-aza-spiro[4.5]decan-1-one;
(5α,8α)-8-Hydroxy-8-propyl-2-[4-(3,3,3-trifluoro-propyl)-phenyl]-2-aza-spiro[4.5]decan-1-one;
(5α,8α)-8-Ethyl-8-hydroxy-2-[6-((S)-2,2,2-trifluoro-1-methyl-ethoxy)-pyridin-3-yl]-2-aza-spiro[4.5]decan-1-one;
(5α,8α)-8-Hydroxy-8-propyl-2-[6-((S)-2,2,2-trifluoro-1-methyl-ethoxy)-pyridin-3-yl]-2-aza-spiro[4.5]decan-1-one;
(5α,8α)-8-Hydroxy-8-trifluoromethyl-2-[6-((S)-2,2,2-trifluoro-1-methyl-ethoxy)-pyridin-3-yl]-2-aza-spiro[4.5]decan-1-one; and
(5α,8α)-8-Hydroxy-8-trifluoromethyl-2-[6-((R)-2,2,2-trifluoro-1-methyl-ethoxy)-pyridin-3-yl]-2-aza-spiro[4.5]decan-1-one.

37. A compound according to claim 1 selected from the group consisting of:
(5α,8α)-8-Ethyl-8-hydroxy-2-[6-((R)-2,2,2-trifluoro-1-methyl-ethoxy)-pyridin-3-yl]-2-aza-spiro[4.5]decan-1-one;
(5α,8α)-8-Hydroxy-8-propyl-2-[6-((R)-2,2,2-trifluoro-1-methyl-ethoxy)-pyridin-3-yl]-2-aza-spiro[4.5]decan-1-one;
(5α,8α)-8-Hydroxy-8-trifluoromethyl-2-[4-(2,2,2-trifluoro-1-methyl-ethoxy)-phenyl]-2-aza-spiro[4.5]decan-1-one;
(5α,8α)-8-Hydroxy-8-trifluoromethyl-2-[4-((S)-2,2,2-trifluoro-1-methyl-ethoxy)-phenyl]-2-aza-spiro[4.5]decan-1-one;
(5α,8α)-8-Hydroxy-8-trifluoromethyl-2-[4-((R)-2,2,2-trifluoro-1-methyl-ethoxy)-phenyl]-2-aza-spiro[4.5]decan-1-one,
(5α,8α)-8-Hydroxy-2-[6-(2,2,2-trifluoro-ethoxy)-pyridin-3-yl]-8-trifluoromethyl-2-aza-spiro[4.5]decan-1-one;
(5α,8α)-8-Cyclopropyl-8-hydroxy-2-[6-((R)-2,2,2-trifluoro-1-methyl-ethoxy)-pyridin-3-yl]-2-aza-spiro[4.5]decan-1-one;
(5α,8α)-8-Cyclopropyl-8-hydroxy-2-[6-((S)-2,2,2-trifluoro-1-methyl-ethoxy)-pyridin-3-yl]-2-aza-spiro[4.5]decan-1-one;
(5α,8α)-8-Cyclopropyl-8-hydroxy-2-[4-(2,2,2-trifluoro-1-methyl-ethoxy)-phenyl]-2-aza-spiro[4.5]decan-1-one; and
(5α,8α)-8-Cyclopropyl-8-hydroxy-2-[4-((R)-2,2,2-trifluoro-1-methyl-ethoxy)-phenyl]-2-aza-spiro[4.5]decan-1-one.

38. A compound according to claim 1 selected from the group consisting of:
4-((5α,8α)-8-hydroxy-1-oxo-8-propyl-2-aza-spiro[4.5]decan-2-yl)phenyl cyclopropanesulfonate;
4-((5α,8α)-8-ethyl-8-hydroxy-1-oxo-2-aza-spiro[4.5]decan-2-yl)phenyl cyclopropanesulfonate;
(5α,8α)-8-hydroxy-2-(4-isopropoxyphenyl)-8-propyl-2-aza-spiro[4.5]decan-1-one;

4-((5α,8β))-8-hydroxy-1-oxo-8-propyl-2-aza-spiro[4.5]
  decan-2-yl)phenyl methanesulfonate;
(5α,8α)-8-Ethyl-8-hydroxy-2-(4-isopropoxy-phenyl)-2-
  aza-spiro[4.5]decan-1-one;
(5α,8α)-2-(4-Ethanesulfonyl-phenyl)-8-hydroxy-8-pro-
  pyl-2-aza-spiro[4.5]decan-1-one;
(5α,8α)-8-hydroxy-8-propyl-2-(4-(trifluoromethoxy)
  benzyl)-2-aza-spiro[4.5]decan-1-one;
4-((5α,8α)-8-hydroxy-1-oxo-8-(trifluoromethyl)-2-aza-
  spiro[4.5]decan-2-yl)phenyl cyclopropanesulfonate;
(5α,8α)-8-butyl-8-hydroxy-2-(4-((R)-2,2,2-trifluoro-1-
  hydroxyethyl)phenyl)-2-aza-spiro[4.5]decan-1-one;
  and
(5α,8α)-2-(4-(2,2-difluoro-1-hydroxypropyl)phenyl)-8-
  hydroxy-8-isopropyl-2-aza-spiro[4.5]decan-1-one.

39. A compound according to claim 1 selected from the group consisting of:
(5α,8α)-2-(4-(2,2-difluoro-1-hydroxypropyl)phenyl)-8-
  hydroxy-8-propyl-2-aza-spiro[4.5]decan-1-one;
(5α,8α)-2-(4-(2,2-difluoro-1-hydroxypropyl)phenyl)-8-
  hydroxy-8-(3,3,3-trifluoropropyl)-2-aza-spiro[4.5]de-
  can-1-one;
(5α,8α)-8-hydroxy-2-(4-((R)-2,2,2-trifluoro-1-hydroxy-
  ethyl)phenyl)-8-(3,3,3-trifluoropropyl)-2-aza-spiro
  [4.5]decan-1-one;
(5α,8α)-2-(4-(2,2-difluoro-1-hydroxyethyl)phenyl)-8-hy-
  droxy-8-propyl-2-aza-spiro[4.5]decan-1-one;
(5α,8α)-8-hydroxy-2-(4-isopropoxyphenyl)-8-isopropyl-
  2-aza-spiro[4.5]decan-1-one;
(5α,8α)-8-cyclopropyl-8-hydroxy-2-(4-isopropoxyphe-
  nyl)-2-aza-spiro[4.5]decan-1-one;
(5α,8α)-8-cyclopentyl-8-hydroxy-2-(4-isopropoxyphe-
  nyl)-2-aza-spiro[4.5]decan-1-one;
(5α,8α)-8-hydroxy-8-isobutyl-2-(4-isopropoxyphenyl)-
  2-aza-spiro[4.5]decan-1-one;
(5α,8α)-8-cyclobutyl-8-hydroxy-2-(4-((R)-2,2,2-trif-
  luoro-1-hydroxyethyl)phenyl)-2-aza-spiro[4.5]decan-
  1-one; and
(5α,8α)-8-cyclopropyl-8-hydroxy-2-(4-((R)-2,2,2-trif-
  luoro-1-hydroxyethyl)phenyl)-2-aza-spiro[4.5]decan-
  1-one.

40. A compound according to claim 1 selected from the group consisting of:
(5α,8α)-8-cyclopentyl-8-hydroxy-2-(4-((R)-2,2,2-trif-
  luoro-1-hydroxyethyl)phenyl)-2-aza-spiro[4.5]decan-
  1-one;
(5α,8α)-8-hydroxy-8-isopropyl-2-(4-isopropylphenyl)-2-
  aza-spiro[4.5]decan-1-one;
(5α,8α)-8-hydroxy-2-(4-isopropylphenyl)-8-propyl-2-
  aza-spiro[4.5]decan-1-one;
(5α,8α)-8-hydroxy-2-(4-isopropylphenyl)-8-phenyl-2-
  aza-spiro[4.5]decan-1-one;
(5α,8α)-8-hydroxy-2-(4-isopropoxyphenyl)-8-phenyl-2-
  aza-spiro[4.5]decan-1-one;
(5α,8α)-2-(4-(2,2-difluoro-1-hydroxyethyl)phenyl)-8-hy-
  droxy-8-isopropyl-2-aza-spiro[4.5]decan-1-one;
(5α,8α)-8-hydroxy-8-propyl-2-(4-(trifluoromethyl)phe-
  nyl)-2-aza-spiro[4.5]decan-1-one;
(5α,8α)-8-hydroxy-8-isopropyl-2-(4-(trifluoromethyl)
  phenyl)-2-aza-spiro[4.5]decan-1-one;
(5α,8α)-8-hydroxy-2-(4-isopropoxyphenyl)-8-(meth-
  oxymethyl)-2-aza-spiro[4.5]decan-1-one; and
(5α,8α)-8-hydroxy-2-(4-isopropoxyphenyl)-8-(thiophen-
  3-yl)-2-aza-spiro[4.5]decan-1-one.

41. A compound according to claim 1 selected from the group consisting of:
(5α,8α)-8-(5-Bromo-3-methyl-3H-[1,2,3]triazol-4-yl)-8-
  hydroxy-2-(4-isopropoxy-phenyl)-2-aza-spiro[4.5]de-
  can-1-one;
(5α,8α)-8-hydroxy-2-(4-isopropoxyphenyl)-8-(1-methyl-
  1H-1,2,3-triazol-4-yl)-2-aza-spiro[4.5]decan-1-one;
(5α,8α)-8-(5-Bromo-3-methyl-3H-[1,2,3]triazol-4-yl)-8-
  hydroxy-2-(4-trifluoromethyl-phenyl)-2-aza-spiro[4.5]
  decan-1-one;
(5α,8α)-8-Hydroxy-8-(3-methyl-3H-[1,2,3]triazol-4-yl)-
  2-(4-trifluoromethyl-phenyl)-2-aza-spiro[4.5]decan-1-
  one;
(5α,8α)-8-hydroxy-2-(4-isopropylphenyl)-8-((2,2,2-trif-
  luoroethoxy)methyl)-2-aza-spiro[4.5]decan-1-one;
(5α,8α)-8-hydroxy-2-(4-isopropoxyphenyl)-8-(1-methyl-
  1H-pyrazol-3-yl)-2-aza-spiro[4.5]decan-1-one;
(5α,8α)-8-hydroxy-2-(4-isopropylphenyl)-8-(methoxym-
  ethyl)-2-aza-spiro[4.5]decan-1-one;
(5α,8α)-8-hydroxy-8-((2,2,2-trifluoroethoxy)methyl)-2-
  (4-(trifluoromethyl)phenyl)-2-aza-spiro[4.5]decan-1-
  one;
(5α,8α)-8-hydroxy-2-(4-isopropoxyphenyl)-8-((5-meth-
  ylisoxazol-3-yl)methyl)-2-aza-spiro[4.5]decan-1-one;
  and
(5α,8β)-8-hydroxy-2-(4-isopropoxyphenyl)-8-((5-meth-
  ylisoxazol-3-yl)methyl)-2-aza-spiro[4.5]decan-1-one.

42. A compound according to claim 1 selected from the group consisting of:
(5α,8α)-8-hydroxy-2-(4-isopropoxyphenyl)-8-(1-methyl-
  4-vinyl-1H-1,2,3-triazol-5-yl)-2-aza-spiro[4.5]decan-
  1-one;
(5α,8α)-2-(4-Cyclopropyl-phenyl)-8-hydroxy-8-meth-
  oxymethyl-2-aza-spiro[4.5]decan-1-one;
(5α,8α)-2-(4-Ethyl-phenyl)-8-hydroxy-8-methoxym-
  ethyl-2-aza-spiro[4.5]decan-1-one;
(5α,8α)-8-Ethoxymethyl-2-(4-ethyl-phenyl)-8-hydroxy-
  2-aza-spiro[4.5]decan-1-one;
(5α,8α)-2-(4-Ethyl-phenyl)-8-hydroxy-8-propoxym-
  ethyl-2-aza-spiro[4.5]decan-1-one;
(5α,8β)-2-(4-Ethyl-phenyl)-8-hydroxy-8-phenoxym-
  ethyl-2-aza-spiro[4.5]decan-1-one;
(5α,8α)-2-(4-Ethyl-phenyl)-8-hydroxy-8-phenoxym-
  ethyl-2-aza-spiro[4.5]decan-1-one;
(5α,8α)-2-(4-Ethyl-phenyl)-8-hydroxy-8-(2-methoxy-
  ethoxymethyl)-2-aza-spiro[4.5]decan-1-one;
(5α,8β)-2-(4-Ethyl-phenyl)-8-hydroxy-8-(2,2,2-trifluoro-
  ethoxymethyl)-2-aza-spiro[4.5]decan-1-one; and
(5α,8α)-2-(4-Ethyl-phenyl)-8-hydroxy-8-(2,2,2-trif-
  luoro-ethoxymethyl)-2-aza-spiro[4.5]decan-1-one.

43. A compound according to claim 1 selected from the group consisting of:
(5α,8β)-8-Hydroxy-8-(2,2,2-trifluoro-ethoxymethyl)-2-
  [4-(2,2,2-trifluoro-ethoxy)-phenyl]-2-aza-spiro[4.5]de-
  can-1-one;
(5α,8α)-8-Hydroxy-8-(2,2,2-trifluoro-ethoxymethyl)-2-
  [4-(2,2,2-trifluoro-ethoxy)-phenyl]-2-aza-spiro[4.5]de-
  can-1-one;
(5α,8α)-8-Ethoxymethyl-8-hydroxy-2-[4-(2,2,2-trif-
  luoro-ethoxy)-phenyl]-2-aza-spiro[4.5]decan-1-one;
(5α,8β)-8-Hydroxy-8-propoxymethyl-2-[4-(2,2,2-trif-
  luoro-ethoxy)-phenyl]-2-aza-spiro[4.5]decan-1-one;
(5α,8α)-8-Hydroxy-8-propoxymethyl-2-[4-(2,2,2-trif-
  luoro-ethoxy)-phenyl]-2-aza-spiro[4.5]decan-1-one,
(5α,8β)-8-Butoxymethyl-8-hydroxy-2-[4-(2,2,2-trif-
  luoro-ethoxy)-phenyl]-2-aza-spiro[4.5]decan-1-one, (5α,8α)-8-Butoxymethyl-8-hydroxy-2-[4-(2,2,2-trifluoro-ethoxy)-phenyl]-2-aza-spiro[4.5]decan-1-one;
(5α,8β)-8-Hydroxy-8-phenoxymethyl-2-[4-(2,2,2-trifluoro-ethoxy)-phenyl]-2-aza-spiro[4.5]decan-1-one;
(5α,8α)-8-Hydroxy-8-phenoxymethyl-2-[4-(2,2,2-trifluoro-ethoxy)-phenyl]-2-aza-spiro[4.5]decan-1-one; and
(5α,8β)-8-Benzyloxymethyl-8-hydroxy-2-[4-(2,2,2-trifluoro-ethoxy)-phenyl]-2-aza-spiro[4.5]decan-1-one.

44. A compound according to claim 1 selected from the group consisting of:
(5α,8α)-8-Benzyloxymethyl-8-hydroxy-2-[4-(2,2,2-trifluoro-ethoxy)-phenyl]-2-aza-spiro[4.5]decan-1-one,
(5α,8β)-8-(2,2-Difluoro-ethoxymethyl)-8-hydroxy-2-[4-(2,2,2-trifluoro-ethoxy)-phenyl]-2-aza-spiro[4.5]decan-1-one,
(5α,8α)-8-(2,2-Difluoro-ethoxymethyl)-8-hydroxy-2-[4-(2,2,2-trifluoro-ethoxy)-phenyl]-2-aza-spiro[4.5]decan-1-one,
(5α,8β)-8-Hydroxy-8-isobutoxymethyl-2-[4-(2,2,2-trifluoro-ethoxy)-phenyl]-2-aza-spiro[4.5]decan-1-one;
(5α,8α)-8-Hydroxy-8-isobutoxymethyl-2-[4-(2,2,2-trifluoro-ethoxy)-phenyl]-2-aza-spiro[4.5]decan-1-one;
(5α,8α)-8-Ethoxymethyl-8-hydroxy-2-[6-(2,2,2-trifluoro-ethoxy)-pyridin-3-yl]-2-aza-spiro[4.5]decan-1-one;
(5α,8β)-8-Ethoxymethyl-8-hydroxy-2-[6-((S)-2,2,2-trifluoro-1-methyl-ethoxy)-pyridin-3-yl]-2-aza-spiro[4.5]decan-1-one,
(5α,8α)-8-Ethoxymethyl-8-hydroxy-2-[6-((S)-2,2,2-trifluoro-1-methyl-ethoxy)-pyridin-3-yl]-2-aza-spiro[4.5]decan-1-one;
(5α,8β)-8-Ethoxymethyl-8-hydroxy-2-[4-((S)-2,2,2-trifluoro-1-methyl-ethoxy)-phenyl]-2-aza-spiro[4.5]decan-1-one; and
(5α,8α)-8-Ethoxymethyl-8-hydroxy-2-[4-((S)-2,2,2-trifluoro-1-methyl-ethoxy)-phenyl]-2-aza-spiro[4.5]decan-1-one.

45. A compound according to claim 1 selected from the group consisting of:
(5α,8β)-8-Ethoxymethyl-8-hydroxy-2-[4-((R)-2,2,2-trifluoro-1-methyl-ethoxy)-phenyl]-2-aza-spiro[4.5]decan-1-one;
(5α,8α)-8-Ethoxymethyl-8-hydroxy-2-[4-((R)-2,2,2-trifluoro-1-methyl-ethoxy)-phenyl]-2-aza-spiro[4.5]decan-1-one;
(5α,8β)-8-[(Cyclobutylmethoxy)methyl]-8-hydroxy-2-[4-(2,2,2-trifluoro-ethoxy)-phenyl]-2-aza-spiro[4.5]decan-1-one;
(5α,8α)-8-[(Cyclobutylmethoxy)methyl]-8-hydroxy-2-[4-(2,2,2-trifluoro-ethoxy)-phenyl]-2-aza-spiro[4.5]decan-1-one;
(5α,8β)-8-[(Cyclopropylmethoxy)methyl]-8-hydroxy-2-[4-(2,2,2-trifluoro-ethoxy)-phenyl]-2-aza-spiro[4.5]decan-1-one;
(5α,8α)-8-[(Cyclopropylmethoxy)methyl]-8-hydroxy-2-[4-(2,2,2-trifluoro-ethoxy)-phenyl]-2-aza-spiro[4.5]decan-1-one;
(5α,8α)-8-Hydroxy-8-methoxymethyl-2-[4-(2,2,2-trifluoro-ethoxy)-phenyl]-2-aza-spiro[4.5]decan-1-one;
(5α,8α)-8-Hydroxy-8-(oxetan-2-ylmethoxymethyl)-2-[4-(2,2,2-trifluoro-ethoxy)-phenyl]-2-aza-spiro[4.5]decan-1-one;
(5α,8α)-8-Hydroxy-8-(3-methyl-oxetan-3-ylmethoxymethyl)-2-[4-(2,2,2-trifluoro-ethoxy)-phenyl]-2-aza-spiro[4.5]decan-1-one; and
(5α,8α)-8-Ethylsulfanylmethyl-8-hydroxy-2-[4-(2,2,2-trifluoro-ethoxy)-phenyl]-2-aza-spiro[4.5]decan-1-one.

46. A compound according to claim 1 selected from the group consisting of:
(5α,8α)-8-(3-Fluoro-phenoxymethyl)-8-hydroxy-2-[4-(2,2,2-trifluoro-ethoxy)-phenyl]-2-aza-spiro[4.5]decan-1-one;
(5α,8α)-8-(4-Fluoro-phenoxymethyl)-8-hydroxy-2-[4-(2,2,2-trifluoro-ethoxy)-phenyl]-2-aza-spiro[4.5]decan-1-one;
(5α,8β)-8-(2,2-Difluoro-ethoxymethyl)-2-(4-ethyl-phenyl)-8-hydroxy-2-aza-spiro[4.5]decan-1-one;
(5α,8α)-8-(2,2-Difluoro-ethoxymethyl)-2-(4-ethyl-phenyl)-8-hydroxy-2-aza-spiro[4.5]decan-1-one;
(5α,8β)-8-Hydroxy-8-propoxymethyl-2-[6-(2,2,2-trifluoro-ethoxy)-pyridin-3-yl]-2-aza-spiro[4.5]decan-1-one;
(5α,8α)-8-Hydroxy-8-propoxymethyl-2-[6-(2,2,2-trifluoro-ethoxy)-pyridin-3-yl]-2-aza-spiro[4.5]decan-1-one;
(5α,8α)-8-Hydroxy-8-propoxymethyl-2-[6-((S)-2,2,2-trifluoro-1-methyl-ethoxy)-pyridin-3-yl]-2-aza-spiro[4.5]decan-1-one;
(5α,8α)-8-Hydroxy-8-propoxymethyl-2-[4-((S)-2,2,2-trifluoro-1-methyl-ethoxy)-phenyl]-2-aza-spiro[4.5]decan-1-one;
(5α,8α)-8-Hydroxy-8-propoxymethyl-2-[4-((R)-2,2,2-trifluoro-1-methyl-ethoxy)-phenyl]-2-aza-spiro[4.5]decan-1-one; and
(5α,8α)-2-(4-Cyclopropyl-phenyl)-8-ethoxymethyl-8-hydroxy-2-aza-spiro[4.5]decan-1-one.

47. A compound according to claim 1 selected from the group consisting of:
(5α,8α)-2-(4-Cyclopropyl-phenyl)-8-hydroxy-8-propoxymethyl-2-aza-spiro[4.5]decan-1-one;
(5α,8α)-8-[(Cyclopentylmethoxy)methyl]-8-hydroxy-2-[4-(2,2,2-trifluoro-ethoxy)-phenyl]-2-aza-spiro[4.5]decan-1-one;
(5α,8α)-8-(2,2-Dimethyl-propoxymethyl)-8-hydroxy-2-[4-(2,2,2-trifluoro-ethoxy)-phenyl]-2-aza-spiro[4.5]decan-1-one;
(5α,8α)-8-Ethanesulfonylmethyl-8-hydroxy-2-[4-(2,2,2-trifluoro-ethoxy)-phenyl]-2-aza-spiro[4.5]decan-1-one;
(5α,8α)-8-Hydroxy-8-isopropoxymethyl-2-[4-(2,2,2-trifluoro-ethoxy)-phenyl]-2-aza-spiro[4.5]decan-1-one;
(5α,8α)-8-Hydroxy-2-[4-(2,2,2-trifluoro-ethoxy)-phenyl]-8-(3,3,3-trifluoro-propoxymethyl)-2-aza-spiro[4.5]decan-1-one;
(5α,8β)-8-Hydroxy-8-(pyridin-2-yloxymethyl)-2-[4-(2,2,2-trifluoro-ethoxy)-phenyl]-2-aza-spiro[4.5]decan-1-one;
(5α,8α)-8-Hydroxy-8-(2,2,2-trifluoro-ethoxymethyl)-2-[6-(2,2,2-trifluoro-ethoxy)-pyridin-3-yl]-2-aza-spiro[4.5]decan-1-one;
(5α,8β)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one; and
(5α,8α)-8-Hydroxy-8-(2,2,2-trifluoro-ethoxymethyl)-2-[6-((S)-2,2,2-trifluoro-1-methyl-ethoxy)-pyridin-3-yl]-2-aza-spiro[4.5]decan-1-one.

48. A compound according to claim 1 selected from the group consisting of:
(5α,8β)-8-Hydroxy-8-(2,2,2-trifluoro-ethoxymethyl)-2-[4-((S)-2,2,2-trifluoro-1-methyl-ethoxy)-phenyl]-2-aza-spiro[4.5]decan-1-one;

(5α,8α)-8-Hydroxy-8-(2,2,2-trifluoro-ethoxymethyl)-2-[4-((S)-2,2,2-trifluoro-1-methyl-ethoxy)-phenyl]-2-aza-spiro[4.5]decan-1-one;

(5α,8β)-8-Hydroxy-8-(2,2,2-trifluoro-ethoxymethyl)-2-[4-((R)-2,2,2-trifluoro-1-methyl-ethoxy)-phenyl]-2-aza-spiro[4.5]decan-1-one;

(5α,8α)-8-Hydroxy-8-(2,2,2-trifluoro-ethoxymethyl)-2-[4-((R)-2,2,2-trifluoro-1-methyl-ethoxy)-phenyl]-2-aza-spiro[4.5]decan-1-one;

(5α,8β)-8-Hydroxy-8-(2,2,2-trifluoro-ethoxymethyl)-2-[4-(2,2,2-trifluoro-ethyl)-phenyl]-2-aza-spiro[4.5]decan-1-one;

(5α,8α)-8-Hydroxy-8-(2,2,2-trifluoro-ethoxymethyl)-2-[4-(2,2,2-trifluoro-ethyl)-phenyl]-2-aza-spiro[4.5]decan-1-one;

(5α,8β)-2-(4-Cyclopropyl-phenyl)-8-hydroxy-8-(2,2,2-trifluoro-ethoxymethyl)-2-aza-spiro[4.5]decan-1-one;

(5α,8α)-2-(4-Cyclopropyl-phenyl)-8-hydroxy-8-(2,2,2-trifluoro-ethoxymethyl)-2-aza-spiro[4.5]decan-1-one; and (5α,8α)-8-(2-Cyclopropyl-ethoxymethyl)-8-hydroxy-2-[4-(2,2,2-trifluoro-ethoxy)-phenyl]-2-aza-spiro[4.5]decan-1-one; and (5α,8α)-8-Hydroxy-8-(3-methyl-butoxymethyl)-2-[4-(2,2,2-trifluoro-ethoxy)-phenyl]-2-aza-spiro[4.5]decan-1-one.

49. A compound according to claim 1 selected from the group consisting of:

(5α,8α)-8-Hydroxy-2-[4-(2,2,2-trifluoro-ethoxy)-phenyl]-8-(2,2,2-trifluoro-1-methyl-ethoxymethyl)-2-aza-spiro[4.5]decan-1-one;

(5α,8α)-8-Hydroxy-8-methylsulfanylmethyl-2-[4-(2,2,2-trifluoro-ethoxy)-phenyl]-2-aza-spiro[4.5]decan-1-one;

(5α,8α)-8-Hydroxy-8-propylsulfanylmethyl-2-[4-(2,2,2-trifluoro-ethoxy)-phenyl]-2-aza-spiro[4.5]decan-1-one;

(5α,8α)-8-(2,2-Difluoro-ethoxymethyl)-8-hydroxy-2-[6-(2,2,2-trifluoro-ethoxy)-pyridin-3-yl]-2-aza-spiro[4.5]decan-1-one;

(5α,8β)-8-(2,2-Difluoro-ethoxymethyl)-8-hydroxy-2-[6-((S)-2,2,2-trifluoro-1-methyl-ethoxy)-pyridin-3-yl]-2-aza-spiro[4.5]decan-1-one;

(5α,8α)-8-(2,2-Difluoro-ethoxymethyl)-8-hydroxy-2-[6-((S)-2,2,2-trifluoro-1-methyl-ethoxy)-pyridin-3-yl]-2-aza-spiro[4.5]decan-1-one;

(5α,8β)-8-(2,2-Difluoro-ethoxymethyl)-8-hydroxy-2-[4-((S)-2,2,2-trifluoro-1-methyl-ethoxy)-phenyl]-2-aza-spiro[4.5]decan-1-one;

(5α,8α)-8-(2,2-Difluoro-ethoxymethyl)-8-hydroxy-2-[4-((S)-2,2,2-trifluoro-1-methyl-ethoxy)-phenyl]-2-aza-spiro[4.5]decan-1-one;

(5α,8β)-8-(2,2-Difluoro-ethoxymethyl)-8-hydroxy-2-[4-((R)-2,2,2-trifluoro-1-methyl-ethoxy)-phenyl]-2-aza-spiro[4.5]decan-1-one; and (5α,8α)-8-(2,2-Difluoro-ethoxymethyl)-8-hydroxy-2-[4-((R)-2,2,2-trifluoro-1-methyl-ethoxy)-phenyl]-2-aza-spiro[4.5]decan-1-one.

50. A compound according to claim 1 selected from the group consisting of:

(5α,8β)-8-(2,2-Difluoro-ethoxymethyl)-8-hydroxy-2-[4-(2,2,2-trifluoro-ethyl)-phenyl]-2-aza-spiro[4.5]decan-1-one;

(5α,8α)-8-(2,2-Difluoro-ethoxymethyl)-8-hydroxy-2-[4-(2,2,2-trifluoro-ethyl)-phenyl]-2-aza-spiro[4.5]decan-1-one;

(5α,8α)-8-Hydroxy-8-methanesulfonylmethyl-2-[4-(2,2,2-trifluoro-ethoxy)-phenyl]-2-aza-spiro[4.5]decan-1-one;

(5α,8α)-8-Hydroxy-8-(propane-1-sulfonylmethyl)-2-[4-(2,2,2-trifluoro-ethoxy)-phenyl]-2-aza-spiro[4.5]decan-1-one;

(5α,8α)-8-Hydroxy-8-isopropylsulfanylmethyl-2-[4-(2,2,2-trifluoro-ethoxy)-phenyl]-2-aza-spiro[4.5]decan-1-one;

(5α,8β)-8-Hydroxy-8-isopropoxymethyl-2-[4-((S)-2,2,2-trifluoro-1-methyl-ethoxy)-phenyl]-2-aza-spiro[4.5]decan-1-one;

(5α,8α)-8-Hydroxy-8-isopropoxymethyl-2-[4-((S)-2,2,2-trifluoro-1-methyl-ethoxy)-phenyl]-2-aza-spiro[4.5]decan-1-one;

(5α,8α)-8-Hydroxy-8-isopropoxymethyl-2-[6-((S)-2,2,2-trifluoro-1-methyl-ethoxy)-pyridin-3-yl]-2-aza-spiro[4.5]decan-1-one;

(5α,8α)-8-Hydroxy-8-isopropoxymethyl-2-[4-((R)-2,2,2-trifluoro-1-methyl-ethoxy)-phenyl]-2-aza-spiro[4.5]decan-1-one; and (5α,8α)-8-Ethoxymethyl-8-hydroxy-2-[6-((R)-2,2,2-trifluoro-1-methyl-ethoxy)-pyridin-3-yl]-2-aza-spiro[4.5]decan-1-one.

51. A compound according to claim 1 selected from the group consisting of:

(5α,8α)-8-Hydroxy-8-propoxymethyl-2-[6-((R)-2,2,2-trifluoro-1-methyl-ethoxy)-pyridin-3-yl]-2-aza-spiro[4.5]decan-1-one;

(5α,8β)-8-(2,2-Difluoro-ethoxymethyl)-8-hydroxy-2-[6-((R)-2,2,2-trifluoro-1-methyl-ethoxy)-pyridin-3-yl]-2-aza-spiro[4.5]decan-1-one;

(5α,8α)-8-(2,2-Difluoro-ethoxymethyl)-8-hydroxy-2-[6-((R)-2,2,2-trifluoro-1-methyl-ethoxy)-pyridin-3-yl]-2-aza-spiro[4.5]decan-1-one;

(5α,8β)-8-Hydroxy-8-isopropoxymethyl-2-[6-((R)-2,2,2-trifluoro-1-methyl-ethoxy)-pyridin-3-yl]-2-aza-spiro[4.5]decan-1-one;

(5α,8α)-8-Hydroxy-8-isopropoxymethyl-2-[6-((R)-2,2,2-trifluoro-1-methyl-ethoxy)-pyridin-3-yl]-2-aza-spiro[4.5]decan-1-one;

(5α,8α)-8-Hydroxy-8-(propane-2-sulfinylmethyl)-2-[4-(2,2,2-trifluoro-ethoxy)-phenyl]-2-aza-spiro[4.5]decan-1-one;

(5α,8α)-8-Hydroxy-8-(propane-2-sulfonylmethyl)-2-[4-(2,2,2-trifluoro-ethoxy)-phenyl]-2-aza-spiro[4.5]decan-1-one;

(5α,8α)-8-tert-Butylsulfanylmethyl-8-hydroxy-2-[4-(2,2,2-trifluoro-ethoxy)-phenyl]-2-aza-spiro[4.5]decan-1-one;

(5α,8α)-8-Hydroxy-8-isopropylsulfanyl methyl-2-[6-((S)-2,2,2-trifluoro-1-methyl-ethoxy)-pyridin-3-yl]-2-aza-spiro[4.5]decan-1-one; and (5α,8α)-8-Hydroxy-8-isopropylsulfanylmethyl-2-[6-((R)-2,2,2-trifluoro-1-methyl-ethoxy)-pyridin-3-yl]-2-aza-spiro[4.5]decan-1-one.

52. A compound according to claim 1 selected from the group consisting of:

(5α,8α)-8-Hydroxy-8-(2-methyl-propane-2-sulfonylmethyl)-2-[4-(2,2,2-trifluoro-ethoxy)-phenyl]-2-aza-spiro[4.5]decan-1-one;

(5α,8α)-8-Hydroxy-8-(propane-2-sulfonylmethyl)-2-[6-((S)-2,2,2-trifluoro-1-methyl-ethoxy)-pyridin-3-yl]-2-aza-spiro[4.5]decan-1-one;

(5α,8α)-8-Hydroxy-8-(propane-2-sulfonylmethyl)-2-[6-((R)-2,2,2-trifluoro-1-methyl-ethoxy)-pyridin-3-yl]-2-aza-spiro[4.5]decan-1-one;

(5α,8α)-8-Hydroxy-8-(2-methyl-propane-2-sulfonylmethyl)-2-[6-((S)-2,2,2-trifluoro-1-methyl-ethoxy)-pyridin-3-yl]-2-aza-spiro[4.5]decan-1-one;

(5α,8α)-8-Hydroxy-8-(2-methyl-propane-2-sulfonylm-
ethyl)-2-[6-((R)-2,2,2-trifluoro-1-methyl-ethoxy)-pyri-
din-3-yl]-2-aza-spiro[4.5]decan-1-one;
(5α,8α)-8-Hydroxy-8-(2,2,2-trifluoro-ethoxymethyl)-2-
[6-((R)-2,2,2-trifluoro-1-methyl-ethoxy)-pyridin-3-yl]-
2-aza-spiro[4.5]decan-1-one;
(5α,8α)-8-(1-Ethyl-propoxymethyl)-8-hydroxy-2-[6-
((S)-2,2,2-trifluoro-1-methyl-ethoxy)-pyridin-3-yl]-2-
aza-spiro[4.5]decan-1-one;
(5α,8α)-8-Hydroxy-2-(6-isopropoxy-pyridin-3-yl)-8-
methoxymethyl-2-aza-spiro[4.5]decan-1-one;
(5α,8α)-8-Ethoxymethyl-8-hydroxy-2-(6-isopropoxy-py-
ridin-3-yl)-2-aza-spiro[4.5]decan-1-one; and
(5α,8α)-2-(4-tert-Butyl-phenyl)-8-hydroxy-8-(propane-
1-sulfonylmethyl)-2-aza-spiro[4.5]decan-1-one.

53. A compound according to claim 1 selected from the group consisting of:
(5α,8α)-2-(4-tert-Butyl-phenyl)-8-hydroxy-8-(2-methyl-
propane-1-sulfonyl methyl)-2-aza-spiro[4.5]decan-1-
one;
(5α,8α)-2-(4-tert-Butyl-phenyl)-8-hydroxy-8-(propane-
2-sulfonylmethyl)-2-aza-spiro[4.5]decan-1-one;
(5α,8α)-2-(4-tert-Butyl-phenyl)-8-hydroxy-8-(2-methyl-
propane-2-sulfonylmethyl)-2-aza-spiro[4.5]decan-1-
one;
(5α,8α)-8-Hydroxy-2-(6-isopropoxy-pyridin-3-yl)-8-
(propane-1-sulfonylmethyl)-2-aza-spiro[4.5]decan-1-
one;
(5α,8α)-2-(2,2-Difluoro-benzo[1,3]dioxol-5-yl)-8-hy-
droxy-8-trifluoromethyl-2-aza-spiro[4.5]decan-1-one;
(5α,8α)-2-(2,2-Difluoro-benzo[1,3]dioxol-5-yl)-8-ethyl-
8-hydroxy-2-aza-spiro[4.5]decan-1-one;
(5α,8α)-8-Acetyl-8-hydroxy-2-[4-(2,2,2-trifluoro-
ethoxy)-phenyl]-2-aza-spiro[4.5]decan-1-one;
(5α,8α)-8-Hydroxy-8-(1-hydroxy-1-methyl-ethyl)-2-[4-
(2,2,2-trifluoro-ethoxy)-phenyl]-2-aza-spiro[4.5]de-
can-1-one;
(5α,8α)-2-[4-(3,3-Difluoro-cyclobutyl)-phenyl]-8-hy-
droxy-8-trifluoromethyl-2-aza-spiro[4.5]decan-1-one; and
(5α,8β)-2-[4-(3,3-Difluoro-cyclobutyl)-phenyl]-8-hy-
droxy-8-trifluoromethyl-2-aza-spiro[4.5]decan-1-one.

54. A compound according to claim 1 selected from the group consisting of:
(5α,8α)-2-[4-(3,3-Difluoro-cyclobutyl)-phenyl]-8-hy-
droxy-8-methoxymethyl-2-aza-spiro[4.5]decan-1-one;
(5α,8α)-2-(4-tert-Butyl-phenyl)-8-hydroxy-8-propyl-2-
aza-spiro[4.5]decan-1-one;
(5α,8α)-2-(4-tert-Butyl-phenyl)-8-hydroxy-8-isopropyl-
2-aza-spiro[4.5]decan-1-one;
(5α,8α)-2-(4-tert-Butyl-phenyl)-8-hydroxy-8-trifluorom-
ethyl-2-aza-spiro[4.5]decan-1-one;
(5α,8α)-2-(4-tert-Butyl-phenyl)-8-hydroxy-8-meth-
oxymethyl-2-aza-spiro[4.5]decan-1-one;
(5α,8α)-2-(4-tert-Butyl-phenyl)-8-hydroxy-8-(2,2,2-trif-
luoro-ethoxymethyl)-2-aza-spiro[4.5]decan-1-one;
(5α,8α)-2-(4-tert-Butyl-phenyl)-8-ethoxymethyl-8-hy-
droxy-2-aza-spiro[4.5]decan-1-one;
(5α,8α)-2-(4-tert-Butyl-phenyl)-8-hydroxy-8-isopro-
poxymethyl-2-aza-spiro[4.5]decan-1-one;
(5α,8α)-2-(4-tert-Butyl-phenyl)-8-hydroxy-8-(2-oxo-
pyrrolidin-1-ylmethyl)-2-aza-spiro[4.5]decan-1-one; and
(5α,8α)-2-(4-tert-Butyl-phenyl)-8-hydroxy-8-(2-oxo-pi-
peridin-1-ylmethyl)-2-aza-spiro[4.5]decan-1-one.

55. A compound according to claim 1 selected from the group consisting of:
(5α,8α)-2-(4-tert-Butyl-phenyl)-8-hydroxy-8-(pyridin-2-
yloxymethyl)-2-aza-spiro[4.5]decan-1-one;
(5α,8α)-2-(4-tert-Butyl-phenyl)-8-hydroxy-8-(2-oxo-2H-
pyridin-1-ylmethyl)-2-aza-spiro[4.5]decan-1-one;
(5α,8α)-2-(4-tert-Butyl-phenyl)-8-hydroxy-8-(pyridin-3-
yloxymethyl)-2-aza-spiro[4.5]decan-1-one;
(5α,8β)-2-(4-tert-Butyl-phenyl)-8-(1-hydroxy-2-methyl-
propyl)-2-aza-spiro[4.5]decan-1-one;
(5α,8α))-2-(4-tert-Butyl-phenyl)-8-(1-hydroxy-2-me-
thyl-propyl)-2-aza-spiro[4.5]decan-1-one;
(5α,8β)-2-(4-tert-Butyl-phenyl)-8-(1-hydroxy-ethyl)-2-
aza-spiro[4.5]decan-1-one;
(5α,8α)-2-(4-tert-Butyl-phenyl)-8-(1-hydroxy-ethyl)-2-
aza-spiro[4.5]decan-1-one;
(5α,8β)-2-(4-tert-Butyl-phenyl)-8-(1-hydroxy-propyl)-2-
aza-spiro[4.5]decan-1-one;
(5α,8β)-2-(4-tert-Butyl-phenyl)-8-(2,2,2-trifluoro-1-hy-
droxy-ethyl)-2-aza-spiro[4.5]decan-1-one; and
(5α,8α)-2-(4-tert-Butyl-phenyl)-8-(2,2,2-trifluoro-1-hy-
droxy-ethyl)-2-aza-spiro[4.5]decan-1-one.

56. A compound according to claim 1 selected from the group consisting of:
2-(4-tert-Butyl-phenyl)-8-(2,2,2-trifluoro-1,1-dihydroxy-
ethyl)-2-aza-spiro[4.5]decan-1-one;
(5α,8β)-2-(4-tert-Butyl-phenyl)-8-[hydroxy-(2H-pyra-
zol-3-yl)-methyl]-2-aza-spiro[4.5]decan-1-one;
(5α,8β)-2-(4-tert-Butyl-phenyl)-8-(2H-pyrazol-3-ylm-
ethyl)-2-aza-spiro[4.5]decan-1-one;
(5α,8β)-8-(1-Hydroxy-propyl)-2-[4-((R)-2,2,2-trifluoro-
1-methyl-ethoxy)-phenyl]-2-aza-spiro[4.5]decan-1-
one;
(5α,8α)-8-(1-Hydroxy-propyl)-2-[4-((R)-2,2,2-trifluoro-
1-methyl-ethoxy)-phenyl]-2-aza-spiro[4.5]decan-1-
one;
(5α,8α)-8-Hydroxy-8-(2-oxo-pyrrolidin-1-ylmethyl)-2-
[4-(2,2,2-trifluoro-ethoxy)-phenyl]-2-aza-spiro[4.5]de-
can-1-one;
(5α,8α)-8-Hydroxy-8-(2-oxo-piperidin-1-ylmethyl)-2-
[4-(2,2,2-trifluoro-ethoxy)-phenyl]-2-aza-spiro[4.5]de-
can-1-one;
(5α,8α)-8-Hydroxy-8-(2-oxo-2H-pyridin-1-ylmethyl)-2-
[4-(2,2,2-trifluoro-ethoxy)-phenyl]-2-aza-spiro[4.5]de-
can-1-one;
(5α,8β)-8-Hydroxy-8-(2-oxo-2H-pyridin-1-ylmethyl)-2-
[4-(2,2,2-trifluoro-ethoxy)-phenyl]-2-aza-spiro[4.5]de-
can-1-one; and
(5α,8α)-8-Hydroxy-8-(pyridin-2-yloxymethyl)-2-[4-(2,2,
2-trifluoro-ethoxy)-phenyl]-2-aza-spiro[4.5]decan-1-
one.

57. A compound according to claim 1 selected from the group consisting of:
(5α,8α)-8-Hydroxy-8-(2,2,2-trifluoro-ethoxymethyl)-2-
[4-((R)-2,2,2-trifluoro-1-methoxy-ethyl)-phenyl]-2-
aza-spiro[4.5]decan-1-one;
(5α,8α)-2-[2-(4-Ethyl-phenyl)-ethyl]-8-hydroxy-8-meth-
oxymethyl-2-aza-spiro[4.5]decan-1-one;
(5α,8α)-8-hydroxy-2-(4-isopropoxyphenyl)-8-(1H-1,2,3-
triazol-4-yl)-2-azaspiro[4.5]decan-1-one; and
(5α,8α)-2-[2-(4-Ethyl-phenyl)-ethyl]-8-hydroxy-8-iso-
propoxymethyl-2-aza-spiro[4.5]decan-1-one.

* * * * *

UNITED STATES PATENT AND TRADEMARK OFFICE
CERTIFICATE OF CORRECTION

PATENT NO. : 8,440,710 B2
APPLICATION NO. : 12/900621
DATED : May 14, 2013
INVENTOR(S) : Jean Ackermann et al.

Page 1 of 1

It is certified that error appears in the above-identified patent and that said Letters Patent is hereby corrected as shown below:

Title Page, item (54) and in the specification at column 1, line 1-2, the title should read as follows:

-- NEW HSL INHIBITORS USEFUL IN THE TREATMENT OF DIABETES --

Title Page, item (75), the city for Inventor Werner Neidhart should read as follows:

-- Hagenthal-le-Bas --

Signed and Sealed this
Sixteenth Day of July, 2013

Teresa Stanek Rea
*Acting Director of the United States Patent and Trademark Office*